United States Patent
Dyckman et al.

(10) Patent No.: US 11,180,474 B2
(45) Date of Patent: Nov. 23, 2021

(54) DIMETHOXYPHENYL SUBSTITUTED INDOLE COMPOUNDS AS TLR7, TLR8 OR TLR9 INHIBITORS

(71) Applicant: BRISTOL-MYERS SQUIBB COMPANY, Princeton, NJ (US)

(72) Inventors: Alaric J. Dyckman, Lawrenceville, NJ (US); Dharmpal S. Dodd, Monmouth Junction, NJ (US); Christopher P. Mussari, Princeton, NJ (US); Tasir S. Haque, Yardley, PA (US); Michael A. Poss, Lawrenceville, NJ (US); Louis J. Lombardo, Belle Mead, NJ (US); John E. Macor, Washington Crossing, PA (US); Laxman Pasunoori, Warangal (IN); Sreekantha Ratna Kumar, Bangalore (IN)

(73) Assignee: Bristol-Myers Squibb Company, Princeton, NJ (US)

( * ) Notice: Subject to any disclaimer, the term of this patent is extended or adjusted under 35 U.S.C. 154(b) by 460 days.

(21) Appl. No.: 16/321,616

(22) PCT Filed: Jul. 27, 2017

(86) PCT No.: PCT/US2017/044091
§ 371 (c)(1),
(2) Date: Jan. 29, 2019

(87) PCT Pub. No.: WO2018/026620
PCT Pub. Date: Feb. 8, 2018

(65) Prior Publication Data
US 2021/0292300 A1    Sep. 23, 2021

(30) Foreign Application Priority Data
Jul. 30, 2016   (IN) ...................................... 1026137

(51) Int. Cl.
| | |
|---|---|
| C07D 401/14 | (2006.01) |
| C07D 405/14 | (2006.01) |
| C07D 417/14 | (2006.01) |
| C07D 451/02 | (2006.01) |
| C07D 401/04 | (2006.01) |
| C07D 413/14 | (2006.01) |
| A61P 37/06 | (2006.01) |
| C07D 409/14 | (2006.01) |

(52) U.S. Cl.
CPC ............ *C07D 401/14* (2013.01); *A61P 37/06* (2018.01); *C07D 401/04* (2013.01); *C07D 405/14* (2013.01); *C07D 409/14* (2013.01); *C07D 413/14* (2013.01); *C07D 417/14* (2013.01); *C07D 451/02* (2013.01)

(58) Field of Classification Search
None
See application file for complete search history.

(56) References Cited

U.S. PATENT DOCUMENTS

| | | |
|---|---|---|
| 6,867,200 B1 | 3/2005 | Allen et al. |
| 7,410,975 B2 | 8/2008 | Lipford et al. |
| 8,138,187 B2 | 3/2012 | Zemolka et al. |
| 8,354,400 B2 | 1/2013 | Zheng et al. |
| 9,126,996 B2 | 9/2015 | Lipford et al. |
| 9,126,999 B2 | 9/2015 | Bolvin et al. |
| 9,241,991 B2 | 1/2016 | Ji et al. |
| 9,353,115 B2 | 5/2016 | Lipford et al. |
| 9,376,398 B2 | 6/2016 | Hori et al. |
| 9,428,495 B2 | 8/2016 | Carlson et al. |
| 9,643,967 B2 | 5/2017 | Koul et al. |
| 2006/0235037 A1 | 10/2006 | Purandare et al. |
| 2010/0160314 A1 | 6/2010 | Lipford et al. |
| 2011/0015219 A1 | 1/2011 | Trawick et al. |
| 2011/0275631 A1 | 11/2011 | Abeywardane et al. |
| 2013/0045986 A1 | 2/2013 | Nagarathnam et al. |
| 2014/0066432 A1 | 3/2014 | Howbert et al. |

(Continued)

FOREIGN PATENT DOCUMENTS

| | | |
|---|---|---|
| EP | 2738172 A1 | 6/2014 |
| WO | WO2006113458 A1 | 10/2006 |

(Continued)

OTHER PUBLICATIONS

International Preliminary Report on Patentability for No. PCT/US2017/044091, dated Feb. 5, 2019.

(Continued)

*Primary Examiner* — Heidi Reese
(74) *Attorney, Agent, or Firm* — Gary Greenblatt

(57) ABSTRACT

Disclosed are compounds of Formula (I) or a salt thereof, wherein $R_1$, $R_3$, $R_4$, $R_5$, m, and n are defined herein. Also disclosed are methods of using such compounds as inhibitors of signaling through Toll-like receptor 7, or 8, or 9, and pharmaceutical compositions comprising such compounds. These compounds are useful in treating inflammatory and autoimmune diseases.

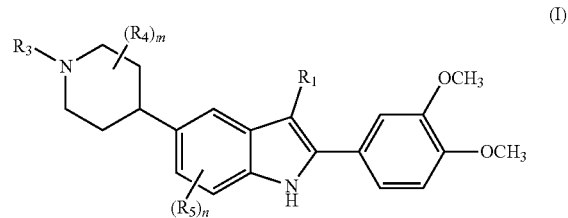

14 Claims, No Drawings

(56) References Cited

U.S. PATENT DOCUMENTS

| | | |
|---|---|---|
| 2014/0088085 A1 | 3/2014 | Burgess et al. |
| 2014/0242121 A1 | 8/2014 | Lipford et al. |
| 2016/0158214 A1 | 6/2016 | Hartman |

FOREIGN PATENT DOCUMENTS

| | | |
|---|---|---|
| WO | WO2007115306 A2 | 10/2007 |
| WO | WO2008065198 A1 | 6/2008 |
| WO | WO2008152471 A1 | 12/2008 |
| WO | WO2009030996 A1 | 3/2009 |
| WO | WO2010149769 A1 | 12/2010 |
| WO | WO2013010904 A1 | 1/2013 |
| WO | WO2013181579 A2 | 12/2013 |
| WO | WO2015088045 A1 | 6/2015 |
| WO | WO2016029077 A1 | 2/2016 |
| WO | WO2018005586 A1 | 1/2018 |
| WO | WO2018026620 A1 | 2/2018 |
| WO | WO2018049089 A1 | 3/2018 |

OTHER PUBLICATIONS

Kawai, T., et al., "The Role of Pattern-Recognition Receptors in Innate Immunity: Update on Toll-like Receptors", Nature Immunol., 2011, 11, 373-384.

Lamphier, M et al., "Novel Small Molecule Inhibitors of TLR7 and TLR9: Mechanism of Action and Efficacy in Vivo", Mol Pharmacol, 2014, 85:429-440.

Patra, Mahesh Chandra, et al., "Recent Progress in the Development of Toll-like Receptor (TLR) antagonists", Exp. Opin. on Therapeutic Patents, 2016, vol. 26, No. 6, 719-730.

Roy, et al., "Design and developmen of benzoxazole derivatives with toll-like receptor 9 antagonism", Eur J Med Chern, 2017, vol. 134, 334-347.

Sims, et al., "The IL-1 Family: Regulators of Immunity", Nature Rev, Immunol., 2010, 10, 89-102.

Ferreira de Freitas, et al., "Discovery of a Potent Class 1 Protein Arginine Methyltransferase Fragment Inhibitor", J. Med. Chem. 2016, 59, pp. 1176-1183.

DIMETHOXYPHENYL SUBSTITUTED INDOLE COMPOUNDS AS TLR7, TLR8 OR TLR9 INHIBITORS

CROSS REFERENCE

This application is a national phase application under 35 U.S.C. § 371 of International Patent Application No. PCT/US2017/044091, filed Jul. 27, 2017, which claims priority to Indian Provisional Application Serial No. 201611026137 filed Jul. 30, 2016, which are expressly incorporated fully herein by reference.

DESCRIPTION

The present invention generally relates to dimethoxyphenyl substituted indole compounds useful as inhibitors of signaling through Toll-like receptor 7, 8, or 9 (TLR7, TLR8, TLR9) or combinations thereof. Provided herein are dimethoxyphenyl substituted indole compounds, compositions comprising such compounds, and methods of their use. The invention further pertains to pharmaceutical compositions containing at least one compound according to the invention that are useful for the treatment of conditions related to TLR modulation, such as inflammatory and autoimmune diseases, and methods of inhibiting the activity of TLRs in a mammal.

Toll/IL-1 receptor family members are important regulators of inflammation and host resistance. The Toll-like receptor family recognizes molecular patterns derived from infectious organisms including bacteria, fungi, parasites, and viruses (reviewed in Kawai, T. et al., *Nature Immunol.*, 11:373-384 (2010)). Ligand binding to the receptor induces dimerization and recruitment of adaptor molecules to a conserved cytoplasmic motif in the receptor termed the Toll/IL-1 receptor (TIR) domain. With the exception of TLR3, all TLRs recruit the adaptor molecule MyD88. The IL-1 receptor family also contains a cytoplasmic TIR motif and recruits MyD88 upon ligand binding (reviewed in Sims, J. E. et al., *Nature Rev. Immunol.*, 10:89-102 (2010)).

Toll-like receptors (TLRs) are a family of evolutionarily conserved, transmembrane innate immune receptors that participate in the first-line defense. As pattern recognition receptors, the TLRs protect against foreign molecules, activated by pathogen associated molecular patterns (PAMPs), or from damaged tissue, activated by danger associated molecular patterns (DAMPs). A total of 13 TLR family members have been identified, 10 in human, that span either the cell surface or the endosomal compartment. TLR7-9 are among the set that are endosomally located and respond to single-stranded RNA (TLR7 and TLR8) or unmethylated single-stranded DNA containing cytosine-phosphate-guanine (CpG) motifs (TLR9).

Activation of TLR7/8/9 can initiate a variety of inflammatory responses (cytokine production, B cell activation and IgG production, Type I interferon response). In the case of autoimmune disorders, the aberrant sustained activation of TLR7/8/9 leads to worsening of disease states. Whereas overexpresion of TLR7 in mice has been shown to exacerbate autoimmune disease, knockout of TLR7 in mice was found to be protective against disease in lupus-prone MRL/lpr mice. Dual knockout of TLR7 and 9 showed further enhanced protection.

As numerous conditions may benefit by treatment involving modulation of cytokines, IFN production and B cell activity, it is immediately apparent that new compounds capable of modulating TLR7 and/or TLR8 and/or TLR9 and methods of using these compounds could provide substantial therapeutic benefits to a wide variety of patients.

The present invention relates to a new class of dimethoxyphenyl substituted indole compounds found to be effective inhibitors of signaling through TLR7/8/9. These compounds are provided to be useful as pharmaceuticals with desirable stability, bioavailability, therapeutic index, and toxicity values that are important to their drugability.

SUMMARY OF THE INVENTION

The present invention provides compounds of Formula (I) that are useful as inhibitors of signaling through Toll-like receptor 7, 8, or 9 and are useful for the treatment of proliferative diseases, allergic diseases, autoimmune diseases and inflammatory diseases, or stereoisomers, tautomers, pharmaceutically acceptable salts, solvates or prodrugs thereof.

The present invention also provides pharmaceutical compositions comprising a pharmaceutically acceptable carrier and at least one of the compounds of the present invention or stereoisomers, tautomers, pharmaceutically acceptable salts, solvates, or prodrugs thereof.

The present invention also provides a method for inhibition of Toll-like receptor 7, 8, or 9 comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method for treating proliferative, metabolic, allergic, autoimmune and inflammatory diseases, comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method of treating a disease or disorder associated with Toll-like receptor 7, 8, or 9 activity, the method comprising administering to a mammal in need thereof, at least one of the compounds of Formula (I) or salts, solvates, and prodrugs thereof.

The present invention also provides processes and intermediates for making the compounds of Formula (I) including salts, solvates, and prodrugs thereof.

The present invention also provides at least one of the compounds of Formula (I) or salts, solvates, and prodrugs thereof, for use in therapy.

The present invention also provides the use of at least one of the compounds of Formula (I) or salts, solvates, and prodrugs thereof, for the manufacture of a medicament for the treatment of prophylaxis of Toll-like receptor 7, 8, or 9 related conditions, such as allergic disease, autoimmune diseases, inflammatory diseases, and proliferative diseases.

The compound of Formula (I) and compositions comprising the compounds of Formula (I) may be used in treating, preventing, or curing various Toll-like receptor 7, 8, or 9 related conditions. Pharmaceutical compositions comprising these compounds are useful for treating, preventing, or slowing the progression of diseases or disorders in a variety of therapeutic areas, such as allergic disease, autoimmune diseases, inflammatory diseases, and proliferative diseases.

These and other features of the invention will be set forth in expanded form as the disclosure continues.

DETAILED DESCRIPTION

The first aspect of the present invention provides at least one compound of Formula (I):

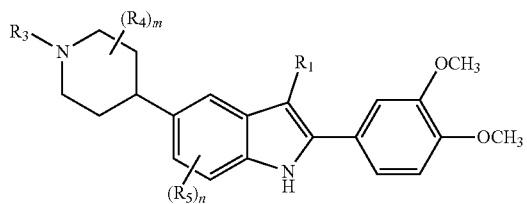

(I)

or a salt thereof, wherein:

$R_1$ is H, Cl, —CN, $C_{1-4}$ alkyl, $C_{1-3}$ fluoroalkyl, $C_{1-3}$ hydroxy-fluoroalkyl, —$CR_z$=$CH_2$, $C_{3-6}$ cycloalkyl, —$CH_2(C_{3-6}$ cycloalkyl), —C(O)O($C_{1-3}$ alkyl), or tetrahydropyranyl;

$R_3$ is:
(a) -$L_1$-A; or
(b) H, $C_{1-6}$ alkyl, $C_{1-3}$ fluoroalkyl, $C_{1-3}$ cyanoalkyl, $C_{1-6}$ hydroxyalkyl, $C_{1-3}$ hydroxy-fluoroalkyl, —$CR_xR_xCR_x$(OH)$CR_x$=$CR_xR_x$, —$(CR_xR_x)_{1-4}$O($C_{1-3}$ alkyl), —$(CR_xR_x)_{1-4}$O($CR_xR_x)_{1-3}$O($C_{1-3}$ alkyl), —$CH_2$CH(OH)$CH_2$O($C_{1-3}$ alkyl), —$(CR_xR_x)_{1-3}$S($C_{1-3}$ alkyl), —$(CH_2)_{1-3}$C(O)OC($CH_3)_3$, —$(CR_xR_x)_{0-3}$NR$_xR_y$, —$(CR_xR_x)_{0-3}$NR$_x$($C_{1-4}$ hydroxyalkyl), —$CH_2$CH(OH)$CH_2$NR$_xR_y$, —$(CR_xR_x)_{1-2}$NHC(O)($CR_xR_x)_{1-4}$C≡CH, —C(O)H, —C(O)($C_{1-6}$ alkyl), —C(O)($C_{1-3}$ hydroxyalkyl), —C(O)($C_{1-3}$ fluoroalkyl), —C(O)($C_{1-3}$ chloroalkyl), —C(O)($C_{1-3}$ cyanoalkyl), —$(CR_xR_x)_{0-3}$C(O)OH, —C(O)($CH_2)_{0-2}$O($C_{1-4}$ alkyl), —C(O)($CR_xR_x)_{0-2}$O($CR_xR_x)_{1-2}$O($C_{1-3}$ alkyl), —C(O)$CR_xR_x$S(O)$_2$($C_{1-3}$ alkyl), —C(O)$CR_xR_x$NR$_x$S(O)$_2$($C_{1-3}$ alkyl), —C(O)$CR_xR_x$OC(O)($C_{1-3}$ alkyl), —C(O)($CR_xR_x)_{0-3}$NR$_xR_y$, —C(O)($CR_xR_x)_{0-1}$NR$_x$($C_{1-3}$ cyanoalkyl), —C(O)($CR_xR_x)_{0-2}$NR$_y$($C_{1-6}$ hydroxyalkyl), —C(O)($CR_xR_x)_{0-1}$NR$_x$($C_{1-3}$ fluoroalkyl), —C(O)($CR_xR_x)_{0-1}$NR$_x$($C_{1-5}$ hydroxy-fluoroalkyl), —C(O)($CR_xR_x)_{0-1}$NR$_x$($CH_2)_{1-2}$O($C_{1-3}$ hydroxyalkyl), —C(O)($CR_xR_x)_{0-1}$NR$_x$($CH_2)_{1-2}$NR$_x$C(O)($C_{1-2}$ alkyl), —C(O)($CR_xR_x)_{0-1}$NR$_x$(($CR_xR_x)_{1-2}$O($C_{1-2}$ alkyl), —C(O)$CR_x$(NH$_2$)($CR_xR_x)_{1-4}$NR$_xR_x$, —C(O)$CR_x$(NH$_2$)($CR_xR_x)_{1-4}$NR$_x$C(O)NR$_xR_x$, —C(O)($CR_xR_x)_{0-3}$NR$_x$($CH_2)_{0-1}$C(O)($C_{1-3}$ alkyl), —C(O)($CR_xR_x)_{0-1}$NR$_x$($CH_2)_{0-1}$C(O)($C_{1-3}$ cyanoalkyl), —C(O)($CR_xR_x)_{0-1}$NR$_x$($CH_2)_{1-2}$C(O)NR$_yR_y$, —C(O)($CR_xR_x)_{1-3}$C(O)NR$_yR_y$, —C(O)($CR_xR_x)_{0-1}$NR$_x$(CHR(CH$_2$OH)), —$(CR_xR_x)_{1-2}$C(O)NR$_yR_y$, —$(CR_xR_x)_{1-2}$C(O)NR$_y$($C_{1-3}$ fluoroalkyl), —$(CR_xR_x)_{1-2}$C(O)NR$_y$($C_{1-4}$ hydroxyalkyl), —$(CR_xR_x)_{1-2}$C(O)NR$_y$($C_{1-3}$ cyanoalkyl), —$(CR_xR_x)_{1-2}$C(O)NR$_x$($CH_2)_{1-2}$O($C_{1-3}$ alkyl), —$(CR_xR_x)_{1-2}$C(O)NR$_x$CH($C_{1-4}$ alkyl)($C_{1-3}$ hydroxyalkyl), —$(CH_2)_{1-2}$C(O)NR$_x$($CH_2)_{1-2}$C(O)NR$_xR_x$, —$(CH_2)_{1-2}$C(O)NR$_x$($CH_2)_{1-2}$S(O)$_2$OH, —$(CH_2)_{1-2}$C(O)NR$_x$($CH_2)_{1-2}$NR$_x$C(O)($C_{1-3}$ alkyl), —$(CH_2)_{1-2}$C(O)NR$_x$($CH_2)_{1-3}$NR$_xR_x$, —$(CH_2)_{1-2}$C(O)N(CH$_2$CH$_3$)($CH_2)_{1-3}$NR$_xR_x$, —$(CH_2)_{0-2}$S(O)$_2$($C_{1-4}$ alkyl), —$(CH_2)_{0-2}$S(O)$_2$($C_{1-3}$ fluoroalkyl), —$(CH_2)_{0-2}$S(O)$_2$NR$_xR_x$, —C(O)C(O)OH, —C(O)C(O)NR$_yR_y$, or —C(O)C(O)NR$_y$($CR_xR_x)_{1-2}$NR$_yR_y$;

$L_1$ is a bond, —$(CR_xR_x)_{1-2}$—, —$(CR_xR_x)_{1-2}$CR$_x$(OH)—, —$(CR_xR_x)_{1-2}$O—, —$CR_xR_x$C(O)—, —$(CR_xR_x)_2$NR$_x$(CR$_xR_x)_{0-1}$—, —$CR_xR_x$C(O)NR$_x$($CR_xR_x)_{0-4}$—, —C(O)($CR_xR_x)_{0-3}$—, —C(O)($CR_xR_x)_{0-2}$NR$_x$($CR_xR_x)_{0-2}$—, —C(O)($CR_xR_x)_{0-2}$N($C_{1-2}$ hydroxyalkyl)($CR_xR_x)_{0-2}$—, —C(O)($CR_xR_x)_{0-2}$NR$_x$($CR_xR_x)_{1-2}$CR$_x$(OH)—, —C(O)($CR_xR_x)_{1-2}$C(O)NR$_x$—, —$(CR_xR_x)_{0-2}$C(O)NR$_x$($CR_xR_x)_{1-2}$CR$_x$(OH)—, —$(CR_xR_x)_{0-2}$C(O)N($C_{1-2}$ hydroxyalkyl)($CR_xR_x)_{1-2}$—, —C(O)($CR_xR_x)_{0-1}$O—, —C(O)($CR_xR_x)_{1-2}$NHS(O)$_2$—, —C(O)$CR_x$(NH$_2$)$CR_xR_x$—, —C(O)C(O)($CR_xR_x)_{0-2}$—, —C(O)NR$_x$($CR_xR_x)_{1-2}$—, or —S(O)$_2$—;

A is 2-oxa-6-azaspiro[3.3]heptanyl, 4-oxaspiro[2.5]octanyl, 7-azaspiro[3.5]nonanyl, 8-azabicyclo[3.2.1]octanyl, 8-oxa-3-azabicyclo[3.2.1]octanyl, 9-azabicyclo[3.3.1]nonanyl, adamantanyl, azepanyl, azetidinyl, $C_{3-6}$ cycloalkyl, diazepanyl, dihydroinonyl, dihydropyrimidinonyl, dioxidoisothiazolidinyl, dioxidothiazinanyl, dioxotetrahydrothiophenyl, dioxotetrahydrothiopyranyl, dioxothiomorpholinyl, furanyl, imidazolyl, imidazolidinonyl, indolyl, isoquinolinyl, isoxazolyl, morpholinyl, morpholinonyl, naphthalenyl, octahydrocyclopenta[b]pyranyl, oxazolidinonyl, oxadiazolyl, oxetanyl, oxazolyl, phenyl, piperidinyl, piperidinonyl, piperazinyl, piperazinonyl, pyrazinyl, pyrazolyl, pyridazinonyl, pyridinonyl, pyridinyl, pyrimidinyl, pyrrolidinonyl, pyrrolidinyl, pyrrolyl, quinolinyl, quinolizinonyl, tetrahydrofuranyl, tetrahydropyranyl, tetrazolyl, thiadiazolyl, thiazolyl, or triazolyl, each substituted with -$L_2$-$R_a$ and zero to 4 $R_b$;

$L_2$ is a bond or —$CR_xR_x$—;

$R_a$ is:
(a) H, F, Cl, —CN, —OH, $C_{1-6}$ alkyl, $C_{1-3}$ fluoroalkyl, $C_{1-5}$ hydroxyalkyl, —$(CH_2)_{0-4}$O($C_{1-3}$ alkyl), —$(CR_xR_x)_{1-3}$S($C_{1-3}$ alkyl), —$(CR_xR_x)_{1-3}$NHC(O)O($C_{1-4}$ alkyl), —$(CR_xR_x)_{1-3}$NR$_xR_y$, —$(CR_xR_x)_{1-3}$C(O)NR$_yR_y$, —O($C_{1-3}$ fluoroalkyl), —S(O)$_2$NR$_xR_x$, —O($CR_xR_x)_{1-3}$NR$_xR_x$, —NHS(O)$_2$($C_{1-3}$ alkyl), —NR$_xR_x$, —NR$_x$($C_{1-4}$ alkyl), —NR$_x$C(O)($C_{1-4}$ alkyl), —$(CR_xR_x)_{0-3}$C(O)OH, —C(O)($C_{1-5}$ alkyl), —C(O)($C_{1-3}$ fluoroalkyl), —C(O)CH$_2$N($C_{1-3}$ alkyl)$_2$, —C(O)O($C_{1-4}$ alkyl), —C(O)NH($C_{1-3}$ cyanoalkyl), —C(O)NR$_yR_y$, —C(O)NR$_x$CH$_2$C(O)NR$_xR_x$, or —C(O)NR$_x$CH$_2$CH$_2$NHC(O)($C_{1-3}$ alkyl);
(b) $C_{3-6}$ cycloalkyl or —C(O)NH($C_{3-6}$ cycloalkyl), wherein each cycloalkyl is substituted with zero to 2 substituents independently selected from —OH, $C_{1-3}$ alkyl, $C_{1-3}$ hydroxyalkyl, $C_{1-3}$ fluoroalkyl, and —C(O)O($C_{1-3}$ alkyl); or
(c) $A_1$, —$CH_2A_1$, —C(O)$A_1$, —NR$_xA_1$, or —C(O)NR$_xA_1$, wherein $A_1$ is furanyl, imidazolyl, indolyl, isoxazolyl, morpholinyl, octahydropyrrolo[3,4-c]pyrrolyl, oxazolyl, oxetanyl, phenyl, piperazinyl, piperidinyl, pyrazolyl, pyridinyl, pyrimidinyl, pyrrolidinyl, pyrrolyl, tetrahydrofuranyl, tetrahydropyranyl, thiadiazolyl, thiazolyl, thiophenyl, or triazolyl, each substituted with zero to three substituents independently selected from —OH, $C_{1-3}$ alkyl, $C_{1-3}$ hydroxyalkyl, —C(O)($C_{1-2}$ alkyl), —C(O)O($C_{1-3}$ alkyl), —NR$_xR_x$, phenyl, trifluoromethyl-phenyl, —CH$_2$(bromophenyl), and —CH$_2$CH$_2$(pyrrolidinyl);

each $R_b$ is independently F, —CH$_3$, —CF$_3$, or —OCH$_3$;
each $R_x$ is independently H or —CH$_3$;
each $R_y$ is independently H or $C_{1-6}$ alkyl;
$R_z$ is H, $C_{1-2}$ alkyl, or $C_{1-2}$ fluoroalkyl;
each $R_4$ is independently F or —OH; or two $R_4$ attached to the same carbon atom form =O;
$R_5$ is F, Cl, —CN, $C_{1-2}$ alkyl, $C_{1-2}$ fluoroalkyl, or —OCH$_3$;
m is zero, 1, 2, 3, or 4; and
n is zero, 1, or 2;
with the proviso that when $R_1$ is —CH$_3$, then $R_3$ is not —CH$_2$CH$_2$NH(CH$_3$).

The second aspect of the present invention provides at least one compound of Formula (I):

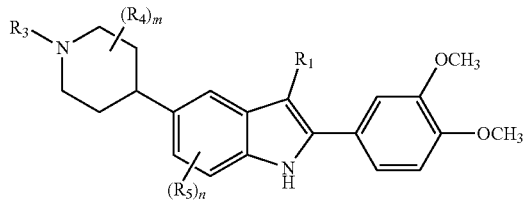

or a salt thereof, wherein:

$R_1$ is H, Cl, —CN, $C_{1-4}$ alkyl, $C_{1-3}$ fluoroalkyl, $C_{1-3}$ hydroxy-fluoroalkyl, —$CR_z$=$CH_2$, $C_{3-6}$ cycloalkyl, —$CH_2(C_{3-6}$ cycloalkyl), —C(O)O($C_{1-3}$ alkyl), or tetrahydropyranyl;

$R_3$ is:
(a) -$L_1$-A; or
(b) H, $C_{1-6}$ alkyl, $C_{1-3}$ fluoroalkyl, $C_{1-3}$ cyanoalkyl, $C_{1-6}$ hydroxyalkyl, $C_{1-3}$ hydroxy-fluoroalkyl, —$CR_xR_xCR_x$(OH)$CR_x$=$CR_xR_x$, —($CR_xR_x)_{1-4}$O($C_{1-3}$ alkyl), —($CR_xR_x)_{1-3}$O($CR_xR_x)_{1-3}$O($C_{1-3}$ alkyl), —$CH_2$CH(OH)$CH_2$O($C_{1-3}$ alkyl), —($CR_xR_x)_{1-3}$S($C_{1-3}$ alkyl), —($CH_2)_{1-3}$C(O)OC(CH_3)_3, —($CR_xR_x)_{0-3}NR_yR_y$, —($CR_xR_x)_{0-3}NR_x(C_{1-4}$ hydroxyalkyl), —$CH_2$CH(OH)$CH_2NR_xR_y$, —C(O)H, —C(O)($C_{1-6}$ alkyl), —C(O)($C_{1-3}$ hydroxyalkyl), —C(O)($C_{1-3}$ fluoroalkyl), —C(O)($C_{1-3}$ chloroalkyl), —C(O)($C_{1-3}$ cyanoalkyl), —($CR_xR_x)_{0-3}$C(O)OH, —C(O)($CH_2)_{0-2}$O($C_{1-4}$ alkyl), —C(O)($CR_xR_x)_{0-2}$O($CR_xR_x)_{1-2}$O($C_{1-3}$ alkyl), —C(O)$CR_xR_xS(O)_2(C_{1-3}$ alkyl), —C(O)$CR_xR_xNR_xS(O)_2(C_{1-3}$ alkyl), —C(O)$CR_xR_xOC(O)(C_{1-3}$ alkyl), —C(O)($CR_xR_x)_{0-3}NR_yR_y$, —C(O)($CR_xR_x)_{0-1}NR_x(C_{1-3}$ cyanoalkyl), —C(O)($CR_xR_x)_{0-2}NR_y(C_{1-6}$ hydroxyalkyl), —C(O)($CR_xR_x)_{0-1}NR_x(C_{1-3}$ fluoroalkyl), —C(O)($CR_xR_x)_{0-1}NR_x(C_{1-5}$ hydroxy-fluoroalkyl), —C(O)($CR_xR_x)_{0-1}NR_x(CH_2)_{1-2}$O($C_{1-3}$ hydroxyalkyl), —C(O)($CR_xR_x)_{0-1}NR_x(CH_2)_{1-2}NR_xC(O)(C_{1-2}$ alkyl), —C(O)($CR_xR_x)_{0-1}NR_x((CR_xR_x)_{1-2}$O($C_{1-2}$ alkyl)), —C(O)$CR_x(NH_2)(CR_xR_x)_{1-4}NR_xR_x$, —C(O)$CR_x(NH_2)(CR_xR_x)_{1-4}NR_xC(O)NR_xR_x$, —C(O)($CR_xR_x)_{0-3}NR_x(CH_2)_{0-1}$C(O)($C_{1-3}$ alkyl), —C(O)($CR_xR_x)_{0-1}NR_x(CH_2)_{0-1}$C(O)($C_{1-3}$ cyanoalkyl), —C(O)($CR_xR_x)_{0-1}NR_x(CH_2)_{1-2}$C(O)$NR_yR_y$, —C(O)($CR_xR_x)_{1-3}$C(O)$NR_yR_y$, —C(O)($CR_xR_x)_{0-1}NR_x(CHR_y(CH_2OH))$, —($CR_xR_x)_{1-2}$C(O)$NR_yR_y$, —($CR_xR_x)_{1-2}$C(O)$NR_y(C_{1-3}$ fluoroalkyl), —($CR_xR_x)_{1-2}$C(O)$NR_y(C_{1-4}$ hydroxyalkyl), —($CR_xR_x)_{1-2}$C(O)$NR_y(C_{1-3}$ cyanoalkyl), —($CR_xR_x)_{1-2}$C(O)$NR_x(CH_2)_{1-2}$O($C_{1-3}$ alkyl), —($CR_xR_x)_{1-2}$C(O)$NR_xCH(C_{1-4}$ alkyl)($C_{1-3}$ hydroxyalkyl), —($CH_2)_{1-2}$C(O)$NR_x(CH_2)_{1-2}$ C(O)$NR_xR_x$, —($CH_2)_{1-2}$C(O)$NR_x(CH_2)_{1-2}$S(O)$_2$OH, —($CH_2)_{1-2}$C(O)$NR_x(CH_2)_{1-2}NR_xC(O)(C_{1-3}$ alkyl), —($CH_2)_{1-2}$C(O)$NR_x(CH_2)_{1-3}NR_xR_x$, —($CH_2)_{1-2}$ C(O)N(CH$_2$CH$_3$)(CH$_2)_{1-3}NR_xR_x$, —($CH_2)_{0-2}$S(O)$_2(C_{1-4}$ alkyl), —($CH_2)_{0-2}$S(O)$_2(C_{1-3}$ fluoroalkyl), —($CH_2)_{0-2}$S(O)$_2NR_xR_x$, —C(O)C(O)OH, —C(O)C(O)$NR_yR_y$, or —C(O)C(O)$NR_y(CR_xR_x)_{1-2}$ $NR_yR_y$;

$L_1$ is a bond, —($CR_xR_x)_{1-2}$—, —($CR_xR_x)_{1-2}CR_x(OH)$—, —($CR_xR_x)_{1-2}$O—, —$CR_xR_xC(O)$—, —($CR_xR_x)_2NR_x$ $(CR_xR_x)_{0-1}$—, —$CR_xR_xC(O)NR_x(CR_xR_x)_{0-4}$—, —C(O) $(CR_xR_x)_{0-3}$—, —C(O)($CR_xR_x)_{0-2}NR_x(CR_xR_x)_{0-2}$—, —C(O)($CR_xR_x)_{0-2}N(C_{1-2}$ hydroxyalkyl)($CR_xR_x)_{0-2}$—, —C(O)($CR_xR_x)_{0-2}NR_x(CR_xR_x)_{1-2}CR_x(OH)$—, —C(O) $(CR_xR_x)_{1-2}C(O)NR_x$—, —($CR_xR_x)_{0-2}C(O)NR_x(CR_xR_x)_{1-2}CR_x(OH)$—, —($CR_xR_x)_{0-2}C(O)N(C_{1-2}$ hydroxyalkyl)($CR_xR_x)_{1-2}$—, —C(O)($CR_xR_x)_{0-1}$O—, —C(O) $(CR_xR_x)_{1-2}NHS(O)_2$—, —C(O)$CR_x(NH_2)CR_xR_x$—, —C(O)C(O)($CR_xR_x)_{0-2}$—, —C(O)$NR_x(CR_xR_x)_{1-2}$—, or —S(O)$_2$—;

A is 2-oxa-6-azaspiro[3.3]heptanyl, 4-oxaspiro[2.5]octanyl, 7-azaspiro[3.5]nonanyl, 8-azabicyclo[3.2.1]octanyl, 8-oxa-3-azabicyclo[3.2.1]octanyl, 9-azabicyclo[3.3.1] nonanyl, adamantanyl, azepanyl, azetidinyl, $C_{3-6}$ cycloalkyl, diazepanyl, dihydroinonyl, dihydropyrimidinonyl, dioxidoisothiazolidinyl, dioxidothiazinanyl, dioxotetrahydrothiophenyl, dioxotetrahydrothiopyranyl, dioxothiomorpholinyl, furanyl, imidazolyl, imidazolidinonyl, indolyl, isoquinolinyl, isoxazolyl, morpholinyl, morpholinonyl, naphthalenyl, octahydrocyclopenta[b] pyranyl, oxazolidinonyl, oxadiazolyl, oxetanyl, oxazolyl, phenyl, piperidinyl, piperidinonyl, piperazinyl, piperazinonyl, pyrazinyl, pyrazolyl, pyridazinonyl, pyridinonyl, pyridinyl, pyrimidinyl, pyrrolidinonyl, pyrrolidinyl, pyrrolyl, quinolinyl, quinolizinonyl, tetrahydrofuranyl, tetrahydropyranyl, tetrazolyl, thiadiazolyl, thiazolyl, or triazolyl, each substituted with -$L_2$-$R_a$ and zero to 4 $R_b$;

$L_2$ is a bond or —$CR_xR_x$—;

$R_a$ is:
(a) H, F, Cl, —CN, —OH, $C_{1-6}$ alkyl, $C_{1-3}$ fluoroalkyl, $C_{1-5}$ hydroxyalkyl, —($CH_2)_{0-4}$O($C_{1-3}$ alkyl), —($CR_xR_x)_{1-3}$S($C_{1-3}$ alkyl), —($CR_xR_x)_{1-3}NHC(O)O$ ($C_{1-4}$ alkyl), —($CR_xR_x)_{1-3}NR_yR_y$, —($CR_xR_x)_{1-3}C(O)$ $NR_yR_y$, —O($C_{1-3}$ fluoroalkyl), —S(O)$_2NR_xR_x$, —O($CR_xR_x)_{1-3}NR_xR_x$, —NHS(O)$_2(C_{1-3}$ alkyl), —$NR_xR_x$, —$NR_x(C_{1-4}$ hydroxyalkyl), —$NR_xC(O)(C_{1-4}$ alkyl), —($CR_xR_x)_{0-3}$C(O)OH, —C(O)($C_{1-5}$ alkyl), —C(O) ($C_{1-3}$ fluoroalkyl), —C(O)O($C_{1-4}$ alkyl), —C(O)NH ($C_{1-3}$ cyanoalkyl), —C(O)$NR_yR_y$, —C(O)$NR_xCH_2C$ (O)$NR_xR_x$, or —C(O)$NR_xCH_2CH_2NHC(O)(C_{1-3}$ alkyl);
(b) $C_{3-6}$ cycloalkyl or —C(O)NH($C_{3-6}$ cycloalkyl), wherein each cycloalkyl is substituted with zero to 2 substituents independently selected from —OH, $C_{1-3}$ alkyl, $C_{1-3}$ hydroxyalkyl, $C_{1-3}$ fluoroalkyl, and —C(O) O($C_{1-3}$ alkyl); or
(c) $A_1$, —$CH_2A_1$, —C(O)$A_1$, —$NR_xA_1$, or —C(O) $NR_xA_1$, wherein $A_1$ is furanyl, imidazolyl, indolyl, isoxazolyl, morpholinyl, octahydropyrrolo[3,4-c]pyrrolyl, oxazolyl, oxetanyl, phenyl, piperazinyl, piperidinyl, pyrazolyl, pyridinyl, pyrimidinyl, pyrrolidinyl, pyrrolyl, tetrahydrofuranyl, tetrahydropyranyl, thiadiazolyl, thiazolyl, thiophenyl, or triazolyl, each substituted with zero to three substituents independently selected from —OH, $C_{1-3}$ alkyl, $C_{1-3}$ hydroxyalkyl, —C(O)($C_{1-2}$ alkyl), —C(O)O($C_{1-3}$ alkyl), —$NR_xR_x$, phenyl, trifluoromethyl-phenyl, —$CH_2$(bromophenyl), and —$CH_2CH_2$(pyrrolidinyl);

each $R_b$ is independently F, —$CH_3$, —$CF_3$, or —$OCH_3$;
each $R_x$ is independently H or —$CH_3$;
each $R_y$ is independently H or $C_{1-6}$ alkyl;
$R_z$ is H, $C_{1-2}$ alkyl, or $C_{1-2}$ fluoroalkyl;
each $R_4$ is independently F or —OH; or two $R_4$ attached to the same carbon atom form =O;
$R_5$ is F, Cl, —CN, $C_{1-2}$ alkyl, $C_{1-2}$ fluoroalkyl, or —$OCH_3$;
m is zero, 1, 2, 3, or 4; and
n is zero, 1, or 2;
with the proviso that when $R_1$ is —$CH_3$, then $R_3$ is not —$CH_2CH_2NH(CH_3)$.

One embodiment provides a compound of Formula (I) or a salt thereof, wherein:

$R_1$ is H, Cl, —CN, $C_{1-4}$ alkyl, $C_{1-3}$ fluoroalkyl, $C_{1-3}$ hydroxy-fluoroalkyl, —CR$_z$=CH$_2$, $C_{3-6}$ cycloalkyl, —CH$_2$($C_{3-6}$ cycloalkyl), —C(O)O($C_{1-3}$ alkyl), or tetrahydropyranyl;

$R_3$ is:

(a) -L$_1$-A; or (b) H, $C_{1-6}$ alkyl, $C_{1-3}$ fluoroalkyl, $C_{1-5}$ hydroxyalkyl, —(CR$_x$R$_x$)$_{1-4}$O($C_{1-3}$ alkyl), —(CR$_x$R$_x$)$_{1-3}$S($C_{1-3}$ alkyl), —(CH$_2$)$_{1-3}$C(O)OC(CH$_3$)$_3$, —(CH$_2$)$_{1-3}$NR$_x$R$_x$, —CHR$_x$CH$_2$NR$_x$($C_{1-4}$ alkyl), —(CH$_2$)$_{1-3}$NR$_x$($C_{1-3}$ alkyl), —(CR$_x$R$_x$)$_{1-2}$NHC(O)(CH$_2$)$_{1-4}$C≡CH, —S(O)$_2$NR$_x$R$_x$, —C(O)O($C_{1-4}$ alkyl), —C(O)($C_{1-3}$ alkyl), —C(O)($C_{1-3}$ hydroxyalkyl), —C(O)($C_{1-3}$ fluoroalkyl), —C(O)($C_{1-3}$ chloroalkyl), —C(O)CH$_2$O($C_{1-3}$ alkyl), —C(O)CH$_2$S(O)$_2$($C_{1-3}$ alkyl), —C(O)($C_{1-3}$ hydroxyalkyl), —C(O)CR$_x$R$_x$OC(O)($C_{1-3}$ alkyl), —C(O)(tetrahydrofuranyl), —C(O)(tetrahydropyranyl), —C(O)(piperidinyl), —C(O)(ethoxypiperidinyl), —C(O)NR$_x$($C_{1-3}$ cyanoalkyl), —C(O)NR$_x$($C_{1-3}$ alkyl), —C(O)NR$_x$CH$_2$C(O)NR$_x$R$_x$, —C(O)NR$_x$CH$_2$CH$_2$NR$_x$C(O)($C_{1-2}$ alkyl), —C(O)N($C_{1-3}$ alkyl)$_2$, —C(O)NR$_x$C(R$_x$)$_3$, —C(O)CH$_2$NR$_x$($C_{1-3}$ cyanoalkyl), —C(O)CH$_2$NR$_x$CH$_2$C(O)($C_{1-3}$ alkyl), —C(O)CH$_2$NR$_x$CH$_2$C(O)N($C_{1-3}$ alkyl)$_2$, —C(O)CH$_2$NR$_x$R$_x$, —C(O)CH$_2$NR$_x$($C_{1-2}$ alkyl), —C(O)CH$_2$NR$_x$($C_{1-3}$ hydroxyalkyl), —C(O)CH$_2$NR$_x$($C_{1-3}$ fluoroalkyl), —C(O)CH$_2$NR$_x$CH$_2$CH$_2$O($C_{1-3}$ hydroxyalkyl), —C(O)CH$_2$NR$_x$CH$_2$CH$_2$C(O)N($C_{1-2}$ alkyl)$_2$, —C(O)CH$_2$NR$_x$(CH(CH$_2$OH)($C_{1-4}$ alkyl)), —C(O)CH$_2$NR$_x$($C_{1-5}$ alkyl), —C(O)CH$_2$NR$_x$($C_{1-5}$ hydroxy-fluoroalkyl), —C(O)CH$_2$NR$_x$($C_{1-6}$ hydroxyalkyl), —C(O)(CH$_2$)$_{1-3}$NR$_x$R$_x$, —C(O)(CH$_2$)$_{1-3}$NR$_x$($C_{1-3}$ alkyl), —C(O)CH$_2$CH(CH$_3$)NR$_x$R$_x$, —C(O)CH$_2$CH$_2$C(O)NR$_x$R$_x$, —CH$_2$C(O)NR$_x$R$_x$, —CH$_2$C(O)NR$_x$($C_{1-3}$ cyanoalkyl), —CH$_2$C(O)NR$_x$CH$_2$C(O)NR$_x$R$_x$, —CH$_2$C(O)NR$_x$($C_{1-3}$ hydroxyalkyl), —CH$_2$C(O)NR$_x$CH$_2$CH$_2$S(O)$_2$OH, —CH$_2$C(O)NR$_x$CH$_2$CH$_2$NR$_x$C(O)($C_{1-3}$ alkyl), —CH$_2$C(O)N(CH$_2$CH$_3$)CH$_2$CH$_2$NR$_x$R$_x$, —CH$_2$C(O)NR$_x$($C_{1-3}$ alkyl), —CH$_2$C(O)NR$_x$(CH$_2$)$_{1-3}$NR$_x$R$_x$, —CH$_2$C(O)NR$_x$($C_{1-5}$ alkyl), —C(O)CH$_2$NR$_x$C(O)($C_{1-3}$ cyanoalkyl), or —C(O)(CH$_2$)$_{1-3}$NR$_x$C(O)($C_{1-3}$ alkyl);

L$_1$ is a bond, —CR$_x$R$_x$—, —CR$_x$R$_x$C(O)—, —(CR$_x$R$_x$)$_2$NR$_x$(CR$_x$R$_x$)$_{0-1}$—, —CR$_x$R$_x$C(O)NR$_x$(CR$_x$R$_x$)$_{0-4}$—, —C(O)(CR$_x$R$_x$)$_{0-3}$—, —C(O)CR$_x$R$_x$NR$_x$—, —C(O)CR$_x$R$_x$O—, or —C(O)NR$_x$(CR$_x$R$_x$)$_{1-2}$—;

A is a ring selected from adamantanyl, 8-azabicyclo[3.2.1]octanyl, azepanyl, $C_{3-6}$ cycloalkyl, diazepanyl, furanyl, imidazolyl, indolyl, isoquinolinyl, morpholinyl, naphthalenyl, oxetanyl, phenyl, piperazinyl, piperidinyl, pyrazinyl, pyrazolyl, pyridinyl, pyrrolidinonyl, pyrrolidinyl, pyrrolyl, quinolinyl, tetrahydropyranyl, tetrazolyl, thiadiazolyl, and thiazolyl, each substituted with -L$_2$-R$_a$ and zero to 4 R$_b$;

L$_2$ is a bond or —CR$_x$R$_x$—;

R$_a$ is:

(a) H, —CN, —OH, $C_{1-6}$ alkyl, $C_{1-3}$ fluoroalkyl, $C_{1-5}$ hydroxyalkyl, —(CH$_2$)$_{1-4}$O($C_{1-3}$ alkyl), —(CR$_x$R$_x$)$_{1-3}$S($C_{1-3}$ alkyl), —(CR$_x$R$_x$)$_{1-3}$NHC(O)O($C_{1-4}$ alkyl), —(CR$_x$R$_x$)$_{1-3}$NH$_2$, —(CR$_x$R$_x$)$_{1-3}$NR$_x$($C_{1-4}$ alkyl), —O($C_{1-3}$ fluoroalkyl), —S(O)$_2$NR$_x$R$_x$, —O(CR$_x$R$_x$)$_{1-3}$NR$_x$R$_x$, —NHS(O)$_2$($C_{1-3}$ alkyl), —NR$_x$R$_x$, —NR$_x$($C_{1-4}$ alkyl), —(CR$_x$R$_x$)$_{1-3}$C(O)OH, —(CR$_x$R$_x$)$_{1-3}$C(O)NH($C_{1-4}$ alkyl), —C(O)OH, —C(O)($C_{1-4}$ alkyl), —C(O)CH$_2$N($C_{1-3}$ alkyl)$_2$, —C(O)O($C_{1-4}$ alkyl), —C(O)NH($C_{1-3}$ cyanoalkyl), —C(O)NR$_x$($C_{1-4}$ alkyl), —C(O)N($C_{1-3}$ alkyl)$_2$, —C(O)NR$_x$CH$_2$C(O)NR$_x$R$_x$, or —C(O)NR$_x$CH$_2$CH$_2$NHC(O)($C_{1-3}$ alkyl);

(b) $C_{3-6}$ cycloalkyl or —C(O)NH($C_{3-6}$ cycloalkyl), wherein each cycloalkyl is substituted with zero to 2 substituents independently selected from —OH, $C_{1-3}$ alkyl, $C_{1-3}$ hydroxyalkyl, $C_{1-3}$ fluoroalkyl, and —C(O)O($C_{1-3}$ alkyl); or (c) A$_1$, —CH$_2$A$_1$, —C(O)A$_1$, or —C(O)NHA$_1$, wherein A$_1$ is furanyl, imidazolyl, indolyl, isoxazolyl, octahydropyrrolo[3,4-c]pyrrolyl, oxazolyl, oxetanyl, phenyl, piperazinyl, piperidinyl, pyrazolyl, pyridinyl, pyrimidinyl, pyrrolidinyl, pyrrolyl, tetrahydrofuranyl, tetrahydropyranyl, thiadiazolyl, thiazolyl, thiophenyl, or triazolyl, each substituted with zero to three substituents independently selected from —OH, $C_{1-3}$ alkyl, $C_{1-3}$ hydroxyalkyl, —C(O)($C_{1-2}$ alkyl), —C(O)O($C_{1-3}$ alkyl), —NR$_x$R$_x$, phenyl, trifluoromethyl-phenyl, —CH$_2$(bromophenyl), and —CH$_2$CH$_2$(pyrrolidinyl);

each R$_4$ is independently F or —OH; or two R$_4$ attached to the same carbon atom form =O;

R$_5$ is F, —CH$_3$, or —OCH$_3$;

R$_b$ is —CH$_3$;

each R$_x$ is independently H or —CH$_3$;

m is zero, 1, or 2; and n is zero or 1;

with the proviso that when $R_1$ is —CH$_3$, then $R_3$ is not —CH$_2$CH$_2$NH(CH$_3$).

One embodiment provides a compound of Formula (I) or a salt thereof, wherein:

$R_1$ is H, Cl, —CN, $C_{1-4}$ alkyl, $C_{1-3}$ fluoroalkyl, $C_{1-3}$ hydroxy-fluoroalkyl, —CR$_z$=CH$_2$, $C_{3-6}$ cycloalkyl, —CH$_2$($C_{3-6}$ cycloalkyl), —C(O)O($C_{1-3}$ alkyl), or tetrahydropyranyl;

$R_3$ is:

(a) -L$_1$-A; or (b) H, $C_{1-6}$ alkyl, $C_{1-3}$ fluoroalkyl, $C_{1-5}$ hydroxyalkyl, —(CR$_x$R$_x$)$_{1-4}$O($C_{1-3}$ alkyl), —(CR$_x$R$_x$)$_{1-3}$S($C_{1-3}$ alkyl), —(CH$_2$)$_{1-3}$C(O)OC(CH$_3$)$_3$, —(CH$_2$)$_{1-3}$NR$_x$R$_x$, —CHR$_x$CH$_2$NR$_x$($C_{1-4}$ alkyl), —(CH$_2$)$_{1-3}$NR$_x$($C_{1-3}$ alkyl), —S(O)$_2$NR$_x$R$_x$, —C(O)O($C_{1-4}$ alkyl), —C(O)($C_{1-3}$ alkyl), —C(O)($C_{1-3}$ hydroxyalkyl), —C(O)($C_{1-3}$ fluoroalkyl), —C(O)($C_{1-3}$ chloroalkyl), —C(O)CH$_2$O($C_{1-3}$ alkyl), —C(O)CH$_2$S(O)$_2$($C_{1-3}$ alkyl), —C(O)($C_{1-3}$ hydroxyalkyl), —C(O)CR$_x$R$_x$OC(O)($C_{1-3}$ alkyl), —C(O)(tetrahydrofuranyl), —C(O)(tetrahydropyranyl), —C(O)(piperidinyl), —C(O)(ethoxypiperidinyl), —C(O)NR$_x$($C_{1-3}$ cyanoalkyl), —C(O)NR$_x$($C_{1-3}$ alkyl), —C(O)NR$_x$CH$_2$C(O)NR$_x$R$_x$, —C(O)NR$_x$CH$_2$CH$_2$NR$_x$C(O)($C_{1-2}$ alkyl), —C(O)N($C_{1-3}$ alkyl)$_2$, —C(O)NR$_x$C(R$_x$)$_3$, —C(O)CH$_2$NR$_x$($C_{1-3}$ cyanoalkyl), —C(O)CH$_2$NR$_x$CH$_2$C(O)($C_{1-3}$ alkyl), —C(O)CH$_2$NR$_x$CH$_2$C(O)N($C_{1-3}$ alkyl)$_2$, —C(O)CH$_2$NR$_x$R$_x$, —C(O)CH$_2$NR$_x$($C_{1-2}$ alkyl), —C(O)CH$_2$NR$_x$($C_{1-3}$ hydroxyalkyl), —C(O)CH$_2$NR$_x$($C_{1-3}$ fluoroalkyl), —C(O)CH$_2$NR$_x$CH$_2$CH$_2$O($C_{1-3}$ hydroxyalkyl), —C(O)CH$_2$NR$_x$CH$_2$CH$_2$C(O)N($C_{1-2}$ alkyl)$_2$, —C(O)CH$_2$NR$_x$(CH(CH$_2$OH)($C_{1-4}$ alkyl)), —C(O)CH$_2$NR$_x$($C_{1-5}$ alkyl), —C(O)CH$_2$NR$_x$($C_{1-5}$ hydroxy-fluoroalkyl), —C(O)CH$_2$NR$_x$($C_{1-6}$ hydroxyalkyl), —C(O)(CH$_2$)$_{1-3}$NR$_x$R$_x$, —C(O)(CH$_2$)$_{1-3}$NR$_x$($C_{1-3}$ alkyl), —C(O)CH$_2$CH(CH$_3$)NR$_x$R$_x$, —C(O)CH$_2$CH$_2$C(O)NR$_x$R$_x$, —CH$_2$C(O)NR$_x$R$_x$, —CH$_2$C(O)NR$_x$($C_{1-3}$ cyanoalkyl), —CH$_2$C(O)NR$_x$CH$_2$C(O)NR$_x$R$_x$, —CH$_2$C(O)NR$_x$($C_{1-3}$ hydroxyalkyl), —CH$_2$C(O)NR$_x$CH$_2$CH$_2$S(O)$_2$OH, —CH$_2$C(O)NR$_x$CH$_2$CH$_2$NR$_x$C(O)($C_{1-3}$ alkyl), —CH$_2$C(O)N $(CH_2CH_3)CH_2CH_2NR_xR_x$, —$CH_2C(O)NR_x(C_{1-3}$ alkyl), —$CH_2C(O)NR_x(CH_2)_{1-3}NR_xR_x$, —$CH_2C(O)NR_x(C_{1-5}$ alkyl), —$C(O)CH_2NR_xC(O)(C_{1-3}$ cyanoalkyl), or —$C(O)(CH_2)_{1-3}NR_xC(O)(C_{1-3}$ alkyl);

$L_1$ is a bond, —$CR_xR_x$—, —$CR_xR_xC(O)$—, —$(CR_xR_x)_2NR_x(CR_xR_x)_{0-1}$—, —$CR_xR_xC(O)NR_x(CR_xR_x)_{0-4}$—, —$C(O)(CR_xR_x)_{0-3}$—, —$C(O)CR_xR_xNR_x$—, —$C(O)CR_xR_xO$—, or —$C(O)NR_x(CR_xR_x)_{1-2}$—;

A is a ring selected from adamantanyl, 8-azabicyclo[3.2.1]octanyl, azepanyl, $C_{3-6}$ cycloalkyl, diazepanyl, furanyl, imidazolyl, indolyl, isoquinolinyl, morpholinyl, naphthalenyl, oxetanyl, phenyl, piperazinyl, piperidinyl, pyrazinyl, pyrazolyl, pyridinyl, pyrrolidinonyl, pyrrolidinyl, pyrrolyl, quinolinyl, tetrahydropyranyl, tetrazolyl, thiadiazolyl, and thiazolyl, each substituted with -$L_2$-$R_a$ and zero to 4 $R_b$;

$L_2$ is a bond or —$CR_xR_x$—;

$R_a$ is:
(a) H, —CN, —OH, $C_{1-6}$ alkyl, $C_{1-3}$ fluoroalkyl, $C_{1-5}$ hydroxyalkyl, —$(CH_2)_{1-4}O(C_{1-3}$ alkyl), —$(CR_xR_x)_{1-3}S(C_{1-3}$ alkyl), —$(CR_xR_x)_{1-3}NHC(O)O(C_{1-4}$ alkyl), —$(CR_xR_x)_{1-3}NH_2$, —$(CR_xR_x)_{1-3}NR_x(C_{1-4}$ alkyl), —$O(C_{1-3}$ fluoroalkyl), —$S(O)_2NR_xR_x$, —$O(CR_xR_x)_{1-3}NR_xR_x$, —$NHS(O)_2(C_{1-3}$ alkyl), —$NR_xR_x$, —$NR_x(C_{1-4}$ alkyl), —$(CR_xR_x)_{1-3}C(O)OH$, —$(CR_xR_x)_{1-3}C(O)NH(C_{1-4}$ alkyl), —$C(O)OH$, —$C(O)(C_{1-4}$ alkyl), —$C(O)O(C_{1-4}$ alkyl), —$C(O)NH(C_{1-3}$ cyanoalkyl), —$C(O)NR_x(C_{1-4}$ alkyl), —$C(O)N(C_{1-3}$ alkyl)$_2$, —$C(O)NR_xCH_2C(O)NR_xR_x$, or —$C(O)NR_xCH_2CH_2NHC(O)(C_{1-3}$ alkyl);
(b) $C_{3-6}$ cycloalkyl or —$C(O)NH(C_{3-6}$ cycloalkyl), wherein each cycloalkyl is substituted with zero to 2 substituents independently selected from —OH, $C_{1-3}$ alkyl, $C_{1-3}$ hydroxyalkyl, $C_{1-3}$ fluoroalkyl, and —$C(O)O(C_{1-3}$ alkyl); or
(c) $A_1$, —$CH_2A_1$, —$C(O)A_1$, or —$C(O)NHA_1$, wherein $A_1$ is furanyl, imidazolyl, indolyl, isoxazolyl, octahydropyrrolo[3,4-c]pyrrolyl, oxazolyl, oxetanyl, phenyl, piperazinyl, piperidinyl, pyrazolyl, pyridinyl, pyrimidinyl, pyrrolidinyl, pyrrolyl, tetrahydrofuranyl, tetrahydropyranyl, thiadiazolyl, thiazolyl, thiophenyl, or triazolyl, each substituted with zero to three substituents independently selected from —OH, $C_{1-3}$ alkyl, $C_{1-3}$ hydroxyalkyl, —$C(O)(C_{1-2}$ alkyl), —$C(O)O(C_{1-3}$ alkyl), —$NR_xR_x$, phenyl, trifluoromethyl-phenyl, —$CH_2$(bromophenyl), and —$CH_2CH_2$(pyrrolidinyl);

each $R_4$ is independently F or —OH; or two $R_4$ attached to the same carbon atom form =O;

$R_5$ is F, —$CH_3$, or —$OCH_3$;

$R_b$ is —$CH_3$;

each $R_x$ is independently H or —$CH_3$;

$R_z$ is H, $C_{1-2}$ alkyl, or —$CF_3$;

m is zero, 1, or 2; and n is zero or 1;

with the proviso that when $R_1$ is —$CH_3$, then $R_3$ is not —$CH_2CH_2NH(CH_3)$.

One embodiment provides a compound of Formula (I) or a salt thereof, wherein:

$R_1$ is H, Cl, —CN, $C_{1-4}$ alkyl, $C_{1-2}$ fluoroalkyl, —$CH(CF_3)OH$, —$CH_2$(cyclopropyl), or tetrahydropyranyl;

$R_3$ is:
(a) -$L_1$-A; or
(b) H, $C_{1-6}$ alkyl, $C_{1-3}$ fluoroalkyl, $C_{1-5}$ hydroxyalkyl, —$(CH_2)_{1-4}OCH_3$, —$(CR_xR_x)_{1-3}SCH_3$, —$CH_2CH_2NHC(O)OC(CH_3)_3$, —$CH_2CH_2NR_xR_x$, —$CHR_xCH_2NR_x(C_{1-4}$ alkyl), —$CH_2CH_2CH_2NH(CH_3)$, —$(CH_2)_{1-2}NHC(O)(CH_2)_{1-4}C≡CH$, —$S(O)_2NR_xR_x$, —$C(O)O(C_{1-4}$ alkyl), —$C(O)(C_{1-2}$ alkyl), —$C(O)(C_{1-3}$ hydroxyalkyl), —$C(O)(C_{1-2}$ chloroalkyl), —$C(O)(C_{1-3}$ fluoroalkyl), —$C(O)CH_2O(C_{1-3}$ alkyl), —$C(O)CH_2S(O)_2(C_{1-2}$ alkyl), —$C(O)CR_xR_xOC(O)(C_{1-2}$ alkyl), —$C(O)$(tetrahydrofuranyl), —$C(O)$(ethoxypiperidinyl), —$C(O)NR_xCH_2CN$, —$C(O)NH(C_{1-3}$ alkyl), —$C(O)NR_xCH_2C(O)NH_2$, —$C(O)NR_xCH_2CH_2NHC(O)(C_{1-2}$ alkyl), —$C(O)N(C_{1-3}$ alkyl)$_2$, —$C(O)NR_xC(R_x)_3$, —$C(O)CH_2NR_xR_x$, —$C(O)CH_2NR_xCH_2CN$, —$C(O)CH_2NR_xCH_2C(O)(C_{1-2}$ alkyl), —$C(O)CH_2NR_xCH_2C(O)N(C_{1-2}$ alkyl)$_2$, —$C(O)CH_2NR_xR_x$, —$C(O)CH_2NR_x(C_{1-2}$ alkyl), —$C(O)CH_2NR_xCH_2CH_2OH$, —$C(O)CH_2NR_x(C_{1-2}$ fluoroalkyl), —$C(O)CH_2NR_xCH_2CH_2OCH_2CH_2OH$, —$C(O)CH_2NR_xCH_2CH_2C(O)N(C_{1-2}$ alkyl)$_2$, —$C(O)CH_2NR_x(CH(CH_2OH)(C_{1-4}$ alkyl)), —$C(O)CH_2NR_x(C_{1-4}$ hydroxyalkyl), —$C(O)CH_2NR_x(C_{1-5}$ alkyl), —$C(O)CH_2NR_xCH_2CHFC(CH_3)_2OH$, —$C(O)CH_2NR_x(C_{1-6}$ hydroxyalkyl), —$C(O)CH_2CH_2NR_xR_x$, —$C(O)CH_2CH_2CH_2NR_xR_x$, —$C(O)CH_2CH_2CH_2NR_x(C_{1-3}$ alkyl), —$C(O)CH_2CH(CH_3)NR_xR_x$, —$C(O)CH_2CH_2C(O)NR_xR_x$, —$CH_2C(O)NR_xR_x$, —$CH_2C(O)NR_xCH_2CN$, —$CH_2C(O)NR_xCH_2C(O)NR_xR_x$, —$CH_2C(O)NR_x(C_{1-3}$ hydroxyalkyl), —$CH_2C(O)NR_xCH_2CH_2S(O)_2OH$, —$CH_2C(O)NR_xCH_2NR_xR_x$, —$CH_2C(O)NR_xCH_2CH_2NR_xC(O)(C_{1-2}$ alkyl), —$CH_2C(O)N(CH_2CH_3)CH_2CH_2NR_xR_x$, —$CH_2C(O)NR_x(C_{1-3}$ alkyl), —$CH_2C(O)NR_xCH_2CH_2NR_xR_x$, —$CH_2C(O)NR_x(C_{1-5}$ alkyl), —$C(O)CH_2NR_xC(O)CH_2CH_2CH_2CN$, or —$C(O)CH_2CH_2CH_2NR_xC(O)(C_{1-2}$ alkyl);

$L_1$ is a bond, —$CHR_x$—, —$CHR_xC(O)$—, —$(CH_2)_2NR_x(CH_2)_{0-1}$—, —$CH_2C(O)NR_x(CH_2)_{0-4}$—, —$C(O)(CH_2)_{0-3}$—, —$C(O)CH_2NR_x$—, —$C(O)CH_2O$—, or —$C(O)NR_x(CH_2)_{1-2}$—;

A is a ring selected from adamantanyl, azabicyclo[3.2.1]octanyl, azepanyl, $C_{3-6}$ cycloalkyl, diazepanyl, furanyl, imidazolyl, indolyl, isoquinolinyl, morpholinyl, naphthalenyl, oxetanyl, phenyl, piperazinyl, piperidinyl, pyrazinyl, pyrazolyl, pyridinyl, pyrrolidinonyl, pyrrolidinyl, pyrrolyl, quinolinyl, tetrahydropyranyl, tetrazolyl, thiadiazolyl, and thiazolyl, each substituted with -$L_2$-$R_a$ and zero to 4 $R_b$;

and $R_a$ is:
(a) H, —CN, —OH, $C_{1-6}$ alkyl, $C_{1-3}$ fluoroalkyl, $C_{1-5}$ hydroxyalkyl, —$(CH_2)_{1-4}OCH_3$, —$(CR_xR_x)_{1-3}SCH_3$, —$CH_2CH_2NHC(O)OC(CH_3)_3$, —$CH_2CH_2NH_2$, —$CHR_xCH_2NR_x(C_{1-4}$ alkyl), —$CH_2CH_2CH_2NH(CH_3)$, —$OCF_3$, —$S(O)_2NR_xR_x$, —$OCH_2CH_2CH_2NR_xR_x$, —$NHS(O)_2(C_{1-2}$ alkyl), —$NR_xR_x$, —$NR_x(C_{1-4}$ alkyl), —$CH_2CH_2C(O)OH$, —$CH_2C(O)NH(C_{1-3}$ alkyl), —$C(O)OH$, —$C(O)(C_{1-3}$ alkyl), —$C(O)CH_2N(C_{1-3}$ alkyl)$_2$, —$C(O)O(C_{1-3}$ alkyl), —$C(O)NHCH_2CN$, —$C(O)NR_x(C_{1-4}$ alkyl), —$C(O)N(C_{1-3}$ alkyl)$_2$, —$C(O)NHCH_2C(O)NR_xR_x$, or —$C(O)NHCH_2CH_2NHC(O)(C_{1-3}$ alkyl);

(b) $C_{3-6}$ cycloalkyl or —$C(O)NH(C_{3-6}$ cycloalkyl), wherein each cycloalkyl is substituted with zero to 1 substituent selected from —OH, $C_{1-3}$ alkyl, $C_{1-3}$ hydroxyalkyl, $C_{1-2}$ fluoroalkyl, and —$C(O)O(C_{1-3}$ alkyl); or (c) $A_1$, —$CH_2A_1$, —$C(O)A_1$, or —$C(O)NHA_1$, wherein $A_1$ is furanyl, imidazolyl, indolyl, isoxazolyl, octahydropyrrolo[3,4-c]pyrrolyl, oxazolyl, oxetanyl, phenyl, piperazinyl, piperidinyl, pyrazolyl, pyridinyl, pyrimidinyl, pyrrolidinyl, pyrrolyl, tetrahydrofuranyl, tetrahydropyranyl, thiadiazolyl, thiazolyl, thiophenyl, or triazolyl, each substituted with zero to three substituents independently selected from —OH, $C_{1-3}$ alkyl, $C_{1-3}$ hydroxyalkyl, —C(O)($C_{1-2}$ alkyl), —C(O)O($C_{1-3}$ alkyl), —NR$_x$R$_x$, phenyl, trifluoromethyl-phenyl, —CH$_2$(bromophenyl), and —CH$_2$CH$_2$(pyrrolidinyl); and R$_4$, R$_5$, R$_b$, R$_x$, m, and n are defined in the first aspect.

One embodiment provides a compound of Formula (I) or a salt thereof, wherein:

R$_1$ is H, Cl, —CN, $C_{1-4}$ alkyl, $C_{1-2}$ fluoroalkyl, —CH(CF$_3$)OH, —CH$_2$(cyclopropyl), or tetrahydropyranyl;

R$_3$ is:
(a) -L$_1$-A; or
(b) H, $C_{1-6}$ alkyl, $C_{1-3}$ fluoroalkyl, $C_{1-5}$ hydroxyalkyl, —(CH$_2$)$_{1-4}$OCH$_3$, —(CR$_x$R$_x$)$_{1-3}$SCH$_3$, —CH$_2$CH$_2$NHC(O)OC(CH$_3$)$_3$, —CH$_2$CH$_2$NH$_2$, —CHR$_x$CH$_2$NR$_x$(C$_{1-4}$ alkyl), —CH$_2$CH$_2$CH$_2$NH(CH$_3$), OCF$_3$, —S(O)$_2$NR$_x$R$_x$, —C(O)O(C$_{1-4}$ alkyl), —C(O)(C$_{1-2}$ alkyl), —C(O)(C$_{1-2}$ hydroxyalkyl), —C(O)(C$_{1-2}$ chloroalkyl), —C(O)(C$_{1-3}$ fluoroalkyl), —C(O)CH$_2$O(C$_{1-3}$ alkyl), —C(O)CH$_2$S(O)$_2$(C$_{1-2}$ alkyl), —C(O)(C$_{1-3}$ hydroxyalkyl), —C(O)CR$_x$R$_x$OC(O)(C$_{1-2}$ alkyl), —C(O)(tetrahydrofuranyl), —C(O)(ethoxypiperidinyl), —C(O)NR$_x$CH$_2$CN, —C(O)NH(C$_{1-3}$ alkyl), —C(O)NR$_x$CH$_2$C(O)NH$_2$, —C(O)NR$_x$CH$_2$CH$_2$NHC(O)(C$_{1-2}$ alkyl), —C(O)N(C$_{1-3}$ alkyl)$_2$, —C(O)NR$_x$C(R$_x$)$_3$, —C(O)CH$_2$NR$_x$R$_x$, —C(O)CH$_2$NR$_x$CH$_2$CN, —C(O)CH$_2$NR$_x$CH$_2$C(O)(C$_{1-2}$ alkyl), —C(O)CH$_2$NR$_x$CH$_2$C(O)N(C$_{1-2}$ alkyl)$_2$, —C(O)CH$_2$NR$_x$R$_x$, —C(O)CH$_2$NR$_x$(C$_{1-2}$ alkyl), —C(O)CH$_2$NR$_x$CH$_2$CH$_2$OH, —C(O)CH$_2$NR$_x$(C$_{1-2}$ fluoroalkyl), —C(O)CH$_2$NR$_x$CH$_2$CH$_2$OCH$_2$CH$_2$OH, —C(O)CH$_2$NR$_x$CH$_2$CH$_2$C(O)N(C$_{1-2}$ alkyl)$_2$, —C(O)CH$_2$NR$_x$(CH(CH$_2$OH)(C$_{1-4}$ alkyl)), —C(O)CH$_2$NR$_x$(C$_{1-4}$ hydroxyalkyl), —C(O)CH$_2$NR$_x$(C$_{1-5}$ alkyl), —C(O)CH$_2$NR$_x$CH$_2$CHFC(CH$_3$)$_2$OH, —C(O)CH$_2$NR$_x$(C$_{1-6}$ hydroxyalkyl), —C(O)CH$_2$CH$_2$NR$_x$R$_x$, —C(O)CH$_2$CH$_2$CH$_2$NR$_x$R$_x$, —C(O)CH$_2$CH$_2$CH$_2$NR$_x$(C$_{1-3}$ alkyl), —C(O)CH$_2$CH(CH$_3$)NR$_x$R$_x$, —C(O)CH$_2$CH$_2$C(O)NR$_x$R$_x$, —CH$_2$C(O)NR$_x$R$_x$, —CH$_2$C(O)NR$_x$CH$_2$CN, —CH$_2$C(O)NR$_x$CH$_2$C(O)NR$_x$R$_x$, —CH$_2$C(O)NR$_x$(C$_{1-3}$ hydroxyalkyl), —CH$_2$C(O)NR$_x$CH$_2$CH$_2$S(O)$_2$OH, —CH$_2$C(O)NR$_x$CH$_2$CH$_2$NR$_x$R$_x$, —CH$_2$C(O)NR$_x$CH$_2$CH$_2$NR$_x$C(O)(C$_{1-2}$ alkyl), —CH$_2$C(O)N(CH$_3$)CH$_2$CH$_2$NR$_x$R$_x$, —CH$_2$C(O)NR$_x$(C$_{1-3}$ alkyl), —CH$_2$C(O)NR$_x$CH$_2$CH$_2$CH$_2$NR$_x$R$_x$, —CH$_2$C(O)NR$_x$(C$_{1-5}$ alkyl), —C(O)CH$_2$NR$_x$C(O)CH$_2$CH$_2$CH$_2$CN, or —C(O)CH$_2$CH$_2$CH$_2$NR$_x$C(O)(C$_{1-2}$ alkyl);

L$_1$ is a bond, —CHR$_x$—, —CHR$_x$C(O)—, —(CH$_2$)$_2$NR$_x$(CH$_2$)$_{0-1}$—, —CH$_2$C(O)NR$_x$(CH$_2$)$_{0-4}$—, —C(O)(CH$_2$)$_{0-3}$—, —C(O)CH$_2$NR$_x$—, —C(O)CH$_2$O—, or —C(O)NR$_x$(CH$_2$)$_{1-2}$—;

A is a ring selected from adamantanyl, azabicyclo[3.2.1]octanyl, azepanyl, $C_{3-6}$ cycloalkyl, diazepanyl, furanyl, imidazolyl, indolyl, isoquinolinyl, morpholinyl, naphthalenyl, oxetanyl, phenyl, piperazinyl, piperidinyl, pyrazinyl, pyrazolyl, pyridinyl, pyrrolidinonyl, pyrrolidinyl, pyrrolyl, quinolinyl, tetrahydropyranyl, tetrazolyl, thiadiazolyl, and thiazolyl, each substituted with -L$_2$-R$_a$ and zero to 4 R$_b$;

L$_2$ is a bond or —CR$_x$R$_x$—;

R$_a$ is:
(a) H, —CN, —OH, $C_{1-6}$ alkyl, $C_{1-3}$ fluoroalkyl, $C_{1-5}$ hydroxyalkyl, —(CH$_2$)$_{1-4}$OCH$_3$, —(CR$_x$R$_x$)$_{1-3}$SCH$_3$, —CH$_2$CH$_2$NHC(O)OC(CH$_3$)$_3$, —CH$_2$CH$_2$NH$_2$, —CHR$_x$CH$_2$NR$_x$(C$_{1-4}$ alkyl), —CH$_2$CH$_2$CH$_2$NH(CH$_3$), —OCF$_3$, —S(O)$_2$NR$_x$R$_x$, —OCH$_2$CH$_2$CH$_2$NR$_x$R$_x$, —NHS(O)$_2$(C$_{1-2}$ alkyl), —NR$_x$R$_x$, —NR$_x$(C$_{1-4}$ alkyl), —CH$_2$CH$_2$CH$_2$C(O)OH, —CH$_2$C(O)NH(C$_{1-3}$ alkyl), —C(O)OH, —C(O)O(C$_{1-3}$ alkyl), —C(O)O(C$_{1-3}$ alkyl), —C(O)NHCH$_2$CN, —C(O)NR$_x$(C$_{1-4}$ alkyl), —C(O)N(C$_{1-3}$ alkyl)$_2$, —C(O)NHCH$_2$C(O)NR$_x$R$_x$, or —C(O)NHCH$_2$CH$_2$NHC(O)(C$_{1-3}$ alkyl);

(b) $C_{3-6}$ cycloalkyl or —C(O)NH(C$_{3-6}$ cycloalkyl), wherein each cycloalkyl is substituted with zero to 1 substituent selected from —OH, $C_{1-3}$ alkyl, $C_{1-3}$ hydroxyalkyl, $C_{1-2}$ fluoroalkyl, and —C(O)O(C$_{1-3}$ alkyl); or (c) A$_1$, —CH$_2$A1, —C(O)A$_1$, or —C(O)NHA$_1$, wherein A$_1$ is furanyl, imidazolyl, indolyl, isoxazolyl, octahydropyrrolo[3,4-c]pyrrolyl, oxazolyl, oxetanyl, phenyl, piperazinyl, piperidinyl, pyrazolyl, pyridinyl, pyrimidinyl, pyrrolidinyl, pyrrolyl, tetrahydrofuranyl, tetrahydropyranyl, thiadiazolyl, thiazolyl, thiophenyl, or triazolyl, each substituted with zero to three substituents independently selected from —OH, $C_{1-3}$ alkyl, $C_{1-3}$ hydroxyalkyl, —C(O)(C$_{1-2}$ alkyl), —C(O)O(C$_{1-3}$ alkyl), —NR$_x$R$_x$, phenyl, trifluoromethyl-phenyl, —CH$_2$(bromophenyl), and —CH$_2$CH$_2$(pyrrolidinyl);

each R$_4$ is independently F or —OH; or two R$_4$ attached to the same carbon atom form =O;

R$_5$ is F, —CH$_3$, or —OCH$_3$;

R$_b$ is —CH$_3$;

each R$_x$ is independently H or —CH$_3$;

m is zero, 1, or 2; and n is zero or 1; with the proviso that when R$_1$ is —CH$_3$, then R$_3$ is not —CH$_2$CH$_2$NH(CH$_3$).

One embodiment provides a compound of Formula (I) or a salt thereof, wherein:

R$_1$ is H, Cl, —CN, —CH$_3$, —CH$_2$CH$_3$, —CH$_2$CH$_2$CH$_3$, —CH(CH$_3$)$_2$, —CH$_2$CH(CH$_3$)$_2$, —CH$_2$CHF$_2$, —CH$_2$CF$_3$, —CH(CF$_3$)OH, —CH$_2$(cyclopropyl), or tetrahydropyranyl;

R$_3$ is:
(a) -L$_1$-A; or
(b) H, —CH$_3$, —CH$_2$CH(CH$_3$)$_2$, —CH$_2$CH(CH$_3$)CF$_3$, —CH$_2$CH$_2$CH$_2$OH, —CH(CH$_3$)CH$_2$OH, —CH$_2$CH$_2$NHC(O)OC(CH$_3$)$_3$, —CH$_2$CH$_2$NH$_2$, —CH$_2$CH$_2$NH(CH$_3$), —CH$_2$CH$_2$N(CH$_3$)$_2$, —CH$_2$CH$_2$N(CH$_3$)(CH$_2$CH$_3$), —CH$_2$CH$_2$N(CH$_3$)(CH$_2$CH(CH$_3$)$_2$), —CH$_2$CH$_2$CH$_2$NH(CH$_3$), —CH(CH$_3$)CH$_2$N(CH$_3$)$_2$, —CH$_2$CH$_2$NHC(O)(CH$_2$)$_4$C≡CH, —C(O)OC(CH$_3$)$_3$, —C(O)CH$_3$, —C(O)CH$_2$OH, —C(O)CH$_2$Cl, —C(O)CH$_2$CF$_3$, —C(O)CH$_2$CH$_2$CF$_3$, —C(O)CH$_2$OCH(CH$_3$)$_2$, —C(O)CH$_2$S(O)$_2$CH$_3$, —C(O)CH$_2$CH(CH$_3$)OH, —C(O)C(CH$_3$)$_2$OC(O)CH$_3$, —C(O)NHCH$_2$CH$_3$, —C(O)NHCH(CH$_3$)$_2$, —C(O)CH$_2$NHCH$_3$, —C(O)CH$_2$NHCH$_2$CN, —C(O)CH$_2$NHCH$_2$C(O)CH$_3$, —C(O)CH$_2$N(CH$_3$)CH$_2$C(O)N(CH$_2$CH$_3$)$_2$, —C(O)CH$_2$N(CH$_3$)$_2$, —C(O)CH$_2$NHCH$_2$CH$_3$, —C(O)CH$_2$NHCH$_2$CH$_2$OH, —C(O)CH$_2$NHCH$_2$CF$_3$, —C(O)CH$_2$NHCH$_2$CH$_2$OCH$_2$CH$_2$OH, —C(O)CH$_2$N(CH$_3$)CH$_2$CH$_2$C(O)N(CH$_2$CH$_3$)$_2$, —C(O)CH$_2$NHCH(CH$_2$OH)CH$_2$CH$_3$, —C(O)CH$_2$NHCH(CH$_2$OH)$_2$, —C(O)CH$_2$N(CH$_3$)CH$_2$CH$_2$OH, —C(O)CH$_2$NHCH$_2$CH(CH$_3$)OH, —C(O)CH$_2$NHCH$_2$CH(OH)CH$_2$OH, —C(O)CH$_2$N(CH$_3$)CH(CH$_3$)$_2$, —C(O)CH$_2$NHCH(CH$_3$)$_2$, —C(O)CH$_2$NHCH(CH$_3$)CH(CH$_3$)$_2$, —C(O)CH$_2$NHCH$_2$CH$_2$CH(CH$_3$)OH, —C(O)CH$_2$NH(CH$_2$OH)(CH$_2$CH$_2$CH$_3$), —C(O)CH$_2$NHCH(CH$_2$OH)CH$_2$CH(CH$_3$)$_2$, —C(O)CH$_2$NH (CH(CH$_2$CH$_3$)$_2$, —C(O)CH$_2$NHCH$_2$CHFC(CH$_3$)$_2$OH, —C(O)CH$_2$NHCH$_2$C(CH$_3$)$_2$CH$_2$OH, —C(O)CH$_2$NHCH(CH$_2$OH)CH$_2$CH(CH$_3$)$_2$, —C(O)CH$_2$CH$_2$N(CH$_3$)$_2$, —C(O)CH$_2$CH$_2$CH$_2$N(CH$_3$)$_2$, —C(O)CH$_2$CH$_2$CH$_2$NHCH(CH$_3$), —C(O)CH$_2$CH(CH$_3$)NH$_2$, —C(O)CH$_2$CH$_2$C(O)NH$_2$, —C(O)CH$_2$CH$_2$C(O)N(CH$_3$)$_2$, —CH$_2$C(O)N(CH$_3$)$_2$, —CH$_2$C(O)NHCH(CH$_3$)$_2$, —CH$_2$C(O)NHCH$_2$CN, —CH$_2$C(O)NHCH$_2$C(O)NH$_2$, —CH$_2$C(O)NHCH$_2$CH$_2$OH, —CH$_2$C(O)NHCH$_2$CH$_2$S(O)$_2$OH, —CH$_2$C(O)NHCH$_2$CH$_2$N(CH$_3$)$_2$, —CH$_2$C(O)NHCH$_2$CH$_2$NHC(O)CH$_3$, —CH$_2$C(O)N(CH$_3$)CH$_2$CH$_2$N(CH$_3$)$_2$, —CH$_2$C(O)N(CH$_2$CH$_3$)CH$_2$CH$_2$N(CH$_3$)$_2$, —CH$_2$C(O)NHCH(CH$_3$)$_2$, —CH$_2$C(O)NHCH$_2$CH$_2$OH, —CH$_2$C(O)NHCH$_2$CH$_2$N(CH$_3$)$_2$, —CH$_2$C(O)N(CH$_3$)CH$_2$CH$_2$CH$_2$N(CH$_3$)$_2$, —CH$_2$C(O)NHCH(CH$_3$)(CH$_2$CH$_3$), —CH$_2$C(O)NHCH(CH$_2$CH$_3$)$_2$, —C(O)CH$_2$NHC(O)CH$_2$CH$_2$CH$_2$CN, —C(O)CH$_2$CH$_2$CH$_2$NHC(O)CH$_3$, or —C(O)CH$_2$CH$_2$CH$_2$C≡CH;

L$_1$ is a bond, —CHR$_x$—, —CH$_2$C(O)—, —(CH$_2$)$_2$NR$_x$(CH$_2$)$_{0-1}$—, —CH$_2$C(O)NR$_x$(CH$_2$)$_{0-4}$—, —C(O)(CH$_2$)$_{0-3}$—, —C(O)CH$_2$NH—, —C(O)CH$_2$O—, or —C(O)NH(CH$_2$)$_{1-2}$—;

A is a ring selected from adamantanyl, azabicyclo[3.2.1]octanyl, azepanyl, cyclohexyl, cyclopentyl, cyclopropyl, diazepanyl, furanyl, imidazolyl, indolyl, isoquinolinyl, morpholinyl, naphthalenyl, oxetanyl, phenyl, piperazinyl, piperidinyl, pyrazinyl, pyrazolyl, pyridinyl, pyrrolidinonyl, pyrrolidinyl, pyrrolyl, quinolinyl, tetrahydropyranyl, tetrazolyl, thiadiazolyl, and thiazolyl, each substituted with -L$_2$-R$_a$ and zero to 4 R$_b$;

L$_2$ is a bond or —CHR$_x$—;

R$_a$ is:
  (a) H, —CN, —OH, C$_{1-6}$ alkyl, —CF$_3$, —CH$_2$CH$_2$CF$_3$, —CH$_2$OH, —C(CH$_3$)$_2$OH, —CH$_2$CH$_2$CH(CH$_3$)OH, —CH$_2$C(CH$_3$)$_2$CH$_2$OH, —CH$_2$CH(OH)CH$_2$OH, —CH(OH)CH$_2$CH$_2$CH$_2$OH, —CH$_2$CH$_2$CH$_2$SCH$_3$, —CH$_2$CH$_2$CH$_2$CH$_2$OCH$_3$, —CH$_2$CH$_2$CH$_2$C(O)OH, —OCF$_3$, —OCH$_2$CH$_2$CH$_2$N(CH$_3$)$_2$, —NH$_2$, —N(CH$_3$)$_2$, —N(CH$_3$)(CH$_2$CH(CH$_3$)$_2$), —NH(CH$_2$CH(CH$_3$)$_2$), —S(O)$_2$NH$_2$, —NHS(O)$_2$CH$_3$, —CH$_2$C(O)NHC(CH$_3$)$_2$, —C(O)OH, —C(O)CH$_3$, —C(O)OCH$_2$CH$_3$, —C(O)CH$_2$N(CH$_3$)$_2$, —C(O)NHCH$_2$CN, —C(O)NHCH(CH$_3$)$_2$, —C(O)N(C$_{1-2}$ alkyl)$_2$, —C(O)N(CH$_3$)CH(CH$_3$)$_2$, —C(O)NHCH$_2$C(O)NH$_2$, or —C(O)NHCH$_2$CH$_2$NHC(O)CH$_3$;
  (b) C$_{3-6}$ cycloalkyl or —C(O)NH(C$_{3-6}$ cycloalkyl), wherein each cycloalkyl is substituted with zero to 1 substituent selected from —OH, —CH$_3$, —CH$_2$OH, —CF$_3$, and —C(O)OCH$_2$CH$_3$; or
  (c) A$_1$, —CH$_2$A$_1$, —C(O)A$_1$, or —C(O)NHA$_1$, wherein A$_1$ is furanyl, imidazolyl, indolyl, isoxazolyl, octahydropyrrolo[3,4-c]pyrrolyl, oxazolyl, oxetanyl, phenyl, piperazinyl, piperidinyl, pyrazolyl, pyridinyl, pyrimidinyl, pyrrolidinyl, pyrrolyl, tetrahydrofuranyl, tetrahydropyranyl, thiadiazolyl, thiazolyl, thiophenyl, or triazolyl, each substituted with zero to three substituents independently selected from —OH, —CH$_3$, —CH(CH$_3$)$_2$, —CH$_2$CH$_2$OH, —C(O)CH$_3$, —C(O)OCH$_2$CH$_3$, —N(CH$_3$)$_2$, phenyl, trifluoromethyl-phenyl, —CH$_2$(bromophenyl), and —CH$_2$CH$_2$(pyrrolidinyl); and each R$_4$ is independently F or —OH; or two R$_4$ attached to the same carbon atom form =O;

and R$_4$, R$_5$, R$_b$, R$_x$, m, and n are defined in the first aspect.

One embodiment provides a compound of Formula (I) or a salt thereof, wherein:

R$_1$ is H, Cl, —CN, —CH$_3$, —CH$_2$CH$_3$, —CH$_2$CH$_2$CH$_3$, —CH(CH$_3$)$_2$, —CH$_2$CH(CH$_3$)$_2$, —CH$_2$CHF$_2$, —CH$_2$CF$_3$, —CH(CF$_3$)OH, —CH$_2$(cyclopropyl), or tetrahydropyranyl;

R$_3$ is:
  (a) -L$_1$-A; or
  (b) H, —CH$_3$, —CH$_2$CH(CH$_3$)$_2$, —CH$_2$CH(CH$_3$)CF$_3$, —CH$_2$CH$_2$CH$_2$OH, —CH(CH$_3$)CH$_2$OH, —CH$_2$CH$_2$NHC(O)OC(CH$_3$)$_3$, —CH$_2$CH$_2$NH$_2$, —CH$_2$CH$_2$NH(CH$_3$), —CH$_2$CH$_2$N(CH$_3$)(CH$_2$CH$_3$), —CH$_2$CH$_2$N(CH$_3$)(CH$_2$CH(CH$_3$)$_2$), —CH$_2$CH$_2$CH$_2$NH(CH$_3$), —CH(CH$_3$)CH$_2$N(CH$_3$)$_2$, —C(O)OC(CH$_3$)$_3$, —C(O)CH$_3$, —C(O)CH$_2$OH, —C(O)CH$_2$C$_1$, —C(O)CH$_2$CF$_3$, —C(O)CH$_2$CH$_2$CF$_3$, —C(O)CH$_2$OCH(CH$_3$)$_2$, —C(O)CH$_2$S(O)$_2$CH$_3$, —C(O)CH$_2$CH(CH$_3$)OH, —C(O)C(CH$_3$)$_2$OC(O)CH$_3$, —C(O)NHCH$_2$CH$_3$, —C(O)NHCH(CH$_3$)$_2$, —C(O)CH$_2$NHCH$_3$, —C(O)CH$_2$NHCH$_2$CN, —C(O)CH$_2$NHCH$_2$C(O)CH$_3$, —C(O)CH$_2$N(CH$_3$)CH$_2$C(O)N(CH$_2$CH$_3$)$_2$, —C(O)CH$_2$N(CH$_3$)$_2$, —C(O)CH$_2$NHCH$_2$CH$_3$, —C(O)CH$_2$NHCH$_2$CH$_2$OH, —C(O)CH$_2$NHCH$_2$CF$_3$, —C(O)CH$_2$NHCH$_2$CH$_2$OCH$_2$CH$_2$OH, —C(O)CH$_2$N(CH$_3$)CH$_2$CH$_2$C(O)N(CH$_2$CH$_3$)$_2$, —C(O)CH$_2$NH(CH$_2$OH)CH$_2$CH$_3$, —C(O)CH$_2$NHCH(CH$_2$OH)$_2$, —C(O)CH$_2$N(CH$_3$)CH$_2$CH$_2$OH, —C(O)CH$_2$NHCH$_2$CH(CH$_3$)OH, —C(O)CH$_2$NHCH$_2$CH(OH)CH$_2$OH, —C(O)CH$_2$N(CH$_3$)CH(CH$_3$)$_2$, —C(O)CH$_2$NHCH$_2$CH(CH$_3$)$_2$, —C(O)CH$_2$NHCH(CH$_3$)CH(CH$_3$)$_2$, —C(O)CH$_2$NHCH$_2$CH(CH$_3$)OH, —C(O)CH$_2$NH(CH$_2$OH)(CH$_2$CH$_2$CH$_3$), —C(O)CH$_2$NH(CH$_2$OH)CH$_2$CH(CH$_3$)$_2$, —C(O)CH$_2$NH(CH(CH$_2$CH$_3$)$_2$, —C(O)CH$_2$NHCH$_2$CHFC(CH$_3$)$_2$OH, —C(O)CH$_2$NHCH$_2$C(CH$_3$)$_2$CH$_2$OH, —C(O)CH$_2$NHCH(CH$_2$OH)CH$_2$CH(CH$_3$)$_2$, —C(O)CH$_2$CH$_2$N(CH$_3$)$_2$, —C(O)CH$_2$CH$_2$CH$_2$N(CH$_3$)$_2$, —C(O)CH$_2$CH$_2$CH$_2$NHCH(CH$_3$)$_2$, —C(O)CH$_2$CH(CH$_3$)NH$_2$, —C(O)CH$_2$CH$_2$C(O)NH$_2$, —C(O)CH$_2$CH$_2$C(O)N(CH$_3$)$_2$, —CH$_2$C(O)N(CH$_3$)$_2$, —CH$_2$C(O)NHCH$_2$CN, —CH$_2$C(O)NHCH$_2$C(O)NH$_2$, —CH$_2$C(O)NHCH$_2$CH$_2$OH, —CH$_2$C(O)NHCH$_2$CH$_2$S(O)$_2$OH, —CH$_2$C(O)NHCH$_2$N(CH$_3$)$_2$, —CH$_2$C(O)NHCH$_2$CH$_2$NHC(O)CH$_3$, —CH$_2$C(O)N(CH$_3$)CH$_2$CH$_2$N(CH$_3$)$_2$, —CH$_2$C(O)N(CH$_2$CH$_3$)CH$_2$CH$_2$N(CH$_3$)$_2$, —CH$_2$C(O)NHCH(CH$_3$)$_2$, —CH$_2$C(O)NHCH$_2$CH$_2$OH, —CH$_2$C(O)NHCH$_2$CH$_2$CH$_2$N(CH$_3$)$_2$, —CH$_2$C(O)N(CH$_3$)CH$_2$CH$_2$CH$_2$N(CH$_3$)$_2$, —CH$_2$C(O)NHCH(CH$_3$)(CH$_2$CH$_3$), —CH$_2$C(O)NHCH(CH$_2$CH$_3$)$_2$, —C(O)CH$_2$NHC(O)CH$_2$CH$_2$CH$_2$CN, or —C(O)CH$_2$CH$_2$CH$_2$NHC(O)CH$_3$;

L$_1$ is a bond, —CHR$_x$—, —CH$_2$C(O)—, —(CH$_2$)$_2$NR$_x$(CH$_2$)$_{0-1}$—, —CH$_2$C(O)NR$_x$(CH$_2$)$_{0-4}$—, —C(O)(CH$_2$)$_{0-3}$—, —C(O)CH$_2$NH—, —C(O)CH$_2$O—, or —C(O)NH(CH$_2$)$_{1-2}$—;

A is a ring selected from adamantanyl, azabicyclo[3.2.1]octanyl, azepanyl, cyclohexyl, cyclopentyl, cyclopropyl, diazepanyl, furanyl, imidazolyl, indolyl, isoquinolinyl, morpholinyl, naphthalenyl, oxetanyl, phenyl, piperazinyl, piperidinyl, pyrazinyl, pyrazolyl, pyridinyl, pyrrolidinonyl, pyrrolidinyl, pyrrolyl, quinolinyl, tetrahydropyranyl, tetrazolyl, thiadiazolyl, and thiazolyl, each substituted with -L$_2$-R$_a$ and zero to 4 R$_b$;

L$_2$ is a bond or —CHR$_x$—;

$R_a$ is:
- (a) H, —CN, —OH, $C_{1-6}$ alkyl, —$CF_3$, —$CH_2CH_2CF_3$, —$CH_2OH$, —$C(CH_3)_2OH$, —$CH_2CH_2CH(CH_3)OH$, —$CH_2C(CH_3)_2CH_2OH$, —$CH_2CH(OH)CH_2OH$, —$CH(OH)CH_2CH_2CH_2OH$, —$CH_2CH_2CH_2SCH_3$, —$CH_2CH_2CH_2CH_2CH_2OCH_3$, —$CH_2CH_2CH_2C(O)OH$, —$OCF_3$, —$OCH_2CH_2CH_2N(CH_3)_2$, —$NH_2$, —$N(CH_3)_2$, —$N(CH_3)(CH_2CH(CH_3)_2)$, —$NH(CH_2CH(CH_3)_2)$, —$S(O)_2NH_2$, —$NHS(O)_2CH_3$, —$CH_2C(O)NHCH(CH_3)_2$, —C(O)OH, —$C(O)CH_3$, —$C(O)OCH_2CH_3$, —$C(O)NHCH_2CN$, —$C(O)NHCH(CH_3)_2$, —$C(O)N(CH_2CH_3)_2$, —$C(O)N(CH_3)CH(CH_3)_2$, —$C(O)NHCH_2C(O)NH_2$, or —$C(O)NHCH_2CH_2NHC(O)CH_3$;
- (b) $C_{3-6}$ cycloalkyl or —$C(O)NH(C_{3-6}$ cycloalkyl), wherein each cycloalkyl is substituted with zero to 1 substituent selected from —OH, —$CH_3$, —$CH_2OH$, —$CF_3$, and —$C(O)OCH_2CH_3$; or
- (c) $A_1$, —$CH_2A_1$, —$C(O)A_1$, or —$C(O)NHA_1$, wherein $A_1$ is furanyl, imidazolyl, indolyl, isoxazolyl, octahydropyrrolo[3,4-c]pyrrolyl, oxazolyl, oxetanyl, phenyl, piperazinyl, piperidinyl, pyrazolyl, pyridinyl, pyrimidinyl, pyrrolidinyl, pyrrolyl, tetrahydrofuranyl, tetrahydropyranyl, thiadiazolyl, thiazolyl, thiophenyl, or triazolyl, each substituted with zero to three substituents independently selected from —OH, —$CH_3$, —$CH(CH_3)_2$, —$CH_2CH_2OH$, —$C(O)CH_3$, —$C(O)OCH_2CH_3$, —$N(CH_3)_2$, phenyl, trifluoromethyl-phenyl, —$CH_2$(bromophenyl), and —$CH_2CH_2$(pyrrolidinyl); and each $R_4$ is independently F or —OH; or two $R_4$ attached to the same carbon atom form =O.

$R_5$ is F, —$CH_3$, or —$OCH_3$;
$R_b$ is —$CH_3$;
each $R_x$ is independently H or —$CH_3$;
m is zero, 1, or 2; and
n is zero or 1.

One embodiment provides a compound of Formula (I) or a salt thereof, wherein: $R_3$ is -$L_1$-A; and $R_1$, $R_4$, $R_5$, $L_1$, A, m, and n are defined in the first aspect.

One embodiment provides a compound of Formula (I) or a salt thereof, wherein $R_3$ is -$L_1$-A; $L_1$ is a bond, —$CR_xR_x$—, —$CR_xR_xC(O)$—, —$(CR_xR_x)_2NR_x(CR_xR_x)_{0-1}$—, —$CR_xR_xC(O)NR_x(CR_xR_x)_{0-4}$—, —$C(O)(CR_xR_x)_{0-3}$—, —$C(O)CR_xR_xNR_x$—, —$C(O)CR_xR_xO$—, or —$C(O)NR_x(CR_xR_x)_{1-2}$—; and $R_1$, $R_4$, $R_5$, $R_x$, A, m, and n are defined in the first aspect. Included in this embodiment are compounds of Formula (I) in which $L_1$ is a bond, —$CHR_x$—, —$CHR_xC(O)$—, —$(CH_2)_2NR_x(CH_2)_{0-1}$—, —$CH_2C(O)NR_x(CH_2)_{0-4}$—, —$C(O)(CH_2)_{0-3}$—, —$C(O)CH_2NR_x$—, —$C(O)CH_2O$—, or —$C(O)NR_x(CH_2)_{1-2}$—. Also included in this embodiment are compounds of Formula (I) in which $L_1$ is a bond, —$CHR_x$—, —$CH_2C(O)$—, —$(CH_2)_2NR_x(CH_2)_{0-1}$—, —$CH_2C(O)NR_x(CH_2)_{0-4}$—, —$C(O)(CH_2)_{0-3}$—, —$C(O)CH_2NH$—, —$C(O)CH_2O$—, or —$C(O)NH(CH_2)_{1-2}$—.

One embodiment provides a compound of Formula (I) or a salt thereof, wherein $R_3$ is -$L_1$-A; $L_1$ is a bond, —$CHR_x$—, —$CH_2C(O)$—, —$(CH_2)_2NR_x(CH_2)_{0-1}$—, —$CH_2C(O)NR_x(CH_2)_{0-4}$—, —$C(O)(CH_2)_{0-3}$—, —$C(O)CH_2NH$—, —$C(O)CH_2O$—, or —$C(O)NH(CH_2)_{1-2}$—; A is a ring selected from adamantanyl, azabicyclo[3.2.1]octanyl, azepanyl, cyclohexyl, cyclopentyl, cyclopropyl, diazepanyl, furanyl, imidazolyl, indolyl, isoquinolinyl, morpholinyl, naphthalenyl, oxetanyl, phenyl, piperazinyl, piperidinyl, pyrazinyl, pyrazolyl, pyridinyl, pyrrolidinonyl, pyrrolidinyl, pyrrolyl, quinolinyl, tetrahydropyranyl, tetrazolyl, thiadiazolyl, and thiazolyl, each substituted with -$L_2$-$R_a$ and zero to 4 $R_b$; and $R_1$, $R_4$, $R_5$, $L_2$, $R_a$, $R_b$ are defined in the first aspect.

One embodiment provides a compound of Formula (I) or a salt thereof, wherein $R_3$ is -$L_1$-A; A is piperidinyl substituted with -$L_2$-$R_a$ and zero to 4 $R_b$; and $R_1$, $R_4$, $R_5$, $L_1$, $L_2$, $R_a$, $R_b$ are defined in the first aspect.

One embodiment provides a compound of Formula (I) or a salt thereof, wherein $R_3$ is -$L_1$-A; A is a ring selected from azepanyl, pyridinyl, piperazinyl, cyclohexyl, imidazolyl, phenyl, pyrrolidinyl, and piperidinyl, each substituted with -$L_2$-$R_a$ and zero to 4 $R_b$; and $R_1$, $R_4$, $R_5$, $L_2$, $R_a$, $R_b$ are defined in the first aspect.

One embodiment provides a compound of Formula (I) or a salt thereof, wherein $R_3$ is -$L_1$-A; $L_2$ is a bond or —$CHR_x$—; and $R_1$, $R_4$, $R_5$, $R_x$ $L_1$, A, m, and n are defined in the first aspect. Included in this embodiment are compounds in which $L_2$ is a bond. Also included in this embodiment are compounds in which $L_2$ is —$CHR_x$—.

One embodiment provides a compound of Formula (I) or a salt thereof, wherein $R_3$ is -$L_1$-A; $R_a$ is (a) H, —CN, —OH, $C_{1-6}$ alkyl, $C_{1-3}$ fluoroalkyl, $C_{1-5}$ hydroxyalkyl, —$(CH_2)_{1-4}OCH_3$, —$(CR_xR_x)_{1-3}SCH_3$, —$CH_2CH_2NHC(O)OC(CH_3)_3$, —$CH_2CH_2NH_2$, —$CHR_xCH_2NR_x(C_{1-4}$ alkyl), —$CH_2CH_2NH(CH_3)$, —$OCF_3$, —$S(O)_2NR_xR_x$, —$OCH_2CH_2CH_2NR_xR_x$, —$NHS(O)_2(C_{1-2}$ alkyl), —$NR_xR_x$, —$NR_x(C_{1-4}$ alkyl), —$CH_2CH_2CH_2C(O)OH$, —$CH_2C(O)NH(C_{1-3}$ alkyl), —C(O)OH, —$C(O)(C_{1-3}$ alkyl), —$C(O)O(C_{1-3}$ alkyl), —$C(O)NHCH_2CN$, —$C(O)NR_x(C_{1-4}$ alkyl), —$C(O)N(C_{1-3}$ alkyl)$_2$, —$C(O)NHCH_2C(O)NR_xR_x$, or —$C(O)NHCH_2CH_2NHC(O)(C_{1-3}$ alkyl); (b) $C_{3-6}$ cycloalkyl or —$C(O)NH(C_{3-6}$ cycloalkyl), wherein each cycloalkyl is substituted with zero to 1 substituent selected from —OH, $C_{1-3}$ alkyl, $C_{1-3}$ hydroxyalkyl, $C_{1-2}$ fluoroalkyl, and —$C(O)O(C_{1-3}$ alkyl); or (c) $A_1$, —$CH_2A_1$, —$C(O)A_1$, or —$C(O)NHA_1$, wherein $A_1$ is furanyl, imidazolyl, indolyl, isoxazolyl, octahydropyrrolo[3,4-c]pyrrolyl, oxazolyl, oxetanyl, phenyl, piperazinyl, piperidinyl, pyrazolyl, pyridinyl, pyrimidinyl, pyrrolidinyl, pyrrolyl, tetrahydrofuranyl, tetrahydropyranyl, thiadiazolyl, thiazolyl, thiophenyl, or triazolyl, each substituted with zero to three substituents independently selected from —OH, $C_{1-3}$ alkyl, $C_{1-3}$ hydroxyalkyl, —$C(O)(C_{1-2}$ alkyl), —$C(O)O(C_{1-3}$ alkyl), —$NR_xR_x$, phenyl, trifluoromethyl-phenyl, —$CH_2$(bromophenyl), and —$CH_2CH_2$(pyrrolidinyl); and $R_1$, $R_4$, $R_5$, $R_x$ $L_1$, A, m, and n are defined in the first aspect. Included in this embodiment are compounds in which $R_a$ is: (a) H, —CN, —OH, $C_{1-6}$ alkyl, —$CF_3$, —$CH_2CH_2CF_3$, —$CH_2OH$, —$C(CH_3)_2OH$, —$CH_2CH_2CH(CH_3)OH$, —$CH_2C(CH_3)_2CH_2OH$, —$CH_2CH(OH)CH_2OH$, —$CH(OH)CH_2CH_2CH_2OH$, —$CH_2CH_2CH_2SCH_3$, —$CH_2CH_2CH_2CH_2CH_2OCH_3$, —$CH_2CH_2CH_2C(O)OH$, —$OCF_3$, —$OCH_2CH_2CH_2N(CH_3)_2$, —$NH_2$, —$N(CH_3)_2$, —$N(CH_3)(CH_2CH(CH_3)_2)$, —$NH(CH_2CH(CH_3)_2)$, —$S(O)_2NH_2$, —$NHS(O)_2CH_3$, —$CH_2C(O)NHCH(CH_3)_2$, —C(O)OH, —$C(O)CH_3$, —$C(O)OCH_2CH_3$, —$C(O)NHCH_2CN$, —$C(O)NHCH(CH_3)_2$, —$C(O)N(CH_2CH_3)_2$, —$C(O)N(CH_3)CH(CH_3)_2$, —$C(O)NHCH_2C(O)NH_2$, or —$C(O)NHCH_2CH_2NHC(O)CH_3$; (b) $C_{3-6}$ cycloalkyl or —$C(O)NH(C_{3-6}$ cycloalkyl), wherein each cycloalkyl is substituted with zero to 1 substituent selected from —OH, —$CH_3$, —$CH_2OH$, —$CF_3$, and —$C(O)OCH_2CH_3$; or (c) $A_1$, —$CH_2A_1$, —$C(O)A_1$, or —$C(O)NHA_1$, wherein $A_1$ is furanyl, imidazolyl, indolyl, isoxazolyl, octahydropyrrolo[3,4-c]pyrrolyl, oxazolyl, oxetanyl, phenyl, piperazinyl, piperidinyl, pyrazolyl, pyridinyl, pyrimidinyl, pyrrolidinyl, pyrrolyl, tetrahydrofuranyl, tetrahydropyranyl, thiadiazolyl, thiazolyl, thiophenyl, or triazolyl, each substituted with zero to three substituents independently selected from —OH, —CH$_3$, —CH(CH$_3$)$_2$, —CH$_2$CH$_2$OH, —C(O)CH$_3$, —C(O)OCH$_2$CH$_3$, —N(CH$_3$)$_2$, phenyl, trifluoromethyl-phenyl, —CH$_2$(bromophenyl), and —CH$_2$CH$_2$(pyrrolidinyl).

One embodiment provides a compound of Formula (I) or a salt thereof, wherein R$_3$ is -L$_1$-A; R$_a$ is H, —OH, C$_{1-6}$ alkyl, C$_{1-3}$ fluoroalkyl, C$_{1-5}$ hydroxyalkyl, —(CH$_2$)$_{1-4}$O (C$_{1-3}$ alkyl), —(CR$_x$R$_x$)$_{1-3}$S(C$_{1-3}$ alkyl), —(CR$_x$R$_x$)$_{1-3}$NHC(O)O(C$_{1-4}$ alkyl), —(CR$_x$R$_x$)$_{1-3}$NI-2, —(CR$_x$R$_x$)$_{1-3}$NR$_x$(C$_{1-4}$ alkyl), —S(O)$_2$NR$_x$R$_x$, —(CR$_x$R$_x$)$_{1-3}$C(O)OH, —(CR$_x$R$_x$)$_{1-3}$C(O)NH(C$_{1-4}$ alkyl), —C(O)OH, —C(O)(C$_{1-4}$ alkyl), —C(O)O(C$_{1-4}$ alkyl), —C(O)NH(C$_{1-3}$ cyanoalkyl), —C(O)NR$_x$(C$_{1-4}$ alkyl), —C(O)N(C$_{1-3}$ alkyl)$_2$, —C(O)NR$_x$CH$_2$C(O)NR$_x$R$_x$, or —C(O)NR$_x$CH$_2$CH$_2$NHC(O)(C$_{1-3}$ alkyl); and R$_1$, R$_4$, R$_5$, L$_1$, A, R$_x$, m, and n are defined in the first aspect. Included in this embodiment are compounds in which R$_a$ is H, —CN, —OH, C$_{1-6}$ alkyl, C$_{1-3}$ fluoroalkyl, C$_{1-5}$ hydroxyalkyl, —(CH$_2$)$_{1-4}$OCH$_3$, —(CR$_x$R$_x$)$_{1-3}$SCH$_3$, —CH$_2$CH$_2$NHC(O)OC(CH$_3$)$_3$, —CH$_2$CH$_2$NH$_2$, —CHR$_x$CH$_2$NR$_x$(C$_{1-4}$ alkyl), —CH$_2$CH$_2$CH$_2$NH(CH$_3$), —OCF$_3$, —S(O)$_2$NR$_x$R$_x$, —OCH$_2$CH$_2$CH$_2$NR$_x$R$_x$, —NHS(O)$_2$(C$_{1-2}$ alkyl), —NR$_x$R$_x$, —NR$_x$(C$_{1-4}$ alkyl), —CH$_2$CH$_2$CH$_2$C(O)OH, —CH$_2$C(O)NH(C$_{1-3}$ alkyl), —C(O)OH, —C(O)(C$_{1-3}$ alkyl), —C(O)O(C$_{1-3}$ alkyl), —C(O)NHCH$_2$CN, —C(O)NR$_x$(C$_{1-4}$ alkyl), —C(O)N(C$_{1-3}$ alkyl)$_2$, —C(O)NHCH$_2$C(O)NR$_x$R$_x$, or —C(O)NHCH$_2$CH$_2$NHC(O)(C$_{1-3}$ alkyl). Also included in this embodiment are compounds in which R$_a$ is A$_1$, —CH$_2$A1, —C(O)A$_1$, or —C(O)NHA$_1$, wherein A$_1$ is furanyl, imidazolyl, indolyl, isoxazolyl, octahydropyrrolo[3,4-c]pyrrolyl, oxazolyl, oxetanyl, phenyl, piperazinyl, piperidinyl, pyrazolyl, pyridinyl, pyrimidinyl, pyrrolidinyl, pyrrolyl, tetrahydrofuranyl, tetrahydropyranyl, thiadiazolyl, thiazolyl, thiophenyl, or triazolyl, each substituted with zero to three substituents independently selected from —OH, C$_{1-3}$ alkyl, C$_{1-3}$ hydroxyalkyl, —C(O)(C$_{1-2}$ alkyl), —C(O)O(C$_{1-3}$ alkyl), —NR$_x$R$_x$, phenyl, trifluoromethyl-phenyl, —CH$_2$(bromophenyl), and —CH$_2$CH$_2$(pyrrolidinyl).

One embodiment provides a compound of Formula (I) or a salt thereof, wherein R$_3$ is -L$_1$-A; R$_a$ is C$_{3-6}$ cycloalkyl or —C(O)NH(C$_{3-6}$ cycloalkyl), wherein each cycloalkyl is substituted with zero to 2 substituents independently selected from —OH, C$_{1-3}$ alkyl, C$_{1-3}$ hydroxyalkyl, C$_{1-3}$ fluoroalkyl, and —C(O)O(C$_{1-3}$ alkyl); and R$_1$, R$_4$, R$_5$, L$_1$, A, m, and n are defined in the first aspect. Included in this embodiment are compounds in which R$_a$ is C$_{3-6}$ cycloalkyl or —C(O)NH(C$_{3-6}$ cycloalkyl), wherein each cycloalkyl is substituted with zero to 1 substituent selected from —OH, C$_{1-3}$ alkyl, C$_{1-3}$ hydroxyalkyl, C$_{1-2}$ fluoroalkyl, and —C(O)O(C$_{1-3}$ alkyl). Also included in this embodiment are compounds in which R$_a$ is C$_{3-6}$ cycloalkyl or —C(O)NH(C$_{3-6}$ cycloalkyl), wherein each cycloalkyl is substituted with zero to 1 substituent selected from —OH, —CH$_3$, —CH$_2$OH, —CF$_3$, and —C(O)OCH$_2$CH$_3$.

One embodiment provides a compound of Formula (I) or a salt thereof, wherein R$_3$ is -L$_1$-A; R$_a$ is A1, —CH$_2$A1, —C(O)A$_1$, or —C(O)NHA$_1$, wherein A$_1$ is furanyl, imidazolyl, indolyl, isoxazolyl, octahydropyrrolo[3,4-c]pyrrolyl, oxazolyl, oxetanyl, phenyl, piperazinyl, piperidinyl, pyrazolyl, pyridinyl, pyrimidinyl, pyrrolidinyl, pyrrolyl, tetrahydrofuranyl, tetrahydropyranyl, thiadiazolyl, thiophenyl, or triazolyl, each substituted with zero to three substituents independently selected from —OH, C$_{1-3}$ alkyl, C$_{1-3}$ hydroxyalkyl, —C(O)(C$_{1-2}$ alkyl), —C(O)O(C$_{1-3}$ alkyl), —NR$_x$R$_x$, phenyl, trifluoromethyl-phenyl, —CH$_2$(bromophenyl), and —CH$_2$CH$_2$(pyrrolidinyl); and R$_1$, R$_4$, R$_5$, L$_1$, A, m, and n are defined in the first aspect. Included in this embodiment are compounds in which R$_a$ is A$_1$, —CH$_2$A1, —C(O)A$_1$, or —C(O)NHA$_1$, wherein A$_1$ is furanyl, imidazolyl, indolyl, isoxazolyl, octahydropyrrolo[3,4-c]pyrrolyl, oxazolyl, oxetanyl, phenyl, piperazinyl, piperidinyl, pyrazolyl, pyridinyl, pyrimidinyl, pyrrolidinyl, pyrrolyl, tetrahydrofuranyl, tetrahydropyranyl, thiadiazolyl, thiazolyl, thiophenyl, or triazolyl, each substituted with zero to three substituents independently selected from —OH, C$_{1-3}$ alkyl, C$_{1-3}$ hydroxyalkyl, —C(O)(C$_{1-2}$ alkyl), —C(O)O(C$_{1-3}$ alkyl), —NR$_x$R$_x$, phenyl, trifluoromethyl-phenyl, —CH$_2$(bromophenyl), and —CH$_2$CH$_2$(pyrrolidinyl). Also included in this embodiment are compounds in which R$_a$ is A$_1$, —CH$_2$A1, —C(O)A$_1$, or —C(O)NHA$_1$, wherein A$_1$ is furanyl, imidazolyl, indolyl, isoxazolyl, octahydropyrrolo[3,4-c]pyrrolyl, oxazolyl, oxetanyl, phenyl, piperazinyl, piperidinyl, pyrazolyl, pyridinyl, pyrimidinyl, pyrrolidinyl, pyrrolyl, tetrahydrofuranyl, tetrahydropyranyl, thiadiazolyl, thiazolyl, thiophenyl, or triazolyl, each substituted with zero to three substituents independently selected from —OH, —CH$_3$, —CH(CH$_3$)$_2$, —CH$_2$CH$_2$OH, —C(O)CH$_3$, —C(O)OCH$_2$CH$_3$, —N(CH$_3$)$_2$, phenyl, trifluoromethyl-phenyl, —CH$_2$(bromophenyl), and —CH$_2$CH$_2$(pyrrolidinyl).

One embodiment provides a compound of Formula (I) or a salt thereof, wherein: R$_3$ is H, C$_{1-6}$ alkyl, C$_{1-3}$ fluoroalkyl, C$_{1-5}$ hydroxyalkyl, —(CR$_x$R$_x$)$_{1-4}$O(C$_{1-3}$ alkyl), —(CR$_x$R$_x$)$_{1-3}$S(C$_{1-3}$ alkyl), —(CH$_2$)$_{1-3}$C(O)OC(CH$_3$)$_3$, —(CH$_2$)$_{1-3}$NR$_x$R$_x$, —CHR$_x$CH$_2$NR$_x$(C$_{1-4}$ alkyl), —(CH$_2$)$_{1-3}$NR$_x$(C$_{1-3}$ alkyl), —S(O)$_2$NR$_x$R$_x$, —C(O)O(C$_{1-4}$ alkyl), —C(O)(C$_{1-3}$ alkyl), —C(O)(C$_{1-3}$ hydroxyalkyl), —C(O)(C$_{1-3}$ chloroalkyl), —C(O)(C$_{1-3}$ fluoroalkyl), —C(O)CH$_2$O(C$_{1-3}$ alkyl), —C(O)CH$_2$S(O)$_2$(C$_{1-3}$ alkyl), —C(O)(C$_{1-3}$ hydroxyalkyl), —C(O)CR$_x$R$_x$OC(O)(C$_{1-3}$ alkyl), —C(O)(tetrahydrofuranyl), —C(O)(tetrahydropyranyl), —C(O)(piperidinyl), —C(O)(ethoxypiperidinyl), —C(O)NR$_x$(C$_{1-3}$ cyanoalkyl), —C(O)NR$_x$(C$_{1-3}$ alkyl), —C(O)NR$_x$CH$_2$C(O)NR$_x$R$_x$, —C(O)NR$_x$CH$_2$CH$_2$NR$_x$C(O)(C$_{1-2}$ alkyl), —C(O)N(C$_{1-3}$ alkyl)$_2$, —C(O)NR$_x$C(R$_x$)$_3$, —C(O)CH$_2$NR$_x$(C$_{1-3}$ cyanoalkyl), —C(O)CH$_2$NR$_x$CH$_2$C(O)(C$_{1-3}$ alkyl), —C(O)CH$_2$NR$_x$CH$_2$C(O)N(C$_{1-3}$ alkyl)$_2$, —C(O)CH$_2$NR$_x$R$_x$, —C(O)CH$_2$NR$_x$(C$_{1-2}$ alkyl), —C(O)CH$_2$NR$_x$(C$_{1-3}$ hydroxyalkyl), —C(O)CH$_2$NR$_x$(C$_{1-3}$ fluoroalkyl), —C(O)CH$_2$NR$_x$CH$_2$CH$_2$O(C$_{1-3}$ hydroxyalkyl), —C(O)CH$_2$NR$_x$CH$_2$CH$_2$C(O)N(C$_{1-2}$ alkyl)$_2$, —C(O)CH$_2$NR$_x$(CH(CH$_2$OH)(C$_{1-4}$ alkyl)), —C(O)CH$_2$NR$_x$(C$_{1-5}$ alkyl), —C(O)CH$_2$NR$_x$(C$_{1-5}$ hydroxy-fluoroalkyl), —C(O)CH$_2$NR$_x$(C$_{1-6}$ hydroxyalkyl), —C(O)(CH$_2$)$_{1-3}$NR$_x$R$_x$, —C(O)(CH$_2$)$_{1-3}$NR$_x$(C$_{1-3}$ alkyl), —C(O)CH$_2$CH(CH$_3$)NR$_x$R$_x$, —C(O)CH$_2$CH$_2$C(O)NR$_x$R$_x$, —CH$_2$C(O)NR$_x$R$_x$, —CH$_2$C(O)NR$_x$(C$_{1-3}$ cyanoalkyl), —CH$_2$C(O)NR$_x$CH$_2$C(O)NR$_x$R$_x$, —CH$_2$C(O)NR$_x$(C$_{1-3}$ hydroxyalkyl), —CH$_2$C(O)NR$_x$CH$_2$CH$_2$S(O)$_2$OH, —CH$_2$C(O)NR$_x$CH$_2$CH$_2$NR$_x$C(O)(C$_{1-3}$ alkyl), —CH$_2$C(O)N(CH$_2$CH$_3$)CH$_2$CH$_2$NR$_x$R$_x$, —CH$_2$C(O)NR$_x$(C$_{1-3}$ alkyl), —CH$_2$C(O)NR(CH$_2$)$_{1-3}$NR$_x$R$_x$, —CH$_2$C(O)NR$_x$(C$_{1-5}$ alkyl), —C(O)CH$_2$NR$_x$C(O)(C$_{1-3}$ cyanoalkyl), or —C(O)(CH$_2$)$_{1-3}$NR$_x$C(O)(C$_{1-3}$ alkyl); and R$_1$, R$_4$, R$_5$, R$_x$, L$_1$, A, m, and n are defined in the first aspect. Included in this embodiment are compounds of Formula (I) in which R$_3$ is H, C$_{1-6}$ alkyl, C$_{1-3}$ fluoroalkyl, C$_{1-5}$ hydroxyalkyl, —(CH$_2$)$_{1-4}$OCH$_3$, —(CR$_x$R$_x$)$_{1-3}$SCH$_3$, —CH$_2$CH$_2$NHC(O)OC(CH$_3$)$_3$, —CH$_2$CH$_2$NH$_2$, —CHR$_x$CH$_2$NR$_x$(C$_{1-4}$ alkyl), —CH$_2$CH$_2$CH$_2$NH(CH$_3$), —S(O)$_2$NR$_x$R$_x$, —C(O)O(C$_{1-4}$ alkyl), —C(O)(C$_{1-2}$ alkyl), —C(O)(C$_{1-2}$ hydroxyalkyl), —C(O)(C$_{1-2}$ chloroalkyl), —C(O)(C$_{1-3}$ fluoroalkyl), —C(O)CH$_2$O(C$_{1-3}$ alkyl), —C(O)CH$_2$S(O)$_2$(C$_{1-2}$ alkyl), —C(O)(C$_{1-3}$ hydroxyalkyl), —C(O)CR$_x$R$_x$OC(O)(C$_{1-2}$ alkyl), —C(O)(tetrahydrofuranyl), —C(O)(ethoxypiperidinyl), —C(O)NR$_x$CH$_2$CN, —C(O)

NH($C_{1-3}$ alkyl), —C(O)NR$_x$CH$_2$C(O)NH$_2$, —C(O)NR$_x$CH$_2$CH$_2$NHC(O)($C_{1-2}$ alkyl), —C(O)N($C_{1-3}$ alkyl)$_2$, —C(O)NR$_x$C(R$_x$)$_3$, —C(O)CH$_2$NR$_x$R$_x$, —C(O)CH$_2$NR$_x$CH$_2$CN, —C(O)CH$_2$NR$_x$CH$_2$C(O)($C_{1-2}$ alkyl), —C(O)CH$_2$NR$_x$CH$_2$C(O)N($C_{1-2}$ alkyl)$_2$, —C(O)CH$_2$NR$_x$R$_x$, —C(O)CH$_2$NR$_x$($C_{1-2}$ alkyl), —C(O)CH$_2$NR$_x$CH$_2$CH$_2$OH, —C(O)CH$_2$NR$_x$($C_{1-2}$ fluoroalkyl), —C(O)CH$_2$NR$_x$CH$_2$CH$_2$OCH$_2$CH$_2$OH, —C(O)CH$_2$NR$_x$CH$_2$CH$_2$C(O)N($C_{1-2}$ alkyl)$_2$, —C(O)CH$_2$NR$_x$(CH(CH$_2$OH)($C_{1-4}$ alkyl)), —C(O)CH$_2$NR$_x$($C_{1-4}$ hydroxyalkyl), —C(O)CH$_2$NR$_x$($C_{1-5}$ alkyl), —C(O)CH$_2$NR$_x$CH$_2$CHFC(CH$_3$)$_2$OH, —C(O)CH$_2$NR$_x$($C_{1-6}$ hydroxyalkyl), —C(O)CH$_2$CH$_2$NR$_x$R$_x$, —C(O)CH$_2$CH$_2$CH$_2$NR$_x$R$_x$, —C(O)CH$_2$CH$_2$CH$_2$NR$_x$($C_{1-3}$ alkyl), —C(O)CH$_2$CH(CH$_3$)NR$_x$R$_x$, —C(O)CH$_2$CH$_2$C(O)NR$_x$R$_x$, —CH$_2$C(O)NR$_x$R$_x$, —CH$_2$C(O)NR$_x$CH$_2$CN, —CH$_2$C(O)NR$_x$CH$_2$C(O)NR$_x$R$_x$, —CH$_2$C(O)NR$_x$($C_{1-3}$ hydroxyalkyl), —CH$_2$C(O)NR$_x$CH$_2$CH$_2$S(O)$_2$OH, —CH$_2$C(O)NR$_x$CH$_2$CH$_2$NR$_x$R$_x$, —CH$_2$C(O)NR$_x$CH$_2$CH$_2$NR$_x$C(O)($C_{1-2}$ alkyl), —CH$_2$C(O)N(CH$_2$CH$_3$)CH$_2$CH$_2$NR$_x$R$_x$, —CH$_2$C(O)NR$_x$($C_{1-3}$ alkyl), —CH$_2$C(O)NR$_x$CH$_2$CH$_2$NR$_x$R$_x$, —CH$_2$C(O)NR$_x$($C_{1-5}$ alkyl), —C(O)CH$_2$NR$_x$C(O)CH$_2$CH$_2$CH$_2$CN, or —C(O)CH$_2$CH$_2$CH$_2$NR$_x$C(O)($C_{1-2}$ alkyl). Also included in this embodiment are compounds of Formula (I) in which R$_3$ is H, —CH$_3$, —CH$_2$CH(CH$_3$)$_2$, —CH$_2$CH(CH$_3$)CF$_3$, —CH$_2$CH$_2$CH$_2$OH, —CH(CH$_3$)CH$_2$OH, —CH$_2$CH$_2$NHC(O)OC(CH$_3$)$_3$, —CH$_2$CH$_2$NH$_2$, —CH$_2$CH$_2$NH(CH$_3$), —CH$_2$CH$_2$N(CH$_3$)(CH$_2$CH$_3$), —CH$_2$CH$_2$N(CH$_3$)(CH$_2$CH(CH$_3$)$_2$), —CH$_2$CH$_2$CH$_2$NH(CH$_3$), —CH(CH$_3$)CH$_2$N(CH$_3$)$_2$, —C(O)OC(CH$_3$)$_3$, —C(O)CH$_3$, —C(O)CH$_2$OH, —C(O)CH$_2$Cl, —C(O)CH$_2$CF$_3$, —C(O)CH$_2$CH$_2$CF$_3$, —C(O)CH$_2$OCH(CH$_3$)$_2$, —C(O)CH$_2$S(O)$_2$CH$_3$, —C(O)CH$_2$CH(CH$_3$)OH, —C(O)C(CH$_3$)$_2$OC(O)CH$_3$, —C(O)NHCH$_2$CH$_3$, —C(O)NHCH(CH$_3$)$_2$, —C(O)CH$_2$NHCH$_3$, —C(O)CH$_2$NHCH$_2$CN, —C(O)CH$_2$NHCH$_2$C(O)CH$_3$, —C(O)CH$_2$N(CH$_3$)CH$_2$C(O)N(CH$_2$CH$_3$)$_2$, —C(O)CH$_2$N(CH$_3$)$_2$, —C(O)CH$_2$NHCH$_2$CH$_3$, —C(O)CH$_2$NHCH$_2$CH$_2$OH, —C(O)CH$_2$NHCH$_2$CF$_3$, —C(O)CH$_2$NHCH$_2$CH$_2$OCH$_2$CH$_2$OH, —C(O)CH$_2$N(CH$_3$)CH$_2$CH$_2$C(O)N(CH$_2$CH$_3$)$_2$, —C(O)CH$_2$NH(CH$_2$OH)CH$_2$CH$_3$, —C(O)CH$_2$NHCH(CH$_2$OH)$_2$, —C(O)CH$_2$N(CH$_3$)CH$_2$CH$_2$OH, —C(O)CH$_2$NHCH$_2$CH(CH$_3$)OH, —C(O)CH$_2$NHCH$_2$CH(OH)CH$_2$OH, —C(O)CH$_2$N(CH$_3$)CH(CH$_3$)$_2$, —C(O)CH$_2$NHCH$_2$CH(CH$_3$)$_2$, —C(O)CH$_2$NHCH(CH$_3$)$_2$, —C(O)CH$_2$NHCH(CH$_3$)CH(CH$_3$)$_2$, —C(O)CH$_2$NHCH$_2$CH(CH$_3$)OH, —C(O)CH$_2$NH(CH$_2$OH)(CH$_2$CH$_2$CH$_3$), —C(O)CH$_2$NH(CH$_2$OH)CH$_2$CH(CH$_3$)$_2$, —C(O)CH$_2$NH(CH(CH$_2$CH$_3$)$_2$), —C(O)CH$_2$NHCH$_2$CHFC(CH$_3$)$_2$OH, —C(O)CH$_2$NHCH$_2$C(CH$_3$)$_2$CH$_2$OH, —C(O)CH$_2$NHCH(CH$_2$OH)CH$_2$CH(CH$_3$)$_2$, —C(O)CH$_2$CH$_2$N(CH$_3$)$_2$, —C(O)CH$_2$CH$_2$CH$_2$N(CH$_3$)$_2$, —C(O)CH$_2$CH$_2$CH$_2$NHCH(CH$_3$)$_2$, —C(O)CH$_2$CH(CH$_3$)NH$_2$, —C(O)CH$_2$CH$_2$C(O)NH$_2$, —C(O)CH$_2$CH$_2$C(O)N(CH$_3$)$_2$, —CH$_2$C(O)N(CH$_3$)$_2$, —CH$_2$C(O)NHCH$_2$CN, —CH$_2$C(O)NHCH$_2$C(O)NH$_2$, —CH$_2$C(O)NHCH$_2$CH$_2$OH, —CH$_2$C(O)NHCH$_2$CH$_2$S(O)$_2$OH, —CH$_2$C(O)NHCH$_2$CH$_2$N(CH$_3$)$_2$, —CH$_2$C(O)NHCH$_2$CH$_2$NHC(O)CH$_3$, —CH$_2$C(O)N(CH$_3$)CH$_2$CH$_2$N(CH$_3$)$_2$, —CH$_2$C(O)N(CH$_2$CH$_3$)CH$_2$CH$_2$N(CH$_3$)$_2$, —CH$_2$C(O)NHCH(CH$_3$)$_2$, —CH$_2$C(O)NHCH$_2$CH$_2$CH$_2$OH, —CH$_2$C(O)NHCH$_2$CH$_2$N(CH$_3$)$_2$, —CH$_2$C(O)N(CH$_3$)CH$_2$CH$_2$CH$_2$N(CH$_3$)$_2$, —CH$_2$C(O)NHCH(CH$_3$)(CH$_2$CH$_3$), —CH$_2$C(O)NHCH(CH$_2$CH$_3$)$_2$, —C(O)CH$_2$NHC(O)CH$_2$CH$_2$CH$_2$CN, or —C(O)CH$_2$CH$_2$NHC(O)CH$_3$.

One embodiment provides a compound of Formula (I) or a salt thereof, wherein R$_1$ is H, Cl, —CN, $C_{1-4}$ alkyl, $C_{1-2}$ fluoroalkyl, —CH(CF$_3$)OH, —CH$_2$(cyclopropyl), or tetrahydropyranyl; and R$_3$, R$_4$, R$_5$, m, and n are defined in the first aspect. Included in this embodiment are compounds in which R$_1$ is H, Cl, —CN, —CH$_3$, —CH$_2$CH$_3$, —CH$_2$CH$_2$CH$_3$, —CH(CH$_3$)$_2$, —CH$_2$CH(CH$_3$)$_2$, —CH$_2$CHF$_2$, —CH$_2$CF$_3$, —CH(CF$_3$)OH, —CH$_2$(cyclopropyl), or tetrahydropyranyl. Also included in this embodiment are compounds in which R$_1$ is $C_{1-4}$ alkyl or $C_{1-2}$ fluoroalkyl; and compounds in which R$_1$ is —CH$_3$, —CH$_2$CH$_3$, —CH(CH$_3$)$_2$, or —CH$_2$CF$_3$.

One embodiment provides a compound of Formula (I) or a salt thereof, wherein R$_1$ is $C_{1-4}$ alkyl or $C_{1-2}$ fluoroalkyl; and R$_3$, R$_4$, R$_5$, m, and n are defined in the first aspect. Included in this embodiment are compounds in which R$_1$ is —CH$_3$, —CH$_2$CH$_3$, —CH(CH$_3$)$_2$, or —CH$_2$CF$_3$.

One embodiment provides a compound of Formula (I) or a salt thereof, wherein R$_1$ is —CH$_3$, —CH$_2$CH$_3$, —CH(CH$_3$)$_2$, or —CH$_2$CF$_3$; and R$_3$, R$_4$, R$_5$, m, and n are defined in the first aspect.

One embodiment provides a compound of Formula (I) or a salt thereof, wherein R$_1$ is —CH$_2$CH$_2$CH$_3$, —CH(CH$_3$)$_2$, —CH$_2$CHF$_2$, or —CH$_2$CF$_3$; and R$_3$, R$_4$, R$_5$, m, and n are defined in the first aspect. Included in this embodiment are compounds in which R$_1$ is —CH(CH$_3$)$_2$ or —CH$_2$CF$_3$.

One embodiment provides a compound of Formula (I) or a salt thereof, wherein R$_1$ is —CH$_2$CHF$_2$; and R$_3$, R$_4$, R$_5$, m, and n are defined in the first aspect.

One embodiment provides a compound of Formula (I) or a salt thereof, wherein R$_1$ is —CH$_2$CF$_3$; and R$_3$, R$_4$, R$_5$, m, and n are defined in the first aspect.

One embodiment provides a compound of Formula (I) or a salt thereof, wherein m is zero; and R$_1$, R$_3$, R$_5$, and n are defined in the first aspect.

One embodiment provides a compound of Formula (I) or a salt thereof, wherein m is 1 or 2; and R$_1$, R$_3$, R$_4$, R$_5$, and n are defined in the first aspect. Included in embodiment are compounds in which m is 1. Also included in this embodiment are compounds in which m is 2.

One embodiment provides a compound of Formula (I) or a salt thereof, wherein n is zero; and R$_1$, R$_3$, R$_4$, and m are defined in the first aspect.

One embodiment provides a compound of Formula (I) or a salt thereof, wherein n is 1; and R$_1$, R$_3$, R$_4$, R$_5$, and m are defined in the first aspect. Included in this embodiment are compounds in which R$_5$ is —CH$_3$.

One embodiment provides a compound of Formula (I) or a salt thereof, wherein R$_1$ is —CH$_3$, —CH$_2$CH$_3$, —CH(CH$_3$)$_2$, or —CH$_2$CF$_3$; m is zero; and R$_3$, R$_5$, and n are defined in the first aspect.

One embodiment provides a compound of Formula (I) or a salt thereof, wherein R$_1$ is —CH$_3$, —CH$_2$CH$_3$, —CH(CH$_3$)$_2$, or —CH$_2$CF$_3$; n is zero; and R$_3$, R$_4$, and m are defined in the first aspect.

One embodiment provides a compound of Formula (I) or a salt thereof, wherein R$_1$ is —CH$_3$, —CH$_2$CH$_3$, —CH(CH$_3$)$_2$, or —CH$_2$CF$_3$; m is zero; n is zero; and R$_3$ is defined in the first aspect.

One embodiment provides a compound of Formula (I) or a salt thereof, wherein R$_3$ is: (a) -L$_1$-A; or (b) H, $C_{1-6}$ alkyl, $C_{1-3}$ fluoroalkyl, $C_{1-5}$ hydroxyalkyl, —(CR$_x$R$_x$)$_{1-4}$O($C_{1-3}$ alkyl), —(CR$_x$R$_x$)$_{1-3}$S($C_{1-3}$ alkyl), —(CH$_2$)$_{1-3}$C(O)OC(CH$_3$)$_3$, —S(O)$_2$NR$_x$R$_x$, —C(O)O($C_{1-4}$ alkyl), —C(O)($C_{1-3}$ alkyl), —C(O)($C_{1-3}$ hydroxyalkyl), —C(O)($C_{1-3}$ chloroalkyl), —C(O)($C_{1-3}$ fluoroalkyl), —C(O)CH$_2$O($C_{1-3}$ alkyl), —C(O)CH$_2$S(O)$_2$($C_{1-3}$ alkyl), —C(O)($C_{1-3}$ hydroxyalkyl), —C(O)CR$_x$R$_x$OC(O)($C_{1-3}$ alkyl), —C(O)(tetrahydrofuranyl), —C(O)(tetrahydropyranyl), —C(O)(piperidinyl), —C(O)(ethoxypiperidinyl), —C(O)NR$_x$($C_{1-3}$ cyanoalkyl), —C(O)NR$_x$(C$_{1-3}$ alkyl), —C(O)NR$_x$CH$_2$C(O)NR$_x$R$_x$, —C(O)NR$_x$CH$_2$CH$_2$NR$_x$C(O)(C$_{1-2}$ alkyl), —C(O)N(C$_{1-3}$ alkyl)$_2$, —C(O)NR$_x$C(R$_x$)$_3$, —C(O)CH$_2$NR$_x$(C$_{1-3}$ cyanoalkyl), —C(O)CH$_2$NR$_x$CH$_2$C(O)(C$_{1-3}$ alkyl), —C(O)CH$_2$NR$_x$CH$_2$C(O)N(C$_{1-3}$ alkyl)$_2$, —C(O)CH$_2$NR$_x$R$_x$, —C(O)CH$_2$NR$_x$(C$_{1-2}$ alkyl), —C(O)CH$_2$NR$_x$(C$_{1-3}$ hydroxyalkyl), —C(O)CH$_2$NR$_x$(C$_{1-3}$ fluoroalkyl), —C(O)CH$_2$NR$_x$CH$_2$CH$_2$O(C$_{1-3}$ hydroxyalkyl), —C(O)CH$_2$NR$_x$CH$_2$CH$_2$C(O)N(C$_{1-2}$ alkyl)$_2$, —C(O)CH$_2$NR$_x$(CH(CH$_2$OH)(C$_{1-4}$ alkyl)), —C(O)CH$_2$NR$_x$(C$_{1-5}$ alkyl), —C(O)CH$_2$NR$_x$(C$_{1-5}$ hydroxy-fluoroalkyl), —C(O)CH$_2$NR$_x$(C$_{1-6}$ hydroxyalkyl), —C(O)(CH$_2$)$_{1-3}$NR$_x$R$_x$, —C(O)(CH$_2$)$_{1-3}$NR$_x$(C$_{1-3}$ alkyl), —C(O)CH$_2$CH(CH$_3$)NR$_x$R$_x$, —C(O)CH$_2$CH$_2$C(O)NR$_x$R$_x$, —CH$_2$C(O)NR$_x$R$_x$, —CH$_2$C(O)NR$_x$(C$_{1-3}$ cyanoalkyl), —CH$_2$C(O)NR$_x$CH$_2$C(O)NR$_x$R$_x$, —CH$_2$C(O)NR$_x$(C$_{1-3}$ hydroxyalkyl), —CH$_2$C(O)NR$_x$CH$_2$CH$_2$S(O)$_2$OH, —CH$_2$C(O)NR$_x$CH$_2$CH$_2$NR$_x$C(O)(C$_{1-3}$ alkyl), —CH$_2$C(O)N(CH$_2$CH$_3$)CH$_2$CH$_2$NR$_x$R$_x$, —CH$_2$C(O)NR$_x$(C$_{1-3}$ alkyl), —CH$_2$C(O)NR$_x$(CH$_2$)$_{1-3}$NR$_x$R$_x$, —CH$_2$C(O)NR$_x$(C$_{1-5}$ alkyl), —CH$_2$C(O)NR$_x$C(O)(C$_{1-3}$ cyanoalkyl), or —C(O)(CH$_2$)$_{1-3}$NR$_x$C(O)(C$_{1-3}$ alkyl); L$_1$ is a bond, —CR$_x$R$_x$—, —CR$_x$R$_x$C(O)—, —CR$_x$R$_x$C(O)NR$_x$(CR$_x$R$_x$)$_{0-4}$—, —C(O)(CR$_x$R$_x$)$_{0-3}$—, —C(O)CR$_x$R$_x$NR$_x$—, —C(O)CR$_x$R$_x$O—, or —C(O)NR$_x$(CR$_x$R$_x$)$_{1-2}$—; and R$_1$, R$_4$, R$_5$, R$_x$, A, m, and n are defined in the first aspect. Included in this embodiment are compounds in which R$_1$ is —CH(CH$_3$)$_2$ or —CH$_2$CF$_3$.

One embodiment provides a compound of Formula (I) or a salt thereof, wherein R$_3$ is: -L$_1$-A; L$_1$ is a bond, —CR$_x$R$_x$—, —CR$_x$R$_x$C(O)—, —CR$_x$R$_x$C(O)NR$_x$(CR$_x$R$_x$)$_{0-4}$—, —C(O)(CR$_x$R$_x$)$_{0-3}$—, —C(O)CR$_x$R$_x$NR$_x$—, —C(O)CR$_x$R$_x$O—, or —C(O)NR$_x$(CR$_x$R$_x$)$_{1-2}$—; and R$_1$, R$_4$, R$_5$, A, m, and n are defined in the first aspect. Included in this embodiment are compounds in which R$_1$ is —CH(CH$_3$)$_2$ or —CH$_2$CF$_3$.

One embodiment provides a compound of Formula (I) or a salt thereof, wherein R$_3$ is: H, C$_{1-6}$ alkyl, C$_{1-3}$ fluoroalkyl, C$_{1-5}$ hydroxyalkyl, —(CR$_x$R$_x$)$_{1-4}$O(C$_{1-3}$ alkyl), —(CR$_x$R$_x$)$_{1-3}$S(C$_{1-3}$ alkyl), —(CH$_2$)$_{1-3}$C(O)OC(CH$_3$)$_3$, —S(O)$_2$NR$_x$R$_x$, —C(O)O(C$_{1-4}$ alkyl), —C(O)(C$_{1-3}$ alkyl), —C(O)(C$_{1-3}$ hydroxyalkyl), —C(O)(C$_{1-3}$ chloroalkyl), —C(O)(C$_{1-3}$ fluoroalkyl), —C(O)CH$_2$O(C$_{1-3}$ alkyl), —C(O)CH$_2$S(O)$_2$(C$_{1-3}$ alkyl), —C(O)(C$_{1-3}$ hydroxyalkyl), —C(O)CR$_x$R$_x$OC(O)(C$_{1-3}$ alkyl), —C(O)(tetrahydrofuranyl), —C(O)(tetrahydropyranyl), —C(O)(piperidinyl), —C(O)(ethoxypiperidinyl), —C(O)NR$_x$(C$_{1-3}$ cyanoalkyl), —C(O)NR$_x$(C$_{1-3}$ alkyl), —C(O)NR$_x$CH$_2$C(O)NR$_x$R$_x$, —C(O)NR$_x$CH$_2$CH$_2$NR$_x$C(O)(C$_{1-2}$ alkyl), —C(O)N(C$_{1-3}$ alkyl)$_2$, —C(O)NR$_x$C(R$_x$)$_3$, —C(O)CH$_2$NR$_x$(C$_{1-3}$ cyanoalkyl), —C(O)CH$_2$NR$_x$CH$_2$C(O)(C$_{1-3}$ alkyl), —C(O)CH$_2$NR$_x$CH$_2$C(O)N(C$_{1-3}$ alkyl)$_2$, —C(O)CH$_2$NR$_x$R$_x$, —C(O)CH$_2$NR$_x$(C$_{1-2}$ alkyl), —C(O)CH$_2$NR$_x$(C$_{1-3}$ hydroxyalkyl), —C(O)CH$_2$NR$_x$(C$_{1-3}$ fluoroalkyl), —C(O)CH$_2$NR$_x$CH$_2$CH$_2$O(C$_{1-3}$ hydroxyalkyl), —C(O)CH$_2$NR$_x$CH$_2$CH$_2$C(O)N(C$_{1-2}$ alkyl)$_2$, —C(O)CH$_2$NR$_x$(CH(CH$_2$OH)(C$_{1-4}$ alkyl)), —C(O)CH$_2$NR$_x$(C$_{1-5}$ alkyl), —C(O)CH$_2$NR$_x$(C$_{1-5}$ hydroxy-fluoroalkyl), —C(O)CH$_2$NR$_x$(C$_{1-6}$ hydroxyalkyl), —C(O)(CH$_2$)$_{1-3}$NR$_x$R$_x$, —C(O)(CH$_2$)$_{1-3}$NR$_x$(C$_{1-3}$ alkyl), —C(O)CH$_2$CH(CH$_3$)NR$_x$R$_x$, —C(O)CH$_2$CH$_2$C(O)NR$_x$R$_x$, —CH$_2$C(O)NR$_x$R$_x$, —CH$_2$C(O)NR$_x$(C$_{1-3}$ cyanoalkyl), —CH$_2$C(O)NR$_x$CH$_2$C(O)NR$_x$R$_x$, —CH$_2$C(O)NR$_x$(C$_{1-3}$ hydroxyalkyl), —CH$_2$C(O)NR$_x$CH$_2$CH$_2$S(O)$_2$OH, —CH$_2$C(O)NR$_x$CH$_2$CH$_2$NR$_x$C(O)(C$_{1-3}$ alkyl), —CH$_2$C(O)N(CH$_2$CH$_3$)CH$_2$CH$_2$NR$_x$R$_x$, —CH$_2$C(O)NR$_x$(C$_{1-3}$ alkyl), —CH$_2$C(O)NR$_x$(CH$_2$)$_{1-3}$NR$_x$R$_x$, —CH$_2$C(O)NR$_x$(C$_{1-5}$ alkyl), —C(O)CH$_2$NR$_x$C(O)(C$_{1-3}$ cyanoalkyl), or —C(O)(CH$_2$)$_{1-3}$NR$_x$C(O)(C$_{1-3}$ alkyl); and R$_1$, R$_4$, R$_5$, R$_x$, L$_1$, A, m, and n are defined in the first aspect. Included in this embodiment are compounds in which R$_1$ is —CH(CH$_3$)$_2$ or —CH$_2$CF$_3$.

One embodiment provides a compound of Formula (I) or a salt thereof, wherein R$_3$ is H, —CH$_3$, —CH$_2$CH(CH$_3$)$_2$, —CH$_2$CH(CH$_3$)CF$_3$, —CH$_2$CH$_2$CH$_2$OH, —CH(CH$_3$)CH$_2$OH, —CH$_2$CH$_2$NHC(O)OC(CH$_3$)$_3$, —C(O)OC(CH$_3$)$_3$, —C(O)CH$_3$, —C(O)CH$_2$OH, —C(O)CH$_2$C$_1$, —C(O)CH$_2$CF$_3$, —C(O)CH$_2$CH$_2$CF$_3$, —C(O)CH$_2$OCH(CH$_3$)$_2$, —C(O)CH$_2$S(O)$_2$CH$_3$, —C(O)CH$_2$CH(CH$_3$)OH, —C(O)C(CH$_3$)$_2$OC(O)CH$_3$, —C(O)NHCH$_2$CH$_3$, —C(O)NHCH(CH$_3$)$_2$, —C(O)CH$_2$NHCH$_3$, —C(O)CH$_2$NHCH$_2$CN, —C(O)CH$_2$NHCH$_2$C(O)CH$_3$, —C(O)CH$_2$N(CH$_3$)CH$_2$C(O)N(CH$_2$CH$_3$)$_2$, —C(O)CH$_2$N(CH$_3$)$_2$, —C(O)CH$_2$NHCH$_2$CH$_3$, —C(O)CH$_2$NHCH$_2$CH$_2$OH, —C(O)CH$_2$NHCH$_2$CF$_3$, —C(O)CH$_2$NHCH$_2$CH$_2$OCH$_2$CH$_2$OH, —C(O)CH$_2$N(CH$_3$)CH$_2$CH$_2$C(O)N(CH$_2$CH$_3$)$_2$, —C(O)CH$_2$NH(CH$_2$OH)CH$_2$CH$_3$, —C(O)CH$_2$NHCH(CH$_2$OH)$_2$, —C(O)CH$_2$N(CH$_3$)CH$_2$CH$_2$OH, —C(O)CH$_2$NHCH$_2$CH(CH$_3$)OH, —C(O)CH$_2$NHCH$_2$CH(OH)CH$_2$OH, —C(O)CH$_2$N(CH$_3$)CH(CH$_3$)$_2$, —C(O)CH$_2$NHCH$_2$CH(CH$_3$)$_2$, —C(O)CH$_2$NHCH(CH$_3$)CH(CH$_3$)$_2$, —C(O)CH$_2$NHCH$_2$CH$_2$CH(CH$_3$)OH, —C(O)CH$_2$NH(CH$_2$OH)(CH$_2$CH$_2$CH$_3$), —C(O)CH$_2$NH(CH$_2$OH)CH$_2$CH(CH$_3$)$_2$, —C(O)CH$_2$NH(CH(CH$_2$CH$_3$)$_2$, —C(O)CH$_2$NHCH$_2$CHFC(CH$_3$)$_2$OH, —C(O)CH$_2$NHCH$_2$C(CH$_3$)$_2$CH$_2$OH, —C(O)CH$_2$NHCH(CH$_2$OH)CH$_2$CH(CH$_3$)$_2$, —C(O)CH$_2$CH$_2$N(CH$_3$)$_2$, —C(O)CH$_2$CH$_2$CH$_2$N(CH$_3$)$_2$, —C(O)CH$_2$CH$_2$CH$_2$NHCH(CH$_3$)$_2$, —C(O)CH$_2$CH(CH$_3$)NH$_2$, —C(O)CH$_2$CH$_2$C(O)NH$_2$, —C(O)CH$_2$CH$_2$C(O)N(CH$_3$)$_2$, —CH$_2$C(O)N(CH$_3$)$_2$, —CH$_2$C(O)NHCH$_2$CN, —CH$_2$C(O)NHCH$_2$C(O)NH$_2$, —CH$_2$C(O)NHCH$_2$CH$_2$OH, —CH$_2$C(O)NHCH$_2$CH$_2$S(O)$_2$OH, —CH$_2$C(O)

NHCH$_2$CH$_2$N(CH$_3$)$_2$, —CH$_2$C(O)NHCH$_2$CH$_2$NHC(O)CH$_3$, —CH$_2$C(O)N(CH$_3$)CH$_2$CH$_2$N(CH$_3$)$_2$, —CH$_2$C(O)N(CH$_2$CH$_3$)CH$_2$CH$_2$N(CH$_3$)$_2$, —CH$_2$C(O)NHCH(CH$_3$)$_2$, —CH$_2$C(O)NHCH$_2$CH$_2$CH$_2$OH, —CH$_2$C(O)NHCH$_2$CH$_2$CH$_2$N(CH$_3$)$_2$, —CH$_2$C(O)N(CH$_3$)CH$_2$CH$_2$CH$_2$N(CH$_3$)$_2$, —CH$_2$C(O)NHCH(CH$_3$)(CH$_2$CH$_3$), —CH$_2$C(O)NHCH(CH$_2$CH$_3$)$_2$, —C(O)CH$_2$NHC(O)CH$_2$CH$_2$CH$_2$CN, or —C(O)CH$_2$CH$_2$CH$_2$NHC(O)CH$_3$; and R$_1$, R$_4$, R$_5$, m, and n are defined in the first aspect. Included in this embodiment are compounds in which R$_1$ is —CH(CH$_3$)$_2$ or —CH$_2$CF$_3$.

One embodiment provides a compound of Formula (I) or a salt thereof, wherein R$_1$ is H, Cl, —CN, C$_{1-4}$ alkyl, C$_{1-2}$ fluoroalkyl, —CH(CF$_3$)OH, —CH$_2$(cyclopropyl), or tetrahydropyranyl; and R$_3$, R$_4$, R$_5$, m, and n are defined in the first aspect. Included in this embodiment are compounds in which R$_1$ is H, Cl, —CN, —CH$_3$, —CH$_2$CH$_3$, —CH$_2$CH$_2$CH$_3$, —CH(CH$_3$)$_2$, —CH$_2$CH(CH$_3$)$_2$, —CH$_2$CHF$_2$, —CH$_2$CF$_3$, —CH(CF$_3$)OH, —CH$_2$(cyclopropyl), or tetrahydropyranyl. Also included in this embodiment are compounds in which R$_1$ is C$_{1-4}$ alkyl or C$_{1-2}$ fluoroalkyl; and compounds in which R$_1$ is —CH$_3$, —CH$_2$CH$_3$, —CH(CH$_3$)$_2$, or —CH$_2$CF$_3$.

One embodiment provides a compound of Formula (I) or a salt thereof, wherein said compound is selected from 2-(3,4-dimethoxyphenyl)-3-methyl-5-(piperidin-4-yl)-1H-indole hydrochloride (1); 5-([1,4'-bipiperidin]-4-yl)-2-(3,4-dimethoxyphenyl)-3-methyl-1H-indole dihydrochloride (2); 5-(1'-(cyclopropylmethyl)-[1,4'-bipiperidin]-4-yl)-2-(3,4-dimethoxyphenyl)-3-methyl-1H-indole (3); 2-(3,4-dimethoxyphenyl)-3-methyl-5-(1-((2-methyl-1H-imidazol-5-yl)methyl)piperidin-4-yl)-1H-indole (4); 3-(4-(2-(3,4-dimethoxyphenyl)-3-methyl-1H-indol-5-yl)piperidin-1-yl)propan-1-ol (5); 2-(3,4-dimethoxyphenyl)-5-(1'-isobutyl-[1,4'-bipiperidin]-4-yl)-3-methyl-1H-indole (6); 2-(3,4-dimethoxyphenyl)-3-methyl-5-(1-(oxetan-3-yl)piperidin-4-yl)-1H-indole (7); 2-(3,4-dimethoxyphenyl)-3-methyl-5-(1-(1-phenylpyrrolidin-3-yl)piperidin-4-yl)-1H-indole (8); 5-(1'-benzyl-[1,4'-bipiperidin]-4-yl)-2-(3,4-dimethoxyphenyl)-3-methyl-1H-indole (9); 2-(3,4-dimethoxyphenyl)-5-(1'-isopropyl-[1,4'-bipiperidin]-4-yl)-3-methyl-1H-indole (10); 2-(3,4-dimethoxyphenyl)-3-methyl-5-(1'-methyl-[1,4'-bipiperidin]-4-yl)-1H-indole (11); 1-(4-(2-(3,4-dimethoxyphenyl)-3-methyl-1H-indol-5-yl)-[1,4'-bipiperidin]-1'-yl)ethan-1-one (12); ethyl 3-(4-(2-(3,4-dimethoxyphenyl)-3-methyl-1H-indol-5-yl)piperidin-1-yl) pyrrolidine-1-carboxylate (13); 4-((4-(2-(3,4-dimethoxyphenyl)-3-methyl-1H-indol-5-yl) piperidin-1-yl)methyl)thiazol-2-amine (14); 5-((4-(2-(3,4-dimethoxyphenyl)-3-methyl-1H-indol-5-yl)piperidin-1-yl)methyl)quinoline (15); 2-(3,4-dimethoxyphenyl)-3-methyl-5-(1-((1-methyl-1H-imidazol-2-yl)methyl)piperidin-4-yl)-1H-indole (16); 2-(3,4-dimethoxyphenyl)-3-methyl-5-(1-((tetrahydro-2H-pyran-4-yl)methyl)piperidin-4-yl)-1H-indole (17); 2-((4-(2-(3,4-dimethoxyphenyl)-3-methyl-1H-indol-5-yl)piperidin-1-yl) methyl)quinoline (18); 4-((4-(2-(3,4-dimethoxyphenyl)-3-methyl-1H-indol-5-yl) piperidin-1-yl)methyl)-N,N-dimethylnaphthalen-1-amine (19); 2-(3,4-dimethoxyphenyl)-3-methyl-5-(1-(pyridin-4-ylmethyl)piperidin-4-yl)-1H-indole (20); 2-(3,4-dimethoxyphenyl)-3-methyl-5-(1-(((1R,5S)-8-methyl-8-azabicyclo[3.2.1]octan-3-yl) piperidin-4-yl)-1H-indole (21); 2-(3,4-dimethoxyphenyl)-3-methyl-5-(1',2',2',6',6'-pentamethyl-[1,4'-bipiperidin]-4-yl)-1H-indole (22); 5-(1'-cyclopropyl-[1,4'-bipiperidin]-4-yl)-2-(3,4-dimethoxyphenyl)-3-methyl-1H-indole (23); 2-(3,4-dimethoxyphenyl)-5-(1'-ethyl-[1,3'-bipiperidin]-4-yl)-3-methyl-1H-indole (24); 3-(4-(2-(3,4-dimethoxyphenyl)-3-methyl-1H-indol-5-yl)piperidin-1-yl)-N,N-dimethylcyclohexan-1-amine (25); 2-(3,4-dimethoxyphenyl)-3-methyl-5-(1'-(tetrahydro-2H-pyran-4-yl)-[1,4'-bipiperidin]-4-yl)-1H-indole (26); 2-(3,4-dimethoxyphenyl)-3-methyl-5-(1-(1-phenylethyl)piperidin-4-yl)-1H-indole (27); 2-(3,4-dimethoxyphenyl)-3-methyl-5-(1-(pyridin-2-ylmethyl)piperidin-4-yl)-1H-indole (28); 2-(3,4-dimethoxyphenyl)-3-methyl-5-(1-((1-methyl-1H-pyrrol-2-yl) methyl)piperidin-4-yl)-1H-indole (29); 2-(4-(2-(3,4-dimethoxyphenyl)-3-methyl-1H-indol-5-yl)piperidin-1-yl)-N,N-dimethylpropan-1-amine (30); 6-((4-(2-(3,4-dimethoxyphenyl)-3-methyl-1H-indol-5-yl)piperidin-1-yl)methyl)isoquinoline (31); 4-((4-(2-(3,4-dimethoxyphenyl)-3-methyl-1H-indol-5-yl) piperidin-1-yl)methyl)quinoline (32); 2-(3,4-dimethoxyphenyl)-3-methyl-5-(1-((1-methyl-1H-indol-2-yl)methyl) piperidin-4-yl)-1H-indole (33); 5-(1-(4-(1H-1,2,4-triazol-1-yl)benzyl)piperidin-4-yl)-2-(3,4-dimethoxyphenyl)-3-methyl-1H-indole (34); 2-((4-(2-(3,4-dimethoxyphenyl)-3-methyl-1H-indol-5-yl)piperidin-1-yl)methyl)quinoline (35); 8-((4-(2-(3,4-dimethoxyphenyl)-3-methyl-1H-indol-5-yl) piperidin-1-yl)methyl)quinoline (36); 4-((4-(2-(3,4-dimethoxyphenyl)-3-methyl-1H-indol-5-yl)piperidin-1-yl) methyl)-N,N-dimethylaniline (37); 3-(4-((4-(2-(3,4-dimethoxyphenyl)-3-methyl-1H-indol-5-yl) piperidin-1-yl) methyl)phenoxy)-N,N-dimethylpropan-1-amine (38); 5-(1-(4-(1H-imidazol-1-yl)benzyl)piperidin-4-yl)-2-(3,4-dimethoxyphenyl)-3-methyl-1H-indole (39); 2-(3,4-dimethoxyphenyl)-3-methyl-5-(1-((1-methyl-1H-imidazol-5-yl)methyl)piperidin-4-yl)-1H-indole (40); 4-((4-(2-(3,4-dimethoxyphenyl)-3-methyl-1H-indol-5-yl)piperidin-1-yl) methyl)-1,2,3-thiadiazole (41); 2-(3,4-dimethoxyphenyl)-3-methyl-5-(1-(4-(4-methylpiperazin-1-yl)benzyl)piperidin-4-yl)-1H-indole (42); 2-(4-(2-(3,4-dimethoxyphenyl)-3-methyl-1H-indol-5-yl)piperidin-1-yl)propan-1-ol (43); 2-(3,4-dimethoxyphenyl)-5-(1'-ethyl-[1,4'-bipiperidin]-4-yl)-3-methyl-1H-indole (44); 5-(1-((1-benzylpyrrolidin-3-yl)methyl)piperidin-4-yl)-2-(3,4-dimethoxyphenyl)-3-methyl-1H-indole (45); 2-(3,4-dimethoxyphenyl)-3-methyl-5-(1-(4-(pyrrolidin-1-yl)benzyl) piperidin-4-yl)-1H-indole (46); 2-(3,4-dimethoxyphenyl)-3-methyl-5-(1-(pyridin-3-ylmethyl)piperidin-4-yl)-1H-indole (47); 2-(3,4-dimethoxyphenyl)-3-methyl-5-(2',2',6',6'-tetramethyl-[1,4'-bipiperidin]-4-yl)-1H-indole (48); 2-(3,4-dimethoxyphenyl)-3-methyl-5-(1-((1-methylpiperidin-2-yl)methyl)piperidin-4-yl)-1H-indole (49); 2-(3,4-dimethoxyphenyl)-3-methyl-5-(1'-(3,3,3-trifluoropropyl)-[1,4'-bipiperidin]-4-yl)-1H-indole (50); 2-(3,4-dimethoxyphenyl)-3-methyl-5-(1'-(2-methylbutyl)-[1,4'-bipiperidin]-4-yl)-1H-indole (51); 3-(4-(2-(3,4-dimethoxyphenyl)-3-methyl-1H-indol-5-yl)-[1,4'-bipiperidin]-1'-yl)propane-1,2-diol (52); 2-(3,4-dimethoxyphenyl)-3-methyl-5-(1'-(3-(methylthio)propyl)-[1,4'-bipiperidin]-4-yl)-1H-indole (53); 2-(3,4-dimethoxyphenyl)-5-(1'-(2-ethylbutyl)-[1,4'-bipiperidin]-4-yl)-3-methyl-1H-indole (54); 2-(3,4-dimethoxyphenyl)-3-methyl-5-(1'-pentyl-[1,4'-bipiperidin]-4-yl)-1H-indole (55); 4-(4-(2-(3,4-dimethoxyphenyl)-3-methyl-1H-indol-5-yl)-[1,4'-bipiperidin]-1'-yl)butan-2-ol (56); 2-(3,4-dimethoxyphenyl)-5-(1'-(5-methoxypentyl)-[1,4'-bipiperidin]-4-yl)-3-methyl-1H-indole (57); 5-(1'-(cyclohexylmethyl)-[1,4'-bipiperidin]-4-yl)-2-(3,4-dimethoxyphenyl)-3-methyl-1H-indole (58); 2-(3,4-dimethoxyphenyl)-3-methyl-5-(1'-((1-methyl-1H-imidazol-5-yl)methyl)-[1,4'-bipiperidin]-4-yl)-1H-indole (59); ethyl 2-((4-(2-(3,4-dimethoxyphenyl)-3-methyl-1H-indol-5-yl)-[1,4'-bipiperidin]-1'-yl)methyl)cyclopropane-1-carboxylate (60); 5-(1'-cyclobutyl-[1,4'-bipiperidin]-4-yl)-2-(3,4-dimethoxyphenyl)-3-methyl-1H-indole (61); 5-(1'-cyclopentyl-[1,4'-bipiperidin]-4-yl)-2-(3,4- dimethoxyphenyl)-3-methyl-1H-indole (62); 2-(3,4-dimethoxyphenyl)-3-methyl-5-(1'-propyl-[1,4'-bipiperidin]-4-yl)-1H-indole (63); 2-(3,4-dimethoxyphenyl)-3-methyl-5-(1'-(thiophen-2-ylmethyl)-[1,4'-bipiperidin]-4-yl)-1H-indole (64); 5-(1'-(cyclopentylmethyl)-[1,4'-bipiperidin]-4-yl)-2-(3,4-dimethoxyphenyl)-3-methyl-1H-indole (65); 5-(1'-(sec-butyl)-[1,4'-bipiperidin]-4-yl)-2-(3,4-dimethoxyphenyl)-3-methyl-1H-indole (66); 2-(3,4-dimethoxyphenyl)-3-methyl-5-(1'-(3-methylcyclohexyl)-[1,4'-bipiperidin]-4-yl)-1H-indole (67); 5-(1'-cyclohexyl-[1,4'-bipiperidin]-4-yl)-2-(3,4-dimethoxyphenyl)-3-methyl-1H-indole (68); 3-(4-(2-(3,4-dimethoxyphenyl)-3-methyl-1H-indol-5-yl)-[1,4'-bipiperidin]-1'-yl)-2,2-dimethylpropan-1-ol (69); 4-(4-(2-(3,4-dimethoxyphenyl)-3-methyl-1H-indol-5-yl)-[1,4'-bipiperidin]-1'-yl)butanoic acid (70); 5-(1'-(sec-butyl)-[1,4'-bipiperidin]-4-yl)-2-(3,4-dimethoxyphenyl)-3-methyl-1H-indole (71); 2-((4-(2-(3,4-dimethoxyphenyl)-3-methyl-1H-indol-5-yl)-[1,4'-bipiperidin]-1'-yl)methyl) thiazole (72); 2-(3,4-dimethoxyphenyl)-3-methyl-5-(1'-(3-(trifluoromethyl)cyclohexyl)-[1,4'-bipiperidin]-4-yl)-1H-indole (73); 2-(3,4-dimethoxyphenyl)-3-methyl-5-(1'-(tetrahydrofuran-3-yl)-[1,4'-bipiperidin]-4-yl)-1H-indole (74); 2-(3,4-dimethoxyphenyl)-3-methyl-5-(1'-neopentyl-[1,4'-bipiperidin]-4-yl)-1H-indole (75); 2-(3,4-dimethoxyphenyl)-5-(1'-(furan-2-ylmethyl)-[1,4'-bipiperidin]-4-yl)-3-methyl-1H-indole (76); 2-(3,4-dimethoxyphenyl)-5-(1'-isopentyl-[1,4'-bipiperidin]-4-yl)-3-methyl-1H-indole (77); 2-(3,4-dimethoxyphenyl)-3-methyl-5-(1'-((1-methyl-1H-pyrrol-2-yl)methyl)-[1,4'-bipiperidin]-4-yl)-1H-indole (78); 2-(3,4-dimethoxyphenyl)-3-methyl-5-(1'-(3-methylcyclohexyl)-[1,4'-bipiperidin]-4-yl)-1H-indole (79); 2-(3,4-dimethoxyphenyl)-3-methyl-5-(1'-(4-methylcyclohexyl)-[1,4'-bipiperidin]-4-yl)-1H-indole (80); 2-(3,4-dimethoxyphenyl)-3-methyl-5-(1"-methyl-[1,4':1',4"-terpiperidin]-4-yl)-1H-indole (81); 5-(1'-butyl-[1,4'-bipiperidin]-4-yl)-2-(3,4-dimethoxyphenyl)-3-methyl-1H-indole (82); 2-(3,4-dimethoxyphenyl)-3-methyl-5-(1'-(oxetan-3-yl)-[1,4'-bipiperidin]-4-yl)-1H-indole (83); 4-(4-(2-(3,4-dimethoxyphenyl)-3-methyl-1H-indol-5-yl)-[1,4'-bipiperidin]-1'-yl)cyclohexan-1-ol (84); 2-(3,4-dimethoxyphenyl)-5-(1-(1-isobutylpyrrolidin-3-yl) piperidin-4-yl)-3-methyl-1H-indole (85); 3-(4-(2-(3,4-dimethoxyphenyl)-3-methyl-1H-indol-5-yl)piperidin-1-yl)-N-isobutyl-N-methylcyclohexan-1-amine (89); 4-(4-(2-(3,4-dimethoxyphenyl)-3-methyl-1H-indol-5-yl)piperidin-1-yl)-N-isobutylcyclohexan-1-amine (90); 2-(3,4-dimethoxyphenyl)-3-methyl-5-(1-(1-methylazepan-4-yl) piperidin-4-yl)-1H-indole (91); 2-(3,4-dimethoxyphenyl)-5-(1-(1-isopropylazepan-4-yl)piperidin-4-yl)-3-methyl-1H-indole (92); 5-(1-(1-cyclopentylazepan-4-yl)piperidin-4-yl)-2-(3,4-dimethoxyphenyl)-3-methyl-1H-indole (93); 5-(1-(1-(cyclopropylmethyl)azepan-4-yl)piperidin-4-yl)-2-(3,4-dimethoxyphenyl)-3-methyl-1H-indole (94); 2-(3,4-dimethoxyphenyl)-5-(1-(1-isobutylazepan-4-yl)piperidin-4-yl)-3-methyl-1H-indole (95); 2-(3,4-dimethoxyphenyl)-3-methyl-5-(1-(1-(oxetan-3-yl)azepan-4-yl)piperidin-4-yl)-1H-indole (96); 2-(3,4-dimethoxyphenyl)-5-(1-(1-ethylazepan-4-yl)piperidin-4-yl)-3-methyl-1H-indole (97); tert-butyl (2-(4-(2-(3,4-dimethoxyphenyl)-3-methyl-1H-indol-5-yl)piperidin-1-yl)ethyl) carbamate (99); 2-(4-(2-(3,4-dimethoxyphenyl)-3-methyl-1H-indol-5-yl)piperidin-1-yl) ethan-1-amine (100); 2-(3,4-dimethoxyphenyl)-3-methyl-5-(1-(piperidin-2-ylmethyl) piperidin-4-yl)-1H-indole (101); 3-(4-(2-(3,4-dimethoxyphenyl)-3-methyl-1H-indol-5-yl) piperidin-1-yl)-N-methylpropan-1-amine (102); 5-(1-(azepan-4-yl)piperidin-4-yl)-2-(3,4-dimethoxyphenyl)-3-methyl-1H-indole (103); 2-(3,4-dimethoxyphenyl)-3-methyl-5-(1-(pyrrolidin-3-yl)piperidin-4-yl)-1H-indole (104); 3-(4-(2-(3,4-dimethoxyphenyl)-3-methyl-1H-indol-5-yl)piperidin-1-yl)cyclohexan-1-amine (105); 5-([1,3'-bipiperidin]-4-yl)-2-(3,4-dimethoxyphenyl)-3-methyl-1H-indole (106); (S)-2-(3,4-dimethoxyphenyl)-3-methyl-5-(1-(pyrrolidin-2-ylmethyl)piperidin-4-yl)-1H-indole (107); (R)-2-(3,4-dimethoxyphenyl)-3-methyl-5-(1-(pyrrolidin-2-ylmethyl)piperidin-4-yl)-1H-indole (108); N-(2-(4-(2-(3,4-dimethoxyphenyl)-3-methyl-1H-indol-5-yl)piperidin-1-yl) ethyl)-N-methyloxetan-3-amine (109); N-(2-(4-(2-(3,4-dimethoxyphenyl)-3-methyl-1H-indol-5-yl)piperidin-1-yl) ethyl)-N,2-dimethylpropan-1-amine (110); 2-(4-(2-(3,4-dimethoxyphenyl)-3-methyl-1H-indol-5-yl)piperidin-1-yl)-N-ethyl-N-methylethan-1-amine (111); N-(cyclopropylmethyl)-2-(4-(2-(3,4-dimethoxyphenyl)-3-methyl-1H-indol-5-yl)piperidin-1-yl)-N-methylethan-1-amine (112); 1-(4-(2-(3,4-dimethoxyphenyl)-3-methyl-1H-indol-5-yl)piperidin-1-yl)-2-(ethylamino)ethan-1-one (113); 2-(4-(2-(3,4-dimethoxyphenyl)-1,3-dimethyl-1H-indol-5-yl)piperidin-1-yl)-N-methylethan-1-amine (114); 2-(3,4-dimethoxyphenyl)-5-(1'-isopropyl-[1,4'-bipiperidin]-4-yl)-3,6-dimethyl-1H-indole-di-trifluoroacetic acid (115); 1-(4-(2-(3,4-dimethoxyphenyl)-3-isobutyl-1H-indol-5-yl)piperidin-1-yl)-2-(ethylamino) ethanone trifluoroacetic acid (116); 2-(4-(3-(cyclopropylmethyl)-2-(3,4-dimethoxyphenyl)-1H-indol-5-yl)piperidin-1-yl)-N-methylethanamine di-trifluoroacetic acid (117); 2-(3,4-dimethoxyphenyl)-5-(1-(2-(methylamino)ethyl)piperidin-4-yl)-1H-indole-3-carbonitrile-di-trifluoroacetic acid (118); 2-(3,4-2-(4-(3-chloro-2-(3,4-dimethoxyphenyl)-1H-indol-5-yl)piperidin-1-yl)-N-methylethanamine-di-trifluoroacetic acid (119); 3-chloro-2-(3,4-dimethoxyphenyl)-5-(1'-isobutyl-[1,4'-bipiperidin]-4-yl)-1H-indole di-trifluoroacetic acid (120); 2-(3,4-dimethoxyphenyl)-5-(1'-isobutyl-[1,4'-bipiperidin]-4-yl)-3-propyl-1H-indole-di-trifluoroacetic acid (121); 2-(3,4-dimethoxyphenyl)-3-ethyl-5-(piperidin-4-yl)-1H-indole (122); 2-(3,4-dimethoxyphenyl)-3-ethyl-5-(1'-isobutyl-[1,4'-bipiperidin]-4-yl)-1H-indole-di-trifluoroacetic acid (123); 5-((4-(2-(3,4-dimethoxyphenyl)-3-ethyl-1H-indol-5-yl)-[1,4'-bipiperidin]-1'-yl)methyl)-2-methyloxazole (124); 5-(1'-((1H-imidazol-4-yl) methyl)-[1,4'-bipiperidin]-4-yl)-2-(3,4-dimethoxyphenyl)-3-ethyl-1H-indole (125); 4-((4-(2-(3,4-dimethoxyphenyl)-3-ethyl-1H-indol-5-yl)-[1,4'-bipiperidin]-1'-yl)methyl)-2-methyloxazole (126); ethyl 5-((4-(2-(3,4-dimethoxyphenyl)-3-ethyl-1H-indol-5-yl)-[1,4'-bipiperidin]-1'-yl)methyl)-2,4-dimethyl-1H-pyrrole-3-carboxylate (127); 5-(1'-((1H-indol-2-yl)methyl)-[1,4'-bipiperidin]-4-yl)-2-(3,4-dimethoxyphenyl)-3-ethyl-1H-indole (128); 2-(3,4-dimethoxyphenyl)-3-ethyl-5-(1'-((2-methyl-1H-indol-3-yl)methyl)-[1,4'-bipiperidin]-4-yl)-1H-indole (129); 4-((4-(2-(3,4-dimethoxyphenyl)-3-ethyl-1H-indol-5-yl)-[1,4'-bipiperidin]-1'-yl)methyl)-1,2,3-thiadiazole (130); 2-(3,4-dimethoxyphenyl)-3-ethyl-5-(1'-((3-methyl-1H-pyrazol-5-yl) methyl)-[1,4'-bipiperidin]-4-yl)-1H-indole (131); 2-(3,4-dimethoxyphenyl)-5-(1'-((1,3-dimethyl-1H-pyrazol-5-yl)methyl)-[1,4'-bipiperidin]-4-yl)-3-ethyl-1H-indole (132); 2-(3,4-dimethoxyphenyl)-3-ethyl-5-(1'-((1-methyl-1H-pyrazol-3-yl)methyl)-[1,4'-bipiperidin]-4-yl)-1H-indole (133); 5-((4-(2-(3,4-dimethoxyphenyl)-3-ethyl-1H-indol-5-yl)-[1,4'-bipiperidin]-1'-yl)methyl)oxazole (134); 2-(1-(4-(2-(3,4-dimethoxyphenyl)-3-ethyl-1H-indol-5-yl)-[1,4'-bipiperidin]-1'-yl)ethyl) oxazole (135); 2-(3,4-dimethoxyphenyl)-3-ethyl-5-(1'-((1-methyl-1H-imidazol-2-yl) methyl)-[1,4'-bipiperidin]-4-yl)-1H-indole (136); 2-(3,4-dimethoxyphenyl)-3-ethyl-5-(1'-((1-methyl-1H-indol-2-yl) methyl)-[1,4'-bipiperidin]-4-yl)-1H-indole (137); 4-((4-(2-(3,4-dimethoxyphenyl)-3-ethyl-1H-indol-5-yl)-[1,4'- bipiperidin]-1'-yl)methyl)-3,5-dimethylisoxazole (138); 2-(3,4-dimethoxyphenyl)-3-ethyl-5-(1'-((3-methylthiophen-2-yl)methyl)-[1,4'-bipiperidin]-4-yl)-1H-indole (139); 2-(3,4-dimethoxyphenyl)-3-ethyl-5-(1'-((5-methylthiophen-2-yl) methyl)-[1,4'-bipiperidin]-4-yl)-1H-indole (140); 2-(3,4-dimethoxyphenyl)-3-ethyl-5-(1'-((5-phenylthiophen-2-yl) methyl)-[1,4'-bipiperidin]-4-yl)-1H-indole (141); 2-(3,4-dimethoxyphenyl)-3-ethyl-5-(1'-(thiophen-3-ylmethyl)-[1,4'-bipiperidin]-4-yl)-1H-indole (142); 2-(3,4-dimethoxyphenyl)-3-ethyl-5-(1'-((5-phenylfuran-2-yl) methyl)-[1,4'-bipiperidin]-4-yl)-1H-indole (143); 2-(3,4-dimethoxyphenyl)-5-(1'-((1,5-dimethyl-1H-pyrazol-3-yl) methyl)-[1,4'-bipiperidin]-4-yl)-3-ethyl-1H-indole (144); 1-(4-(2-(3,4-dimethoxyphenyl)-3-ethyl-1H-indol-5-yl)-[1, 4'-bipiperidin]-1'-yl)butane-1,4-diol (145); 2-(3,4-dimethoxyphenyl)-3-ethyl-5-(1'-(furan-3-ylmethyl)-[1,4'-bipiperidin]-4-yl)-1H-indole (146); 5-(1'-benzyl-[1,4'-bipiperidin]-4-yl)-2-(3,4-dimethoxyphenyl)-3-ethyl-1H-indole (147); 2-(3,4-dimethoxyphenyl)-3-ethyl-5-(1'-ethyl-[1,4'-bipiperidin]-4-yl)-1H-indole (149); 2-(3,4-dimethoxyphenyl)-3-ethyl-5-(1'-methyl-[1,4'-bipiperidin]-4-yl)-1H-indole (150); 2-(3,4-dimethoxyphenyl)-3-ethyl-5-(1'-isopropyl-[1,4'-bipiperidin]-4-yl)-1H-indole (151); 5-(1'-cyclopentyl-[1,4'-bipiperidin]-4-yl)-2-(3,4-dimethoxyphenyl)-3-ethyl-1H-indole (152); 2-(3,4-dimethoxyphenyl)-3-ethyl-5-(1'-((2-methyl-1H-imidazol-5-yl)methyl)-[1,4'-bipiperidin]-4-yl)-1H-indole (153); 2-(4-(2-(3,4-dimethoxyphenyl)-3-ethyl-1H-indol-5-yl)piperidin-1-yl)-N-methylethanamine di-trifluoroacetic acid (155); 1-(4-(2-(3,4-dimethoxyphenyl)-3-ethyl-1H-indol-5-yl) piperidin-1-yl)-2-((2-hydroxypropyl)amino)ethan-1-one (157); 2-([1,4'-bipiperidin]-1'-yl)-1-(4-(2-(3,4-dimethoxyphenyl)-3-ethyl-1H-indol-5-yl)piperidin-1-yl)ethan-1-one (158); 1-(4-(2-(3,4-dimethoxyphenyl)-3-ethyl-1H-indol-5-yl)piperidin-1-yl)-2-((2-hydroxyethyl)amino) ethan-1-one (159); 1-(4-(2-(3,4-dimethoxyphenyl)-3-ethyl-1H-indol-5-yl)piperidin-1-yl)-2-((1-(hydroxymethyl)cyclopentyl)amino) ethan-1-one (160); 2-((2-(4-(2-(3,4-dimethoxyphenyl)-3-ethyl-1H-indol-5-yl)piperidin-1-yl)-2-oxoethyl) amino) acetonitrile (161); 1-(4-(2-(3,4-dimethoxyphenyl)-3-ethyl-1H-indol-5-yl) piperidin-1-yl)-2-((4-(dimethylamino) cyclohexyl)amino)ethan-1-one (162); 1-(4-(2-(3,4-dimethoxyphenyl)-3-ethyl-1H-indol-5-yl)piperidin-1-yl)-2-(((1r,3s,5R,7S)-3-hydroxyadamantan-1-yl)amino) ethan-1-one (163); 1-(4-(2-(3,4-dimethoxyphenyl)-3-ethyl-1H-indol-5-yl)piperidin-1-yl)-2-((3-hydroxy-2,2-dimethylpropyl)amino)ethan-1-one (164); 2-((1,3-dihydroxypropan-2-yl)amino)-1-(4-(2-(3,4-dimethoxyphenyl)-3-ethyl-1H-indol-5-yl)piperidin-1-yl) ethan-1-one (165); 2-(4-acetyl-1,4-diazepan-1-yl)-1-(4-(2-(3,4-dimethoxyphenyl)-3-ethyl-1H-indol-5-yl)piperidin-1-yl)ethan-1-one (166); 1-(4-(2-(3,4-dimethoxyphenyl)-3-ethyl-1H-indol-5-yl)piperidin-1-yl)-2-morpholinoethan-1-one (167); 1-(2-(4-(2-(3,4-dimethoxyphenyl)-3-ethyl-1H-indol-5-yl)piperidin-1-yl)-2-oxoethyl)-N,N-diethylpiperidine-3-carboxamide (168); 1-(4-(2-(3,4-dimethoxyphenyl)-3-ethyl-1H-indol-5-yl)piperidin-1-yl)-2-(3-(hydroxymethyl)piperidin-1-yl)ethan-1-one (169); 1-(4-(2-(3,4-dimethoxyphenyl)-3-ethyl-1H-indol-5-yl)piperidin-1-yl)-2-(isopropyl(methyl)amino) ethan-1-one (170); 2-(4-acetylpiperazin-1-yl)-1-(4-(2-(3,4-dimethoxyphenyl)-3-ethyl-1H-indol-5-yl)piperidin-1-yl)ethan-1-one (171); 1-(4-(2-(3,4-dimethoxyphenyl)-3-ethyl-1H-indol-5-yl)piperidin-1-yl)-2-(4-(tetrahydrofuran-2-carbonyl)piperazin-1-yl) ethan-1-one (172); (R)-1-(4-(2-(3,4-dimethoxyphenyl)-3-ethyl-1H-indol-5-yl)piperidin-1-yl)-2-(3-hydroxypyrrolidin-1-yl)ethan-1-one (173); (S)-1-(4-(2-(3,4-dimethoxyphenyl)-3-ethyl-1H-indol-5-yl)piperidin-1-yl)-2-((1-hydroxyhexan-2-yl)amino)ethan-1-one (174); 1-(4-(2-(3,4-dimethoxyphenyl)-3-ethyl-1H-indol-5-yl) piperidin-1-yl)-2-methyl-1-oxopropan-2-yl acetate (175); 1-(2-(4-(2-(3,4-dimethoxyphenyl)-3-ethyl-1H-indol-5-yl)piperidin-1-yl)-2-oxoethyl)piperidine-3-carboxylic acid (176); 1-(4-(2-(3,4-dimethoxyphenyl)-3-ethyl-1H-indol-5-yl)piperidin-1-yl)-2-(thiazol-2-ylamino)ethanone (177); 1-(2-(4-(2-(3,4-dimethoxyphenyl)-3-ethyl-1H-indol-5-yl)piperidin-1-yl)-2-oxoethyl)-N,N-diethylpiperidine-3-carboxamide (178 and 179); 2-(3,4-dimethoxyphenyl)-3-ethyl-5-(1-(3,3,3-trifluoro-2-methylpropyl)piperidin-4-yl)-1H-indole (180); 1-(4-(2-(3,4-dimethoxyphenyl)-3-ethyl-1H-indol-5-yl)piperidin-1-yl)-2-(dimethylamino) ethanone (181); 4-(2-(3,4-dimethoxyphenyl)-3-ethyl-1H-indol-5-yl)-N-isopropylpiperidine-1-carboxamide (182); (4-(2-(3,4-dimethoxyphenyl)-3-ethyl-1H-indol-5-yl)piperidin-1-yl)(pyridin-4-yl) methanone (183); tert-butyl 3-(4-(2-(3,4-dimethoxyphenyl)-3-ethyl-1H-indol-5-yl)piperidine-1-carbonyl)piperidine-1-carboxylate (184); 1-(4-(2-(3,4-dimethoxyphenyl)-3-ethyl-1H-indol-5-yl)piperidin-1-yl)ethan-1-one (185); (4-(2-(3,4-dimethoxyphenyl)-3-ethyl-1H-indol-5-yl)piperidin-1-yl) (piperidin-4-yl) methanone (186); (4-(2-(3,4-dimethoxyphenyl)-3-ethyl-1H-indol-5-yl)piperidin-1-yl)(4-methylpiperidin-4-yl)methanone (187); 2-(4-(2-(3,4-dimethoxyphenyl)-3-ethyl-6-methyl-1H-indol-5-yl) piperidin-1-yl)-N-methylethanamine-di-trifluoroacetic acid (188); 2-(3,4-dimethoxyphenyl)-3-ethyl-7-fluoro-5-(piperidin-4-yl)-1H-indole (189); 2-(3,4-dimethoxyphenyl)-3-ethyl-7-fluoro-5-(1'-isobutyl-[1,4'-bipiperidin]-4-yl)-1H-indole (190); 2-(4-(2-(3,4-dimethoxyphenyl)-3-ethyl-7-fluoro-1H-indol-5-yl)piperidin-1-yl)-N-methylethan-1-amine (191); 2-(3,4-dimethoxyphenyl)-3-ethyl-5-(1'-isopropyl-[1,4'-bipiperidin]-4-yl)-6-methoxy-1H-indole (192); 2-(4-(2-(3,4-dimethoxyphenyl)-3-ethyl-6-methoxy-1H-indol-5-yl)piperidin-1-yl)-N-methylethanamine (193); 2-(3,4-dimethoxyphenyl)-3-isopropyl-5-(piperidin-4-yl)-1H-indole hydrochloride (194); 2-(4-(2-(3,4-dimethoxyphenyl)-3-isopropyl-1H-indol-5-yl)piperidin-1-yl)-N-methyl-ethan-1-amine (195); 5-([1,4'-bipiperidin]-4-yl)-2-(3,4-dimethoxyphenyl)-3-isopropyl-1H-indole dihydrochloride (197); 5-(1'-(cyclopropylmethyl)-[1,4'-bipiperidin]-4-yl)-2-(3,4-dimethoxyphenyl)-3-isopropyl-1H-indole di trifluoroacetic acid (198); 2-(3,4-dimethoxyphenyl)-5-(1'-isobutyl-[1,4'-bipiperidin]-4-yl)-3-isopropyl-1H-indole (199); 2-(3, 4-dimethoxyphenyl)-3-isopropyl-5-(1'-methyl-[1,4'-bipiperidin]-4-yl)-1H-indole (200); 2-(3,4-dimethoxyphenyl)-3-isopropyl-5-(1'-isopropyl-[1,4'-bipiperidin]-4-yl)-1H-indole (201); 5-(1'-cyclopentyl-[1,4'-bipiperidin]-4-yl)-2-(3,4-dimethoxyphenyl)-3-isopropyl-1H-indole (202); 2-((2-(4-(2-(3,4-dimethoxyphenyl)-3-isopropyl-1H-indol-5-yl) piperidin-1-yl)-2-oxoethyl)(methyl)amino)-N,N-diethylacetamide, TFA (203); 3-((2-(4-(2-(3,4-dimethoxyphenyl)-3-isopropyl-1H-indol-5-yl) piperidin-1-yl)-2-oxoethyl)(methyl) amino)-N,N-diethylpropanamide (204); 2-(3,4-dimethoxyphenyl)-3-isopropyl-6-methyl-5-(piperidin-4-yl)-1H-indole (205); 2-(3,4-dimethoxyphenyl)-3-isopropyl-5-(1'-isopropyl-[1,4'-bipiperidin]-4-yl)-6-methyl-1H-indole di trifluoroacetic acid (206); 2-(3,4-dimethoxyphenyl)-3-isopropyl-5-(1'-isopropyl-[1,4'-bipiperidin]-4-yl)-6-methyl-1H-indole-ditrifluoroacteic acid (207); 2-(4-(2-(3,4-dimethoxyphenyl)-6-fluoro-3-isopropyl-1H-indol-5-yl)piperidin-1-yl)-N-methylethan-1-amine (208); 1-(4-(2-(3,4-dimethoxyphenyl)-3-isopropyl-1H-indol-5-yl)piperidin-1-yl)-2-(dimethylamino)ethan-1-one (209); 1-(4-(2-(3,4-dimethoxyphenyl)-3-isopropyl-1H-indol-5-yl)piperidin-1-yl)-2-((2-hydroxypropyl)amino)

ethan-1-one (210); 2-([1,4'-bipiperidin]-1'-yl)-1-(4-(2-(3,4-dimethoxyphenyl)-3-isopropyl-1H-indol-5-yl)piperidin-1-yl)ethan-1-one (211); 1-(4-(2-(3,4-dimethoxyphenyl)-3-isopropyl-1H-indol-5-yl)piperidin-1-yl)-2-((2-hydroxyethyl) amino)ethan-1-one (212); 1-(4-(2-(3,4-dimethoxyphenyl)-3-isopropyl-1H-indol-5-yl) piperidin-1-yl)-2-((1-(hydroxymethyl)cyclopentyl)amino)ethan-1-one (213); 2-((2-(4-(2-(3,4-dimethoxyphenyl)-3-isopropyl-1H-indol-5-yl) piperidin-1-yl)-2-oxoethyl)amino) acetonitrile (214); 1-(4-(2-(3,4-dimethoxyphenyl)-3-isopropyl-1H-indol-5-yl) piperidin-1-yl)-2-((4-(dimethylamino)cyclohexyl)amino) ethan-1-one (215); 2-((3-(tert-butyl)-1H-pyrazol-5-yl)amino)-1-(4-(2-(3,4-dimethoxyphenyl)-3-isopropyl-1H-indol-5-yl)piperidin-1-yl)ethan-1-one (216); 2-(((3s,5s,7s)-adamantan-1-yl)amino)-1-(4-(2-(3,4-dimethoxyphenyl)-3-isopropyl-1H-indol-5-yl)piperidin-1-yl)ethan-1-one (217); 1-(4-(2-(3,4-dimethoxyphenyl)-3-isopropyl-1H-indol-5-yl)piperidin-1-yl)-2-(((1r,3s,5R,7S)-3-hydroxyadamantan-1-yl)amino)ethan-1-one (218); 1-(4-(2-(3,4-dimethoxyphenyl)-3-isopropyl-1H-indol-5-yl)piperidin-1-yl)-2-((3-hydroxy-2,2-dimethylpropyl)amino)ethan-1-one (219); 2-((1,3-dihydroxypropan-2-yl)amino)-1-(4-(2-(3,4-dimethoxyphenyl)-3-isopropyl-1H-indol-5-yl)piperidin-1-yl) ethan-1-one (220); 1-(4-(2-(3,4-dimethoxyphenyl)-3-isopropyl-1H-indol-5-yl)piperidin-1-yl)-2-((2,2,2-trifluoroethyl) amino)ethan-1-one (221); 2-(4-acetyl-1,4-diazepan-1-yl)-1-(4-(2-(3,4-dimethoxyphenyl)-3-isopropyl-1H-indol-5-yl)piperidin-1-yl)ethan-1-one (222); 1-(4-(2-(3,4-dimethoxyphenyl)-3-isopropyl-1H-indol-5-yl)piperidin-1-yl)-2-morpholinoethan-1-one (223); 1-(2-(4-(2-(3,4-dimethoxyphenyl)-3-isopropyl-1H-indol-5-yl)piperidin-1-yl)-2-oxoethyl)-N,N-diethylpiperidine-3-carboxamide (224); 1-(4-(2-(3,4-dimethoxyphenyl)-3-isopropyl-1H-indol-5-yl)piperidin-1-yl)-2-(((S)-1-methylpyrrolidin-2-yl)methyl) piperidin-1-yl)ethan-1-one (225); 1-(4-(2-(3,4-dimethoxyphenyl)-3-isopropyl-1H-indol-5-yl)piperidin-1-yl)-2-(3-(hydroxymethyl)piperidin-1-yl)ethan-1-one (226); 1-(4-(2-(3,4-dimethoxyphenyl)-3-isopropyl-1H-indol-5-yl)piperidin-1-yl)-2-(isopropyl(methyl)amino) ethan-1-one (227); 2-((2-(4-(2-(3,4-dimethoxyphenyl)-3-isopropyl-1H-indol-5-yl) piperidin-1-yl)-2-oxoethyl)amino)acetamide (228); 2-(4-(2-(4-(2-(3,4-dimethoxyphenyl)-3-isopropyl-1H-indol-5-yl)piperidin-1-yl)-2-oxoethyl)piperazin-1-yl)-N-isopropylacetamide (229); 1-(4-(2-(3,4-dimethoxyphenyl)-3-isopropyl-1H-indol-5-yl) piperidin-1-yl)-2-((2-(2-hydroxyethoxy)ethyl)amino)ethan-1-one (230); (S)-1-(4-(2-(3,4-dimethoxyphenyl)-3-isopropyl-1H-indol-5-yl) piperidin-1-yl)-2-((1-hydroxy-4-methylpentan-2-yl)amino) ethan-1-one (231); 2-(((1r,4r)-4-aminocyclohexyl)amino)-1-(4-(2-(3,4-dimethoxyphenyl)-3-isopropyl-1H-indol-5-yl)piperidin-1-yl)ethan-1-one (232); 1-(4-(2-(3,4-dimethoxyphenyl)-3-isopropyl-1H-indol-5-yl)piperidin-1-yl)-2-((1-hydroxybutan-2-yl)amino)ethan-1-one (233); (R)-1-(4-(2-(3,4-dimethoxyphenyl)-3-isopropyl-1H-indol-5-yl)piperidin-1-yl)-2-((1-hydroxy-4-methylpentan-2-yl)amino) ethan-1-one (234); (S)-2-((2,3-dihydroxypropyl)amino)-1-(4-(2-(3,4-dimethoxyphenyl)-3-isopropyl-1H-indol-5-yl)piperidin-1-yl)ethan-1-one (235); 1-(4-(2-(3,4-dimethoxyphenyl)-3-isopropyl-1H-indol-5-yl)piperidin-1-yl)-2-((2-hydroxycyclopentyl) amino)ethan-1-one (236); 1-(4-(2-(3,4-dimethoxyphenyl)-3-isopropyl-1H-indol-5-yl) piperidin-1-yl)-2-((3-hydroxybutyl)amino)ethan-1-one (237); 1-(4-(2-(3,4-dimethoxyphenyl)-3-isopropyl-1H-indol-5-yl) piperidin-1-yl)-2-(4-hydroxypiperidin-1-yl) ethan-1-one (238); 1-(4-(2-(3,4-dimethoxyphenyl)-3-isopropyl-1H-indol-5-yl)piperidin-1-yl)-2-(4-methyl-1,4-diazepan-1-yl) ethan-1-one (239); 1-(4-(2-(3,4-dimethoxyphenyl)-3-isopropyl-1H-indol-5-yl)piperidin-1-yl)-2-(4-isopropylpiperazin-1-yl)ethan-1-one (240); 1-(4-(2-(3,4-dimethoxyphenyl)-3-isopropyl-1H-indol-5-yl)piperidin-1-yl)-2-(4-(4-methylpiperazin-1-yl)piperidin-1-yl)ethan-1-one (241); 1-(4-(2-(3,4-dimethoxyphenyl)-3-isopropyl-1H-indol-5-yl)piperidin-1-yl)-2-((2-hydroxyethyl)(methyl)amino)ethan-1-one (242); 1-(4-(2-(3,4-dimethoxyphenyl)-3-isopropyl-1H-indol-5-yl)piperidin-1-yl)-2-(4-(hydroxymethyl)piperidin-1-yl)ethan-1-one (243); 1-(4-(2-(3,4-dimethoxyphenyl)-3-isopropyl-1H-indol-5-yl)piperidin-1-yl)-2-(4-(dimethylamino)piperidin-1-yl)ethan-1-one (244); 1-(4-(2-(3,4-dimethoxyphenyl)-3-isopropyl-1H-indol-5-yl)piperidin-1-yl)-2-((4-(2-hydroxypropan-2-yl)cyclohexyl)amino)ethan-1-one (245); 1-(4-(2-(3,4-dimethoxyphenyl)-3-isopropyl-1H-indol-5-yl)piperidin-1-yl)-2-((4-hydroxycyclohexyl) amino)ethan-1-one (246); 1-(2-(4-(2-(3,4-dimethoxyphenyl)-3-isopropyl-1H-indol-5-yl) piperidin-1-yl)-2-oxoethyl)-N,N-diethylpiperidine-3-carboxamide (247 and 248); 1-(4-(2-(3,4-dimethoxyphenyl)-3-isopropyl-1H-indol-5-yl)piperidin-1-yl)-2-(3-(hydroxymethyl) piperidin-1-yl)ethan-1-one (249 and 250); (R)-1-(4-(2-(3,4-dimethoxyphenyl)-3-isopropyl-1H-indol-5-yl)piperidin-1-yl)-2-((2-fluoro-3-hydroxy-3-methylbutyl) amino) ethan-1-one (251); N-(2-(4-(2-(3,4-dimethoxyphenyl)-3-isopropyl-1H-indol-5-yl) piperidin-1-yl)-2-oxoethyl) hex-5-ynamide (252); (S)-3-amino-1-(4-(2-(3,4-dimethoxyphenyl)-3-isopropyl-1H-indol-5-yl)piperidin-1-yl)butan-1-one (253); (S)-1-(4-(2-(3,4-dimethoxyphenyl)-3-isopropyl-1H-indol-5-yl)piperidin-1-yl)-3-hydroxybutan-1-one (254 and 255); 1-(4-(2-(3,4-dimethoxyphenyl)-3-isopropyl-1H-indol-5-yl)piperidin-1-yl)-2-(methylamino) ethan-1-one (256); 1-(4-(2-(3,4-dimethoxyphenyl)-3-isopropyl-1H-indol-5-yl)piperidin-1-yl)-4-(isopropylamino) butan-1-one (257); 2-(3,4-dimethoxyphenyl)-3-isopropyl-5-(1-((1-methyl-1H-imidazol-5-yl)methyl)piperidin-4-yl)-1H-indole (258); 2-(3,4-dimethoxyphenyl)-3-isopropyl-5-(1-((1-methyl-1H-pyrazol-4-yl) methyl)piperidin-4-yl)-1H-indole (259); N-(3-((4-(2-(3,4-dimethoxyphenyl)-3-isopropyl-1H-indol-5-yl)piperidin-1-yl)methyl)phenyl) methanesulfonamide (260); 2-((4-(2-(3,4-dimethoxyphenyl)-3-isopropyl-1H-indol-5-yl)piperidin-1-yl)methyl)thiazole (261); 2-(3,4-dimethoxyphenyl)-3-isopropyl-5-(1-((1-methyl-1H-imidazol-2-yl)methyl) piperidin-4-yl)-1H-indole (262); 5-(1-(4-(1H-imidazol-1-yl) benzyl)piperidin-4-yl)-2-(3,4-dimethoxyphenyl)-3-isopropyl-1H-indole (263); 3-(4-(2-(3,4-dimethoxyphenyl)-3-isopropyl-1H-indol-5-yl)piperidin-1-yl)methyl)benzonitrile (264); 2-(3,4-dimethoxyphenyl)-5-(1-(2-ethylbutyl)piperidin-4-yl)-3-isopropyl-1H-indole (265); 2-(3,4-dimethoxyphenyl)-3-isopropyl-5-(1-((2-methyl-1H-imidazol-5-yl)methyl)piperidin-4-yl)-1H-indole (266); 2-(3,4-dimethoxyphenyl)-3-isopropyl-5-(1-((4-methyl-1H-imidazol-5-yl)methyl)piperidin-4-yl)-1H-indole (267); 5-(1-((1H-imidazol-5-yl)methyl) piperidin-4-yl)-2-(3,4-dimethoxyphenyl)-3-isopropyl-1H-indole (268); 2-(3,4-dimethoxyphenyl)-3-isopropyl-5-(1-(3-(trifluoromethyl) benzyl)piperidin-4-yl)-1H-indole (269); 4-((4-(2-(3,4-dimethoxyphenyl)-3-isopropyl-1H-indol-5-yl)piperidin-1-yl)methyl)-N,N-dimethylaniline (270); 2-(3,4-dimethoxyphenyl)-3-isopropyl-5-(1-(4-(trifluoromethoxy) benzyl)piperidin-4-yl)-1H-indole (271); 1-(2-(4-(2-(3,4-dimethoxyphenyl)-3-isopropyl-1H-indol-5-yl)piperidin-1-yl)acetyl)-N,N-diethylpiperidine-3-carboxamide (272); 2-(4-(2-(3,4-dimethoxyphenyl)-3-isopropyl-1H-indol-5-yl) piperidin-1-yl)-N-(1-isopropylpiperidin-4-yl)acetamide (273); 2-(4-(2-(3,4-dimethoxyphenyl)-3-isopropyl-1H-indol-5-yl)piperidin-1-yl)-1-(4-methylpiperazin-1-yl) ethan- 1-one (274); 2-(4-(2-(3,4-dimethoxyphenyl)-3-isopropyl-1H-indol-5-yl)piperidin-1-yl)-1-(3-(hydroxymethyl)piperidin-1-yl)ethan-1-one (275); 2-(4-(2-(3,4-dimethoxyphenyl)-3-isopropyl-1H-indol-5-yl)piperidin-1-yl)-N-(2-hydroxyethyl) acetamide (276); 2-(4-(2-(3,4-dimethoxyphenyl)-3-isopropyl-1H-indol-5-yl)piperidin-1-yl)-N-(3-hydroxypropyl)acetamide (277); (S)-2-(4-(2-(3,4-dimethoxyphenyl)-3-isopropyl-1H-indol-5-yl)piperidin-1-yl)-1-(3-hydroxypyrrolidin-1-yl)ethan-1-one (278); 2-(4-(2-(3,4-dimethoxyphenyl)-3-isopropyl-1H-indol-5-yl)piperidin-1-yl)-N-((1r,4r)-4-(2-hydroxypropan-2-yl)cyclohexyl)acetamide (279); 1-(2-(4-(2-(3,4-dimethoxyphenyl)-3-isopropyl-1H-indol-5-yl)piperidin-1-yl)-2-oxoethyl)-N-(1-isopropylpiperidin-4-yl) piperidine-3-carboxamide (280 and 281); 1-(4-(2-(3,4-dimethoxyphenyl)-3-isopropyl-1H-indol-5-yl)piperidin-1-yl)-2-(3-(3-hydroxypyrrolidine-1-carbonyl)piperidin-1-yl)ethan-1-one (282 and 283); (S)-2-(3-(4-acetylpiperazine-1-carbonyl)piperidin-1-yl)-1-(4-(2-(3,4-dimethoxyphenyl)-3-isopropyl-1H-indol-5-yl)piperidin-1-yl)ethan-1-one (284); (S)-1-(2-(4-(2-(3,4-dimethoxyphenyl)-3-isopropyl-1H-indol-5-yl)piperidin-1-yl)-2-oxoethyl)-N-isopropylpiperidine-3-carboxamide (285); (S)-1-(4-(2-(3,4-dimethoxyphenyl)-3-isopropyl-1H-indol-5-yl)piperidin-1-yl)-2-(3-(4-isopropylpiperazine-1-carbonyl)piperidin-1-yl)ethan-1-one (286); (S)-1-(4-(2-(3,4-dimethoxyphenyl)-3-isopropyl-1H-indol-5-yl)piperidin-1-yl)-2-(3-(pyrrolidine-1-carbonyl)piperidin-1-yl)ethan-1-one (287); (S)-1-(2-(4-(2-(3,4-dimethoxyphenyl)-3-isopropyl-1H-indol-5-yl)piperidin-1-yl)-2-oxoethyl)-N-isopropyl-N-methylpiperidine-3-carboxamide (288); (S)-1-(4-(2-(3,4-dimethoxyphenyl)-3-isopropyl-1H-indol-5-yl) piperidin-1-yl)-2-(3-(4-(dimethylamino)piperidine-1-carbonyl)piperidin-1-yl)ethan-1-one (289); (S)-1-(4-(2-(3,4-dimethoxyphenyl)-3-isopropyl-1H-indol-5-yl)piperidin-1-yl)-2-(3-(4-(3-(trifluoromethyl)phenyl)piperazine-1-carbonyl)piperidin-1-yl)ethan-1-one (290); (S)-1-(4-(2-(3,4-dimethoxyphenyl)-3-isopropyl-1H-indol-5-yl)piperidin-1-yl)-2-(3-(4-(2-hydroxyethyl)piperidine-1-carbonyl)piperidin-1-yl)ethan-1-one (291); 1-(4-(2-(3,4-dimethoxyphenyl)-3-isopropyl-1H-indol-5-yl)piperidin-1-yl)-2-((3S)-3-(3-hydroxypiperidine-1-carbonyl)piperidin-1-yl)ethan-1-one (292); (S)-1-(4-(2-(3,4-dimethoxyphenyl)-3-isopropyl-1H-indol-5-yl)piperidin-1-yl)-2-(3-(4-(2-(pyrrolidin-1-yl) ethyl)piperazine-1-carbonyl)piperidin-1-yl)ethan-1-one (293); (S)-2-(3-(4-(4-bromobenzyl)piperazine-1-carbonyl)piperidin-1-yl)-1-(4-(2-(3,4-dimethoxyphenyl)-3-isopropyl-1H-indol-5-yl)piperidin-1-yl)ethan-1-one (294); (S)—N-(2-acetamidoethyl)-1-(2-(4-(2-(3,4-dimethoxyphenyl)-3-isopropyl-1H-indol-5-yl) piperidin-1-yl)-2-oxoethyl) piperidine-3-carboxamide (295); (S)-1-(2-(4-(2-(3,4-dimethoxyphenyl)-3-isopropyl-1H-indol-5-yl)piperidin-1-yl)-2-oxoethyl)-N-(1-(hydroxymethyl)cyclopentyl)piperidine-3-carboxamide (296); (S)—N-(cyanomethyl)-1-(2-(4-(2-(3,4-dimethoxyphenyl)-3-isopropyl-1H-indol-5-yl)piperidin-1-yl)-2-oxoethyl)piperidine-3-carboxamide (297); (S)—N-(2-amino-2-oxoethyl)-1-(2-(4-(2-(3,4-dimethoxyphenyl)-3-isopropyl-1H-indol-5-yl) piperidin-1-yl)-2-oxoethyl)piperidine-3-carboxamide (298): 1-(4-(2-(3,4-dimethoxyphenyl)-3-isopropyl-1H-indol-5-yl)piperidin-1-yl)-2-((3 S)-3-(octahydropyrrolo[3,4-c]pyrrole-2-carbonyl)piperidin-1-yl)ethan-1-one (299); 1-(4-(2-(3,4-dimethoxyphenyl)-3-isopropyl-1H-indol-5-yl)piperidin-1-yl)-2-((3S)-3-(2,5-dimethylpyrrolidine-1-carbonyl)piperidin-1-yl)ethan-1-one (300); 1-(4-(2-(3,4-dimethoxyphenyl)-3-isopropyl-1H-indol-5-yl)piperidin-1-yl)-2-((S)-3-((S)-3-hydroxypyrrolidine-1-carbonyl)piperidin-1-yl)ethan-1-one (301); (R)-1-(4-(2-(3,4-dimethoxyphenyl)-3-isopropyl-1H-indol-5-yl)piperidin-1-yl)-2-(3-(4-isopropylpiperazine-1-carbonyl)piperidin-1-yl)ethan-1-one (302); (R)-1-(4-(2-(3,4-dimethoxyphenyl)-3-isopropyl-1H-indol-5-yl)piperidin-1-yl)-2-(3-(pyrrolidine-1-carbonyl)piperidin-1-yl)ethan-1-one (303); (R)-1-(2-(4-(2-(3,4-dimethoxyphenyl)-3-isopropyl-1H-indol-5-yl)piperidin-1-yl)-2-oxoethyl)-N-isopropyl-N-methylpiperidine-3-carboxamide (304); (R)-1-(4-(2-(3,4-dimethoxyphenyl)-3-isopropyl-1H-indol-5-yl) piperidin-1-yl)-2-(3-(4-(dimethylamino)piperidine-1-carbonyl)piperidin-1-yl)ethan-1-one (305); (R)-1-(4-(2-(3,4-dimethoxyphenyl)-3-isopropyl-1H-indol-5-yl)piperidin-1-yl)-2-(3-(4-(2-hydroxyethyl)piperidine-1-carbonyl)piperidin-1-yl)ethan-1-one (306); (R)-1-(4-(2-(3,4-dimethoxyphenyl)-3-isopropyl-1H-indol-5-yl)piperidin-1-yl)-2-(3-(4-(2-(pyrrolidin-1-yl)ethyl)piperazine-1-carbonyl)piperidin-1-yl)ethan-1-one (307); (R)—N-(cyanomethyl)-1-(2-(4-(2-(3,4-dimethoxyphenyl)-3-isopropyl-1H-indol-5-yl)piperidin-1-yl)-2-oxoethyl)piperidine-3-carboxamide (308); (R)—N-(2-amino-2-oxoethyl)-1-(2-(4-(2-(3,4-dimethoxyphenyl)-3-isopropyl-1H-indol-5-yl)piperidin-1-yl)-2-oxoethyl)piperidine-3-carboxamide (309); 1-(4-(2-(3,4-dimethoxyphenyl)-3-isopropyl-1H-indol-5-yl) piperidin-1-yl)-2-((3R)-3-(octahydropyrrolo[3,4-c]pyrrole-2-carbonyl)piperidin-1-yl) ethan-1-one (310); 1-(4-(2-(3,4-dimethoxyphenyl)-3-isopropyl-1H-indol-5-yl)piperidin-1-yl)-2-((3R)-3-(2,5-dimethylpyrrolidine-1-carbonyl)piperidin-1-yl)ethan-1-one (311); 2-(4-(2-(3,4-dimethoxyphenyl)-3-isopropyl-1H-indol-5-yl)piperidin-1-yl)-N,N-dimethylacetamide (312); 1-(4-(2-(3,4-dimethoxyphenyl)-3-isopropyl-1H-indol-5-yl) piperidin-1-yl)-2-hydroxyethanone (313); 1-(4-(2-(3,4-dimethoxyphenyl)-3-isopropyl-1H-indol-5-yl) piperidin-1-yl)-2-isopropoxyethan-1-one (314); 1-(4-(2-(3,4-dimethoxyphenyl)-3-isopropyl-1H-indol-5-yl)piperidin-1-yl)-2-((1-methylpiperidin-4-yl) oxy)ethan-1-one (315); tert-butyl 5-(1-(tert-butoxycarbonyl)-3-hydroxypiperidin-4-yl)-2-(3,4-dimethoxyphenyl)-3-isopropyl-1H-indole-1-carboxylate (316); 4-(2-(3,4-dimethoxyphenyl)-3-isopropyl-1H-indol-5-yl)piperidin-3-ol 2,2,2-trifluoroacetate (317 and 318); 2-(3,4-dimethoxyphenyl)-5-(3-fluoropiperidin-4-yl)-3-isopropyl-1H-indole (319 and 320); 2-(3,4-dimethoxyphenyl)-5-(3-fluoropiperidin-4-yl)-3-isopropyl-1H-indole (321, 322, 323, and 324); 5-(3,3-difluoropiperidin-4-yl)-2-(3,4-dimethoxyphenyl)-3-isopropyl-1H-indole (325); 4-(2-(3,4-dimethoxyphenyl)-3-isopropyl-1H-indol-5-yl) piperidin-2-one (326); 3-(2,2-difluoroethyl)-2-(3,4-dimethoxyphenyl)-5-(piperidin-4-yl)-1H-indole (328); 2-(3,4-dimethoxyphenyl)-5-(piperidin-4-yl)-3-(2,2,2-trifluoroethyl)-1H-indole (329); 1-(4-(2-(3,4-dimethoxyphenyl)-3-(2,2,2-trifluoroethyl)-1H-indol-5-yl)piperidin-1-yl)-3-(piperidin-1-yl)propan-1-one (330); 1-(4-(2-(3,4-dimethoxyphenyl)-3-(2,2,2-trifluoroethyl)-1H-indol-5-yl)piperidin-1-yl)-4-(1H-imidazol-1-yl)butan-1-one (331); 1-(4-(2-(3,4-dimethoxyphenyl)-3-(2,2,2-trifluoroethyl)-1H-indol-5-yl)piperidin-1-yl)-2-(1H-indol-3-yl)ethan-1-one (332); 4-(4-(2-(3,4-dimethoxyphenyl)-3-(2,2,2-trifluoroethyl)-1H-indol-5-yl)piperidin-1-yl)-4-oxobutanamide (333); 1-(4-(2-(3,4-dimethoxyphenyl)-3-(2,2,2-trifluoroethyl)-1H-indol-5-yl)piperidin-1-yl)-2-(1H-imidazol-4-yl)ethan-1-one (334); 1-(4-(2-(3,4-dimethoxyphenyl)-3-(2,2,2-trifluoroethyl)-1H-indol-5-yl)piperidin-1-yl)-2-(pyridin-3-yl)ethan-1-one (335); (S)-1-(2-(4-(2-(3,4-dimethoxyphenyl)-3-(2,2,2-trifluoroethyl)-1H-indol-5-yl)piperidine-1-carbonyl) pyrrolidin-1-yl)ethan-1-one (336); 1-(4-(2-(3,4-dimethoxyphenyl)-3-(2,2,2-trifluoroethyl)-1H-indol-5-yl)piperidin-1-yl)-3-(1H-indol- 1-yl)propan-1-one (337); 1-(4-(2-(3,4-dimethoxyphenyl)-3-(2,2,2-trifluoroethyl)-1H-indol-5-yl)piperidin-1-yl)-2-(4-(dimethylamino)phenyl)ethan-1-one (338); 1-(4-(2-(3,4-dimethoxyphenyl)-3-(2,2,2-trifluoroethyl)-1H-indol-5-yl)piperidin-1-yl)-3,3,3-trifluoropropan-1-one (339); 1-(4-(2-(3,4-dimethoxyphenyl)-3-(2,2,2-trifluoroethyl)-1H-indol-5-yl)piperidin-1-yl)-3-(dimethylamino)propan-1-one (340); 1-(4-(2-(3,4-dimethoxyphenyl)-3-(2,2,2-trifluoroethyl)-1H-indol-5-yl)piperidin-1-yl)-2-(1H-tetrazol-5-yl)ethan-1-one (341); 1-(4-(2-(3,4-dimethoxyphenyl)-3-(2,2,2-trifluoroethyl)-1H-indol-5-yl)piperidin-1-yl)-2-(pyrazin-2-yl)ethan-1-one (342); N-(4-(4-(2-(3,4-dimethoxyphenyl)-3-(2,2,2-trifluoroethyl)-1H-indol-5-yl)piperidin-1-yl)-4-oxobutyl) acetamide (343); 1-(4-(2-(3,4-dimethoxyphenyl)-3-(2,2,2-trifluoroethyl)-1H-indol-5-yl)piperidin-1-yl)-3-(1H-pyrrol-1-yl)propan-1-one (344); 1-(4-(4-(2-(3,4-dimethoxyphenyl)-3-(2,2,2-trifluoroethyl)-1H-indol-5-yl)piperidine-1-carbonyl)piperidin-1-yl)ethan-1-one (345); 4-(4-(2-(3,4-dimethoxyphenyl)-3-(2,2,2-trifluoroethyl)-1H-indol-5-yl)piperidin-1-yl)-N,N-dimethyl-4-oxobutanamide (346); 1-(4-(2-(3,4-dimethoxyphenyl)-3-(2,2,2-trifluoroethyl)-1H-indol-5-yl)piperidin-1-yl)-2-(methylsulfonyl)ethan-1-one (347); 1-(4-(2-(3,4-dimethoxyphenyl)-3-(2,2,2-trifluoroethyl)-1H-indol-5-yl)piperidin-1-yl)-3-(pyridin-3-yl) propan-1-one (348); 1-(4-(2-(3,4-dimethoxyphenyl)-3-(2,2,2-trifluoroethyl)-1H-indol-5-yl)piperidin-1-yl)-2-(pyridin-3-yloxy)ethan-1-one (349); 1-(4-(2-(3,4-dimethoxyphenyl)-3-(2,2,2-trifluoroethyl)-1H-indol-5-yl)piperidin-1-yl)-4,4,4-trifluorobutan-1-one (350); 1-(4-(2-(3,4-dimethoxyphenyl)-3-(2,2,2-trifluoroethyl)-1H-indol-5-yl)piperidin-1-yl)-4-(dimethylamino)butan-1-one (351); (S)-1-(4-(2-(3,4-dimethoxyphenyl)-3-(2,2,2-trifluoroethyl)-1H-indol-5-yl)piperidin-1-yl)-3-hydroxybutan-1-one (352); (R)-1-(4-(2-(3,4-dimethoxyphenyl)-3-(2,2,2-trifluoroethyl)-1H-indol-5-yl)piperidin-1-yl)-3-hydroxybutan-1-one (353); 1-(4-(2-(3,4-dimethoxyphenyl)-3-(2,2,2-trifluoroethyl)-1H-indol-5-yl)piperidin-1-yl)-2-(dimethylamino)ethan-1-one (354); 2-(3,4-dimethoxyphenyl)-5-(1-methylpiperidin-4-yl)-3-(2,2,2-trifluoroethyl)-1H-indole (355); 4-(2-(3,4-dimethoxyphenyl)-3-(2,2,2-trifluoroethyl)-1H-indol-5-yl)-N-ethylpiperidine-1-carboxamide (356); 4-(2-(3,4-dimethoxyphenyl)-3-(2,2,2-trifluoroethyl)-1H-indol-5-yl)-N-phenethylpiperidine-1-carboxamide (357); 4-(2-(3,4-dimethoxyphenyl)-3-(2,2,2-trifluoroethyl)-1H-indol-5-yl)-N-(furan-2-ylmethyl)piperidine-1-carboxamide (358); 1-([1,4'-bipiperidin]-1'-yl)-2-(4-(2-(3,4-dimethoxyphenyl)-3-(2,2,2-trifluoroethyl)-1H-indol-5-yl)piperidin-1-yl)ethan-1-one (359); 2-(4-(2-(3,4-dimethoxyphenyl)-3-(2,2,2-trifluoroethyl)-1H-indol-5-yl)piperidin-1-yl)-N-(2-(1-methylpyrrolidin-2-yl)ethyl) acetamide (360); 1-(4-acetylpiperazin-1-yl)-2-(4-(2-(3,4-dimethoxyphenyl)-3-(2,2,2-trifluoroethyl)-1H-indol-5-yl)piperidin-1-yl)ethan-1-one (361); 2-(4-(2-(3,4-dimethoxyphenyl)-3-(2,2,2-trifluoroethyl)-1H-indol-5-yl)piperidin-1-yl)-1-(4-isopropylpiperazin-1-yl)ethan-1-one (362); 2-(4-(2-(3,4-dimethoxyphenyl)-3-(2,2,2-trifluoroethyl)-1H-indol-5-yl)piperidin-1-yl)-1-(4-(4-methylpiperazin-1-yl)piperidin-1-yl) ethan-1-one (363); 2-(4-(2-(3,4-dimethoxyphenyl)-3-(2,2,2-trifluoroethyl)-1H-indol-5-yl) piperidin-1-yl)-1-(4-(dimethylamino)piperidin-1-yl)ethan-1-one (364); 2-(4-(2-(3,4-dimethoxyphenyl)-3-(2,2,2-trifluoroethyl)-1H-indol-5-yl)piperidin-1-yl)-N-(3-(dimethylamino)propyl)-N-methylacetamide (365); 2-(4-(2-(3,4-dimethoxyphenyl)-3-(2,2,2-trifluoroethyl)-1H-indol-5-yl)piperidin-1-yl)-1-(4-(pyridin-4-yl)piperazin-1-yl) ethan-1-one (366); 2-(4-(2-(3,4-dimethoxyphenyl)-3-(2,2,2-trifluoroethyl)-1H-indol-5-yl)piperidin-1-yl)-N-(2-(dimethylamino)ethyl)-N-methylacet-amide (367); 2-(4-(2-(3,4-dimethoxyphenyl)-3-(2,2,2-trifluoroethyl)-1H-indol-5-yl)piperidin-1-yl)-1-(4-(pyrimidin-2-yl)piperazin-1-yl)ethan-1-one (368); 1-(2-(4-(2-(3,4-dimethoxyphenyl)-3-(2,2,2-trifluoroethyl)-1H-indol-5-yl)piperidin-1-yl)acetyl)piperidine-4-carboxamide (369); 2-(4-(2-(3,4-dimethoxyphenyl)-3-(2,2,2-trifluoroethyl)-1H-indol-5-yl)piperidin-1-yl)-N-methyl-N-(1-methylpyrrolidin-3-yl)acetamide (370); (R)-2-(4-(2-(3,4-dimethoxyphenyl)-3-(2,2,2-trifluoroethyl)-1H-indol-5-yl)piperidin-1-yl)-1-(2-(hydroxymethyl)pyrrolidin-1-yl)ethan-1-one (371); 2-(4-(2-(3,4-dimethoxyphenyl)-3-(2,2,2-trifluoroethyl)-1H-indol-5-yl)piperidin-1-yl)-N-(2-(dimethylamino)ethyl)-N-ethylacetamide (372); (R)-2-(4-(2-(3,4-dimethoxyphenyl)-3-(2,2,2-trifluoroethyl)-1H-indol-5-yl)piperidin-1-yl)-1-(3-(dimethylamino)pyrrolidin-1-yl)ethan-1-one (373); (S)-2-(4-(2-(3,4-dimethoxyphenyl)-3-(2,2,2-trifluoroethyl)-1H-indol-5-yl)piperidin-1-yl)-1-(3-(dimethylamino)pyrrolidin-1-yl) ethan-1-one (374); 2-(4-(2-(3,4-dimethoxyphenyl)-3-(2,2,2-trifluoroethyl)-1H-indol-5-yl) piperidin-1-yl)-N-(2-(pyrrolidin-1-yl)ethyl)acetamide (375); 2-(4-(2-(3,4-dimethoxyphenyl)-3-(2,2,2-trifluoroethyl)-1H-indol-5-yl)piperidin-1-yl)-N-(3-(2-oxopyrrolidin-1-yl)propyl)acetamide (376); N-(sec-butyl)-2-(4-(2-(3,4-dimethoxyphenyl)-3-(2,2,2-trifluoroethyl)-1H-indol-5-yl)piperidin-1-yl)acetamide (377); 2-(4-(2-(3,4-dimethoxyphenyl)-3-(2,2,2-trifluoroethyl)-1H-indol-5-yl)piperidin-1-yl)-N-(pentan-3-yl)acetamide (378); N-(2-acetamidoethyl)-2-(4-(2-(3,4-dimethoxyphenyl)-3-(2,2,2-trifluoroethyl)-1H-indol-5-yl)piperidin-1-yl)acetamide (379); 2-(4-(2-(3,4-dimethoxyphenyl)-3-(2,2,2-trifluoroethyl)-1H-indol-5-yl)piperidin-1-yl)-N-(2-(dimethylamino)ethyl)acetamide (380); N-(cyanomethyl)-2-(4-(2-(3,4-dimethoxyphenyl)-3-(2,2,2-trifluoroethyl)-1H-indol-5-yl)piperidin-1-yl)acetamide (381); 2-(4-(2-(3,4-dimethoxyphenyl)-3-(2,2,2-trifluoroethyl)-1H-indol-5-yl)piperidin-1-yl)-N-(3-(dimethylamino)propyl)acetamide (382); N-(3-(1H-imidazol-1-yl)propyl)-2-(4-(2-(3,4-dimethoxyphenyl)-3-(2,2,2-trifluoroethyl)-1H-indol-5-yl)piperidin-1-yl)acetamide (383); 2-(4-(2-(3,4-dimethoxyphenyl)-3-(2,2,2-trifluoroethyl)-1H-indol-5-yl)piperidin-1-yl)-N-(4-sulfamoylphenethyl)acetamide (384); N-(2-amino-2-oxoethyl)-2-(4-(2-(3,4-dimethoxyphenyl)-3-(2,2,2-trifluoroethyl)-1H-indol-5-yl)piperidin-1-yl)acetamide (385); 2-(2-(4-(2-(3,4-dimethoxyphenyl)-3-(2,2,2-trifluoroethyl)-1H-indol-5-yl)piperidin-1-yl) acetamido)ethane-1-sulfonic acid (386); N-(5-(tert-butyl)-1H-pyrazol-3-yl)-2-(4-(2-(3,4-dimethoxyphenyl)-3-(2,2,2-trifluoroethyl)-1H-indol-5-yl)piperidin-1-yl)acetamide (387); 2-(4-(2-(3,4-dimethoxyphenyl)-3-(2,2,2-trifluoroethyl)-1H-indol-5-yl)piperidin-1-yl)-N-(4-(pyrrolidin-1-yl)butyl)acetamide (388); 2-(3,4-dimethoxyphenyl)-5-(piperidin-4-yl)-3-(tetrahydro-2H-pyran-4-yl)-1H-indole (389); 1-(2-(4-(2-(3,4-dimethoxyphenyl)-3-(tetrahydro-2H-pyran-4-yl)-1H-indol-5-yl)piperidin-1-yl)-2-oxoethyl)-N,N-diethylpiperidine-3-carboxamide (391 and 392); 1-(4-(2-(3,4-dimethoxyphenyl)-3-(tetrahydro-2H-pyran-4-yl)-1H-indol-5-yl)piperidin-1-yl)-2-(dimethylamino)ethan-1-one (393); (R)-1-(4-(2-(3,4-dimethoxyphenyl)-3-(tetrahydro-2H-pyran-4-yl)-1H-indol-5-yl) piperidin-1-yl)-2-((3-methylbutan-2-yl)amino)ethan-1-one (394); 1-(4-(2-(3,4-dimethoxyphenyl)-3-(2,2,2-trifluoro-1-hydroxyethyl)-1H-indol-5-yl)piperidin-1-yl)-2-(dimethylamino)ethan-1-one (395); 2-(3,4-dimethoxyphenyl)-3-ethyl-6-methyl-5-(piperidin-4-yl)-1H-indole (396); 2-(3,4-dimethoxyphenyl)-3-ethyl-6-methoxy-5-(piperidin-4-yl)-1H-indole (397); 2-(3,4-dimethoxyphenyl)-3-ethyl-5-(1'-isopropyl-[1,4'-bipiperidin]-4-yl)-6-methoxy-1H-indole (398); 1-(4-(3-(2,2- difluoroethyl)-2-(3,4-dimethoxyphenyl)-1H-indol-5-yl) piperidin-1-yl)-2-(dimethylamino)ethan-1-one (399); 2-(4-(3-(2,2-difluoroethyl)-2-(3,4-dimethoxyphenyl)-1H-indol-5-yl)piperidin-1-yl)-N,N-dimethylacetamide (400); 2-(4-(3-(2,2-difluoroethyl)-2-(3,4-dimethoxyphenyl)-1H-indol-5-yl)piperidin-1-yl)-N-methylacetamide (401); 1-(4-(2-(3,4-dimethoxyphenyl)-3-methyl-1H-indol-5-yl)piperidin-1-yl)-2-(dimethylamino)ethan-1-one (402); 1-(2-(4-(2-(3,4-dimethoxyphenyl)-3-methyl-1H-indol-5-yl)piperidin-1-yl)-2-oxoethyl)-N,N-diethylpiperidine-3-carboxamide (404); (R)-2-((2,3-dihydroxypropyl) amino)-1-(4-(2-(3,4-dimethoxyphenyl)-3-methyl-1H-indol-5-yl)piperidin-1-yl)ethan-1-one (405); 1-(4-(2-(3,4-dimethoxyphenyl)-3-methyl-1H-indol-5-yl)piperidin-1-yl)-2-((3-hydroxybutyl) amino) ethan-1-one (406); 1-(4-(2-(3,4-dimethoxyphenyl)-3-methyl-1H-indol-5-yl) piperidin-1-yl)-2-(4-(dimethylamino)piperidin-1-yl)ethan-1-one (407); 1-(4-(2-(3,4-dimethoxyphenyl)-3-methyl-1H-indol-5-yl)piperidin-1-yl)-2-((2-hydroxyethyl)(methyl) amino)ethan-1-one (408); 1-(4-(2-(3,4-dimethoxyphenyl)-3-methyl-1H-indol-5-yl) piperidin-1-yl)-2-(4-methylpiperazin-1-yl)ethan-1-one (409); 1-(4-(2-(3,4-dimethoxyphenyl)-3-methyl-1H-indol-5-yl)piperidin-1-yl)-2-(4-methyl-1,4-diazepan-1-yl)ethan-1-one (410); N-(2-(4-(2-(3,4-dimethoxyphenyl)-3-isopropyl-1H-indol-5-yl) piperidin-1-yl)ethyl)hept-6-ynamide (411); 2-(3,4-dimethoxyphenyl)-5-(1'-isopropyl-[1,4'-bipiperidin]-4-yl)-3-(2,2,2-trifluoroethyl)-1H-indole (412); 2-(4-(2-(3,4-dimethoxyphenyl)-3-(2,2,2-trifluoroethyl)-1H-indol-5-yl)piperidin-1-yl)-N-methylethanamine (413); tert-butyl (2-(4-(2-(3,4-dimethoxyphenyl)-3-(2,2,2-trifluoroethyl)-1H-indol-5-yl) piperidin-1-yl)-2-oxoethyl) (methyl)carbamate (414); 2-(4-(2-(3,4-dimethoxyphenyl)-3-methyl-1H-indol-5-yl)piperidin-1-yl)-N,N-dimethylethan-1-amine (415); 2-(3,4-dimethoxyphenyl)-5-(1'-isobutyl-[1, 3'-bipiperidin]-4-yl)-3-methyl-1H-indole (416); 2-(3,4-dimethoxyphenyl)-5-(1'-isobutyl-[1,3'-bipiperidin]-4-yl)-3-methyl-1H-indole (417); 1-(2-(4-(2-(3,4-dimethoxyphenyl)-3-(2,2,2-trifluoroethyl)-1H-indol-5-yl)piperidin-1-yl)-2-oxoethyl)-N,N-diethylpiperidine-3-carboxamide (418 and 420-421); and 1-(2-(4-(2-(3,4-dimethoxyphenyl)-3-(2,2,2-trifluoroethyl)-1H-indol-5-yl) piperidin-1-yl)-2-oxoethyl)-N,N-dimethylpiperidine-3-carboxamide (419).

The present invention may be embodied in other specific forms without departing from the spirit or essential attributes thereof. The invention encompasses all combinations of the aspects and/or embodiments of the invention noted herein. It is understood that any and all embodiments of the present invention may be taken in conjunction with any other embodiment or embodiments to describe additional embodiments. It is also to be understood that each individual element of the embodiments is meant to be combined with any and all other elements from any embodiment to describe an additional embodiment.

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phrase "compounds" refers to at least one compound. For example, a compound of Formula (I) includes a compound of Formula (I) and two or more compounds of Formula (I).

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The terms "halo" and "halogen," as used herein, refer to F, Cl, Br, and I.

The term "cyano" refers to the group —CN.

The term "amino" refers to the group —NH$_2$.

The term "oxo" refers to the group =O.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "C$_{1-6}$ alkyl" denotes straight and branched chain alkyl groups with one to six carbon atoms.

The term "fluoroalkyl" as used herein is intended to include both branched and straight-chain saturated aliphatic hydrocarbon groups substituted with one or more fluorine atoms. For example, "C$_{1-4}$ fluoroalkyl" is intended to include C$_1$, C$_2$, C$_3$, and C$_4$ alkyl groups substituted with one or more fluorine atoms. Representative examples of fluoroalkyl groups include, but are not limited to, —CF$_3$ and —CH$_2$CF$_3$.

The term "chloroalkyl" as used herein is intended to include both branched and straight-chain saturated aliphatic hydrocarbon groups substituted with one or more chlorine atoms. For example, "C$_{1-4}$ chloroalkyl" is intended to include C$_1$, C$_2$, C$_3$, and C$_4$ alkyl groups substituted with one or more chlorine atoms. Representative examples of fluoroalkyl groups include, but are not limited to, —CCl$_3$ and —CH$_2$CCl$_3$.

The term "cyanoalkyl" includes both branched and straight-chain saturated alkyl groups substituted with one or more cyano groups. For example, "cyanoalkyl" includes —CH$_2$CN, —CH$_2$CH$_2$CN, and C$_{1-4}$ cyanoalkyl.

The term "aminoalkyl" includes both branched and straight-chain saturated alkyl groups substituted with one or more amine groups. For example, "aminoalkyl" includes —CH$_2$NH$_2$, —CH$_2$CH$_2$NH$_2$, and C$_{1-4}$ aminoalkyl.

The term "hydroxyalkyl" includes both branched and straight-chain saturated alkyl groups substituted with one or more hydroxyl groups. For example, "hydroxyalkyl" includes —CH$_2$OH, —CH$_2$CH$_2$OH, and C$_{1-4}$ hydroxyalkyl.

The term "hydroxy-fluoroalkyl" includes both branched and straight-chain saturated alkyl groups substituted with one or more hydroxyl groups and one or more fluorine atoms. For example, "hydroxy-fluoroalkyl" includes —CHFCH$_2$OH, —CH$_2$CHFC(CH$_3$)$_2$OH, and C$_{1-4}$ hydroxyfluoroalkyl.

The term "cycloalkyl," as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "C$_3$-C$_6$ cycloalkyl" denotes cycloalkyl groups with three to six carbon atoms.

The term "alkoxy," as used herein, refers to an alkyl group attached to the parent molecular moiety through an oxygen atom, for example, methoxy group (—OCH$_3$). For example, "C$_{1-3}$ alkoxy" denotes alkoxy groups with one to three carbon atoms.

The terms "fluoroalkoxy" and "—O(fluoroalkyl)" represent a fluoroalkyl group as defined above attached through an oxygen linkage (—O—). For example, "C$_{1-4}$ fluoroalkoxy" is intended to include C$_1$, C$_2$, C$_3$, and C$_4$ fluoroalkoxy groups.

The term "alkoxyalkoxy," as used herein, refers to an alkoxy group attached through its oxygen atom to a carbon atom in a second alkoxy group, which is attached to the parent molecular moiety through an oxygen atom, for example, methoxymethoxy group (—OCH$_2$OCH$_3$). For example, "C$_{2-4}$ alkoxyalkoxy" denotes alkoxyalkoxy groups with two to four carbon atoms, such as —OCH$_2$OCH$_3$, —OCH$_2$CH$_2$OCH$_3$, —OCH$_2$OCH$_2$CH$_3$, and —OCH$_2$CH$_2$OCH$_2$CH$_3$.

The term "benzyl," as used herein, refers to a methyl group in which one of the hydrogen atoms is replaced by a phenyl group. The phenyl ring may be unsubstituted or may contain one or more substituents as valence allows.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can be provided as amorphous solids or crystalline solids. Lyophilization can be employed to provide the compounds of Formula (I) as amorphous solids.

It should further be understood that solvates (e.g., hydrates) of the compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Various forms of prodrugs are well known in the art and are described in:

a) *The Practice of Medicinal Chemistry*, Camille G. Wermuth et al., Ch 31, (Academic Press, 1996);

b) *Design of Prodrugs*, edited by H. Bundgaard, (Elsevier, 1985);

c) *A Textbook of Drug Design and Development*, P. Krogsgaard-Larson and H. Bundgaard, eds. Ch 5, pgs 113-191 (Harwood Academic Publishers, 1991); and d) *Hydrolysis in Drug and Prodrug Metabolism*, Bernard Testa and Joachim M. Mayer, (Wiley-VCH, 2003).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an inhibitor to TLR7/8/9, or effective to treat or prevent autoimmune and/or inflammatory disease states, such as SLE, IBD, multiple sclerosis (MS), and Sjögren's syndrome, and rheumatoid arthritis.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. For example, methyl (—CH$_3$) also includes deuterated methyl groups such as —CD$_3$.

Utility

The human immune system has evolved to defend the body from micro-organisms, viruses, and parasites that can cause infection, disease or death. Complex regulatory mechanisms ensure that the various cellular components of the immune system target the foreign substances or organisms, while not causing permanent or significant damage to the individual. While the initiating events are not well understood at this time, in autoimmune disease states the immune system directs its inflammatory response to target organs in the afflicted individual. Different autoimmune diseases are typically characterized by the predominate or initial target organ or tissues affected; such as the joint in the case of rheumatoid arthritis, the thyroid gland in the case of Hashimoto's thyroiditis, the central nervous system in the case of multiple sclerosis, the pancreas in the case of type I diabetes, and the bowel in the case of inflammatory bowel disease.

The compounds of the invention inhibit signaling through Toll-like receptor 7, or 8, or 9 (TLR7, TLR8, TLR9) or combinations thereof. Accordingly, compounds of Formula (I) have utility in treating conditions associated with the inhibition of signaling through one or more of TLR7, TLR8, or TLR9. Such conditions include TLR7, TLR8, or TLR9 receptor associated diseases in which cytokine levels are modulated as a consequence of intracellular signaling.

As used herein, the terms "treating" or "treatment" encompass the treatment of a disease state in a mammal, particularly in a human, and include: (a) preventing or delaying the occurrence of the disease state in a mammal, in particular, when such mammal is predisposed to the disease state but has not yet been diagnosed as having it; (b) inhibiting the disease state, i.e., arresting its development; and/or (c) achieving a full or partial reduction of the symptoms or disease state, and/or alleviating, ameliorating, lessening, or curing the disease or disorder and/or its symptoms.

In view of their activity as selective inhibitors of TLR7, TLR8, or TLR9, compounds of Formula (I) are useful in treating TLR7, TLR8, or TLR9 family receptor associated diseases, but not limited to, inflammatory diseases such as Crohn's disease, ulcerative colitis, asthma, graft versus host disease, allograft rejection, chronic obstructive pulmonary disease; autoimmune diseases such as Graves' disease, rheumatoid arthritis, systemic lupus erythematosis, lupus nephritis, cutaneous lupus, psoriasis; auto-inflammatory diseases including Cryopyrin-Associated Periodic Syndromes (CAPS), TNF Receptor Associated Periodic Syndrome (TRAPS), Familial Mediterranean Fever (FMF), adult onset stills, systemic onset juvenile idiopathic arthritis, gout, gouty arthritis; metabolic diseases including type 2 diabetes, atherosclerosis, myocardial infarction; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders such as angiogenic disorders including solid tumors, ocular neovascularization, and infantile haemangiomas; infectious diseases such as sepsis, septic shock, and Shigellosis; neurodegenerative diseases such as Alzheimer's disease, Parkinson's disease, cerebral ischemias or neurodegenerative disease caused by traumatic injury, oncologic and viral diseases such as metastatic melanoma, Kaposi's sarcoma, multiple myeloma, and HIV infection and CMV retinitis, AIDS, respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosis, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic 3-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoidosis, bone resorption disease, allograft rejections, fever and myalgias due to infection, cachexia secondary to infection, keloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hypoxia, vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris. Included in this embodiment are methods of treatment in which the condition is selected from lupus including lupus nephritis and systemic lupus erythematosus (SLE), Crohn's disease, ulcerative colitis, allograft rejection, rheumatoid arthritis, psoriasis, ankylosing spondylitis, psoriatic arthritis, and pemphigus vulgaris. Also included are methods of treatment in which the condition is selected from ischemia reperfusion injury, including cerebral ischemia reperfusions injury arising from stroke and cardiac ischemia reperfusion injury arising from myocardial infarction. Another method of treatment is one in which the condition is multiple myeloma.

In one embodiment, the compounds of Formula (I) are useful in treating cancer, including Waldenstrom's Macroglobulinemia (WM), diffuse large B cell lymphoma (DLBCL), chronic lymphocytic leukemia (CLL), cutaneous diffuse large B cell lymphoma, and primary CNS lymphoma.

In addition, the TLR7, TLR8, or TLR9 inhibitors of the present invention inhibit the expression of inducible pro-inflammatory proteins such as prostaglandin endoperoxide synthase-2 (PGHS-2), also referred to as cyclooxygenase-2 (COX-2), IL-1, IL-6, IL-18, chemokines. Accordingly, additional TLR7/8/9 associated conditions include edema, analgesia, fever and pain, such as neuromuscular pain, headache, pain caused by cancer, dental pain and arthritis pain. The inventive compounds also may be used to treat veterinary viral infections, such as lentivirus infections, including, but not limited to equine infectious anemia virus; or retrovirus infections, including feline immunodeficiency virus, bovine immunodeficiency virus, and canine immunodeficiency virus.

The present invention thus provides methods for treating such conditions, comprising administering to a subject in need thereof a therapeutically-effective amount of at least one compound of Formula (I) or a salt thereof. "Therapeutically effective amount" is intended to include an amount of a compound of the present invention that is effective when administered alone or in combination to inhibit autoimmune disease or chronic inflammatory disease.

The methods of treating TLR7, TLR8, or TLR9 associated conditions may comprise administering compounds of Formula (I) alone or in combination with each other and/or other suitable therapeutic agents useful in treating such conditions. Accordingly, "therapeutically effective amount" is also intended to include an amount of the combination of compounds claimed that is effective to inhibit TLR7, TLR8, or TLR9 and/or treat diseases associated with TLR7, TLR8, or TLR9.

Exemplary of such other therapeutic agents include corticosteroids, rolipram, calphostin, cytokine-suppressive anti-inflammatory drugs (CSAIDs), Interleukin-10, glucocorticoids, salicylates, nitric oxide, and other immunosuppressants; nuclear translocation inhibitors, such as deoxyspergualin (DSG); non-steroidal anti-inflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, PRO-GRAF®); anti-malarials such as hydroxychloroquine; cytotoxic drugs such as azathiprine and cyclophosphamide; TNF-α inhibitors such as tenidap, anti-TNF antibodies or soluble TNF receptor, and rapamycin (sirolimus or RAPA-MUNE®) or derivatives thereof.

The above other therapeutic agents, when employed in combination with the compounds of the present invention, may be used, for example, in those amounts indicated in the *Physicians' Desk Reference* (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating TLR7/8/9 receptor-associated conditions, including IL-1 family receptor mediated diseases as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula (I) and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 17th Edition (1985), which is incorporated herein by reference in its entirety.

Compounds in accordance with Formula (I) can be administered by any means suitable for the condition to be treated, which can depend on the need for site-specific treatment or quantity of Formula (I) compound to be delivered.

Also embraced within this invention is a class of pharmaceutical compositions comprising a compound of Formula (I) and one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g. magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium crosscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) with at least one inert solid diluent, such as, for example, calcium carbonate; calcium phosphate; and kaolin.

Soft gelatin capsules can, for example, be prepared by mixing at least one compound of Formula (I) with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) in either a vegetable oil, such as, for example, *arachis* oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an antioxidant, such as, for example, butylated hydroxyanisol, and alpha-tocopherol.

Dispersible powders and granules can, for example, be prepared by admixing at least one compound of Formula (I) with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) thereof can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and arachis oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two day cycle.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise at least one compound of Formula (I) and optionally an additional agent selected from any pharmaceutically acceptable carrier, adjuvant, and vehicle. Alternate compositions of this invention comprise a compound of the Formula (I) described herein, or a prodrug thereof, and a pharmaceutically acceptable carrier, adjuvant, or vehicle.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and (c) a package insert stating that the pharmaceutical composition can be used for the treatment of a cardiovascular and/or inflammatory disorder (as defined previously). In another embodiment, the package insert states that the pharmaceutical composition can be used in combination (as defined previously) with a second therapeutic agent to treat cardiovascular and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). In one embodiment, the package insert specifically recites the indications for which the pharmaceutical composition has been approved. The package insert may be made of any material on which a person can read information contained therein or thereon. For example, the package insert is a printable material (e.g., paper, plastic, cardboard, foil, adhesive-backed paper or plastic, etc.) on which the desired information has been formed (e.g., printed or applied).

Methods of Preparation

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Third Edition, Wiley and Sons, 1999).

Compounds of Formula (I) may be prepared by reference to the methods illustrated in the following Schemes. As shown therein the end product is a compound having the same structural formula as Formula (I). It will be understood that compounds of Formula (I) may be produced by the schemes by the suitable selection of reagents with appropriate substitution. Solvents, temperatures, pressures, and other reaction conditions may readily be selected by one of ordinary skill in the art. Starting materials are commercially available or readily prepared by one of ordinary skill in the art. Constituents of compounds are as defined herein or elsewhere in the specification.

As shown in Scheme 1, compounds of Formula I may be produced, starting with the substituted 5-bromoindoles (2). 2 can be prepared from the 3-formyl indoles (via reduction) or from the 3-H indoles, via alkylation. Transition metal catalyzed cross coupling of 2 and boronate 3 followed by olefin reduction and Boc deprotection affords 4, which can then be coupled with 3,4-dimethoxyphenyl boronic acid and deprotected to give 6. Alkylation or acylation of 6 leads to the production of the compounds of Formula I.

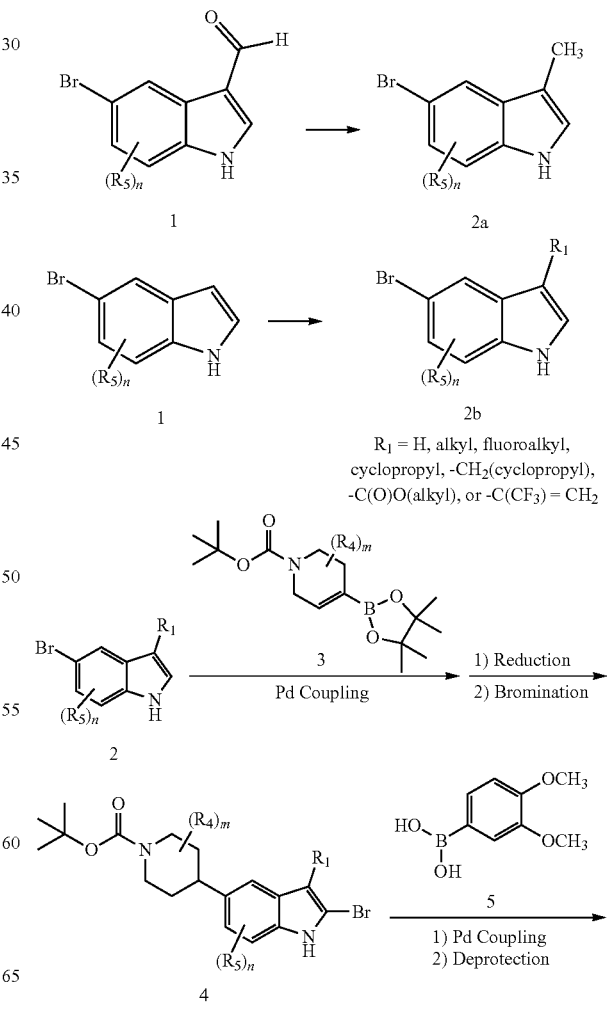

SCHEME 1

-continued

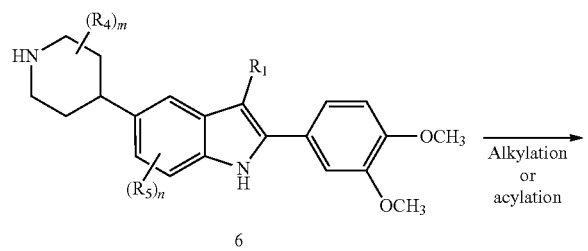

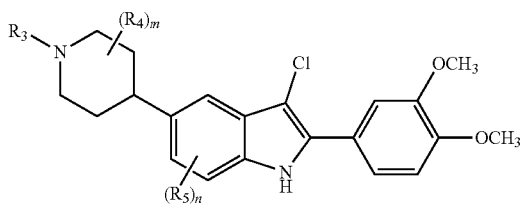

In an alternative preparation, bromoindole 2b can first be coupled with boronate 3 and reduced. Chlorination proceeds selectively on the 3-position, with bromination then providing the di-halogenated compound 7. The target compounds are then obtained by the chemistry outlined above.

The target compounds may also be obtained through synthesis of the indole core. Friedel-Crafts acylation of 1,2-dimethoxybenzene affords ketones 11 which react with (4-bromophenyl)hydrazine to give 5-bromoindoles 12. Elaboration as described above via cross coupling, reduction, deprotection, and alkylation or acylation leads to the desired products.

SCHEME 2

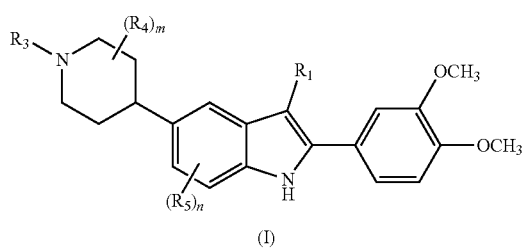

SCHEME 3

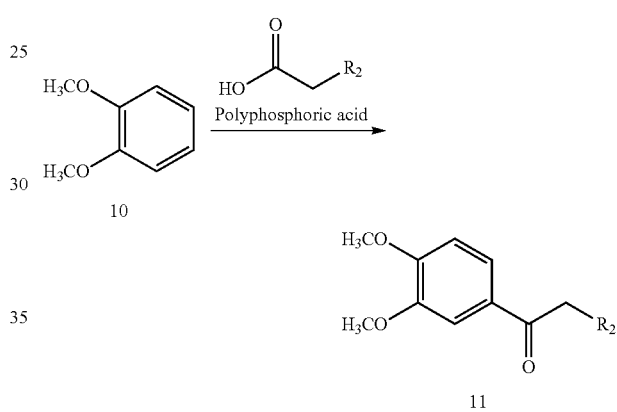

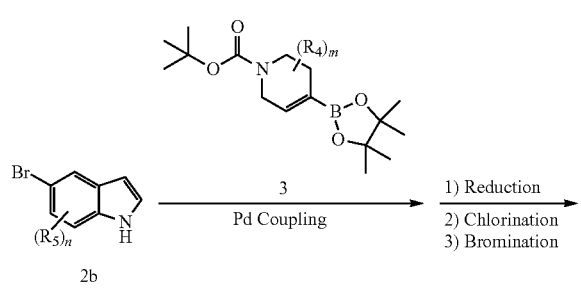

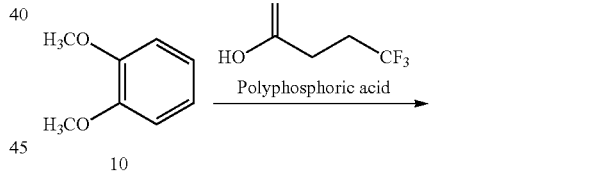

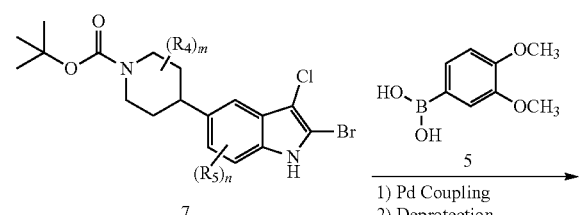

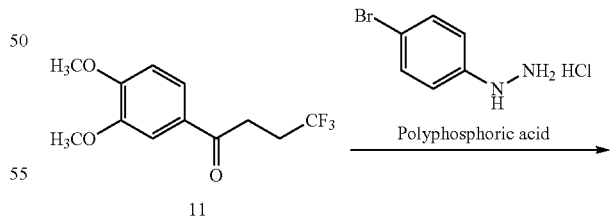

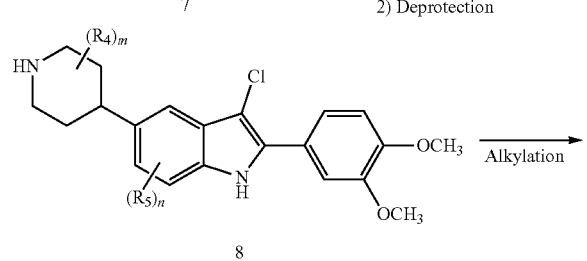

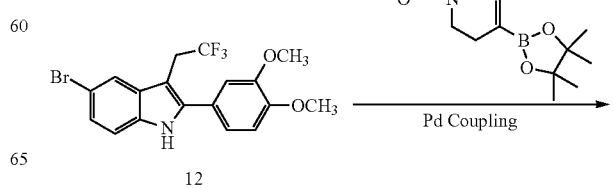

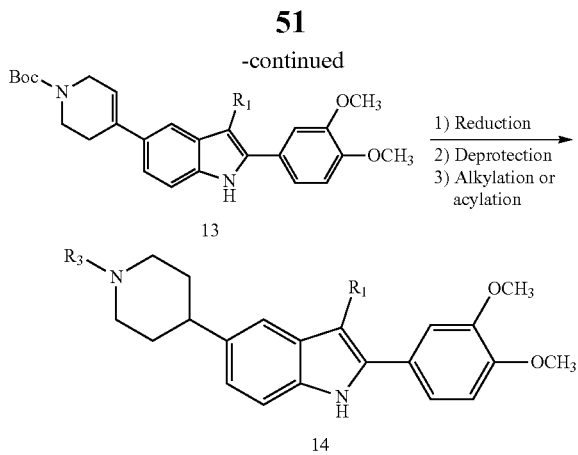

Examples

Preparation of compounds of Formula (I), and intermediates used in the preparation of compounds of Formula (I), can be prepared using procedures shown in the following Examples and related procedures. The methods and conditions used in these examples, and the actual compounds prepared in these Examples, are not meant to be limiting, but are meant to demonstrate how the compounds of Formula (I) can be prepared. Starting materials and reagents used in these examples, when not prepared by a procedure described herein, are generally either commercially available, or are reported in the chemical literature, or may be prepared by using procedures described in the chemical literature.

Abbreviations

Ac acetyl
ACN acetonitrile
AcOH acetic acid
anhyd. anhydrous
aq. aqueous
BH$_3$DMS boron dimethylsulfide
Bn benzyl
Bu butyl
Boc tert-butoxycarbonyl
BOP benzotriazol-1-yloxytris-(dimethylamino)-phosphonium hexafluorophosphate
CV Column Volumes
DAST (diethylamino)sulfur trifluoride
DCE dichloroethane
DCM dichloromethane
DMAP dimethylaminopyridine
DEA diethylamine
DIPEA diisopropylethylamine
DMF dimethylformamide
DMSO dimethylsulfoxide
EDC 1-(3-dimethylaminopropyl)-3-ethylcarbodiimide hydrochloride
EtOAc ethyl acetate
Et ethyl
EtOH ethanol
H or H$_2$ hydrogen
h, hr or hrs hour(s)
HATU O-(7-azabenzotriazol-1-yl)-N, N, N',N'-tetramethyluronium hexafluorophosphate
HCTU O-(6-Chlorobenzotriazol-1-yl)-N,N,N',N'-tetramethyluronium hexafluorophosphate
hex hexane
i iso
IPA isopropyl alcohol
HOAc acetic acid
HCl hydrochloric acid
HPLC high pressure liquid chromatography
LC liquid chromatography
LCMS liquid chromatography mass spectrometry
M molar
mL or ml milliliter
mM millimolar
Me methyl
MeOH methanol
MHz megahertz
min. minute(s)
mins minute(s)
M$^{+1}$ (M+H)$^+$
MS mass spectrometry
n or N normal
NBS n-bromosuccinimide
nm nanometer
nM nanomolar
NCS N-chlorosuccinimide
NMP N-methylpyrrolidine
Pd/C palladium on carbon
PdCl$_2$(dppf)$_2$ [1,1'-bis(diphenylphosphino)ferrocene]dichloropalladium(II)
Pd(PPh$_3$)$_4$ tetrakis(triphenylphosphine)palladium
Ph phenyl
PPh$_3$ triphenylphosphine
Pr propyl
PSI pounds per square inch
PyBOP bromotripyrrolidinophosphonium hexafluorophosphate
Ret Time retention time
sat. saturated
SFC supercritical fluid chromatography
TEA triethylamine
TFA trifluoroacetic acid
THF tetrahydrofuran
TsCl 4-toluenesulfonyl chloride Analytical and Preparative HPLC Conditions:
Method A1: L3 Acquity: Column: (LCMS) BEH C18, 2.1×50 mm, 1.7 μm particles; Mobile Phase: (A) water; (B) acetonitrile; Buffer: 0.05% TFA; Gradient Range: 2%-98% B (0 to 1 min) 98% B (to 1.5 min) 98%-2% B (to 1.6 min); Gradient Time: 1.6 min; Flow Rate: 0.8 mL/min; Analysis Time: 2.2 min; Detection: Detector 1: UV at 254 nm; Detector 2: MS (ESI$^+$).
Method B1: L2 Aquity (4); Column: (LCMS) BEH C18, 2.1×50 mm, 1.7 μm particles; Mobile Phase: (A) water; (B) acetonitrile; Buffer: 0.05% TFA; Gradient Range: 2%-98% B (0 to 1 min) 98% B (to 1.5 min) 98%-2% B (to 1.5 min); Gradient Time: 1.8 min; Flow Rate: 0.8 mL/min; Analysis Time: 2.2 min; Detection: Detector 1: UV at 254 nm; Detector 2: MS (ESI$^+$).
Method C1 SCP: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate. Temperature: 50° C.; Gradient: 0-100% B over 3 minutes, then a 0.75-minute hold at 100% B; Flow: 1.11 mL/min; Detection: UV at 220 nm.
Method D1 SCP: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.11 mL/min; Detection: UV at 220 nm.
Method E1 iPAC: Column: Waters Xbridge C18 4.6×50 mm 5 um particles; Mobile Phase A: 5:95 acetonitrile:water with 10 mM ammonium acetate; Mobile Phase B: 95:5 acetonitrile:water with 10 mM ammonium acetate. Temperature: 50° C.; Gradient: 0-100% B over 1 minute; Flow: 4 mL/min; Detection: UV at 220 nm.
Method F1 iPAC: Column: Waters Acquity BEH C18 2.1× 50 mm 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 2.20 minutes; Flow: 0.800 mL/min; Detection: UV at 220 nm.
Method F1 iPAC: Column: Waters Acquity BEH C18 2.1× 50 mm 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 2.20 minutes; Flow: 0.800 mL/min; Detection: UV at 220 nm.
Waters Acquity SDS: Run Time: 2.20 min; Comment: Generic gradient; Solvent Selection A: A1; Solvent Selection B: B1; Low Pressure Limit: 0 psi; High Pressure Limit: 15000 psi; Solvent Name A: 100% H$_2$O w/0.05% TFA; Solvent Name B: 100% ACN w/0.05% TFA; Switch 1: No Change; Switch 2: No Change; Switch 3: No Change; Seal Wash: 5.0 min; Chart Out 1: System Pressure; Chart Out 2: % B; System Pressure Data Channel: Yes; Flow Rate Data Channel: No; % A Data Channel: No; % B Data Channel: No; Primary A Pressure Data Channel: No; Accumulator A Pressure Data Channel: No; Primary B Pressure Data Channel: No; Accumulator B Pressure Data Channel: No; Degasser Pressure Data Channel: No; Gradient Time (min) Flow A % B % Curve Rate: Initial 0.800 98.0 2.0; 1.00 0.800 2.0 98.0 6; 1.50 0.800 2.0 98.0 6; 1.60 0.800 98.0 2.0 11; Run Events: Yes;
(A): Column-Ascentis Express C18 (50×2.1 mm-2.7 m) Mphase A: 10 mM NH$_4$COOH in water: ACN (98:02); Mphase B: 10 mM NH$_4$COOH in water: ACN (02:98), Gradient: 0-100% B over 3 minutes, Flow=1 mL/min.
(B): Waters Acquity BEH C18 (2.1×50 mm) 1.7 micron; Buffer: 5 mM ammonium acetate pH 5 adjusted with HCOOH, Solvent A: Buffer:ACN (95:5), Solvent B: Buffer: ACN (5:95), Method:% B: 0 min-5%:1.1 min-95%: 1.7 min-95%, Flow: 0.8 mL/min.
(C): Column-Ascentis Express C18 (50×2.1 mm-2.7 m) Mobile phase A: 0.1% HCOOH in water; Mobile phase B: ACN. Temperature: 50° C.; Gradient: 0-100% B over 3 minutes; Flow rate: 1.0 mL/min.
(D): Kinetex XB-C18 (75×3 mm) 2.6 micron; Solvent A: 10 mM ammonium formate in water: acetonitrile (98:02); Mobile Phase B: 10 mM ammonium formate in water: acetonitrile (02:98); Temperature: 50° C.; Gradient: 0-100% B over 3 minutes; Flow rate: 1.1 mL/min; Detection: UV at 220 nm.
(E): Column: Ascentis Express C18 (50×2.1) mm, 2.7 m; Mobile Phase A: 5:95 acetonitrile: water with 10 mM NH$_4$OAc; Mobile Phase B: 95:5 acetonitrile: water with 10 mM NH$_4$OAc; Temperature: 50° C.; Gradient:0-100% B over 3 minutes; Flow: 1.1 ml/min.
(F): Column: Ascentis Express C18 (50×2.1) mm, 2.7 μm; Mobile Phase A: 5:95 acetonitrile: water with 0.1% TFA; Mobile Phase B: 95:5 acetonitrile: water with 0.1% TFA; Temperature: 50° C.; Gradient:0-100% B over 3 minutes; Flow:1.1 ml/min.
(G): Column: Waters Acquity UPLC BEH C18 (2.1×50 mm), 1.7 micron; Solvent A=100% water with 0.05% TFA; Solvent B=100% acetonitrile with 0.05% TFA; gradient=2-98% B over 1 minute, then a 0.5-minute hold at 98% B; Flow rate: 0.8 mL/min; Detection: UV at 220 nm.
(H): Column: Acentis Express C18 (50×2.1 mm) 1.7 m, Acentis C8 NH$_4$COOH 5 min. M, Mobile Phase A: –10 mM ammonium formate: ACN (98:2), Mobile Phase B: –10 mM ammonium formate: ACN (2:98), Flow: 1 ml/min.
(I) Column: Sunfire C18 (4.6×150) mm, 3.5 m; Mobile Phase A: 5:95 acetonitrile: water with 0.05% TFA; Mobile Phase B: 95:5 acetonitrile: water with 0.05% TFA; Temperature: 50° C.; Gradient:10-100% B over 12 minutes; Flow:1 ml/min.
(J) Column: Sunfire C18 (4.6×150) mm, 3.5 m; Mobile Phase A: 5:95 acetonitrile: water with 0.05% TFA; Mobile Phase B: 95:5 acetonitrile: water with 0.05% TFA; Temperature: 50° C.; Gradient:10-100% B over 25 minutes; Flow:1 ml/min.

Example 1

2-(3,4-dimethoxyphenyl)-3-methyl-5-(piperidin-4-yl)-1H-indole hydrochloride

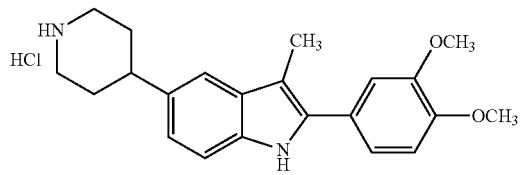

(1)

Intermediate 1A: 5-bromo-3-methyl-1H-indole

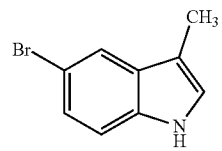

(1A)

A solution of 5-bromo-1H-indole-3-carbaldehyde (13.12 g, 58.6 mmol) in THF (100 mL) was added to a refluxing mixture of LiAlH$_4$ (4.89 g, 129 mmol) in THF (100 mL) (reflux condenser fitted to a two neck flask) over 30 min. The reaction mixture was refluxed for 8 hours, cooled to room temperature and treated with diethyl ether (~50 mL). The reaction mixture was acidified to ~pH 3 with 1N HCl, while cooling in an ice bath. The reaction mixture was diluted with ethyl acetate (125 mL), poured into a separatory funnel and washed with water (2×50 mL) and saturated aqueous sodium chloride solution (50 mL), dried over anhydrous sodium sulfate and filtered. The filtrate was concentrated in vacuo to give crude product. The crude product was dissolved in a small amount of DCM and charged to an ISCO silica gel (80 g) column, which was eluted over 15 minutes using a gradient of 0-50% ethyl acetate/heptane. The combined fractions were concentrated to give 5-bromo-3-methyl-1H- indole (5.5 g, 44.7% yield). LC retention time 1.0 min [Method A1]. MS (E⁻) m/z: 210/212 (M–H).

Intermediate 1B: tert-butyl 4-(3-methyl-1H-indol-5-yl)-3,6-dihydropyridine-1(2H)-carboxylate

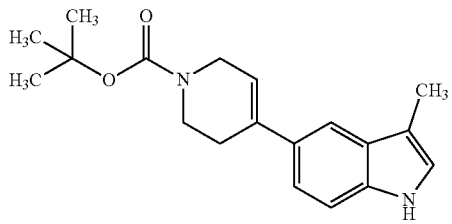

(1B)

To a mixture of 5-bromo-3-methyl-1H-indole (0.417 g, 1.985 mmol), PdCl₂(dppf)-CH₂Cl₂ adduct (0.041 g, 0.050 mmol), and tert-butyl 4-(4,4,5,5-tetramethyl-1,3,2-dioxaborolan-2-yl)-5,6-dihydropyridine-1(2H)-carboxylate (0.675 g, 2.183 mmol) in a 40 ml reaction vial was added THF (10 mL) followed by a 3M aqueous solution of tripotassium phosphate (1.985 mL, 5.95 mmol). The vial was fitted with a Teflon-lined septum cap. The system was evacuated under vacuum (via a needle from a nitrogen/vacuum manifold line) and back-filled with nitrogen gas. The procedure was repeated three times. The needle was removed and the vial was heated at 75° C. for 18 hours. The reaction mixture was cooled to room temperature and diluted with ethyl acetate (125 mL). The mixture was poured into a separatory funnel and washed with water (2×50 mL) and saturated aqueous sodium chloride solution (50 mL), dried over anhydrous sodium sulfate and filtered. The filtrate was concentrated in vacuo to give crude product. The crude product was dissolved in a small amount of DCM and charged to an ISCO silica gel (24 g) column, which was eluted over 20 minutes using a gradient of 0-50% ethyl acetate/heptane. The combined fractions were concentrated to give tert-butyl 4-(3-methyl-1H-indol-5-yl)-5,6-dihydropyridine-1(2H)-carboxylate (0.510 g, 82% yield) as a tan oil. LC retention time 1.10 min [Method A1]. MS (E⁻) m/z: 313 (M–H).

Intermediate 1C: tert-butyl 4-(3-methyl-1H-indol-5-yl)piperidine-1-carboxylate

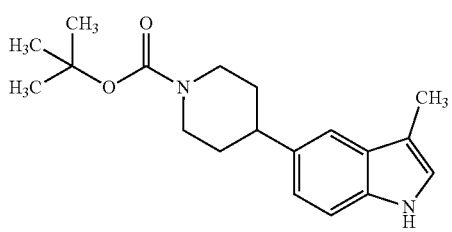

(1C)

In a 250 ml round bottom flask was added tert-butyl 4-(3-methyl-1H-indol-5-yl)-5,6-dihydropyridine-1(2H)-carboxylate (1.300 g, 4.16 mmol) and ethyl acetate (20 mL). The flask was purged with nitrogen gas and Pd/C (0.325 g, 0.305 mmol) was added. Following pump/purging with nitrogen gas three times, hydrogen gas was introduced via a balloon. The reaction mixture was stirred at room temperature overnight. The flask was evacuated and filled with nitrogen gas. The suspension was filtered through fluted filter paper and the filtrate was concentrated in vacuo. Collected tert-butyl 4-(3-methyl-1H-indol-5-yl)piperidine-1-carboxylate (1.10 g, 88% yield) as an off-white solid. LC retention time 1.15 min [Method A1]. MS (E⁻) m/z: 315 (M–H).

Intermediate 1D: tert-butyl 4-(2-bromo-3-methyl-1H-indol-5-yl)piperidine-1-carboxylate

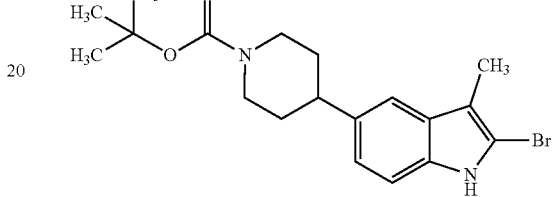

(1D)

In a 100 ml round bottom flask was added tert-butyl 4-(3-methyl-1H-indol-5-yl) piperidine-1-carboxylate (1.100 g, 3.50 mmol) and DCE (20 mL). NBS (0.560 g, 3.15 mmol) was dissolved in 15 ml of DCE and added to the reaction drop-wise, via an addition funnel over a 15 minute period. Following this addition, the reaction mixture was stirred at room temperature for 15 minutes, then quenched with a 10% aqueous sodium sulfite solution (1.0 ml). The mixture was diluted with DCM (100 mL), poured into a separatory funnel and washed with water (2×50 mL) and then, saturated aqueous sodium chloride solution (50 mL), dried over anhydrous sodium sulfate and filtered. The filtrate was concentrated in vacuo to give crude product. The crude product was dissolved in a small amount of DCM and charged to an ISCO silica gel column (40 g), which was eluted over a 30 min gradient with 0%-50% EtOAc/hexanes to give tert-butyl 4-(2-bromo-3-methyl-1H-indol-5-yl)piperidine-1-carboxylate (1.05 g, 76% yield) as a white solid. LC retention time 1.16 min [Method A1]. MS (E⁻) m/z: 337/339 (M–H).

Intermediate 1E: tert-butyl 4-(2-(3,4-dimethoxyphenyl)-3-methyl-1H-indol-5-yl) piperidine-1-carboxylate

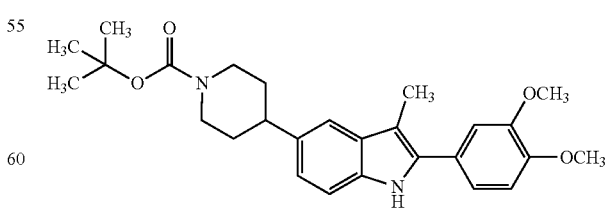

(1E)

In a 40 ml reaction vial, tert-butyl 4-(2-bromo-3-methyl-1H-indol-5-yl)piperidine-1-carboxylate (1.16 g, 2.94 mmol) was taken in THF (10 mL) and (3,4-dimethoxyphenyl) boronic acid (0.589 g, 3.24 mmol, PdCl₂(dppf)-CH₂Cl₂ adduct (0.156 g, 0.191 mmol), and a 3M dipotassium phosphate solution (2.94 mL, 8.82 mmol) were added and the mixture was sealed with a Teflon-lined cap and pump/purged with nitrogen gas three times. The reaction mixture was set to heat at 65° C. for 1 hour. The mixture was cooled to room temperature, diluted with EtOAc (100 mL), poured into a separatory funnel and washed with water (2×50 mL) and saturated aqueous sodium chloride solution (50 mL), dried over anhydrous sodium sulfate and filtered. The filtrate was concentrated in vacuo to give crude product. The crude product was dissolved in a small amount of DCM and charged to an ISCO silica gel column (40 g), which was eluted over a 30 minute gradient with 0-50% EtOAc/hexanes to give tert-butyl 4-(2-(3,4-dimethoxyphenyl)-3-methyl-1H-indol-5-yl)piperidine-1-carboxylate (0.996 g, 75% yield). LC retention time 1.16 min [Method A1]. MS (E⁻) m/z: 451 (M−H).

Example 1

In a 40 ml reaction vial was added tert-butyl 4-(2-(3,4-dimethoxyphenyl)-3-methyl-1H-indol-5-yl)piperidine-1-carboxylate (1.21 g, 2.77 mmol) followed by DCM (5 ml) and 4M HCl/dioxane (1.70 mL, 6.94 mmol). The reaction mixture was stirred at room temperature for 60 minutes, then concentrated to dryness under a stream of nitrogen gas to give 2-(3,4-dimethoxyphenyl)-3-methyl-5-(piperidin-4-yl)-1H-indole, HCl (0.973 g, 91% yield). LC retention time 0.71 min [Method A1]. MS (E⁻) m/z: 351 (M−H). Further purification (10.0 mg) was performed using preparative LC-MS with the following conditions: Column: Waters XBridge C18, 19×200 mm, 5-μm particles; Mobile Phase A: 5:95 acetonitrile:water with 0.1% ammonium acetate; Mobile Phase B: 95:5 acetonitrile:water with 0.1% ammonium acetate; Gradient: 15-100% B over 25 minutes, then a 5-minute hold at 100% B; Flow: 20 mL/min. Fractions containing the desired product were combined and dried via centrifugal evaporation to give 2-(3,4-dimethoxyphenyl)-3-methyl-5-(piperidin-4-yl)-1H-indole (5.7 mg, 57%). Two analytical LC/MS injections were used to determine the final purity: LC retention time 1.18 min [C1]. MS (E+) m/z: 351 (M+H); LC retention time=1.18 min [D1]. MS (E+) m/z: 351 (M+H).

Example 2

5-([1,4'-bipiperidin]-4-yl)-2-(3,4-dimethoxyphenyl)-3-methyl-1H-indole dihydrochloride (2)

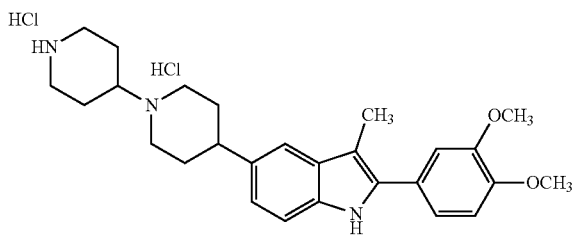

Intermediate 2A: tert-butyl 4-(2-(3,4-dimethoxyphenyl)-3-methyl-1H-indol-5-yl)-[1,4'-bipiperidine]-1'-carboxylate (2A)

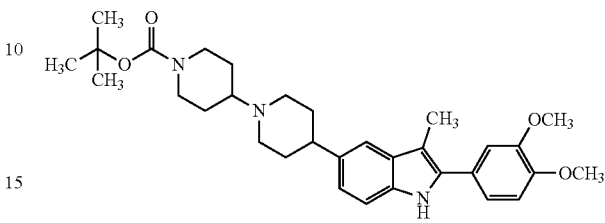

In a 40 ml reaction vial was added 2-(3,4-dimethoxyphenyl)-3-methyl-5-(piperidin-4-yl)-1H-indole, HCl (0.612 g, 1.358 mmol) and DCM (5 mL). TEA (0.947 mL, 6.79 mmol) was added, followed by tert-butyl 4-oxopiperidine-1-carboxylate (0.406 g, 2.037 mmol) and acetic acid (0.078 mL, 1.358 mmol). The mixture was stirred at room temperature for 15 minutes and sodium cyanoborohydride (0.256 g, 4.07 mmol) was added. The reaction mixture was stirred at 50° C. for 2 hours, diluted with water and DCM and the contents was transferred to a separatory funnel. The layers were separated and the organics were washed with a saturated sodium chloride solution. The organics were collected, dried over anhydrous sodium sulfate and concentrated to a brownish residue. The residue was diluted with DCM (1 ml) and charged to an ISCO silica gel column (12 g), which was eluted with 0-20% MeOH/DCM. Following concentration of the combined fractions, tert-butyl 4-(2-(3,4-dimethoxyphenyl)-3-methyl-1H-indol-5-yl)-[1,4'-bipiperidine]-1'-carboxylate (0.72 g, 100% yield) was collected as a tan solid. LC retention time 0.85 min [Method A1]. MS (E⁻) m/z: 534 (M−H).

Example 2

In a 40 ml reaction vial were added tert-butyl 4-(2-(3,4-dimethoxyphenyl)-3-methyl-1H-indol-5-yl)-[1,4'-bipiperidine]-1'-carboxylate (0.700 g, 1.312 mmol followed by DCM (5 ml) and 4M HCl/dioxane (3.28 mL, 13.12 mmol). The reaction mixture was stirred at room temperature for 60 minutes, then concentrated to dryness under a stream of nitrogen gas. The residue was taken up in DMF (1 mL) and the solids were filtered through a 0.45 micron syringe filter and the crude material was purified via preparative LC/MS with the following conditions: Column: Waters XBridge C18, 19×200 mm, 5-m particles; Mobile Phase A: 5:95 acetonitrile: water with 0.1% trifluoroacetic acid; Mobile Phase B: 95:5 acetonitrile: water with 0.1% trifluoroacetic acid; Gradient: 0-100% B over 15 minutes, then a 5-minute hold at 100% B; Flow: 20 mL/min. Fractions containing the desired product were combined and dried via centrifugal evaporation to afford 5-([1,4'-bipiperidin]-4-yl)-2-(3,4-dimethoxyphenyl)-3-methyl-1H-indole, bis trifluoroacetic acid (0.515 g, 78% yield). Two analytical LC/MS injections were used to determine the final purity. (1) LC retention time 1.18 min [C1]. MS (E⁻) m/z: 434 (M−H). (2) LC retention time=1.04 min [D1]. MS (E⁻) m/z: 434 (M−H).

Example 3

5-(1'-(cyclopropylmethyl)-[1,4'-bipiperidin]-4-yl)-2-(3,4-dimethoxyphenyl)-3-methyl-1H-indole

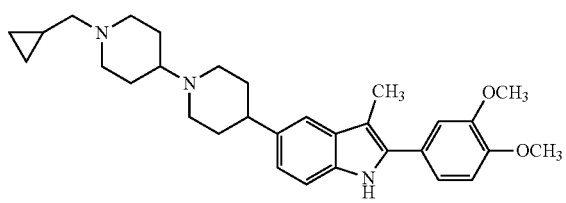

(3)

To a 2 dram reaction vial were added 5-([1,4'-bipiperidin]-4-yl)-2-(3,4-dimethoxyphenyl)-3-methyl-1H-indole dihydrochloride (0.015 g, 0.030 mmol), DCE, TEA (0.025 ml, 0.178 mmol), cyclopropanecarbaldehyde (4.15 mg, 0.059 mmol) and acetic acid (1.695 μl, 0.030 mmol). With stirring, sodium cyanoborohydride (7.44 mg, 0.118 mmol) was added after 15 minutes. The reaction mixture was allowed to heat at 50° C. for 1 hour. The reaction was quenched with MeOH (0.1 ml) and concentrated to dryness. The crude material was purified via preparative LC/MS with the following conditions: Column: Waters XBridge C18, 19×200 mm, 5-μm particles; Mobile Phase A: 5:95 acetonitrile:water with 0.1% ammonium hydroxide; Mobile Phase B: 95:5 acetonitrile:water with 0.1% ammonium hydroxide; Gradient: 15-100% B over 25 minutes, then a 5-minute hold at 100% B; Flow: 20 mL/min. Fractions containing the desired product were combined and dried via centrifugal evaporation. 5-(1'-(cyclopropylmethyl)-[1,4'-bipiperidin]-4-yl)-2-(3,4-dimethoxyphenyl)-3-methyl-1H-indole di trifluoroacetic acid (0.045 g, 30% yield). Two analytical LC/MS injections were used to determine the final purity. (1) LC retention time 1.11 min [C1]. MS (E⁻) m/z: 488 (M–H). (2) LC retention time=1.35 min [D1]. MS (E⁻) m/z: 488 (M–H).

The following examples were prepared according to the general procedure of Example 2 using 2-(3,4-dimethoxyphenyl)-3-methyl-5-(piperidin-4-yl)-1H-indole, HCl as the starting intermediate.

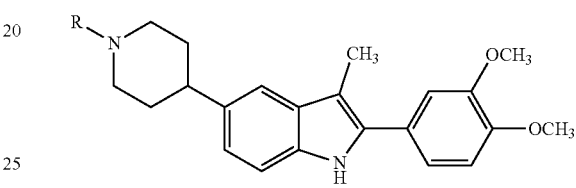

TABLE 1

| Ex. No. | R | M⁺¹ | RT Method | Method |
|---|---|---|---|---|
| 4 | ![H3C-imidazole-CH2] | 445.2 | 1.18 | B |
| 5 | HO-(CH2)3- | 408.2 | 1.18 | B |
| 6 | (CH3)2CH-CH2-N-piperidine- | 490.3 | 1.25 | B |
| 7 | oxetan-3-yl | 406.4 | 1.35 | A |
| 8 | 1-phenylpyrrolidin-3-yl | 496.3 | 2.29 | A |
| 9 | 1-benzylpiperidin-4-yl | 524.3 | 1.76 | A |

TABLE 1-continued

| Ex. No. | R | M$^{+1}$ | RT Method | Method |
|---|---|---|---|---|
| 10 | H$_3$C-CH(CH$_3$)-N-piperidinyl | 476.3 | 1.41 | A |
| 11 | H$_3$C-N-piperidinyl | 448.3 | 1.33 | A |
| 12 | H$_3$C-C(O)-N-piperidinyl | 476.3 | 1.32 | A |
| 13 | H$_3$C-CH$_2$-O-C(O)-N-pyrrolidinyl | 492.2 | 1.47 | B |
| 14 | 2-amino-thiazol-4-yl-methyl | 463.3 | 1.43 | A |
| 15 | quinolin-5-ylmethyl | 492.2 | 1.28 | B |
| 16 | (1-methyl-imidazol-2-yl)methyl | 445.2 | 1.59 | A |
| 17 | (tetrahydropyran-4-yl)methyl | 449.5 | 1.4 | |
| 18 | quinolin-2-ylmethyl | 493.3 | 2.18 | A |
| 19 | (4-dimethylamino-isoquinolin-1-yl)methyl | 534.4 | 1.58 | B |
| 20 | pyridin-4-ylmethyl | 442.3 | 1.92 | A |

TABLE 1-continued

| Ex. No. | R | M+1 | RT Method | Method |
|---|---|---|---|---|
| 21 | H3C—N, piperidine bicyclic (tropane-like) | 474.0 | 1.06 | B1 |
| 22 | 1,2,2,6,6-pentamethylpiperidin-4-yl | 504 | 1.11 | B1 |
| 23 | 1-cyclopropylpiperidin-4-yl | 474 | 1.08 | B1 |
| 24 | 1-ethylpiperidin-3-yl (Rac) | 462 | 1.19 | B1 |
| 25 | (1R,2R/1S,2S)-2-(dimethylamino)cyclohexyl (Rac) | 476 | 1.11 | B1 |
| 26 | 1-(tetrahydro-2H-pyran-4-yl)piperidin-4-yl | 518.4 | 1.45 | A |
| 27 | 1-phenylethyl | 457.3 | 1.31 | B |
| 28 | pyridin-2-ylmethyl | 442.3 | 1.41 | B |
| 29 | (1-methyl-1H-pyrrol-2-yl)methyl | 444.3 | 1.53 | B |
| 30 | 3-(dimethylamino)-2-methylpropyl | 436.4 | 1.68 | A |
| 31 | isoquinolin-6-ylmethyl | 492.3 | 2.06 | A |

TABLE 1-continued
| Ex. No. | R | M⁺¹ | RT Method | Method |
|---|---|---|---|---|
| 32 | 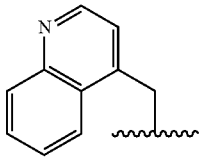 [SMILES: *Cc1ccnc2ccccc12] | 492.3 | 2.41 | A |
| 33 | 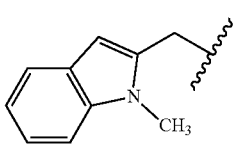 | 494.3 | 2.62 | A |
| 34 | 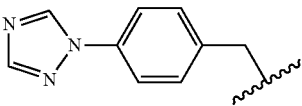 [SMILES: *Cc1ccc(-n2cncn2)cc1] | 508.3 | 1.91 | A |
| 35 | 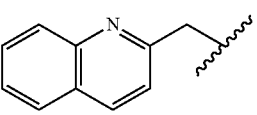 [SMILES: *Cc1ccc2ccccc2n1] | 492.3 | 1.68 | B |
| 36 | 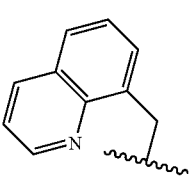 [SMILES: *Cc1cccc2cccnc12] | 492.3 | 1.69 | A |
| 37 | 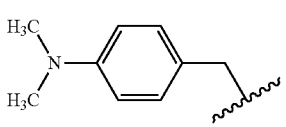 [SMILES: *Cc1ccc(N(C)C)cc1] | 484.4 | 1.36 | B |
| 38 | 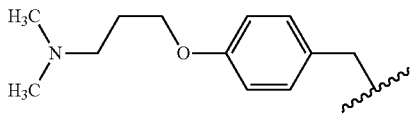 | 542.4 | 1.47 | A |
| 39 | 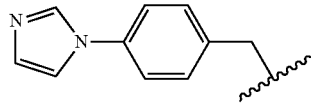 [SMILES: *Cc1ccc(-n2ccnc2)cc1] | 507.4 | 1.12 | B |
| 40 | 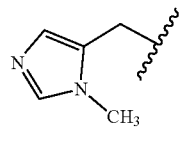 | 445.4 | 1.08 | B |
| 41 | 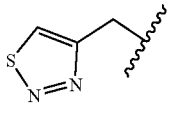 | 449.3 | 1.9 | A |
| 42 | 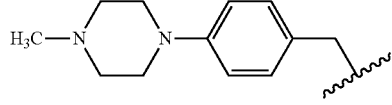 [SMILES: *Cc1ccc(N2CCN(C)CC2)cc1] | 539.4 | 1.56 | A |

TABLE 1-continued

| Ex. No. | R | M+1 | RT Method | Method |
|---|---|---|---|---|
| 43 | HO-CH(CH3)-CH2- (2-hydroxy-1-methylethyl) | 409.3 | 1.23 | A |
| 44 | 1-ethylpiperidin-4-yl | 462.4 | 1.1 | B |
| 45 | (1-benzylpyrrolidin-3-yl)methyl | 510.4 | 1.29 | B |
| 46 | (4-(pyrrolidin-1-yl)phenyl)methyl | 510.4 | 1.83 | B |
| 47 | (pyridin-3-yl)methyl | 442.3 | 1.15 | B |
| 48 | 2,2,6,6-tetramethylpiperidin-4-yl | 490 | 0.67 | A1 |
| 49 | (1-methylpiperidin-2-yl)methyl | 462 | 1.01 | D1 |

The following Examples were prepared according to the general procedure of Example 3 using 5-([1,4'-bipiperidin]-4-yl)-2-(3,4-dimethoxyphenyl)-3-methyl-1H-indole dihydrochloride as the starting intermediate.

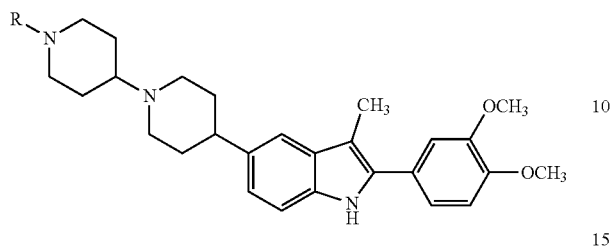

TABLE 2

| Ex. No. | R | M + 1 | RT Method | Method |
|---|---|---|---|---|
| 50 | —CH₂CH₂CF₃ | 530.4 | 1.18 | B |
| 51 | —CH₂CH(CH₃)CH₂CH₃ | 504.4 | 1.23 | B |
| 52 | —CH₂CH(OH)CH₂OH | 508.4 | 1.06 | B |
| 53 | —CH₂CH₂CH₂SCH₃ | 522.4 | 1.19 | B |
| 54 | —CH₂CH(CH₂CH₃)₂ | 518.3 | 1.35 | B |
| 55 | —(CH₂)₄CH₃ | 504.4 | 1.26 | B |
| 56 | —CH₂CH₂CH(OH)CH₃ | 506.4 | 1.42 | A |
| 57 | —(CH₂)₅OCH₃ | 520.4 | 1.11 | B |
| 58 | cyclohexylmethyl | 530.5 | 1.31 | B |
| 59 | (1-methyl-1H-imidazol-5-yl)methyl | 528.4 | 1.4 | A |
| 60 | ethyl cyclopropanecarboxylate-CH₂- | 560.4 | 1.23 | B |
| 61 | cyclobutyl | 488.4 | 1.1 | B |
| 62 | cyclopentyl | 502.4 | 1.18 | B |
| 63 | CH₃CH₂CH₂CH₂- | 476.4 | 1.59 | A |
| 64 | (thiophen-2-yl)methyl | 530.4 | 1.21 | B |

TABLE 2-continued

| Ex. No. | R | M + 1 | RT Method | Method |
|---|---|---|---|---|
| 65 | cyclopentyl-CH₂- | 516.3 | 1.74 | A |
| 66 | CH₃CH₂-CH(CH₃)- | 494.4 | 1.08 | B |
| 67 | 3-methylcyclohexyl- | 530.4 | 1.22 | B |
| 68 | cyclohexyl- | 516.4 | 1.22 | B |
| 69 | HOCH₂-C(CH₃)₂-CH₂- | 520.4 | 1.14 | B |
| 70 | HOOC-(CH₂)₃- | 520.4 | 1.11 | B |
| 71 | CH₃CH₂-CH(CH₃)- | 490.4 | 1.16 | B |
| 72 | thiazol-2-yl-CH₂- | 531.3 | 1.57 | A |
| 73 | 3-(trifluoromethyl)cyclohexyl- | 584.4 | 1.97 | A |
| 74 | tetrahydrofuran-3-yl-CH₂- | 518.4 | 1.11 | B |
| 75 | (CH₃)₃C-CH₂- | 504.4 | 2.1 | A |
| 76 | furan-2-yl-CH₂- | 514.4 | 1.17 | B |

TABLE 2-continued
| Ex. No. | R | M + 1 | RT Method | Method |
|---|---|---|---|---|
| 77 | (isobutyl-methyl group with CH3, H3C) | 504.4 | 1.83 | A |
| 78 | (1-methyl-pyrrol-2-yl-methyl, H3C-N) | 527.4 | 1.21 | B |
| 79 | (3-trifluoromethylcyclohexyl, F3C) | 584.5 | 2.13 | A |
| 80 | (4-methylcyclohexyl, H3C) | 530.4 | 1.23 | B |
| 81 | (1-methylpiperidin-4-yl, H3C—N) | 531.4 | 0.97 | B |
| 82 | (n-butyl, H3C) | 490.4 | 1.13 | B |
| 83 | (oxetan-3-yl, O) | 490 | 1.20 | D1 |
| 84 | (4-hydroxycyclohexyl, HO) | 532.4 | 1.06 | B |
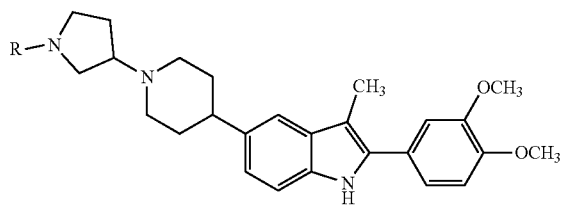
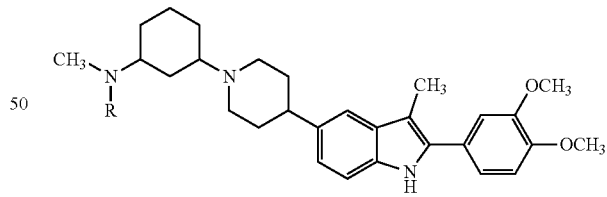
| TABLE 3 | | | | | | TABLE 4 | | | | |
|---|---|---|---|---|---|---|---|---|---|---|
| Ex. No. | R | M + 1 | RT Method | Method | | Ex. No. | R | M+1 | RT Method | Method |
| 85 | —CH2CH(CH3)2 | 476 | 1.16 | D1 | | 89 | —CH2CH(CH3)2 | 518 | 1.21 | D1 |

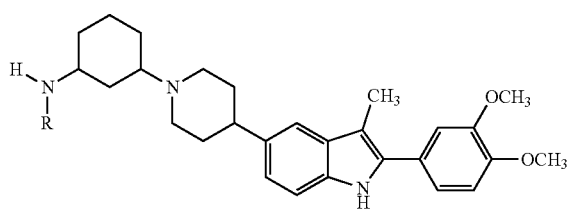

TABLE 5

| Ex. No. | R | M+1 | RT Method | Method |
|---|---|---|---|---|
| 90 | —CH₂CH(CH₃)₂ | 504 | 1.20 | D1 |

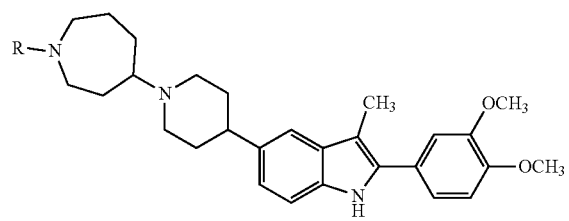

TABLE 6

| Ex. No. | R | M+1 | RT Method | Method |
|---|---|---|---|---|
| 91 | —CH₃ | 462 | 1.05 | D1 |
| 92 | —CH(CH₃)₂ | 490 | 1.08 | D1 |
| 93 | cyclopentyl | 516 | 1.15 | D1 |
| 94 | cyclopropylmethyl | 502 | 1.12 | D1 |
| 95 | isobutyl | 504 | 1.13 | D1 |
| 96 | oxetanyl | 504 | 1.05 | D1 |
| 97 | —CH₂CH₃ | 476 | 1.02 | D1 |

Example 99 tert-butyl (2-(4-(2-(3,4-dimethoxyphenyl)-3-methyl-1H-indol-5-yl)piperidin-1-yl) ethyl)carbamate

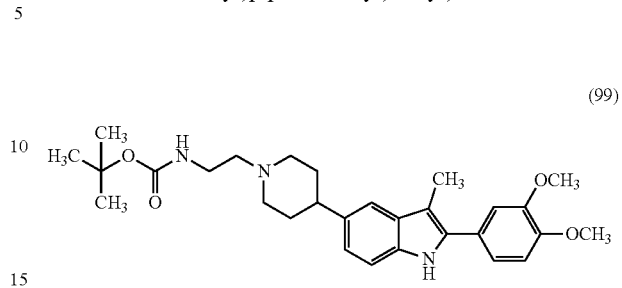

(99)

Tert-butyl (2-(4-(2-(3,4-dimethoxyphenyl)-3-methyl-1H-indol-5-yl)piperidin-1-yl)ethyl)carbamate was prepared according to the general procedure of Example 98 using tert-butyl-(2-oxoethyl)carbamate as the starting material. The crude material was purified via preparative LC/MS with the following conditions: Column: Waters XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 25-100% B over 25 minutes, then a 5-minute hold at 100% B; Flow: 20 mL/min. Fractions containing the desired product were combined and dried via centrifugal evaporation. tert-butyl (2-(4-(2-(3,4-dimethoxyphenyl)-3-methyl-1H-indol-5-yl)piperidin-1-yl)ethyl)carbamate hydrochloride (0.078 g, 75% yield). Two analytical LC/MS injections were used to determine the final purity. (1) LC retention time 1.88 min [C1]. MS (E⁻) m/z: 494 (M–H). (2) LC retention time=1.60 min [D1]. MS (E⁻) m/z: 494 (M–H).

Example 100

2-(4-(2-(3,4-dimethoxyphenyl)-3-methyl-1H-indol-5-yl)piperidin-1-yl)ethan-1-amine

(100)

To a 2 dram reaction vial were added tert-butyl-(2-(4-(2-(3,4-dimethoxyphenyl)-3-methyl-1H-indol-5-yl)piperidin-1-yl)ethyl)carbamate (0.070 g, 0.142 mmol) followed by DCM (0.5 ml) and 4M HCl/Dioxane (0.355 mL, 1.42 mmol). The reaction mixture was stirred at room temperature for 60 minutes, then concentrated to dryness under a stream of nitrogen gas. The residue was taken up in DMF (1 mL) and the solids were filtered through a 0.45 micron syringe filter and the crude material was purified via preparative LC/MS with the following conditions: Column: Waters XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 0%-100% B over 15 minutes, then a 0-minute hold at 100% B; Flow: 20 mL/min.

Fractions containing the desired product were combined and dried via centrifugal evaporation to afford 2-(4-(2-(3,4-dimethoxyphenyl)-3-methyl-1H-indol-5-yl) piperidin-1-yl) ethanamine (0.0055 g, 9.5% yield). Two analytical LC/MS injections were used to determine the final purity. (1) LC retention time 1.39 min [C1]. MS (E⁻) m/z: 394 (M–H). (2) LC retention time=1.08 min [D1]. MS (E⁻) m/z: 394 (M–H).

The following Examples were prepared according to the general procedure of Example 98 using 4-(2-(3,4-dimethoxyphenyl)-3-methyl-1H-indol-5-yl) piperidine hydrochloride as the starting intermediate.

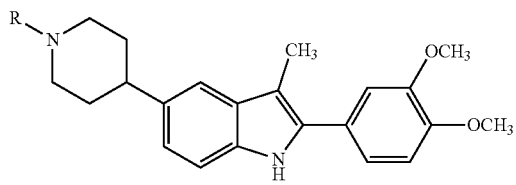

TABLE 7

| Ex. No. | R | M⁺¹ | RT Method | Method |
|---|---|---|---|---|
| 101 | (2-piperidinyl-methyl) | 448.2 | 1.69 | A |
| 102 | —CH₂CH₂CH₂NH(CH₃) | 422.3 | 1.14 | A |
| 103 | (azepan-4-yl) | 448 | 1.06 | D1 |
| 104 | (pyrrolidin-3-yl) | 420 | 1.04 | D1 |
| 105 | (3-aminocyclohexyl) | 448 | 1.06 | D1 |
| 106 | (piperidin-3-ylmethyl) | 434 | 1.00 | D1 |
| 107 | (pyrrolidin-2-ylmethyl) | 434 | 1.01 | D1 |
| 108 | (pyrrolidin-2-ylmethyl) | 434 | 0.99 | D1 |

Example 109

N-(2-(4-(2-(3,4-dimethoxyphenyl)-3-methyl-1H-indol-5-yl)piperidin-1-yl)ethyl)-N-methyloxetan-3-amine

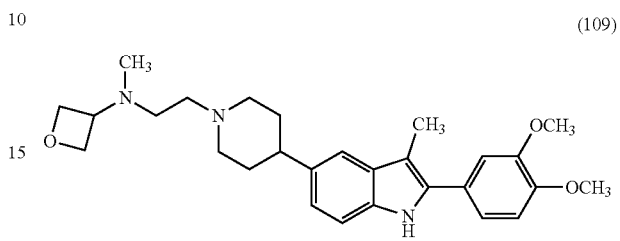

(109)

To a 2 dram vial were added 2-(4-(2-(3,4-dimethoxyphenyl)-3-methyl-1H-indol-5-yl)piperidin-1-yl)-N-methylethanamine dihydrochloride (0.018 g, 0.037 mmol), DMF (1 mL), TEA (0.026 mL, 0.187 mmol), oxetan-3-one (4.05 mg, 0.056 mmol) and acetic acid (2.145 µl, 0.037 mmol) and in that order. To this with stirring was added sodium cyanoborohydride (7.06 mg, 0.112 mmol) and the reaction mixture was stirred at room temperature for 30 minutes. Following the reaction completion, the reaction mixture was diluted with MeOH and the crude material was purified via preparative LC/MS with the following conditions: Column: Waters XBridge C18, 19×200 mm, 5-µm particles; Mobile Phase A: 5:95 acetonitrile:water with 0.1% ammonium acetate; Mobile Phase B: 95:5 acetonitrile:water with 0.1% ammonium acetate; Gradient: 15-100% B over 25 minutes, then a 5-minute hold at 100% B; Flow: 20 mL/min. Fractions containing the desired product were combined and dried via centrifugal evaporation to afford N-(2-(4-(2-(3,4-dimethoxyphenyl)-3-methyl-1H-indol-5-yl)piperidin-1-yl)ethyl)-N-methyloxetan-3-amine di trifluoroacetic acid (0.0079 g, 44% yield). Two analytical LC/MS injections were used to determine the final purity. (1) LC retention time 1.00 min [C1]. MS (E⁻) m/z: 464 (M–H). (2) LC retention time=1.00 min [D1]. MS (E⁻) m/z: 464 (M–H).

The following examples were prepared according to the general procedure for Example 109 using 2-(4-(2-(3,4-dimethoxyphenyl)-3-methyl-1H-indol-5-yl)piperidin-1-yl)-N-methylethanamine dihydrochloride as the starting intermediate.

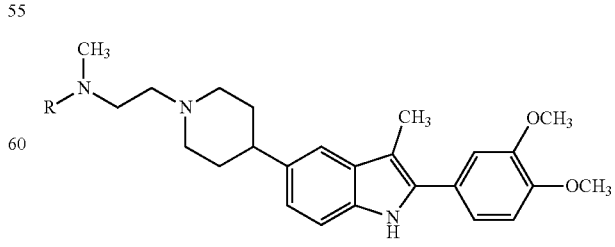

TABLE 8

| Ex. No. | R | M+1 | RT Method | Method |
|---------|---|-----|-----------|--------|
| 110 | —CH₂CH(CH₃)₂ | 464 | 1.16 | D1 |
| 111 | —CH₂CH₃ | 436 | 1.05 | D1 |
| 112 | ⟨cyclopropylmethyl⟩ | 462 | 1.14 | D1 |

Example 113

1-(4-(2-(3,4-dimethoxyphenyl)-3-methyl-1H-indol-5-yl)piperidin-1-yl)-2-(ethylamino)ethan-1-one (113)

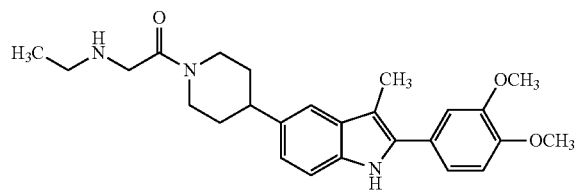

To a 2 dram reaction vial were added 2-(3,4-dimethoxyphenyl)-3-methyl-5-(piperidin-4-yl)-1H-indole hydrochloride (0.020 g, 0.052 mmol) and THF (5 mL). To this were added TEA (0.018 mL, 0.129 mmol) followed by 2-((tert-butoxycarbonyl) (ethyl)amino)acetic acid (0.016 g, 0.078 mmol), HCTU (0.064 g, 0.155 mmol) and DMAP (0.032 g, 0.258 mmol). The mixture was stirred at room temperature for 30 minutes. The reaction mixture was concentrated, diluted with water and ethyl acetate and the layers were separated. The organics were washed with saturated NaCl solution, dried over anhydrous Na2SO4, filtered and concentrated. The residue was diluted with 1 ml of DCM and 1 ml of TFA and stirred for 15 minutes. The reaction mixture was concentrated, diluted with 1 ml of DMSO and filtered through a 0.45 micron syringe filter. The crude material was purified via preparative LC/MS with the following conditions: Column: Waters XBridge C18, 19×200 mm, 5-μm particles; Mobile Phase A: 5:95 acetonitrile:water with 0.1% ammonium hydroxide; Mobile Phase B: 95:5 acetonitrile: water with 0.1% ammonium hydroxide; Gradient: 15-100% B over 25 minutes, then a 5-minute hold at 100% B; Flow: 20 mL/min. Fractions containing the desired product were combined and dried via centrifugal evaporation. 1-(4-(2-(3,4-dimethoxyphenyl)-3-methyl-1H-indol-5-yl) piperidin-1-yl)-2-(ethylamino)ethanone trifluoroacetic acid (0.0112 g, 45% yield). Two analytical LC/MS injections were used to determine the final purity. (1) LC retention time 1.42 min [C1]. MS (E⁻) m/z: 436 (M–H). (2) LC retention time=1.36 min [D1]. MS (E⁻) m/z: 436 (M–H).

Example 114

2-(4-(2-(3,4-dimethoxyphenyl)-1,3-dimethyl-1H-indol-5-yl)piperidin-1-yl)-N-methylethan-1-amine (114)

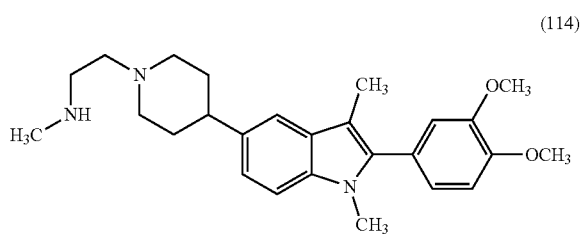 [SMILES: CNCCN1CCC(c2ccc3c(c2)c(C)c(-c2ccc(OC)c(OC)c2)n3C)CC1]

To a 2 dram vial were added tert-butyl (2-(4-(2-(3,4-dimethoxyphenyl)-3-methyl-1H-indol-5-yl)piperidin-1-yl) ethyl)(methyl)carbamate (0.055 g, 0.108 mmol), DMF (1 ml) and at 0° C., NaH (6.50 mg, 0.271 mmol). Under a nitrogen atmosphere, the anion was allowed to form and equilibrate over 20 minutes at 0° C. To this was added methyl iodide (0.020 ml, 0.325 mmol) and the reaction mixture was allowed to warm to room temperature and stirred for 1 hour. The reaction was quenched carefully with water and the mixture was concentrated to dryness under a stream of nitrogen gas. To the residue was added DCM (1 ml) and TFA (0.5 ml). The reaction vessel was capped and the reaction mixture was stirred for 30 minutes followed by removal of the volatiles under a stream of nitrogen gas. The residue was diluted with 1 ml of DMF. The solids were filtered off and the crude material was purified via preparative LC/MS with the following conditions: Column: Waters XBridge C18, 19×250 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 0-60% B over 30 minutes, then a 6-minute hold at 100% B; Flow: 20 mL/min. Fractions containing the desired product were combined and dried via centrifugal evaporation. 2-(4-(2-(3,4-dimethoxyphenyl)-1,3-dimethyl-1H-indol-5-yl)piperidin-1-yl)-N-methylethanamine (0.0246 g, 52% yield). Two analytical LC/MS injections were used to determine the final purity. (1) LC retention time 1.57 min [C1]. MS (E⁻) m/z: 422 (M–H). (2) LC retention time=1.25 min [D1]. MS (E⁻) m/z: 422 (M–H).

Example 115

2-(3,4-dimethoxyphenyl)-5-(1'-isopropyl-[1,4'-bipiperidin]-4-yl)-3,6-dimethyl-1H-indole-di-trifluoroacetic acid (115)

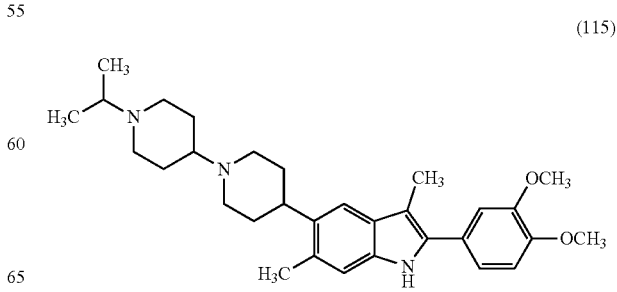

Intermediate 115A: 3,6-dimethyl-1H-indole

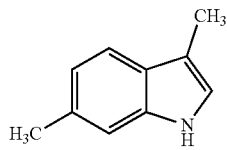
(115A)

A solution of 6-methyl-1H-indole-3-carbaldehyde (4.00 g, 25.1 mmol) in THF (50 mL) was added to a refluxing mixture of LiAlH₄ (2.098 g, 55.3 mmol) in THF (50 mL) (reflux condenser fitted to a two neck flask) over 30 min. The reaction mixture was refluxed for 8 hours, cooled to room temperature and treated with ether (~50 mL). The reaction mixture was acidified to ~pH 3 with 1N HCl while cooling in an ice bath. The reaction mixture was diluted with EtOAc (125 mL), poured into a separatory funnel and washed with water (2×50 mL) and saturated aqueous NaCl solution (50 mL), dried over anhydrous sodium sulfate, filtered and the filtrate concentrated in vacuo to give crude product. The crude product was dissolved in a small amount of DCM and charged to an ISCO silica gel 80G column which was eluted over a 25 min gradient with 0%-50% ethyl acetate/heptane to give 3,6-dimethyl-1H-indole (2.6 g, 71.3% yield). LC retention time 0.96 min [1A]. MS (E⁻) m/z: 146 (M−H).

Intermediate 115B: 2-bromo-3,6-dimethyl-1H-indole

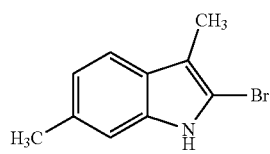
(115B)

In a 100 ml round bottom flask were added 3,6-dimethyl-1H-indole (1.000 g, 6.89 mmol) and DCM (20 mL). NBS (1.164 g, 6.54 mmol) was dissolved in 5 ml of DCE and added to the reaction drop-wise via an addition funnel over 15 minutes. The reaction was quenched with 5 ml of a 10% sodium sulfite solution. The mixture was diluted with DCM (50 ml). The contents of the flask was transferred to a separatory funnel and the layers were separated. The organics were washed with water, then brine, dried over anhydrous sodium sulfate, filtered and concentrated. The residue was taken up in minimal DCM and charged to a 24G ISCO column, which was eluted over 15 minutes using 0-50% ethyl acetate/heptane. Following concentration of the fractions, collected 2-bromo-3,6-dimethyl-1H-indole as a white foam (1.3 g, 84% yield).

Intermediate 115C: 2-(3,4-dimethoxyphenyl)-3,6-dimethyl-1H-indole

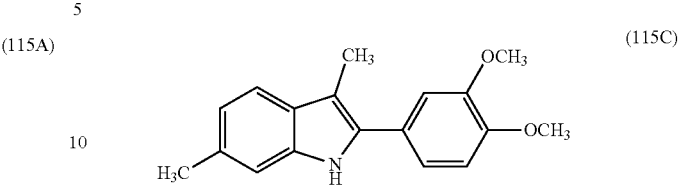
(115C)

In a 2 dram reaction vial, 2-bromo-3,6-dimethyl-1H-indole (0.737 g, 3.29 mmol) was taken in THF (7 mL) and to this was added (3,4-dimethoxyphenyl)boronic acid (0.628 g, 3.45 mmol), PdCl₂(dppf)-CH₂Cl₂ adduct (0.067 g, 0.082 mmol), and a 3M tripotassium phosphate solution (3.29 mL, 9.87 mmol). The mixture was capped and pump/purged with nitrogen gas three times. The reaction mixture heated at 50° C. for 1 hour. The mixture was concentrated in vacuo and the crude residue was diluted with 1 ml of DCM and charged to a 24G ISCO column, which was eluted over a 15 minute gradient using 0-50% ethyl acetate/hexane. Following concentration of the fractions, collected 2-(3,4-dimethoxyphenyl)-3,6-dimethyl-1H-indole as a white solid (0.425 g, 46% yield). LC retention time 1.07 min [1A]. MS (E⁻) m/z: 282 (M−H).

Intermediate 115D: tert-butyl 5-bromo-2-(3,4-dimethoxyphenyl)-3,6-dimethyl-1H-indole-1-carboxylate

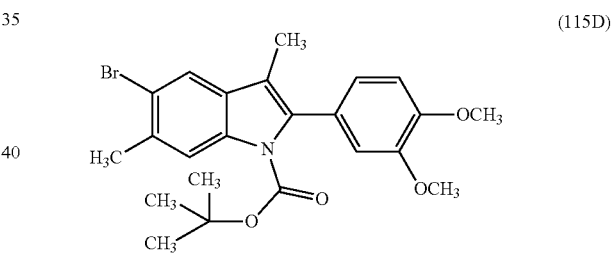
(115D)

To a 100 ml round bottom flask were added 2-(3,4-dimethoxyphenyl)-3,6-dimethyl-1H-indole (0.200 g, 0.711 mmol), THF (5 ml), a crystal of DMAP and boc-anhydride (0.186 g, 0.853 mmol). The reaction mixture was stirred for 2 hours at room temperature, then diluted with ethyl acetate and dilute 1N HCl. The contents of the flask was transferred to a separatory funnel and the layers were separated. The organics were washed with water, then brine, dried over anhydrous sodium sulfate, filtered and concentrated in vacuo. To this was added DCM (3 mL) and NBS (0.120 g, 0.675 mmol) (The NBS was dissolved in 2 ml of DCE and added drop-wise via an addition funnel over 15 minutes to the reaction). The reaction was quenched with 5 ml of a 10% sodium sulfite solution and diluted with DCM (50 ml). The contents of the flask was transferred to a separatory funnel and the layers were separated. The organics were washed with water, then brine, dried over anhydrous sodium sulfate, filtered and concentrated. The residue was taken up in minimal DCM and charged to a 24G ISCO column, which was eluted over 15 minutes using 0-50% ethyl acetate/heptane. Following concentration of the fractions, collected tert-butyl 5-bromo-2-(3,4-dimethoxyphenyl)-3,6-dimethyl- 1H-indole-1-carboxylate (0.05 g, 15.28% yield). LC retention time 1.16 min [1A]. MS (E⁻) m/z: 461 (M–H).

Intermediate 115E: tert-butyl 5-(1-(tert-butoxycarbonyl)-1,2,3,6-tetrahydropyridin-4-yl)-2-(3,4-dimethoxyphenyl)-3,6-dimethyl-1H-indole-1-carboxylate

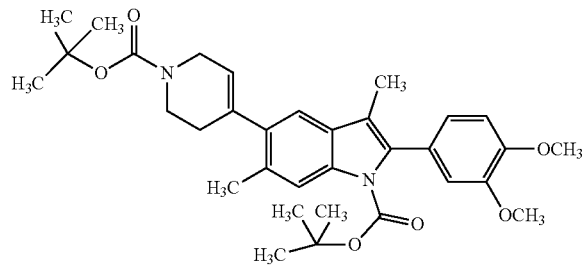
(115E)

To a mixture of 5-bromo-2-(3,4-dimethoxyphenyl)-3,6-dimethyl-1H-indole-1-carboxylate (0.648 g, 1.799 mmol), PdCl$_2$(dppf)-CH$_2$Cl$_2$ adduct (0.037 g, 0.045 mmol) and tert-butyl 4-(4,4,5,5-tetramethyl-1,3,2-dioxaborolan-2-yl)-5,6-dihydropyridine-1(2H)-carboxylate (0.584 g, 1.889 mmol) in a 40 ml reaction vial were added THF (35 mL) followed by an aqueous solution of 3M tripotassium phosphate (1.799 mL, 5.40 mmol). The vial was fitted with a Teflon-lined septum cap. The system was evacuated under vacuum (via a needle from a nitrogen/vacuum manifold line) and back-filled with nitrogen gas. The procedure was repeated three times. The needle was removed and the vial was heated at 75° C. for 18 hours. The reaction mixture was diluted with EtOAc (100 mL), poured into a separatory funnel and washed with water (2×50 mL) and saturated aqueous NaCl solution (50 mL), dried over anhydrous sodium sulfate, filtered and the filtrate concentrated in vacuo to give crude product (0.070 g, 10%). ¹H NMR (400 MHz, DMSO-d$_6$) δ 10.84 (s, 1H), 7.23-7.15 (m, 3H), 7.13-7.06 (m, 2H), 5.76 (s, 1H), 3.86 (s, 3H), 3.82-3.80 (m, 3H), 3.64-3.59 (m, 4H), 1.80-1.73 (m, 2H), 1.50 (s, 3H), 1.46 (s, 9H), 1.44 (s, 3H).

Intermediate 115F: 2-(3,4-dimethoxyphenyl)-3,6-dimethyl-5-(piperidin-4-yl)-1H-indole hydrochloride

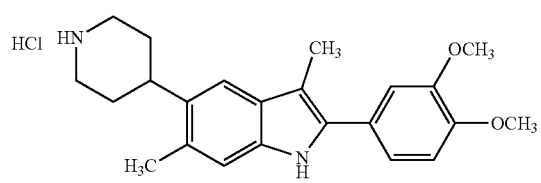
(115F)

To a 100 ml round bottom flask were added tert-butyl 4-(2-(3,4-dimethoxyphenyl)-3, 6-dimethyl-1H-indol-5-yl)-5,6-dihydropyridine-1(2H)-carboxylate (0.070 g, 0.151 mmol) and ethyl acetate (5 mL). The flask was purged with nitrogen gas and Pd/C (8.05 mg, 7.57 μmol) were added. Following pump/purging with nitrogen gas three times, hydrogen gas was introduced via a balloon. The reaction mixture was stirred at room temperature overnight. The flask was evacuated and filled with nitrogen gas. The suspension was filtered through fluted filter paper and the filtrate was concentrated. To this was added 4M hydrogen chloride solution in 1,4-dioxane (1.892 mL, 7.57 mmol) and the reaction mixture was stirred at room temperature for 1 hour, then concentrated to dryness under a stream of nitrogen gas to give product (0.05 g, 15.28% yield). LC retention time 0.73 min [1A]. MS (E⁻) m/z: 365 (M–H).

Example 115

To a 2 dram vial were added 2-(3,4-dimethoxyphenyl)-3,6-dimethyl-5-(piperidin-4-yl)-1H-indole hydrochloride (0.030 g, 0.075 mmol) and DMF (1 mL). To this were added TEA (0.052 mL, 0.374 mmol) and 1-isopropylpiperidin-4-one (10.57 mg, 0.075 mmol) and 1 drop of acetic acid. The reaction mixture was stirred for 1 hour at room temperature and sodium cyanoborohydride (0.014 g, 0.224 mmol) was added. The reaction mixture was stirred overnight at room temperature. The reaction was quenched with water, concentrated to a residue and diluted with 1 ml of DMSO. The solids were filtered off the crude material was purified via preparative LC/MS with the following conditions: Column: Waters XBridge C18, 19×200 mm, 5-μm particles; Mobile Phase A: 5:95 acetonitrile:water with 0.1% ammonium acetate; Mobile Phase B: 95:5 acetonitrile:water with 0.1% ammonium acetate; Gradient: 15-100% B over 25 minutes, then a 5-minute hold at 100% B; Flow: 20 mL/min. Fractions containing the desired product were combined and dried via centrifugal evaporation. 2-(3,4-dimethoxyphenyl)-5-(1'-isopropyl-[1,4'-bipiperidin]-4-yl)-3,6-dimethyl-1H-indole-di-trifluoroacetic acid (0.0065 g, 17% yield). Two analytical LC/MS injections were used to determine the final purity. (1) LC retention time 1.42 min [C1]. MS (E⁻) m/z: 490 (M–H). (2) LC retention time=1.05 min [D1]. MS (E⁻) m/z: 490 (M–H).

Example 116

1-(4-(2-(3,4-dimethoxyphenyl)-3-isobutyl-1H-indol-5-yl)piperidin-1-yl)-2-(ethylamino)ethanone trifluoroacetic acid

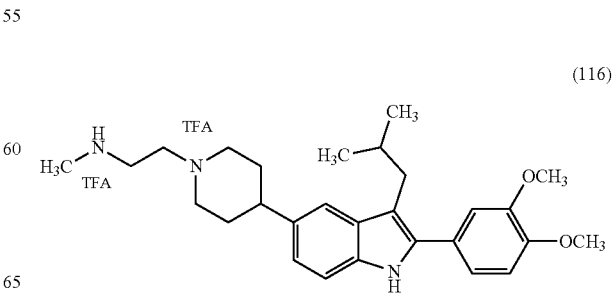
(116)

Intermediate 116A: 5-bromo-3-isobutyl-1H-indole

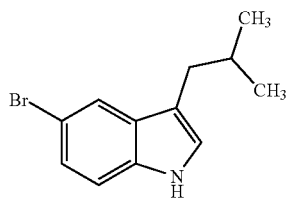

To a 2 dram vial were added 5-bromo-1H-indole (0.257 g, 1.311 mmol), Shvo's Catalyst (0.014 g, 0.013 mmol), potassium carbonate (9.06 mg, 0.066 mmol) and diisobutylamine (0.458 ml, 2.62 mmol). The reaction mixture was purged with nitrogen gas and heated to 155° C. for 48 hours. The reaction mixture was concentrated under a stream of nitrogen gas. The resulting residue was diluted with DCM and charged to 12G ISCO column, which was eluted with 0-50% ethyl acetate/hexane. Following concentration of the fractions, collected product as a yellowish oil (0.068 g, 21%). LC retention time=1.15 min [Method A1]. MS (E⁻) m/z: 253 (M−H).

Intermediate 116B: tert-butyl 4-(3-isobutyl-1H-indol-5-yl)-3,6-dihydropyridine-1(2H)-carboxylate

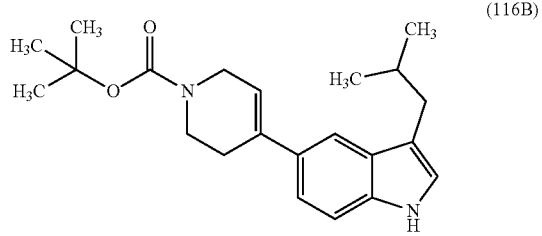 [SMILES: CC(C)Cc1c[nH]c2ccc(C3=CCN(C(=O)OC(C)(C)C)CC3)cc12]

Tert-butyl 4-(3-isobutyl-1H-indol-5-yl)-5,6-dihydropyridine-1(2H)-carboxylate was prepared according to the general procedure described in Intermediate 1B for tert-butyl 4-(3-isopropyl-1H-indol-5-yl)-5,6-dihydropyridine-1(2H)-carboxylate using 5-bromo-3-isobutyl-1H-indole as the starting intermediate (0.080 g, 84% yield). LC retention time 1.19 min [Method A1]. MS (E⁻) m/z: 355 (M−H).

Intermediate 116C: tert-butyl 4-(3-isobutyl-1H-indol-5-yl)piperidine-1-carboxylate

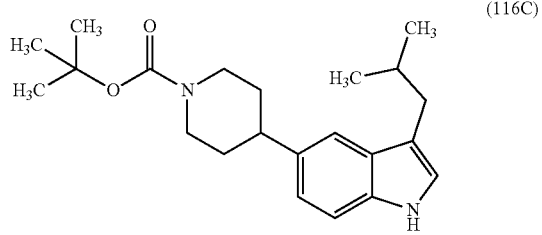 [SMILES: CC(C)Cc1c[nH]c2ccc(C3CCN(C(=O)OC(C)(C)C)CC3)cc12]

Tert-butyl 4-(3-isobutyl-1H-indol-5-yl)piperidine-1-carboxylate was prepared according to the general procedure described in Intermediate 1C for tert-butyl 4-(3-isopropyl-1H-indol-5-yl) piperidine-1-carboxylate using tert-butyl 4-(3-isobutyl-1H-indol-5-yl)-5,6-dihydropyridine-1(2H)-carboxylate as the starting intermediate (0.072 g, 97%). LC retention time 1.20 min [Method A1]. MS (E⁻) m/z: 357 (M−H).

Intermediate 116D: tert-butyl 4-(2-bromo-3-isobutyl-1H-indol-5-yl)piperidine-1-carboxylate

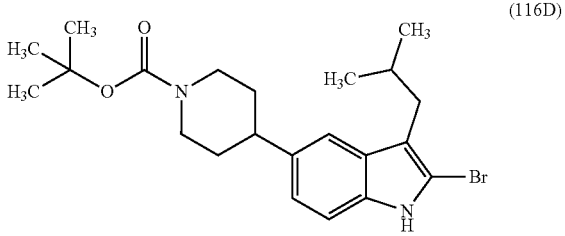 [SMILES: CC(C)Cc1c(Br)[nH]c2ccc(C3CCN(C(=O)OC(C)(C)C)CC3)cc12]

Tert-butyl 4-(2-bromo-3-isobutyl-1H-indol-5-yl)piperidine-1-carboxylate was prepared according to the general procedure described in Intermediate 1D for tert-butyl 4-(2-bromo-3-isopropyl-1H-indol-5-yl)piperidine-1-carboxylate using tert-butyl 4-(3-isobutyl-1H-indol-5-yl)piperidine-1-carboxylate as the starting intermediate (0.020 g, 20% yield). LC retention time 1.26 min [Method A1]. MS (E⁻) m/z: 435/437 (M−H).

Intermediate 116E: tert-butyl 4-(2-(3,4-dimethoxyphenyl)-3-isobutyl-1H-indol-5-yl) piperidine-1-carboxylate

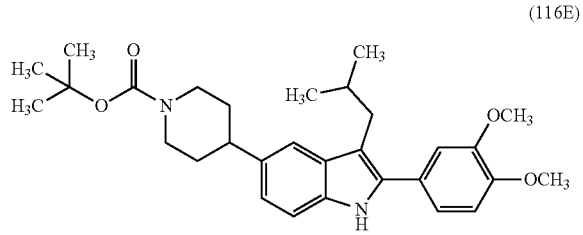 [SMILES: COc1ccc(-c2[nH]c3ccc(C4CCN(C(=O)OC(C)(C)C)CC4)cc3c2CC(C)C)cc1OC]

Tert-butyl 4-(2-(3,4-dimethoxyphenyl)-3-isobutyl-1H-indol-5-yl)piperidine-1-carboxylate was prepared according to the general procedure described in Intermediate 1E for tert-butyl 4-(2-(3,4-dimethoxyphenyl)-3-isopropyl-1H-indol-5-yl)piperidine-1-carboxylate using tert-butyl 4-(2-bromo-3-isobutyl-1H-indol-5-yl)piperidine-1-carboxylate as the starting intermediate. LC retention time 1.24 min [Method A1]. MS (E⁻) m/z: 493 (M−H).

Intermediate 116F: 2-(3,4-dimethoxyphenyl)-3-isobutyl-5-(piperidin-4-yl)-1H-indole hydrochloride

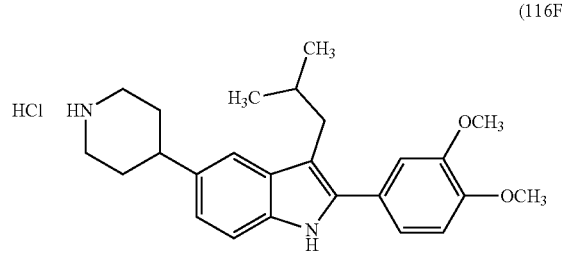 [SMILES: Cl ; COc1ccc(-c2[nH]c3ccc(C4CCNCC4)cc3c2CC(C)C)cc1OC]

(116F)

2-(3,4-dimethoxyphenyl)-3-isobutyl-5-(piperidin-4-yl)-1H-indole, HCl was prepared according to the general procedure described in Intermediate 1F for tert-butyl 4-(2-(3,4-dimethoxyphenyl)-3-isopropyl-1H-indol-5-yl)piperidine-1-carboxylate using Tert-butyl 4-(2-(3,4-dimethoxyphenyl)-3-isobutyl-1H-indol-5-yl)piperidine-1-carboxylate as the starting intermediate (0.031 g, 100% yield). LC retention time 0.9 min [Method A1]. MS (E⁻) m/z: 393 (M−H).

Example 116

2-(4-(2-(3,4-dimethoxyphenyl)-3-isobutyl-1H-indol-5-yl)piperidin-1-yl)-N-methylethanamine di trifluoroacetic acid was prepared according to the general procedure described in Example 98 for 2-(4-(2-(3,4-dimethoxyphenyl)-3-methyl-1H-indol-5-yl)piperidin-1-yl)-N-methyl-ethanamine dihydrochloride using 2-(3,4-dimethoxyphenyl)-3-isobutyl-5-(piperidin-4-yl)-1H-indole, HCl as the starting intermediate.

The crude material was purified via preparative LC/MS with the following conditions: Column: Waters XBridge C18, 19×200 mm, 5-μm particles; Mobile Phase A: 5:95 acetonitrile:water with 0.1% ammonium acetate; Mobile Phase B: 95:5 acetonitrile:water with 0.1% ammonium acetate; Gradient: 15-100% B over 25 minutes, then a 5-minute hold at 100% B; Flow: 20 mL/min. Fractions containing the desired product were combined and dried via centrifugal evaporation. The crude material was purified via preparative LC/MS with the following conditions: Column: Waters XBridge C18, 19×200 mm, 5-μm particles; Mobile Phase A: 5:95 acetonitrile:water with 0.1% ammonium hydroxide; Mobile Phase B: 95:5 acetonitrile:water with 0.1% ammonium hydroxide; Gradient: 15-100% B over 25 minutes, then a 5-minute hold at 100% B; Flow: 20 mL/min. Fractions containing the desired product were combined and dried via centrifugal evaporation. 1-(4-(2-(3,4-dimethoxyphenyl)-3-isobutyl-1H-indol-5-yl)piperidin-1-yl)-2-(ethylamino)ethanone trifluoroacetic acid (0.0024 g, 12% yield). Two analytical LC/MS injections were used to determine the final purity. (1) LC retention time 1.21 min [C1]. MS (E⁻) m/z: 450 (M−H). (2) LC retention time=1.38 min [D1]. MS (E⁻) m/z: 450 (M−H).

Example 117

2-(4-(3-(cyclopropylmethyl)-2-(3,4-dimethoxyphenyl)-1H-indol-5-yl)piperidin-1-yl)-N-methyl-ethanamine di-trifluoroacetic acid

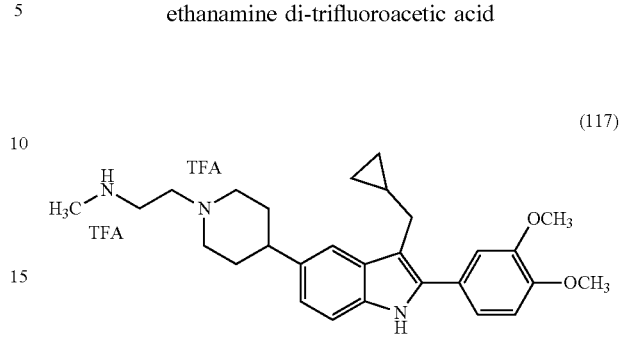

(117)

Intermediate 117A: 5-bromo-3-cyclopropylmethyl-1H-indole

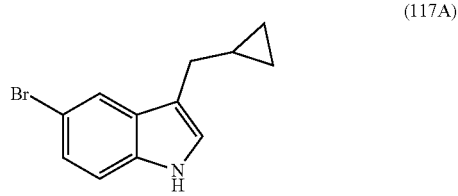 [SMILES: Brc1ccc2[nH]cc(CC3CC3)c2c1]

(117A)

To a 30 ml pressure tube were added 5-bromo-1H-indole (1.000 g, 5.10 mmol), Shvo's Catalyst (0.055 g, 0.051 mmol), potassium carbonate (0.035 g, 0.255 mmol) and cyclopropyl methanamine (1.451 g, 20.40 mmol). The reaction mixture was purged with nitrogen gas and heated to 155° C. for 48 hours. The reaction mixture was diluted with DCM, washed with 1N HCl and the combined organics were dried over anhydrous Na2SO4. The solids were filtered and the filtrate was concentrated. The residue was diluted with DCM and charged to 40G ISCO column, which was eluted with 0-50% ethyl acetate/hexane. Following concentration of the fractions, collected 5-bromo-3-cyclopropylmethyl-1H-indole as a tannish oil.

Intermediate 117B: tert-butyl 4-(3-cyclopropylmethyl-1H-indol-5-yl)-5,6-dihydropyridine-1(2H)-carboxylate

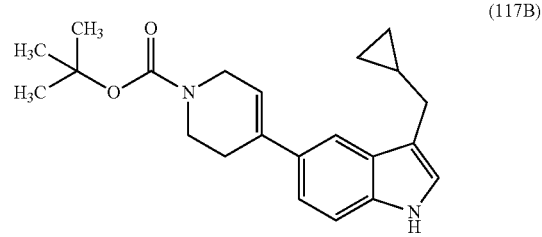 [SMILES: CC(C)(C)OC(=O)N1CC=C(c2ccc3[nH]cc(CC4CC4)c3c2)CC1]

(117B)

Tert-butyl 4-(3-cyclopropylmethyl-1H-indol-5-yl)-5,6-dihydropyridine-1(2H)-carboxylate was prepared according to the general procedure described in Intermediate 1B for tert-butyl 4-(3-isopropyl-1H-indol-5-yl)-5,6-dihydropyridine-1(2H)-carboxylate using 5-bromo-3-cyclopropylmethyl-1H-indole as the starting intermediate (0.205 g, 43% yield). LC retention time 1.28 min [Method A1]. MS (E⁻) m/z: 353 (M−H).

Intermediate 117C: tert-butyl 4-(3-(cyclopropylmethyl)-1H-indol-5-yl)piperidine-1-carboxylate

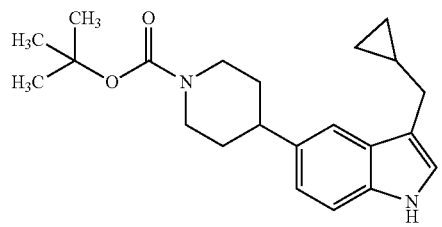

(117C)

Tert-butyl 4-(3-cyclopropylmethyl-1H-indol-5-yl)piperidine-1-carboxylate was prepared according to the general procedure described in Intermediate 1C for tert-butyl 4-(3-isopropyl-1H-indol-5-yl)piperidine-1-carboxylate using tert-butyl 4-(3-cyclopropyl-1H-indol-5-yl)-5,6-dihydropyridine-1(2H)-carboxylate as the starting intermediate.

Intermediate 117D: tert-butyl 4-(2-bromo-3-(cyclopropylmethyl)-1H-indol-5-yl) piperidine-1-carboxylate

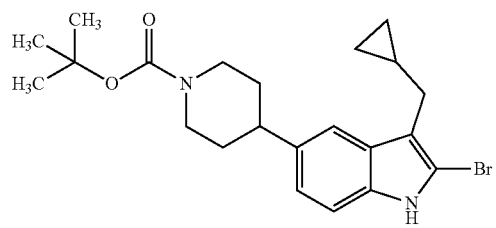

(117D)

Tert-butyl 4-(2-bromo-3-cyclopropylmethyl1-1H-indol-5-yl)piperidine-1-carboxylate was prepared according to the general procedure described in Intermediate 1D for tert-butyl 4-(2-bromo-3-isopropyl-1H-indol-5-yl)piperidine-1-carboxylate using tert-butyl 4-(3-cyclopropylmethyl-1H-indol-5-yl)piperidine-1-carboxylate as the starting intermediate (0.214 g, 88% yield). LC retention time 1.28 min [Method A1]. MS (E⁻) m/z: 377/379 (M−H).

Intermediate 117E: tert-butyl (2-(4-(2-bromo-3-(cyclopropylmethyl)-1H-indol-5-yl) piperidin-1-yl) ethyl)(methyl)carbamate

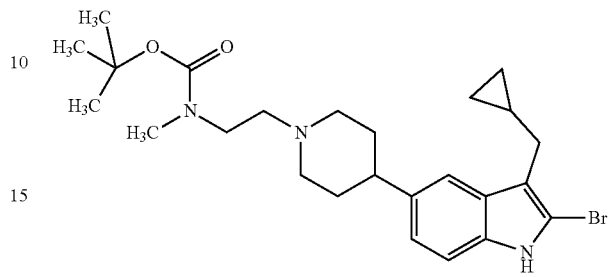

(117E)

To a 2 dram vial were added tert-butyl 4-(2-bromo-3-(cyclopropylmethyl)-1H-indol-5-yl)piperidine-1-carboxylate (0.065 g, 0.150 mmol) and DCM (5 mL). The reaction mixture was placed under a nitrogen atmosphere, cooled to 0° C. and hydrobromic acid in acetic acid (0.037 mL, 0.225 mmol) was added drop-wise via syringe. The reaction mixture was stirred at 0° C. for 15 minutes. The reaction was quenched with TEA (0.105 mL, 0.750 mmol). To the mixture was added tert-butyl methyl(2-oxoethyl)carbamate (0.029 g, 0.165 mmol) in 1 ml of DCM. The reaction mixture was stirred at room temperature for 15 minutes and sodium triacetoxyborohydride (0.095 g, 0.450 mmol) was added. The reaction mixture was stirred at room temperature for 1 hour. The reaction mixture was diluted with water and DCM and the layers were separated. The combined organics were washed with a saturated NaCl solution, dried over anhydrous Na₂SO₄, filtered and concentrated. The residue was diluted with 1 ml of DCM and charged to a 12G ISCO column, which was then eluted with 0-20% MeOH/DCM. Following concentration of the fractions, (2-(4-(2-bromo-3-(cyclopropylmethyl)-1H-indol-5-yl)piperidin-1-yl)ethyl)(methyl)carbamate (0.067 g, 91% yield) was collected as a yellowish solid.

Example 117

In a 2 dram vial, tert-butyl (2-(4-(2-bromo-3-(cyclopropylmethyl)-1H-indol-5-yl) piperidin-1-yl)ethyl)(methyl)carbamate (0.020 g, 0.041 mmol) was taken in THF (1 mL) and 2-(3,4-dimethoxyphenyl)-4,4,5,5-tetramethyl-1,3,2-dioxaborolane (0.013 g, 0.049 mmol), di-tert-butyl-di-phosphino palladium dichloride (1.329 mg, 2.039 µmol), and 3M potassium phosphate solution (0.041 mL, 0.122 mmol) were added. The vial was capped and pump/purged with nitrogen gas three times. The reaction mixture was set to heat at 70° C. for 1 hour. The mixture was concentrated. The crude residue was diluted with DCM and to this was added 0.1 ml of TFA. The reaction mixture was stirred at room temperature for 30 minutes, then concentrated to dryness. The crude material was purified via preparative LC/MS with the following conditions: Column: Waters XBridge C18, 19×200 mm, 5-µm particles; Mobile Phase A: 5:95 acetonitrile:water with 0.1% ammonium acetate; Mobile Phase B: 95:5 acetonitrile:water with 0.1% ammonium acetate; Gradient: 15-100% B over 25 minutes, then a 5-minute hold at 100% B; Flow: 20 mL/min. Fractions containing the desired product were combined and dried via centrifugal evaporation. 2-(4-(3-(cyclopropylmethyl)-2-(3,4-dimethoxyphenyl)-1H- indol-5-yl)piperidin-1-yl)-N-methylethanamine di-trifluoroacetic acid (0.009 g, 47% yield). Two analytical LC/MS injections were used to determine the final purity. (1) LC retention time 1.63 min [C1]. MS (E⁻) m/z: 448 (M–H). (2) LC retention time=1.63 min [D1]. MS (E⁻) m/z: 448 (M–H).

Example 118

2-(3,4-dimethoxyphenyl)-5-(1-(2-(methylamino) ethyl)piperidin-4-yl)-1H-indole-3-carbonitrile-di-trifluoroacetic acid

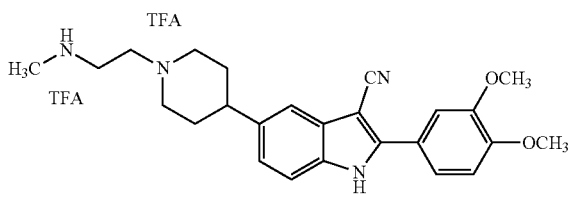

(118)

Intermediate 118A: tert-butyl 4-(3-cyano-1H-indol-5-yl)piperidine-1-carboxylate

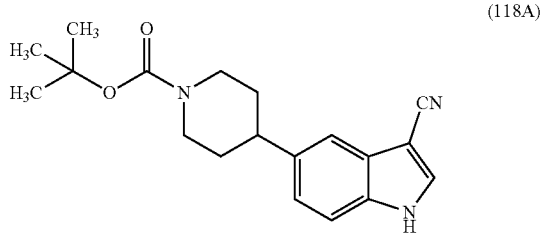 [SMILES: CC(C)(C)OC(=O)N1CCC(c2ccc3[nH]cc(C#N)c3c2)CC1]

(118A)

In a 2 dram vial, 5-bromo-1H-indole-3-carbonitrile (0.500 g, 2.262 mmol) was taken in THF (2 mL) and tert-butyl 4-(4,4,5,5-tetramethyl-1,3,2-dioxaborolan-2-yl)-5,6-dihydropyridine-1(2H)-carboxylate (0.190 g, 0.614 mmol), PdCl₂(dppf)-CH₂Cl₂ adduct (0.023 g, 0.028 mmol), and 3M dipotassium phosphate solution (0.559 mL, 1.676 mmol) were added. The vial was capped and pump/purged with nitrogen gas three times. The reaction mixture was set to heat at 50° C. for 1 hour. The mixture was cooled to room temperature and concentrated under a stream of nitrogen gas. The crude residue was diluted with DCM and charged to a 40G ISCO column, which was eluted with 0-70% ethyl acetate/hexane. Following concentration of the fractions, product was collected as a clear oil. The oil was transferred to a 100 ml round bottom flask with EtOAc. Following a nitrogen purge, Pd/C (0.059 g, 0.559 mmol) was introduced and the vessel was pump/purged with nitrogen gas then back-filled with hydrogen gas via balloon. The reaction mixture was allowed to stir at atmospheric pressure overnight. The suspension was filtered and the cake was rinsed with MeOH. The material was concentrated to dryness via rota-evaporation and used as such in the next step. (0.145 g, 80% yield). LC retention time 0.98 min [Method A1]. MS (E⁻) m/z: 326 (M–H).

Intermediate 118B: isopropyl 4-(2-bromo-3-cyano-1H-indol-5-yl)piperidine-1-carboxylate

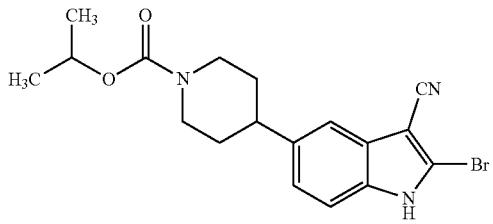

(118B)

To a 100 ml round bottom flask were added tert-butyl 4-(3-cyano-1H-indol-5-yl) piperidine-1-carboxylate (0.550 g, 1.690 mmol) and DCE (7 mL). NBS (0.286 g, 1.606 mmol) was dissolved in 2 ml of DCE and added to the reaction mixture drop-wise via an addition funnel over 15 minutes. The reaction mixture was allowed to heat at 50° C. for 1 hour. The reaction was quenched with 5 ml of a 10% sodium sulfite solution and the volatiles were removed in vacuo. The residue was dissolved in DCM (1 ml), filtered and loaded onto a 24G ISCO column, which was eluted using 0-50% ethyl acetate/heptane. Following concentration of the fractions, collected product as a white foam (0.245 g, 36%). LC retention time 1.04 min [Method A1]. MS (E⁻) m/z: 405/407 (M–H).

Intermediate 118C: 2-(3,4-dimethoxyphenyl)-5-(piperidin-4-yl)-1H-indole-3-carbonitrile hydrochloride

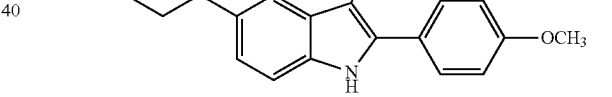

(118C)

To a 40 ml reaction vial were added tert-butyl 4-(2-bromo-3-cyano-1H-indol-5-yl)piperidine-1-carboxylate (0.040 g, 0.099 mmol), (3,4-dimethoxyphenyl)boronic acid (0.020 g, 0.109 mmol), THF (15 mL), PdCl₂(dppf)-CH₂Cl₂ adduct (4.04 mg, 4.95 µmol) and 3M potassium phosphate solution (0.099 mL, 0.297 mmol). The vial was capped with a Teflon-lined cap and flushed with nitrogen for 1 minute. The reaction mixture was set to heat at 50° C. for 1 hour. The mixture was cooled to room temperature and concentrated. The crude residue was diluted with DCM and charged to a 4G ISCO column, which was eluted with 0-70% ethyl acetate/hexane. Following concentration of the fractions, collected product as a clear oil. To this were added DCM (0.5 ml) and 4M HCl in dioxane (0.5 ml). The reaction mixture was stirred at room temperature for 30 minutes, then concentrated to dryness under a stream of nitrogen to give 2-(3,4-dimethoxyphenyl)-5-(piperidin-4-yl)-1H-indole-3-carbonitrile hydrochloride (0.022 g, 60%). LC retention time 0.67 min [Method A1]. MS (E⁻) m/z: 362 (M–H).

Example 118

To a 40 ml reaction vial were added 2-(3,4-dimethoxyphenyl)-5-(piperidin-4-yl)-1H-indole-3-carbonitrile hydrochloride (10.00 mg, 0.025 mmol) and DCM (1 mL). To this were added TEA (0.018 mL, 0.126 mmol) followed by tert-butyl(2-oxoethyl) carbamate (4.80 mg, 0.030 mmol) and acetic acid (1.439 µl, 0.025 mmol). The mixture was stirred at room temperature for 15 minutes and sodium triacetoxyborohydride (0.016 g, 0.075 mmol) was added. The reaction mixture was stirred at room temperature for 4 hours. The reaction mixture was diluted with water and ethyl acetate and the layers were separated. The organics were combined and washed with saturated sodium chloride solution, dried over anhydrous sodium sulfate, filtered and the filtrate was concentrated in vacuo. The residue was diluted with 1 ml of DCM and 1 ml of TFA and stirred for 25 minutes at room temperature, then concentrated to a viscous oil. The crude material was purified via preparative LC/MS with the following conditions: Column: Waters XBridge C18, 19×200 mm, 5-µm particles; Mobile Phase A: 5:95 acetonitrile:water with 0.1% ammonium acetate; Mobile Phase B: 95:5 acetonitrile:water with 0.1% ammonium acetate; Gradient: 15-100% B over 25 minutes, then a 5-minute hold at 100% B; Flow: 20 mL/min. Fractions containing the desired product were combined and dried via centrifugal evaporation. 2-(3,4-dimethoxyphenyl)-5-(1-(2-(methylamino)ethyl)piperidin-4-yl)-1H-indole-3-carbonitrile-di-trifluoroacetic acid (0.0052 g, 47% yield). Two analytical LC/MS injections were used to determine the final purity. (1) LC retention time 1.33 min [C1]. MS (E⁻) m/z: 419 (M–H). (2) LC retention time=0.95 min [D1]. MS (E⁻) m/z: 419 (M–H).

Example 119

2-(3,4-2-(4-(3-chloro-2-(3,4-dimethoxyphenyl)-1H-indol-5-yl)piperidin-1-yl)-N-methylethanamine-di-trifluoroacetic acid

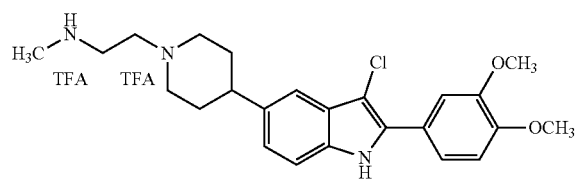

(119)

Intermediate 119A: tert-butyl 4-(1H-indol-5-yl)-5,6-dihydropyridine-1(2H)-carboxylate

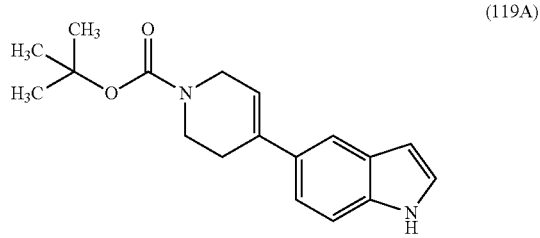 [SMILES: CC(C)(C)OC(=O)N1CC=C(c2ccc3[nH]ccc3c2)CC1]

(119A)

To a mixture of 5-bromo-1H-indole (1.060 g, 5.41 mmol), PdCl₂(dppf)-CH₂Cl₂ adduct (0.110 g, 0.135 mmol), and tert-butyl 4-(4,4,5,5-tetramethyl-1,3,2-dioxaborolan-2-yl)-5,6-dihydropyridine-1(2H)-carboxylate (1.839 g, 5.95 mmol) in a screw cap vial were added THF (13 mL) followed by an aqueous solution of 3M tripotassium phosphate (5.41 mL, 16.22 mmol). The vial was fitted with a Teflon-lined septum cap. The system was evacuated under vacuum (via a needle from a nitrogen/vacuum manifold line) and back-filled with nitrogen gas. The procedure was repeated three times. The needle was removed and the vial was heated at 70° C. for 18 h. The reaction mixture was diluted with EtOAc (100 mL), poured into a separatory funnel and washed with water (2×50 mL) and saturated aqueous NaCl solution (50 mL), dried over anhydrous sodium sulfate and filtered. The filtrate was concentrated in vacuo to give crude product. The crude product was dissolved in a small amount of DCM and charged to an ISCO silica gel column (24G), which was eluted over a 20 min gradient with 0%-50% EtOAc/hexanes to give tert-butyl 4-(1H-indol-5-yl)-5,6-dihydropyridine-1(2H)-carboxylate (1.42 g, 88% yield). LC retention time 1.03 min [Method A1]. MS (E⁻) m/z: 299 (M–H).

Intermediate 119B: tert-butyl 4-(1H-indol-5-yl)piperidine-1-carboxylate

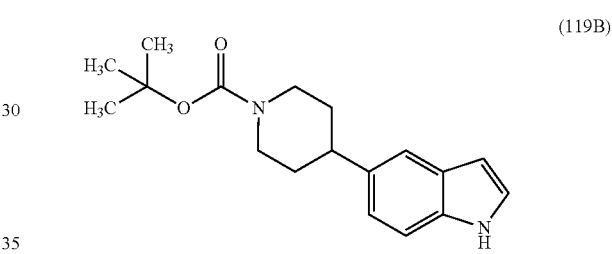

(119B)

To a 250 ml round bottom flask were added tert-butyl 4-(1H-indol-5-yl)-5,6-dihydropyridine-1(2H)-carboxylate (1.300 g, 4.36 mmol) and ethyl acetate (20 mL). The flask was purged with nitrogen gas and Pd/C (0.325 g, 0.305 mmol) was added. Following pump/purging with nitrogen gas three times, hydrogen gas was introduced via a balloon. The reaction mixture was stirred at room temperature overnight. The flask was evacuated and filled with nitrogen gas. The suspension was filtered through fluted filter paper and the filtrate was concentrated in vacuo. Collected tert-butyl 4-(1H-indol-5-yl)piperidine-1-carboxylate as an off-white solid (1.15 g, 88% yield). LC retention time 1.04 min [Method A1]. MS (E⁻) m/z: 301 (M–H).

Intermediate 119C: tert-butyl 4-(3-chloro-1H-indol-5-yl)piperidine-1-carboxylate

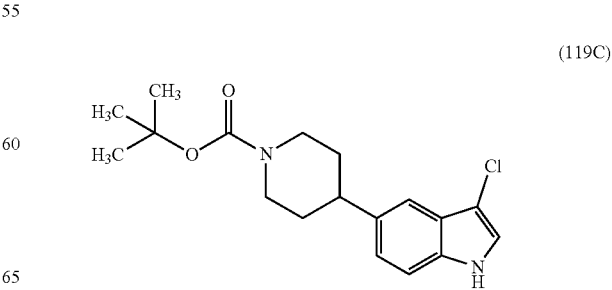

(119C)

To a 100 ml round bottom flask were added tert-butyl 4-(1H-indol-5-yl)piperidine-1-carboxylate (0.210 g, 0.699 mmol) and DCM (6 mL). NCS (0.093 g, 0.699 mmol) was dissolved in 2 ml of DCE and added to the reaction mixture drop-wise via an addition funnel over 15 minutes. The reaction was quenched with 5 ml of a 10% sodium sulfite solution and the volatiles were removed in vacuo. The residue was taken up in DCM (5 ml), filtered and loaded onto a 24G ISCO column, which was eluted over a 15 minute gradient using 0-50% ethyl acetate/heptane. Following concentration of the fractions, collected tert-butyl 4-(3-chloro-1H-indol-5-yl)piperidine-1-carboxylate as a white foam (0.201 g, 86% yield). LC retention time 1.10 min [Method A1]. MS (E⁻) m/z: 335 (M−H).

Intermediate 119D: tert-butyl-4-(2-bromo-3-chloro-1H-indol-5-yl)piperidine-1-carboxylate

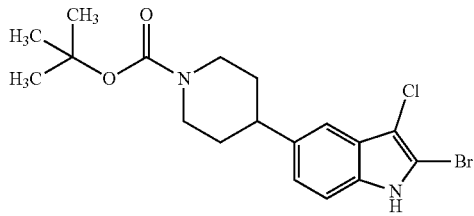

(119D)

To a 100 ml round bottom flask were added tert-butyl 4-(3-chloro-1H-indol-5-yl) piperidine-1-carboxylate (0.130 g, 0.388 mmol) and DCE (6 mL). NBS (0.066 g, 0.369 mmol) was dissolved in 2 ml of DCE and added to the reaction mixture drop-wise via an addition funnel over 15 minutes. The reaction was quenched with 5 ml of a 10% sodium sulfite solution and the volatiles were removed in vacuo. The residue was taken up in DCM (5 ml), filtered and loaded onto a 12G ISCO column, which was eluted over a 15 minute gradient using 0-50% ethyl acetate/heptane. Following concentration of the fractions, collected tert-butyl-4-(2-bromo-3-chloro-1H-indol-5-yl)piperidine-1-carboxylate as a white foam (0.060 g, 37% yield). LC retention time 1.17 min [Method A1]. MS (E⁻) m/z: 414/416 (M−H).

Intermediate 119E: tert-butyl 4-(3-chloro-2-(3,4-dimethoxyphenyl)-1H-indol-5-yl) piperidine-1-carboxylate

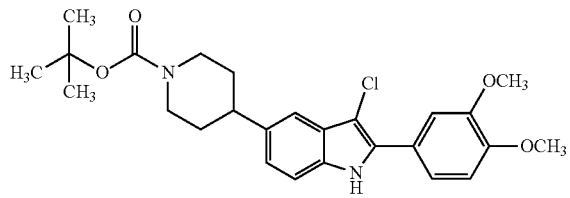

(119E)

To a 2 dram vial were added tert-butyl 4-(2-bromo-3-chloro-1H-indol-5-yl) piperidine-1-carboxylate (0.075 g, 0.181 mmol), (3,4-dimethoxyphenyl)boronic acid (0.040 g, 0.218 mmol), and PdCl₂(dppf)-CH₂Cl₂ adduct (7.40 mg, 9.06 μmol). To this mixture and under a nitrogen gas atmosphere were added THF (1 ml) and a 3M potassium phosphate solution (0.181 mL, 0.544 mmol). The vial was capped and pump/purged with nitrogen gas three times. The reaction mixture was set to heat at 50° C. for 1 hour. Upon cooling, the mixture was concentrated under a stream of nitrogen gas and the crude residue was diluted with 1 ml of DCM and charged to a 12G ISCO column, which was eluted over a 15 minute gradient using 0-50% ethyl acetate/hexane. Following concentration of the fractions, collected tert-butyl 4-(3-chloro-2-(3,4-dimethoxyphenyl)-1H-indol-5-yl)piperidine-1-carboxylate as an off-white solid (0.072 g, 84% yield). LC retention time 1.17 min [Method A1]. MS (E⁻) m/z: 471 (M−H).

Example 119

To a 40 ml reaction vial were added tert-butyl 4-(3-chloro-2-(3,4-dimethoxyphenyl)-1H-indol-5-yl)piperidine-1-carboxylate 3 (0.027 g, 0.073 mmol), DCM (0.55 mL) and TFA (0.5 ml). The reaction mixture was stirred for 15 minutes, then concentrated to dryness under a stream of nitrogen gas. To this residue were added DCM (1 ml), TEA (0.051 mL, 0.364 mmol) and tert-butyl (2-oxoethyl)carbamate (0.014 g, 0.087 mmol). Acetic acid (4.17 μl, 0.073 mmol) was added and the mixture was stirred at room temperature for 15 minutes and then sodium triacetoxyborohydride (0.046 g, 0.218 mmol) was added. The reaction mixture was stirred at room temperature for 4 hours. The reaction was quenched with MeOH and concentrated to dryness. The residue was diluted with 1 ml of DCM and to this was added 0.5 ml of TFA. The mixture was stirred for 15 minutes and concentrated under a stream of nitrogen gas. The residue was diluted with 2 ml of DMSO and filtered through a 0.45 micron syringe filter. The crude material was purified via preparative LC/MS with the following conditions: Column: Waters XBridge C18, 19×200 mm, 5-μm particles; Mobile Phase A: 5:95 acetonitrile:water with 0.1% ammonium hydroxide; Mobile Phase B: 95:5 acetonitrile:water with 0.1% ammonium hydroxide; Gradient: 15-100% B over 25 minutes, then a 5-minute hold at 100% B; Flow: 20 mL/min. Fractions containing the desired product were combined and dried via centrifugal evaporation to give 2-(3,4-2-(4-(3-chloro-2-(3,4-dimethoxyphenyl)-1H-indol-5-yl)piperidin-1-yl)-N-methylethanamine-di-trifluoroacetic acid (0.026 g, 81% yield). Two analytical LC/MS injections were used to determine the final purity. (1) LC retention time 1.41 min [C1]. MS (E⁻) m/z: 428 (M−H). (2) LC retention time=1.10 min [D1]. MS (E⁻) m/z: 428 (M−H).

Example 120

3-chloro-2-(3,4-dimethoxyphenyl)-5-(1'-isobutyl-[1,4'-bipiperidin]-4-yl)-1H-indole di-trifluoroacetic acid

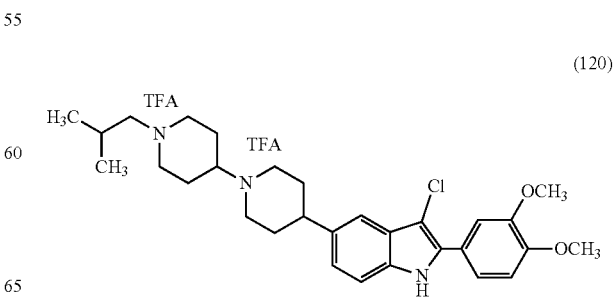

(120)

To a 4 ml reaction vial were added tert-butyl 4-(3-chloro-2-(3,4-dimethoxyphenyl)-1H-indol-5-yl)piperidine-1-carboxylate 3 (0.018 g, 0.038 mmol), DCM (0.55 mL) and TFA (0.5 ml). The reaction mixture was stirred for 15 minutes, then concentrated to dryness under a stream of nitrogen gas. To this residue were added DCM (1 ml) and TEA (0.027 mL, 0.192 mmol) followed by 4-isobutyl-piperidone (7.35 mg, 0.046 mmol) and acetic acid (2.202 µl, 0.038 mmol). The mixture was stirred at room temperature for 15 minutes and sodium cyanoborohydride (7.25 mg, 0.115 mmol) was added. The reaction mixture was stirred at room temperature for 4 hours. The reaction was quenched with MeOH and concentrated to dryness under a stream of nitrogen gas. The residue was diluted with 2 ml of DMSO and filtered through a 0.45 micron syringe filter. The crude material was purified via preparative LC/MS with the following conditions: Column: Waters XBridge C18, 19×200 mm, 5-µm particles; Mobile Phase A: 5:95 acetonitrile:water with 0.1% ammonium hydroxide; Mobile Phase B: 95:5 acetonitrile:water with 0.1% ammonium hydroxide; Gradient: 15-100% B over 25 minutes, then a 5-minute hold at 100% B; Flow: 20 mL/min. Fractions containing the desired product were combined and dried via centrifugal evaporation to afford 3-chloro-2-(3,4-dimethoxyphenyl)-5-(1'-isobutyl-[1,4'-bipiperidin]-4-yl)-1H-indole di-trifluoroacetic acid (0.018 g, 92% yield). Two analytical LC/MS injections were used to determine the final purity. (1) LC retention time 1.57 min [C1]. MS (E⁻) m/z: 510 (M–H). (2) LC retention time=1.17 min [D1]. MS (E⁻) m/z: 510 (M–H).

Example 121

2-(3,4-dimethoxyphenyl)-5-(1'-isobutyl-[1,4'-bipiperidin]-4-yl)-3-propyl-1H-indole-di-trifluoroacetic acid

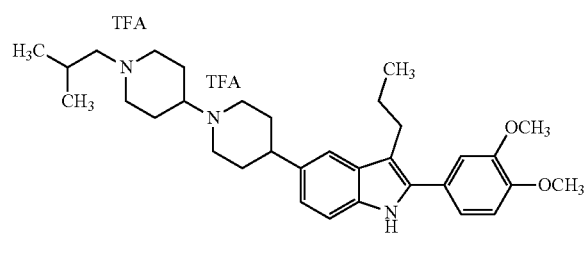

(121)

Intermediate 121A: 5-bromo-3-propyl-1H-indole

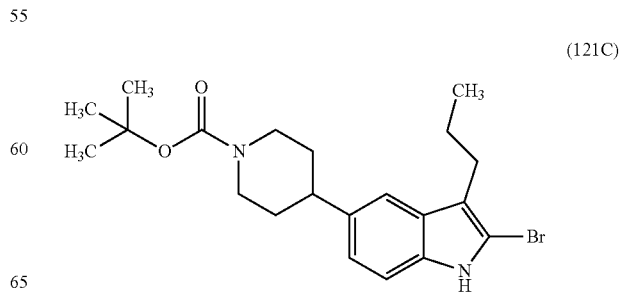

(121A)

To a tall reaction vial were added 5-bromo-1H-indole (2.00 g, 10.20 mmol), Shvo's Catalyst (0.111 g, 0.102 mmol), potassium carbonate (70.0 mg, 0.510 mmol), and dipropylamine (2.06 g, 20.40 mmol). The reaction mixture was purged with nitrogen gas and heated to 155° C. for 48 hours. The mixture was concentrated under a stream of nitrogen gas. The resulting residue was diluted with DCM and charged to a 120G ISCO column, which was eluted with 0-100% ethyl acetate/hexane. Following concentration of the fractions, collected 5-bromo-3-propyl-1H-indole as a yellowish oil (0.500 g, 21%). LC retention time=1.16 min [E1]. MS (E⁻) m/z: 238/240 (M–H).

Intermediate 121B: tert-butyl 4-(3-propyl-1H-indol-5-yl)-5,6-dihydropyridine-1(2H)-carboxylate

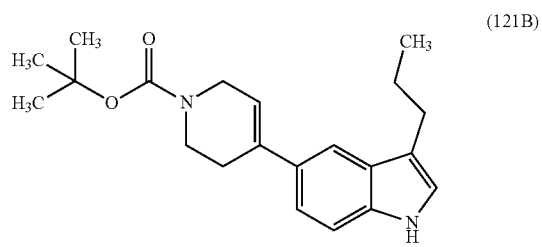 [SMILES: CCCc1c[nH]c2ccc(C3=CCN(C(=O)OC(C)(C)C)CC3)cc12]

(121B)

To a mixture of 5-bromo-3-propyl-1H-indole (0.648 g, 2.72 mmol), PdCl₂(dppf)-CH₂Cl₂ adduct (0.056 g, 0.068 mmol), and tert-butyl 4-(4,4,5,5-tetramethyl-1,3,2-dioxaborolan-2-yl)-5,6-dihydropyridine-1(2H)-carboxylate (0.884 g, 2.86 mmol) in a 100 ml round bottom flask were added THF (35 mL) followed by an aqueous 3M solution of tripotassium phosphate (2.72 mL, 8.16 mmol). The vial was fitted with a Teflon-lined septum cap. The system was evacuated under vacuum (via a needle from a nitrogen/vacuum manifold line) and back-filled with nitrogen gas. The procedure was repeated three times. The needle was removed and the vial was heated at 75° C. for 18 hours. The reaction mixture was diluted with EtOAc (100 mL), poured into a separatory funnel and washed with water (2×50 mL) and saturated aqueous NaCl solution (50 mL). The organics were collected and dried over anhydrous sodium sulfate. The suspension was filtered and the filtrate concentrated in vacuo to give crude product. The crude product was purified using a 40G ISCO silica gel column, which was eluted with 0-100% ethyl acetate/hexane. Following concentration of the fractions, collected tert-butyl 4-(3-propyl-1H-indol-5-yl)-5,6-dihydropyridine-1(2H)-carboxylate as a tan solid (0.768 g, 83%). LC retention time=1.25 min [F1]. MS (E⁻) m/z: 341 (M–H).

Intermediate 121C: tert-butyl 4-(2-bromo-3-propyl-1H-indol-5-yl)piperidine-1-carboxylate (121C)

To a 250 ml round bottom flask were added tert-butyl 4-(3-propyl-1H-indol-5-yl)-5,6-dihydropyridine-1(2H)-carboxylate (0.75 g, 2.20 mmol) and ethyl acetate (5 mL). The flask was purged with nitrogen gas and Pd/C (0.20 g, 0.250 mmol) was added. Following pump/purging with nitrogen gas three times, hydrogen gas was introduced via a balloon. The reaction mixture was stirred at room temperature overnight. The flask was evacuated and filled with nitrogen gas. The suspension was filtered through fluted filter paper and the filtrate was concentrated in vacuo. In a 100 ml round bottom flask were added tert-butyl 4-(3-propyl-1H-indol-5-yl)piperidine-1-carboxylate (0.700 g, 2.044 mmol) and DCE (10 mL). NBS (0.346 g, 1.942 mmol) was dissolved in 10 ml of DCE and added to the reaction mixture drop-wise via an addition funnel over 15 minutes. The reaction was quenched with 5 ml of a 10% sodium sulfite solution and the volatiles were removed in vacuo. The residue was taken up in DCM (2 ml), filtered and loaded onto a 24G ISCO column, which was eluted using 0-50% ethyl acetate/heptane. Following concentration of fractions, collected tert-butyl 4-(2-bromo-3-propyl-1H-indol-5-yl) piperidine-1-carboxylate as an off-white solid (0.79 g, 92% yield). LC retention time 1.25 min [Method A1]. MS (E$^-$) m/z: 422 (M−H).

Example 121

To a 2 dram vial were added tert-butyl 4-(2-bromo-3-propyl-1H-indol-5-yl) piperidine-1-carboxylate (0.039 g, 0.093 mmol), (3,4-dimethoxyphenyl)boronic acid (0.020 g, 0.111 mmol), PdCl$_2$(dppf)-CH$_2$Cl$_2$ adduct (3.78 mg, 4.63 µmol), and THF (1 ml). To this was added a 3M potassium phosphate solution (0.093 mL, 0.278 mmol) and the vial was capped and pump/purged with nitrogen three times. The reaction mixture was heated at 70° C. for 1 hour. The mixture was concentrated under a stream of nitrogen gas. The crude residue was diluted with DCM and the organics were washed with water and then brine. The combined extracts were dried over anhydrous sodium sulfate, filtered and concentrated in vacuo. To this was added 1 ml DCM and TFA (0.071 mL, 0.926 mmol). The reaction mixture was stirred at room temperature for 30 minutes, then concentrated to dryness under a stream of nitrogen gas. The residue was taken up in DMF (1 mL) and to this were added TEA (0.065 mL, 0.463 mmol), 1 drop of acetic acid, and 1-isobutylpiperidin-4-one (0.029 g, 0.185 mmol). The reaction mixture was stirred at room temperature for 1 hour then sodium cyanoborohydride (0.017 g, 0.278 mmol) was added. The vial was capped and mixture was stirred at room temperature overnight. The suspension was filtered through a 0.45 micron syringe filter and the crude material was purified via preparative LC/MS with the following conditions: Column: Waters XBridge C18, 19×200 mm, 5-µm particles; Mobile Phase A: 5:95 acetonitrile:water with 0.1% ammonium hydroxide; Mobile Phase B: 95:5 acetonitrile:water with 0.1% ammonium hydroxide; Gradient: 15-100% B over 25 minutes, then a 5-minute hold at 100% B; Flow: 20 mL/min. Fractions containing the desired product were combined and dried via centrifugal evaporation to afford 2-(3,4-dimethoxyphenyl)-5-(1'-isobutyl-[1,4'-bipiperidin]-4-yl)-3-propyl-1H-indole-di-trifluoroacetic acid (0.0098 g, 20% yield). Two analytical LC/MS injections were used to determine the final purity. (1) LC retention time 1.68 min [C1]. MS (E$^-$) m/z: 518 (M−H). (2) LC retention time=1.25 min [D1]. MS (E$^-$) m/z: 518 (M−H).

Example 122

2-(3,4-dimethoxyphenyl)-3-ethyl-5-(piperidin-4-yl)-1H-indole

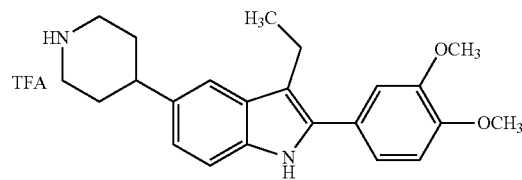

Intermediate 122A: 5-bromo-3-ethyl-1H-indole

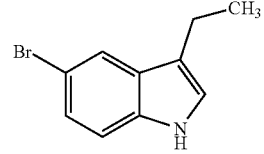

5-bromo-1H-indole (2.80 g, 14.28 mmol), Shvo's Catalyst (0.155 g, 0.143 mmol), potassium carbonate (0.099 g, 0.714 mmol) and diethylamine (2.089 g, 28.6 mmol) were added in a 30 mL pressure tube. The reaction mixture was purged with nitrogen and heated to 155° C. for 20 hours. The reaction mixture was diluted with dichloromethane and washed with 1N HCl. The organic phase was dried over Na$_2$SO$_4$, filtered and concentrated. The residue was purified using silica gel chromatography eluting with 0-50% ethyl acetate/hexane. The product fractions were combined and concentrated to provide white solid product (2.1 g, 9.37 mmol, 65.6% yield). LC retention time 1.06 min [1A]. MS (E$^-$) m/z: 224/226 (M−H).

Intermediate 122B: tert-butyl 4-(3-ethyl-1H-indol-5-yl)-3,6-dihydropyridine-1(2H)-carboxylate

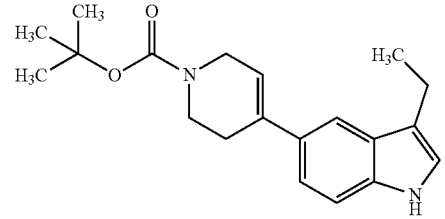

THF (35 mL) was added to a mixture of 5-bromo-3-ethyl-1H-indole (1.950 g, 8.70 mmol), PdCl$_2$(dppf)-CH$_2$Cl$_2$ adduct (0.178 g, 0.218 mmol) and tert-butyl 4-(4,4,5,5-tetramethyl-1,3,2-dioxaborolan-2-yl)-5,6-dihydropyridine-1 (2H)-carboxylate (2.83 g, 9.14 mmol) in a 100 ml round bottom flask. An aqueous solution of 3M tripotassium phosphate (8.70 mL, 26.1 mmol) was added to the reaction mixture. The vial was fitted with a Teflon lined septum cap.

The system was evacuated under vacuum (via a needle from a nitrogen/vacuum manifold line) and backfilled with nitrogen gas. The procedure was repeated three times. The needle was removed and the vial was heated at 75° C. for 18 hours. The reaction mixture was diluted with ethyl acetate (100 mL) and poured into a separatory funnel. The mixture was washed with water (2×50 mL) and saturated aqueous NaCl solution (50 mL), dried (Na$_2$SO$_4$) and filtered. The filtrate was concentrated in vacuum to give crude product. The crude product was purified with silica gel chromatography eluting with 0%-50% ethyl acetate/hexanes over 20 minutes to give tert-butyl 4-(3-ethyl-1H-indol-5-yl)-5,6-dihydropyridine-1(2H)-carboxylate (2.3 g, 7.05 mmol, 81% yield). LC retention time 1.12 min [1A]. MS (E$^-$) m/z: 327 (M–H).

Intermediate 122C: tert-butyl 4-(3-ethyl-1H-indol-5-yl)piperidine-1-carboxylate

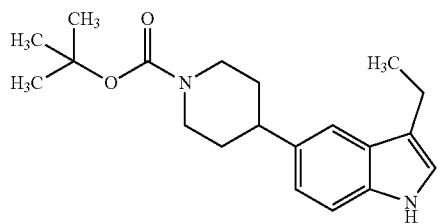

(122C)

Tert-butyl 4-(3-ethyl-1H-indol-5-yl)-5,6-dihydropyridine-1(2H)-carboxylate (2.100 g, 6.43 mmol) and ethyl acetate (20 mL) were added to a 250 mL round-bottom flask. The flask was purged with nitrogen gas. Pd/C (0.479 g, 0.450 mmol) was added to the reaction flask, followed by pump/purging with nitrogen gas, three times. Hydrogen gas was introduced via a balloon. The reaction mixture was stirred at room temperature overnight. The flask was evacuated and back-filled with nitrogen gas. The suspension was filtered through fluted filter paper and the filtrate was concentrated. The residue was purified with flash chromatography (ISCO) eluting with 0-40% ethyl acetate/hexane. The product fractions were combined and concentrated to provide the product as a white solid (1.15 g, 3.50 mmol, 54.4% yield). LC retention time 1.13 min [1A]. MS (E$^-$) m/z: 329 (M–H).

Intermediate 122D: tert-butyl 4-(2-bromo-3-ethyl-1H-indol-5-yl)piperidine-1-carboxylate

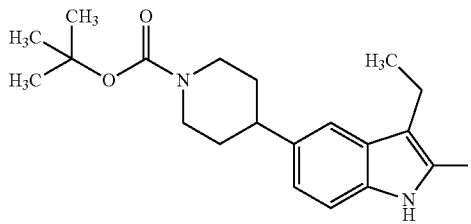

(122D)

Tert-butyl 4-(3-ethyl-1H-indol-5-yl)piperidine-1-carboxylate (1.820 g, 5.54 mmol) and 1,2-dichloroethane (DCE, 10 mL) were added to a 100 mL round-bottom flask. N-bromosuccinimide (NBS, 0.986 g, 5.54 mmol) was dissolved in 10 mL of DCE. The solution of NBS was added to the reaction mixture drop-wise via an addition funnel over 15 minutes. The reaction was quenched with 5 mL of a 10% sodium sulfite solution and the volatiles were removed. The residue was taken up in dichloromethane (5 mL), filtered and loaded onto a silica gel column. The column was eluted with 0-50% ethyl acetate/heptanes. The product fractions were combined and concentrated to provide the product as white foam (1.95 g, 4.79 mmol, 86% yield). LC retention time 1.20 min [1A]. MS (E$^-$) m/z: 408 (M–H).

Intermediate 122E: tert-butyl 4-(2-(3,4-dimethoxyphenyl)-3-ethyl-1H-indol-5-yl) piperidine-1-carboxylate

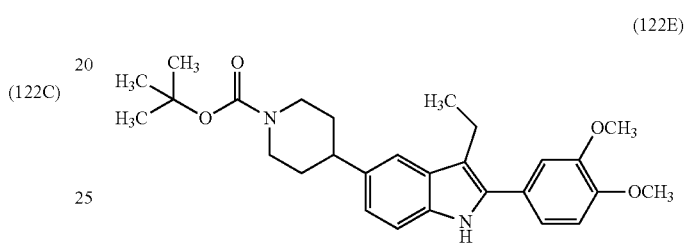

(122E)

To a 2 dram vial were added tert-butyl 4-(2-bromo-3-ethyl-1H-indol-5-yl) piperidine-1-carboxylate (0.014 g, 0.034 mmol), THF (1 mL), (3,4-dimethoxyphenyl) boronic acid (7.51 mg, 0.041 mmol), PdCl$_2$(dppf)-CH$_2$Cl$_2$ adduct (1.120 mg, 1.718 µmol), and 3M tripotassium phosphate solution (0.034 mL, 0.103 mmol). The vessel was capped with a Teflon-lined cap and the mixture was pump/purged with nitrogen gas three times. Following heating at 55° C. for one hour, the mixture was concentrated under a stream of nitrogen gas. The crude residue was diluted with DCM and neutralized with 1N HCl. The organics were collected, then dried over anhydrous sodium sulfate, filtered and concentrated. The crude residue was diluted with DCM and charged to a 24G ISCO column, which was eluted with 0-50% ethyl acetate/hexane. Following concentration of the fractions, the product was collected as a white solid. LC retention time 1.19 min [A1]. MS (E$^-$) m/z: 465 (M–H).

Example 122

To a 2 dram reaction vial was added tert-butyl 4-(2-(3,4-dimethoxyphenyl)-3-ethyl-1H-indol-5-yl)piperidine-1-carboxylate and a 1:1 mixture of DCM and TFA. The reaction mixture was stirred at room temperature for 3 hours, then concentrated to dryness under a stream of nitrogen. Further purification of 20 mg was performed using preparative LC-MS with the following conditions: Column: XBridge C18, 19×200 mm, 5-µm particles; Mobile Phase A: 5:95 acetonitrile: water with 0.1% trifluoroacetic acid; Mobile Phase B: 95:5 acetonitrile: water with 0.1% trifluoroacetic acid; Gradient: 10-100% B over 19 minutes, then a 5-minute hold at 100% B; Flow: 20 mL/min. Fractions containing the desired product were combined and dried via centrifugal evaporation to give 2-(3,4-dimethoxyphenyl)-3-ethyl-5-(piperidin-4-yl)-1H-indole, trifluoroacetic acid (16.0 mg, 85%). Two analytical LC/MS injections were used to determine the final purity: LC retention time 1.32 min [C1]. MS (E+) m/z: 365 (M+H); LC retention time=1.31 min [D1]. MS (E+) m/z: 365 (M+H).

Example 123

2-(3,4-dimethoxyphenyl)-3-ethyl-5-(1'-isobutyl-[1,4'-bipiperidin]-4-yl)-1H-indole-di-trifluoroacetic acid

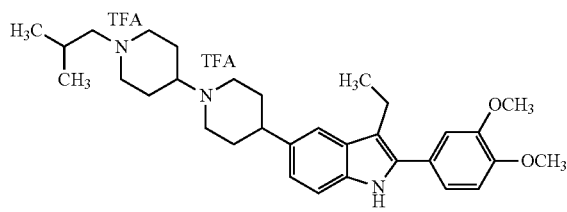

(123)

Intermediate 122E (16.0 mg) was added to DCM (1 mL) and TFA (0.026 mL, 0.344 mmol) was added drop-wise. The reaction mixture was stirred for 30 minutes and concentrated to dryness. To this residue were added DMF (1.0 ml), and TEA (0.048 mL, 0.344 mmol) followed by 1-isobutylpiperidin-4-one (10.67 mg, 0.069 mmol) and 1 drop of acetic acid. The mixture was stirred for 1 hour at room temperature and then sodium cyanoborohydride (6.48 mg, 0.103 mmol) was added. The reaction mixture was set to heat at 50° C. for two hours. Methanol was added and the volatiles were removed under a stream of nitrogen gas. The residue was taken up in 1 ml of DMSO. The solids were filtered off and the crude material was purified via preparative LC/MS with the following conditions: Column: Waters XBridge C18, 19×200 mm, 5-μm particles; Mobile Phase A: 5:95 acetonitrile:water with 0.1% ammonium hydroxide; Mobile Phase B: 95:5 acetonitrile:water with 0.1% ammonium hydroxide; Gradient: 15-100% B over 25 minutes, then a 5-minute hold at 100% B; Flow: 20 mL/min. Fractions containing the desired product were combined and dried via centrifugal evaporation to afford 2-(3,4-dimethoxyphenyl)-3-ethyl-5-(1'-isobutyl-[1,4'-bipiperidin]-4-yl)-1H-indole-di-trifluoroacetic acid (0.0032 g, 18% yield). Two analytical LC/MS injections were used to determine the final purity. (1) LC retention time 1.65 min [C1]. MS (E$^-$) m/z: 504 (M-H). (2) LC retention time=1.22 min [D1]. MS (E$^-$) m/z: 504 (M-H).

The following Examples were prepared according to the general procedure described in Example 123 using 2-(3,4-dimethoxyphenyl)-3-ethyl-5-(piperidin-4-yl)-1H-indole, trifluoroacetic acid as the starting intermediate.

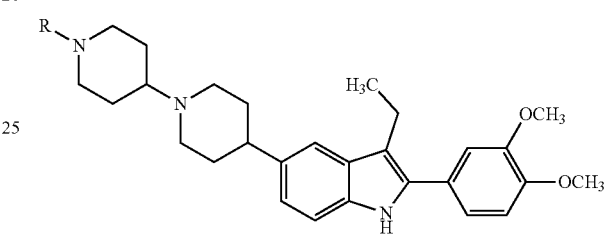

TABLE 9

| Ex. No. | R | M$^{+1}$ | RT (min) | Method |
|---|---|---|---|---|
| 124 | ![oxazole-methyl] H$_3$C-oxazole-CH$_2$- | 543.5 | 1.19 | B |
| 125 | ![imidazole-methyl] | 528.5 | 1.1 | B |
| 126 | ![methyloxazole] H$_3$C-oxazole-CH$_2$- | 543.5 | 1.48 | A |
| 127 | ![pyrrole ester] | 627.6 | 1.85 | A |
| 128 | ![indole-methyl] | 577.6 | 1.43 | B |

TABLE 9-continued

| Ex. No. | R | M⁺¹ | RT (min) | Method |
|---|---|---|---|---|
| 129 | 2-methyl-1H-indol-3-yl-ethyl | 591.5 | 1.4 | B |
| 130 | 1,2,3-thiadiazol-4-yl-methyl | 546.3 | 1.18 | B |
| 131 | 3-methyl-1H-pyrazol-5-yl-methyl | 542.5 | 1.2 | B |
| 132 | 1,3-dimethyl-1H-pyrazol-5-yl-methyl | 556.5 | 1.22 | B |
| 133 | 1-methyl-1H-pyrazol-3-yl-methyl | 542.4 | 1.16 | B |
| 134 | oxazol-5-yl-methyl | 543.3 | 1.18 | B |
| 135 | 1-(oxazol-2-yl)ethyl | 529.4 | 1.38 | A |
| 136 | 1-methyl-1H-imidazol-2-yl-methyl | 542.4 | 1.19 | B |
| 137 | 1-methyl-1H-indol-2-yl-methyl | 591.4 | 1.42 | B |
| 138 | 3,5-dimethylisoxazol-4-yl-methyl | 557.4 | 1.19 | B |
| 139 | 3-methylthiophen-2-yl-methyl | 558.5 | 1.95 | A |

TABLE 9-continued
| Ex. No. | R | M⁺¹ | RT (min) | Method |
|---|---|---|---|---|
| 140 | 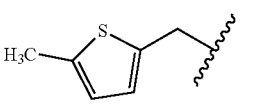 [SMILES: *Cc1ccc(C)s1] | 558.5 | 1.34 | B |
| 141 | 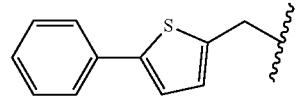 [SMILES: *Cc1ccc(-c2ccccc2)s1] | 620.5 | 2.23 | A |
| 142 | 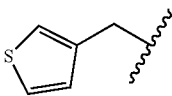 [SMILES: *Cc1ccsc1] | 544.4 | 1.28 | B |
| 143 | 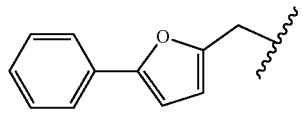 [SMILES: *Cc1ccc(-c2ccccc2)o1] | 604.6 | 1.5 | B |
| 144 | 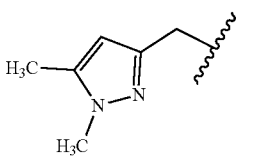 [SMILES: *Cc1cc(C)n(C)n1] | 556.5 | 1.24 | B |
| 145 | —CH(OH)CH₂CH₂CH₂OH | 534.4 | 1.37 | A |
| 146 | 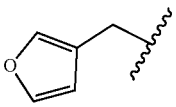 | 528.5 | 1.24 | B |
| 147 | 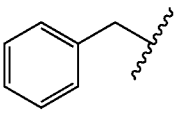 [SMILES: *Cc1ccccc1] | 539.5 | 1.13 | B |
| 149 | —CH₂CH₃ | 476 | 1.11 | D1 |
| 150 | —CH₃ | 462 | 1.09 | D1 |
| 151 | —CH(CH₃)₂ | 490 | 1.19 | D1 |
| 152 | 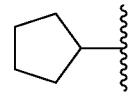 | 516 | 1.17 | D1 |
| 153 | 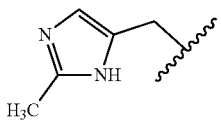 | 542.5 | 1.13 | A |

Example 155

2-(4-(2-(3,4-dimethoxyphenyl)-3-ethyl-1H-indol-5-yl)piperidin-1-yl)-N-methylethanamine di-trifluoroacetic acid

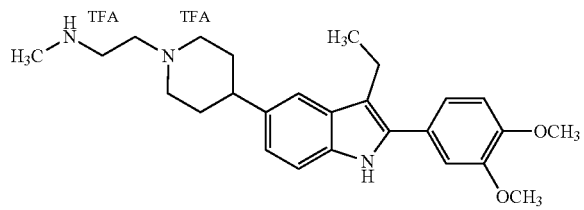

(155)

Intermediate 155A: tert-butyl (2-(4-(2-bromo-3-ethyl-1H-indol-5-yl)piperidin-1-yl) ethyl)(methyl)carbamate

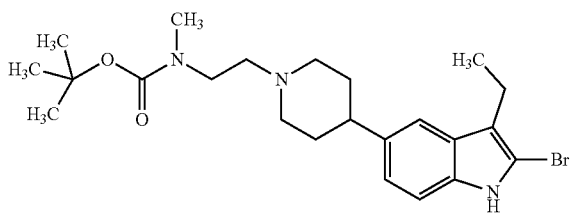

(155A)

To a 2 dram vial were added tert-butyl 4-(2-bromo-3-ethyl-1H-indol-5-yl) piperidine-1-carboxylate (0.323 g, 0.793 mmol) and DCM (5 mL). The reaction mixture was placed under a nitrogen atmosphere, cooled to 0° C. and 48% hydrobromic acid in acetic acid (0.196 mL, 1.189 mmol) was added drop-wise via syringe. The reaction mixture was stirred at 0° C. for 15 minutes. While maintaining the temperature at 0° C., the reaction was quenched with TEA (0.553 mL, 3.96 mmol). Next, tert-butyl methyl(2-oxoethyl)carbamate (0.151 g, 0.872 mmol) in 1 ml of DCM was added. The bath was removed and the reaction mixture was allowed to stir at room temperature for 15 minutes and then sodium triacetoxyborohydride (0.504 g, 2.379 mmol) was added. The reaction mixture was stirred at room temperature for 1 hour. The reaction mixture was diluted with water and DCM and the contents added to a separatory funnel. The layers were separated and the combined organics were washed with a saturated sodium chloride solution, dried over anhydrous sodium sulfate, filtered and concentrated. The residue was diluted with 1 ml of DCM and charged to a 12G ISCO column, which was eluted with 0-20% MeOH/DCM. Following concentration of the combined fractions, collected tert-butyl (2-(4-(2-bromo-3-ethyl-1H-indol-5-yl)piperidin-1-yl)ethyl)(methyl)carbamate (0.291 g, 79% yield) as a yellow solid. LC retention time 0.87 min [Method A1]. MS (E⁻) m/z: 464/466 (M–H).

Example 155

To a 2 dram vial were added tert-butyl (2-(4-(2-bromo-3-ethyl-1H-indol-5-yl) piperidin-1-yl)ethyl)(methyl)carbamate (0.022 g, 0.047 mmol), THF (1 mL), (3,4-dimethoxyphenyl)boronic acid (10.34 mg, 0.057 mmol), PdCl₂(dppf)-CH₂Cl₂ adduct (1.544 mg, 2.368 µmol) and a 3M tripotassium phosphate solution (0.047 mL, 0.142 mmol). The vessel was capped with a Teflon-lined cap and the mixture was pump/purged with nitrogen gas three times. The vial was set to heat at 70° C. for 1 hour, cooled to room temperature and the mixture was concentrated. The crude residue was diluted with DCM and to this was added 0.1 ml of TFA. The reaction mixture was stirred at room temperature for 30 minutes, then concentrated to dryness under a stream of nitrogen gas. The residue was diluted with 1 ml of DMF. The solids were filtered off and the crude material was purified via preparative LC/MS with the following conditions: Column: Waters XBridge C18, 19×200 mm, 5-µm particles; Mobile Phase A: 5:95 acetonitrile:water with 0.1% ammonium hydroxide; Mobile Phase B: 95:5 acetonitrile:water with 0.1% ammonium hydroxide; Gradient: 15-100% B over 25 minutes, then a 5-minute hold at 100% B; Flow: 20 mL/min. Fractions containing the desired product were combined and dried via centrifugal evaporation to afford 2-(4-(2-(3,4-dimethoxyphenyl)-3-ethyl-1H-indol-5-yl)piperidin-1-yl)-N-methylethanamine-di-trifluoroacetic acid (0.0142 g, 68% yield). Two analytical LC/MS injections were used to determine the final purity. (1) LC retention time 1.53 min [C1]. MS (E⁻) m/z: 422 (M–H). (2) LC retention time=1.23 min [D1]. MS (E⁻) m/z: 422 (M–H).

Example 157

1-(4-(2-(3,4-dimethoxyphenyl)-3-ethyl-1H-indol-5-yl)piperidin-1-yl)-2-((2-hydroxypropyl)amino)ethan-1-one

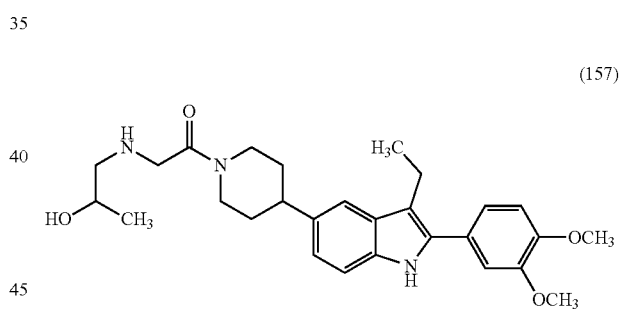

(157)

Intermediate 157A: 2-(3,4-dimethoxyphenyl)-3-ethyl-5-(piperidin-4-yl)-1H-indole hydrochloride

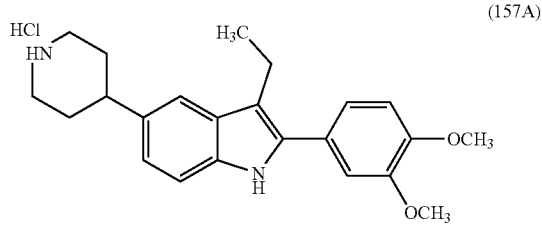 [SMILES: Cl ; CCc1c(-c2ccc(OC)c(OC)c2)[nH]c2ccc(C3CCNCC3)cc12]

(157A)

Tert-butyl 4-(2-(3,4-dimethoxyphenyl)-3-ethyl-1H-indol-5-yl)piperidine-1-carboxylate (0.220 g, 0.474 mmol) and dichloromethane (1 mL) were added in a 2-dram reaction vial. HCl/dioxane (4 N, 1.184 mL, 4.74 mmol) was added dropwise. The reaction mixture was stirred at room temperature for 2 h and then concentrated to dryness. The crude product was used as such in subsequent steps (0.188 g, 0.469 mmol, 99% yield). LC retention time 0.77 min [F]. MS (E⁻) m/z: 379.3 (M+H).

Intermediate 157B: 2-chloro-1-(4-(2-(3,4-dimethoxyphenyl)-3-ethyl-1H-indol-5-yl) piperidin-1-yl) ethanone

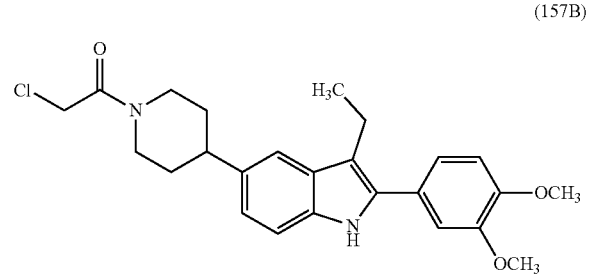 [SMILES: CCc1c(-c2ccc(OC)c(OC)c2)[nH]c2ccc(C3CCN(C(=O)CCl)CC3)cc12]

(157B)

DIPEA (0.096 ml, 0.549 mmol) was added to 2-(3,4-dimethoxyphenyl)-3-ethyl-5-(piperidin-4-yl)-1H-indole (40 mg, 0.110 mmol) in THF (5 mL) followed by chloroacetyl chloride (0.018 ml, 0.219 mmol) at room temperature. The reaction mixture was then stirred at ambient temperature for 12 h. The reaction mass was concentrated and purified with flash chromatography eluting with pet ether:ethyl acetate (6:4). The product fractions were combined and concentrated to provide 2-chloro-1-(4-(2-(3,4-dimethoxyphenyl)-3-ethyl-1H-indol-5-yl)piperidin-1-yl)ethanone (40 mg, 0.091 mmol, 83% yield). LC retention time 2.41 min [A]. MS (E⁻) m/z: 441.2 (M+H).

Example 157

Mixture of 2-chloro-1-(4-(2-(3,4-dimethoxyphenyl)-3-ethyl-1H-indol-5-yl) piperidin-1-yl)ethanone (10 mg, 0.023 mmol), 1-aminopropan-2-ol (2.55 mg, 0.034 mmol), DIPEA (0.012 mL, 0.068 mmol) and acetonitrile (0.5 mL) in a microwave vial was capped and placed in a sand bath and preheated to 100° C. for 3 h. The reaction sample was purified by reverse phase preparative HPLC to provide the desired product (4.89 mg, 9.78 µmol, 43.1% yield). LC retention time 1.356 min [E]. MS (E⁻) m/z: 480.2 (M+H).

The following Examples were prepared according to the general procedure described in Example 157.

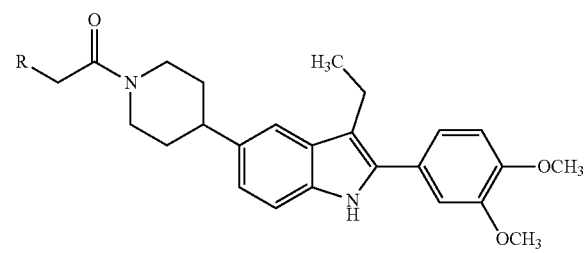

TABLE 10

| Ex. No. | R | M⁺¹ | RT (min) | Method |
|---|---|---|---|---|
| 158 | (piperidinyl-piperidinyl) | 573.3 | 1.436 | E |
| 159 | —NH(CH₂CH₂OH) | 466.2 | 1.303 | E |
| 160 | (1-(hydroxymethyl)cyclopentyl)amino | 520.2 | 1.558 | E |
| 161 | —NH(CH₂CN) | 461.2 | 1.589 | E |
| 162 | 4-(dimethylamino)cyclohexylamino | 547.2 | 1.158 | E |
| 163 | (3-hydroxyadamantyl)amino | 572.2 | 1.516 | E |
| 164 | —NHCH₂C(CH₃)₂CH₂OH | 508.2 | 1.512 | E |
| 165 | —NHCH(CH₂OH)₂ | 496.2 | 1.319 | E |

TABLE 10-continued

| Ex. No. | R | M$^{+1}$ | RT (min) | Method |
|---|---|---|---|---|
| 166 | 4-acetyl-1,4-diazepan-1-yl | 547.2 | 1.57 | E |
| 167 | morpholin-4-yl | 492.2 | 1.682 | E |
| 168 | 3-(N,N-diethylcarbamoyl)piperidin-1-yl | 589.2 | 1.788 | E |
| 169 | 3-(hydroxymethyl)piperidin-1-yl | 520.2 | 1.498 | E |
| 170 | —N(CH$_3$)CH(CH$_3$)$_2$ | 478.2 | 1.504 | E |
| 171 | 4-acetylpiperazin-1-yl | 533.2 | 1.548 | E |
| 172 | 4-(tetrahydrofuran-2-carbonyl)piperazin-1-yl | 589.2 | 1.623 | E |
| 173 | (3S)-3-hydroxypyrrolidin-1-yl | 492.2 | 1.34 | E |
| 174 | —NH(CH$_2$OH)CH$_2$CH$_2$CH$_3$ | 522.2 | 1.706 | E |

Example 175

1-(4-(2-(3,4-dimethoxyphenyl)-3-ethyl-1H-indol-5-yl)piperidin-1-yl)-2-methyl-1-oxopropan-2-yl acetate (175)

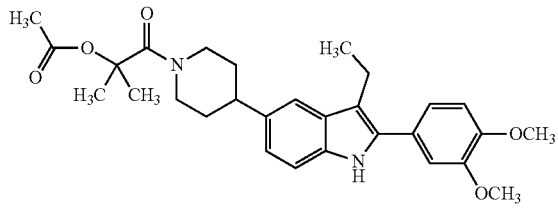

DIPEA (0.096 mL, 0.549 mmol) was added to a solution of 2-(2,3-dimethoxyphenyl)-3-ethyl-5-(piperidin-4-yl)-1H-indole (40 mg, 0.110 mmol) in dichloromethane (50 mL) followed by addition of 2-acetoxyisobutyryl chloride (18.06 mg, 0.110 mmol) at room temperature. The reaction mixture was then stirred at ambient temperature for 12 h. The reaction mass was concentrated and purified by prep HPLC to provide the desired product (17.5 mg, 0.036 mmol, 32.4% yield). $^1$H NMR (400 MHz, DMSO-d$_6$) δ=10.90 (s, 1H), 7.33 (s, 1H), 7.27 (d, J=8.3 Hz, 1H), 7.18-7.07 (m, 3H), 6.95 (dd, J=1.5, 8.4 Hz, 1H), 3.83 (d, J=12.8 Hz, 6H), 2.89-2.78 (m, 5H), 2.07 (s, 3H), 1.86 (d, J=13.1 Hz, 2H), 1.53 (s, 8H), 1.26 (t, J=7.5 Hz, 3H). LC retention time 2.32 min [A]. MS (E) m/z: 493.4 (M+H).

Example 176

1-(2-(4-(2-(3,4-dimethoxyphenyl)-3-ethyl-1H-indol-5-yl)piperidin-1-yl)-2-oxoethyl)piperidine-3-carboxylic acid (176)

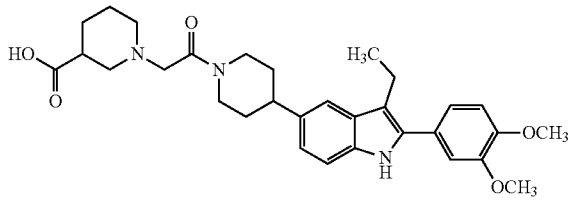

Intermediate 176A: ethyl 1-(2-(4-(2-(3,4-dimethoxyphenyl)-3-ethyl-1H-indol-5-yl) piperidin-1-yl)-2-oxoethyl) piperidine-3-carboxylate (176A)

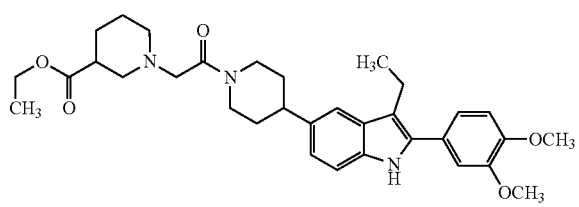

DIPEA (0.091 mL, 0.522 mmol) was added to 2-chloro-1-(4-(2-(3,4-dimethoxyphenyl)-3-ethyl-1H-indol-5-yl)piperidin-1-yl)ethanone (115 mg, 0.261 mmol) in THF (2 mL) followed by addition of ethyl piperidine-3-carboxylate (61.5 mg, 0.391 mmol) at room temperature. The reaction mixture was stirred at room temperature for 12 h. The reaction mass was concentrated to afford crude compound, which was purified by flash chromatography. The compound was eluted with petroleum ether:ethyl acetate (6:4), the fractions was collected and concentrated to afford racemic compound ethyl 1-(2-(4-(2-(3,4-dimethoxyphenyl)-3-ethyl-1H-indol-5-yl)piperidin-1-yl)-2-oxoethyl) piperidine-3-carboxylate (80 mg, 0.107 mmol, 41% yield) as an off-white solid. LC retention time 2.41 min [A]. MS (E$^-$) m/z: 560.2 (M–H).

Example 176

Aqueous LiOH (12.79 mg, 0.534 mmol) was added to ethyl 1-(2-(4-(2-(3,4-dimethoxyphenyl)-3-ethyl-1H-indol-5-yl)piperidin-1-yl)-2-oxoethyl)piperidine-3-carboxylate (150 mg, 0.267 mmol) in THF (2 mL) and MeOH (2.000 mL). The reaction temperature was raised to room temperature and the reaction mixture was stirred for 12 h. The reaction mass was concentrated, and the residue obtained was purified by prep HPLC to provide racemic 1-(2-(4-(2-(3,4-dimethoxyphenyl)-3-ethyl-1H-indol-5-yl)piperidin-1-yl)-2-oxoethyl)piperidine-3-carboxylic acid (120 mg, 0.225 mmol, 84% yield) as a pale yellow solid. $^1$H NMR (400 MHz, DMSO-d$_6$) δ=1.26 (t, J=7.60 Hz, 3H), 1.52-1.57 (m, 2H), 1.57-0.00 (m, 1H), 1.72-1.89 (m, 4H), 2.80-2.86 (m, 7H), 3.24-0.00 (m, 2H), 3.49-0.00 (m, 2H), 3.80 (s, 6H), 4.34-4.54 (m, 2H), 6.97 (t, J=4.40 Hz, 1H), 7.07-7.12 (m, 1H), 7.14-0.00 (m, 2H), 7.27 (d, J=8.40 Hz, 1H), 7.34 (s, 1H). LC retention time 1.94 min [C1]. MS (E$^-$) m/z: 534.2 (M+H).

Example 177

1-(4-(2-(3,4-dimethoxyphenyl)-3-ethyl-1H-indol-5-yl)piperidin-1-yl)-2-(thiazol-2-ylamino)ethanone (177)

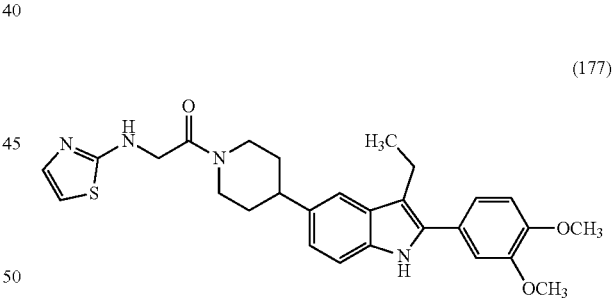

DIPEA (0.032 mL, 0.181 mmol) was added to 2-chloro-1-(4-(2-(3,4-dimethoxyphenyl)-3-ethyl-1H-indol-5-yl)piperidin-1-yl)ethanone (40 mg, 0.091 mmol) in THF (2 mL) followed by addition of thiazol-2-amine (13.63 mg, 0.136 mmol) at room temperature. The reaction mixture was stirred at room temperature for 12 h. The reaction mass was concentrated, and the residue obtained was dissolved in methanol and purified with preparative HPLC to provide 1-(4-(2-(3,4-dimethoxyphenyl)-3-ethyl-1H-indol-5-yl)piperidin-1-yl)-2-(thiazol-2-ylamino)ethanone (17 mg, 0.032 mmol, 35.3% yield) as a pale yellow solid. $^1$H NMR (400 MHz, DMSO-d$_6$) δ=1.26 (t, J=7.60 Hz, 3H), 1.90-1.86 (m, 6H), 2.86-0.00 (m, 1H), 2.88-0.00 (m, 3H), 3.60-3.67 (m, 2H), 3.85 (s, 6H), 4.34-4.54 (m, 4H), 5.94 (d, J=4.80 Hz, 1H), 7.09 (d, J=8.40 Hz, 1H), 7.12-0.00 (m, 3H), 7.27 (d, J=8.40 Hz, 1H), 7.34 (s, 1H). LC retention time 2.215 min [C1]. MS (E⁻) m/z: 505.2 (M+H).

Examples 178 and 179

1-(2-(4-(2-(3,4-dimethoxyphenyl)-3-ethyl-1H-indol-5-yl)piperidin-1-yl)-2-oxoethyl)-N,N-diethylpiperidine-3-carboxamide

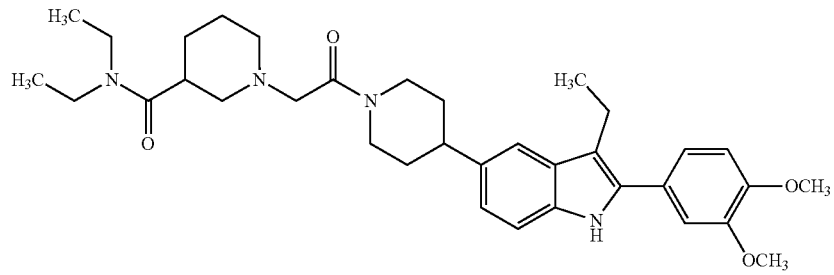

(178 and 179)

Diethylamine (0.020 mL, 0.187 mmol) and DIPEA (0.033 mL, 0.187 mmol) were added to 1-(2-(4-(2-(3,4-dimethoxyphenyl)-3-ethyl-1H-indol-5-yl)piperidin-1-yl)-2-oxoethyl) piperidine-3-carboxylic acid (50 mg, 0.094 mmol) in DMF (2 mL). Next, HATU (53.4 mg, 0.141 mmol) was added to the reaction mixture. The reaction mixture was stirred for 12 h. The reaction was quenched with ice cold water. The mixture was extracted with ethyl acetate, the organic layer was dried over sodium sulfate and concentrated to afford the crude product (40 mg, 0.068 mmol, 72.5% yield) as a racemic mixture. The crude product containing 3.5 mg of racemates was resolved using chiral SFC column to provide the two homochiral products: Example 178 (0.83 mg, 1.269 µmol, 21.34% yield, 90% purity); LC retention time 2.010 min [A]. MS (E⁻) m/z: 603.5 (M+H); Example 179 (0.71 mg, 1.085 µmol, 18.26% yield). LC retention time 2.010 min [A]. MS (E⁻) m/z: 603.5 (M+H).

Example 180

2-(3,4-dimethoxyphenyl)-3-ethyl-5-(1-(3,3,3-trifluoro-2-methylpropyl)piperidin-4-yl)-1H-indole

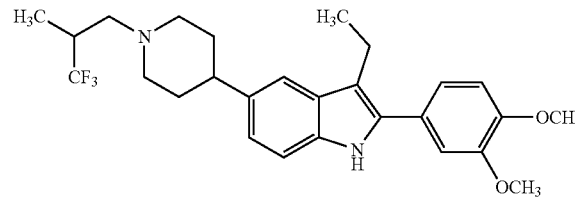

(180)

2-(trifluoromethyl)propionaldehyde (20.75 mg, 0.165 mmol) and acetic acid (9.42 µl, 0.165 mmol) were added to 2-(2,3-dimethoxyphenyl)-3-ethyl-5-(piperidin-4-yl)-1H-indole (40 mg, 0.110 mmol) in dichloromethane (5 mL) followed by addition of sodium triacetoxyborohydride (93 mg, 0.439 mmol) at room temperature. The reaction mixture was stirred at room temperature for 12 h. The reaction mixture was diluted with dichloromethane (10 mL), quenched with water, and washed with saturated NaHCO₃. The organic layer was dried over sodium sulfate, concentrated and purified by prep HPLC to provide 2-(3,4-dimethoxyphenyl)-3-ethyl-5-(1-(3,3,3-trifluoro-2-methylpropyl) piperidin-4-yl)-1H-indole (8.9 mg, 0.019 mmol, 17.09% yield) as a white solid. ¹H NMR (400 MHz, DMSO-d₆) δ=10.88 (s, 1H), 7.36 (s, 1H), 7.26 (d, J=8.3 Hz, 1H), 7.18-7.07 (m, 3H), 6.98 (dd, J=1.5, 8.3 Hz, 1H), 3.83 (d, J=13.0 Hz, 6H), 2.85 (d, J=7.5 Hz, 2H), 2.47 (d, J=4.6 Hz, 1H), 2.38-2.29 (m, 2H), 2.25-2.15 (m, 2H), 2.02-1.88 (m, 2H), 1.79 (br. s., 5H), 1.27 (t, J=7.5 Hz, 3H), 1.14 (d, J=6.8 Hz, 3H). LC retention time 2.574 min [A]. MS (E⁻) m/z: 475.4 (M+H).

Example 181

1-(4-(2-(3,4-dimethoxyphenyl)-3-ethyl-1H-indol-5-yl)piperidin-1-yl)-2-(dimethylamino) ethanone

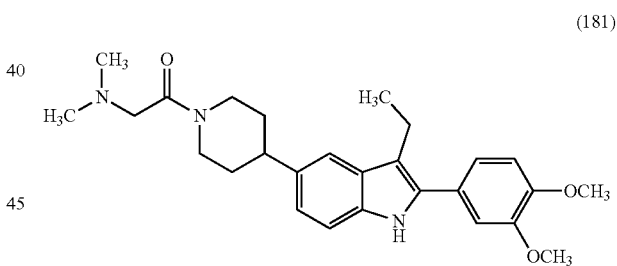

(181)

DIPEA (0.024 mL, 0.136 mmol) was added to 2-chloro-1-(4-(2-(3,4-dimethoxyphenyl)-3-ethyl-1H-indol-5-yl)piperidin-1-yl)ethanone (30 mg, 0.068 mmol) in THF (2 mL), followed by addition of dimethylamine (0.102 mL, 0.204 mmol) at room temperature. The reaction mixture was stirred at room temperature for 12 h. The reaction mixture was concentrated, and the residue obtained was purified by prep HPLC to provide 1-(4-(2-(3,4-dimethoxyphenyl)-3-ethyl-1H-indol-5-yl)piperidin-1-yl)-2-(dimethylamino)ethanone (20 mg, 0.044 mmol, 65.4% yield) as a white solid ¹H NMR (400 MHz, DMSO-d₆) δ=10.89 (s, 1H), 7.35 (s, 1H), 7.27 (d, J=8.2 Hz, 1H), 7.18-7.07 (m, 4H), 6.97 (dd, J=1.5, 8.4 Hz, 1H), 4.54 (d, J=12.3 Hz, 1H), 4.24-4.16 (m, 1H), 3.83 (d, J=12.7 Hz, 8H), 3.15-3.05 (m, 3H), 2.85 (q, J=7.3 Hz, 4H), 2.70-2.60 (m, 1H), 2.22 (s, 6H), 1.85 (d, J=11.8 Hz, 2H), 1.71-1.62 (m, 1H), 1.54-1.46 (m, 1H), 1.37 (s, 1H), 1.27 (t, J=7.5 Hz, 3H). LC retention time 1.779 min [C]. MS (E⁻) m/z: 464.2 (M+H).

Example 182

4-(2-(3,4-dimethoxyphenyl)-3-ethyl-1H-indol-5-yl)-N-isopropylpiperidine-1-carboxamide (182)

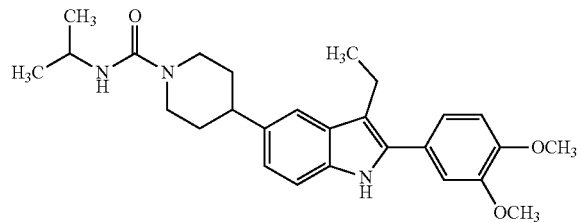

Triethylamine (TEA, 30.6 μl, 0.219 mmol) was added to 2-(2,3-dimethoxyphenyl)-3-ethyl-5-(piperidin-4-yl)-1H-indole (40 mg, 0.110 mmol) in dichloromethane (5 mL) followed by addition of isopropyl isocyanate (21.72 μl, 0.219 mmol) at room temperature. The reaction mixture was stirred at room temperature for 12 h. The reaction mass was diluted with dichloromethane (10 mL), washed with water, the organic layer was separated, dried over sodium sulfate and concentrated to afford the crude compound. The crude material was purified by prep HPLC to provide 4-(2-(3,4-dimethoxyphenyl)-3-ethyl-1H-indol-5-yl)-N-isopropylpiperidine-1-carboxamide (25 mg, 0.056 mmol, 50.7% yield) as a pale yellow solid. LC retention time 2.143 min [C]. MS (E$^-$) m/z: 450.2 (M+H).

Example 183

(4-(2-(3,4-dimethoxyphenyl)-3-ethyl-1H-indol-5-yl)piperidin-1-yl)(pyridin-4-yl) methanone (183)

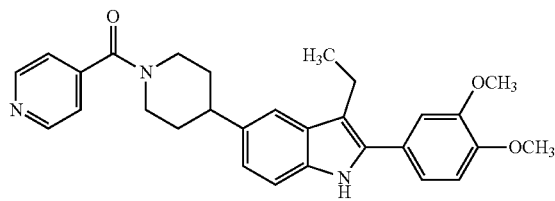

Intermediate 183A: 2-(3,4-dimethoxyphenyl)-3-ethyl-5-(piperidin-4-yl)-1H-indole, TFA salt (183A)

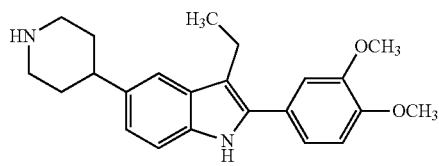

(4-(2-(3,4-dimethoxyphenyl)-3-ethyl-1H-indol-5-yl)piperidin-1-yl)(pyridin-4-yl) methanone: tert-butyl 5-(1-(tert-butoxycarbonyl)piperidin-4-yl)-2-(3,4-dimethoxyphenyl)-3-ethyl-1H-indole-1-carboxylate (17.5 mg, 0.031 mmol) was Boc-deprotected with 2:1 TFA/DCM (1.2 mL, 0.031 mmol) for 45 min. Excess solvent and TFA were evaporated from the reaction mixture under an $N_2$ stream. Obtained 2-(3,4-dimethoxyphenyl)-3-ethyl-5-(piperidin-4-yl)-1H-indole, TFA salt (14.8 mg), which was carried directly into the subsequent amidation reaction. m/z [M+H]=365.2.

Example 183

(4-(2-(3,4-dimethoxyphenyl)-3-ethyl-1H-indol-5-yl)piperidin-1-yl)(pyridin-4-yl) methanone: 2-(3,4-dimethoxyphenyl)-3-ethyl-5-(piperidin-4-yl)-1H-indole, TFA salt (14.8 mg, 0.031 mmol) was taken up in a solution of $CH_2Cl_2$ (0.500 mL) and N,N-diisopropylethylamine (0.016 mL, 0.093 mmol) containing isonicotinic acid (4.58 mg, 0.037 mmol) and PyBOP (19.35 mg, 0.037 mmol) in a 1-dram vial. The vial was capped and the reaction mixture was stirred at room temperature. Upon completion of the amide coupling reaction (as monitored by analytical LCMS), $CH_2Cl_2$ (1.0 mL) was added to the vial, the reaction mixture was washed with water (2×1 mL), and the excess solvent was evaporated from the organic phase under an $N_2$ stream. The crude material was taken up in DMF (1 mL) and purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 35-75% B over 20 minutes, then a 5-minute hold at 100% B; Flow: 20 mL/min. Fractions containing the desired product were combined and dried via centrifugal evaporation. The yield of the product was 11.3 mg, and its estimated purity by LCMS analysis was 97%. Two analytical LC/MS injections were used to determine the final purity. Injection 1 conditions: Method C1 SCP. Injection 2 conditions: Method D1 SCP. Obtained (4-(2-(3,4-dimethoxyphenyl)-3-ethyl-1H-indol-5-yl) piperidin-1-yl)(pyridin-4-yl)methanone (11.3 mg, 75% yield over 2 steps). M z [M+H]$^+$=470.1. $^1$H NMR (500 MHz, DMSO-$d_6$) δ 10.93 (s, 1H), 8.69 (d, J=5.6 Hz, 2H), 7.47 (d, J=5.7 Hz, 2H), 7.40 (s, 1H), 7.27 (d, J=8.2 Hz, 1H), 7.17-7.12 (m, 2H), 7.09 (d, J=8.2 Hz, 1H), 7.02 (d, J=8.3 Hz, 1H), 4.66 (d, J=10.4 Hz, 1H), 3.87-3.83 (m, 4H), 3.81 (s, 3H), 3.25-3.15 (m, 1H), 2.95-2.81 (m, 4H), 1.98-1.89 (m, 1H), 1.73 (d, J=16.8 Hz, 3H), 1.27 (t, J=7.4 Hz, 3H).

Example 184 tert-butyl 3-(4-(2-(3,4-dimethoxyphenyl)-3-ethyl-1H-indol-5-yl)piperidine-1-carbonyl)piperidine-1-carboxylate (184)

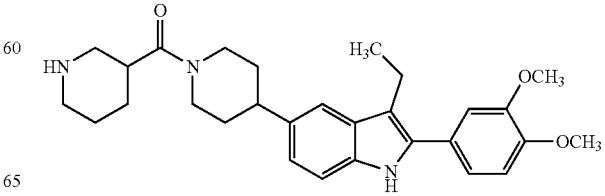

Intermediate 184A: 2-(3,4-dimethoxyphenyl)-3-ethyl-5-(piperidin-4-yl)-1H-indole, TFA salt

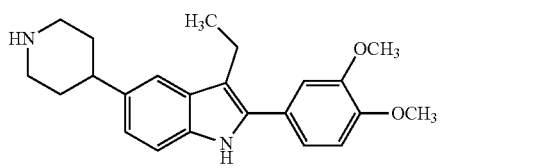

(184A)

tert-butyl 5-(1-(tert-butoxycarbonyl)piperidin-4-yl)-2-(3,4-dimethoxyphenyl)-3-ethyl-1H-indole-1-carboxylate (17.5 mg, 0.031 mmol) was Boc-deprotected with 2:1 trifluoroacetic acid/dichloromethane (1.2 mL, 0.031 mmol) for 45 min. Excess solvent and TFA were evaporated from the reaction mixture under an $N_2$ stream to afford 2-(3,4-dimethoxyphenyl)-3-ethyl-5-(piperidin-4-yl)-1H-indole, TFA salt (0.031 mmol). m/z [M+H]+=365.2.

Intermediate 184B: tert-butyl 3-(4-(2-(3,4-dimethoxyphenyl)-3-ethyl-1H-indol-5-yl) piperidine-1-carbonyl)piperidine-1-carboxylate

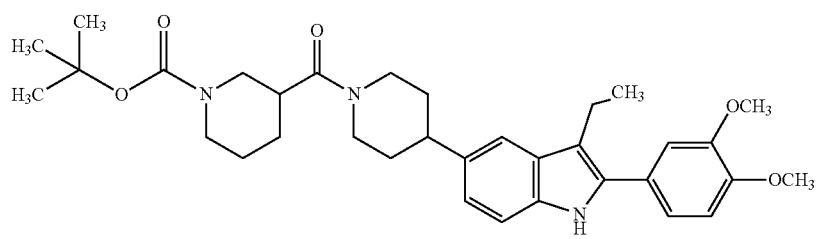

(184B)

2-(3,4-dimethoxyphenyl)-3-ethyl-5-(piperidin-4-yl)-1H-indole, TFA salt (14.8 mg, 0.031 mmol) was taken up in a solution of dichloromethane (0.500 mL) and N,N-diisopropylethylamine (0.016 mL, 0.093 mmol) containing 1-Boc-piperidine-3-carboxylic acid (8.53 mg, 0.037 mmol) and PyBOP (19.35 mg, 0.037 mmol) in a 1-dram vial. The vial was capped and the reaction mixture stirred at room temperature. Upon completion of the amide coupling reaction, dichloromethane (1.0 mL) was added to the vial, the reaction mixture was washed with water (2×1 mL), and the excess solvent was evaporated from the organic phase. Obtained tert-butyl 3-(4-(2-(3,4-dimethoxyphenyl)-3-ethyl-1H-indol-5-yl)piperidine-1-carbonyl)piperidine-1-carboxylate (17.8 mg, 0.031 mmol (100% unpurified yield)). m/z [M+H]+ =576.6.

Example 184

Intermediate 184B, tert-butyl 3-(4-(2-(3,4-dimethoxyphenyl)-3-ethyl-1H-indol-5-yl)piperidine-1-carbonyl)piperidine-1-carboxylate, was Boc-deprotected with 2:1 TFA/DCM (1.5 mL, 0.031 mmol) for 1 h. Excess solvent was evaporated from the reaction mixture, and the residue was taken up in DMF (1 mL) and purified via preparative LC/MS with the following conditions: Column: XBridge C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 15-100% B over 20 minutes, then a 5-minute hold at 100% B; Flow: 20 mL/min. Fractions containing the desired product were combined and dried via centrifugal evaporation. The yield of the product was 24.1 mg, and its estimated purity by LCMS analysis was 96%. Two analytical LC/MS injections were used to determine the final purity. Injection 1 conditions: Column: Waters Acquity UPLC BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.11 mL/min; Detection: UV at 220 nm. Injection 2 conditions: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.11 mL/min; Detection: UV at 220 nm. Proton NMR was acquired in deuterated DMSO. Obtained (4-(2-(3,4-dimethoxyphenyl)-3-ethyl-1H-indol-5-yl)piperidin-1-yl)(piperidin-3-yl)methanone (24.1 mg, 99% yield).

$^1$H NMR (500 MHz, DMSO-$d_6$) δ 10.93 (s, 1H), 7.35 (s, 1H), 7.27 (d, J=8.2 Hz, 1H), 7.16-7.11 (m, 2H), 7.10-7.06 (m, 11H), 6.97 (d, J=8.2 Hz, 11H), 4.56 (d, J=12.2 Hz, 11H), 4.06 (d, J=13.3 Hz, 1H), 3.84 (s, 3H), 3.80 (s, 3H), 3.64-3.50 (m, 1H), 3.22-3.11 (m, 1H), 2.97 (br. s., 1H), 2.83 (d, J=7.4 Hz, 4H), 2.77-2.57 (m, 3H), 1.90 (br. s., 1H), 1.82 (br. s., 2H), 1.67-1.44 (m, 5H), 1.25 (t, J=7.4 Hz, 3H).

The following Examples were prepared according to the general procedure described in Example 184.

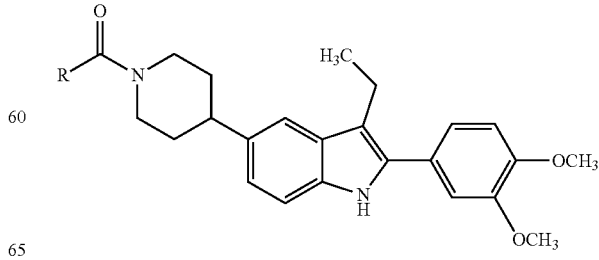

TABLE 11

| Ex. No. | R | M+1 | RT (min) | Method |
|---|---|---|---|---|
| 185 | —CH₃ | 407 | 1.71 | G |
| 186 | (piperidin-4-yl) | 476 | 1.46 | G |
| 187 | (4-methylpiperidin-4-yl) | 490 | 1.53 | G |

Example 188

2-(4-(2-(3,4-dimethoxyphenyl)-3-ethyl-6-methyl-1H-indol-5-yl)piperidin-1-yl)-N-methylethanamine-di-trifluoroacetic acid

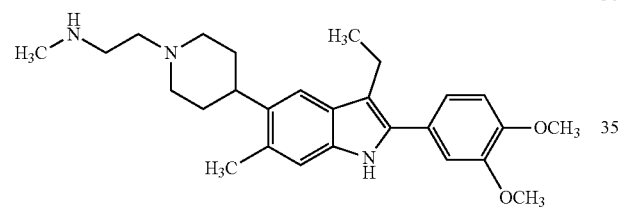

(188)

Intermediate 188A: 3-ethyl-6-methyl-1H-indole

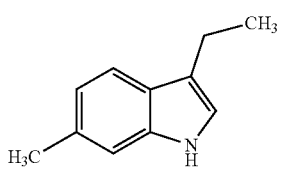

(188A)

To a 30 ml pressure tube were added 6-methyl-1H-indole (1.300 g, 9.91 mmol), Shvo's catalyst (0.107 g, 0.099 mmol), potassium carbonate (0.068 g, 0.496 mmol), and diethylamine (1.450 g, 19.82 mmol). The reaction mixture was purged with nitrogen gas and heated to 155° C. for 48 hrs. The reaction mixture was cooled to room temperature, diluted with DCM and washed with 1N HCl. The organics were dried over anhydrous sodium sulfate, filtered and concentrated. The residue was purified on a 120G ISCO column eluting with 0-70% ethyl acetate/hexane. Following concentration of the fractions, collected 3-ethyl-6-methyl-1H-indole (0.493 g, 31% yield). LC retention time 1.01 min [F1]. MS (E⁻) m/z: 160 (M–H).

Intermediate 188B:
2-bromo-3-ethyl-6-methyl-1H-indole

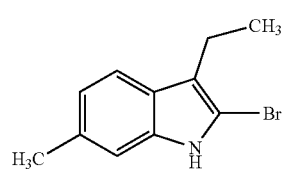

(188B)

To a 100 ml round bottom flask were added 3-ethyl-6-methyl-1H-indole (0.593 g, 3.72 mmol) and DCE (15 mL). NBS (0.630 g, 3.54 mmol) was dissolved in 5 ml of DCE and added to the reaction mixture drop-wise via an addition funnel over 15 minutes. The reaction mixture was allowed to stir for an additional 15 minutes. The reaction was quenched with 5 ml of a 10% sodium sulfite solution. The contents was added to a separatory funnel and the layers were separated. The organics were washed with water, followed by brine. The combined organics were dried over anhydrous sodium sulfate, filtered and concentrated. The residue was taken up in minimal DCM and charged to a 24G ISCO column eluting with 0-50% ethyl acetate/heptane. Following concentration of the fractions, collected 2-bromo-3-ethyl-6-methyl-1H-indole as a white foam (0.660 g 74.4% yield). LC retention time 1.20 min [Method A1]. MS (E⁻) m/z: 238/240 (M–H).

Intermediate 188C:
2-(3,4-dimethoxyphenyl)-3-ethyl-6-methyl-1H-indole

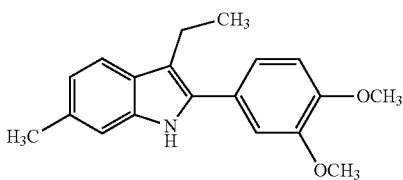

(188C)

To a 40 ml reaction vial fitted with a Teflon-lined cap, 2-bromo-3-ethyl-6-methyl-1H-indole (0.737 g, 3.10 mmol) was taken in THF (7 mL) and (3,4-dimethoxyphenyl) boronic acid (0.591 g, 3.25 mmol), PdCl₂(dppf)-CH₂Cl₂ adduct (0.063 g, 0.077 mmol), and potassium phosphate solution (3.10 mL, 9.29 mmol) were added. The vial was capped and pump/purged with nitrogen gas three times. The reaction mixture was set to heat at 50° C. for 1 hour. The mixture was cooled to room temperature and concentrated under a stream of nitrogen gas. The crude residue was diluted with 1 ml of DCM and charged to a 24G ISCO column, eluting with 0-50% ethyl acetate/hexane. Following concentration of the fractions, collected product as a white solid (0.425 g, 46% yield). LC retention time 2.26 min [C1]. MS (E⁻) m/z: 296 (M–H).

Intermediate 188D: 5-bromo-2-(3,4-dimethoxyphenyl)-3-ethyl-6-methyl-1H-indole

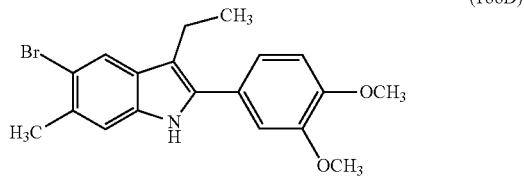

(188D)

To a 100 ml round bottom flask were added 2-(3,4-dimethoxyphenyl)-3-ethyl-6-methyl-1H-indole (0.230 g, 0.779 mmol) and DCE (3 mL). NBS (0.132 g, 0.740 mmol) was dissolved in 2 ml of DCE and was added to the reaction mixture drop-wise via an addition funnel over 15 minutes. The reaction mixture was allowed to stir for an additional 15 minutes, then quenched with 5 ml of a 10% sodium sulfite solution. The contents was added to a separatory funnel and the layers were separated. The organics were washed with water, followed by brine. The combined organics were dried over anhydrous sodium sulfate, filtered and concentrated. The residue was taken up in minimal DCM and charged to a 24G ISCO column eluting with 0-50% ethyl acetate/heptane. Following concentration of the fractions, collected 5-bromo-2-(3,4-dimethoxyphenyl)-3-ethyl-6-methyl-1H-indole as a white foam (0.050 g, 17.16% yield). LC retention time 1.22 min [Method A1]. MS (E⁻) m/z: 375 (M–H).

Intermediate 188E: tert-butyl-4-(2-(3,4-dimethoxyphenyl)-3-ethyl-6-methyl-1H-indol-5-yl)-5,6-dihydropyridine-1(2H)-carboxylate

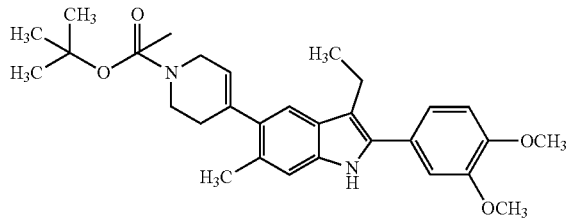

(188E)

To a mixture of 5-bromo-2-(3,4-dimethoxyphenyl)-3-ethyl-6-methyl-1H-indole (0.400 g, 1.069 mmol), PdCl₂(dppf)-CH₂Cl₂ adduct (0.022 g, 0.027 mmol), and tert-butyl 4-(4,4,5,5-tetramethyl-1,3,2-dioxaborolan-2-yl)-5,6-dihydropyridine-1(2H)-carboxylate (0.347 g, 1.122 mmol) in a 100 ml round bottom flask was added THF (35 mL) followed by aqueous solution of tripotassium phosphate (1.069 mL, 3.21 mmol). The vial was fitted with a Teflon-lined septum cap. The system was evacuated under vacuum (via a needle from a nitrogen/vacuum manifold line) and backfilled with nitrogen gas. The procedure was repeated three times. The needle was removed and the vial was heated at 75° C. for 18 h. The reaction mixture was diluted with EtOAc (100 mL), poured into a separatory funnel and washed with water (2×50 mL) and saturated aqueous sodium chloride solution (50 mL) dried over anhydrous sodium sulfate and filtered. The filtrate was concentrated in vacuo to give crude product. The crude material was dissolved in a small amount of DCM and charged to an ISCO silica gel 24G ISCO column which was eluted over a 20 min gradient with 0%-50% EtOAc/hexanes to afford tert-butyl-4-(2-(3,4-dimethoxyphenyl)-3-ethyl-6-methyl-1H-indol-5-yl)-5,6-dihydropyridine-1(2H)-carboxylate (0.350 g, 68.7% yield). LC retention time 1.20 min [Method A1]. MS (E⁻) m/z: 477 (M–H).

Intermediate 188F: 2-(3,4-dimethoxyphenyl)-3-ethyl-6-methyl-5-(piperidin-4-yl)-1H-indole HCl

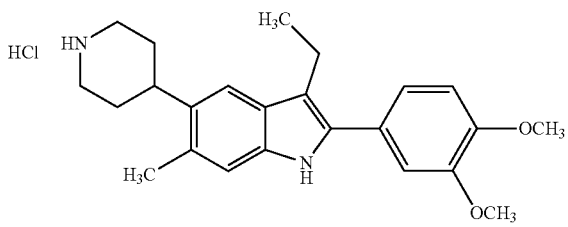

(188F)

To a 250 ml round bottom flask were added tert-butyl 4-(2-(3,4-dimethoxyphenyl)-3-ethyl-6-methyl-1H-indol-5-yl)-5,6-dihydropyridine-1(2H)-carboxylate (0.400 g, 0.839 mmol) and ethyl acetate (5 mL). The flask was purged with nitrogen gas and Pd/C (0.045 g, 0.042 mmol) was added. Following pump/purging with nitrogen gas three times, hydrogen gas was introduced via a balloon. The reaction mixture was stirred at room temperature overnight. The flask was evacuated and filled with nitrogen gas. The suspension was filtered through fluted filter paper and the filtrate was concentrated. To this was added 4 M HCl/dioxane (2.098 mL, 8.39 mmol) and the flask was capped and stirred for 1 hour at room temperature. The volatiles were removed to afford 2-(3,4-dimethoxyphenyl)-3-ethyl-6-methyl-5-(piperidin-4-yl)-1H-indole HCl (0.29 g, 91% yield). LC retention time 1.19 min [Method A1]. MS (E⁻) m/z: 379 (M–H).

Example 188

To a 2 dram vial were added 2-(3,4-dimethoxyphenyl)-3-ethyl-6-methyl-5-(piperidin-4-yl)-1H-indole (0.030 g, 0.079 mmol), DCM (1 mL), TEA (0.055 mL, 0.396 mmol), tert-butyl methyl(2-oxoethyl)carbamate (0.021 g, 0.119 mmol) and 1 drop of acetic acid. After 5 minutes, sodium triacetoxyborohydride (0.067 g, 0.317 mmol) was added and the reaction mixture was stirred at room temperature for 1 hour. The mixture was diluted with water and DCM was added. The layers were separated and the organics were washed with brine, dried over anhydrous sodium sulfate and filtered. The residue was diluted with 1 ml of DCM and treated with 1 ml of HCl (4M/dioxane). The reaction mixture was stirred at room temperature for 30 minutes, then concentrated to dryness and diluted with 1 ml of DMF. The solids were filtered off and the crude material was purified via preparative LC/MS with the following conditions: Column: Waters XBridge C18, 19×200 mm, 5-μm particles; Mobile Phase A: 5:95 acetonitrile: water with 0.1% trifluoroacetic acid; Mobile Phase B: 95:5 acetonitrile: water with 0.1% trifluoroacetic acid; Gradient: 5-40% B over 25 minutes, then a 5-minute hold at 40% B; Flow: 20 mL/min. Fractions containing the desired product were combined and dried via centrifugal evaporation to afford 2-(4-(2-(3,4-dimethoxyphenyl)-3-ethyl-6-methyl-1H-indol-5-yl)piperidin-1-yl)-N-methylethanamine-di-trifluoroacetic acid (0.0217 g, 63% yield). Two analytical LC/MS injections were used to determine the final purity. (1) LC retention time 1.41 min [C1]. MS (E⁻) m/z: 436 (M–H). (2) LC retention time=1.10 min [D1]. MS (E⁻) m/z: 436 (M–H).

Example 189

2-(3,4-dimethoxyphenyl)-3-ethyl-7-fluoro-5-(piperidin-4-yl)-1H-indole

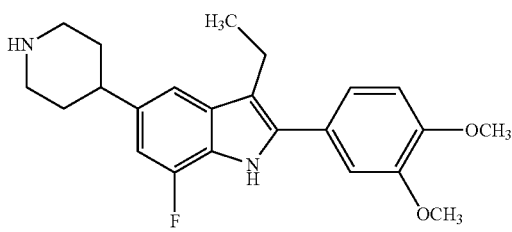

(189)

Intermediate 189A: 5-bromo-3-ethyl-7-fluoro-1H-indole

(189A)

To a tall reaction vial were added 5-bromo-7-fluoro-1H-indole (1.000 g, 4.67 mmol), Shvo's Catalyst (0.051 g, 0.047 mmol), potassium carbonate (0.032 g, 0.234 mmol), and diethylamine (0.683 g, 9.34 mmol). The reaction mixture was purged with nitrogen gas and heated to 155° C. for 12 hours. The reaction mixture was concentrated under a stream of nitrogen gas. The resulting residue was diluted with DCM and charged to 40G ISCO column, which was eluted with 0-100% ethyl acetate/hexane. Following concentration of the fractions, collected 5-bromo-3-ethyl-7-fluoro-1H-indole as a brownish oil (0.650 g, 57%). LC retention time=1.42 min [Method A1]. MS (E⁻) m/z: 243 (M–H).

Intermediate 189B: tert-butyl 4-(3-ethyl-7-fluoro-1H-indol-5-yl)piperidine-1-carboxylate

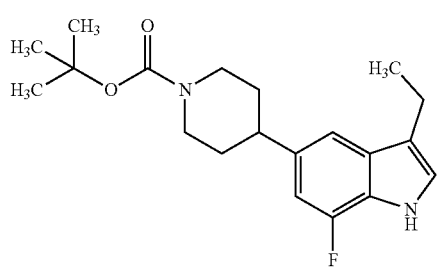

(189B)

To a mixture of 5-bromo-3-ethyl-7-fluoro-1H-indole (0.149 g, 0.615 mmol), PdCl₂(dppf)-CH₂Cl₂ adduct (0.013 g, 0.015 mmol), and tert-butyl 4-(4,4,5,5-tetramethyl-1,3,2-dioxaborolan-2-yl)-5,6-dihydropyridine-1(2H)-carboxylate (0.200 g, 0.646 mmol) in a 40 ml reaction vial were added THF (5 mL) followed by an aqueous 3 M solution of tripotassium phosphate (0.615 mL, 1.85 mmol). The vial was fitted with a Teflon-lined septum cap. The system was evacuated under vacuum (via a needle from a nitrogen/vacuum manifold line) and back-filled with nitrogen gas. The procedure was repeated three times. The needle was removed and the vial was heated at 75° C. for 18 hours. The reaction mixture was diluted with EtOAc (100 mL), poured into a separatory funnel and washed with water (2×50 mL) and saturated aqueous sodium chloride solution (50 mL). The organics were collected and dried over anhydrous sodium sulfate. The suspension was filtered and the filtrate concentrated in vacuo to give crude product. The crude product was purified using a 24G ISCO silica gel column, which was eluted with 0-50% ethyl acetate/hexane over a 20 minute period. Following concentration of the fractions, collected tert-butyl 4-(3-ethyl-7-fluoro-1H-indol-5-yl)-5,6-dihydropyridine-1(2H)-carboxylate. LC retention time=1.52 min [Method A1]. MS (E⁻) m/z: 345 (M–H).

In a 100 ml round bottom flask was added tert-butyl 4-(3-ethyl-7-fluoro-1H-indol-5-yl)-5,6-dihydropyridine-1(2H)-carboxylate and ethyl acetate (5 ml). The flask was purged with nitrogen gas and Pd/C (0.033 g, 0.031 mmol) was added. Following pump/purging with nitrogen gas three times, hydrogen gas was introduced via a balloon. The reaction mixture was stirred at room temperature overnight. The flask was evacuated and filled with nitrogen gas. The suspension was filtered through fluted filter paper and the filtrate was concentrated in vacuo to give tert-butyl 4-(3-ethyl-7-fluoro-1H-indol-5-yl)piperidine-1-carboxylate (0.189 g, 89% yield). LC retention time=1.52 min [Method A1]. MS (E⁻) m/z: 347 (M–H).

Intermediate 189C: tert-butyl 4-(2-bromo-3-ethyl-7-fluoro-1H-indol-5-yl)piperidine-1-carboxylate

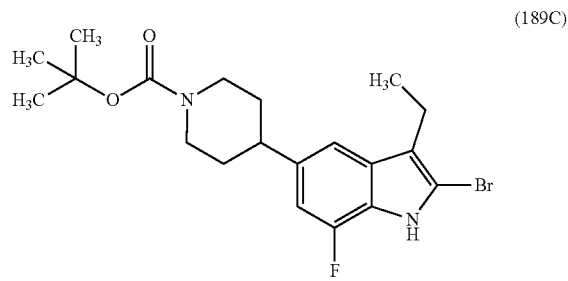 [SMILES: CCc1c(Br)[nH]c2c(F)cc(C3CCN(C(=O)OC(C)(C)C)CC3)cc12]

(189C)

To a 100 ml round bottom flask were added tert-butyl 4-(3-ethyl-7-fluoro-1H-indol-5-yl)piperidine-1-carboxylate (0.189 g, 0.546 mmol) and DCE (4 mL). NBS (0.092 g, 0.518 mmol) was dissolved in 1 ml of DCE and added to the reaction mixture drop-wise via a pipet over 2 minutes. The reaction was quenched with 2 ml of a 10% sodium sulfite solution and the volatiles were removed in vacuo. The residue was taken up in DCM (1 ml), filtered and loaded onto a 24G ISCO column, which was eluted using 0-50% ethyl acetate/heptane. Following concentration of fractions, collected tert-butyl 4-(2-bromo-3-ethyl-7-fluoro-1H-indol-5-yl)piperidine-1-carboxylate (0.210 g, 91% yield) as a white foam. LC retention time 1.61 min [Method A1]. MS (E⁻) m/z: 425/427 (M–H).

Intermediate 189D: tert-butyl 4-(2-(3,4-dimethoxyphenyl)-3-ethyl-7-fluoro-1H-indol-5-yl)piperidine-1-carboxylate

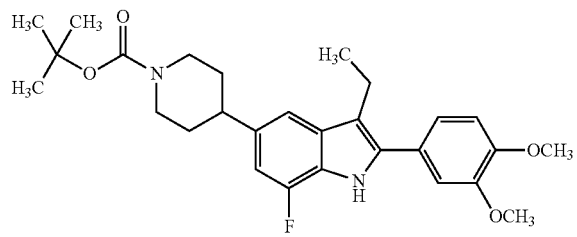

(189D)

To a 2 dram vial were added tert-butyl 4-(2-bromo-3-ethyl-7-fluoro-1H-indol-5-yl)piperidine-1-carboxylate (0.100 g, 0.235 mmol), (3,4-dimethoxyphenyl)boronic acid (0.047 g, 0.259 mmol), PdCl$_2$(dppf)-CH$_2$Cl$_2$ adduct (0.096 g, 0.120 mmol), and THF (2 ml). To this was added a 3M potassium phosphate solution (0.24 mL, 0.705 mmol) and the vial was capped and pump/purged with nitrogen three times. The reaction mixture was heated at 50° C. for 1 hour. The mixture was concentrated under a stream of nitrogen gas. The crude residue was diluted with DCM and the organics were washed with water, then brine. The combined extracts were dried over anhydrous sodium sulfate, filtered and concentrated in vacuo. The crude product was solid-loaded onto a 24G ISCO column, which was eluted using 0-20% DCM/MeOH. Following concentration of fractions, collected tert-butyl 4-(2-(3,4-dimethoxyphenyl)-3-ethyl-7-fluoro-1H-indol-5-yl)piperidine-1-carboxylate (0.086 g, 76% yield) as a white foam. LC retention time 1.26 min [F1]. MS (E$^-$) m/z: 483 (M−H).

Example 189

To Intermediate 189C (0.086 g) were added 1 ml DCM and 4 M HCl/dioxane (0.071 mL, 0.926 mmol). The reaction mixture was stirred at room temperature for 60 minutes, then concentrated to dryness under a stream of nitrogen gas. The residue was taken up in DMF (1 mL) and the solids were filtered through a 0.45 micron syringe filter and the crude material was purified via preparative LC/MS with the following conditions: Column: Waters XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 0-100% B over 20 minutes, then a 0-minute hold at 100% B; Flow: 20 mL/min. Fractions containing the desired product were combined and dried via centrifugal evaporation. 2-(3,4-dimethoxyphenyl)-3-ethyl-7-fluoro-5-(piperidin-4-yl)-1H-indole (0.021 g, 65% yield). Two analytical LC/MS injections were used to determine the final purity. (1) LC retention time 1.34 min [C1]. MS (E$^-$) m/z: 383 (M−H). (2) LC retention time=1.28 min [D1]. MS (E$^-$) m/z: 383 (M−H).

Example 190

2-(3,4-dimethoxyphenyl)-3-ethyl-7-fluoro-5-(1'-isobutyl-[1,4'-bipiperidin]-4-yl)-1H-indole

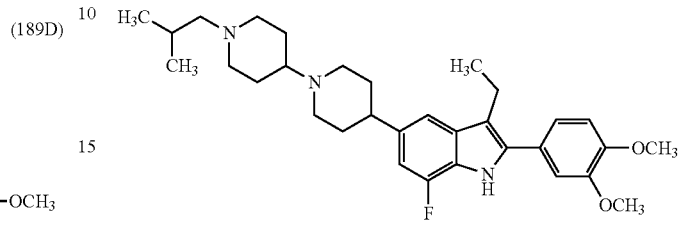

(190)

To a 2 dram reaction vial were added 2-(3,4-dimethoxyphenyl)-3-ethyl-7-fluoro-5-(piperidin-4-yl)-1H-indole (0.017 g, 0.041 mmol) and DMF (1 ml). To this were added TEA (0.028 mL, 0.203 mmol), 1 drop of acetic acid and 1-isobutylpiperidin-4-one (0.0063 g, 0.041 mmol). The reaction mixture was stirred at room temperature for 1 hour. Next, sodium cyanoborohydride (0.0076 g, 0.122 mmol) was added. The vial was capped and stirred at room temperature overnight. The suspension was filtered through a 0.45 micron syringe filter. The crude material was purified via preparative LC/MS with the following conditions: Column: Waters XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 20-100% B over 19 minutes, then a 5-minute hold at 100% B; Flow: 20 mL/min. Fractions containing the desired product were combined and dried via centrifugal evaporation to afford 2-(3,4-dimethoxyphenyl)-3-ethyl-7-fluoro-5-(1'-isobutyl-[1,4'-bipiperidin]-4-yl)-1H-indole (0.0039 g, 18% yield). Two analytical LC/MS injections were used to determine the final purity. (1) LC retention time 1.79 min [C1]. MS (E$^-$) m/z: 522 (M−H). (2) LC retention time=1.28 min [D1]. MS (E$^-$) m/z: 522 (M−H).

Example 191

2-(4-(2-(3,4-dimethoxyphenyl)-3-ethyl-7-fluoro-1H-indol-5-yl)piperidin-1-yl)-N-methylethan-1-amine

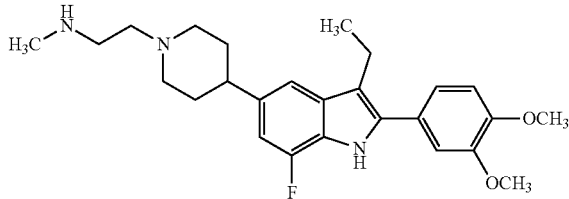

(191)

Intermediate 191A: tert-butyl-(2-(4-(2-(3,4-dimethoxyphenyl)-3-ethyl-7-fluoro-1H-indol-5-yl)piperidin-1-yl)ethyl)(methyl)carbamate (191A)

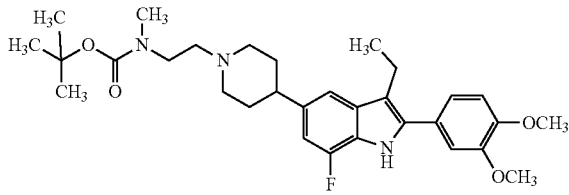

Tert-butyl-(2-(4-(2-(3,4-dimethoxyphenyl)-3-ethyl-7-fluoro-1H-indol-5-yl) piperidin-1-yl)ethyl)(methyl)carbamate (0.020 g, 20% yield) was prepared according to the general process of Example 98 using tert-butyl methyl(2-oxoethyl)carbamate as the starting material. LC retention time 0.89 min [Method A1]. MS (E⁻) m/z: 540 (M−H).

Example 191

To a 2 dram reaction vial were added tert-butyl-(2-(4-(2-(3,4-dimethoxyphenyl)-3-ethyl-7-fluoro-1H-indol-5-yl)piperidin-1-yl)ethyl)(methyl)carbamate (0.014 g, 0.026 mmol) followed by DCM (0.5 ml) and 4M HCl/dioxane (0.071 mL, 0.926 mmol). The reaction mixture was stirred at room temperature for 60 minutes, then concentrated to dryness under a stream of nitrogen gas. The residue was taken up in DMF (1 mL) and the solids were filtered through a 0.45 micron syringe filter and the crude material was purified via preparative LC/MS with the following conditions: Column: Waters XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 15-55%% B over 25 minutes, then a 0-minute hold at 100% B; Flow: 20 mL/min. Fractions containing the desired product were combined and dried via centrifugal evaporation to afford 2-(4-(2-(3,4-dimethoxyphenyl)-3-ethyl-7-fluoro-1H-indol-5-yl)piperidin-1-yl)-N-methylethanamine (0.0104 g, 88% yield). Two analytical LC/MS injections were used to determine the final purity. (1) LC retention time 1.51 min [C1]. MS (E⁻) m/z: 440 (M−H). (2) LC retention time=1.20 min [D1]. MS (E⁻) m/z: 440 (M−H).

Example 192

2-(3,4-dimethoxyphenyl)-3-ethyl-5-(1'-isopropyl-[1,4'-bipiperidin]-4-yl)-6-methoxy-1H-indole (192)

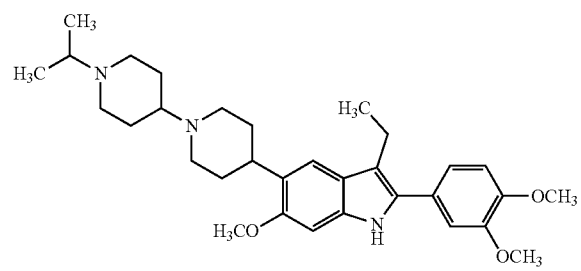

Intermediate 192A:
5-bromo-3-ethyl-6-methoxy-1H-indole (192A)

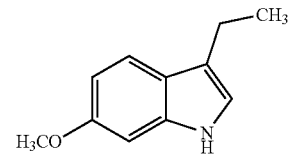

In four separate 30 ml pressure tubes (800 mg each) was added 6-methoxy-1H-indole (3.20 g, 21.74 mmol), Shvo's Catalyst (0.236 g, 0.217 mmol), potassium carbonate (0.150 g, 1.087 mmol) and diethylamine (3.18 g, 43.5 mmol). The reaction mixture was purged with nitrogen gas and heated to 155° C. for 12 hours. The reaction mixture was concentrated under a stream of nitrogen gas. The resulting residue was charged to 220G ISCO column (solid loading on celite), which was eluted with 0-55% ethyl acetate/hexane. Following concentration of the fractions, collected 5-bromo-3-ethyl-6-methoxy-1H-indole as a brownish oil (2.65 g, 70%). LC retention time=1.07 min [F1]. MS (E⁻) m/z: 176 (M−H).

Intermediate 192B:
2,5-dibromo-3-ethyl-6-methoxy-1H-indole (192B)

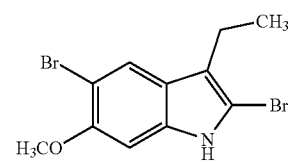

To a 100 ml round bottom flask were added 3-ethyl-6-methoxy-1H-indole (0.150 g, 0.856 mmol) and DCM (4 mL). The reaction mixture was cooled to 0° C. and NBS (0.289 g, 1.626 mmol) in 2 ml of DCM was added drop-wise via a pipet over 5 minutes. After 5 minutes of additional stirring at 0° C., the reaction was quenched with 2 ml of 10% sodium sulfite solution. The mixture was diluted with EtOAc (100 mL), poured into a separatory funnel and washed with water (2×50 mL) and saturated aqueous NaCl solution (50 mL). The organics were collected and dried over anhydrous sodium sulfate. The suspension was filtered and the filtrate concentrated in vacuo to give 2,5-dibromo-3-ethyl-6-methoxy-1H-indole as a purplish solid. LC retention time 1.11 min [B1]. MS (E⁻) m/z: 333 (M−H).

Intermediate 192C: tert-butyl 4-(2-(3,4-dimethoxyphenyl)-3-ethyl-6-methoxy-1H-indol-5-yl)-5,6-dihydropyridine-1(2H)-carboxylate (192C)

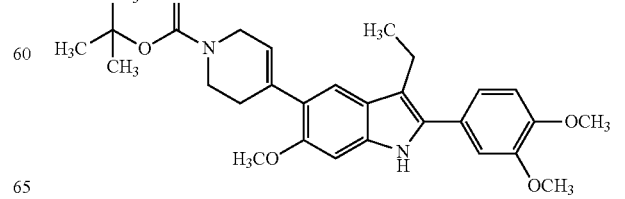

In a 2 dram vial was added 2,5-dibromo-3-ethyl-6-methoxy-1H-indole, (3,4-dimethoxyphenyl)boronic acid (0.156 g, 0.856 mmol), PdCl$_2$(dppf)-CH$_2$Cl$_2$ adduct (0.070 g, 0.086 mmol) and 5 ml of THF. The vial was capped with a Teflon-lined cap and to this was added a 3M tripotassium phosphate solution (0.90 mL). The mixture was pump/purged with nitrogen gas three times. The reaction mixture was heated at 50° C. for 1 hour. The mixture was cooled to room temperature and to this was added tert-butyl 4-(4,4,5,5-tetramethyl-1,3,2-dioxaborolan-2-yl)-5,6-dihydropyridine-1(2H)-carboxylate (0.397 g, 1.284 mmol), PdCl$_2$(dppf)-CH$_2$Cl$_2$ adduct (0.070 g, 0.086 mmol) and a 3M tripotassium phosphate solution (0.90 mL) was added. The mixture was pump/purged with nitrogen gas three times. The reaction mixture was heated at 75° C. for 1 hour. The mixture was cooled to room temperature and diluted with EtOAc (100 mL), poured into a separatory funnel and washed with water (2×50 mL) and saturated aqueous NaCl solution (50 mL). The organics were collected and dried over anhydrous sodium sulfate. The suspension was filtered and the filtrate concentrated in vacuo to give crude product. The crude product was purified using a 24G ISCO silica gel column, which was eluted with 0-50% ethyl acetate/hexane over a 20 minute period. Following concentration of the fractions, collected tert-butyl 4-(2-(3,4-dimethoxyphenyl)-3-ethyl-6-methoxy-1H-indol-5-yl)-5,6-dihydropyridine-1(2H)-carboxylate (0.100 g, 24%) as a tan solid. LC retention time=1.18 min [B1]. MS (E$^-$) m/z: 393 (M–H). 90% yield). LC retention time=1.18 min [B1]. MS (E$^-$) m/z: 395 (M–H).

Intermediate 19D: 2-(3,4-dimethoxyphenyl)-3-ethyl-6-methoxy-5-(piperidin-4-yl)-1H-indole·HCl salt

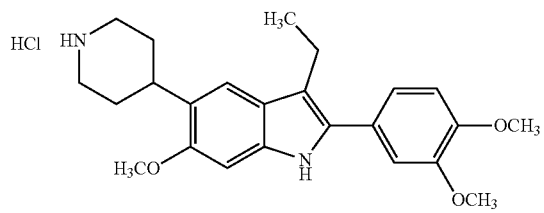

(192D)

To a Parr bottle were added tert-butyl 4-(2-(3,4-dimethoxyphenyl)-3-ethyl-6-methoxy-1H-indol-5-yl)-5,6-dihydropyridine-1(2H)-carboxylate (0.100 g, 0.203 mmol) and methanol (5 ml). The bottle was purged with nitrogen gas and Pd(OH)$_2$ (0.014 g, 0.020 mmol) was added. The bottle was situated on the Parr apparatus and following pump/purging with nitrogen gas three times, the vessel was pressurized to 55 psi with hydrogen gas. The reaction mixture was allowed to shake at this pressure for 18 hours. The flask was evacuated and filled with nitrogen gas. The suspension was filtered through fluted filter paper. The filtrate was concentrated and diluted with 0.5 ml of DCM and 1 ml of 4M HCl/Dioxane. The reaction was capped and stirred for 1 hr at room temperature, then concentrated to dryness and used as such in next step.

Example 192

To a 2 dram reaction vial were added 2-(3,4-dimethoxyphenyl)-3-ethyl-6-methoxy-5-(piperidin-4-yl)-1H-indole (0.020 g, 0.046 mmol) and DMF (1 ml). To this were added TEA (0.028 mL, 0.203 mmol), 1 drop of acetic acid, and 1-isopropylpiperidin-4-one (0.0063 g, 0.041 mmol). The reaction mixture was stirred at room temperature for 1 hour. Next, sodium cyanoborohydride (0.0076 g, 0.122 mmol) was added. The vial was capped and stirred at room temperature overnight. The suspension was filtered through a 0.45 micron syringe filter and the crude material was purified via preparative LC/MS with the following conditions: Column: Waters XBridge C18, 19×200 mm, 5-µm particles; Mobile Phase A: 5:95 acetonitrile: water with 0.1% trifluoroacetic acid; Mobile Phase B: 95:5 acetonitrile: water with 0.1% trifluoroacetic acid; Gradient: 5-45% B over 25 minutes, then a 5-minute hold at 45% B; Flow: 20 mL/min. Fractions containing the desired product were combined and dried via centrifugal evaporation to afford 2-(3,4-dimethoxyphenyl)-3-ethyl-6-methoxy-5-(1'-isopropyl-[1,4'-bipiperidin]-4-yl)-1H-indole (0.0134 g, 55% yield). Two analytical LC/MS injections were used to determine the final purity. (1) LC retention time 1.44 min [C1]. MS (E$^-$) m/z: 520 (M–H). (2) LC retention time=1.19 min [D1]. MS (E$^-$) m/z: 520 (M–H).

Example 193

2-(4-(2-(3,4-dimethoxyphenyl)-3-ethyl-6-methoxy-1H-indol-5-yl)piperidin-1-yl)-N-methylethanamine

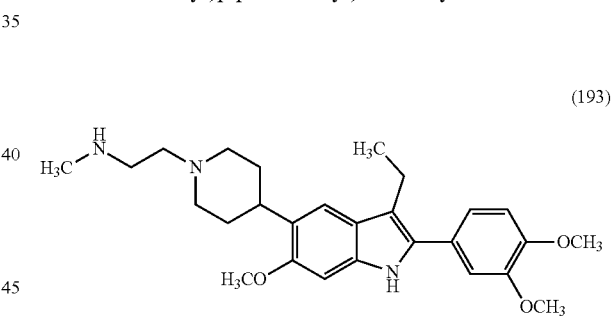

(193)

2-(4-(2-(3,4-dimethoxyphenyl)-3-ethyl-6-methoxy-1H-indol-5-yl)piperidin-1-yl)-N-methylethanamine was prepared according to the general procedure of Example 98 using tert-butyl methyl(2-oxoethyl)carbamate as the starting material. The crude material was purified via preparative LC/MS with the following conditions: Column: Waters XBridge C18, 19×200 mm, 5-µm particles; Mobile Phase A: 5:95 acetonitrile: water with 0.1% trifluoroacetic acid; Mobile Phase B: 95:5 acetonitrile: water with 0.1% trifluoroacetic acid; Gradient: 5-55% B over 25 minutes, then a 5-minute hold at 45% B; Flow: 20 mL/min. Fractions containing the desired product were combined and dried via centrifugal evaporation to afford 2-(4-(2-(3,4-dimethoxyphenyl)-3-ethyl-6-methoxy-1H-indol-5-yl)piperidin-1-yl)-N-methylethanamine (0.0072 g, 31% yield). Two analytical LC/MS injections were used to determine the final purity. (1) LC retention time 1.42 min [C1]. MS (E$^-$) m/z: 452 (M–H). (2) LC retention time=1.12 min [D1]. MS (E$^-$) m/z: 452 (M–H).

Example 194

2-(3,4-dimethoxyphenyl)-3-isopropyl-5-(piperidin-4-yl)-1H-indole hydrochloride

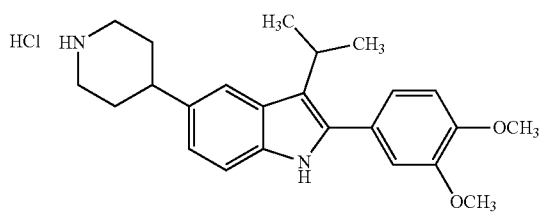
(194)

Intermediate 194A: 5-bromo-3-isopropyl-1H-indole

(194A)

A 250 ml round bottom flask was charged with triethylsilane (8.90 g, 77 mmol), trichloroacetic acid (6.25 g, 38.3 mmol) and toluene (50 mL). The solution was heated to 70° C., then a solution of 5-bromo-H-indole (5.0 g, 25.5 mmol) and acetone (2.247 mL, 30.6 mmol) in toluene (30 mL) was added drop wise via an addition funnel. The resulting brown solution was heated at 70° C. for 1.5 h. The solution was cooled to 10° C., quenched with 10% sodium bicarbonate and diluted with diethyl ether. The organic layer was separated, dried and concentrated under vacuum to get crude compound. The crude was purified using silica gel chromatography eluting with 500 ethyl acetate in hexanes to give 5-bromo-3-isopropyl-1H-indole (5.5 g, 23.10 mmol 95% yield) as an oil. LC retention time 1.42 min [D]. MS (E⁻) m/z: 238.2 (M+H).

Intermediate 194B3: tert-butyl 4-(3-isopropyl-1H-indol-5-yl)-5,6-dihydropyridine-1(2H)-carboxylate

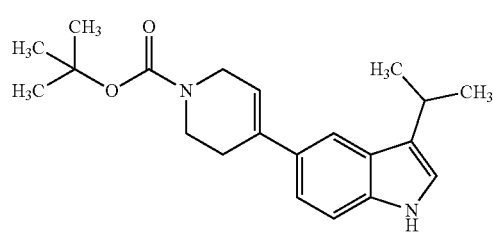
(194B)

To a mixture of 5-bromo-3-isopropyl-H-indole (5.5 g, 23.10 mmol), tert-butyl 4-(4,4,5,5-tetramethyl-1,3,2-dioxaborolan-2-yl)-5,6-dihydropyridine-1(2H)-carboxylate (7.50 g, 24.2c mmol) in a 250 ml round bottom flask were added THE (50 mL) followed by aqueous solution of potassium phosphate, dibasic (12.07 g, 69.3 mmol, 20 mL). The resulting reaction mixture was degassed for 10 minutes with nitrogen gas, then PdCl₂(dppf)-CH₂Cl₂ adduct, (0.472 g, 0.577 mmol) was added. The mixture was degassed again for 5 min. The resulting reaction mixture was heated at 75° C. for 18 hours. The reaction mixture was diluted with ethyl acetate (100 mL), poured into a separate funnel and was washed with water (2×50 mL), brine (50 mL), dried over sodium sulfate, and concentrated to give crude product. The crude material was purified using silica gel chromatography, eluting with 15% ethyl acetate in hexane. The fractions were collected and concentrated to give tert-butyl 4-(3-isopropyl-1H-indol-5-yl)-5,6-dihydropyridine-1(2H)-carboxylate (6.5 g, 83% yield) as an oil. LCMS retention time 1.21 min [B]. MS (E⁻) m/z: 339 (M–H).

Intermediate 194C: tert-butyl 4-(3-isopropyl-1H-indol-5-yl)piperidine-1-carboxylate

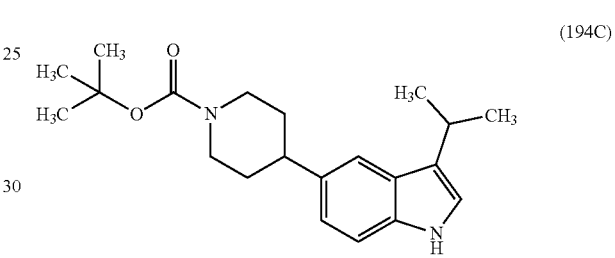
(194C)

To a solution of tert-butyl 4-(3-isopropyl-1H-indol-5-yl)-5,6-dihydropyridine-1(2H)-carboxylate (7.9 g, 23.20 mmol) in ethyl acetate (150 mL), under a nitrogen atmosphere, was added palladium on carbon (0.617 g, 0.580 mmol). The vessel was pimp/purged three times with nitrogen gas then evacuated. Hydrogen gas was introduced via a balloon and the mixture was stirred at room temperature for 5 hours. The suspension was filtered through celite and the filtrate was concentrated to give crude compound. The crude residue was purified by ISCO using a 40 g silica column, eluting with 15% ethyl acetate in hexane. The combined fractions were collected and concentrated to give tert-butyl 4-(3-isopropyl-1H-indol-5-yl)piperidine-1-carboxylate (6.5 g, 82% yield) as a white solid. LCMS retention time 2.48 min [C]. MS (E⁻) m/z: 341 (M–H).

Intermediate 194D: tert-butyl 4-(2-bromo-3-isopropyl-1H-indol-5-yl)piperidine-1-carboxylate

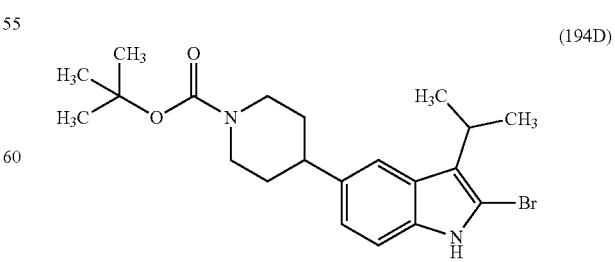
(194D)

To a solution of tert-butyl 4-(3-isopropyl-1H-indol-5-yl)piperidine-1-carboxylate (6.3 g, 18.40 mmol) in DCE (60 mL) at 0° C., was added NBS (3.27 g, 18.40 mmol) in DCE (50 mL) drop-wise via an addition funnel over 10 minutes. The resulting brown solution was stirred at room temperature for 20 minutes. The reaction was quenched with a 10% sodium sulfite solution (15 mL) and the volatiles were removed. The residue was taken up in DCM (50 mL) and the mixture was poured into a separatory funnel and the aqueous layer was separated. The organic layer was dried over $Na_2SO_4$ and concentrated to give crude compound. The crude material was purified by ISCO using 40 g silica column, eluting with 15% ethyl acetate in petroleum ether. The combined fractions were concentrated to give tert-butyl 4-(2-bromo-3-isopropyl-1H-indol-5-yl)piperidine-1-carboxylate (6.4 g, 83% yield) as a white solid. LCMS retention time 3.944 min [D]. MS (E$^-$) m/z: 421.2 (M–H).

Intermediate 194E: tert-butyl 4-(2-(3,4-dimethoxyphenyl)-3-isopropyl-1H-indol-5-yl) piperidine-1-carboxylate

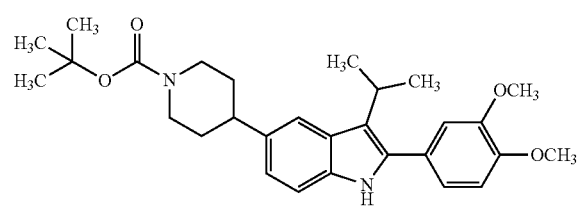

(194E)

To a degassed solution (nitrogen gas, 10 minutes) of tert-butyl 4-(2-bromo-3-isopropyl-1H-indol-5-yl)piperidine-1-carboxylate (2.0 g, 4.75 mmol), (3,4-dimethoxyphenyl)boronic acid (0.950 g, 5.22 mmol) and potassium carbonate (1.968 g, 14.24 mmol) in THF (40 mL) and water (10 mL), was added $PdCl_2$(dppf)-$CH_2Cl_2$ adduct (0.194 g, 0.237 mmol). The reaction mixture was degassed for an additional 5 minutes and then heated at 70° C. for 5 hours. The reaction mixture was concentrated. The residue was dissolved in ethyl acetate and the solution was washed with water. The organic layer was collected, dried over $Na_2SO_4$ and concentrated to give crude compound. The crude material was purified by flash chromatography, using a 24 g silica column and eluting with 18% ethyl acetate in petroleum ether. The combined fractions were concentrated to give tert-butyl 4-(2-(3,4-dimethoxyphenyl)-3-isopropyl-1H-indol-5-yl) piperidine-1-carboxylate (1.4 g, 2.93 mmol, 61.6% yield) as a white solid. LCMS retention time 3.871 min [D]. MS (E$^-$) m/z: 479.2 (M+H).

Example 194

To a solution of tert-butyl 4-(2-(3,4-dimethoxyphenyl)-3-isopropyl-1H-indol-5-yl)piperidine-1-carboxylate (1.4 g, 2.93 mmol) in DCM (5 mL) was added 4M HCl in dioxane (3.66 mL, 14.63 mmol). The mixture was stirred at room temperature for 1 hour. The resulting slurry was concentrated and the residue was triturated with diethyl ether (2×10 mL) to afford 2-(3,4-dimethoxyphenyl)-3-isopropyl-5-(piperidin-4-yl)-1H-indole hydrochloride (1.1 g, 99% yield) as a pale yellow solid. LC retention time=1.41 min [B1]. MS (E$^-$) m/z: 379 (M–H).

Example 196

2-(4-(2-(3,4-dimethoxyphenyl)-3-isopropyl-1H-indol-5-yl)piperidin-1-yl)-N-methylethan-1-amine

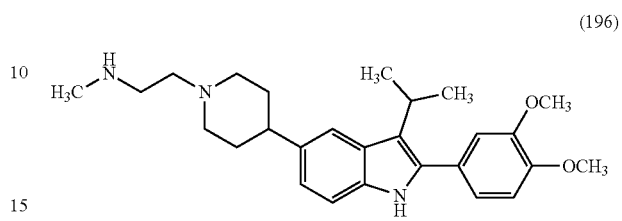

(196)

2-(4-(2-(3,4-dimethoxyphenyl)-3-isopropyl-1H-indol-5-yl)piperidin-1-yl)-N-methylethanamine was prepared according to the general process of Example 98 using tert-butyl methyl(2-oxoethyl)carbamate as the starting material. The crude material was purified via flash chromatography (ISCO) using a 40G silica column and eluting with 0-100% DCM:20% $NH_3$ in MeOH over a gradient time of 35 minutes. Fractions containing the desired product were combined and concentrated in vacuo to give 2-(4-(2-(3,4-dimethoxyphenyl)-3-isopropyl-1H-indol-5-yl)piperidin-1-yl)-N-methylethanamine ((0.086 g, 44% yield) as a whitish solid. LCMS retention time 1.22 min [E1]. MS (E$^-$) m/z: 339 (M–H).

Example 197

5-([1,4'-bipiperidin]-4-yl)-2-(3,4-dimethoxyphenyl)-3-isopropyl-1H-indole dihydrochloride

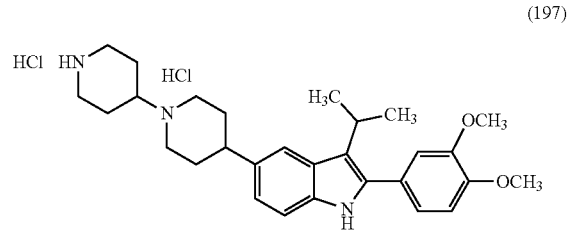 [SMILES: Cl ; COc1ccc(-c2[nH]c3ccc(C4CCN(C5CCNCC5)CC4)cc3c2C(C)C)cc1OC ; Cl]

(197)

To a 40 ml reaction vial were added 2-(3,4-dimethoxyphenyl)-3-isopropyl-5-(piperidin-4-yl)-1H-indole hydrochloride (0.125 g, 0.301 mmol) and DMF (1 mL). TEA (0.210 mL, 1.506 mmol) was added followed by the addition of tert-butyl 4-oxopiperidine-1-carboxylate (0.072 g, 0.361 mmol) and acetic acid (0.017 mL, 0.301 mmol). The mixture was stirred at room temperature for 15 minutes and sodium cyanoborohydride (0.057 g, 0.904 mmol) was added. The reaction mixture was stirred at room temperature for 4 hours, diluted with water and ethyl acetate and the contents was transferred to a separatory funnel. The layers were separated and the organics were washed with a saturated sodium chloride solution. The organics were collected, dried over anhydrous sodium sulfate and concentrated to a brownish residue. The residue was diluted with DCM (1 ml) and to this was added 4 M HCl/dioxane (2 ml) and the reaction mixture was stirred at room temperature for 1 hour, then the solvent was decanted. Following removal of residual solvent under a stream of nitrogen gas, 5-([1,4'-bipiperidin]-4-yl)-

2-(3,4-dimethoxyphenyl)-3-isopropyl-1H-indole, 2 HCl (0.12 g, 85% yield) was collected as a yellow solid. LC retention time 0.69 min [Method A1]. MS (E⁻) m/z: 462 (M–H).

Example 198

5-(1'-(cyclopropylmethyl)-[1,4'-bipiperidin]-4-yl)-2-(3,4-dimethoxyphenyl)-3-isopropyl-1H-indole di trifluoroacetic acid

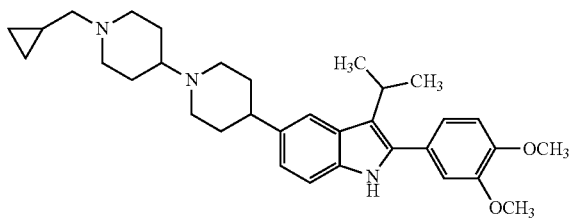

(198)

5-(1'-(cyclopropylmethyl)-[1,4'-bipiperidin]-4-yl)-2-(3,4-dimethoxyphenyl)-3-isopropyl-1H-indole di trifluoroacetic acid was prepared according to the general procedure described in Example 3 using 5-([1,4'-bipiperidin]-4-yl)-2-(3,4-dimethoxyphenyl)-3-isopropyl-1H-indole as the starting intermediate (0.011 g, 56% yield). Two analytical LC/MS injections were used to determine the final purity. (1) LC retention time 1.48 min [C1]. MS (E⁻) m/z: 516 (M–H). (2) LC retention time=1.21 min [D1]. MS (E⁻) m/z: 516 (M–H).

The following Examples were prepared according to the general procedure described in Example 198.

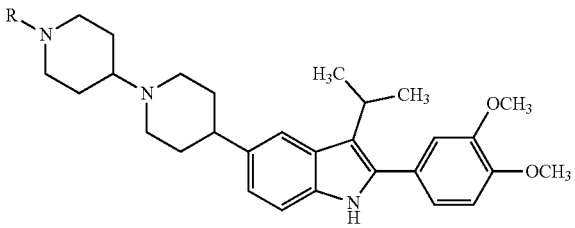

TABLE 12

| Ex. No. | R | M⁺¹ | RT (min) | Method |
|---|---|---|---|---|
| 199 | —CH₂CH(CH₃)₂ | 518 | 1.24 | D1 |
| 200 | —CH₃ | 476 | 1.16 | D1 |
| 201 | —CH(CH₃)₂ | 504 | 1.20 | D1 |
| 202 | cyclopentyl-CH₂ | 530 | 1.24 | D1 |

Example 203

2-((2-(4-(2-(3,4-dimethoxyphenyl)-3-isopropyl-1H-indol-5-yl)piperidin-1-yl)-2-oxoethyl)(methyl)amino)-N,N-diethylacetamide, TFA

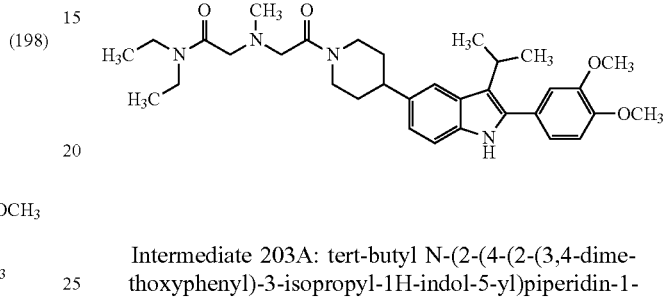

(203)

Intermediate 203A: tert-butyl N-(2-(4-(2-(3,4-dimethoxyphenyl)-3-isopropyl-1H-indol-5-yl)piperidin-1-yl)-2-oxoethyl)-N-methylglycinate

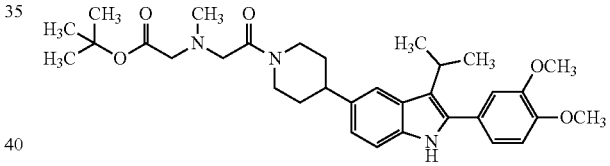

(203A)

2-chloro-1-(4-(2-(3,4-dimethoxyphenyl)-3-isopropyl-1H-indol-5-yl)piperidin-1-yl)ethanone (16.8 mg, 0.037 mmol) was suspended in DCM (369 µl) in a 1-dram vial containing a Teflon-coated stir bar. Next, tert-butyl 2-(methylamino)acetate, HCl (6.71 mg, 0.037 mmol) was added to the reaction vial, followed by DIPEA (19.35 µl, 0.111 mmol). The vial was capped and the reaction mixture was stirred at room temperature for 20 h. Additional DCM (~250 µL) was added to the vial. Additional tert-butyl 2-(methylamino)acetate, HCl (4 mg) was added to the vial, and the reaction mixture was stirred at room temperature for 22 h. Additional DIPEA (19.35 µl, 0.111 mmol) was added and the reaction mixture was heated to 40° C. for 40 min. The stirring was continued at room temperature for 26 h. Excess solvent was evaporated from the reaction. The resulting yellow residue was dissolved in DMF (~1.2 mL) and purified by preparative HPLC on an LCMS system, triggering fraction collection on the desired product mass ion. Product-containing fractions were consolidated into a tarred 20 mL scintillation vial using a Biotage V-10 evaporator to afford tert-butyl 2-((2-(4-(2-(3,4-dimethoxyphenyl)-3-isopropyl-1H-indol-5-yl)piperidin-1-yl)-2-oxoethyl)(methyl)amino) acetate, TFA salt (19.2 mg, 0.017 mmol, 46.0% yield) as a bright yellow solid. LC retention time 0.93 min [B1]. M z [M+H]⁺=564.5.

141

Intermediate 203B: N-(2-(4-(2-(3,4-dimethoxyphenyl)-3-isopropyl-1H-indol-5-yl) piperidin-1-yl)-2-oxoethyl)-N-methylglycine

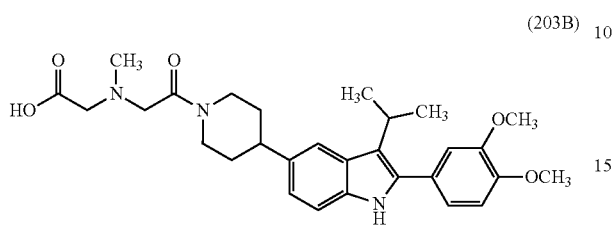

(203B)

The reaction mixture was set up in a 1-dram vial containing a Teflon-coated stir bar. Tert-butyl 2-((2-(4-(2-(3,4-dimethoxyphenyl)-3-isopropyl-1H-indol-5-yl)piperidin-1-yl)-2-oxoethyl)(methyl)amino) acetate, TFA (19.2 mg, 0.028 mmol) was weighed into the vial. The t-butyl group was removed using 4 N HCl in dioxane (500 µL, 2.000 mmol) for 40 min. Triisopropyl silane (10 µL) was then added to the reaction mixture, and stirring was continued at room temperature for another 1.5 h. Excess solvent and HCl were evaporated off to afford crude N-(2-(4-(2-(3,4-dimethoxyphenyl)-3-isopropyl-1H-indol-5-yl)piperidin-1-yl)-2-oxoethyl)-N-methylglycine, HCl salt (14.2 mg, 0.28 mmol), which was carried directly into the subsequent coupling reaction. LC retention time 0.81 min [B1]. m/z [M+H]$^+$= 508.4.

Example 203

N-(2-(4-(2-(3,4-dimethoxyphenyl)-3-isopropyl-1H-indol-5-yl)piperidin-1-yl)-2-oxoethyl)-N-methylglycine, HCl salt (14.2 mg, 0.28 mmol) was dissolved in DCM (500 µL) and DIPEA (14.84 µL, 0.085 mmol). Diethylamine (7.40 µL, 0.071 mmol) was added to the reaction mixture. Next, HATU (16.16 mg, 0.042 mmol) was added to the reaction mixture followed by the addition of DMF (500 µL). The reaction mixture was stirred at room temperature overnight. Excess DCM was evaporated off under a nitrogen stream, and DMF (~0.6 mL) was added to the remaining solution. The product was purified by preparative HPLC, and solvent was evaporated from product-containing fractions under reduced pressure to afford 2-((2-(4-(2-(3,4-dimethoxyphenyl)-3-isopropyl-1H-indol-5-yl) piperidin-1-yl)-2-oxoethyl)(methyl)amino)-N,N-diethylacetamide, TFA (5.0 mg, 6.65 µmol, 23.47% yield) as a bright yellow glass. LC retention time 0.89 min [B1]. M z [M+H]=563.5. $^1$H NMR (400 MHz, METHANOL-d$_4$) δ 7.58 (s, 1H), 7.30 (d, J=8.4 Hz, 1H), 7.11 (s, 1H), 7.10-7.05 (m, 2H), 7.03-6.98 (m, 1H), 4.70 (d, J=13.0 Hz, 1H), 4.35 (br. s., 4H), 3.97-3.93 (m, 1H), 3.91 (s, 3H), 3.91 (s, 3H), 3.85-3.77 (m, 1H), 3.49 (q, J=6.7 Hz, 2H), 3.42-3.35 (m, 2H), 3.31-3.26 (m, 1H), 3.07 (s, 3H), 2.98-2.85 (m, 2H), 2.07-1.98 (m, 2H), 1.85 (td, J=12.9, 4.4 Hz, 1H), 1.74 (td, J=12.9, 4.1 Hz, 1H), 1.48 (d, J=7.3 Hz, 6H), 1.26 (t, J=7.2 Hz, 3H), 1.20 (t, J=7.2 Hz, 3H).

142

Example 204

3-((2-(4-(2-(3,4-dimethoxyphenyl)-3-isopropyl-1H-indol-5-yl)piperidin-1-yl)-2-oxoethyl)(methyl)amino)-N,N-diethylpropanamide

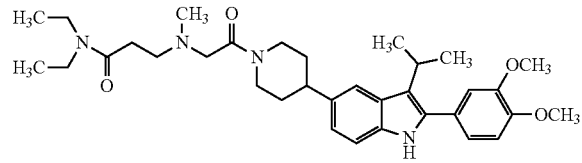

(204)

Intermediate 204A: tert-butyl 4-(2-(3,4-dimethoxyphenyl)-3-isopropyl-1H-indol-5-yl)-3,6-dihydropyridine-1(2H)-carboxylate

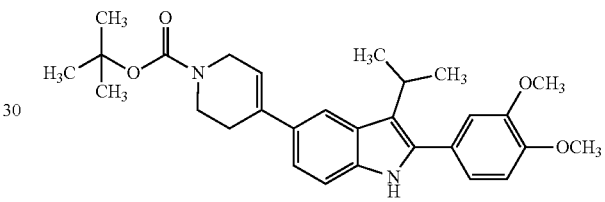

(204A)

5-chloro-2-(3,4-dimethoxyphenyl)-3-isopropyl-1H-indole (110 mg, 0.334 mmol) was dissolved in THF (3335 µl) in a 2-dram vial containing a Teflon-covered stir bar. tert-butyl 4-(4,4,5,5-tetramethyl-1,3,2-dioxaborolan-2-yl)-5,6-dihydropyridine-1(2H)-carboxylate (155 mg, 0.500 mmol) was added to the vial, followed by tripotassium phosphate (500 µl, 1.001 mmol). The reaction mixture was degassed using an N$_2$ stream bubbled through the solution for 1 min, then second generation Xphos precatalyst (7.87 mg, 10.01 µmol) was added to the reaction mixture. The reaction mixture was placed under an N$_2$ atmosphere, and heated to 60° C. with stirring for 16 h. The reaction mixture was allowed to cool to room temperature. Excess THF was evaporated from the reaction mixture under an N$_2$ stream. EtOAc (~3 mL) and water (1 mL) were added to the reaction mixture, and the resulting organic and aqueous phases were separated. Excess solvent was evaporated from the organic phase. The residue was dissolved in DCM (~4 mL) and purified by flash chromatography on an Isco Rf instrument using a 24 g SiO$_2$ column and eluting with ethyl acetate and hexanes. Obtained tert-butyl 4-(2-(3,4-dimethoxyphenyl)-3-isopropyl-1H-indol-5-yl)-5,6-dihydropyridine-1(2H)-carboxylate (114.1 mg, 0.215 mmol, 64.6% yield) as a light pink solid. LC retention time 1.25 min [B1]. m/z [M+H]$^+$= 477.2. $^1$H NMR (400 MHz, chloroform-d) δ 7.90 (s, 1H), 7.78 (s, 1H), 7.33 (d, J=8.4 Hz, 1H), 7.26 (dd, J=8.6, 1.8 Hz, 1H), 7.08 (dd, J=7.9, 1.8 Hz, 1H), 7.04 (d, J=2.0 Hz, 1H), 6.99 (d, J=8.4 Hz, 1H), 6.03 (br. s., 1H), 4.13 (d, J=2.4 Hz, 2H), 3.97 (s, 3H), 3.95 (s, 3H), 3.71 (t, J=5.7 Hz, 2H), 3.38 (quin, J=7.1 Hz, 1H), 2.67 (br. s., 2H), 1.53 (s, 9H), 1.51 (d, J=7.0 Hz, 6H).

Intermediate 204B: 2-chloro-1-(4-(2-(3,4-dimethoxyphenyl)-3-isopropyl-1H-indol-5-yl)-3,6-dihydropyridin-1(2H)-yl)ethan-1-one

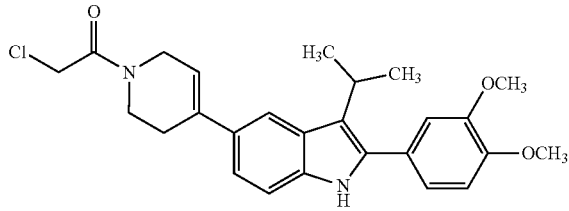

(204B)

tert-butyl 4-(2-(3,4-dimethoxyphenyl)-3-isopropyl-1H-indol-5-yl)-5,6-dihydropyridine-1(2H)-carboxylate (35 mg, 0.073 mmol) was added to a 1-dram vial containing a Teflon-coated stir bar. Next, 4N HCl in 1,4-dioxane (184 µl, 0.734 mmol) was added to the vial and the vial was capped. The reaction mixture was stirred at room temperature for 40 min. Excess solvent and HCl were evaporated from the reaction. The residue was suspended in DCM (1836 µl), and DIPEA (32.1 µl, 0.184 mmol) was added (color change from green to yellow suspension), followed by chloroacetyl chloride (6.44 µl, 0.081 mmol) (solid in suspension gradually dissolved). The reaction mixture was stirred at room temperature for 1.75 h. Additional chloroacetyl chloride (2.5 µL) was added to the reaction mixture, and the reaction mixture was stirred for 1 h. Excess solvent was evaporated from the reaction. The residue was partitioned between EtOAc and saturated aqueous NaHCO₃ (1.5 mL of each), separated, and the aqueous phase was extracted 2 additional times with EtOAc (2×1.5 mL). The combined organic extracts were dried over Na₂SO₄, filtered, and excess solvent was evaporated off. Obtained 2-chloro-1-(4-(2-(3,4-dimethoxyphenyl)-3-isopropyl-1H-indol-5-yl)-5,6-dihydropyridin-1(2H)-yl)ethanone (37.5 mg, 0.066 mmol, 90% yield) as a brown solid. LC retention time 1.05 min [B1]. m/z [M+H]⁺=453.2.

Intermediate 204C: 3-((2-(4-(2-(3,4-dimethoxyphenyl)-3-isopropyl-1H-indol-5-yl)-3,6-dihydropyridin-1(2H)-yl)-2-oxoethyl)(methyl)amino)propanoic acid

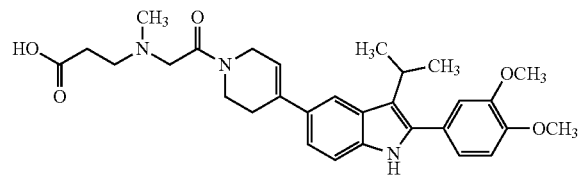

(204C)

2-chloro-1-(4-(2-(3,4-dimethoxyphenyl)-3-isopropyl-1H-indol-5-yl)-5,6-dihydropyridin-1(2H)-yl)ethanone (37.5 mg, 0.083 mmol) was dissolved in NMP (394 µl) in a 2-dram vial containing a Teflon-coated stir bar. 3-(methylamino) propanoic acid (12.81 mg, 0.124 mmol) and DIPEA (21.69 µl, 0.124 mmol) were added to the reaction mixture, the reaction mixture was degassed with N₂, then heated to 65° C. overnight (16 h). The reaction mixture was allowed to cool to room temperature. DMF (1.2 mL) was added to the reaction and the reaction mixture was purified by HPLC. Product-containing fractions were consolidated into a tarred 20 mL scintillation vial using a Biotage V-10 concentrator. Obtained 3-((2-(4-(2-(3,4-dimethoxyphenyl)-3-isopropyl-1H-indol-5-yl)-5,6-dihydropyridin-1(2H)-yl)-2-oxoethyl) (methyl)amino)propanoic acid (17.1 mg, 0.033 mmol, 39.8% yield) as a bright yellow solid. LC retention time 0.81 min [B1]. m/z [M+H]⁺=520.4.

Example 204

The reaction mixture was set up in a 1-dram vial containing a Teflon-coated stir bar. 3-((2-(4-(2-(3,4-dimethoxyphenyl)-3-isopropyl-1H-indol-5-yl)-5,6-dihydropyridin-1(2H)-yl)-2-oxoethyl)(methyl)amino) propanoic acid (17.1 mg, 0.033 mmol) was transferred into the vial. DCM (329 µl) and DIPEA (17.24 µl, 0.099 mmol) were added to the vial, followed by PyBOP (22.26 mg, 0.043 mmol), then diethylamine (6.88 µl, 0.066 mmol). The vial was capped and the reaction mixture (a transparent orange solution) was stirred at room temperature for 2.5 h. Additional diethylamine (6.88 µl, 0.066 mmol) was added to the reaction mixture. The reaction mixture was stirred at room temperature for 18 h. Excess solvent was evaporated from the reaction mixture. The residue was partitioned between EtOAc and aqueous saturated NaHCO₃ (1.5 mL of each), the phases were separated, and the aqueous phase was extracted with 3×1 mL EtOAc. Excess solvent was evaporated from the combined organic extracts. 5% Palladium on Carbon, wet (10 mg, 0.033 mmol), MeOH (1.5 mL), and ammonium formate (20.75 mg, 0.329 mmol) were added to the vial containing the residue, and the vial was capped and heated to 65° C. for 2 h. The reaction mixture was allowed to cool to room temperature and filtered through celite, and excess solvent was evaporated from the filtrate under an N₂ stream. The crude material was purified via preparative LC/MS with the following conditions: Column: Waters XBridge C18, 19×200 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 31-71% B over 20 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 acetonitrile: water with 0.1% trifluoroacetic acid; Mobile Phase B: 95:5 acetonitrile: water with 0.1% trifluoroacetic acid; Gradient: 30-70% B over 20 minutes, then a 5-minute hold at 100% B; Flow: 20 mL/min. Fractions containing the desired product were combined and dried via centrifugal evaporation. The yield of the product was 4.2 mg, and its estimated purity by LCMS analysis was 90%. Proton NMR was acquired in deuterated DMSO. LC retention time 1.85 min [B1]. M/z [M+H]⁺=577.3.

Example 205

2-(3,4-dimethoxyphenyl)-3-isopropyl-6-methyl-5-(piperidin-4-yl)-1H-indole

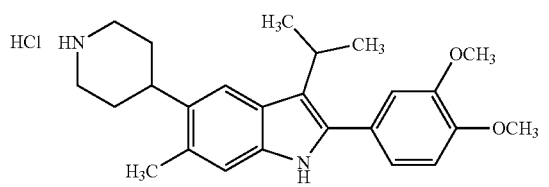
(205)

Intermediate 205A: 6-methyl-3-isopropyl-1H-indole

(205A)

A 250 ml round bottom flask was charged with triethylsilane (29.4 ml, 184 mmol), trichloroacetic acid (15.0 g, 92.0 mmol) and toluene (75 mL). The solution was heated to 70° C., then a solution of 5-bromo-1H-indole (8.0 g, 61.0 mmol) and acetone (4.27 g, 73.6 mmol) in toluene (25 mL) was added drop-wise via an addition funnel. The resulting brown solution was heated at 90° C. for 4 h. The solution was cooled to 10° C., quenched with 2M potassium phosphate solution and diluted with diethyl ether. The organic layer was separated, dried and concentrated under vacuum to get crude compound. The crude was purified using silica gel chromatography (ISCO 750 g column) eluting with 0-15% ethyl acetate in hexanes over a run time of 12 minutes to give 6-methyl-3-isopropyl-1H-indole (5.41 g, 31% yield) as a tan solid. LCMS retention time 1.17 min. MS (E⁻) m/z: 174 (M−H).

Intermediate 205B: 2-bromo-5-chloro-3-isopropyl-6-methyl-1H-indole

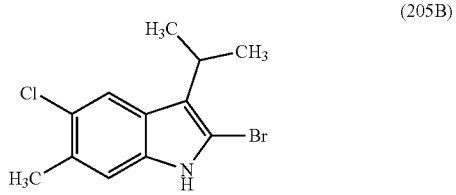
(205B)

To a 100 ml round bottom flask were added 3-isopropyl-6-methyl-1H-indole (1.090 g, 6.29 mmol) and acetonitrile (10 mL). NBS (1.064 g, 5.98 mmol) was dissolved in 5 ml of acetonitrile and added to the reaction mixture drop-wise via a pipet over 3 minutes. To this purple/brown liquid was then added NCS (0.840 g, 6.29 mmol) and the vial was capped and heated at 80° C. for 35 minutes. The reaction was quenched with a 10% sodium sulfite solution (2 ml). The reaction mixture was diluted with ethyl acetate and the contents poured in a separatory funnel. Water was added and the layers were separated. The organics were washed with a saturated sodium chloride solution, dried over anhydrous sodium sulfate, filtered and concentrated to afford 2-bromo-5-chloro-3-isopropyl-6-methyl-1H-indole (1.88 g, 100% yield). The material was stored at −35° C. due to reduce decomposition. LCMS retention time 1.20 min. MS (E⁻) m/z: 278 (M−H).

Intermediate 205C: 5-chloro-2-(3,4-dimethoxyphenyl)-3-isopropyl-6-methyl-1H-indole

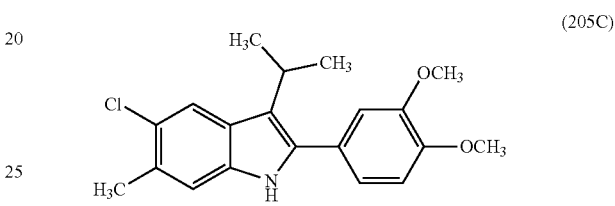
(205C)

To a 40 ml reaction vial were added 2-bromo-5-chloro-3-isopropyl-6-methyl-1H-indole (0.400 g, 1.396 mmol), (3,4-dimethoxyphenyl)boronic acid (0.267 g, 1.465 mmol), PdCl₂(dppf)-CH₂Cl₂ adduct (0.028 g, 0.035 mmol), THF (7 ml) and a 3M tribasic potassium phosphate solution (1.396 mL, 4.19 mmol). The reaction mixture was degassed with nitrogen gas for 5 minutes and then heated at 60° C. for 2 hours. The reaction mixture was cooled to room temperature and diluted with ethyl acetate and water. The mixture was transferred to a separatory funnel and the layers were separated. The organics were then washed with a saturated sodium chloride solution, dried over anhydrous sodium sulfate, filtered and concentrated to dryness. The residue was solid loaded onto a 40 g ISCO column, which was eluted with 0-30% ethyl acetate/hexane with a run time of 12 minutes. The combined fractions were concentrated to afford 5-chloro-2-(3,4-dimethoxyphenyl)-3-isopropyl-6-methyl-1H-indole (0.112 g, 23% yield) as a white solid. LCMS retention time 1.27 min. MS (E⁻) m/z: 344 (M−H).

Intermediate 205D: tert-butyl 4-(3-isopropyl-2-(3,4-dimethoxyphenyl)-1H-indol-5-yl)-5,6-dihydropyridine-1(2H)-carboxylate

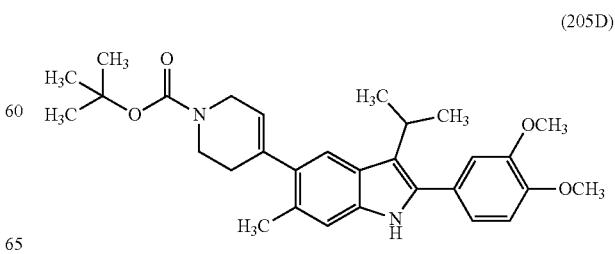
(205D)

To a mixture of 5-bromo-3-isopropyl-1H-indole (0.112 g, 0.326 mmol), tert-butyl 4-(4,4,5,5-tetramethyl-1,3,2-dioxaborolan-2-yl)-5,6-dihydropyridine-1(2H)-carboxylate (0.121 g, 0.391 mmol) in a 40 ml reaction vial were added THF (3 mL) followed by a 3M aqueous solution of potassium phosphate, tribasic (0.326 ml, 0.927 mmol). The resulting reaction mixture was sealed with a Teflon-lined pressure cap and degassed for 10 minutes with nitrogen gas. PdCl$_2$ (dppf)-CH$_2$Cl$_2$ adduct, (0.013 g, 0.016 mmol) was then added and the resulting suspension was degassed again for 5 minutes. The resulting reaction mixture was heated at 80° C. for 16 hours. The mixture was cooled to room temperature, diluted with ethyl acetate (100 mL), poured into a separatory funnel and was washed with water (2×50 mL). The collected organics were then washed with a saturated sodium chloride solution (50 mL), dried over anhydrous sodium sulfate, filtered and concentrated to give crude product. The crude material was purified using silica gel chromatography (12 g ISCO column), eluting with 0-50% ethyl acetate in hexane. The fractions were collected and concentrated to give tert-butyl 4-(3-isopropyl-2-(3,4-dimethoxyphenyl)-1H-indol-5-yl)-5,6-dihydropyridine-1(2H)-carboxylate as a tan solid. LCMS retention time 1.19 min [F1]. MS (E$^-$) m/z: 490 (M–H).

Example 205

Tert-butyl-4-(3-isopropyl-2-(3,4-dimethoxyphenyl)-1H-indol-5-yl)-5,6-dihydropyridine-1(2H)-carboxylate was dissolved in methanol and under a nitrogen atmosphere was added Pd(OH)$_2$ (0.023 g, 0.033 mmol). The vessel was placed on the Parr apparatus and pump/purged with nitrogen gas three times. This was followed by a second pump/purge with hydrogen gas. The vessel was evacuated and charged to 55 psi with hydrogen gas. The reaction mixture was allowed to shake at room temperature for 16 hours. The suspension was filtered thru fluted paper and concentrated to dryness. To this was added 4 M HCl/dioxane (2 ml) and the reaction mixture was stirred for 30 minutes at room temperature. The volatiles were removed and 2-(3,4-dimethoxyphenyl)-3-isopropyl-6-methyl-5-(piperidin-4-yl)-1H-indole (0.056 g, 43% yield) was collected as a tannish residue. 20 mg of the crude solid was further purified via preparative LC/MS with the following conditions: Column: Waters XBridge C18, 19×250 mm, 5-µm particles; Mobile Phase A: 5:95 acetonitrile: water with 10-mM ammonium acetate; Mobile Phase B: 95:5 acetonitrile: water with 10-mM ammonium acetate; Gradient: 15-100% B over 20 minutes, then a 5-minute hold at 100% B; Flow: 20 mL/min. Fractions containing the desired product were combined and dried via centrifugal evaporation to afford 2-(3,4-dimethoxyphenyl)-3-isopropyl-6-methyl-5-(piperidin-4-yl)-1H-indole. Two analytical LC/MS injections were used to determine the final purity. (1) LC retention time 1.49 min. MS (E$^-$) m/z: 393 (M–H). (2) LC retention time=1.46 min. MS (E$^-$) m/z: 393 (M–H).

Example 206

2-(3,4-dimethoxyphenyl)-3-isopropyl-5-(1'-isopropyl-[1,4'-bipiperidin]-4-yl)-6-methyl-1H-indole di trifluoroacetic acid

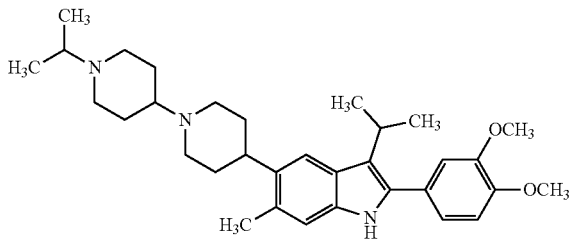

(206)

To a 2 dram reaction vial were added 2-(3,4-dimethoxyphenyl)-3-isopropyl-6-methyl-5-(piperidin-4-yl)-1H-indole hydrochloride (0.050 g, 0.117 mmol) and DMF (1 mL). To this were added TEA (0.081 mL, 0.583 mmol) and 1-isopropylpiperidin-4-one (0.016 g, 0.117 mmol) and drop of acetic acid. The reaction mixture was stirred for 1 hour at room temperature and sodium cyanoborohydride (0.022 g, 0.350 mmol) was added, and stirring was continued for 16 hours at room temperature. Methanol (0.1 ml) was added and the sample was concentrated to dryness. The crude material was purified via preparative LC/MS with the following conditions: Column: Waters XBridge C18, 19×200 mm, 5-µm particles; Mobile Phase A: 5:95 acetonitrile: water with 0.1% trifluoroacetic acid; Mobile Phase B: 95:5 acetonitrile: water with 0.1% trifluoroacetic acid; Gradient: 0-100% B over 20 minutes, then a 3-minute hold at 100% B; Flow: 20 mL/min. Fractions containing the desired product were combined and dried via centrifugal evaporation to afford 2-(3,4-dimethoxyphenyl)-3-isopropyl-5-(1'-isopropyl-[1,4'-bipiperidin]-4-yl)-6-methyl-1H-indole di trifluoroacetic acid (0.0104 g, 17% yield). Two analytical LC/MS injections were used to determine the final purity. (1) LC retention time 1.73 min [C1]. MS (E$^-$) m/z: 518 (M–H). (2) LC retention time=1.33 min [D1]. MS (E$^-$) m/z: 518 (M–H).

Example 207

2-(4-(2-(3,4-dimethoxyphenyl)-3-isopropyl-6-methyl-1H-indol-5-yl)piperidin-1-yl)-N-methyl-ethan-1-amine

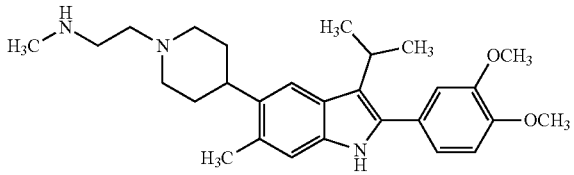

(207)

To a 2 dram vial were added 2-(3,4-dimethoxyphenyl)-3-isopropyl-6-methyl-5-(piperidin-4-yl)-1H-indole hydrochloride (0.050 g, 0.117 mmol), DCM (5 mL), TEA (0.425 mL, 3.05 mmol), tert-butyl methyl(2-oxoethyl)carbamate (0.030 g, 0.175 mmol) and acetic acid (0.035 mL, 0.610 mmol). The mixture was stirred for 1 hour at room temperature and then sodium triacetoxyborohydride (0.388 g, 1.831 mmol) was added. The reaction mixture was set to stir at room temperature overnight. The reaction mixture was diluted with DCM and water and the contents transferred to a separatory funnel. The layers were separated and the organics were washed with a saturated sodium chloride solution. The combined organics were dried over anhydrous sodium sulfate, filtered and concentrated to approximately 1 ml and to this was added 4M HCl in dioxane (2 ml). The reaction mixture was stirred at room temperature for 60 minutes then concentrated. The residue was taken up in DMF (1 mL) and the solids were filtered through a 0.45 micron syringe filter. The crude material was purified via preparative LC/MS with the following conditions: Column: Waters XBridge C18, 19×200 mm, 5-m particles; Mobile Phase A: 5:95 acetonitrile: water with 0.1% trifluoroacetic acid; Mobile Phase B: 95:5 acetonitrile: water with 0.1% trifluoroacetic acid; Gradient: 0-100% B over 20 minutes, then a 3-minute hold at 100% B; Flow: 20 mL/min. Fractions containing the desired product were combined and dried via centrifugal evaporation to afford 2-(3,4-dimethoxyphenyl)-3-isopropyl-5-(1'-isopropyl-[1,4'-bipiperidin]-4-yl)-6-methyl-1H-indole-ditrifluoroacteic acid (0.0165 g, 31% yield). Two analytical LC/MS injections were used to determine the final purity. (1) LC retention time 1.67 min [C$_{1]}$ MS (E$^-$) m/z: 450 (M–H). (2) LC retention time=1.30 min [D1]. MS (E$^-$) m/z: 450 (M–H).

Example 208

2-(4-(2-(3,4-dimethoxyphenyl)-6-fluoro-3-isopropyl-1H-indol-5-yl)piperidin-1-yl)-N-methylethan-1-amine (208)

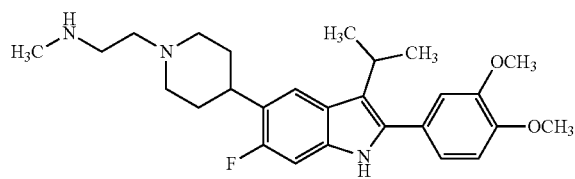

Intermediate 208A:
5-chloro-6-fluoro-3-isopropyl-1H-indole (208A)

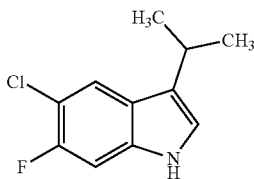

A 250 ml round bottom flask was charged with triethylsilane (2.83 ml, 17.69 mmol), trichloroacetic acid (1.45 g, 8.85 mmol) and toluene (10 mL). The solution was heated to 70° C., then a solution of 5-chloro-6-fluoro-1H-indole (1.0 g, 5.90 mmol) and acetone (0.52 g, 7.08 mmol) in toluene (20 mL) was added drop-wise via an addition funnel. The resulting brown solution was heated at 90° C. for 2.5 hours. The solution was cooled to 10° C. The reaction was quenched with 2M potassium phosphate solution. The mixture was diluted with diethyl ether. The organic layer was separated, dried and concentrated under vacuum to get crude compound. The crude was purified using silica gel chromatography (ISCO 24 g column) eluting with 0-40% ethyl acetate in hexanes over a run time of 10 minutes to give 5-chloro-6-fluoro-3-isopropyl-1H-indole (1.1 g, 88% yield) as an oil. LCMS retention time 1.21 min [B1]. MS (E$^-$) m/z: 212/214 (M–H).

Intermediate 208B: tert-butyl 4-(6-fluoro-3-isopropyl-2-(3,4-dimethoxyphenyl)-1H-indol-5-yl)-5,6-dihydropyridine-1(2H)-carboxylate (208B)

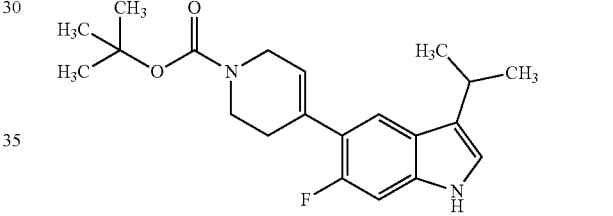

To a mixture of 5-chloro-6-fluoro-3-isopropyl-1H-indole (1.790 g, 8.46 mmol), 2nd generation XPhos precatalyst (0.166 g, 0.211 mmol) and tert-butyl 4-(4,4,5,5-tetramethyl-1,3,2-dioxaborolan-2-yl)-5,6-dihydropyridine-1(2H)-carboxylate (2.75 g, 8.88 mmol) in a 250 ml round bottom flask were added THF (25 mL), followed by a 3M aqueous solution of tripotassium phosphate (8.46 mL, 25.4 mmol). The flask was fitted with a reflux condenser and septum. The system was evacuated under vacuum (via a needle from a nitrogen/vacuum manifold line) and back-filled with nitrogen gas. The procedure was repeated three times. The needle was removed and the reaction mixture was heated at 50° C. for 1 hour. The reaction mixture was diluted with ethyl acetate (100 mL), poured into a separatory funnel and washed with water (2×50 mL) and saturated aqueous sodium chloride solution (50 mL). The combined organics were dried over anhydrous sodium sulfate, filtered and the filtrate was concentrated in vacuo to give crude product. The crude was purified using silica gel chromatography (ISCO 40 g column) eluting with 0-50% ethyl acetate in hexanes over a run time of 12 minutes to give tert-butyl 4-(6-fluoro-3-isopropyl-2-(3,4-dimethoxyphenyl)-1H-indol-5-yl)-5,6-dihydropyridine-1(2H)-carboxylate (1.4 g, 55% yield) as an oil. LCMS retention time 1.24 min [B1]. MS (E$^-$) m/z: 359 (M–H).

Intermediate 208C: tert-butyl 4-(6-fluoro-3-isopropyl-1H-indol-5-yl)piperidine-1-carboxylate

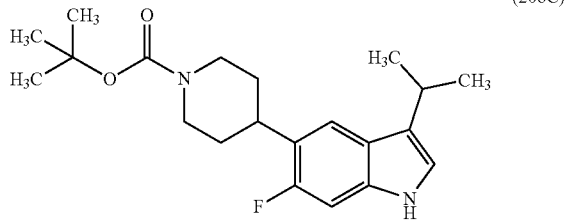

(208C)

To a 100 ml round bottom flask were added tert-butyl 4-(6-fluoro-3-isopropyl-2-(3,4-dimethoxyphenyl)-1H-indol-5-yl)-5,6-dihydropyridine-1(2H)-carboxylate (1.4 g, 3.91 mmol) and ethyl acetate (5 ml). The flask was purged with nitrogen gas and Pd/C (0.325 g, 0.305 mmol) was added. Following pump/purging with nitrogen gas three times, hydrogen gas was introduced via a balloon. The reaction mixture was stirred at room temperature overnight. The flask was evacuated and filled with nitrogen gas. The suspension was diluted with methanol (100 ml) and filtered through fluted filter paper and the filtrate was concentrated in vacuo. Collected tert-butyl 4-(6-fluoro-3-isopropyl-1H-indol-5-yl)piperidine-1-carboxylate (1.10 g, 88% yield) as an off-white solid. LC retention time 1.25 min [B1]. MS (E$^-$) m/z: 361 (M−H).

Intermediate 208D: tert-butyl 4-(2-bromo-6-fluoro-3-isopropyl-1H-indol-5-yl)piperidine-1-carboxylate

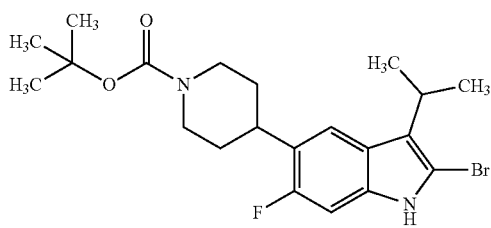

(208D)

To a solution of tert-butyl 4-(6-fluoro-3-isopropyl-1H-indol-5-yl)piperidine-1-carboxylate (1.00 g, 2.77 mmol) in DCM (20 mL) at 0° C., was added NBS (0.469 g, 2.64 mmol) in DCM (20 mL) drop-wise via an addition funnel over 10 minutes. The resulting brown solution was stirred at room temperature for 15 minutes. The reaction was quenched with a 10% sodium sulfite solution (5 mL). The residue was diluted with DCM (50 mL) and water (20 ml) and the mixture was poured into a separatory funnel. The aqueous layer was separated. The organics were then washed with a saturated sodium chloride solution (20 ml), dried over anhydrous sodium sulfate, filtered and concentrated to give crude compound. The crude material was purified by ISCO using a 24 g silica column, eluting with 0-100% ethyl acetate in hexanes. The combined fractions were concentrated to give tert-butyl 4-(2-bromo-6-fluoro-3-isopropyl-1H-indol-5-yl) piperidine-1-carboxylate (0.4 g, 33% yield) as a tan solid. LC retention time 1.23 min [B1]. MS (E$^-$) m/z: 439/441 (M−H).

Example 208

To a 2 dram reaction vial were added tert-butyl 4-(2-bromo-6-fluoro-3-isopropyl-1H-indol-5-yl)piperidine-1-carboxylate (0.300 g, 0.683 mmol), (3,4-dimethoxyphenyl)boronic acid (0.128 g, 0.683 mmol), PdCl$_2$(dppf)-CH$_2$Cl$_2$ adduct (0.028 g, 0.034 mmol), THF (7 ml) and a 3M tribasic potassium phosphate solution (0.68 mL, 2.05 mmol). The reaction mixture was degassed with nitrogen gas for 5 minutes and then heated at 60° C. for 2 hours. The reaction mixture was cooled to room temperature and diluted with ethyl acetate and water. The mixture was transferred to a separatory funnel and the layers were separated. The organics were then washed with a saturated sodium chloride solution, dried over anhydrous sodium sulfate, filtered and concentrated to dryness. The residue was dissolved in DCM (1 ml) and loaded onto a 12 g ISCO column, which was eluted with 0-50% ethyl acetate/hexane with a run time of 10 minutes. The combined fractions were concentrated to give tert-butyl (2-(4-(2-(3,4-dimethoxyphenyl)-6-fluoro-3-isopropyl-1H-indol-5-yl)piperidin-1-yl)ethyl)(methyl)carbamate (0.175 g, 52% yield) as a white solid. To this was added DCM (0.5 ml) and 4M HCl in dioxane (2 ml) The reaction mixture was capped and stirred at room temperature for 1 hour, then concentrated to dryness under a stream of nitrogen gas to give 2-(3,4-dimethoxyphenyl)-6-fluoro-3-isopropyl-1H-indole-5-yl)piperidin-1-carboxylate (0.112 g, 45% yield). To this intermediate (0.025 g, 0.063 mmol), in a 2 dram reaction vial, were added DCM (1 mL), TEA (0.040 mL, 0.503 mmol), tert-butyl methyl(2-oxoethyl)carbamate (0.013 g, 0.076 mmol) and 1 drop of acetic acid. The mixture was stirred for 1 hour at room temperature and then sodium triacetoxyborohydride (0.043 g, 0.201 mmol) was added. The reaction mixture was set to stir at room temperature overnight. The reaction mixture was diluted with DCM and water and the contents transferred to a separatory funnel. The layers were separated and the organics were washed with a saturated sodium chloride solution. The combined organics were dried over anhydrous sodium sulfate, filtered and concentrated to approximately 1 ml. Next, 4M HCl in dioxane (2 ml) was added. The reaction mixture was stirred at room temperature for 60 minutes then concentrated. The residue was taken up in DMF (1 mL) and the solids were filtered through a 0.45 micron syringe filter. The crude material was purified via preparative LC/MS with the following conditions: Column: XBridge C18, 19×200 mm, 5-μm particles; Mobile Phase A: 5:95 acetonitrile: water with 10-mM ammonium acetate; Mobile Phase B: 95:5 acetonitrile: water with 10-mM ammonium acetate; Gradient: 20-60% B over 19 minutes, then a 5-minute hold at 100% B; Flow: 20 mL/min. Fractions containing the desired product were combined and dried via centrifugal evaporation to give 2-(4-(2-(3,4-dimethoxyphenyl)-6-fluoro-3-isopropyl-1H-indol-5-yl)piperidin-1-yl)-N-methylethanamine (0.006 g, 25% yield). Two analytical LC/MS injections were used to determine the final purity. (1) LC retention time 1.65 min [C1]. MS (E$^-$) m/z: 454 (M−H). (2) LC retention time=1.22 min [D1]. MS (E$^-$) m/z: 454 (M−H).

Example 209

1-(4-(2-(3,4-dimethoxyphenyl)-3-isopropyl-1H-indol-5-yl)piperidin-1-yl)-2-(dimethylamino)ethan-1-one

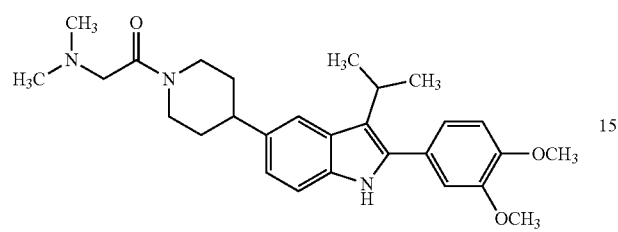

(209)

2-chloro-1-(4-(2-(3,4-dimethoxyphenyl)-3-isopropyl-1H-indol-5-yl)piperidin-1-yl)ethanone (0.02 g, 0.044 mmol) and DIPEA (0.012 mL, 0.066 mmol) were added to THF (1 mL). The solution was stirred. Dimethylamine (2.378 mg, 0.053 mmol) was added to the reaction solution. The resulting reaction mixture was stirred at 25° C. for 4 h. The reaction mixture was concentrated. The crude was dissolved in ethyl acetate. It was washed with water. The organic layer was dried over Na$_2$SO$_4$ and concentrated. The crude was purified using prep TLC plate eluting with 5% methanol: 95% chloroform. The product was collected (2.5 g, 12.3% yield). LC retention time=1.779 min [C]. MS (E$^-$) m/z: 464.2 (M+H).

The following Examples were prepared according to the general procedure described in Example 209.

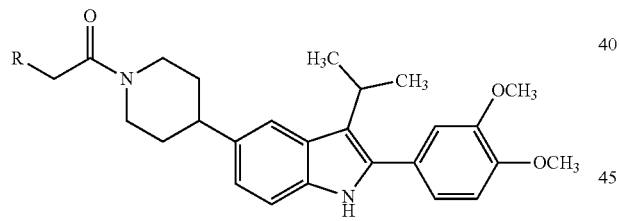

TABLE 13

| Ex. No. | R | M$^{+1}$ | RT (min) | Method |
|---|---|---|---|---|
| 210 | —NH(CH$_2$CH(OH)CH$_3$) | 494.2 | 1.332 | F |
| 211 | (piperidin-4-yl)piperidine | 587.4 | 1.201 | F |
| 212 | —NH(CH$_2$CH$_2$OH) | 480.2 | 1.246 | F |
| 213 | HO-cyclopentyl-NH- | 534.2 | 1.46 | F |
| 214 | —NH(CH$_2$CN) | 475.2 | 1.402 | F |

TABLE 13-continued

| Ex. No. | R | M$^{+1}$ | RT (min) | Method |
|---|---|---|---|---|
| 215 | (CH$_3$)$_2$N-cyclohexyl-NH- | 561.2 | 1.187 | F |
| 216 | (dimethylpyrazol-yl)NH- | 558.2 | 1.557 | F |
| 217 | bicycloalkyl-NH- | 570.2 | 1.704 | F |
| 218 | HO-bicycloalkyl-NH- | 586.2 | 1.397 | F |
| 219 | —NH(CH$_2$C(CH$_3$)$_2$CH$_2$OH) | 522.2 | 1.442 | F |
| 220 | —NH(CH(CH$_2$OH)$_2$) | 510.2 | 1.297 | F |
| 221 | —NH(CH$_2$CF$_3$) | 518.2 | 1.575 | F |
| 222 | acetyl-diazepan-yl | 561.2 | 1.342 | F |
| 223 | morpholin-yl | 506.2 | 1.363 | F |
| 224 | N,N-diethylcarboxamide piperidin-yl | 603.4 | 1.609 | F |
| 225 | N-methylpyrrolidin-ylmethyl-piperidin-yl | 601.4 | 1.283 | F |
| 226 | HO-methyl-piperidin-yl | 534.2 | 1.365 | F |
| 227 | —N(CH$_3$)CH(CH$_3$)$_2$ | 492.2 | 1.445 | F |
| 228 | —NH(CH$_2$C(O)NH$_2$) | 493.2 | 1.417 | E |

TABLE 13-continued

| Ex. No. | R | M+1 | RT (min) | Method |
|---|---|---|---|---|
| 229 | HN-C(=O)-CH2-N(piperazine)-, isopropyl on HN | 604.3 | 1.746 | E |
| 230 | —NH(CH2CH2OCH2CH2OH) | 524.2 | 1.364 | E |
| 231 | (CH3)2CH-CH2-CH(NH-)-CH2OH | 536.2 | 1.723 | E |
| 232 | H2N-cyclohexyl-NH- | 533.2 | 1.261 | E |
| 233 | —NH(CH(CH2OH)CH2CH3) | 508.2 | 1.526 | E |
| 234 | (CH3)2CH-CH2-CH(NH-)-CH2OH | 536.2 | 1.733 | E |
| 235 | HOCH2-CH(OH)-CH2-NH- | 510.2 | 1.318 | E |
| 236 | 2-hydroxycyclopentyl-NH- | 520.2 | 1.512 | E |
| 237 | —NH(CH2CH2CH(OH)CH3) | 508.2 | 1.38 | E |
| 238 | 4-hydroxypiperidin-1-yl | 520.2 | 1.456 | E |
| 239 | 4-methyl-1,4-diazepan-1-yl | 533.2 | 1.424 | E |
| 240 | 4-isopropylpiperazin-1-yl | 547.2 | 1.53 | E |
| 241 | 4-(4-methylpiperazin-1-yl)piperidin-1-yl | 602.4 | 1.43 | E |
| 242 | —N(CH3)CH2CH2OH | 494.2 | 1.479 | E |
| 243 | 4-(hydroxymethyl)piperidin-1-yl | 534.2 | 1.449 | E |
| 244 | 4-(dimethylamino)piperidin-1-yl | 547.3 | 1.406 | E |
| 245 | 4-(2-hydroxypropan-2-yl)cyclohexyl-NH- | 576.2 | 1.589 | E |
| 246 | 4-hydroxycyclohexyl-NH- | 534.2 | 1.406 | E |
| 247 | 3-(N,N-diethylcarbamoyl)piperidin-1-yl, Homochiral | 603.5 | 2.01 | E |
| 248 | 3-(N,N-diethylcarbamoyl)piperidin-1-yl, Homochiral | 603.5 | 2.01 | E |
| 249 | 3-(hydroxymethyl)piperidin-1-yl, Homochiral | 534.4 | 2.21 | E |
| 250 | 3-(hydroxymethyl)piperidin-1-yl, Homochiral | 534.4 | 2.26 | E |
| 251 | (CH3)2C(OH)-CHF-CH2-NH- | 540.4 | 1.728 | C1 |

Example 252

N-(2-(4-(2-(3,4-dimethoxyphenyl)-3-isopropyl-1H-indol-5-yl)piperidin-1-yl)-2-oxoethyl)hex-5-ynamide

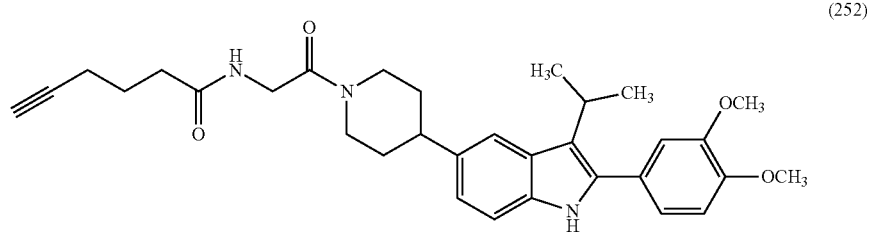 [SMILES: C#CCCCC(=O)NCC(=O)N1CCC(c2ccc3[nH]c(-c4ccc(OC)c(OC)c4)c(C(C)C)c3c2)CC1]

(252)

Intermediate 252A: tert-butyl (2-(4-(2-(3,4-dimethoxyphenyl)-3-isopropyl-1H-indol-5-yl) piperidin-1-yl)-2-oxoethyl)carbamate

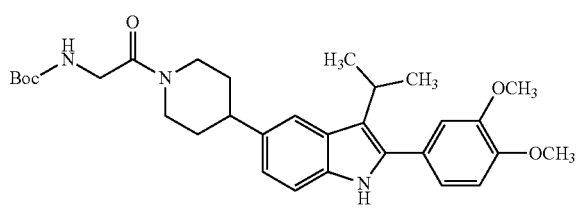

(252A)

To a solution of 2-(3,4-dimethoxyphenyl)-3-isopropyl-5-(piperidin-4-yl)-1H-indole (0.2 g, 0.528 mmol) and 2-((tert-butoxycarbonyl)amino)acetic acid (0.093 g, 0.528 mmol) in DMF (3 mL) were added DIPEA (0.277 mL, 1.585 mmol) and HATU (0.201 g, 0.528 mmol) at room temperature. The mixture was stirred at room temperature for 4 h.

DMF was removed under vacuum. The reaction was quenched with ice water. The mixture was extracted with ethyl acetate. The ethyl acetate layer was dried over Na2SO4 and concentrated to afford the crude compound. The crude material was purified by flash chromatography using 12 g silica column. The compound was eluted in 5% methanol in $CHCl_3$, the fractions combined and concentrated to provide tert-butyl (2-(4-(2-(3,4-dimethoxyphenyl)-3-isopropyl-1H-indol-5-yl)piperidin-1-yl)-2-oxoethyl)carbamate (0.18 g, 63.6% yield) as an off white solid. LC retention time=1.16 min [B]. MS (E⁻) m/z: 536.3 (M+H).

Intermediate 252B: 2-amino-1-(4-(2-(3,4-dimethoxyphenyl)-3-isopropyl-1H-indol-5-yl) piperidin-1-yl)ethan-1-one

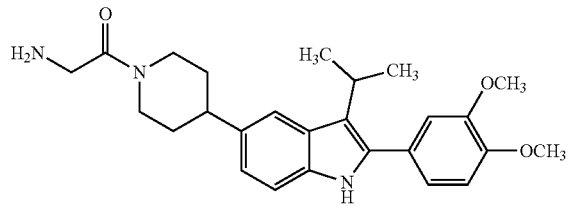

(252B)

To a solution of tert-butyl (2-(4-(2-(3,4-dimethoxyphenyl)-3-isopropyl-1H-indol-5-yl)piperidin-1-yl)-2-oxoethyl)carbamate (0.2 g, 0.373 mmol) in DCM (5 mL) was added TFA (0.029 mL, 0.373 mmol) at room temperature. The mixture was stirred at room temperature for 2 h. The reaction mass was concentrated to afford crude compound. The crude was triturated with diethyl ether (2×5 mL) and then dried to afford 2-amino-1-(4-(2-(3,4-dimethoxyphenyl)-3-isopropyl-1H-indol-5-yl)piperidin-1-yl)ethanone (0.16 g, 98% yield) as an off white solid. LC retention time=1.00 min [B]. MS (E⁻) m/z: 436.3 (M+H).

Example 252

To a solution of 2-amino-1-(4-(2-(3,4-dimethoxyphenyl)-3-isopropyl-1H-indol-5-yl)piperidin-1-yl)ethanone (0.2 g, 0.459 mmol) in DMF (2 mL) were added hex-5-ynoic acid (0.051 g, 0.459 mmol), DIPEA (0.241 mL, 1.378 mmol) and HATU (0.175 g, 0.459 mmol) at room temperature. The reaction mixture was stirred at the room temperature for 2 h. DMF was removed under vacuum and the residue was diluted with 10% $NaHCO_3$ (10 mL) and extracted with ethyl acetate (2×20 mL). The combined organic extracts was dried ($Na_2SO_4$) and concentrated to get crude compound. The crude product was purified by prep HPLC to provide N-(2-(4-(2-(3,4-dimethoxyphenyl)-3-isopropyl-1H-indol-5-yl)piperidin-1-yl)-2-oxoethyl)hex-5-ynamide (46 mg, 18.91% yield) as an off white solid. LC retention time=1.93 min [F]

The following examples were prepared according to the general procedure described in Example 252 using 2-(3,4-dimethoxyphenyl)-3-isopropyl-5-(piperidin-4-yl)-1H-indole.

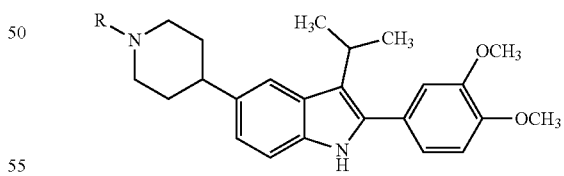

TABLE 14

| Ex. No. | R | M⁺¹ | RT (min) | Method |
|---|---|---|---|---|
| 253 | ![NH2 group structure] | 464.40 | 1.57 | E |

TABLE 14-continued

| Ex. No. | R | M+1 | RT (min) | Method |
|---|---|---|---|---|
| 254 | OH O / H3C (S) | 465.2 | 1.814 | E |
| 255 | OH O / H3C (R) | 465.2 | 1.828 | E |
| 256 | —C(O)CH2NH(CH3) | 450.4 | 1.425 | E |

Example 257

1-(4-(2-(3,4-dimethoxyphenyl)-3-isopropyl-1H-indol-5-yl)piperidin-1-yl)-4-(isopropylamino)butan-1-one

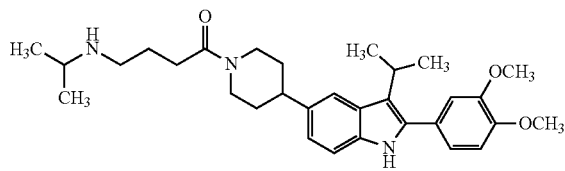

(257)

Intermediate 257A: tert-butyl (4-(4-(2-(3,4-dimethoxyphenyl)-3-isopropyl-1H-indol-5-yl) piperidin-1-yl)-4-oxobutyl)carbamate

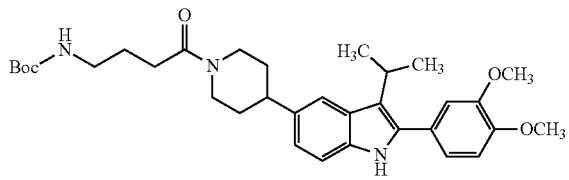

(257A)

2-(3,4-dimethoxyphenyl)-3-isopropyl-5-(piperidin-4-yl)-1H-indole (0.1 g, 0.264 mmol) was dissolved in DMF (2 mL). DIPEA (0.231 mL, 1.321 mmol) and BOP (0.140 g, 0.317 mmol) were added to the reaction solution followed by drop wise addition of 4-((tert-butoxycarbonyl)amino) butanoic acid (0.054 g, 0.264 mmol). The resulting reaction mixture was stirred at 25° C. for 12 h. The reaction mixture was concentrated. The crude was dissolved in ethyl acetate and the solution was washed with water. The organic layer was dried over Na2SO4 and concentrated to get tert-butyl (4-(4-(2-(3,4-dimethoxyphenyl)-3-isopropyl-1H-indol-5-yl) piperidin-1-yl)-4-oxobutyl)carbamate (0.14 g, 94% yield) as an off white solid. LC retention time=2.184 min [A]. MS (E⁻) m/z: 564.6 (M+H).

Intermediate 257B: 4-amino-1-(4-(2-(3,4-dimethoxyphenyl)-3-isopropyl-1H-indol-5-yl) piperidin-1-yl)butan-1-one

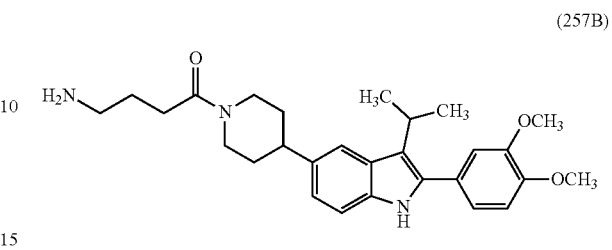

(257B)

Tert-butyl (4-(4-(2-(3,4-dimethoxyphenyl)-3-isopropyl-1H-indol-5-yl)piperidin-1-yl)-4-oxobutyl)carbamate (0.14 g, 0.248 mmol) was dissolved in DCM (2 mL). Next, 4M HCl in dioxane (0.310 mL, 1.242 mmol) was added to the solution. The reaction mixture was stirred at room temperature for 30 min. The reaction mixture was diluted with DCM and 10% sodium bicarbonate was added. The organic layer was separated, the aqueous layer was extracted twice with DCM (2×20 mL), combined organic extracts was dried over Na2SO4 and concentrated to afford 4-amino-1-(4-(2-(3,4-dimethoxyphenyl)-3-isopropyl-1H-indol-5-yl)piperidin-1-yl)butan-1-one (0.05 g, 0.108 mmol) as a pale yellow solid. LC retention time=0.94 min [B]. MS (E⁻) m/z: 464.2 (M+H).

Example 257

4-amino-1-(4-(2-(3,4-dimethoxyphenyl)-3-isopropyl-1H-indol-5-yl)piperidin-1-yl)butan-1-one (0.05 g, 0.108 mmol) and propan-2-one (6.26 mg, 0.108 mmol) were dissolved in THF (1 mL). Titanium(IV) isopropoxide (0.077 g, 0.270 mmol) was added to the reaction and the reaction mixture was stirred under nitrogen at 60° C. for 12 h. After reaching to 25° C., sodium cyanoborohydride (0.014 g, 0.216 mmol) was added and stirred at the 25° C. for 4 h. The reaction mixture was diluted with ethyl acetate (20 mL) and washed with water (2×10 mL), the organic layer was dried over Na2SO4, filtered and the filtrate was concentrated in vacuum to give crude product. The crude was purified with prep HPLC to 1-(4-(2-(3,4-dimethoxyphenyl)-3-isopropyl-1H-indol-5-yl)piperidin-1-yl)-4-(isopropylamino)butan-1-one (2 mg, 3.67% yield) as an off white solid. LC retention time=1.562 min [C1]. MS (E⁻) m/z: 506.2 (M+H).

Example 258

2-(3,4-dimethoxyphenyl)-3-isopropyl-5-(1-((1-methyl-1H-imidazol-5-yl)methyl)piperidin-4-yl)-1H-indole

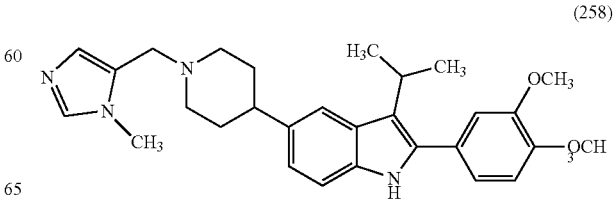

(258)

A solution of 2-(3,4-dimethoxyphenyl)-3-isopropyl-5-(piperidin-4-yl)-1H-indole, HCl (25 mg, 0.060 mmol) in DCM (0.5 mL) was neutralized by adding triethylamine drop wise (checked by pH paper). The solution was added to a vial containing 1-methyl-1H-imidazole-5-carbaldehyde (9.95 mg, 0.090 mmol), acetic acid (0.01 ml, 0.175 mmol) at room temperature. The mixture was stirred at room temperature for 16 h. Sodium triacetoxyborohydride (19.15 mg, 0.090 mmol) was added to the reaction mixture and the mixture was stirred for another 6 h at room temperature. The reaction mixture was purified by reverse phase prep LCMS to provide 2-(3,4-dimethoxyphenyl)-3-isopropyl-5-(1-((1-methyl-1H-imidazol-5-yl)methyl)piperidin-4-yl)-1H-indole (1.27 mg, 4.3400 yield, 97.25 purity) as a pale solid. LC retention time=1.734 min [E]. MS (E) mz: 473.2 (M+H).

The following Examples were prepared according to the general procedure described in Example 258.

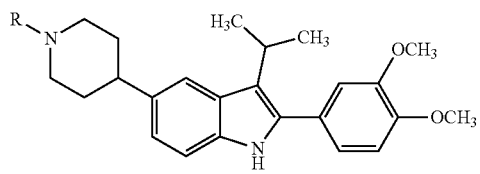

TABLE 15

| Ex. No. | R | M$^{+1}$ | RT (min) | Method |
|---|---|---|---|---|
| 259 | | 473.2 | 1.415 | E |
| 260 | | 562.2 | 1.853 | E |
| 261 | | 476.2 | 2.114 | E |
| 262 | | 473.2 | 1.731 | E |
| 263 | | 535.2 | 1.938 | E |
| 264 | | 494.2 | 2.316 | E |
| 265 | —CH$_2$CH(CH$_2$CH$_3$)$_2$ | 463.2 | 2.203 | E |
| 266 | | 473 | 1.21 | D1 |
| 267 | | 473 | 1.22 | D1 |
| 268 | | 459 | 1.19 | D1 |
| 269 | | 537.2 | 2.633 | E |

Example 270

4-((4-(2-(3,4-dimethoxyphenyl)-3-isopropyl-1H-indol-5-yl)piperidin-1-yl)methyl)-N,N-dimethylaniline (270)

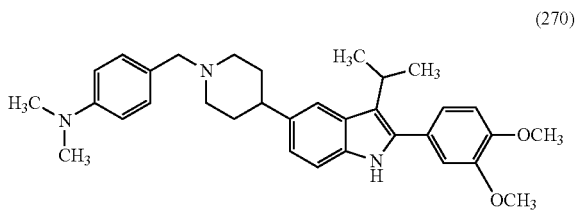

To a solution of 2-(3,4-dimethoxyphenyl)-3-isopropyl-5-(piperidin-4-yl)-1H-indole HCl (25 mg, 0.060 mmol) in DCM (1 ml) was neutralized with triethyl amine, then diluted with water (2 mL), extracted with DCM (2×10 mL). The solvent was evaporated to afford the compound. In a separate vial, zinc chloride (10 mg) and sodium cyanoborohydride (25 mg) were taken in methanol (0.5 mL), stirred for 1 h at room temperature. The contents of the vial were then added to a vial containing the above compound and 4-(dimethylamino)benzaldehyde (13.48 mg, 0.090 mmol) in DCM (0.5 mL). The reaction mixture was stirred for 6 h at room temperature. The reaction mixture was purified by Prep HPLC to afford 4-((4-(2-(3,4-dimethoxyphenyl)-3-isopropyl-1H-indol-5-yl)piperidin-1-yl)methyl)-N,N-dimethylaniline (8.99 mg, 29.1% yield, 99.7% purity) as a pale solid. LC retention time=1.962 min [E]. MS (E$^-$) m/z: 512.2 (M+H).

The following Examples were prepared according to the general procedure in Example 270.

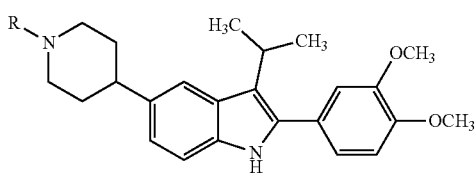

TABLE 16

| Ex. No. | R | M+1 | RT (min) | Method |
|---------|---|-----|----------|--------|
| 271 | 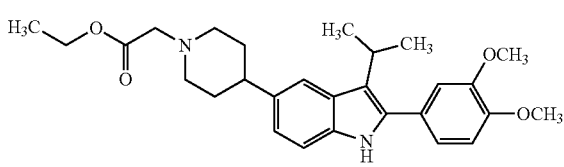 | 553.2 | 2.632 | E |

Example 272

1-(2-(4-(2-(3,4-dimethoxyphenyl)-3-isopropyl-1H-indol-5-yl)piperidin-1-yl)acetyl)-N,N-diethylpiperidine-3-carboxamide

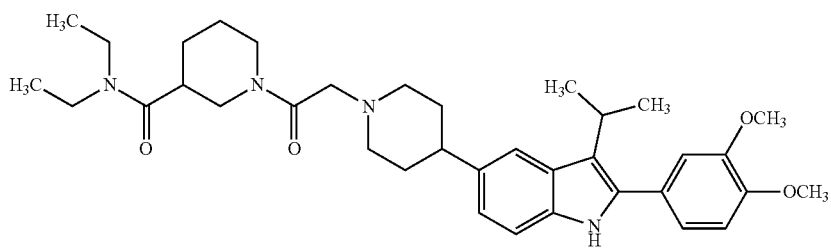

(272)

Intermediate 272A: ethyl 2-(4-(2-(3,4-dimethoxyphenyl)-3-isopropyl-1H-indol-5-yl) piperidin-1-yl) acetate (272A)

A 25 mL two-necked flask equipped with a condenser and a nitrogen U tube with a rubber septum was charged with a solution of 2-(3,4-dimethoxyphenyl)-3-isopropyl-5-(piperidin-4-yl)-1H-indole hydrochloride (400 mg, 0.964 mmol) in THF (10 mL). To this was added DIPEA (3.87 mL, 22.17 mmol) and ethyl 2-bromoacetate (0.129 mL, 1.157 mmol). The mixture was stirred at room temperature for 16 h, then was quenched with water (10 mL), extracted with ethyl acetate (3×30 mL), the combined organic extracts was dried with sodium sulfate and concentrated under reduced pressure to get crude compound (3.2 g). The crude product was purified by flash chromatography, using 24 g silica column, the compound was eluted in 20-25% ethyl acetate in hexanes, the fractions were collected and concentrated to afford ethyl 2-(4-(2-(3,4-dimethoxyphenyl)-3-isopropyl-1H-indol-5-yl)piperidin-1-yl)acetate (350 mg, 78% yield) as a pale yellow solid. LC retention time=2.128 min [A]. MS (E−) m/z: 465.4 (M+H).

Intermediate 272B: 2-(4-(2-(3,4-dimethoxyphenyl)-3-isopropyl-1H-indol-5-yl)piperidin-1-yl)acetic acid

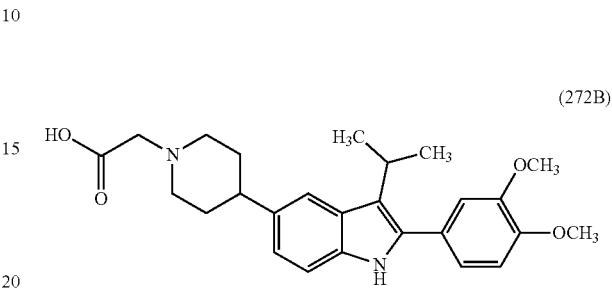

(272B)

To a solution of ethyl 2-(4-(2-(3,4-dimethoxyphenyl)-3-isopropyl-1H-indol-5-yl)piperidin-1-yl)acetate (250 mg, 0.538 mmol) in MeOH (2 mL), THF (8.00 mL), and water (8.00 mL) was added lithium hydroxide (38.7 mg, 1.614 mmol) at room temperature. The mixture was stirred at the room temperature for 16 h. The reaction mass was concentrated, extracted with DCM (3×30 mL), washed with water (30 mL), dried (Na2SO4) and concentrated to afford 2-(4-(2-(3,4-dimethoxyphenyl)-3-isopropyl-1H-indol-5-yl)piperidin-1-yl)acetic acid (175 mg, 73% yield and 98% purity) as an off white solid. LC retention time=1.745 min [A]. MS (E−) m/z: 437.2 (M+H).

Example 272

To a mixture of 2-(4-(2-(3,4-dimethoxyphenyl)-3-isopropyl-1H-indol-5-yl) piperidin-1-yl)acetic acid (20 mg, 0.046 mmol) and N,N-diethylpiperidine-3-carboxamide (8.44 mg, 0.046 mmol) in DCM (1 mL) and DMF (1 mL), was added EDC (8.78 mg, 0.046 mmol). The reaction mixture was stirred at room temperature for 16 h. The reaction mixture was purified with prep HPLC to provide 1-(2-(4-(2-(3,4-dimethoxyphenyl)-3-isopropyl-1H-indol-5-yl)piperidin-1-yl)acetyl)-N,N-diethylpiperidine-3-carboxamide (7 mg, 24.8% yield and 98% purity) as a pale solid. LC retention time=2.741 min [E]. MS (E−) m/z: 603.4 (M+H).

The following Examples were prepared according to the general procedure in Example 272.

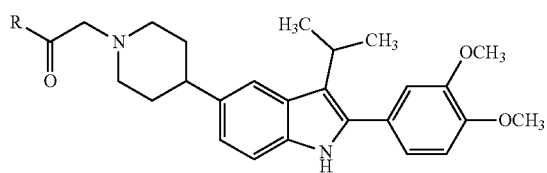

TABLE 17

| Ex. No. | R | M+1 | RT (min) | Method |
|---|---|---|---|---|
| 273 | (isopropylpiperidinyl-NH-) | 561.4 | 1.955 | F |
| 274 | (4-methylpiperazinyl-) | 519.2 | 1.931 | F |
| 275 | (3-(hydroxymethyl)piperidinyl-) | 534.2 | 2.177 | F |

TABLE 17-continued

| Ex. No. | R | M+1 | RT (min) | Method |
|---|---|---|---|---|
| 276 | —NH(CH$_2$CH$_2$OH) | 480.2 | 2.049 | F |
| 277 | —NH(CH$_2$CH$_2$CH$_2$OH) | 494.2 | 2.046 | F |
| 278 | (3-hydroxypyrrolidinyl-) | 506.2 | 2.076 | F |
| 279 | (2-hydroxypropan-2-yl-cyclohexyl-NH-) | 576.2 | 2.286 | F |

Examples 280 and 281

1-(2-(4-(2-(3,4-dimethoxyphenyl)-3-isopropyl-1H-indol-5-yl)piperidin-1-yl)-2-oxoethyl)-N-(1-isopropylpiperidin-4-yl)piperidine-3-carboxamide (enantiomers 1 and 2)

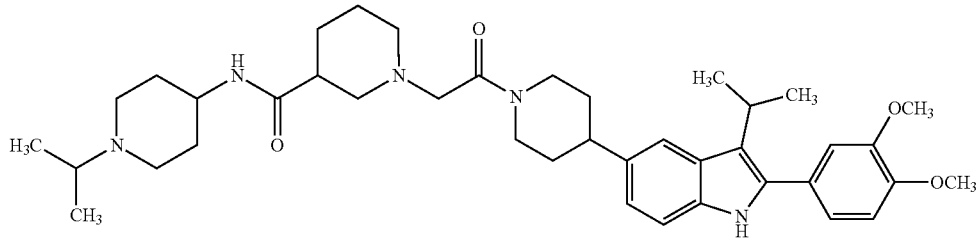

(280 and 281)

Intermediate 280A: methyl 1-(2-(4-(2-(3,4-dimethoxyphenyl)-3-isopropyl-1H-indol-5-yl) piperidin-1-yl)-2-oxoethyl)piperidine-3-carboxylate

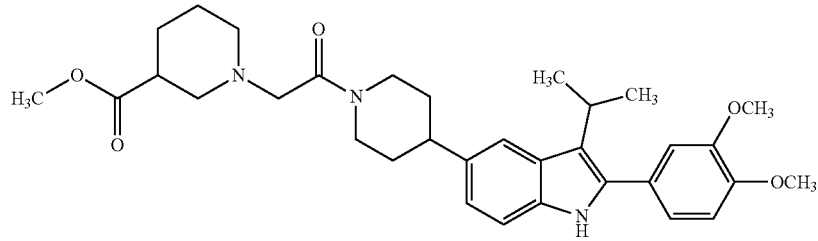

(280A)

To a mixture of 2-chloro-1-(4-(2-(3,4-dimethoxyphenyl)-3-isopropyl-1H-indol-5-yl) piperidin-1-yl)ethanone (0.25 g, 0.549 mmol) and methyl piperidine-3-carboxylate (0.079 g, 0.549 mmol) in THF (5 mL) was added DIPEA (0.288 mL, 1.648 mmol) at room temperature. The resulting mixture was stirred at room temperature for 2.5 days. The reaction mixture was diluted with ethyl acetate (20 mL), washed with water (2×10 mL), dried over Na$_2$SO$_4$, filtered and the filtrate was concentrated to get the crude compound. The crude material was purified by flash chromatography using 12 g silica column. The compound was eluted in 28% ethyl acetate in Pet ether, the fractions were combined and concentrated to provide methyl 1-(2-(4-(2-(3,4-dimethoxyphenyl)-3-isopropyl-1H-indol-5-yl)piperidin-1-yl)-2-oxoethyl) piperidine-3-carboxylate (0.19 g, 61.6% yield) as a pale yellow solid. LC retention time=2.114 min [A]. MS (E$^-$) m/z: 562.5 (M+H).

Intermediate 280B: 1-(2-(4-(2-(3,4-dimethoxyphenyl)-3-isopropyl-1H-indol-5-yl) piperidin-1-yl)-2-oxoethyl)piperidine-3-carboxylic acid (280B)

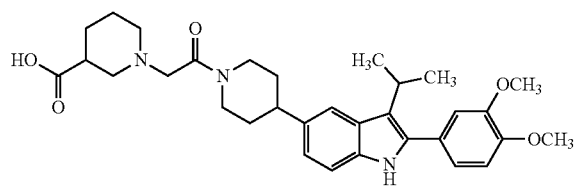

To a mixture of methyl 1-(2-(4-(2-(3,4-dimethoxyphenyl)-3-isopropyl-1H-indol-5-yl)piperidin-1-yl)-2-oxoethyl) piperidine-3-carboxylate (0.19 g, 0.338 mmol) in methanol (1 mL) and THF (1 mL) solvent mixture was added lithium hydroxide (0.024 g, 1.015 mmol) at room temperature. The resulting mixture was stirred at room temperature for 16 h. The reaction mixture was concentrated under vacuum to remove solvent, the residue was taken in 1 ml water, and the water solution was acidified and extracted with ethyl acetate (2×20 mL). The combined organic extracts was dried over Na2SO4, filtered and the filtrate was concentrated to afford 1-(2-(4-(2-(3,4-dimethoxyphenyl)-3-isopropyl-1H-indol-5-yl)piperidin-1-yl)-2-oxoethyl)piperidine-3-carboxylic acid (0.16 g, 86% yield) as an off white solid. LC retention time=2.046 min [A]. MS (E$^-$) m/z: 548.2 (M+H).

Examples 280 and 281

1-(2-(4-(2-(3,4-dimethoxyphenyl)-3-isopropyl-1H-indol-5-yl)piperidin-1-yl)-2-oxoethyl) piperidine-3-carboxylic acid (0.05 g, 0.091 mmol) was dissolved in DMF (2 mL). DIPEA (0.080 mL, 0.456 mmol) and HATU (0.035 g, 0.091 mmol) were added to the reaction solution followed by the addition of 1-isopropylpiperidin-4-amine hydrochloride (0.016 g, 0.091 mmol). The resulting reaction mixture was stirred at 25° C. for 12 h. The reaction mixture was concentrated; the residue was dissolved in ethyl acetate and washed with water, the organic layer was dried over Na$_2$SO$_4$ and concentrated to afford the crude compound. The crude compound was purified by Prep HPLC purification, the fractions was collected, concentrated and lyophilized to afford the racemic compound. The racemic compound was then separated by Chiral SFC to yield Enantiomer-1 (Example 280, 4 mg, 6.52% yield), LC retention time=2.517 min [A]. MS (E$^-$) m/z: 672.4 (M+H) and Enantiomer-2 (Example 281, 3 mg, 4.89% yield), LC retention time=2.518 min [A]. MS (E$^-$) m/z: 672.4 (M+H)

The following Examples were prepared according to the general procedure described in Examples 280 and 281.

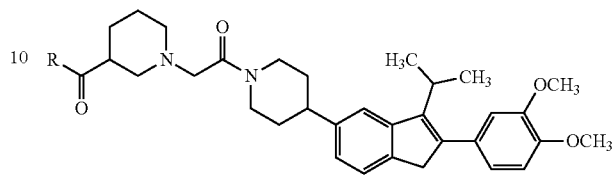

TABLE 18

| Ex. No. | R | M$^{+1}$ | RT (min) | Method |
|---|---|---|---|---|
| 282 | ![HO-pyrrolidine] | 617.4 | 2.44 | E |
| 283 | ![HO-pyrrolidine] | 617.4 | 2.45 | E |

Example 284

(S)-2-(3-(4-acetylpiperazine-1-carbonyl)piperidin-1-yl)-1-(4-(2-(3,4-dimethoxyphenyl)-3-isopropyl-1H-indol-5-yl)piperidin-1-yl)ethan-1-one (284)

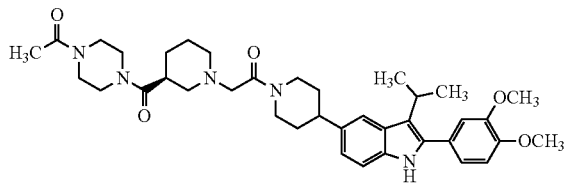

Intermediates 284A-1 and 284A-2: tert-butyl (S)-1-(2-(4-(2-(3,4-dimethoxyphenyl)-3-isopropyl-1H-indol-5-yl)piperidin-1-yl)-2-oxoethyl)piperidine-3-carboxylate and tert-butyl (R)-1-(2-(4-(2-(3,4-dimethoxyphenyl)-3-isopropyl-1H-indol-5-yl) piperidin-1-yl)-2-oxoethyl)piperidine-3-carboxylate (284A-1)

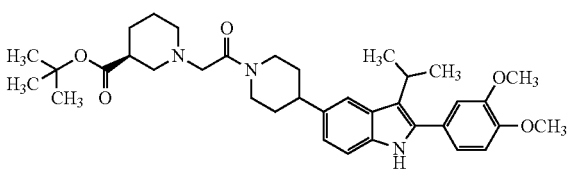

-continued (284A-2)

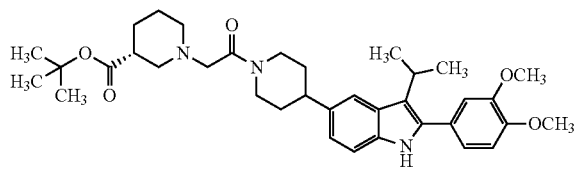

A 25 ml two necked flask equipped with a condenser and a nitrogen U tube with a rubber septum was charged with a solution of 2-chloro-1-(4-(2-(3,4-dimethoxyphenyl)-3-isopropyl-1H-indol-5-yl)piperidin-1-yl)ethanone (700 mg, 1.538 mmol) in dichloromethane (20 mL). Next, DIPEA (1.344 mL, 7.69 mmol) and tert-butyl piperidine-3-carboxylate (855 mg, 4.62 mmol) were added at room temperature. The resulting mixture was stirred at room temperature under nitrogen for 16 h. The reaction was quenched with water (10 mL). The reaction mixture was extracted with ethyl acetate (3×30 mL), dried (Na$_2$SO$_4$) and concentrated to afford crude compound. The crude material was purified by flash chromatography using 24 g silica column, compound was eluted in 35%-65% ethyl acetate in hexanes, the fractions was collected and concentrated to afford racemic compound tert-butyl 1-(2-(4-(2-(3,4-dimethoxyphenyl)-3-isopropyl-1H-indol-5-yl) piperidin-1-yl)-2-oxoethyl)piperidine-3-carboxylate (590 mg, 0.977 mmol, 63.5% yield) as dark solid. The racemic compound was subjected to chiral separation using chiral SFC to afford Intermediate 284A-1 (enantiomer 1) (240 mg) as a white solid, LC retention time=0.96 min [G]. MS (E⁻) m/z: 604.8 (M+H) and Intermediate 284B-2 (enantiomer-2) (230 mg) as a white solid, LC retention time=0.96 min [G]. MS (E⁻) m/z: 604.8 (M+H).

Intermediate 284B: (S)-1-(2-(4-(2-(3,4-dimethoxyphenyl)-3-isopropyl-1H-indol-5-yl) piperidin-1-yl)-2-oxoethyl)piperidine-3-carboxylic acid (284B)

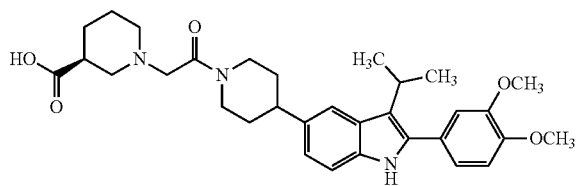

To a solution of tert-butyl (S)-1-(2-(4-(2-(3,4-dimethoxyphenyl)-3-isopropyl-1H-indol-5-yl)piperidin-1-yl)-2-oxoethyl)piperidine-3-carboxylate (Intermediate 284A-1) (238 mg, 0.394 mmol) in DCM (10 mL) was added 4M HCl in dioxane (8.00 mmol, 2 mL) at room temperature, then the mixture was stirred at the room temperature under nitrogen for 16 h. The reaction mixture was concentrated to yield crude compound. The crude compound was triturated with diethyl ether (3×10 mL), dried under vacuum to afford (S)-1-(2-(4-(2-(3,4-dimethoxyphenyl)-3-isopropyl-1H-indol-5-yl)piperidin-1-yl)-2-oxoethyl)piperidine-3-carboxylic acid (185 mg, 0.338 mmol, 86% yield) as a white solid. LC retention time=0.85 min [G]. MS (E⁻) m/z: 548.7 (M+H).

Example 284

(S)-1-(2-(4-(2-(3,4-dimethoxyphenyl)-3-isopropyl-1H-indol-5-yl)piperidin-1-yl)-2-oxoethyl)piperidine-3-carboxylic acid (10 mg, 0.018 mmol) and HATU (10.41 mg, 0.027 mmol) were dissolved in DMF (1 mL). Next, 1-(piperazin-1-yl)ethanone (4.68 mg, 0.037 mmol) was added to the reaction mixture followed by the addition of DIPEA (9.57 μl, 0.055 mmol). The resulting reaction mixture was stirred for 3 h at room temperature. The solvent was removed from the reaction mixture to give a crude sample. The crude material was purified by prep HPLC to afford (S)-2-(3-(4-acetylpiperazine-1-carbonyl) piperidin-1-yl)-1-(4-(2-(3,4-dimethoxyphenyl)-3-isopropyl-1H-indol-5-yl)piperidin-1-yl) ethanone (5 mg, 39.1% yield, 94% purity) as a pale solid. LC retention time=1.615 min [E]. MS (E⁻) m/z: 658.5 (M+H).

The following Examples were prepared according to the general procedure described in Example 284.

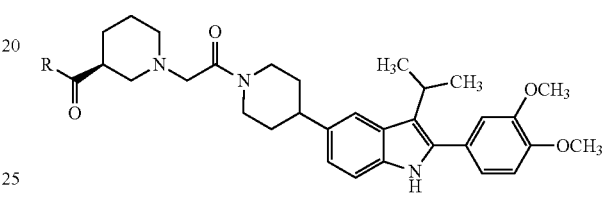

TABLE 19

| Ex. No. | R | M⁺¹ | RT (min) | Method |
|---|---|---|---|---|
| 285 | —NH(CH(CH₃)₂) | 589.5 | 1.914 | E |
| 286 | ![H₃C-CH(CH₃)-piperazinyl] | 658.5 | 1.828 | E |
| 287 | ![pyrrolidinyl] | 601.5 | 1.547 | F |
| 288 | —N(CH₃)CH(CH₃)₂ | 603.5 | 1.636 | F |
| 289 | ![(CH₃)₂N-piperidinyl] | 658.5 | 1.246 | F |
| 290 | ![3-CF₃-phenyl-piperazinyl] | 760.5 | 1.947 | F |
| 291 | ![HO-ethyl-piperidinyl] | 659.5 | 1.493 | F |
| 292 | ![3-hydroxypiperidinyl] | 631.5 | 1.444 | F |

TABLE 19-continued

| Ex. No. | R | M+1 | RT (min) | Method |
|---|---|---|---|---|
| 293 | 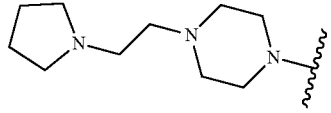 [SMILES: *N1CCN(CCN2CCCC2)CC1] | 713.8 | 1.586 | E |
| 294 | 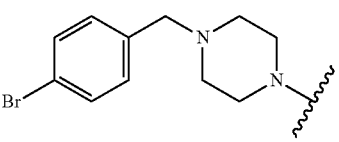 [SMILES: *N1CCN(Cc2ccc(Br)cc2)CC1] | 784.5 | 2.299 | E |
| 295 | —NH(CH₂CH₂NHC(O)CH₃) | 632.5 | 1.632 | E |
| 296 | 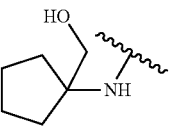 [SMILES: *NC1(CO)CCCC1] | 645.5 | 1.560 | F |
| 297 | —NH(CH₂CN) | 586.6 | 1.845 | E |
| 298 | —NH(CH₂C(O)NH₂) | 604.5 | 1.320 | F |
| 299 | 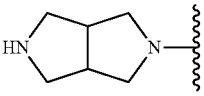 [SMILES: *N1CC2CNCC2C1] | 642.5 | 1.473 | E |
| 300 | 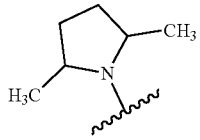 | 629.5 | 2.031 | E |
| 301 | 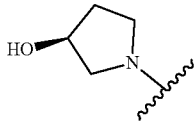 | 617.5 | 1.571 | E |

The following Examples were prepared according to the general procedure described in Example 284.

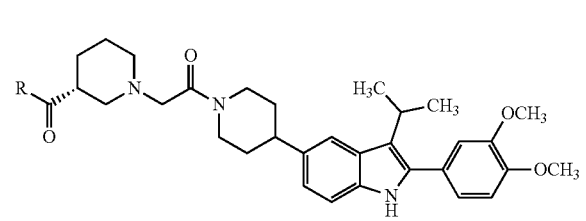

TABLE 20

| Ex. No. | R | M+1 | RT (min) | Method |
|---|---|---|---|---|
| 302 | 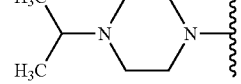 | 658.5 | 1.292 | F |
| 303 | 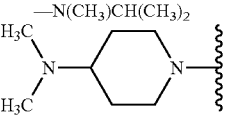 | 601.5 | 1.564 | F |
| 304 | —N(CH₃)CH(CH₃)₂ | 603.5 | 1.649 | E |
| 305 | 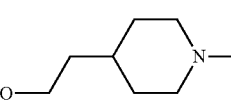 | 658.5 | 1.280 | F |
| 306 | 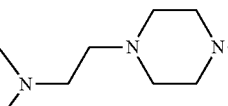 | 659.5 | 1.511 | F |
| 307 | 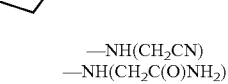 | 713.5 | 1.242 | F |
| 308 | —NH(CH₂CN) | 586.5 | 1.462 | F |
| 309 | —NH(CH₂C(O)NH₂) | 604.5 | 1.344 | F |
| 310 | 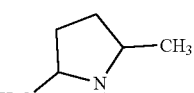 | 642.5 | 1.245 | F |
| 311 |  | 629.5 | 1.725 | F |

Example 312

2-(4-(2-(3,4-dimethoxyphenyl)-3-isopropyl-1H-indol-5-yl)piperidin-1-yl)-N,N-dimethylacetamide

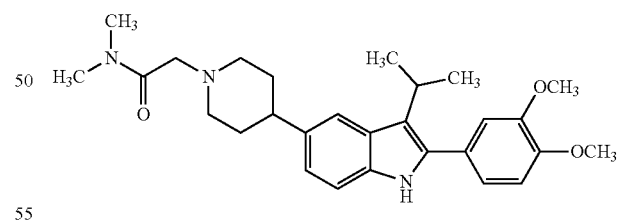

(312)

To a solution of 2-(3,4-dimethoxyphenyl)-3-isopropyl-5-(piperidin-4-yl)-1H-indole (30 mg, 0.079 mmol) in THF (2 mL), were added DTPEA (0.069 mL, 0.396 mmol) and 2-chloro-N,N-dimethylacetamide (19.27 mg, 0.159 mmol) at room temperature. The mixture was stirred at room temperature for 2 h. The reaction mixture was purified by prep HPLC to afford 2-(4-(2-(3,4-dimethoxyphenyl)-3-isopropyl-1H-indol-5-yl) piperidin-1-yl)-N,N-dimethylacetamide (15 mg, 0.030 mmol, 38.4% yield, 94% purity) as off white solid. LC retention time=3.099 min [D]. MS (E⁻) m/z: 464.2 (M+H).

Examples 313 and 314

1-(4-(2-(3,4-dimethoxyphenyl)-3-isopropyl-1H-indol-5-yl)piperidin-1-yl)-2-hydroxyethanone (313) and 1-(4-(2-(3,4-dimethoxyphenyl)-3-isopropyl-1H-indol-5-yl) piperidin-1-yl)-2-isopropoxyethan-1-one (314)

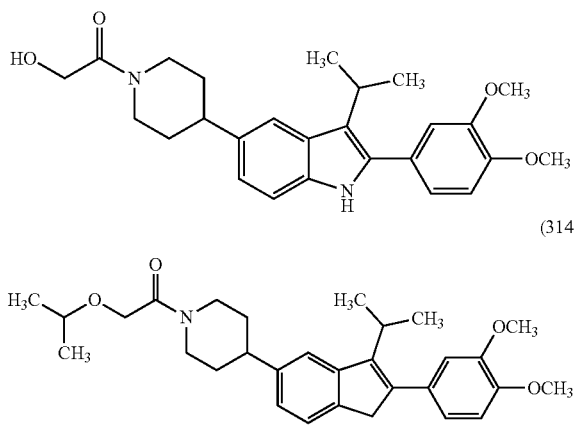

To a solution of 2-chloro-1-(4-(2-(3,4-dimethoxyphenyl)-3-isopropyl-1H-indol-5-yl)piperidin-1-yl)ethanone (50 mg, 0.110 mmol) in DMF (1 mL) were added propan-2-ol (6.60 mg, 0.110 mmol) and $Cs_2CO_3$ (35.8 mg, 0.110 mmol) at room temperature. The mixture was stirred at to 100° C. in a microwave for 1 h. The reaction mixture was purified with preparative HPLC. The reaction provided two products: 1-(4-(2-(3,4-dimethoxyphenyl)-3-isopropyl-1H-indol-5-yl) piperidin-1-yl)-2-isopropoxyethan-1-one (5 mg, 10.45 μmol, 9.51% yield), LC retention time=2.057 min [C1]. MS (E⁻) m/z: 479.4 (M+H), and 1-(4-(2-(3,4-dimethoxyphenyl)-3-isopropyl-1H-indol-5-yl)piperidin-1-yl)-2-hydroxyethanone (1 mg, 2.291 μmol, 2.085% yield) LC retention time=1.742 min [C1]. MS (E⁻) m/z: 437.3 (M+H).

The following Examples were prepared according to the general procedure described in Examples 313 and 314.

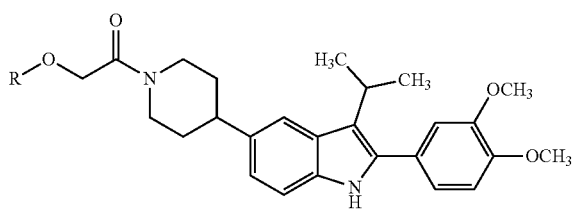

TABLE 21

| Ex. No. | R | M⁺¹ | RT (min) | Method |
|---|---|---|---|---|
| 315 | 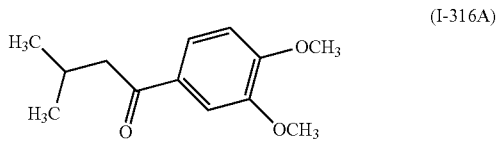 | 534.5 | 1.454 | C1 |

Intermediate 316 tert-butyl 5-(1-(tert-butoxycarbonyl)-3-hydroxypiperidin-4-yl)-2-(3,4-dimethoxyphenyl)-3-isopropyl-1H-indole-1-carboxylate

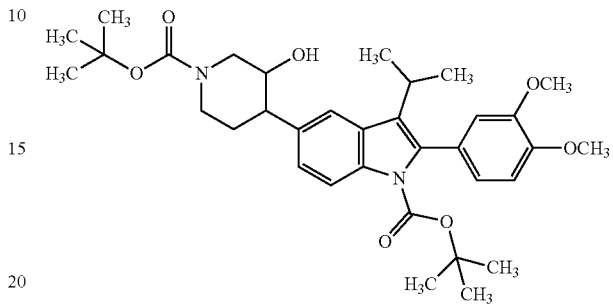

Intermediate 316A:
1-(3,4-dimethoxyphenyl)-3-methylbutan-1-one

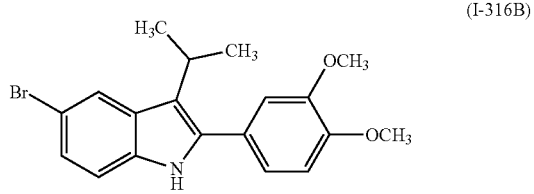 [SMILES: COc1ccc(-c2[nH]c3ccc(Br)cc3c2C(C)C)cc1OC]

To a solution of 3-methylbutanoyl chloride (8.91 mL, 72.4 mmol) in DCM (26 mL) was added portion wise $AlCl_3$ (9.65 g, 72.4 mmol) at 0° C. The suspension was stirred for 10 min, then a solution of 1,2-dimethoxybenzene (9.26 mL, 72.4 mmol) in DCM (26 mL) was added drop wise via an addition funnel over an approximate 10 min. After the complete addition of the starting material, the reaction was quenched with ice water (20 mL) and the solution was extracted with ethyl acetate (3×30 mL), the combined organic extracts was dried with sodium sulfate and concentrated to afford crude compound (1.2 g). The crude material was purified by flash chromatography using 80 g silica column, compound was eluted in 15% ethyl acetate in hexanes, the fractions was collected and concentrated under reduced pressure to afford 1-(3,4-dimethoxyphenyl)-3-methylbutan-1-one (10 g, 45.0 mmol, 62.2% yield) as an oil. ¹H NMR (400 MHz, $CDCl_3$) δ=7.59-7.53 (m, 2H), 6.88 (d, J=8.4 Hz, 1H), 3.95 (s, 3H), 3.94 (s, 3H), 2.79 (d, J=6.8 Hz, 2H), 2.32-2.25 (m, 1H), 0.99 (d, J=6.8 Hz, 6H).

Intermediate 316B: 5-bromo-2-(3,4-dimethoxyphenyl)-3-isopropyl-1H-indole

A mixture of (2-(4-bromophenyl)hydrazinyl)chloronium (10.51 g, 47.2 mmol) and 1-(3,4-dimethoxyphenyl)-3-methylbutan-1-one (7 g, 31.5 mmol) in polyphosphoric acid (1.699 ml, 31.5 mmol) was stirred at 155° C. for 1 h. After the complete addition of starting material, the reaction was quenched with ice (500 g) and the mixture was extracted with ethyl acetate (7×100 mL), dried (Na₂SO₄) and concentrated to afford crude compound (8 g). The crude was purified by flash chromatography using 120 g silica column, compound was eluted in 15% ethyl acetate in hexanes, the fractions was collected and concentrated under reduced pressure to afford 5-bromo-2-(3,4-dimethoxyphenyl)-3-isopropyl-1H-indole (5 g, 13.36 mmol, 42.4% yield) as an orange solid. LC retention time=2.807 min [A]. MS (E⁻) m/z: 374.0 (M+H).

Intermediate 316C: tert-butyl 4-(2-(3,4-dimethoxyphenyl)-3-isopropyl-1H-indol-5-yl)-3,6-dihydropyridine-1(2H)-carboxylate

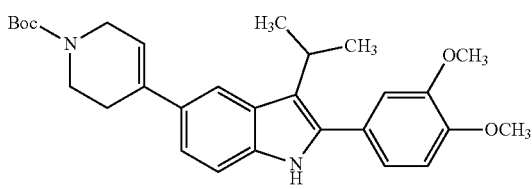

(I-316C)

To a mixture of 5-bromo-2-(3,4-dimethoxyphenyl)-3-isopropyl-1H-indole (0.2 g, 0.534 mmol), and tert-butyl 4-(4,4,5,5-tetramethyl-1,3,2-dioxaborolan-2-yl)-5,6-dihydropyridine-1(2H)-carboxylate (0.198 g, 0.641 mmol) in dioxane (12 mL) was added aqueous solution of K₃PO₄ (0.227 g, 1.069 mmol, 4 mL). The mixture was degassed with argon for 20 minutes prior to the addition of PdCl₂ (dppf)-CH₂Cl₂ adduct (0.044 g, 0.053 mmol) and after addition another 5 min, then the mixture was stirred at 75° C. for 12 h. The reaction mixture was diluted with ethyl acetate (50 mL), poured into a separate funnel and washed with water (2×50 mL), brine (50 mL), dried (Na₂SO₄), and concentrated in vacuum to get crude compound. The crude compound was purified with flash chromatography using 12 g silica column, compound was eluted in 50% ethyl acetate in hexanes, the fractions was collected and concentrated to yield tert-butyl 4-(2-(3,4-dimethoxyphenyl)-3-isopropyl-1H-indol-5-yl)-5,6-dihydropyridine-1(2H)-carboxylate (150 mg, 0.280 mmol, 52.4% yield, 89% purity) as an off white solid. LC retention time=2.238 min [A]. MS (E⁻) m/z: 477.4 (M+H).

Intermediate 316D: tert-butyl 5-(1-(tert-butoxycarbonyl)-1,2,3,6-tetrahydropyridin-4-yl)-2-(3,4-dimethoxyphenyl)-3-isopropyl-1H-indole-1-carboxylate

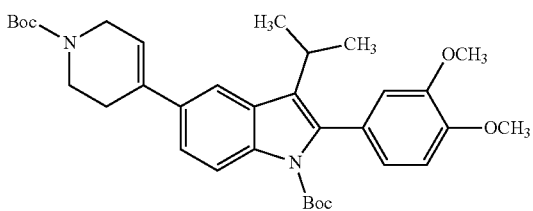

(I-316D)

To a solution of tert-butyl 4-(2-(3,4-dimethoxyphenyl)-3-isopropyl-1H-indol-5-yl)-5,6-dihydropyridine-1(2H)-carboxylate (1 g, 2.098 mmol) in THF (50 mL) were added DMAP (0.7 g, 5.73 mmol) and Boc₂O (0.633 mL, 2.73 mmol) at room temperature. The mixture was stirred at room temperature for 12 h. The reaction mixture was concentrated to yield crude compound, the crude material was purified by flash chromatography using 24 g silica column, compound was eluted in pet ether:ethyl acetate (8:2), the fractions was collected and concentrated to afford tert-butyl 5-(1-(tert-butoxycarbonyl)-1,2,3,6-tetrahydropyridin-4-yl)-2-(3,4-dimethoxyphenyl)-3-isopropyl-1H-indole-1-carboxylate (0.8 g, 1.387 mmol, 66.1% yield) as an off white solid. LC retention time=2.619 min [A]. MS (E⁻) m/z: 577.4 (M+H).

Intermediate 316

Borane-methyl sulfide complex (0.659 mL, 6.94 mmol) was added to a solution of tert-butyl 5-(1-(tert-butoxycarbonyl)-1,2,3,6-tetrahydropyridin-4-yl)-2-(3,4-dimethoxyphenyl)-3-isopropyl-1H-indole-1-carboxylate (0.8 g, 1.387 mmol) in THF (15 ml) at 0° C., then stirred at room temperature for 3 h. After the complete addition of the starting material, hydrogen peroxide (5 mL, 82 mmol) was added drop wise at −10° C. Effervescence were observed during addition. Next, sodium hydroxide (5 mL, 1.387 mmol) was added drop wise, then the reaction mixture was stirred at room temperature for 10 h. The reaction mixture was diluted with ethyl acetate, organic layer was separated, dried and concentrated to get crude compound. The crude material was purified by ISCO, using 12 g silica column; compound was eluted in pet ether: ethylacetate (8:2), the fractions was collected and concentrated to afford diastereomeric mixture tert-butyl 5-(1-(tert-butoxycarbonyl)-3-hydroxypiperidin-4-yl)-2-(3,4-dimethoxyphenyl)-3-isopropyl-1H-indole-1-carboxylate (0.65 g, 1.093 mmol, 79% yield) as a white solid. LC retention time=4.104 min [D]. MS (E⁻) m/z: 495.2 (M+H-Boc).

Examples 317 and 318

4-(2-(3,4-dimethoxyphenyl)-3-isopropyl-1H-indol-5-yl)piperidin-3-ol 2,2,2-trifluoroacetate (Racemate; diastereomer 1)

4-(2-(3,4-dimethoxyphenyl)-3-isopropyl-1H-indol-5-yl)piperidin-3-ol 2,2,2-trifluoroacetate (Racemate; diastereomer 2)

Isomer 1

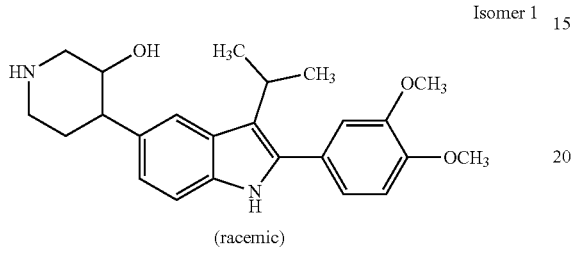
(racemic)

Isomer 2

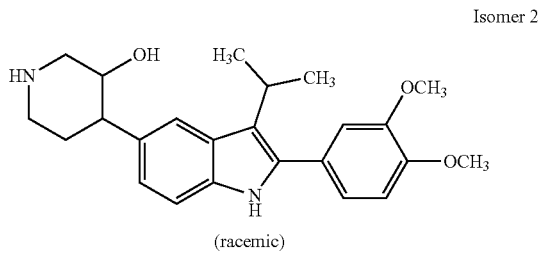
(racemic)

Obtained through TFA deprotection of tert-butyl 5-(1-(tert-butoxycarbonyl)-3-hydroxypiperidin-4-yl)-2-(3,4-dimethoxyphenyl)-3-isopropyl-1H-indole-1-carboxylate and subsequent Prep HPLC purification to obtain the diastereomeric racemates.

Example 317: LC retention time=1.20 min [E]. MS (E$^-$) m/z: 395.30 (M+H).

Example 318: LC retention time=1.27 min [E]. MS (E$^-$) m/z: 395.30 (M+H).

Examples 319 and 320

2-(3,4-dimethoxyphenyl)-5-(3-fluoropiperidin-4-yl)-3-isopropyl-1H-indole

Isomer 1

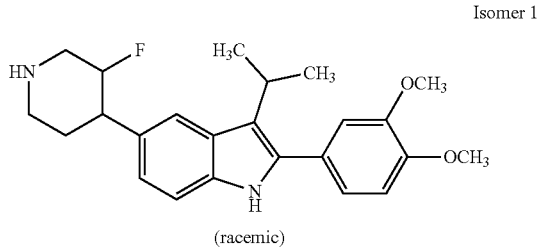
(racemic)

Isomer 2

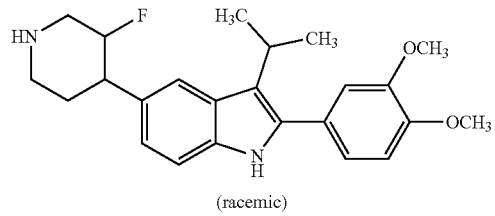
(racemic)

Intermediate 319A: tert-butyl 5-(1-(tert-butoxycarbonyl)-3-fluoropiperidin-4-yl)-2-(3,4-dimethoxyphenyl)-3-isopropyl-1H-indole-1-carboxylate (319A)

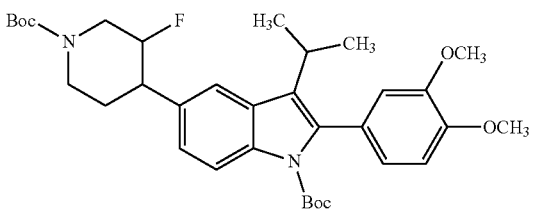

DAST (0.233 mL, 1.765 mmol) was added to a solution of tert-butyl 5-(1-(tert-butoxycarbonyl)-3-hydroxypiperidin-4-yl)-2-(3,4-dimethoxyphenyl)-3-isopropyl-1H-indole-1-carboxylate (0.35 g, 0.588 mmol) in DCM (15 mL) at −78° C. The reaction mixture was stirred at room temperature for 12 h. The reaction was quenched with ice-cold water and the mixture was concentrated to provide crude product. The crude material was taken to next step without further purification. LC retention time=2.307 min [D]. MS (E$^-$) m/z: 597.4 (M+H-Boc).

Examples 319 and 320

A mixture of tert-butyl 5-(1-(tert-butoxycarbonyl)-3-fluoropiperidin-4-yl)-2-(3,4-dimethoxyphenyl)-3-isopropyl-1H-indole-1-carboxylate (60 mg, 0.101 mmol) and 4M HCl in dioxane (5 mL) was stirred at room temperature for 2 h. The reaction mixture was concentrated to yield crude compound as a diastereomeric mixture.

The diastereomeric mixture was separated by Prep HPLC purification to isolated two racemic compounds (racemate 1) 2-(3,4-dimethoxyphenyl)-5-(3-fluoropiperidin-4-yl)-3-isopropyl-1H-indole (Example 319, 5 mg, 0.012 mmol, 12.42% yield, 99% purity), LC retention time=1.466 min [C1]. MS (E$^-$) m/z: 397.3 (M+H) and (racemate 2) 2-(3,4-dimethoxyphenyl)-5-(3-fluoropiperidin-4-yl)-3-isopropyl-1H-indole (Example 320, 0.45 mg, 1.090 mmol, 1.084% yield, 96% purity) as a white solid, LC retention time=1.647 min [C1]. MS (E$^-$) m/z: 397.3 (M+H).

The following Examples were obtained from Examples 319 and 320, isolated as single stereoisomers through chiral chromatographic separation.

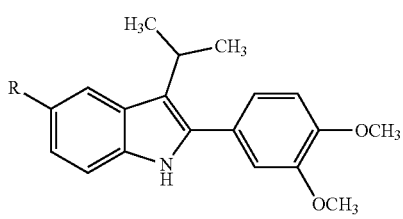

TABLE 22

| Ex. No. | R | M+1 | RT (min) | Method |
|---|---|---|---|---|
| 321 | HN—[piperidine-F] | 397.30 | 1.48 | E |
| 322 | HN—[piperidine-F] | 397.30 | 1.48 | E |
| 323 | HN—[piperidine-F] | 397.30 | 1.62 | E |
| 324 | HN—[piperidine-F] | 397.30 | 1.59 | E |

Example 325

5-(3,3-difluoropiperidin-4-yl)-2-(3,4-dimethoxyphenyl)-3-isopropyl-1H-indole (325)

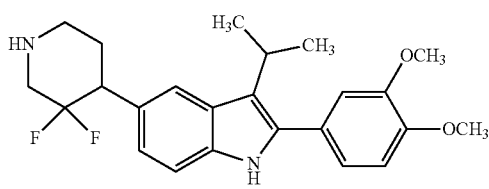

Intermediate 325A: tert-butyl 5-(1-(tert-butoxycarbonyl)-3-oxopiperidin-4-yl)-2-(3,4-dimethoxyphenyl)-3-isopropyl-1H-indole-1-carboxylate (325A)

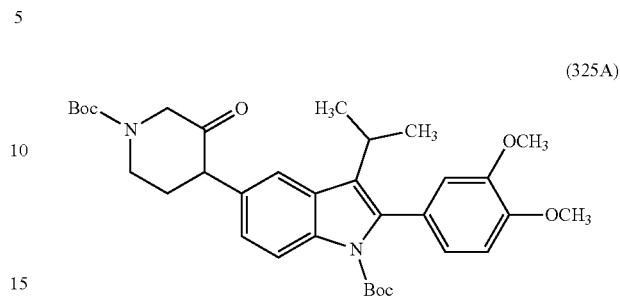

To a solution of tert-butyl 5-(1-(tert-butoxycarbonyl)-3-hydroxypiperidin-4-yl)-2-(3,4-dimethoxyphenyl)-3-isopropyl-1H-indole-1-carboxylate (20 mg, 0.034 mmol) in DCM (5 mL) was added Dess-Martin Periodinane (28.5 mg, 0.067 mmol), at room temperature. The reaction mixture was stirred at room temperature for 12 h. The reaction mass was concentrated and purified by flash chromatograph. The material was eluted in pet ether/ethyl acetate (8:2), fractions was collected and concentrated to yield tert-butyl 5-(1-(tert-butoxycarbonyl)-3-oxopiperidin-4-yl)-2-(3,4-dimethoxyphenyl)-3-isopropyl-1H-indole-1-carboxylate (15 mg, 0.025 mmol, 75% yield) as an off white solid. LC retention time 3.96 min [D]. MS (E−) m/z: 593.2 (M+H).

Intermediate 325B: tert-butyl 5-(1-(tert-butoxycarbonyl)-3,3-difluoropiperidin-4-yl)-2-(3,4-dimethoxyphenyl)-3-isopropyl-1H-indole-1-carboxylate (325B)

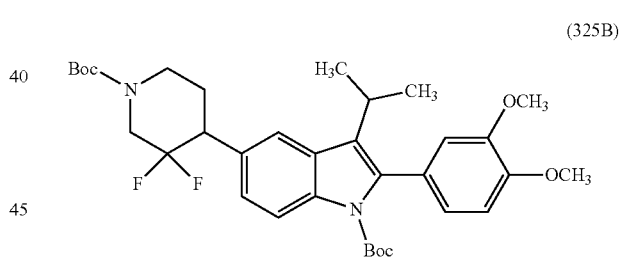

DAST (0.033 mL, 0.253 mmol) was added to a solution of tert-butyl 5-(1-(tert-butoxycarbonyl)-3-oxopiperidin-4-yl)-2-(3,4-dimethoxyphenyl)-3-isopropyl-1H-indole-1-carboxylate (0.05 g, 0.084 mmol) in DCM (5 mL) at −78° C. The mixture was stirred at room temperature for 12 h. The reaction was quenched with ice-cold water, and the mixture was extracted with dichloromethane and concentrated to afford crude compound. The crude material was taken to next step without further purification. LC retention time 4.09 min [D]. MS (E−) m/z: 615.2 (M+H).

Example 325

Tert-butyl 5-(1-(tert-butoxycarbonyl)-3,3-difluoropiperidin-4-yl)-2-(3,4-dimethoxyphenyl)-3-isopropyl-1H-indole-1-carboxylate (40 mg, 0.065 mmol) in 4M HCl in dioxane (5 mL) was stirred at room temperature for 2 h. The reaction mixture was concentrated and purified by prep HPLC to afford 5-(3,3-difluoropiperidin-4-yl)-2-(3,4-dimethoxyphenyl)-3-isopropyl-1H-indole (1 mg, 2.413 μmol, 3.71% yield) as a pale solid. LC retention time=1.789 min [C1]. MS (E⁻) m/z: 415.3 (M+H).

Example 326

4-(2-(3,4-dimethoxyphenyl)-3-isopropyl-1H-indol-5-yl)piperidin-2-one

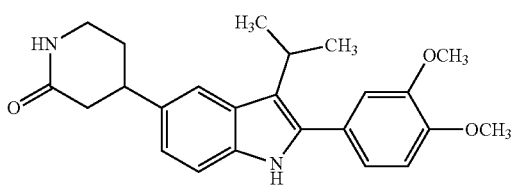

(326)

Intermediate 326A: tert-butyl 4-(2-(3,4-dimethoxyphenyl)-3-isopropyl-1H-indol-5-yl)-6-oxo-3,6-dihydropyridine-1(2H)-carboxylate

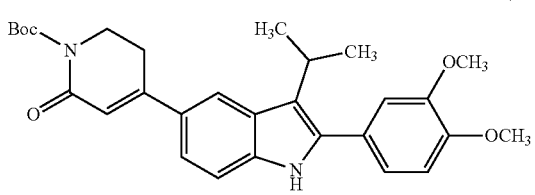

(326A)

Mixture of 5-bromo-2-(3,4-dimethoxyphenyl)-3-isopropyl-1H-indole (230 mg, 0.615 mmol), tert-butyl 2-oxo-4-(4,4,5,5-tetramethyl-1,3,2-dioxaborolan-2-yl)-5,6-dihydropyridine-1(2H)-carboxylate (238 mg, 0.737 mmol) and sodium carbonate (195 mg, 1.844 mmol) in DME (5 mL) and water (0.5 mL) was degassed with nitrogen for 10 min, then Pd(PPh₃)₄ (71.0 mg, 0.061 mmol) was added to the reaction mixture and again degassed for 10 min. Next, the reaction mixture was stirred at 80° C. for 16 h. The reaction mixture was filtered through celite bed, the celite bed was washed with ethyl acetate, the filtrate was collected and concentrated to yield crude compound. The crude mass was purified by flash chromatography to provide tert-butyl 4-(2-(3,4-dimethoxyphenyl)-3-isopropyl-1H-indol-5-yl)-2-oxo-5,6-dihydropyridine-1(2H)-carboxylate (30 mg, 0.061 mmol, 9.95% yield) as an off white solid. LC retention time=1.20 min [D]. MS (E⁻) m/z: 435.4 (M+H-tBu).

Intermediate 326B: tert-butyl 4-(2-(3,4-dimethoxyphenyl)-3-isopropyl-1H-indol-5-yl)-2-oxopiperidine-1-carboxylate

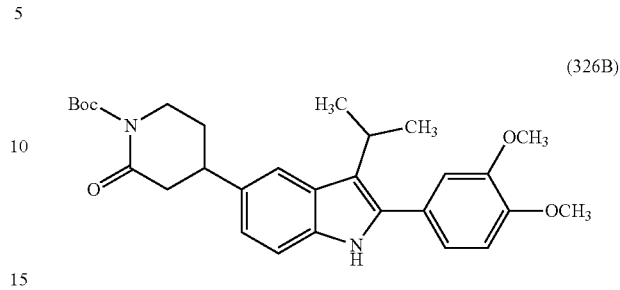

(326B)

Pd/C (21.69 mg, 0.204 mmol) was added to a solution of tert-butyl 4-(2-(3,4-dimethoxyphenyl)-3-isopropyl-1H-indol-5-yl)-2-oxo-5,6-dihydropyridine-1(2H)-carboxylate (100 mg, 0.204 mmol) in ethyl acetate (10 mL). The reaction mixture was stirred under hydrogen gas for 16 h. The reaction mass was filtered through a celite bed, washed with methanol, the filtrate was collected and concentrated to yield crude compound. The crude compound was purified by flash chromatography to afford tert-butyl 4-(2-(3,4-dimethoxyphenyl)-3-isopropyl-1H-indol-5-yl)-2-oxopiperidine-1-carboxylate (100 mg, 0.203 mmol, 100% yield). LC retention time=1.21 min [D]. MS (E⁻) m/z: 393.3 (M+H-Boc).

Example 326

4 M HCl in dioxane (0.2 mL) was added to a stirred solution of tert-butyl 4-(2-(3,4-dimethoxyphenyl)-3-isopropyl-1H-indol-5-yl)-2-oxopiperidine-1-carboxylate (100 mg, 0.203 mmol) in DCM (1 mL). The reaction mixture was stirred at room temperature for 16 h. The reaction mixture was concentrated to yield crude compound. The crude compound was purified with prep HPLC to get 4-(2-(3,4-dimethoxyphenyl)-3-isopropyl-1H-indol-5-yl)piperidin-2-one (13 mg, 0.032 mmol, 15.99% yield) as a white solid. 1H NMR (400 MHz, DMSO-d₆) δ=10.85 (s, 1H), 7.54 (s, 2H), 7.27 (d, J=8.5 Hz, 1H), 7.13-6.94 (m, 3H), 3.82 (d, J=7.5 Hz, 6H), 3.22 (dd, J=12.3, 3.8 Hz, 2H), 3.15-3.08 (m, 1H), 2.42-2.30 (m, 2H), 2.02-1.82 (m, 1H), 1.82-1.79 (m, 2H), 1.48-1.35 (m, 6H). LC retention time=1.645 min [C1]. MS (E⁻) m/z: 393.3 (M+H).

Example 328

3-(2,2-difluoroethyl)-2-(3,4-dimethoxyphenyl)-5-(piperidin-4-yl)-1H-indole

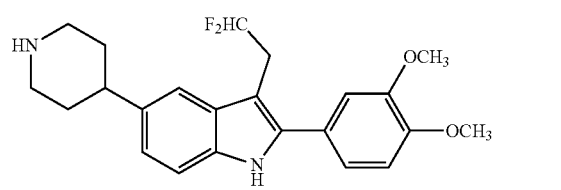

(328)

Intermediate 328A: 5-bromo-1-tosyl-1H-indole

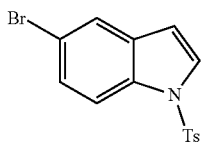
(328A)

To a stirred solution of 5-bromo-1H-indole (5.0 g, 25.5 mmol), TsCl (6.03 g, 31.6 mmol), and tetrabutylammonium hydrogen sulfate (0.63 g, 1.855 mmol) in toluene (100 mL) was added NaOH (50% solution in water, 10.20 g, 255 mmol) dropwise. The mixture was stirred for 16 h at room temperature. The reaction was quenched with water (20 mL). The layers were separated, the aqueous layer was extracted with EtOAc (2×50 mL), the combined organic extracts was dried (Na$_2$SO$_4$) and concentrated to yield crude material. The crude material was purified by ISCO using 40 g silica column, compound was eluted in 4% EA in hexanes, the fractions was collected and concentrated to afford 5-bromo-1-tosyl-1H-indole (7.1 g, 20.27 mmol) as white solid. LC retention time=2.230 min [A]. MS (E$^-$) m/z: 393.3 (M–H).

Intermediate 328B: 1-(5-bromo-1-tosyl-1H-indol-3-yl)-2,2-difluoroethan-1-one

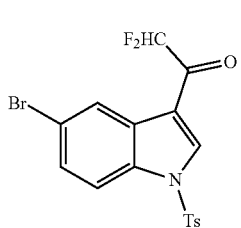
(328B)

To a suspension of AlCl$_3$ (6.85 g, 51.4 mmol) in DCM (50 mL) was added difluoroacetic anhydride (4.47 g, 25.7 mmol). The reaction mixture was stirred for 15 min, then a solution of 5-bromo-1-tosyl-1H-indole (3 g, 8.57 mmol)) in DCM (30 mL) was added. The reaction mixture was stirred for 1 h at ambient temperature. The reaction was quenched with ice-water, and the mixture was extracted with DCM (2×50 mL), combined extracts was washed with aqueous NaHCO$_3$, brine, dried over MgSO$_4$, filtered and concentrated to yield crude material. The crude material was purified by ISCO using silica column, the compound was eluted in 10% EtOAc in hexane, the fraction was collected and concentrated to afford 1-(5-bromo-1-tosyl-1H-indol-3-yl)-2,2-difluoroethanone (2.21 g, 4.1 mmol) as a crystalline solid. LC retention time=2.732 min [A]. MS (E$^-$) m/z: 428.0 (M+H).

Intermediate 328C: 1-(5-bromo-1H-indol-3-yl)-2,2-difluoroethan-1-one

(328C)

To a solution of 1-(5-bromo-1-tosyl-1H-indol-3-yl)-2,2-difluoroethanone (0.2 g, 0.467 mmol) in THF (4 mL) and MeOH (4.00 mL) solvent mixture was added Cs$_2$CO$_3$ (0.45 g, 1.381 mmol) at room temperature. The mixture was stirred at room temperature for 12 h. The reaction mixture was concentrated, the residue was diluted with minimum amount of water and undissolved solids were filtered and dried under vacuum to afford 1-(5-bromo-1H-indol-3-yl)-2,2-difluoroethanone (105 mg, 0.244 mmol) as a white solid. LC retention time=2.233 min [A]. MS (E$^-$) m/z: 276 (M+2H).

Intermediate 328D: 5-bromo-3-(2,2-difluoroethyl)-1H-indole

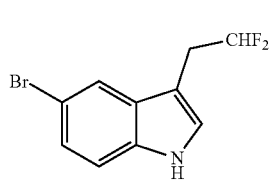
(328D)

To the stirred solution of 1-(5-bromo-1H-indol-3-yl)-2,2-difluoroethanone (0.25 g, 0.912 mmol) in THF (10 mL) was added BH$_3$DMS (1.368 mL, 2.74 mmol) at 0° C. under nitrogen, then the mixture was stirred at 80° C. for 20 h. The reaction was quenched with water (2 ml) at 0° C., diluted with ethyl acetate (100 ml), washed with sodium bicarbonate (2×25 ml) and water (2×25 ml), combined organic extracts was dried over anhydrous sodium sulphate, filtered and concentrated to yield crude compound. The crude material was purified on ISCO by using 24 g silica gel column, the compound was eluted at 8% ethyl acetate/hexane, the fractions was collected and concentrated to afford 5-bromo-3-(2,2-difluoroethyl)-1H-indole (120 mg, 0.438 mmol) as an oil. LC retention time=2.802 min [D]. MS (E$^-$) m/z: 260 (M+H).

Intermediate 328E: tert-butyl 4-(3-(2,2-difluoro-ethyl)-1H-indol-5-yl)-3,6-dihydropyridine-1(2H)-carboxylate

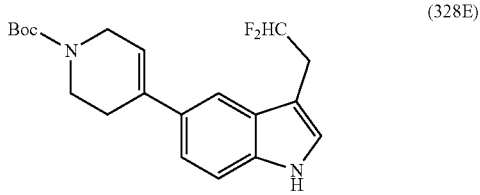 [SMILES: CC(C)(C)OC(=O)N1CC=C(c2ccc3[nH]cc(CC(F)F)c3c2)CC1]

Tert-butyl 4-(3-(2,2-difluoroethyl)-1H-indol-5-yl)-5,6-dihydropyridine-1(2H)-carboxylate was prepared according to the general procedure described in Intermediates 194A and 194B using 5-bromo-3-(2,2-difluoroethyl)-1H-indole as the starting intermediate (0.14 g, 80% yield). LC retention time 3.075 min [D]. MS (E⁻) m/z: 361.2 (M–H).

Intermediate 328F: tert-butyl 4-(3-(2,2-difluoro-ethyl)-1H-indol-5-yl)piperidine-1-carboxylate

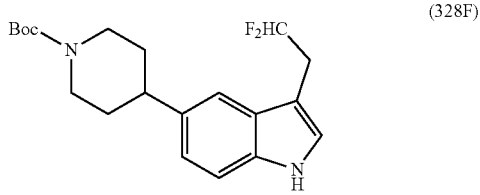 [SMILES: CC(C)(C)OC(=O)N1CCC(c2ccc3[nH]cc(CC(F)F)c3c2)CC1]

Tert-butyl 4-(3-(2,2-difluoroethyl)-1H-indol-5-yl)piperidine-1-carboxylate was prepared according to the general procedure described in Intermediate 194C using tert-butyl 4-(3-(2,2-difluoroethyl)-1H-indol-5-yl)-5,6-dihydropyridine-1(2H)-carboxylate as the starting intermediate (0.9 g, 88% yield). LC retention time 3.282 min [D]. MS (E⁻) m/z: 265.0 (M+H-Boc).

Intermediate 328G: tert-butyl 4-(2-bromo-3-(2,2-difluoroethyl)-1H-indol-5-yl)piperidine-1-carboxylate

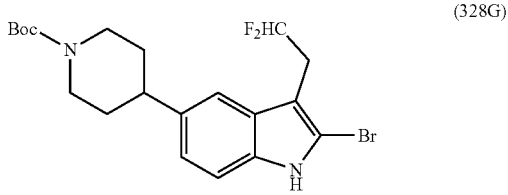 [SMILES: CC(C)(C)OC(=O)N1CCC(c2ccc3[nH]c(Br)c(CC(F)F)c3c2)CC1]

Tert-butyl 4-(2-bromo-3-(2,2-difluoroethyl)-1H-indol-5-yl)piperidine-1-carboxylate was prepared according to the general procedure described in Intermediate 194D using tert-butyl 4-(3-(2,2-difluoroethyl)-1H-indol-5-yl)piperidine-1-carboxylate as the starting intermediate (0.3 g, 52% yield). LC retention time 1.10 min [G]. MS (E⁻) m/z: 389.0 (M+2H-tBu).

Intermediate 328H: tert-butyl 4-(3-(2,2-difluoro-ethyl)-2-(3,4-dimethoxyphenyl)-1H-indol-5-yl)piperidine-1-carboxylate

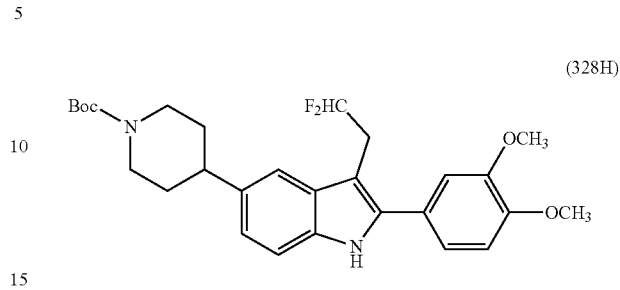

Tert-butyl 4-(3-(2,2-difluoroethyl)-2-(3,4-dimethoxyphenyl)-1H-indol-5-yl) piperidine-1-carboxylate was prepared according to the general procedure described in Intermediate 194E using tert-butyl 4-(2-bromo-3-(2,2-difluoroethyl)-1H-indol-5-yl) piperidine-1-carboxylate as the starting intermediate (0.3 g, 56.5% yield). LC retention time 3.434 min [A]. MS (E⁻) m/z: 501.3 (M+H).

Example 328

3-(2,2-difluoroethyl)-2-(3,4-dimethoxyphenyl)-5-(piperidin-4-yl)-1H-indole was prepared as described in Example 194 using tert-butyl 4-(3-(2,2-difluoroethyl)-2-(3,4-dimethoxyphenyl)-1H-indol-5-yl)piperidine-1-carboxylate as the starting intermediate (0.3 g, 56.5% yield). LC retention time=1.102 min [C1]. MS (E⁻) m/z: 401.3 (M+H).

Example 329

2-(3,4-dimethoxyphenyl)-5-(piperidin-4-yl)-3-(2,2,2-trifluoroethyl)-1H-indole

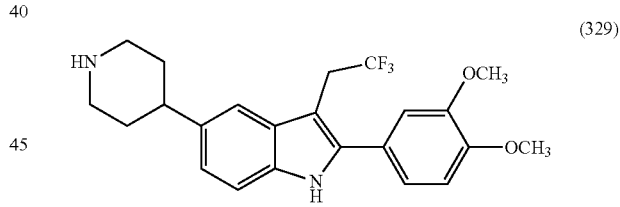

Intermediate 329A: 1-(3,4-dimethoxyphenyl)-4,4,4-trifluorobutan-1-one

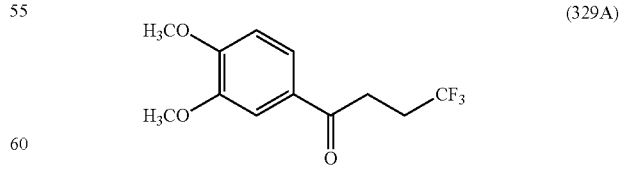

To a solution of 4,4,4-trifluorobutanoic acid (10 g, 70.4 mmol) in toluene (100 mL) at 0° C. was added 1,2-dimethoxybenzene (9.00 mL, 70.4 mmol) in a portion wise manner. The suspension was stirred for 10 min at 0° C., then polyphosphoric acid (141 mmol) was added. The reaction mixture was heated at 75° C. for 16 h. The reaction was quenched with water (50 mL), extracted with ethyl acetate (3×100 mL), the combined organic extracts was dried with sodium sulfate and concentrated under reduced pressure to yield a colorless liquid as a crude compound (15.2 g). The crude compound was purified with flash chromatography, using 120 g silica column. The compound was eluted in 15% ethyl acetate/Pet ether, the fractions were collected and concentrated to afford 1-(3,4-dimethoxyphenyl)-4,4,4-trifluorobutan-1-one (8 g, 30.5 mmol, 43.3% yield) as an oil. LC retention time 2.305 min [D]. MS (E⁻) m/z: 263.2 (M+H).

Intermediate 329B: 5-bromo-2-(3,4-dimethoxyphenyl)-3-(2,2,2-trifluoroethyl)-1H-indole

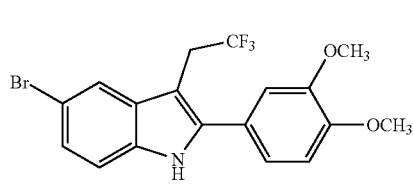
(329B)

To a mixture of (4-bromophenyl)hydrazine (1.070 g, 5.72 mmol), 1-(3,4-dimethoxyphenyl)-4,4,4-trifluorobutan-1-one (1.5 g, 5.72 mmol), and (4-bromophenyl) hydrazine (1.070 g, 5.72 mmol) at room temperature was added polyphosphoric acid (3.40 ml, 5.72 mmol) in a portion wise manner. The suspension was stirred for 10 minutes at room temperature, then stirred at 155° C. for 10-20 min. Then, the reaction was quenched with water (20 mL), and the mixture was extracted with ethyl acetate (3×50 mL). The combined organic extracts was dried with sodium sulfate and concentrated under reduced pressure to yield crude compound (15.2 g). The crude compound was purified by flash chromatography using a 40 g silica column. The compound was eluted in 20-25% ethyl acetate/Pet ether, the fractions were collected and concentrated to afford 5-bromo-2-(3,4-dimethoxyphenyl)-3-(2,2,2-trifluoroethyl)-1H-indole (900 mg, 2.173 mmol, 38.0% yield) as a brown solid. LC retention time 3.404 min [D]. MS (E⁻) m/z: 413.0 (M–H).

Intermediate 329C: tert-butyl 4-(2-(3,4-dimethoxyphenyl)-3-(2,2,2-trifluoroethyl)-1H-indol-5-yl)-3,6-dihydropyridine-1(2H)-carboxylate

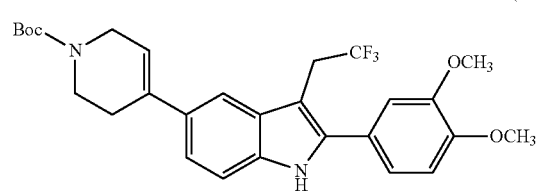
(329C)

A mixture of 5-bromo-2-(3,4-dimethoxyphenyl)-3-(2,2,2-trifluoroethyl)-1H-indole (900 mg, 2.173 mmol), tert-butyl 4-(4,4,5,5-tetramethyl-1,3,2-dioxaborolan-2-yl)-5,6-dihydropyridine-1(2H)-carboxylate (1344 mg, 4.35 mmol), and K₂CO₃ (901 mg, 6.52 mmol) in 1,4-dioxane (50 mL) and water (10.00 mL) was purged under nitrogen for 10 min. Next, 1,1'-(PdCl₂(dppf)-CH₂Cl₂ (177 mg, 0.217 mmol) was added to the reaction mixture, then the mixture was stirred at 90° C. for 20-30 min. The reaction mixture was diluted with water (20 mL), extracted with ethyl acetate (3×50 mL), the combined organic extracts was dried with sodium sulfate and concentrated under reduced pressure to yield crude compound. The crude compound was purified by flash chromatography, using 24 g silica column. The compound was eluted in 35%-65% ethyl acetate/Pet ether, the fractions were collected and concentrated to afford tert-butyl 4-(2-(3,4-dimethoxyphenyl)-3-(2,2,2-trifluoroethyl)-1H-indol-5-yl)-5,6-dihydropyridine-1(2H)-carboxylate (900 mg, 1.742 mmol, 80% yield) as light yellow solid. LC retention time 2.177 min [A]. MS (E⁻) m/z: 515.2 (M–H).

Intermediate 329D: tert-butyl 4-(2-(3,4-dimethoxyphenyl)-3-(2,2,2-trifluoroethyl)-1H-indol-5-yl) piperidine-1-carboxylate

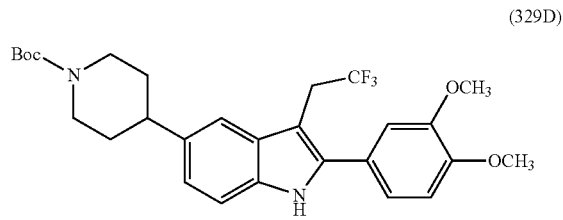 [SMILES: COc1ccc(-c2[nH]c3ccc(C4CCN(C(=O)OC(C)(C)C)CC4)cc3c2CC(F)(F)F)cc1OC]
(329D)

To a solution of tert-butyl 4-(2-(3,4-dimethoxyphenyl)-3-(2,2,2-trifluoroethyl)-1H-indol-5-yl)-5,6-dihydropyridine-1 (2H)-carboxylate (1 g, 1.936 mmol) in ethyl acetate (50 mL) and methanol (50.0 mL) solvent mixture was added Pd/C (300 mg, 2.82 mmol). The reaction mixture was stirred at room temperature under a hydrogen bladder for 16 h. The reaction mixture was filtered through celite pad, washed with methanol (20 mL), the filtrates were collected and concentrated under reduced pressure to yield tert-butyl 4-(2-(3,4-dimethoxyphenyl)-3-(2,2,2-trifluoroethyl)-1H-indol-5-yl)piperidine-1-carboxylate (900 mg, 1.736 mmol, 90% yield) as a light yellow solid. LC retention time 2.207 min [A]. MS (E⁻) m/z: 517.2 (M–H).

Example 329

To a solution of tert-butyl 4-(2-(3,4-dimethoxyphenyl)-3-(2,2,2-trifluoroethyl)-1H-indol-5-yl)piperidine-1-carboxylate (900 mg, 1.736 mmol) in DCM (10 mL) was added 4M HCl in dioxane (2 mL, 8.00 mmol). The mixture was stirred at room temperature for 1 h. The reaction mixture was concentrated under reduced pressure to yield crude compound. The crude mixture was washed with diethyl ether (3×10 mL), and dried under vacuum to afford 2-(3,4-dimethoxyphenyl)-5-(piperidin-4-yl)-3-(2,2,2-trifluoroethyl)-1H-indole, HCl (700 mg, 1.400 mmol, 81% yield) as a white solid. LC retention time 1.842 min [A]. MS (E⁻) m/z: 418.2 (M+H).

Example 330

1-(4-(2-(3,4-dimethoxyphenyl)-3-(2,2,2-trifluoro-ethyl)-1H-indol-5-yl)piperidin-1-yl)-3-(piperidin-1-yl)propan-1-one

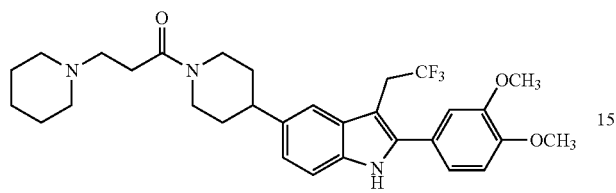

(330)

DIPEA (3.84 μl, 0.022 mmol) and DMF (1 mL) were added to a vial containing 2-(3,4-dimethoxyphenyl)-5-(piperidin-4-yl)-3-(2,2,2-trifluoroethyl)-1H-indole, HCl (10 mg, 0.022 mmol), HATU (8.36 mg, 0.022 mmol) and 3-(piperidin-1-yl)propanoic acid (4.15 mg, 0.026 mmol). The reaction mixture was stirred for 12 h at room temperature. The sample was purified by reverse phase prep HPLC to provide 1-(4-(2-(3,4-dimethoxyphenyl)-3-(2,2,2-trifluoroethyl)-1H-indol-5-yl)piperidin-1-yl)-3-(piperidin-1-yl)propan-1-one (8 mg, 0.014 mmol, 58.2% yield, 97% purity). LC retention time 1.562 min [A]. MS (E⁻) m/z: 558.4 (M+H).

The following Examples were prepared according to the general procedure described in Example 330M

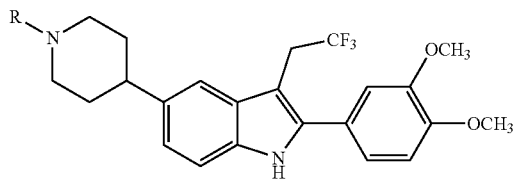

TABLE 23

| Ex. No. | R | M$^{+1}$ | RT (min) | Method |
|---|---|---|---|---|
| 331 | ![imidazole-butanone] | 555.4 | 1.675 | E |
| 332 | ![indole-acetyl] | 576.4 | 2.704 | F |
| 333 | —C(O)CH$_2$CH$_2$C(O)NH$_2$ | 518.4 | 2.142 | F |
| 334 | ![imidazole-acetyl] | 527.4 | 2.145 | E |

TABLE 23-continued

| Ex. No. | R | M$^{+1}$ | RT (min) | Method |
|---|---|---|---|---|
| 335 | ![pyridine-acetyl] | 538.4 | 1.998 | F |
| 336 | ![N-acetyl-prolyl] | 558.4 | 2.31 | E |
| 337 | ![indole-N-propanoyl] | 590.4 | 2.953 | E |
| 338 | ![dimethylamino-phenyl-acetyl] | 580.4 | 2.886 | E |
| 339 | —C(O)CH$_2$CF$_3$ | 529.3 | 2.694 | E |
| 340 | —C(O)CH$_2$CH$_2$N(CH$_3$)$_2$ | 518.3 | 2.102 | E |
| 341 | ![tetrazole-acetyl] | 529.3 | 1.831 | E |
| 342 | ![pyrazine-acetyl] | 539.3 | 2.365 | E |
| 343 | —C(O)CH$_2$CH$_2$CH$_2$NHC(O)CH$_3$ | 546.4 | 2.217 | E |
| 344 | ![pyrrole-propanoyl] | 540.4 | 2.741 | E |
| 345 | ![N-acetyl-piperidine-carbonyl] | 572.4 | 2.333 | E |
| 346 | —C(O)CH$_2$CH$_2$C(O)N(CH$_3$)$_2$ | 546.4 | 2.332 | F |
| 347 | —C(O)CH$_2$S(O)$_2$CH$_3$ | 539.3 | 2.324 | F |
| 348 | ![pyridine-propanoyl] | 552.3 | 2.503 | E |

TABLE 23-continued

| Ex. No. | R | M+1 | RT (min) | Method |
|---|---|---|---|---|
| 349 | ![pyridinyloxy acetyl] | 554.4 | 2.436 | E |
| 350 | F3C-CH2CH2-C(O)- | 543.4 | 2.838 | F |
| 351 | —C(O)CH2CH2CH2N(CH3)2 | 532.4 | 2.001 | F |
| 352 | (R)-OH CH3 CH2 C(O)- | 505.3 | 1.735 | E |
| 353 | (S)-OH CH3 CH2 C(O)- | 505.3 | 1.744 | E |
| 354 | —C(O)CH2N(CH3)2 | 504.2 | 2.257 | E |

Example 355

2-(3,4-dimethoxyphenyl)-5-(1-methylpiperidin-4-yl)-3-(2,2,2-trifluoroethyl)-1H-indole

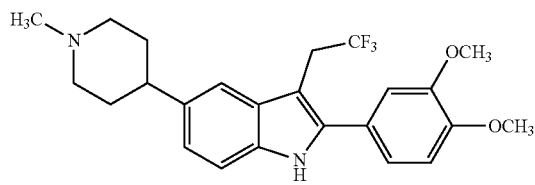

(355)

To a solution of 2-(3,4-dimethoxyphenyl)-5-(piperidin-4-yl)-3-(2,2,2-trifluoroethyl)-1H-indole hydrochloride (30 mg, 0.066 mmol) and HCHO (0.1 mL, 40% solution in water) in MeOH (2 mL), was added AcOH (0.038 mL, 0.659 mmol) at 0° C. The reaction mixture was stirred at room temperature for 4 h. NaCN(BH)$_3$ (12.5 mg, 0.33 mmol) was added at 0° C. and the reaction mixture was stirred at room temperature for 16 h. The reaction mixture was concentrated and purified by Prep LCMS to afford 2-(3,4-dimethoxyphenyl)-5-(1-methylpiperidin-4-yl)-3-(2,2,2-trifluoroethyl)-1H-indole (8 mg, 30% yield) as an off white solid. LC retention time 2.043 min [C1]. MS (E$^-$) m/z: 433.2 (M+H).

The following Examples were prepared according to the general procedure described in Example 355.

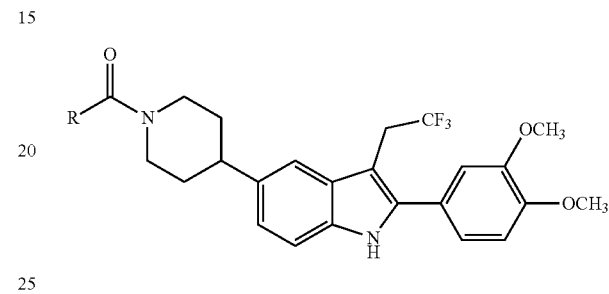

TABLE 24

| Ex. No. | R | M+1 | RT (min) | Method |
|---|---|---|---|---|
| 356 | —NHCH2CH3 | 555.4 | 1.675 | E |
| 357 | PhCH2CH2NH- | 576.4 | 2.704 | F |
| 358 | furan-2-ylmethyl-NH- | 518.4 | 2.142 | F |

Example 359

1-([1,4'-bipiperidin]-1'-yl)-2-(4-(2-(3,4-dimethoxyphenyl)-3-(2,2,2-trifluoroethyl)-1H-indol-5-yl)piperidin-1-yl)ethan-1-one

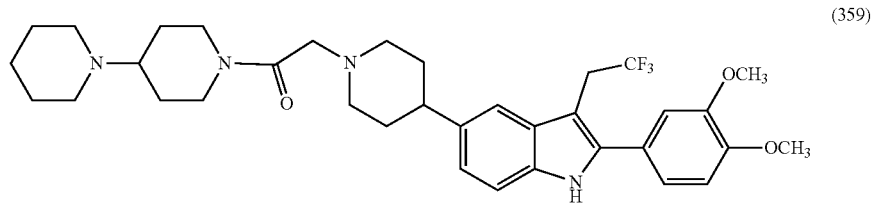 [SMILES: COc1ccc(-c2[nH]c3ccc(C4CCN(CC(=O)N5CCC(N6CCCCC6)CC5)CC4)cc3c2CC(F)(F)F)cc1OC]

(359)

193

Intermediate 359A: tert-butyl 2-(4-(2-(3,4-dimethoxyphenyl)-3-(2,2,2-trifluoroethyl)-1H-indol-5-yl)piperidin-1-yl)acetate

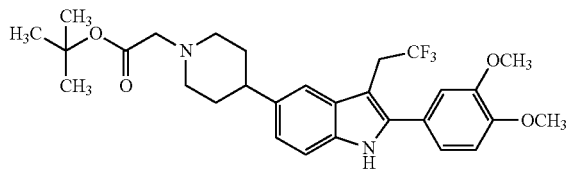
(359A)

To a solution of 2-(3,4-dimethoxyphenyl)-5-(piperidin-4-yl)-3-(2,2,2-trifluoroethyl)-1H-indole (300 mg, 0.717 mmol) in DCM (20 mL) were added DIPEA (0.501 mL, 2.87 mmol) and tert-butyl 2-bromoacetate (0.151 mL, 1.075 mmol) at room temperature. The reaction mixture was stirred at room temperature for 16 h. The reaction was quenched with water (10 mL). The mixture was extracted with ethyl acetate (3×30 mL), the combined organic extracts was dried with sodium sulfate and concentrated under reduced pressure to yield crude product. The crude product was purified by flash chromatography using 12 g silica column. The compound was eluted in 70% EtOAc in pet ether, the fractions was collected and concentrated under reduced pressure to afford tert-butyl 2-(4-(2-(3,4-dimethoxyphenyl)-3-(2,2,2-trifluoroethyl)-1H-indol-5-yl)piperidin-1-yl)acetate (310 mg, 0.582 mmol, 81% yield) as a brown solid. LC retention time 0.90 min [G]. MS (E$^-$) m/z: 533.7 (M+H).

Intermediate 359B: 2-(4-(2-(3,4-dimethoxyphenyl)-3-(2,2,2-trifluoroethyl)-1H-indol-5-yl)piperidin-1-yl) acetic acid To a solution of tert-butyl 2-(4-(2-(3,4-dimethoxyphenyl)-3-(2,2,2-trifluoroethyl)-1H-indol-5-yl)piperidin-1-yl) acetate (350 mg, 0.657 mmol)) in DCM (15 mL) was added 4M HCl in dioxane (0.164 mL, 0.657 mmol) at room temperature. The reaction mixture was stirred at room temperature for 2 h. The reaction mixture was concentrated and triturated with diethyl ether (2×10 mL) to afford 2-(4-(2-(3,4-dimethoxyphenyl)-3-(2,2,2-trifluoroethyl)-1H-indol-5-yl)piperidin-1-yl)acetic acid (300 mg, 0.630 mmol, 96% yield) as an off white solid. LC retention time 0.79 min [B]. MS (E$^-$) m/z: 477.2 (M+H).

Example 359

To a solution of 2-(4-(2-(3,4-dimethoxyphenyl)-3-isopropyl-1H-indol-5-yl) piperidin-1-yl)acetic acid (20 mg, 0.046 mmol) in DMF (1 mL) were added TEA (0.032 ml, 0.23 mmol), 1,4'-bipiperidine (7.74 mg, 0.046 mmol) and HATU (35 mg, 0.092 mmol) at room temperature. The mixture was stirred at room temperature for 16 h. The reaction mixture was purified with prep HPLC to provide 1-([1,4'-bipiperidin]-1'-yl)-2-(4-(2-(3,4-dimethoxyphenyl)-3-(2,2,2-trifluoroethyl)-1H-indol-5-yl)piperidin-1-yl) ethanone (7 mg, 24.8% yield and 98% purity) as an off white solid. LC retention time 1.231 min [C1]. MS (E$^-$) m/z: 627.5 (M+H).

The following Examples were prepared according to the general procedure described in Example 359.

(359B)

TABLE 25

| Ex. No. | R | M$^{+1}$ | RT (min) | Method |
|---|---|---|---|---|
| 360 | (pyrrolidine with N-CH$_3$, ethyl linker to NH) | 587.4 | 1.586 | E |
| 361 | (N-acetyl piperazine) | 587.4 | 1.542 | E |

TABLE 25-continued

| Ex. No. | R | M$^{+1}$ | RT (min) | Method |
|---|---|---|---|---|
| 362 | (CH(CH₃)₂)-piperazinyl | 587.5 | 1.789 | E |
| 363 | 4-(4-methylpiperazin-1-yl)piperidinyl | 642.5 | 1.144 | F |
| 364 | 4-(dimethylamino)piperidinyl | 587.4 | 1.187 | F |
| 365 | —NH(CH₃)CH₂CH₂CH₂N(CH₃)₂ | 575.4 | 1.188 | F |
| 366 | 4-(pyridin-3-yl)piperazinyl | 622.4 | 1.218 | F |
| 367 | —N(CH₃)CH₂CH₂N(CH₃)₂ | 561.4 | 1.177 | F |
| 368 | 4-(pyrimidin-2-yl)piperazinyl | 623.4 | 1.871 | E |
| 369 | 4-carbamoylpiperidinyl | 587.4 | 1.449 | E |
| 370 | N-methyl-N-(1-methylpyrrolidin-3-yl)amino | 573.4 | 1.18 | F |
| 371 | 2-(hydroxymethyl)pyrrolidinyl | 560.4 | 1.362 | F |
| 372 | —N(CH₂CH₃)CH₂CH₂N(CH₃)₂ | 575.4 | 1.217 | F |
| 373 | (S)-3-(dimethylamino)pyrrolidinyl | 573.4 | 1.657 | E |
| 374 | (R)-3-(dimethylamino)pyrrolidinyl | 573.4 | 1.168 | F |
| 375 | 2-(pyrrolidin-1-yl)ethylamino | 573.4 | 1.192 | F |
| 376 | 3-(2-oxopyrrolidin-1-yl)propylamino | 601.4 | 1.715 | E |

TABLE 25-continued

| Ex. No. | R | M+1 | RT (min) | Method |
|---|---|---|---|---|
| 377 | —NHCH(CH$_3$)CH$_2$CH$_3$ | 532.4 | 2.036 | E |
| 378 | —NH(CH(CH$_2$CH$_3$)$_2$ | 546.4 | 2.124 | E |
| 379 | —NH(CH$_2$CH$_2$NHC(O)CH$_3$) | 561.4 | 1.606 | E |
| 380 | —NH(CH$_2$CH$_2$N(CH$_3$)$_2$) | 547.4 | 1.142 | F |
| 381 | —NH(CH$_2$CN) | 514.3 | 1.368 | F |
| 382 | —NH(CH$_2$CH$_2$CH$_2$N(CH$_3$)$_2$) | 561.4 | 1.568 | E |
| 383 | | 584.4 | 1.7 | E |
| 384 | | 659.3 | 1.781 | E |
| 385 | —NH(CH$_2$C(O)NH$_2$) | 533.3 | 1.564 | E |
| 386 | —NHCH$_2$CH$_2$S(O)$_2$OH | 584.3 | 1.239 | F |
| 387 | | 598.4 | 2.075 | E |
| 388 | | 601.5 | 1.614 | E |

Example 389

2-(3,4-dimethoxyphenyl)-5-(piperidin-4-yl)-3-(tetrahydro-2H-pyran-4-yl)-1H-indole (389)

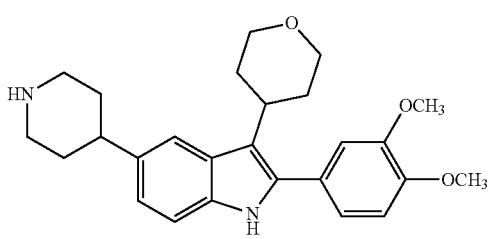

Intermediate 389A: 5-bromo-3-(tetrahydro-2H-pyran-4-yl)-1H-indole

A 250 ml round bottom flask charged with triethylsilane (2.444 mL, 15.30 mmol) and trichloroacetic acid (1.250 g, 7.65 mmol) in toluene (10 mL) was heated to 70° C. To the flask was added a mixture of 5-bromo-1H-indole (1 g, 5.10 mmol) and tetrahydro-4H-pyran-4-one (0.613 g, 6.12 mmol) in toluene (10 mL) at 70° C. dropwise. The reaction mixture was heated to 70° C. for 2 h. Progression of the reaction was monitored by LC/MS. The resulting brown solution was heated at 70° C. for 1.5 h. The solution was cooled to 10° C., quenched with 10% sodium bicarbonate and diluted with diethyl ether. The organic layer was separated, dried and concentrated under vacuum to yield crude compound. The crude compound was purified using silica gel chromatography eluting with 5% ethyl acetate in hexanes to afford 5-bromo-3-(tetrahydro-2H-pyran-4-yl)-1H-indole (0.6 g, 2.142 mmol 42% yield) as an oil. LCMS retention time 3.01 min [B]. MS (E$^-$) m/z: 280 (M+H).

Intermediate 389B: tert-butyl 4-(3-(tetrahydro-2H-pyran-4-yl)-1H-indol-5-yl)-3,6-dihydropyridine-1(2H)-carboxylate

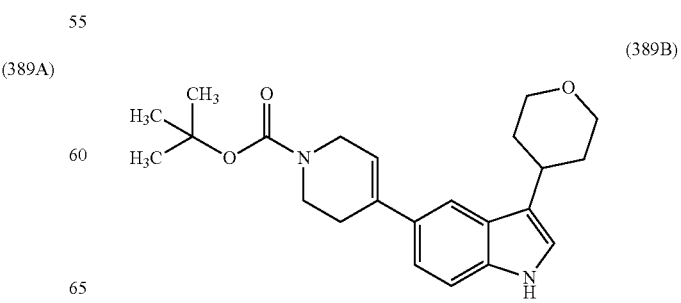

To a mixture of 5-bromo-3-(tetrahydro-2H-pyran-4-yl)-1H-indole (0.5 g, 1.85 mmol) and tert-butyl-4-(4,4,5,5-tetramethyl-1,3,2-dioxaborolan-2-yl)-5,6-dihydropyridine-1(2H)-carboxylate (0.63 g, 2.042 mmol) in a 250 ml round bottom flask was added THE (10 mL) followed by an aqueous solution of potassium phosphate, dibasic (0.47 g, 2.27 mmol). The resulting reaction mixture was degassed for 10 minutes with nitrogen, followed by the addition of $PdCl_2$(dppf)-$CH_2Cl_2$ adduct, 0.152 g, 0.186 mmol). The reaction mixture was degassed again for 5 min. The resulting reaction mixture was heated at 75° C. for 18 h. The reaction mixture was diluted with ethyl acetate (10 mL), poured into a separate funnel and was washed with water (2×5 mL), brine (5 mL), dried over sodium sulfate, and concentrated to yield crude product. The crude material was purified using silica gel chromatography, eluting with 15% ethyl acetate in hexane, the fractions was collected and concentrated to afford tert-butyl 4-(3-(tetrahydro-2H-pyran-4-yl)-1H-indol-5-yl)-5,6-dihydropyridine-1(2H)-carboxylate (0.4 g, 1.046 mmol, 56.3% yield) as an oil. LCMS retention time 2.18 min [C]. MS ($E^-$) m/z: 283 (M-Boc).

Intermediate 389C: tert-butyl 4-(3-(tetrahydro-2H-pyran-4-yl)-1H-indol-5-yl)piperidine-1-carboxylate

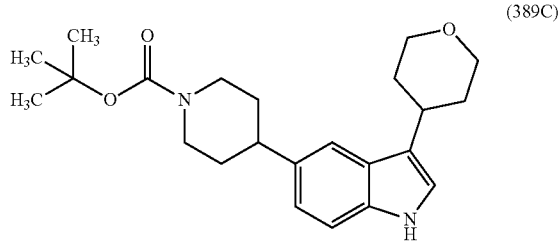 [SMILES: CC(C)(C)OC(=O)N1CCC(c2ccc3[nH]cc(C4CCOCC4)c3c2)CC1]

(389C)

A solution of tert-butyl 4-(3-(tetrahydro-2H-pyran-4-yl)-1H-indol-5-yl)-5,6-dihydropyridine-1(2H)-carboxylate (1 g, 2.61 mmol) in ethyl acetate (15 mL) was purged with nitrogen. Next, palladium on carbon (0.1 g, 0.65 mmol) was added and the mixture was purged with $N_2$ three times. Hydrogen gas was introduced via a balloon to the mixture. The reaction mixture was stirred at room temperature for 5 h. The suspension was filtered through celite, the filtrate was collected and concentrated to provide crude compound. The crude compound was purified by ISCO using 40 g silica column, the compound was eluted in 15% ethyl acetate in hexane, the fractions was collected and concentrated to afford tert-butyl 4-(3-(tetrahydro-2H-pyran-4-yl)-1H-indol-5-yl) piperidine-1-carboxylate (0.7 g, 69% yield) as a white solid. LCMS retention time 2.50 min [H]. MS ($E^-$) m/z: 383 (M–H).

Intermediate 389D: tert-butyl 4-(2-bromo-3-(tetrahydro-2H-pyran-4-yl)-1H-indol-5-yl)piperidine-1-carboxylate

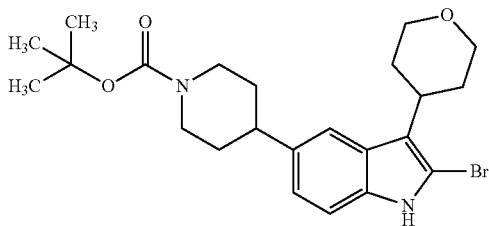

(389D)

To a solution of tert-butyl 4-(3-(tetrahydro-2H-pyran-4-yl)-1H-indol-5-yl) piperidine-1-carboxylate (2.1 g, 5.46 mmol) in DCE (20 mL) was added NBS (1 g, 5.46 mmol) dissolved in DCE (20 mL) drop wise via an addition funnel over 10 min at 0° C. The resulting brown solution was stirred at room temperature for 20 min. The reaction was quenched with sodium sulfite solution (15 mL) and the volatiles were removed. The residue was taken up in DCM (20 mL) and the aqueous layer was separated. The organic layer was dried over Na2SO4 and concentrated to yield crude compound. The crude material was purified by ISCO using 40 g silica column, the compound was eluted in 15% ethyl acetate in Pet ether, the fractions were collected and concentrated to yield tert-butyl 4-(2-bromo-3-(tetrahydro-2H-pyran-4-yl)-1H-indol-5-yl)piperidine-1-carboxylate (1.8 g, 71% yield) as a white solid. LCMS retention time 3.0 min [C]. MS ($E^-$) m/z: 363 (M-Boc).

Intermediate 389E: tert-butyl 4-(2-(3,4-dimethoxyphenyl)-3-(tetrahydro-2H-pyran-4-yl)-1H-indol-5-yl) piperidine-1-carboxylate (389E)

A solution of tert-butyl 4-(2-bromo-3-(tetrahydro-2H-pyran-4-yl)-1H-indol-5-yl) piperidine-1-carboxylate (0.8 g, 1.72 mmol), (3,4-dimethoxyphenyl)boronic acid (0.72 g, 3.97 mmol) and cesium carbonate (1.968 g, 5.18 mmol) in dioxane (40 mL) and water (10 mL) was degassed with $N_2$ for 10 min. Next, tetrakis(triphenylphosphine)palladium (0.194 g, 0.173 mmol) was added and the mixture was degassed again for 5 min. The resulting reaction mixture was heated at 70° C. for 5 h. The reaction mixture was concentrated. The residue was dissolved in ethyl acetate and the solution was washed with water. The organic layer was collected, dried over $Na_2SO_4$ and concentrated to yield crude compound. The crude material was purified by flash chromatography using a 24 g silica column. The compound was eluted in 18% ethyl acetate in Pet ether, the fractions were combined and concentrated to provide tert-butyl 4-(2-(2,3-dimethoxyphenyl)-3-(tetrahydro-2H-pyran-4-yl)-1H-indol-5-yl)piperidine-1-carboxylate (0.6 g, 2.93 mmol, 66% yield) as a white solid. LCMS retention time 3.14 min [H]. MS (E⁻) m/z: 519 (M–H).

Example 389

To a solution of tert-butyl 4-(2-(2,3-dimethoxyphenyl)-3-(tetrahydro-2H-pyran-4-yl)-1H-indol-5-yl)piperidine-1-carboxylate (0.1 g, 0.192 mmol) in DCM (5 mL) was added TFA (0.2 ml) at room temperature. The reaction mixture was stirred at room temperature for 1 h, and solid was observed to slowly precipitate from the reaction mixture. The slurry was concentrated and the residue was triturated with diethyl ether (2×10 mL) to afford 2-(3,4-dimethoxyphenyl)-3-isopropyl-5-(piperidin-4-yl)-1H-indole (0.05 g, 55% yield) as a pale yellow solid. LCMS retention time 2.19 min [H]. MS (E⁻) m/z: 421 (M+H).

Intermediate 390

2-chloro-1-(4-(2-(3,4-dimethoxyphenyl)-3-(tetrahydro-2H-pyran-4-yl)-1H-indol-5-yl) piperidin-1-yl) ethan-1-one

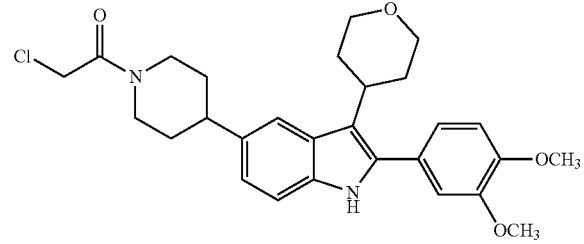

(I-390)

To a solution of 2-(2,3-dimethoxyphenyl)-5-(piperidin-4-yl)-3-(tetrahydro-2H-pyran-4-yl)-1H-indole (0.5 g, 0.95 mmol) in THF (15 mL) were added DIPEA (0.8 mL, 0.769 mol) and chloroacetyl chloride (0.15 mL, 0.269 mol). The reaction mixture was stirred at ambient temperature for 12 h. The mixture was concentrated. The residue was dissolved in ethyl acetate and the solution was washed with water. The organic layer was collected, dried over Na₂SO₄ and concentrated to provide crude compound. The crude material was purified by flash chromatography using 24 g silica column, compound was eluted in 50% ethyl acetate in Pet ether, the fractions were combined and concentrated to afford 2-chloro-1-(4-(2-(3,4-dimethoxyphenyl)-3-(tetrahydro-2H-pyran-4-yl)-1H-indol-5-yl) piperidin-1-yl)ethan-1-one (0.49 g, 84% yield) as a pale yellow solid. LCMS retention time 2.30 min [H]. MS (E⁻) m/z: 497 (M+H).

The following Examples were prepared according to the general procedure described in Example 157 using 2-chloro-1-(4-(2-(3,4-dimethoxyphenyl)-3-(tetrahydro-2H-pyran-4-yl)-1H-indol-5-yl)piperidin-1-yl)ethan-1-one.

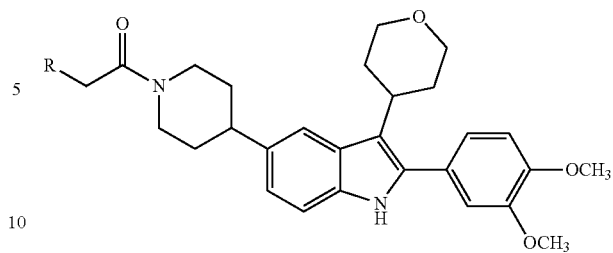

TABLE 26

| Ex. No. | R | M⁺¹ | RT (min) | Method |
|---|---|---|---|---|
| 391 | H₃C-CH₂-N(CH₂-CH₃)-C(O)- piperidin-3-yl (Isomer 1) | 645.4 | 7.67 | I |
| 392 | H₃C-CH₂-N(CH₂-CH₃)-C(O)- piperidin-3-yl (Isomer 2) | 645.4 | 11.96 | J |
| 393 | —N(CH₃)₂ | 506.2 | 7.26 | I |
| 394 | pyrrolidin-1-yl-CH₂CH₂-NH— | 548.4 | 7.41 | I |

Example 395

1-(4-(2-(3,4-dimethoxyphenyl)-3-(2,2,2-trifluoro-1-hydroxyethyl)-1H-indol-5-yl) piperidin-1-yl)-2-(dimethylamino)ethan-1-one (395)

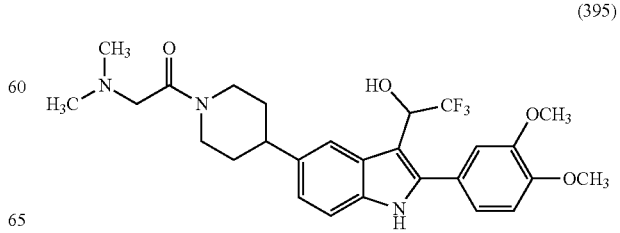

Intermediate 395A:
1-(5-bromo-1H-indol-3-yl)-2,2,2-trifluoroethanone

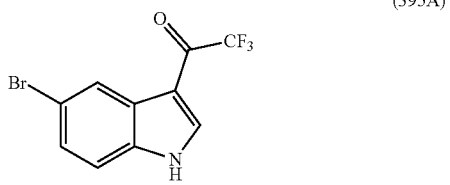

(395A)

To a stirred solution of 5-bromo-1H-indole (5.0 g, 25.5 mmol) in DMF (50 mL) was added trifluoroacetic anhydride (5.4 mL, 38.3 mmol) dropwise at room temperature. The mixture was stirred at room temperature for 2 h. The reaction mixture was poured onto crushed ice, the resulting solid material was filtered, washed with water and dried under vacuum to provide 1-(5-bromo-1H-indol-3-yl)-2,2,2-trifluoroethanone (5.2 g, 17.81 mmol 69% yield) as a white solid. LCMS retention time 2.875 min [D]. MS (E⁻) m/z: 290.0 (M−2H).

Intermediate 395B:
1-(5-bromo-1H-indol-3-yl)-2,2,2-trifluoroethanol

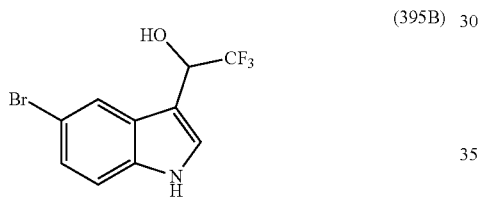

(395B)

To a stirred solution of 1-(5-bromo-1H-indol-3-yl)-2,2,2-trifluoroethanone (1 g, 3.42 mmol) in MeOH (5 mL) was added NaBH₄ (0.259 g, 6.85 mmol) at room temperature. The reaction mixture was stirred at room temperature for 3 h. The reaction was quenched with water (2 ml), and the mixture was concentrated under reduced pressure to remove MeOH, the residue was diluted with ethyl acetate (25 ml), washed with water (2×10 ml), dried over anhydrous sodium sulphate, filtered and concentrated to afford 1-(5-bromo-1H-indol-3-yl)-2,2,2-trifluoroethanol (0.6 g, 2.142 mmol 42% yield) as an off white solid. LCMS retention time 2.644 min [D]. MS (E⁻) m/z: 292.0 (M−2H).

Intermediate 395C: tert-butyl 4-(3-(2,2,2-trifluoro-1-hydroxyethyl)-1H-indol-5-yl)-3,6-dihydropyridine-1(2H)-carboxylate

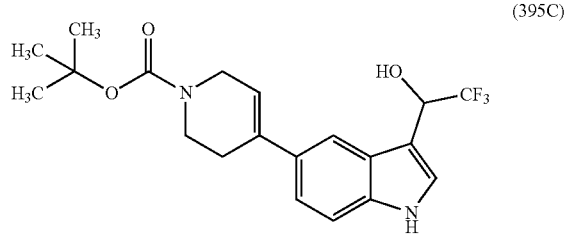 [SMILES: CC(C)(C)OC(=O)N1CC=C(c2ccc3[nH]cc(C(O)C(F)(F)F)c3c2)CC1]

(395C)

To a mixture of 1-(5-bromo-1H-indol-3-yl)-2,2,2-trifluoroethanol (0.9 g, 3.06 mmol) and tert-butyl-4-(4,4,5,5-tetramethyl-1,3,2-dioxaborolan-2-yl)-5,6-dihydropyridine-1(2H)-carboxylate (1.04 g, 3.37 mmol) in a 250 ml round bottom flask was added THF (25 mL) followed by the addition of an aqueous solution of potassium phosphate, dibasic (0.78 g, 3.67 mmol). The resulting reaction mixture was degassed for 10 minutes with nitrogen, then PdCl₂ (dppf)-CH₂Cl₂ adduct (0.252 g, 0.30 mmol) was added and the reaction mixture was degassed again for 5 min. The resulting reaction mixture was heated at 75° C. for 18 h. The reaction mixture was diluted with ethyl acetate (10 mL), poured into a separate funnel and was washed with water (2×5 mL), brine (5 mL), dried over sodium sulfate, and concentrated to afford crude product. The crude material was purified using silica gel chromatography, eluted with 15% ethyl acetate in hexane, the fractions were collected and concentrated to yield tert-butyl 4-(3-(2,2,2-trifluoro-1-hydroxyethyl)-1H-indol-5-yl)-5,6-dihydropyridine-1(2H)-carboxylate (0.45 g, 1.046 mmol, 33.3% yield) as an oil. LCMS retention time 2.30 min [H]. MS (E⁻) m/z: 395 (M−H).

Intermediate 395D: tert-butyl 4-(3-(2,2,2-trifluoro-1-hydroxyethyl)-1H-indol-5-yl) piperidine-1-carboxylate

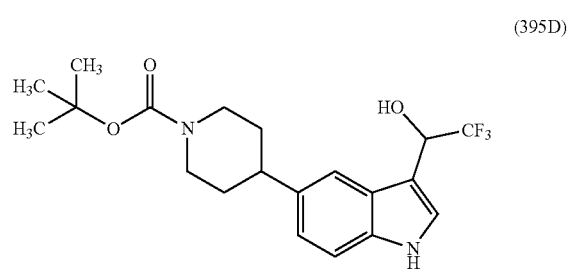 [SMILES: CC(C)(C)OC(=O)N1CCC(c2ccc3[nH]cc(C(O)C(F)(F)F)c3c2)CC1]

(395D)

A solution of tert-butyl 4-(3-(2,2,2-trifluoro-1-hydroxyethyl)-1H-indol-5-yl)-5,6-dihydropyridine-1(2H)-carboxylate (0.45 g, 11.35 mmol) in ethyl acetate (15 mL) was purged with nitrogen. Next, palladium on carbon (0.18 g, 1.70 mmol) was added and the mixture was purged with N₂ three times. Hydrogen gas was introduced via a balloon to the mixture and the reaction mixture was stirred at room temperature for 5 h. The suspension was filtered through celite be, the filtrate was collected and concentrated to provide crude compound. The crude material was purified by ISCO using 40 g silica column, the compound was eluted in 15% ethyl acetate in hexane, the fractions were collected and concentrated to afford tert-butyl 4-(3-(2,2,2-trifluoro-1-hydroxyethyl)-1H-indol-5-yl)piperidine-1-carboxylate (0.3 g, 66% yield) as a white solid. LCMS retention time 2.1 min [H]. MS (E⁻) m/z: 397 (M−H).

Intermediate 395E: tert-butyl 4-(2-bromo-3-(2,2,2-trifluoro-1-hydroxyethyl)-1H-indol-5-yl)piperidine-1-carboxylate

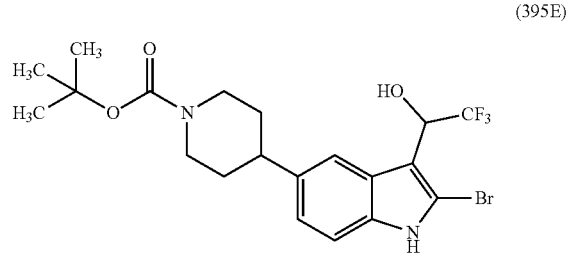 [SMILES: CC(C)(C)OC(=O)N1CCC(c2ccc3[nH]c(Br)c(C(O)C(F)(F)F)c3c2)CC1]

(395E)

To a solution tert-butyl 4-(3-(2,2,2-trifluoro-1-hydroxyethyl)-1H-indol-5-yl) piperidine-1-carboxylate (0.3 g, 0.75 mmol) in DCE (10 mL), was added NBS (0.13 g, 0.75 mmol) dissolved in DCE (10 mL) drop wise via an addition funnel over 10 min at 0° C. The resulting brown solution was stirred at room temperature for 20 min. The reaction was quenched with sodium sulfite solution (15 mL). The volatiles were removed from the reaction mixture, the residue was taken up in DCM (20 mL) and the aqueous layer was separated. The organic layer was dried over $Na_2SO_4$ and concentrated to yield crude compound. The crude material was purified by ISCO using 40 g silica column, the compound was eluted in 15% ethyl acetate in Pet ether, the fractions were collected and concentrated to afford tert-butyl 4-(2-bromo-3-(2,2,2-trifluoro-1-hydroxyethyl)-1H-indol-5-yl)piperidine-1-carboxylate (0.12 g, 22% yield) as a pale yellow solid. LCMS retention time 2.51 min [C]. MS (E$^-$) m/z: 477 (M+H).

Intermediate 395F: tert-butyl 4-(2-(3,4-dimethoxyphenyl)-3-(2,2,2-trifluoro-1-hydroxyethyl)-1H-indol-5-yl)piperidine-1-carboxylate

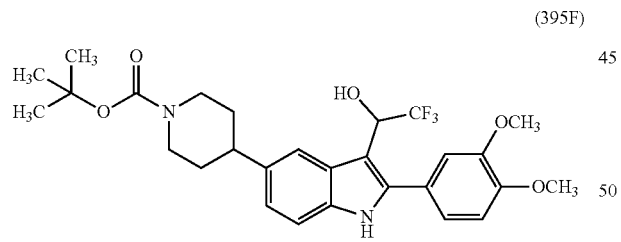

(395F)

A solution of tert-butyl 4-(2-bromo-3-(2,2,2-trifluoro-1-hydroxyethyl)-1H-indol-5-yl)piperidine-1-carboxylate (0.1 g, 0.21 mmol), (3,4-dimethoxyphenyl)boronic acid (0.082 g, 0.48 mmol), and cesium carbonate (0.20 g, 0.62 mmol) in dioxane (4 mL) and water (1 mL) was degassed with $N_2$ for 10 min. Next, tetrakis(triphenylphosphine) palladium (0.024 g, 0.021 mmol) was added and the mixture was again degassed for 5 min. The resulting reaction mixture was heated at 70° C. for 5 h. The reaction mixture was concentrated. The residue was dissolved in ethyl acetate and the solution was washed with water. The organic layer was collected, dried over $Na_2SO_4$ and concentrated to get crude compound. The crude material was purified by flash chromatography, using 12 g silica column, the compound was eluted in 18% ethyl acetate in Pet ether, the fractions were combined and concentrated to afford tert-butyl 4-(2-(2,3-dimethoxyphenyl)-3-(2,2,2-trifluoro-1-hydroxyethyl)-1H-indol-5-yl) piperidine-1-carboxylate (0.07 g, 44% yield) as a white solid. LCMS retention time 2.47 min [H]. MS (E$^-$) m/z: 533 (M–H).

Intermediate 395G: 1-(2-(3,4-dimethoxyphenyl)-5-(piperidin-4-yl)-1H-indol-3-yl)-2,2,2-trifluoroethan-1-ol hydrochloride

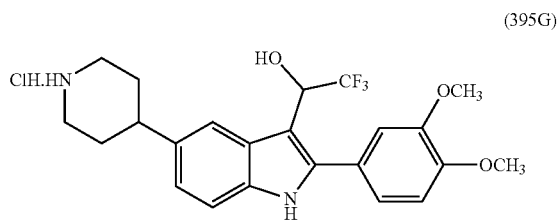

(395G)

To a solution of tert-butyl 4-(2-(3,4-dimethoxyphenyl)-3-(2,2,2-trifluoro-1-hydroxyethyl)-1H-indol-5-yl)piperidine-1-carboxylate (0.07 g, 0.131 mmol) in DCM (5 mL) was added TFA (0.2 ml) at room temperature, then the mixture was stirred at room temperature for 1 h. Solid material was observed to slowly precipitate from the reaction mixture. The slurry was concentrated and the residue was triturated with diethyl ether (2×10 mL) to afford 1-(2-(3,4-dimethoxyphenyl)-5-(piperidin-4-yl)-1H-indol-3-yl)-2,2,2-trifluoroethanol (0.05 g, 88% yield) as a pale yellow solid. LCMS retention time 1.94 min [H]. MS (E$^-$) m/z: 435 (M+H).

Intermediate 395H: 2-chloro-1-(4-(2-(3,4-dimethoxyphenyl)-3-(2,2,2-trifluoro-1-hydroxyethyl)-1H-indol-5-yl)piperidin-1-yl)ethan-1-one

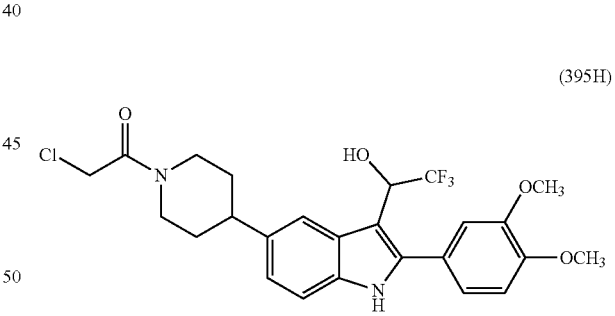

(395H)

To a solution of 1-(2-(2,3-dimethoxyphenyl)-5-(piperidin-4-yl)-1H-indol-3-yl)-2,2,2-trifluoroethanol (0.05 g, 0.095 mmol) in THF (5 mL), were added DIPEA (0.08 mL, 0.460 mmol) and chloroacetyl chloride (0.015 mL, 0.184 mmol). The reaction mixture was stirred at ambient temperature for 12 h. The mixture was concentrated. The residue was dissolved in ethyl acetate and the solution was washed with water. The organic layer was collected, dried over Na2SO4 and concentrated to yield crude compound. The crude material was purified by flash chromatography using 24 g silica column and the compound was eluted in 50% ethyl acetate in Pet ether, the fractions were combined and concentrated to afford 2-chloro-1-(4-(2-(3,4-dimethoxyphenyl)-3-(2,2,2-trifluoro-1-hydroxyethyl)-1H-indol-5-yl)piperidin-1-yl)ethan-1-one (0.049 g, 84% yield) as a pale yellow solid. LCMS retention time 2.31 min [H]. MS (E⁻) m/z: 509 (M–H).

Example 395

To 2-chloro-1-(4-(2-(3,4-dimethoxyphenyl)-3-(2,2,2-trifluoro-1-hydroxyethyl)-1H-indol-5-yl)piperidin-1-yl)ethanone (40 mg, 0.078 mmol) in THF (2 mL) was added DIPEA (0.027 mL, 0.157 mmol), followed by dimethylamine (0.117 mL, 0.235 mmol) dropwise and the reaction mixture was stirred at room temperature for 12 h. The reaction mass was concentrated, and the residue obtained purified by preparative HPLC. LCMS retention time 1.855 min [H]. MS (E⁻) m/z: 520 (M+H).

Example 396

2-(3,4-dimethoxyphenyl)-3-ethyl-6-methyl-5-(piperidin-4-yl)-1H-indole, HCl

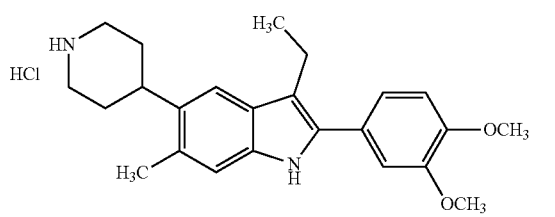

(396)

Preparation 396A: 3-ethyl-6-methyl-1H-indole

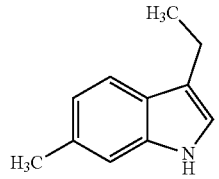

(396A)

To a 30 ml pressure tube were added 6-methyl-1H-indole (1.300 g, 9.91 mmol), Shvo's catalyst (0.107 g, 0.099 mmol), potassium carbonate (0.068 g, 0.496 mmol) and diethylamine (1.450 g, 19.82 mmol). The reaction mixture was purged with nitrogen gas and heated to 155° C. for 48 hrs. The reaction mixture was cooled to room temperature, diluted with DCM and washed with 1N HCl. The organics were dried over anhydrous sodium sulfate, filtered and concentrated. The residue was purified on a 120G ISCO column eluting with 0-70% ethyl acetate/hexane. Following concentration of the fractions, collected 3-ethyl-6-methyl-1H-indole (0.493 g, 31% yield). LC retention time 1.01 min [B1]. MS (E⁻) m/z: 160 (M–H).

Preparation 396B:
2-bromo-3-ethyl-6-methyl-1H-indole

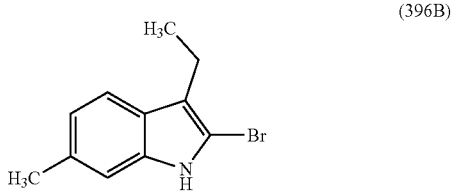

(396B)

In a 100 ml round bottom flask were added 3-ethyl-6-methyl-1H-indole (0.593 g, 3.72 mmol) and DCE (15 mL). NBS (0.630 g, 3.54 mmol) was dissolved in 5 ml of DCE and added to the reaction drop-wise via an addition funnel over 15 minutes. The reaction mixture was stirred for an additional 15 minutes, then quenched with 5 ml of a 10% sodium sulfite solution. The mixture was added to a separatory funnel and the layers were separated. The organics were washed with water, followed by brine. The combined organics were dried over anhydrous sodium sulfate, filtered and concentrated. The residue was taken up in minimal DCM and charged to a 24G ISCO column eluting with 0-50% ethyl acetate/heptane. Following concentration of the fractions, collected 2-bromo-3-ethyl-6-methyl-1H-indole as a white foam (0.660 g 74.4% yield). LC retention time 1.20 min [B1]. MS (E⁻) m/z: 238/240 (M–H).

Preparation 396C:
2-(3,4-dimethoxyphenyl)-3-ethyl-6-methyl-1H-indole

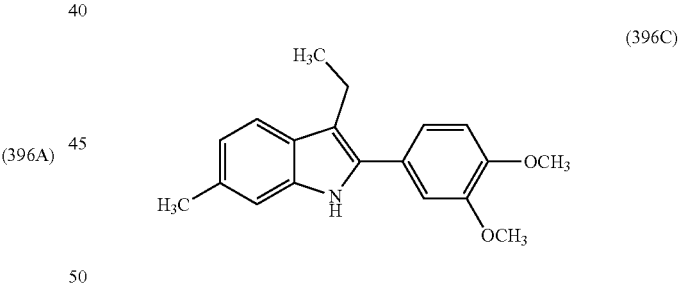

(396C)

In a 40 ml reaction vial fitted with a teflon-lined cap, 2-bromo-3-ethyl-6-methyl-1H-indole (0.737 g, 3.10 mmol) was taken in THF (7 mL). Next, (3,4-dimethoxyphenyl) boronic acid (0.591 g, 3.25 mmol), PdCl₂(dppf)-CH₂Cl₂ adduct (0.063 g, 0.077 mmol), and potassium phosphate solution (3.10 mL, 9.29 mmol) were added and the mixture was capped and pump/purged with nitrogen gas three times. The reaction mixture was heated at 50° C. for 1 hour. The mixture was cooled to room temperature and concentrated under a stream of nitrogen gas. The crude residue was diluted with 1 ml of DCM and charged to a 24G ISCO column, eluting with 0-50% ethyl acetate/hexane. Following concentration of the fractions, 2-(3,4-dimethoxyphenyl)-3-ethyl-6-methyl-1H-indole was collected as a white solid (0.425 g, 46% yield). LC retention time 2.26 min [B1]. MS (E⁻) m/z: 296 (M–H).

Preparation 396D: 5-bromo-2-(3,4-dimethoxyphenyl)-3-ethyl-6-methyl-1H-indole

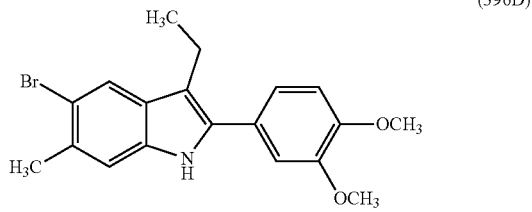

(396D)

In a 100 ml round bottom flask were added 2-(3,4-dimethoxyphenyl)-3-ethyl-6-methyl-1H-indole (0.230 g, 0.779 mmol) and DCE (3 mL). NBS (0.132 g, 0.740 mmol) was dissolved in 2 ml of DCE and added to the reaction mixture drop-wise via an addition funnel over 15 minutes. The reaction mixture was stirred for an additional 15 minutes. The reaction was quenched with the addition of 5 ml of a 10% sodium sulfite solution. The mixture was added to a separatory funnel and the layers were separated. The organics were washed with water, followed by brine. The combined organics were dried over anhydrous sodium sulfate, filtered and concentrated. The residue was taken up in minimal DCM and charged to a 24G ISCO column eluting with 0-50% ethyl acetate/heptane. Following concentration of the fractions, 5-bromo-2-(3,4-dimethoxyphenyl)-3-ethyl-6-methyl-1H-indole was collected as a white foam (0.050 g, 17.16% yield). LC retention time 1.22 min [B1]. MS (E$^-$) m/z: 375 (M–H).

Preparation 396E: tert-butyl-4-(2-(3,4-dimethoxyphenyl)-3-ethyl-6-methyl-1H-indol-5-yl)-5,6-dihydropyridine-1(2H)-carboxylate

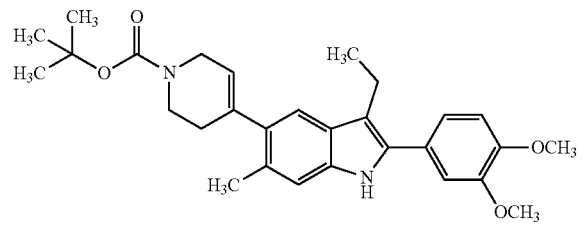

(396E)

To a mixture of 5-bromo-2-(3,4-dimethoxyphenyl)-3-ethyl-6-methyl-1H-indole (0.400 g, 1.069 mmol), PdCl$_2$(dppf)-CH$_2$Cl$_2$ adduct (0.022 g, 0.027 mmol), and tert-butyl 4-(4,4,5,5-tetramethyl-1,3,2-dioxaborolan-2-yl)-5,6-dihydropyridine-1(2H)-carboxylate (0.347 g, 1.122 mmol) in a 100 ml round bottom flask was added THF (35 mL) followed by an aqueous solution of tripotassium phosphate (1.069 mL, 3.21 mmol). The flask was fitted with a teflon-lined septum cap. The system was evacuated under vacuum (via a needle from a nitrogen/vacuum manifold line) and backfilled with nitrogen gas. The procedure was repeated three times. The needle was removed and the flask was heated at 75° C. for 18 h. The reaction mixture was diluted with EtOAc (100 mL), poured into a separatory funnel and washed with water (2×50 mL) and saturated aqueous sodium chloride solution (50 mL), dried over anhydrous sodium sulfate and filtered. The filtrate was concentrated in vacuo to give crude product. The crude material was dissolved in a small amount of DCM and charged to an ISCO silica gel 24G ISCO column, and was eluted over a 20 min gradient with 0%-50% EtOAc/hexanes to afford tert-butyl-4-(2-(3,4-dimethoxyphenyl)-3-ethyl-6-methyl-1H-indol-5-yl)-5,6-dihydropyridine-1(2H)-carboxylate (0.350 g, 68.7% yield). LC retention time 1.20 min [B1]. MS (E$^-$) m/z: 477 (M–H).

Example 396

To a 250 ml round bottom flask were added tert-butyl 4-(2-(3,4-dimethoxyphenyl)-3-ethyl-6-methyl-1H-indol-5-yl)-5,6-dihydropyridine-1(2H)-carboxylate (0.400 g, 0.839 mmol) and ethyl acetate (5 mL). The flask was purged with nitrogen gas and Pd/C (0.045 g, 0.042 mmol) was added. Following pump/purging with nitrogen gas three times, hydrogen gas was introduced via a balloon. The reaction mixture was stirred at room temperature overnight. The flask was evacuated and filled with nitrogen gas. The suspension was filtered through fluted filter paper and the filtrate was concentrated. To this was added 4M HCl/dioxane (2.098 mL, 8.39 mmol) and the reaction vessel was capped and the mixture was stirred for 1 hour at room temperature. The volitiles were removed to afford 2-(3,4-dimethoxyphenyl)-3-ethyl-6-methyl-5-(piperidin-4-yl)-1H-indole, HCl (0.29 g, 91% yield). LC retention time 1.19 min [B1]. MS (E$^-$) m/z: 379 (M–H).

Example 397

2-(3,4-dimethoxyphenyl)-3-ethyl-6-methoxy-5-(piperidin-4-yl)-1H-indole

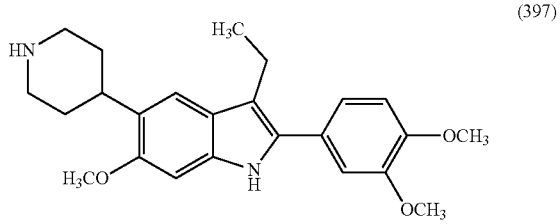 [SMILES: CCc1c(-c2ccc(OC)c(OC)c2)[nH]c2cc(OC)c(C3CCNCC3)cc12]

(397)

Preparation 397A: 5-bromo-3-ethyl-6-methoxy-11H-indole

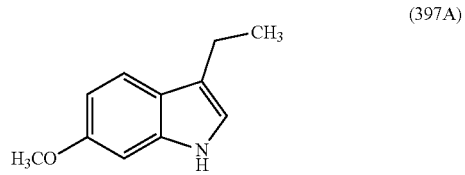

(397A)

To four separate 30 ml pressure tubes (800 mg each) were added 6-methoxy-1H-indole (3.20 g, 21.74 mmol), Shvo's Catalyst (0.236 g, 0.217 mmol), potassium carbonate (0.150 g, 1.087 mmol) and diethylamine (3.18 g, 43.5 mmol). The reaction mixtures were purged with nitrogen gas and heated to 155° C. for 12 hours. The reaction mixtures were concentrated under a stream of nitrogen gas. The resulting residue was charged to a 220G ISCO column (solid loading on celite), which was eluted with 0-55% ethyl acetate/hexane. Following concentration of the fractions, 5-bromo-3-ethyl-6-methoxy-1H-indole was collected as a brownish oil (2.65 g, 70%). LC retention time=1.07 min [B1]. MS (E⁻) m/z: 176 (M–H).

Preparation 397B:
2,5-dibromo-3-ethyl-6-methoxy-1H-indole

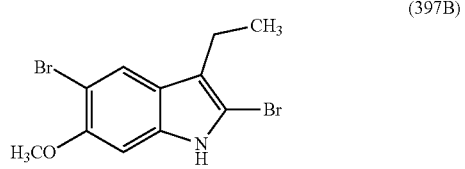

(397B)

To a 100 ml round bottom flask were added 3-ethyl-6-methoxy-1H-indole (0.150 g, 0.856 mmol) and DCM (4 mL). The reaction mixture was cooled to 0° C. and NBS (0.289 g, 1.626 mmol) in 2 ml of DCM was added drop-wise via a pipet over 5 minutes. After 5 minutes of additional stirring at 0° C., the reaction was quenched by the addition of 2 ml of a 10% sodium sulfite solution. The reaction mixture was diluted with EtOAc (100 mL), poured into a separatory funnel and washed with water (2×50 mL) and saturated aqueous NaCl solution (50 mL). The organics were collected and dried over anhydrous sodium sulfate. The suspension was filtered and the filtrate concentrated in vacuo to give 2,5-dibromo-3-ethyl-6-methoxy-1H-indole as a purplish solid. LC retention time 1.11 min [B1]. MS (E⁻) m/z: 333 (M–H).

Preparation 397C: tert-butyl 4-(2-(3,4-dimethoxyphenyl)-3-ethyl-6-methoxy-1H-indol-5-yl)-5,6-dihydropyridine-1(2H)-carboxylate

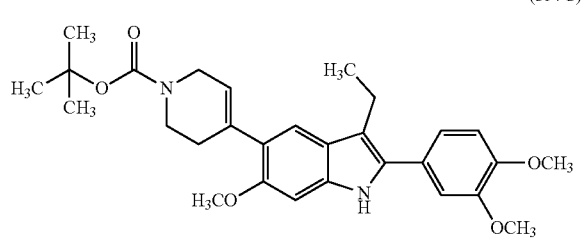

(397C)

To a 2 dram vial were added 2,5-dibromo-3-ethyl-6-methoxy-1H-indole, (3,4-dimethoxyphenyl)boronic acid (0.156 g, 0.856 mmol), PdCl₂(dppf)-CH₂Cl₂ adduct (0.070 g, 0.086 mmol) and 5 ml of THF. The vial was capped with a Teflon-lined cap and 3M tripotassium phosphate solution (0.90 mL) was added. The mixture was pump/purged with nitrogen gas three times. The reaction mixture was heated at 50° C. for 1 hour. The mixture was cooled to room temperature and tert-butyl 4-(4,4,5,5-tetramethyl-1,3,2-dioxaborolan-2-yl)-5,6-dihydropyridine-1(2H)-carboxylate (0.397 g, 1.284 mmol), PdCl₂(dppf)-CH₂Cl₂ adduct (0.070 g, 0.086 mmol) and a 3M tripotassium phosphate solution (0.90 mL) were added. The mixture was pump/purged with nitrogen gas three times. The reaction mixture was heated at 75° C. for 1 hour. The mixture was cooled to room temperature and diluted with EtOAc (100 mL), poured into a separatory funnel and washed with water (2×50 mL) and saturated aqueous NaCl solution (50 mL). The organics were collected and dried over anhydrous sodium sulfate. The suspension was filtered and the filtrate concentrated in vacuo to give crude product. The crude product was purified using a 24G ISCO silica gel column, which was eluted with 0-50% ethyl acetate/hexane over a 20 minute period. Following concentration of the fractions, tert-butyl 4-(2-(3,4-dimethoxyphenyl)-3-ethyl-6-methoxy-1H-indol-5-yl)-5,6-dihydropyridine-1(2H)-carboxylate (0.100 g, 24%) was collected as a tan solid. LC retention time=1.18 min [B1]. MS (E⁻) m/z: 393 (M–H).

Preparation 397D: 2-(3,4-dimethoxyphenyl)-3-ethyl-6-methoxy-5-(piperidin-4-yl)-1H-indole

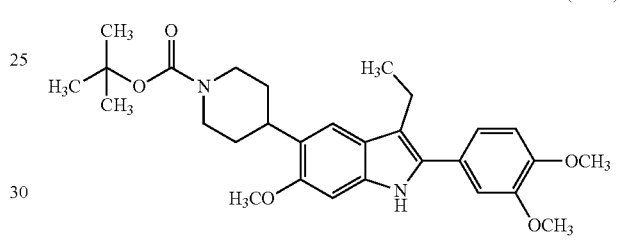

(397D)

To a Parr bottle were added tert-butyl 4-(2-(3,4-dimethoxyphenyl)-3-ethyl-6-methoxy-1H-indol-5-yl)-5,6-dihydropyridine-1(2H)-carboxylate (0.100 g, 0.203 mmol) and methanol (5 ml). The bottle was purged with nitrogen gas and Pd(OH)₂ (0.014 g, 0.020 mmol) was added. The bottle was situated on the Parr apparatus and following pump/purging with nitrogen gas three times, the vessel was pressurized to 50 psi with hydrogen gas. The reaction mixture was allowed to shake at this pressure for 18 hours. The flask was evacuated and filled with nitrogen gas. The suspension was diluted with methanol (50 ml) and filtered through fluted filter paper. The filter cake was washed several times with additional methanol. The filtrate was concentrated in vacuo to afford 2-(3,4-dimethoxyphenyl)-3-ethyl-6-methoxy-5-(piperidin-4-yl)-1H-indole (0.090 g, 90% yield). LC retention time=1.18 min [B1]. MS (E⁻) m/z: 395 (M–H).

Example 397

To a 2 dram reaction vial was added 2-(3,4-dimethoxyphenyl)-3-ethyl-6-methoxy-5-(piperidin-4-yl)-1H-indole (0.090, 0.180 mmol) and DCM (1 ml), followed by the addition of 4M HCl/Dioxane (0.071 mL, 0.926 mmol). The reaction mixture was stirred at room temperature for 60 minutes, then concentrated to dryness under a stream of nitrogen gas. The residue was taken up in DMF (1 mL) and the solids were filtered through a 0.45 micron syringe filter and the crude material was purified via preparative LC/MS with the following conditions: Column: Waters XBridge C18, 19×200 mm, 5-m particles; Mobile Phase A: 5:95 acetonitrile: water with 0.1% trifluoroacetic acid; Mobile Phase B: 95:5 acetonitrile: water with 0.1% trifluoroacetic acid; Gradient: 10-50% B over 25 minutes, then a 5-minute

Example 398

2-(3,4-dimethoxyphenyl)-3-ethyl-5-(1'-isopropyl-[1,4'-bipiperidin]-4-yl)-6-methoxy-1H-indole hold at 50% B; Flow: 20 mL/min. Fractions containing the desired product were combined and dried via centrifugal evaporation to afford 2-(3,4-dimethoxyphenyl)-3-ethyl-6-methoxy-5-(piperidin-4-yl)-1H-indole-trifluoroacetic acid salt (0.080 g, 100% yield). Two analytical LC/MS injections were used to determine the final purity. (1) LC retention time 1.28 min [C1]. MS (E⁻) m/z: 395 (M−H). (2) LC retention time=1.27 min [B1]. MS (E⁻) m/z: 395 (M−H).

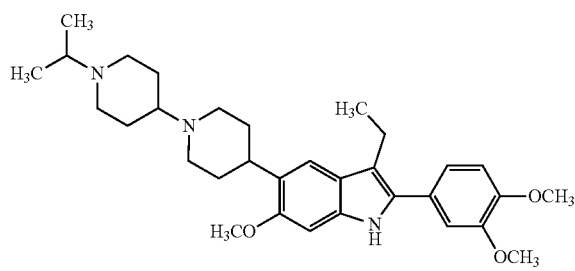

(398)

To a 2 dram reaction vial were added 2-(3,4-dimethoxyphenyl)-3-ethyl-6-methoxy-5-(piperidin-4-yl)-1H-indole (0.020 g, 0.046 mmol) and DMF (1 ml). To this were added TEA (0.028 mL, 0.203 mmol), 1 drop of acetic acid and 1-isopropylpiperidin-4-one (0.0063 g, 0.041 mmol). The reaction mixture was stirred at room temperature for 1 hour, and sodium cyanoborohydride (0.0076 g, 0.122 mmol) was added. The reaction vial was capped and the reaction mixture was stirred at room temperature overnight. The suspension was filtered through a 0.45 micron syringe filter and the crude material was purified via preparative LC/MS with the following conditions: Column: Waters XBridge C18, 19×200 mm, 5-µm particles; Mobile Phase A: 5:95 acetonitrile: water with 0.1% trifluoroacetic acid; Mobile Phase B: 95:5 acetonitrile: water with 0.1% trifluoroacetic acid; Gradient: 5-45% B over 25 minutes, then a 5-minute hold at 45% B; Flow: 20 mL/min. Fractions containing the desired product were combined and dried via centrifugal evaporation to afford 2-(3,4-dimethoxyphenyl)-3-ethyl-6-methoxy-5-(1'-isopropyl-[1,4'-bipiperidin]-4-yl)-1H-indole (0.0134 g, 55% yield). Two analytical LC/MS injections were used to determine the final purity. (1) LC retention time 1.44 min [C1]. MS (E⁻) m/z: 520 (M−H). (2) LC retention time=1.19 min [D1]. MS (E⁻) m/z: 520 (M−H).

Example 399

1-(4-(3-(2,2-difluoroethyl)-2-(3,4-dimethoxyphenyl)-1H-indol-5-yl)piperidin-1-yl)-2-(dimethylamino)ethan-1-one

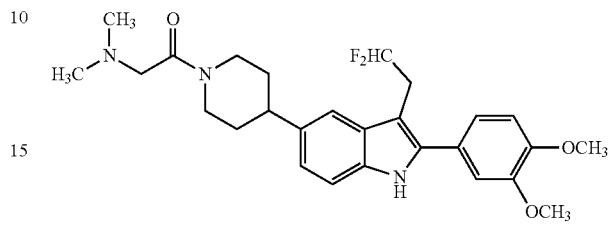

(399)

To a stirred solution of 3-(2,2-difluoroethyl)-2-(3,4-dimethoxyphenyl)-5-(piperidin-4-yl)-1H-indole (40 mg, 0.100 mmol) in DMF (3 mL) were added 2-(dimethylamino)acetic acid (10.30 mg, 0.100 mmol), HATU (76 mg, 0.200 mmol) and TEA (0.042 mL, 0.300 mmol) at room temperature under nitrogen atmosphere. The reaction mixture was stirred for 16 h. The reaction mixture was diluted with ethyl acetate (20 ml), washed with ice cold water (2×10 ml). The separated organic layer was dried over anhydrous sodium sulphate, concentrated and purified by prep LCMS with the following conditions: Waters Xbridge C18, 19×150 mm, 5 m; Guard Column: Waters XBridge C18, 19×10 mm, 5 m; Mobile Phase A:5:95 Acetonitrile:water with 0.1% TFA; Mobile Phase B: 95:5 Acetonitrile:water with 0.1% TFA; Gradient:15-50% B over 25 minutes, followed by a 10 minute hold at 50% B and 5 minute hold at 100% B; Flow: 15 ml/min. Fractions containing the product were combined and dried using a Genevac centrifugal evaporator to afford 1-(4-(3-(2,2-difluoroethyl)-2-(3,4-dimethoxyphenyl)-1H-indol-5-yl)piperidin-1-yl)-2-(dimethylamino)ethanone (12 mg, 0.025 mmol, 24% yield) as a white solid. ¹H NMR (400 MHz, DMSO-d₆) δ ppm 1.50-1.81 (m, 2H) 1.86-1.96 (m, 2H) 2.79-2.89 (m, 8H) 3.13-3.28 (m, 1H) 3.29-3.34 (m, 1H) 3.83 (d, J=5.84 Hz, 6H) 4.25-4.44 (m, 2H) 4.50-4.64 (m, 1H) 6.15-6.51 (m, 1H) 7.00-7.07 (m, 1H) 7.08-7.14 (m, 1H) 7.14-7.21 (m, 1H) 7.28-7.34 (m, 1H) 7.39-7.46 (m, 1H) 10.91-11.58 (m, 1H). LC retention time 1.385 min [E]. MS (E⁻) m/z: 486.4 (M+H).

Example 400

2-(4-(3-(2,2-difluoroethyl)-2-(3,4-dimethoxyphenyl)-1H-indol-5-yl)piperidin-1-yl)-N,N-dimethylacetamide

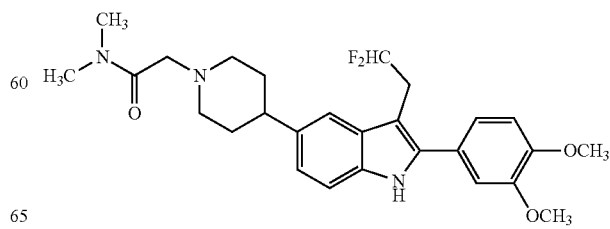

(400)

To a stirred solution of 3-(2,2-difluoroethyl)-2-(3,4-dimethoxyphenyl)-5-(piperidin-4-yl)-1H-indole (20 mg, 0.050 mmol) in THF (3 mL) were added 2-chloro-N,N-dimethylacetamide (7.29 mg, 0.060 mmol) and DIPEA (0.013 mL, 0.075 mmol) at room temperature under nitrogen atmosphere. The reaction mixture was stirred at room temperature for 2 h. The reaction mixture was diluted with ethyl acetate (20 ml), washed with ice cold water (2×10 ml). The separated organic layer was dried over anhydrous sodium sulphate, concentrated and purified by preparative LCMS with the following conditions: Waters Xbridge C18, 19×150 mm, 5 m; Guard Column: Waters XBridge C18, 19×10 mm, 5 m; Mobile Phase A:5:95 Methanol:water with 10 mM NH$_4$OAc; Mobile Phase B: 95:5 Methanol:water with 10 mM NH$_4$OAc; Gradient:15-65% B over 25 minutes, followed by a 10 minute hold at 65% B and 5 minute hold at 100% B; Flow: 15 ml/min. Fractions containing the product were combined and dried using a Genevac centrifugal evaporator to afford 2-(4-(3-(2,2-difluoroethyl)-2-(3,4-dimethoxyphenyl)-1H-indol-5-yl)piperidin-1-yl)-N,N-dimethylacetamide (14 mg, 0.028 mmol, 46% yield) as a white solid. $^1$H NMR (400 MHz, DMSO-d$_6$) δ ppm 11.15-11.19 (m, 1H) 7.41-7.45 (m, 1H) 7.24-7.32 (m, 1H) 7.14-7.20 (m, 1H) 7.07-7.13 (m, 1H) 6.99-7.05 (m, 1H) 3.12-3.18 (m, 2H) 3.03-3.09 (m, 3H) 2.91-2.98 (m, 2H) 2.78-2.84 (m, 3H) 2.64-2.71 (m, 2H) 2.31-2.37 (m, 4H) 2.05-2.22 (m, 1H) 1.62-1.79 (m, 1H). LC retention time 1.424 min [E]. MS (E$^-$) m/z: 486.4 (M+H).

Example 401

2-(4-(3-(2,2-difluoroethyl)-2-(3,4-dimethoxyphenyl)-1H-indol-5-yl)piperidin-1-yl)-N-methylacetamide (401)

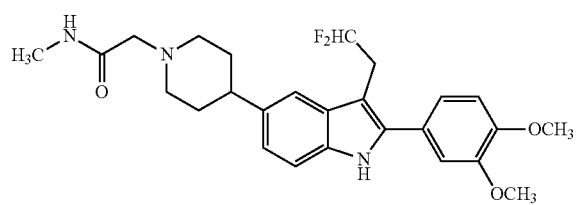

2-(4-(3-(2,2-difluoroethyl)-2-(3,4-dimethoxyphenyl)-1H-indol-5-yl)piperidin-1-yl)-N-methylacetamide (6 mg, 0.013 mmol, 25% yield) was prepared according to the general procedure described Example 400 using 3-(2,2-difluoroethyl)-2-(3,4-dimethoxyphenyl)-5-(piperidin-4-yl)-1H-indole (20 mg, 0.050 mmol), 2-chloro-N-methylacetamide (6.44 mg, 0.060 mmol) and DIPEA (0.013 mL, 0.075 mmol). $^1$H NMR (400 MHz, DMSO-d$_6$) δ ppm 11.12-11.24 (m, 1H) 7.38-7.48 (m, 1H) 7.25-7.33 (m, 1H) 7.15-7.24 (m, 1H) 7.07-7.15 (m, 1H) 6.96-7.05 (m, 1H) 6.05-6.54 (m, 1H) 3.24-3.45 (m, 2H) 2.88-3.09 (m, 2H) 2.51-2.78 (m, 3H) 2.37-2.48 (m, 2H) 1.94-2.13 (m, 2H) 1.69-1.81 (m, 3H). LC retention time=1.595 min [E]. MS (E$^-$) m/z: 472.3 (M+H).

Example 402

1-(4-(2-(3,4-dimethoxyphenyl)-3-methyl-1H-indol-5-yl)piperidin-1-yl)-2-(dimethylamino)ethan-1-one (402)

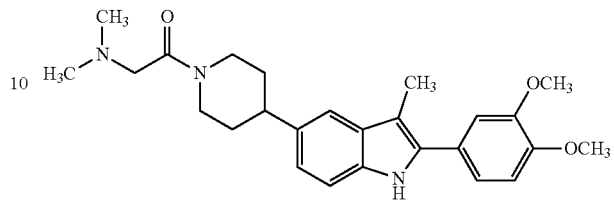

Preparation 402A: 2-chloro-1-(4-(2-(3,4-dimethoxyphenyl)-3-methyl-1H-indol-5-yl) piperidin-1-yl) ethanone (402A)

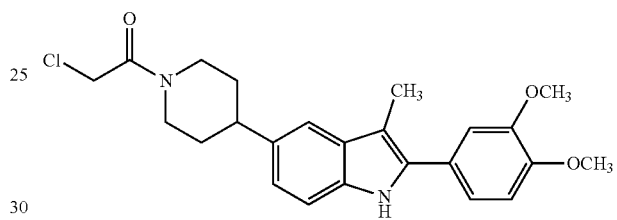

To a solution of 2-(3,4-dimethoxyphenyl)-3-methyl-5-(piperidin-4-yl)-1H-indole (0.3 g, 0.856 mmol) in THF (5 mL), were added DIPEA (0.449 mL, 2.57 mmol) and 2-chloroacetyl chloride (0.116 g, 1.027 mmol). The reaction mixture was stirred at ambient temperature for 12 h. The mixture was concentrated and the residue was dissolved in ethyl acetate. The solution was washed with water, the organic layer was collected, dried over Na2SO4 and concentrated to afford crude compound. The crude material was purified by combiflash, using 24 g silica column. The compound was eluted in 50% ethyl acetate in Pet ether, the fractions was combined and concentrated to afford 2-chloro-1-(4-(2-(3,4-dimethoxyphenyl)-3-methyl-1H-indol-5-yl)piperidin-1-yl)ethanone as a pale yellow solid. (0.29 g, 84% yield). LCMS retention time 1.10 min [H]. MS (E$^-$) m/z: 427 (M+H).

Example 402

To a solution of 2-chloro-1-(4-(2-(3,4-dimethoxyphenyl)-3-methyl-1H-indol-5-yl) piperidin-1-yl)ethanone (0.1 g, 0.234 mmol) in THF (2 mL) was added DIPEA (0.123 mL, 0.703 mmol) followed by the addition of dimethylamine (10.56 mg, 0.234 mmol). The reaction mixture was stirred at ambient temperature for 12 h. The residue was diluted with ethyl acetate and the solution was washed with water. The organic layer was collected, dried over Na$_2$SO$_4$ and concentrated to get crude compound. The crude material was purified by SCP to afford 1-(4-(2-(3,4-dimethoxyphenyl)-3-methyl-1H-indol-5-yl)piperidin-1-yl)-2-(dimethylamino) ethanone (0.021 g, 20% yield) as a pale yellow solid. LCMS retention time 2.69 min [F]. MS (E$^-$) m/z: 436.2 (M+H).

The following Examples were according to the general procedure described in Example 402.

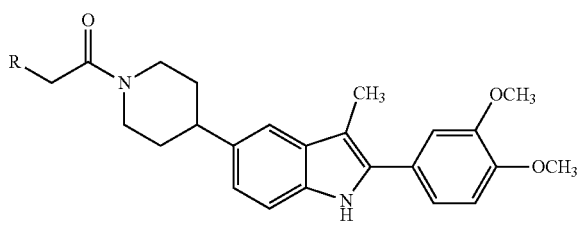

TABLE 27

| Ex. No. | R | M⁺¹ | RT | Method |
|---|---|---|---|---|
| 404 | (piperidine-3-carboxamide with N,N-diethyl) | 575 | 2.89 | F |
| 405 | —NHCH₂CH(OH)CH₂OH (R) | 482 | 1.92 | F |
| 406 | —NHCH₂CH₂CH(OH)CH₃ | 480 | 2.00 | F |
| 407 | 4-(dimethylamino)piperidin-1-yl | 519 | 2.19 | E |
| 408 | —N(CH₃)CH₂CH₂OH | 466 | 2.27 | F |
| 409 | 4-methylpiperazin-1-yl | 491 | 1.94 | F |
| 410 | 4-methyl-1,4-diazepan-1-yl | 505 | 2.26 | E |

Example 411

N-(2-(4-(2-(3,4-dimethoxyphenyl)-3-isopropyl-1H-indol-5-yl)piperidin-1-yl)ethyl)hept-6-ynamide Preparation 411A: tert-butyl (2-(4-(2-(3,4-dimethoxyphenyl)-3-isopropyl-1H-indol-5-yl) piperidin-1-yl)ethyl)carbamate (411A)

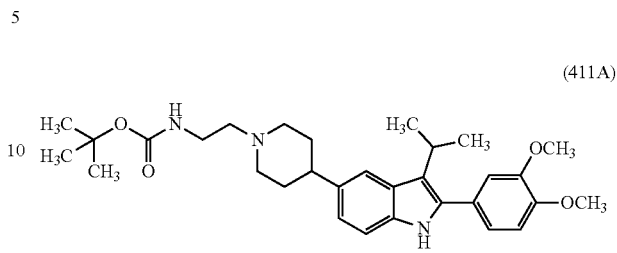

To a solution of 2-(3,4-dimethoxyphenyl)-3-isopropyl-5-(piperidin-4-yl)-1H-indole (0.5 g, 1.321 mmol) in acetonitrile (5 mL) was added K₂CO₃ (0.183 g, 1.321 mmol) followed by tert-butyl (2-bromoethyl)carbamate (0.296 g, 1.321 mmol). The reaction mixture was stirred at ambient temperature for 12 h. The residue containing acetonitrile was evaporated to afford the crude compound. The crude compound was purified by combiflash using n-hexane:ethyl acetate as eluent to afford tert-butyl(2-(4-(2-(3,4-dimethoxyphenyl)-3-isopropyl-1H-indol-5-yl)piperidin-1-yl)ethyl)carbamate as a pale yellow solid (0.3 g, 44%). LCMS retention time 0.99 min [H]. MS (E⁻) m/z: 522 (M+H).

Preparation 411B: 2-(4-(2-(3,4-dimethoxyphenyl)-3-isopropyl-1H-indol-5-yl)piperidin-1-yl)ethan-1-amine (411B)

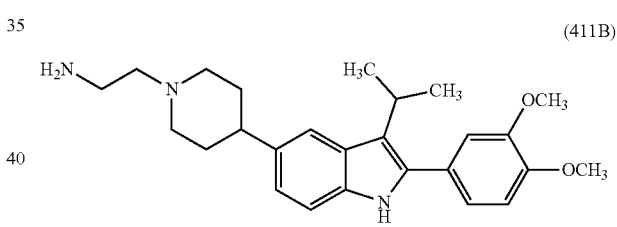

To a solution of tert-butyl(2-(4-(2-(3,4-dimethoxyphenyl)-3-isopropyl-1H-indol-5-yl)piperidin-1-yl)ethyl)carbamate (0.3 g, 0.575 mmol) in DCM (5 mL), was added TFA (0.25 ml, 2.87 mmol). The reaction mixture was stirred at ambient temperature for 12 h. The residue containing TFA and DCM was evaporated to afford 2-(4-(2-(3,4-dimethoxyphenyl)-3-isopropyl-1H-indol-5-yl)piperidin-1-yl)ethan-1-

(411)

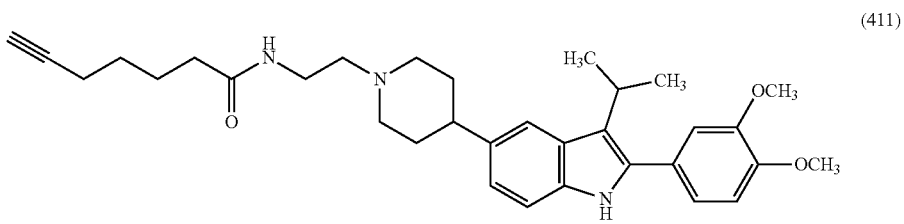 [SMILES: C#CCCCCC(=O)NCCN1CCC(c2ccc3[nH]c(-c4ccc(OC)c(OC)c4)c(C(C)C)c3c2)CC1]

amine (0.21 g, 87% yield) as a brown solid. LCMS retention time 1.04 min [H]. MS (E⁻) m/z: 422 (M+H).

Example 411

To a solution of 2-(4-(2-(3,4-dimethoxyphenyl)-3-isopropyl-1H-indol-5-yl) piperidin-1-yl)ethanamine (0.1 g, 0.237 mmol) in DMF (2 mL) was added hept-6-ynoic acid (0.030 g, 0.237 mmol) followed by HATU (0.090 g, 0.237 mmol) and DIPEA (0.041 mL, 0.237 mmol). The reaction mixture was stirred at ambient temperature for 12 h. The residue containing DMF was evaporated to afford crude compound. The crude material was purified by SCP to afford N-(2-(4-(2-(3,4-dimethoxyphenyl)-3-isopropyl-1H-indol-5-yl)piperidin-1-yl)ethyl)hept-6-ynamide (0.012 g, 8% yield) as a pale yellow solid. 1H NMR (400 MHz, DMSO-d₆) δ 10.79 (s, 1H), 7.72 (t, J=5.5 Hz, 1H), 7.49 (s, 1H), 7.24 (d, J=8.3 Hz, 1H), 7.11-6.98 (m, 3H), 6.95 (dd, J=8.3, 1.5 Hz, 1H), 3.82 (d, J=7.5 Hz, 6H), 3.31 (dt, J=14.1, 7.0 Hz, 1H), 3.23-3.15 (m, 2H), 2.98 (d, J=11.0 Hz, 2H), 2.73 (t, J=2.6 Hz, 1H), 2.37 (t, J=6.9 Hz, 2H), 2.17 (td, J=7.0, 2.5 Hz, 2H), 2.12-1.99 (m, 4H), 1.87-1.76 (m, 6H), 1.71-1.63 (m, 2H), 1.61-1.53 (m, 2H), 1.50-1.36 (m, 6H). LCMS retention time 2.18 min [F]. MS (E⁻) m/z: 530 (M+H).

Example 412

2-(3,4-dimethoxyphenyl)-5-(1'-isopropyl-[1,4'-bipiperidin]-4-yl)-3-(2,2,2-trifluoroethyl)-1H-indole

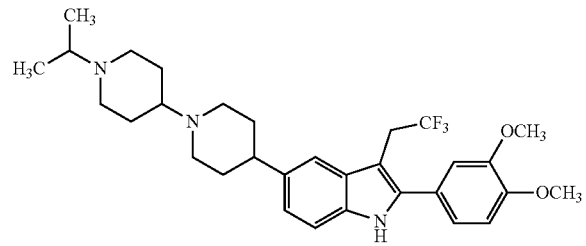

(412)

To a solution of 2-(3,4-dimethoxyphenyl)-5-(piperidin-4-yl)-3-(2,2,2-trifluoroethyl)-1H-indole hydrochloride (30 mg, 0.066 mmol) and 1-isopropylpiperidin-4-one (13.99 mg, 0.099 mmol) in MeOH (2 mL), was added titanium(IV) isopropoxide (0.048 mL, 0.165 mmol). The reaction mixture was heated at 50° C. for 5 h. The reaction mass was brought to ambient temperature and sodium cyanoborohydride (8.29 mg, 0.132 mmol) was added. The reaction mixture was stirred at ambient temperature for 12 h. The residue containing methanol was evaporated to afford crude compound. The crude material was purified by SCP to afford 2-(3,4-dimethoxyphenyl)-5-(1'-isopropyl-[1,4'-bipiperidin]-4-yl)-3-(2,2,2-trifluoroethyl)-1H-indole. 0.008 g, 22% yield) as white solid. ¹H NMR (400 MHz, DMSO-d₆) δ 11.28 (s, 1H), 7.42 (s, 1H), 7.29 (d, J=8.3 Hz, 1H), 7.19-7.07 (m, 3H), 3.82 (d, J=3.8 Hz, 6H), 3.80-3.69 (m, 2H), 2.66-2.62 (m, 3H), 2.31-2.15 (m, 2H), 2.13-2.02 (m, 6H), 1.89 (s, 6H), 1.83-1.59 (m, 2H), 1.48-1.35 (m, 1H), 0.95 (d, J=6.5 Hz, 6H). LCMS retention time 1.07 min [H]. MS (E⁻) m/z: 544 (M+H).

Example 413

2-(4-(2-(3,4-dimethoxyphenyl)-3-(2,2,2-trifluoroethyl)-1H-indol-5-yl)piperidin-1-yl)-N-methylethanamine

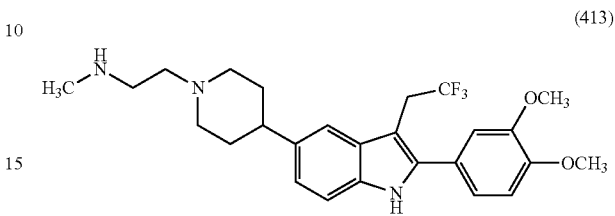

(413)

Preparation 413A: tert-butyl (2-(4-(2-(3,4-dimethoxyphenyl)-3-(2,2,2-trifluoroethyl)-1H-indol-5-yl)_piperidin-1-yl)ethyl)(methyl)carbamate

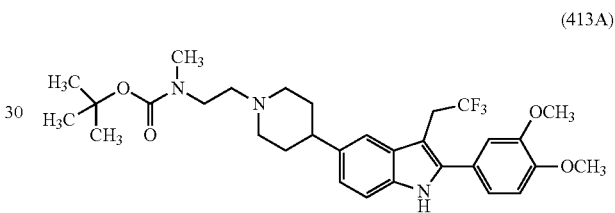

(413A)

To a solution of 2-(3,4-dimethoxyphenyl)-5-(piperidin-4-yl)-3-(2,2,2-trifluoroethyl)-1H-indole hydrochloride (40 mg, 0.088 mmol) in MeOH (2 mL), was added tert-butyl methyl(2-oxoethyl)carbamate (15.23 mg, 0.088 mmol) followed by the addition of titanium(IV) isopropoxide (0.064 mL, 0.220 mmol). The reaction mixture was heated to 50° C. for 5 h. The reaction mixture was cooled to ambient temperature. Sodium cyanoborohydride (11.05 mg, 0.176 mmol) was added and the reaction mixture was stirred at ambient temperature for 12 h. The residue containing methanol was evaporated to afford crude compound. The crude material was purified by combiflash to afford tert-butyl (2-(4-(2-(3,4-dimethoxyphenyl)-3-(2,2,2-trifluoroethyl)-1H-indol-5-yl) piperidin-1-yl)ethyl)(methyl)carbamate (0.0042 g, 79% yield) as white solid. LCMS retention time 1.01 min [H]. MS (E⁻) m/z: 576 (M+H).

Example 413

To a solution of tert-butyl (2-(4-(2-(3,4-dimethoxyphenyl)-3-(2,2,2-trifluoroethyl)-1H-indol-5-yl)piperidin-1-yl) ethyl)(methyl)carbamate (40 mg, 0.069 mmol) in DCM (1 mL), was added TFA (0.5 ml, 6.49 mmol). The reaction mixture was stirred at ambient temperature for 12 h. The residue containing TFA and DCM was evaporated to afford crude compound. The crude material was purified by SCP to afford 2-(4-(2-(3,4-dimethoxyphenyl)-3-(2,2,2-trifluoroethyl)-1H-indol-5-yl)piperidin-1-yl)-N-methylethanamine (0.007 g, 21% yield) as a white solid. ¹H NMR (400 MHz, DMSO-d₆) δ 11.39 (br. s., 1H), 8.68 (br. s., 1H), 7.35 (d, J=8.3 Hz, 2H), 7.23-7.07 (m, 4H), 3.83 (d, J=3.3 Hz, 6H), 3.81-3.71 (m, 3H), 2.66-2.62 (m, 6H), 2.08 (br. s., 3H), 1.91 (m, 6H). LCMS retention time 1.04 min [H]. MS (E⁻) m/z: 476 (M+H).

Example 414 tert-butyl (2-(4-(2-(3,4-dimethoxyphenyl)-3-(2,2,2-trifluoroethyl)-1H-indol-5-yl) piperidin-1-yl)-2-oxoethyl)(methyl)carbamate

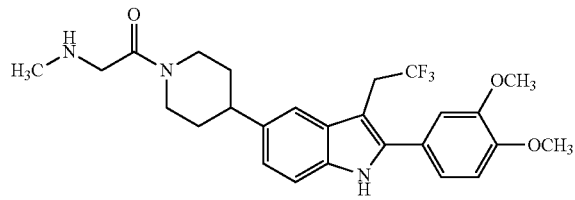

(414)

Preparation 414A: tert-butyl (2-(4-(2-(3,4-dimethoxyphenyl)-3-(2,2,2-trifluoroethyl)-1H-indol-5-yl) piperidin-1-yl)-2-oxoethyl)(methyl)carbamate

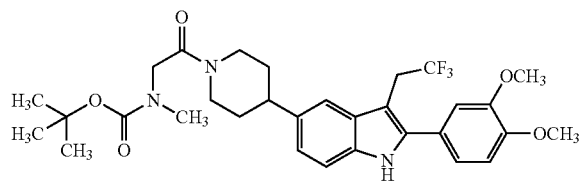

(414A)

To a solution of 2-(3,4-dimethoxyphenyl)-5-(piperidin-4-yl)-3-(2,2,2-trifluoroethyl)-1H-indole hydrochloride (40 mg, 0.088 mmol) in DMF (2 mL) were added BOC-SAR-OH (16.64 mg, 0.088 mmol), TEA (60 mg, 0.44 mmol), HATU (33.4 mg, 0.088 mmol). The reaction mixture was stirred at ambient temperature for 12 h. The residue containing DMF was concentrated to afford the crude product. The crude product was further treated with ice cold water and the resulting yellow solid precipitated was filtered and dried to afford tert-butyl (2-(4-(2-(3,4-dimethoxyphenyl)-3-(2,2,2-trifluoroethyl)-1H-indol-5-yl)piperidin-1-yl)-2-oxoethyl)(methyl)carbamate (45 mg, 87% yield). LCMS retention time 4.08 min [H]. MS (E⁻) m/z: 588 (M–H).

Example 414

To a solution of tert-butyl (2-(4-(2-(3,4-dimethoxyphenyl)-3-(2,2,2-trifluoroethyl)-1H-indol-5-yl)piperidin-1-yl)-2-oxoethyl)(methyl)carbamate (40 mg, 0.068 mmol) in DCM (2 mL) was added HCl (0.2 mL, 4 M in Dioxane). The reaction mixture was stirred at ambient temperature for 12 h. The residue containing dioxane was concentrated to afford the crude product. The crude material was purified by SCP to afford 1-(4-(2-(3,4-dimethoxyphenyl)-3-(2,2,2-trifluoroethyl)-1H-indol-5-yl)piperidin-1-yl)-2-(methylamino)ethanone (0.0021 g, 11% yield) as white solid. $^1$H NMR (400 MHz, DMSO-d₆) δ 11.32 (s, 1H), 7.42 (s, 1H), 7.31 (d, J=8.3 Hz, 1H), 7.19-7.08 (m, 3H), 7.03 (dd, J=8.3, 1.5 Hz, 1H), 4.56 (d, J=12.3 Hz, 1H), 3.93 (d, J=13.3 Hz, 1H), 3.83 (d, J=3.5 Hz, 8H), 3.80-3.70 (m, 2H), 3.50-3.34 (m, 1H), 3.10 (t, J=12.3 Hz, 1H), 2.90-2.80 (m, 1H), 2.73-2.62 (m, 1H), 2.32 (s, 3H), 1.92-1.88 (m, 2H), 1.64 (dd, J=12.3, 3.3 Hz, 1H), 1.52 (dd, J=12.5, 3.8 Hz, 1H). LCMS retention time 1.37 min [H]. MS (E⁻) m/z: 490 (M+H).

The following examples were prepared according to the general procedures of the indicated tables.

TABLE 28

| Ex. No. | R | M⁺¹ | R_T (min) | HPLC Method | Table |
|---|---|---|---|---|---|
| 415 | ![structure] | 422.3 | 1.42 | C1 | 8 |
| 416 | ![structure] | 490.4 | 1.72 | C1 | 7 |

TABLE 28-continued

| Ex. No. | R | M+1 | RT (min) | HPLC Method | Table |
|---|---|---|---|---|---|
| 417 | (structure) | 490.4 | 1.99 | C1 | 7 |
| 418 | (structure) Racemate | 643 | 2.02 | A | 24 |
| 419 | (structure) | 504 | 1.87 | A | 25 |
| 420 | (structure) Isomer 1 | 643 | 1.98 | A | 24 |
| 421 | (structure) Isomer 2 | 643 | 1.99 | A | 24 |

Biological Assays

The pharmacological properties of the compounds of this invention may be confirmed by a number of biological assays. The exemplified biological assays, which follow, have been carried out with compounds of the invention.

TLR7/8/9 Inhibition Reporter Assays

HEK-Blue™-cells (Invivogen) overexpressing human TLR7, TLR8 or TLR9 receptors were used for screening inhibitors of these receptors using an inducible SEAP (secreted embryonic alkaline phosphatase) reporter gene under the control of the IFN-β minimal promoter fused to five NF-κB and AP-1-binding sites. Briefly, cells are seeded into Greiner 384 well plates (15000 cells per well for TLR7, 20,000 for TLR8 and 25,000 for TLR9) and then treated with test compounds in DMSO to yield a final dose response concentration range of 0.05 nM-50 μM. After a 30 minute compound pre-treatment at room temperature, the cells are then stimulated with a TLR7 ligand (gardiquimod at a final concentration of 7.5 μM), TLR8 ligand (R848 at a final concentration of 15.9 μM) or TLR9 ligand (ODN2006 at a final concentration of 5 nM) to activate NF-κB and AP-1 which induce the production of SEAP. After a 22 hour incubation at 37° C., 5% $CO_2$, SEAP levels are determined with the addition of HEK-Blue™ Detection reagent (Invivogen), a cell culture medium that allows for detection of SEAP, according to manufacturer's specifications. The percent inhibition is determined as the % reduction in the HEK-Blue signal present in wells treated with agonist plus DMSO alone compared to wells treated with a known inhibitor.

TABLE 29

TLR7/8/9 Inhibition Data

| Ex. No. | TLR7 $IC_{50}$ (nM) | TLR8 $IC_{50}$ (nM) | TLR9 $IC_{50}$ (nM) |
|---|---|---|---|
| 1 | 583 | — | 5910 |
| 2 | 985 | — | 206 |
| 3 | 339 | 216 | 117 |
| 4 | 3771 | — | 190 |
| 5 | 1706 | — | 447 |
| 6 | 1227 | 247 | 221 |
| 7 | 2160 | — | 569 |
| 8 | 50000 | — | 50000 |
| 9 | 1548 | 457 | 360 |
| 10 | 606 | 201 | 202 |
| 11 | 934 | — | 216 |
| 12 | 1335 | — | 649 |
| 13 | 50000 | — | 1081 |
| 14 | 2108 | — | 1093 |
| 15 | 8303 | — | 602 |
| 16 | — | — | 1966 |
| 17 | 368 | — | 729 |
| 18 | 6449 | — | 1199 |
| 19 | 10497 | — | 2554 |
| 20 | 2225 | 978 | 1736 |
| 21 | 72 | 242 | 83 |
| 22 | 1163 | — | 1115 |
| 23 | 101 | 151 | 154 |
| 24 | 50000 | 27864 | 17478 |
| 25 | 317 | — | 169 |
| 26 | 348 | — | 318 |
| 27 | 850 | — | 2804 |
| 28 | 638 | — | 1008 |
| 29 | 1635 | — | 787 |
| 30 | 666 | — | 860 |
| 31 | 347 | — | 225 |
| 32 | 2478 | — | 3588 |
| 33 | 50000 | — | 3719 |
| 34 | 673 | — | 347 |
| 35 | 2685 | — | 1429 |
| 36 | 1156 | — | 348 |
| 37 | 1055 | — | 637 |
| 38 | 663 | — | 210 |
| 39 | 1976 | — | 251 |
| 40 | 512 | — | 2014 |
| 41 | 2341 | — | 3840 |
| 42 | 687 | — | 120 |
| 43 | 1161 | 926 | 2759 |
| 44 | 468 | 926 | 301 |
| 45 | 648 | — | 309 |
| 46 | 3287 | — | 746 |
| 47 | 589 | — | 1079 |
| 48 | 560 | 616 | 435 |
| 49 | 1364 | 260 | 550 |
| 50 | 1091 | 510 | 442 |
| 51 | 240 | — | 89 |
| 52 | 230 | 333 | 268 |
| 53 | 188 | — | 116 |
| 54 | 595 | — | 238 |
| 55 | 86 | 293 | 72 |
| 56 | 409 | — | 217 |
| 57 | 62 | — | 213 |
| 58 | 266 | 258 | 86 |
| 59 | 477 | 187 | 180 |
| 60 | 270 | — | 111 |
| 61 | 1586 | — | 555 |
| 62 | 225 | 217 | 196 |
| 63 | 321 | — | 132 |
| 64 | 163 | 195 | 112 |
| 65 | 23968 | 41356 | 112 |
| 66 | 521 | — | 233 |
| 67 | 1955 | — | 70 |
| 68 | 288 | 182 | 88 |
| 69 | 238 | 317 | 174 |
| 70 | 3745 | — | 2284 |
| 71 | 537 | — | 97 |
| 72 | 563 | 312 | 356 |
| 73 | 5089 | — | 100 |
| 74 | 1084 | 102 | 62 |
| 75 | 734 | 325 | 169 |
| 76 | 147 | 238 | 172 |
| 77 | 522 | — | 218 |
| 78 | 223 | 143 | 130 |
| 79 | 2322 | — | 122 |
| 80 | 433 | 284 | 80 |
| 81 | 538 | — | 190 |
| 82 | 145 | — | 165 |
| 83 | 2629 | — | 1555 |
| 84 | 490 | 143 | 192 |
| 85 | 907 | — | 247 |
| 91 | 829 | 352 | 313 |
| 92 | 576 | — | 59 |
| 93 | 903 | 302 | 237 |
| 94 | 1774 | 281 | 195 |
| 95 | 819 | 195 | 115 |
| 96 | 2534 | — | 186 |
| 97 | 931 | 196 | 397 |
| 99 | 938 | — | 1017 |
| 100 | 175 | — | 543 |
| 101 | 1793 | — | 209 |
| 102 | 559 | — | 382 |
| 103 | 344 | — | 157 |
| 104 | 2174 | — | 1049 |
| 105 | 144 | — | 385 |
| 106 | 905 | — | 307 |
| 107 | 1313 | — | 614 |
| 108 | 3541 | — | 861 |
| 109 | 50000 | — | 16950 |
| 110 | 1123 | — | 288 |
| 111 | 387 | — | 1506 |
| 112 | 250 | — | 319 |
| 113 | 371 | — | 885 |
| 114 | 5259 | 958 | 737 |
| 115 | 132 | 2228 | 77 |
| 116 | 1288 | 95 | 830 |
| 117 | 1343 | — | 882 |
| 118 | — | 347 | 260 |
| 119 | 1999 | 555 | 409 |
| 120 | 2739 | 1264 | 157 |
| 121 | 661 | 65 | 378 |
| 122 | 57 | 26 | 1413 |
| 123 | 398 | 150 | 170 |
| 124 | 1872 | 248 | 1281 |
| 125 | 182 | 150 | 410 |
| 126 | 920 | 114 | 481 |
| 127 | 1619 | 345 | 267 |
| 128 | 3278 | 629 | 947 |
| 129 | 1137 | 378 | — |
| 130 | 4168 | 792 | 6232 |
| 131 | 371 | 56 | 447 |
| 132 | 50000 | 50000 | 695 |
| 133 | 208 | 160 | 657 |
| 134 | 1692 | 399 | 7896 |
| 135 | 2914 | 635 | 7147 |
| 136 | 735 | 330 | — |

TABLE 29-continued

TLR7/8/9 Inhibition Data

| Ex. No. | TLR7 IC$_{50}$ (nM) | TLR8 IC$_{50}$ (nM) | TLR9 IC$_{50}$ (nM) |
|---|---|---|---|
| 137 | 4692 | 1293 | 2596 |
| 138 | 3511 | 268 | 1397 |
| 139 | 579 | 206 | 444 |
| 140 | 1024 | 240 | 479 |
| 141 | 3742 | 9781 | 50000 |
| 142 | 898 | 101 | 133 |
| 143 | 1264 | 706 | 730 |
| 144 | 473 | 73 | 495 |
| 145 | 8173 | 261 | — |
| 146 | 586 | 178 | — |
| 147 | 292 | 101 | 552 |
| 149 | 345 | 31 | 152 |
| 150 | 7978 | 1355 | 2335 |
| 151 | 507 | 403 | 556 |
| 152 | 590 | 33 | 233 |
| 153 | 1467 | 364 | 547 |
| 155 | 134 | 29 | 492 |
| 157 | 71 | — | 2839 |
| 158 | 219 | — | 678 |
| 159 | 42 | 26 | 3385 |
| 160 | 118 | — | 1900 |
| 161 | 1210 | 332 | 50000 |
| 162 | 88 | 23 | 402 |
| 163 | 280 | — | 2166 |
| 164 | 160 | — | 2129 |
| 165 | 107 | — | 5170 |
| 166 | 300 | — | 6440 |
| 167 | 179 | — | 33197 |
| 168 | 142 | 41 | 870 |
| 169 | 144 | — | 2097 |
| 170 | 257 | — | 1666 |
| 171 | 488 | — | 50000 |
| 172 | 263 | — | 19340 |
| 173 | 43 | 25 | 2237 |
| 174 | 1182 | | 2567 |
| 175 | 1694 | 2060 | 14141 |
| 176 | 8919 | 6554 | 50000 |
| 177 | 121 | 36 | 3358 |
| 178 | 480 | 131 | 5226 |
| 179 | 280 | 68 | 747 |
| 180 | 50000 | 776 | 50000 |
| 181 | 52 | 66 | 2266 |
| 182 | 610 | — | 50000 |
| 183 | 533 | 838 | 10175 |
| 184 | 191 | 136 | 2069 |
| 185 | 273 | 837 | 32440 |
| 186 | 96 | 132 | 991 |
| 187 | 167 | 162 | 1281 |
| 188 | 70 | 213 | 613 |
| 189 | 430 | 620 | 1153 |
| 190 | 588 | 1759 | 280 |
| 191 | 1190 | 110 | 1223 |
| 192 | 171 | 194 | 260 |
| 194 | 73 | 54 | 5006 |
| 196 | 12 | 16 | 521 |
| 197 | 113 | 25 | 653 |
| 198 | 379 | 22 | 490 |
| 199 | 120 | 19 | 257 |
| 200 | 101 | 27 | 1259 |
| 201 | 119 | 17 | 650 |
| 202 | 155 | 13 | 340 |
| 203 | 128 | 286 | 6662 |
| 204 | 160 | 112 | 1996 |
| 205 | 2371 | 6867 | 966 |
| 206 | 3575 | 14481 | 1001 |
| 207 | 7301 | 46877 | 2293 |
| 208 | 9 | 35 | 374 |
| 209 | 12 | 24 | 1661 |
| 210 | 13 | 25 | 1935 |
| 211 | 14 | 25 | 990 |
| 212 | 13 | 20 | 1187 |
| 213 | 31 | 18 | 2074 |
| 214 | 21 | 256 | 50000 |
| 215 | 36 | 163 | 2020 |
| 216 | 212 | — | 50000 |
| 217 | 409 | 379 | 2133 |
| 218 | 44 | 54 | 1279 |
| 219 | 33 | 39 | 2104 |
| 220 | 25 | 21 | 5577 |
| 221 | 162 | — | 50000 |
| 222 | 45 | 67 | 6881 |
| 223 | 48 | 98 | 50000 |
| 224 | 46 | 27 | 403 |
| 225 | 445 | — | 3228 |
| 226 | 16 | 17 | 1419 |
| 227 | 29 | 24 | 1734 |
| 228 | 46 | 118 | 15072 |
| 229 | 25 | 43 | 4981 |
| 230 | 19 | 18 | 2197 |
| 231 | 96 | 63 | 1931 |
| 232 | 120 | 169 | 307 |
| 233 | 23 | 27 | 877 |
| 234 | 172 | 63 | 1880 |
| 235 | 15 | 39 | 774 |
| 236 | 29 | 38 | 1384 |
| 237 | 15 | 22 | 1161 |
| 238 | 36 | 5 | 1425 |
| 239 | 11 | 17 | 516 |
| 240 | 11 | 34 | 1386 |
| 241 | 12 | 13 | 571 |
| 242 | 23 | 14 | 976 |
| 243 | 55 | 16 | 1505 |
| 244 | 6 | 16 | 381 |
| 245 | 26 | 26 | 1140 |
| 246 | 11 | 19 | 664 |
| 247 | 40 | 38 | 4132 |
| 248 | 33 | 22 | 163 |
| 249 | 21 | 17 | 780 |
| 251 | 372 | 750 | 15321 |
| 253 | 10 | 19 | 445 |
| 254 | 105 | 483 | 45215 |
| 255 | 34 | 480 | 50000 |
| 256 | 11 | 35 | 2323 |
| 258 | 18 | 17 | 1444 |
| 259 | 40 | 11 | 2028 |
| 260 | 64 | — | 2701 |
| 261 | 180 | — | 5759 |
| 262 | 61 | 23 | 2967 |
| 263 | 82 | — | 790 |
| 264 | 364 | — | 5088 |
| 265 | 180 | — | 50000 |
| 266 | 48 | 20 | 1261 |
| 267 | | 25 | |
| 268 | 31 | 15 | 1485 |
| 269 | 2694 | — | 18627 |
| 270 | 191 | — | 1940 |
| 271 | 2377 | — | 10558 |
| 272 | 83 | 37 | 3401 |
| 273 | 7 | 29 | 565 |
| 274 | 68 | 228 | 829 |
| 275 | 17 | 22 | 1663 |
| 276 | 17 | 27 | 3577 |
| 277 | 16 | 37 | 4982 |
| 278 | 8 | 11 | 2868 |
| 279 | 495 | 1163 | 17953 |
| 280 | 26 | 22 | 417 |
| 281 | 17 | 20 | 586 |
| 282 | 29 | 33 | 3979 |
| 283 | 25 | 24 | 3901 |
| 284 | 39 | 25 | 4612 |
| 285 | 55 | 37 | 4953 |
| 286 | 5 | 17 | 603 |
| 287 | 38 | 33 | 2277 |
| 288 | 44 | 32 | 633 |
| 289 | 13 | 14 | 502 |
| 290 | 1743 | 803 | 5337 |
| 291 | 36 | 17 | 2312 |
| 292 | 22 | 22 | 1812 |

TABLE 29-continued

TLR7/8/9 Inhibition Data

| Ex. No. | TLR7 IC$_{50}$ (nM) | TLR8 IC$_{50}$ (nM) | TLR9 IC$_{50}$ (nM) |
|---|---|---|---|
| 293 | 28 | 33 | 777 |
| 294 | 1204 | 554 | 2217 |
| 295 | 50 | 22 | 5313 |
| 296 | 35 | 22 | 3030 |
| 297 | 48 | 19 | 3053 |
| 298 | 47 | 27 | 3941 |
| 299 | 204 | 128 | 6985 |
| 300 | 85 | 70 | 321 |
| 301 | 66 | 19 | 3121 |
| 302 | 40 | 18 | 564 |
| 303 | 30 | 31 | 1790 |
| 304 | 64 | 61 | 2750 |
| 305 | 27 | 26 | 561 |
| 306 | 153 | 73 | 2681 |
| 307 | 52 | 38 | 579 |
| 308 | 37 | 41 | 2609 |
| 309 | 31 | 59 | 6917 |
| 310 | 290 | 488 | 5231 |
| 311 | 148 | 60 | 2482 |
| 312 | 8 | 28 | 1373 |
| 313 | 73 | 496 | 48350 |
| 314 | 284 | 657 | 26620 |
| 315 | 538 | 824 | — |
| 317 | 38 | 82 | 4719 |
| 318 | 3282 | 6075 | 11161 |
| 319 | 45 | 46 | 9112 |
| 320 | 71 | 124 | 5019 |
| 321 | 22 | 21 | 4499 |
| 322 | 21 | 22 | 2794 |
| 323 | 42 | 20 | 2869 |
| 324 | 51 | 20 | 3533 |
| 325 | 269 | 147 | 50000 |
| 326 | 127 | 192 | 50000 |
| 329 | 15 | 19 | 1158 |
| 330 | 57 | 84 | 1614 |
| 331 | 33 | 221 | 5234 |
| 332 | 1855 | 4106 | 50000 |
| 333 | 94 | 702 | 50000 |
| 334 | 130 | 412 | 7768 |
| 335 | 331 | 632 | 15252 |
| 336 | 359 | 697 | 27827 |
| 337 | 3571 | 5077 | 50000 |
| 338 | 1494 | 1463 | 50000 |
| 339 | 331 | 822 | 50000 |
| 340 | 22 | 32 | 914 |
| 341 | 5027 | 9388 | 50000 |
| 342 | 240 | 591 | 26434 |
| 343 | 174 | 371 | 40842 |
| 344 | 881 | 1420 | 50000 |
| 345 | 256 | 1034 | 25198 |
| 346 | 213 | 529 | 2937 |
| 347 | 155 | 767 | 39078 |
| 348 | 413 | 1420 | 15314 |
| 349 | 291 | 671 | 9728 |
| 350 | 624 | 2052 | 50000 |
| 351 | 17 | 57 | 1562 |
| 352 | 458 | 765 | 28933 |
| 353 | 229 | 964 | 39951 |
| 354 | 22 | 82 | 2150 |
| 355 | 19 | 41 | 2280 |
| 356 | 618 | 626 | 50000 |
| 357 | 690 | 943 | 50000 |
| 358 | 50000 | 2920 | 50000 |
| 359 | 19 | 63 | 267 |
| 360 | 16 | 43 | 392 |
| 361 | 100 | 109 | 2423 |
| 362 | 65 | 109 | 1146 |
| 363 | 8 | 44 | 268 |
| 364 | 23 | 76 | 563 |
| 365 | 14 | 24 | 190 |
| 366 | 4 | 23 | 141 |
| 367 | 23 | 36 | 441 |
| 368 | 159 | 74 | 1331 |
| 369 | 101 | 43 | 1954 |
| 370 | 27 | 55 | 399 |
| 371 | 79 | 52 | 2456 |
| 372 | 13 | 25 | 335 |
| 373 | 16 | 44 | 370 |
| 374 | 9 | 35 | 252 |
| 375 | 29 | 117 | 701 |
| 376 | 178 | 65 | 2900 |
| 377 | 233 | 204 | 8653 |
| 378 | 622 | 451 | 14385 |
| 379 | 94 | 39 | 4227 |
| 380 | 33 | 55 | 745 |
| 381 | 63 | 76 | 5912 |
| 382 | 17 | 62 | 555 |
| 383 | 13 | 30 | 660 |
| 384 | 150 | 81 | 2312 |
| 385 | 61 | 41 | 4252 |
| 386 | 557 | 590 | 50000 |
| 387 | 994 | 587 | 8427 |
| 388 | 9 | 40 | 288 |
| 389 | 300 | — | 1641 |
| 391 | 626 | 356 | 5399 |
| 392 | 681 | 196 | 1796 |
| 393 | 248 | — | 4853 |
| 394 | 1390 | 660 | 2757 |
| 395 | 61 | 438 | 13169 |
| 396 | 47 | 295 | 3427 |
| 399 | 106 | 82 | 2168 |
| 400 | 157 | 110 | 3956 |
| 401 | 132 | 128 | 5294 |
| 402 | 544 | 2284 | 5821 |
| 404 | 3147 | 3750 | 8635 |
| 405 | 18260 | 29185 | 13510 |
| 406 | 1183 | 2052 | 3888 |
| 407 | 12315 | 50000 | 11489 |
| 408 | 898 | 4771 | 2004 |
| 409 | 1014 | 11158 | 2348 |
| 410 | 3861 | 21141 | 5252 |
| 411 | 63 | 36 | 3891 |
| 412 | 19 | 21 | 247 |
| 413 | 83 | 28 | 626 |
| 414 | 58 | 86 | 1168 |
| 415 | 2132 | — | 1074 |
| 416 | 677 | — | 291 |
| 417 | 1176 | — | 565 |
| 418 | 79 | 77 | 1451 |
| 419 | 31 | 47 | 2950 |
| 420 | 66 | 25 | 279 |
| 421 | 114 | 71 | 2278 |

In Vivo Mouse TLR7 and TLR9 PD Model:

Adult male C57BL/6 mice were used for the experiments. Mice (7 to 10 per group) were randomized into different treatment groups based on body weight. Mice from the respective treatment groups were administered orally with vehicle or test compound. Thirty min after the oral administration of vehicle or test compound, mice were challenged with intraperitoneal injection of gardiquimod for TLR7 PD model and CpG-ODN for TLR9 PD model. Ninety minutes after gardiquimod injection and 120 minutes after CpG-ODN injection, mice were bled under isoflurane anaesthesia and plasma IL-6 level was estimated by using commercially available ELISA kit (BD Biosciences). At the end of experiment, mean cytokine data was plotted and one way ANOVA with Dunnett's test was performed to calculate the significance of test compound treated group vs. vehicle control group. Percent inhibition of cytokine induction was calculated for test compound treated group vs vehicle control group. Data from multiple studies with different test compounds is shown in Table 30.

TABLE 30

Percent inhibition of IL-6 in mouse TLR7 and TLR9 PD model

| TLR7 PD model | | | TLR9 PD model | | |
|---|---|---|---|---|---|
| Ex. No. | Dose (mg/kg) | % inhibition of IL6 | Ex. No | Dose (mg/kg) | % inhibition of IL6 |
| 196 | 0.03 | 38 | 196 | 1 | 47 |
|  | 0.1 | 34 |  | 3 | 75 |
|  | 0.3 | 55 |  | 10 | 83 |
|  | 1 | 68 |  | 30 | 88 |
|  | 3 | 88 |  | 100 | 62 |
|  | 10 | 97 |  | — | — |
|  | 30 | 99 |  | — | — |
| 209 | 0.001 | 11 | 209 | 1 | 29 |
|  | 0.01 | 21 |  | 10 | 37 |
|  | 0.1 | 61 |  | 30 | 37 |
|  | 1 | 86 |  | 100 | 51 |
| 312 | 0.001 | 34 |  |  |  |
|  | 0.01 | 39 |  |  |  |
|  | 0.1 | 59 |  |  |  |
|  | 1 | 82 |  |  |  |

Imiquimod Induced Psoriasis:

Male C57BL/6 mice of 8-9 week age were used to evaluate the impact of TLR7/8/9 inhibitors on Imiquimod-induced psoriasis. Mice (7 to 10 per group) were randomized into different treatment groups based on body weight. Mice from the respective treatment groups were treated orally, once daily for 6 days with vehicle or test compound. Psoriasis was induced by application of imiquimod cream on the shaved back region of the mice everyday for 6 days. Disease severity was monitored daily by recording of skin thickness, erythema and scaling. A cumulative disease score was also calculated to reflect the impact on the overall severity of inflammation in this model. At the end of experiment, all mice were euthanized by $CO_2$ asphyxiation and skin samples were subjected for histology. At the end of experiment, one way ANOVA with Dunnett's test was performed to calculate the significance of test compound treated group vs. vehicle control group. Overall percent reduction in imiquimod induced psoriasis was calculated for test compound treated group vs vehicle control group. Data from various studies with different test compounds is shown in Table 31.

TABLE 31

Inhibition of Imiquimod-induced Psoriasis

| Example No. | Dose (mg/kg) | Scaling | Erythema | Skin Thickness | % inhibition Cumulative Score |
|---|---|---|---|---|---|
| Ex. 196 | 1 | 35 | 31 | 16 | 27 |
|  | 3 | 50 | 40 | 20 | 36 |
|  | 10 | 60 | 48 | 30 | 46 |
|  | 30 | 70 | 55 | 39 | 55 |
| Ex. 209 | 0.1 | 13 | 3 | 0 | 3 |
|  | 1 | 38 | 26 | 18 | 27 |
|  | 10 | 50 | 41 | 29 | 40 |
|  | 30 | 63 | 53 | 32 | 49 |

MRL/Lpr Model of Systemic Lupus Erythematosus (SLE)

Male MRL/lpr mice of 12-14 weeks age were screened and randomized based on the titers of anti-dsDNA antibodies and urinary NGAL (Neutrophil Gelatinase Associated Lipocalin). Mice were treated orally, once daily for 8 weeks with vehicle or test compound. The effect of test compound on disease severity was assessed by measuring end points including proteinuria, urinary-NGAL, anti-dsDNA Ab titer, and lymphadenopathy. These end points were assessed before the start of treatment and after 4 and 8 weeks of treatment. At the end of experiment, all mice were euthanized by $CO_2$ asphyxiation and kidney samples were subjected for histology. At the end of experiment, one way ANOVA with Dunnett's test was performed to calculate the significance of test compound treated group vs. vehicle control group. Percent reduction in disease severity was calculated for each parameter, for test compound treated group vs vehicle control group. A cumulative disease score and the percent reduction in cumulative disease score was calculated by considering the average inhibition in all parameters except lymphadenopathy to reflect the impact on the overall severity of disease progression. Data from multiple studies with different test compounds is shown in Table 32.

TABLE 32

Inhibition disease development in MRL/lpr model of Systemic Lupus Erythematosus

| | | % inhibition | | | | | | |
|---|---|---|---|---|---|---|---|---|
| Ex. No. | Dose (mg/kg) | Anti-dsDNA antibody titer | Urinary NGAL | Proteinuria | IL-12p40 | IL-10 | Lymphadenopathy | Cumulative score |
| 196 | 1 | 14 | 33 | 36 | 20 | 28 | 24 | 28 |
|  | 3 | 30 | 41 | 55 | 22 | 35 | 37 | 42 |
|  | 10 | 54 | 65 | 76 | 24 | 49 | 41 | 61 |
|  | 30 | 84 | 67 | 82 | 51 | 73 | 59 | 76 |
| 209 | 1 | 44 | 36 | 46 | 13 | 10 | 35 | 42 |
|  | 2 | 57 | 52 | 57 | 24 | 22 | 38 | 55 |
|  | 5 | 67 | 54 | 61 | 18 | 36 | 50 | 61 |
|  | 7.5 | 70 | 62 | 68 | 27 | 36 | 58 | 67 |

What is claimed is:

1. A compound of Formula (I)

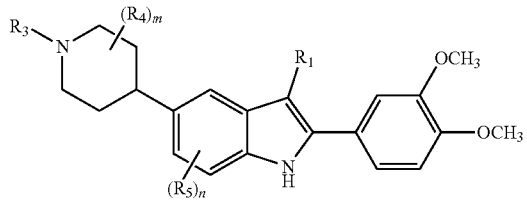

or a salt thereof, wherein:

$R_1$ is H, Cl, —CN, $C_{1-4}$ alkyl, $C_{1-3}$ fluoroalkyl, $C_{1-3}$ hydroxy-fluoroalkyl, —$CR_z$=$CH_2$, $C_{3-6}$ cycloalkyl, —$CH_2(C_{3-6}$ cycloalkyl), —C(O)O($C_{1-3}$ alkyl), or tetrahydropyranyl;

$R_3$ is:

(a) -$L_1$-A; or (b) H, $C_{1-6}$ alkyl, $C_{1-3}$ fluoroalkyl, $C_{1-3}$ cyanoalkyl, $C_{1-6}$ hydroxyalkyl, $C_{1-3}$ hydroxy-fluoroalkyl, —$CR_xR_x$-$CR_x(OH)CR_x$=$CR_xR_x$, —$(CR_xR_x)_{1-4}O(C_{1-3}$ alkyl), —$(CR_xR_x)_{1-4}O(CR_xR_x)_{1-3}O(C_{1-3}$ alkyl), —$CH_2CH(OH)CH_2O(C_{1-3}$ alkyl), —$(CR_xR_x)_{1-3}S(C_{1-3}$ alkyl), —$(CH_2)_{1-3}C(O)OC(CH_3)_3$, —$(CR_xR_x)_{0-3}NR_xR_y$, —$(CR_xR_x)_{0-3}NR_x(C_{1-4}$ hydroxyalkyl), —$CH_2CH(OH)CH_2NR_xR_y$, —$(CR_xR_x)_{1-2}NHC(O)(CR_xR_x)_{1-4}$C≡CH, —C(O)H, —C(O)($C_{1-6}$ alkyl), —C(O)($C_{1-3}$ hydroxyalkyl), —C(O)($C_{1-3}$ fluoroalkyl), —C(O)($C_{1-3}$ chloroalkyl), —C(O)($C_{1-3}$ cyanoalkyl), —$(CR_xR_x)_{0-3}C(O)OH$, —C(O)$(CH_2)_{0-2}O(C_{1-4}$ alkyl), —C(O)$(CR_xR_x)_{0-2}O(CR_xR_x)_{1-2}O(C_{1-3}$ alkyl), —C(O)$CR_xR_xS(O)_2(C_{1-3}$ alkyl), —C(O)$CR_xR_xNR_xS(O)_2(C_{1-3}$ alkyl), —C(O)$CR_xR_xOC(O)(C_{1-3}$ alkyl), —C(O)$(CR_xR_x)_{0-3}NR_xR_y$, —C(O)$(CR_xR_x)_{0-1}NR_x(C_{1-3}$ cyanoalkyl), —C(O)$(CR_xR_x)_{0-2}NR_y(C_{1-6}$ hydroxyalkyl), —C(O)$(CR_xR_x)_{0-1}NR_x(C_{1-3}$ fluoroalkyl), —C(O)$(CR_xR_x)_{0-1}NR_x(C_{1-5}$ hydroxy-fluoroalkyl), —C(O)$(CR_xR_x)_{0-1}NR_x(CH_2)_{1-2}O(C_{1-3}$ hydroxyalkyl), —C(O)$(CR_xR_x)_{0-1}NR_x(CH_2)_{1-2}NR_xC(O)(C_{1-2}$ alkyl), —C(O)$(CR_xR_x)_{0-1}NR_x((CR_xR_x)_{1-2}O(C_{1-2}$ alkyl)), —C(O)$CR_x(NH_2)(CR_xR_x)_{1-4}NR_xR_x$, —C(O)$CR_x(NH_2)(CR_xR_x)_{1-4}NR_xC(O)NR_xR_x$, —C(O)$(CR_xR_x)_{0-3}NR_x(CH_2)_{0-1}C(O)(C_{1-3}$ alkyl), —C(O)$(CR_xR_x)_{0-1}NR_x(CH_2)_{0-1}C(O)(C_{1-3}$ cyanoalkyl), —C(O)$(CR_xR_x)_{0-1}NR_x(CH_2)_{1-2}C(O)NR_yR_y$, —C(O)$(CR_xR_x)_{1-3}C(O)NR_yR_y$, —C(O)$(CR_xR_x)_{0-1}NR_x(CHR_y(CH_2OH))$, —$(CR_xR_x)_{1-2}C(O)NR_yR_y$, —$(CR_xR_x)_{1-2}C(O)NR_y(C_{1-3}$ fluoroalkyl), —$(CR_xR_x)_{1-2}C(O)NR_y(C_{1-4}$ hydroxyalkyl), —$(CR_xR_x)_{1-2}C(O)NR_y(C_{1-3}$ cyanoalkyl), —$(CR_xR_x)_{1-2}C(O)NR_x(CH_2)_{1-2}O(C_{1-3}$ alkyl), —$(CR_xR_x)_{1-2}C(O)NR_xCH(C_{1-4}$ alkyl)($C_{1-3}$ hydroxyalkyl), —$(CH_2)_{1-2}C(O)NR_x(CH_2)_{1-2}C(O)NR_xR_x$, —$(CH_2)_{1-2}C(O)NR_x(CH_2)_{1-2}S(O)_2OH$, —$(CH_2)_{1-2}C(O)NR_x(CH_2)_{1-2}NR_xC(O)(C_{1-3}$ alkyl), —$(CH_2)_{1-2}C(O)NR_x(CH_2)_{1-3}NR_xR_x$, —$(CH_2)_{1-2}C(O)N(CH_2CH_3)(CH_2)_{1-3}NR_xR_x$, —$(CH_2)_{0-2}S(O)_2(C_{1-4}$ alkyl), —$(CH_2)_{0-2}S(O)_2(C_{1-3}$ fluoroalkyl), —$(CH_2)_{0-2}S(O)_2NR_xR_x$, —C(O)C(O)OH, —C(O)C(O)$NR_yR_y$, or —C(O)C(O)$NR_y(CR_xR_x)_{1-2}NR_yR_y$;

$L_1$ is a bond, —$(CR_xR_x)_{1-2}$—, —$(CR_xR_x)_{1-2}CR_x(OH)$—, —$(CR_xR_x)_{1-2}O$—, —$CR_xR_xC(O)$—, —$(CR_xR_x)_2NR_x(CR_xR_x)_{0-1}$—, —$CR_xR_xC(O)NR_x(CR_xR_x)_{0-4}$—, —C(O)$(CR_xR_x)_{0-3}$—, —C(O)$(CR_xR_x)_{0-2}NR_x(CR_xR_x)_{0-2}$—, —C(O)$(CR_xR_x)_{0-2}N(C_{1-2}$ hydroxyalkyl)$(CR_xR_x)_{0-2}$—, —C(O)$(CR_xR_x)_{0-2}NR_x(CR_xR_x)_{1-2}CR_x(OH)$—, —C(O)$(CR_xR_x)_{1-2}C(O)NR_x$—, —$(CR_xR_x)_{0-2}C(O)NR_x(CR_xR_x)_{1-2}CR_x(OH)$—, —$(CR_xR_x)_{0-2}C(O)N(C_{1-2}$ hydroxyalkyl)$(CR_xR_x)_{1-2}$—, —C(O)$(CR_xR_x)_{0-1}O$—, —C(O)$(CR_xR_x)_{1-2}NHS(O)_2$—, —C(O)$CR_x(NH_2)CR_xR_x$—, —C(O)C(O)$(CR_xR_x)_{0-2}$—, —C(O)$NR_x(CR_xR_x)_{1-2}$—, or —S(O)$_2$—;

A is 2-oxa-6-azaspiro[3.3]heptanyl, 4-oxaspiro[2.5]octanyl, 7-azaspiro[3.5]nonanyl, 8-azabicyclo[3.2.1]octanyl, 8-oxa-3-azabicyclo[3.2.1]octanyl, 9-azabicyclo[3.3.1]nonanyl, adamantanyl, azepanyl, azetidinyl, $C_{3-6}$ cycloalkyl, diazepanyl, dihydroinonyl, dihydropyrimidinonyl, dioxidoisothiazolidinyl, dioxidothiazinanyl, dioxotetrahydrothiophenyl, dioxotetrahydrothiopyranyl, dioxothiomorpholinyl, furanyl, imidazolyl, imidazolidinonyl, indolyl, isoquinolinyl, isoxazolyl, morpholinyl, morpholinonyl, naphthalenyl, octahydrocyclopenta[b]pyranyl, oxazolidinonyl, oxadiazolyl, oxetanyl, oxazolyl, phenyl, piperidinyl, piperidinonyl, piperazinyl, piperazinonyl, pyrazinyl, pyrazolyl, pyridazinonyl, pyridinonyl, pyridinyl, pyrimidinyl, pyrrolidinonyl, pyrrolidinyl, pyrrolyl, quinolinyl, quinolizinonyl, tetrahydrofuranyl, tetrahydropyranyl, tetrazolyl, thiadiazolyl, thiazolyl, or triazolyl, each substituted with -$L_2$-$R_a$ and zero to 4 $R_b$;

$L_2$ is a bond or —$CR_xR_x$—;

$R_a$ is:

(a) H, F, Cl, —CN, —OH, $C_{1-6}$ alkyl, $C_{1-3}$ fluoroalkyl, $C_{1-5}$ hydroxyalkyl, —$(CH_2)_{0-4}O(C_{1-3}$ alkyl), —$(CR_xR_x)_{1-3}S(C_{1-3}$ alkyl), —$(CR_xR_x)_{1-3}NHC(O)O(C_{1-4}$ alkyl), —$(CR_xR_x)_{1-3}NR_yR_y$, —$(CR_xR_x)_{1-3}C(O)NR_yR_y$, —O($C_{1-3}$ fluoroalkyl), —S(O)$_2NR_xR_x$, —O$(CR_xR_x)_{1-3}NR_xR_x$, —NHS(O)$_2(C_{1-3}$ alkyl), —$NR_xR_x$, —$NR_x(C_{1-4}$ alkyl), —$NR_xC(O)(C_{1-4}$ alkyl), —$(CR_xR_x)_{0-3}C(O)OH$, —C(O)($C_{1-5}$ alkyl), —C(O)($C_{1-3}$ fluoroalkyl), —C(O)$CH_2N(C_{1-3}$ alkyl)$_2$, —C(O)O($C_{1-4}$ alkyl), —C(O)NH($C_{1-3}$ cyanoalkyl), —C(O)$NR_yR_y$, —C(O)$NR_xCH_2C(O)NR_yR_x$, or —C(O)$NR_xCH_2CH_2NHC(O)(C_{1-3}$ alkyl);

(b) $C_{3-6}$ cycloalkyl or —C(O)NH($C_{3-6}$ cycloalkyl), wherein each cycloalkyl is substituted with zero to 2 substituents independently selected from —OH, $C_{1-3}$ alkyl, $C_{1-3}$ hydroxyalkyl, $C_{1-3}$ fluoroalkyl, and —C(O)O($C_{1-3}$ alkyl); or (c) $A_1$, —$CH_2A_1$, —C(O)$A_1$, —$NR_xA_1$, or —C(O)$NR_xA_1$, wherein $A_1$ is furanyl, imidazolyl, indolyl, isoxazolyl, morpholinyl, octahydropyrrolo[3,4-c]pyrrolyl, oxazolyl, oxetanyl, phenyl, piperazinyl, piperidinyl, pyrazolyl, pyridinyl, pyrimidinyl, pyrrolidinyl, pyrrolyl, tetrahydrofuranyl, tetrahydropyranyl, thiadiazolyl, thiazolyl, thiophenyl, or triazolyl, each substituted with zero to three substituents independently selected from —OH, $C_{1-3}$ alkyl, $C_{1-3}$ hydroxyalkyl, —C(O)($C_{1-2}$ alkyl), —C(O)O($C_{1-3}$ alkyl), —$NR_xR_x$, phenyl, trifluoromethyl-phenyl, —$CH_2$(bromophenyl), and —$CH_2CH_2$(pyrrolidinyl);

each $R_b$ is independently F, —$CH_3$, —$CF_3$, or —$OCH_3$;

each $R_x$ is independently H or —$CH_3$;

each $R_y$ is independently H or $C_{1-6}$ alkyl;

$R_z$ is H, $C_{1-2}$ alkyl, or $C_{1-2}$ fluoroalkyl;

each $R_4$ is independently F or —OH; or two $R_4$ attached to the same carbon atom form =O;

$R_5$ is F, Cl, —CN, $C_{1-2}$ alkyl, $C_{1-2}$ fluoroalkyl, or —$OCH_3$;

m is zero, 1, 2, 3, or 4; and n is zero, 1, or 2;

with the proviso that when $R_1$ is —$CH_3$, then $R_3$ is not —$CH_2CH_2NH(CH_3)$.

2. The compound according to claim 1 or a salt thereof, wherein:

$R_1$ is H, Cl, —CN, $C_{1-4}$ alkyl, $C_{1-3}$ fluoroalkyl, $C_{1-3}$ hydroxy-fluoroalkyl, —$CR_z$=$CH_2$, $C_{3-6}$ cycloalkyl, —$CH_2(C_{3-6}$ cycloalkyl), —C(O)O($C_{1-3}$ alkyl), or tetrahydropyranyl;

$R_3$ is:

(a) -$L_1$-A; or (b) H, $C_{1-6}$ alkyl, $C_{1-3}$ fluoroalkyl, $C_{1-5}$ hydroxyalkyl, —$(CR_xR_x)_{1-4}O(C_{1-3}$ alkyl), —$(CR_xR_x)_{1-3}S(C_{1-3}$ alkyl), —$(CH_2)_{1-3}C(O)OC(CH_3)_3$, —$(CH_2)_{1-3}NR_xR_x$, —$CHR_xCH_2NR_x(C_{1-4}$ alkyl), —$(CH_2)_{1-3}NR_x(C_{1-3}$ alkyl), —$(CR_xR_x)_{1-2}NHC(O)(CH_2)_{1-4}C$≡$CH$, —$S(O)_2NR_xR_x$, —C(O)O($C_{1-4}$ alkyl), —C(O)($C_{1-3}$ alkyl), —C(O)($C_{1-3}$ hydroxyalkyl), —C(O)($C_{1-3}$ fluoroalkyl), —C(O)($C_{1-3}$ chloroalkyl), —C(O)$CH_2O(C_{1-3}$ alkyl), —C(O)$CH_2S(O)_2(C_{1-3}$ alkyl), —C(O)($C_{1-3}$ hydroxyalkyl), —C(O)$CR_xR_xOC(O)(C_{1-3}$ alkyl), —C(O)(tetrahydrofuranyl), —C(O)(tetrahydropyranyl), —C(O)(piperidinyl), —C(O)(ethoxypiperidinyl), —C(O)$NR_x(C_{1-3}$ cyanoalkyl), —C(O)$NR_x(C_{1-3}$ alkyl), —C(O)$NR_xCH_2C(O)NR_xR_x$, —C(O)$NR_xCH_2CH_2NR_xC(O)(C_{1-2}$ alkyl), —C(O)N($C_{1-3}$ alkyl)$_2$, —C(O)$NR_xC(R_x)_3$, —C(O)$CH_2NR_x(C_{1-3}$ cyanoalkyl), —C(O)$CH_2NR_xCH_2C(O)(C_{1-3}$ alkyl), —C(O)$CH_2NR_xCH_2C(O)N(C_{1-3}$ alkyl)$_2$, —C(O)$CH_2NR_xR_x$, —C(O)$CH_2NR_x(C_{1-2}$ alkyl), —C(O)$CH_2NR_x(C_{1-3}$ hydroxyalkyl), —C(O)$CH_2NR_x(C_{1-3}$ fluoroalkyl), —C(O)$CH_2NR_xCH_2CH_2O(C_{1-3}$ hydroxyalkyl), —C(O)$CH_2NR_xCH_2CH_2C(O)N(C_{1-2}$ alkyl)$_2$, —C(O)$CH_2NR_x(CH(CH_2OH)(C_{1-4}$ alkyl)), —C(O)$CH_2NR_x(C_{1-5}$ alkyl), —C(O)$CH_2NR_x(C_{1-5}$ hydroxy-fluoroalkyl), —C(O)$CH_2NR_x(C_{1-6}$ hydroxyalkyl), —C(O)$(CH_2)_{1-3}NR_xR_x$, —C(O)$(CH_2)_{1-3}NR_x(C_{1-3}$ alkyl), —C(O)$CH_2CH(CH_3)NR_xR_x$, —C(O)$CH_2CH_2C(O)NR_xR_x$, —$CH_2C(O)NR_xR_x$, —$CH_2C(O)NR_x(C_{1-3}$ cyanoalkyl), —$CH_2C(O)NR_xCH_2C(O)NR_xR_x$, —$CH_2C(O)NR_x(C_{1-3}$ hydroxyalkyl), —$CH_2C(O)NR_xCH_2CH_2S(O)_2OH$, —$CH_2C(O)NR_xCH_2CH_2C(O)(C_{1-3}$ alkyl), —$CH_2C(O)N(CH_2CH_3)CH_2CH_2NR_xR_x$, —$CH_2C(O)NR_x(C_{1-3}$ alkyl), —$CH_2C(O)NR_x(CH_2)_{1-3}NR_xR_x$, —$CH_2C(O)NR_x(C_{1-5}$ alkyl), —C(O)$CH_2NR_xC(O)(C_{1-3}$ cyanoalkyl), or —C(O)$(CH_2)_{1-3}NR_xC(O)(C_{1-3}$ alkyl);

$L_1$ is a bond, —$CR_xR_x$—, —$CR_xR_xC(O)$—, —$(CR_xR_x)_2NR_x(CR_xR_x)_{0-1}$—, —$CR_xR_xC(O)NR_x(CR_xR_x)_{0-4}$—, —C(O)$(CR_xR_x)_{0-3}$—, —C(O)$CR_xR_xNR_x$—, —C(O)$CR_xR_xO$—, or —C(O)$NR_x(CR_xR_x)_{1-2}$—;

A is a ring selected from adamantanyl, 8-azabicyclo[3.2.1]octanyl, azepanyl, $C_{3-6}$ cycloalkyl, diazepanyl, furanyl, imidazolyl, indolyl, isoquinolinyl, morpholinyl, naphthalenyl, oxetanyl, phenyl, piperazinyl, piperidinyl, pyrazinyl, pyrazolyl, pyridinyl, pyrrolidinonyl, pyrrolidinyl, pyrrolyl, quinolinyl, tetrahydropyranyl, tetrazolyl, thiadiazolyl, and thiazolyl, each substituted with -$L_2$-$R_a$ and zero to 4 $R_b$;

$L_2$ is a bond or —$CR_xR_x$—;

$R_a$ is:

(a) H, —CN, —OH, $C_{1-6}$ alkyl, $C_{1-3}$ fluoroalkyl, $C_{1-5}$ hydroxyalkyl, —$(CH_2)_{1-4}O(C_{1-3}$ alkyl), —$(CR_xR_x)_{1-3}S(C_{1-3}$ alkyl), —$(CR_xR_x)_{1-3}NHC(O)O(C_{1-4}$ alkyl), —$(CR_xR_x)_{1-3}NH_2$, —$(CR_xR_x)_{1-3}NR_x(C_{1-4}$ alkyl), —O($C_{1-3}$ fluoroalkyl), —$S(O)_2NR_xR_x$, —O($CR_xR_x)_{1-3}NR_xR_x$, —$NHS(O)_2(C_{1-3}$ alkyl), —$NR_xR_x$, —$NR_x(C_{1-4}$ alkyl), —$(CR_xR_x)_{1-3}C(O)OH$, —$(CR_xR_x)_{1-3}C(O)NH(C_{1-4}$ alkyl), —C(O)OH, —C(O)($C_{1-4}$ alkyl), —C(O)$CH_2N(C_{1-3}$ alkyl)$_2$, —C(O)O($C_{1-4}$ alkyl), —C(O)NH($C_{1-3}$ cyanoalkyl), —C(O)$NR_x(C_{1-4}$ alkyl), —C(O)N($C_{1-3}$ alkyl)$_2$, —C(O)$NR_xCH_2C(O)NR_xR_x$, or —C(O)$NR_xCH_2CH_2NHC(O)(C_{1-3}$ alkyl);

(b) $C_{3-6}$ cycloalkyl or —C(O)NH($C_{3-6}$ cycloalkyl), wherein each cycloalkyl is substituted with zero to 2 substituents independently selected from —OH, $C_{1-3}$ alkyl, $C_{1-3}$ hydroxyalkyl, $C_{1-3}$ fluoroalkyl, and —C(O)O($C_{1-3}$ alkyl); or (c) $A_1$, —$CH_2A_1$, —C(O)$A_1$, or —C(O)$NHA_1$, wherein $A_1$ is furanyl, imidazolyl, indolyl, isoxazolyl, octahydropyrrolo[3,4-c]pyrrolyl, oxazolyl, oxetanyl, phenyl, piperazinyl, piperidinyl, pyrazolyl, pyridinyl, pyrimidinyl, pyrrolidinyl, pyrrolyl, tetrahydrofuranyl, tetrahydropyranyl, thiadiazolyl, thiazolyl, thiophenyl, or triazolyl, each substituted with zero to three substituents independently selected from —OH, $C_{1-3}$ alkyl, $C_{1-3}$ hydroxyalkyl, —C(O)($C_{1-2}$ alkyl), —C(O)O($C_{1-3}$ alkyl), —$NR_xR_x$, phenyl, trifluoromethyl-phenyl, —$CH_2$(bromophenyl), and —$CH_2CH_2$(pyrrolidinyl);

each $R_4$ is independently F or —OH; or two $R_4$ attached to the same carbon atom form =O;

$R_5$ is F, —$CH_3$, or —$OCH_3$;

$R_b$ is —$CH_3$;

each $R_x$ is independently H or —$CH_3$;

m is zero, 1, or 2; and n is zero or 1;

with the proviso that when $R_1$ is —$CH_3$, then $R_3$ is not —$CH_2CH_2NH(CH_3)$.

3. The compound according to claim 1 or a salt thereof, wherein:

$R_1$ is H, Cl, —CN, $C_{1-4}$ alkyl, $C_{1-2}$ fluoroalkyl, —CH(CF$_3$)OH, —$CH_2$(cyclopropyl), or tetrahydropyranyl;

$R_3$ is:

(a) -$L_1$-A; or (b) H, $C_{1-6}$ alkyl, $C_{1-3}$ fluoroalkyl, $C_{1-5}$ hydroxyalkyl, —$(CH_2)_{1-4}OCH_3$, —$(CR_xR_x)_{1-3}SCH_3$, —$CH_2CH_2NHC(O)OC(CH_3)_3$, —$CH_2CH_2NR_xR_x$, —$CHR_xCH_2NR_x(C_{1-4}$ alkyl), —$CH_2CH_2CH_2NH(CH_3)$, —$(CH_2)_{1-2}NHC(O)(CH_2)_{1-4}C$≡$CH$, —$S(O)_2NR_xR_x$, —C(O)O($C_{1-4}$ alkyl), —C(O)($C_{1-2}$ alkyl), —C(O)($C_{1-3}$ hydroxyalkyl), —C(O)($C_{1-2}$ chloroalkyl), —C(O)($C_{1-3}$ fluoroalkyl), —C(O)$CH_2O(C_{1-3}$ alkyl), —C(O)$CH_2S(O)_2(C_{1-2}$ alkyl), —C(O)$CR_xR_xOC(O)(C_{1-2}$ alkyl), —C(O)(tetrahydrofuranyl), —C(O)(ethoxypiperidinyl), —C(O)$NR_xCH_2CN$, —C(O)NH($C_{1-3}$ alkyl), —C(O)$NR_xCH_2C(O)NH_2$, —C(O)$NR_xCH_2CH_2NHC(O)(C_{1-2}$ alkyl), —C(O)N($C_{1-3}$ alkyl)$_2$, —C(O)$NR_xC(R_x)_3$, —C(O)$CH_2NR_xR_x$, —C(O)$CH_2NR_xCH_2CN$, —C(O)$CH_2NR_xCH_2C(O)(C_{1-2}$ alkyl), —C(O)$CH_2NR_xC(O)N(C_{1-2}$ alkyl)$_2$, —C(O)$CH_2NR_xR_x$, —C(O)$CH_2NR_x(C_{1-2}$ alkyl), —C(O)$CH_2NR_xCH_2CH_2OH$, —C(O)$CH_2NR_x(C_{1-2}$ fluoroalkyl), —C(O)$CH_2NR_xCH_2CH_2OCH_2CH_2OH$, —C(O)$CH_2NR_xCH_2C(O)N(C_{1-2}$ alkyl)$_2$, —C(O)$CH_2NR_x(CH(CH_2OH)(C_{1-4}$ alkyl)), —C(O)$CH_2NR_x(C_{1-4}$ hydroxyalkyl), —C(O)$CH_2NR_x(C_{1-5}$ alkyl), —C(O)$CH_2NR_xCH_2CHFC(CH_3)_2OH$, —C(O)

CH$_2$NR$_x$(C$_{1-6}$ hydroxyalkyl), —C(O)CH$_2$CH$_2$NR$_x$R$_x$, —C(O)CH$_2$CH$_2$CH$_2$NR$_x$R$_x$, —C(O)CH$_2$CH$_2$CH$_2$NR$_x$(C$_{1-3}$ alkyl), —C(O)CH$_2$CH(CH$_3$)NR$_x$R$_x$, —C(O)CH$_2$CH$_2$C(O)NR$_x$R$_x$, —CH$_2$C(O)NR$_x$R$_x$, —CH$_2$C(O)NR$_x$CH$_2$CN, —CH$_2$C(O)NR$_x$CH$_2$C(O)NR$_x$R$_x$, —CH$_2$C(O)NR$_x$(C$_{1-3}$ hydroxyalkyl), —CH$_2$C(O)NR$_x$CH$_2$CH$_2$S(O)$_2$OH, —CH$_2$C(O)NR$_x$CH$_2$CH$_2$NR$_x$R$_x$, —CH$_2$C(O)NR$_x$CH$_2$CH$_2$NR$_x$C(O)(C$_{1-2}$ alkyl), —CH$_2$C(O)N(CH$_2$CH$_3$)CH$_2$CH$_2$NR$_x$R$_x$, —CH$_2$C(O)NR$_x$(C$_{1-3}$ alkyl), —CH$_2$C(O)NR$_x$CH$_2$CH$_2$CH$_2$NR$_x$R$_x$, —CH$_2$C(O)NR$_x$(C$_{1-5}$ alkyl), —C(O)CH$_2$NR$_x$C(O)CH$_2$CH$_2$CH$_2$CN, or —C(O)CH$_2$CH$_2$CH$_2$NR$_x$C(O)(C$_{1-2}$ alkyl);

L$_1$ is a bond, —CHR$_x$—, —CHR$_x$C(O)—, —(CH$_2$)$_2$NR$_x$(CH$_2$)$_{0-1}$—, —CH$_2$C(O)NR$_x$(CH$_2$)$_{0-4}$—, —C(O)(CH$_2$)$_{0-3}$—, —C(O)CH$_2$NR$_x$—, —C(O)CH$_2$O—, or —C(O)NR$_x$(CH$_2$)$_{1-2}$—;

A is a ring selected from adamantanyl, azabicyclo[3.2.1]octanyl, azepanyl, C$_{3-6}$ cycloalkyl, diazepanyl, furanyl, imidazolyl, indolyl, isoquinolinyl, morpholinyl, naphthalenyl, oxetanyl, phenyl, piperazinyl, piperidinyl, pyrazinyl, pyrazolyl, pyridinyl, pyrrolidinonyl, pyrrolidinyl, pyrrolyl, quinolinyl, tetrahydropyranyl, tetrazolyl, thiadiazolyl, and thiazolyl, each substituted with -L$_2$-R$_a$ and zero to 4 R$_b$;

and

R$_a$ is:
(a) H, —CN, —OH, C$_{1-6}$ alkyl, C$_{1-3}$ fluoroalkyl, C$_{1-5}$ hydroxyalkyl, —(CH$_2$)$_{1-4}$OCH$_3$, —(CR$_x$R$_x$)$_{1-3}$SCH$_3$, —CH$_2$CH$_2$NHC(O)OC(CH$_3$)$_3$, —CH$_2$CH$_2$NH$_2$, —CHR$_x$CH$_2$NR$_x$(C$_{1-4}$ alkyl), —CH$_2$CH$_2$CH$_2$NH(CH$_3$), —OCF$_3$, —S(O)$_2$NR$_x$R$_x$, —OCH$_2$CH$_2$CH$_2$NR$_x$R$_x$, —NHS(O)$_2$(C$_{1-2}$ alkyl), —NR$_x$R$_x$, —NR$_x$(C$_{1-4}$ alkyl), —CH$_2$CH$_2$C(O)OH, —CH$_2$C(O)NH(C$_{1-3}$ alkyl), —C(O)OH, —C(O)(C$_{1-3}$ alkyl), —C(O)CH$_2$N(C$_{1-3}$ alkyl)$_2$, —C(O)O(C$_{1-3}$ alkyl), —C(O)NHCH$_2$CN, —C(O)NR$_x$(C$_{1-4}$ alkyl), —C(O)N(C$_{1-3}$ alkyl)$_2$, —C(O)NHCH$_2$C(O)NR$_x$R$_x$, or —C(O)NHCH$_2$CH$_2$NHC(O)(C$_{1-3}$ alkyl);
(b) C$_{3-6}$ cycloalkyl or —C(O)NH(C$_{3-6}$ cycloalkyl), wherein each cycloalkyl is substituted with zero to 1 substituent selected from —OH, C$_{1-3}$ alkyl, C$_{1-3}$ hydroxyalkyl, C$_{1-2}$ fluoroalkyl, and —C(O)O(C$_{1-3}$ alkyl); or
(c) A$_1$, —CH$_2$A$_1$, —C(O)A$_1$, or —C(O)NHA$_1$, wherein A$_1$ is furanyl, imidazolyl, indolyl, isoxazolyl, octahydropyrrolo[3,4-c]pyrrolyl, oxazolyl, oxetanyl, phenyl, piperazinyl, piperidinyl, pyrazolyl, pyridinyl, pyrimidinyl, pyrrolidinyl, pyrrolyl, tetrahydrofuranyl, tetrahydropyranyl, thiadiazolyl, thiazolyl, thiophenyl, or triazolyl, each substituted with zero to three substituents independently selected from —OH, C$_{1-3}$ alkyl, C$_{1-3}$ hydroxyalkyl, —C(O)(C$_{1-2}$ alkyl), —C(O)O(C$_{1-3}$ alkyl), —NR$_x$R$_x$, phenyl, trifluoromethyl-phenyl, —CH$_2$(bromophenyl), and —CH$_2$CH$_2$(pyrrolidinyl).

4. The compound according to claim 1 or a salt thereof, wherein:
R$_1$ is H, Cl, —CN, —CH$_3$, —CH$_2$CH$_3$, —CH$_2$CH$_2$CH$_3$, —CH(CH$_3$)$_2$, —CH$_2$CH(CH$_3$)$_2$, —CH$_2$CHF$_2$, —CH$_2$CF$_3$, —CH(CF$_3$)OH, —CH$_2$(cyclopropyl), or tetrahydropyranyl;

R$_3$ is:
(a) -L$_1$-A; or
(b) H, —CH$_3$, —CH$_2$CH(CH$_3$)$_2$, —CH$_2$CH(CH$_3$)CF$_3$, —CH$_2$CH$_2$CH$_2$OH, —CH(CH$_3$)CH$_2$OH, —CH$_2$CH$_2$NHC(O)OC(CH$_3$)$_3$, —CH$_2$CH$_2$NH$_2$, —CH$_2$CH$_2$NH(CH$_3$), —CH$_2$CH$_2$N(CH$_3$)$_2$, —CH$_2$CH$_2$N(CH$_3$)(CH$_2$CH$_3$), —CH$_2$CH$_2$N(CH$_3$)(CH$_2$CH(CH$_3$)$_2$), —CH$_2$CH$_2$CH$_2$N(CH$_3$), —CH(CH$_3$)CH$_2$N(CH$_3$)$_2$, —CH$_2$CH$_2$NHC(O)(CH$_2$)$_4$C≡CH, —C(O)OC(CH$_3$)$_3$, —C(O)CH$_3$, —C(O)CH$_2$OH, —C(O)CH$_2$Cl, —C(O)CH$_2$CF$_3$, —C(O)CH$_2$CH$_2$CF$_3$, —C(O)CH$_2$OCH(CH$_3$)$_2$, —C(O)CH$_2$S(O)$_2$CH$_3$, —C(O)CH$_2$CH(CH$_3$)OH, —C(O)C(CH$_3$)$_2$OC(O)CH$_3$, —C(O)NHCH$_2$CH$_3$, —C(O)NHCH(CH$_3$)$_2$, —C(O)CH$_2$NHCH$_3$, —C(O)CH$_2$NHCH$_2$CN, —C(O)CH$_2$NHCH$_2$C(O)CH$_3$, —C(O)CH$_2$N(CH$_3$)CH$_2$C(O)N(CH$_2$CH$_3$)$_2$, —C(O)CH$_2$N(CH$_3$)$_2$, —C(O)CH$_2$NHCH$_2$CH$_3$, —C(O)CH$_2$NHCH$_2$CH$_2$OH, —C(O)CH$_2$NHCH$_2$CF$_3$, —C(O)CH$_2$NHCH$_2$CH$_2$OCH$_2$CH$_2$OH, —C(O)CH$_2$N(CH$_3$)CH$_2$CH$_2$C(O)N(CH$_2$CH$_3$)$_2$, —C(O)CH$_2$NHCH(CH$_2$OH)CH$_2$CH$_3$, —C(O)CH$_2$NHCH(CH$_2$OH)$_2$, —C(O)CH$_2$N(CH$_3$)CH$_2$CH$_2$OH, —C(O)CH$_2$NHCH$_2$CH(CH$_3$)OH, —C(O)CH$_2$NHCH$_2$CH(OH)CH$_2$OH, —C(O)CH$_2$N(CH$_3$)CH(CH$_3$)$_2$, —C(O)CH$_2$NHCH$_2$CH(CH$_3$)$_2$, —C(O)CH$_2$NHCH(CH$_3$)CH(CH$_3$)$_2$, —C(O)CH$_2$NHCH$_2$CH$_2$CH(CH$_3$)OH, —C(O)CH$_2$NH(CH$_2$OH)(CH$_2$CH$_2$CH$_3$), —C(O)CH$_2$NHCH(CH$_2$OH)CH$_2$CH(CH$_3$)$_2$, —C(O)CH$_2$NH(CH(CH$_2$CH$_3$)$_2$, —C(O)CH$_2$NHCH$_2$CHFC(CH$_3$)$_2$OH, —C(O)CH$_2$NHCH$_2$C(CH$_3$)$_2$CH$_2$OH, —C(O)CH$_2$NHCH(CH$_2$OH)CH(CH$_3$)$_2$, —C(O)CH$_2$CH$_2$N(CH$_3$)$_2$, —C(O)CH$_2$CH$_2$CH$_2$N(CH$_3$)$_2$, —C(O)CH$_2$CH$_2$CH$_2$NHCH(CH$_3$)$_2$, —C(O)CH$_2$CH(CH$_3$)NH$_2$, —C(O)CH$_2$CH$_2$C(O)NH$_2$, —C(O)CH$_2$CH$_2$C(O)N(CH$_3$)$_2$, —CH$_2$C(O)N(CH$_3$)$_2$, —CH$_2$C(O)NHC(CH$_3$)$_3$, —CH$_2$C(O)NHCH$_2$CN, —CH$_2$C(O)NHCH$_2$C(O)NH$_2$, —CH$_2$C(O)NHCH$_2$CH$_2$OH, —CH$_2$C(O)NHCH$_2$CH$_2$S(O)$_2$OH, —CH$_2$C(O)NHCH$_2$CH$_2$N(CH$_3$)$_2$, —CH$_2$C(O)NHCH$_2$CH$_2$NHC(O)CH$_3$, —CH$_2$C(O)N(CH$_3$)CH$_2$CH$_2$N(CH$_3$)$_2$, —CH$_2$C(O)N(CH$_2$CH$_3$)CH$_2$CH$_2$N(CH$_3$)$_2$, —CH$_2$C(O)NHCH(CH$_3$)$_2$, —CH$_2$C(O)NHCH$_2$CH$_2$OH, —CH$_2$C(O)NHCH$_2$CH$_2$N(CH$_3$)$_2$, —CH$_2$C(O)N(CH$_3$)CH$_2$CH$_2$N(CH$_3$)$_2$, —CH$_2$C(O)NHCH(CH$_3$)(CH$_2$CH$_3$), —CH$_2$C(O)NHCH(CH$_2$CH$_3$)$_2$, —C(O)CH$_2$NHC(O)CH$_2$CH$_2$CH$_2$CN, —C(O)CH$_2$CH$_2$CH$_2$NHC(O)CH$_3$, or —CH$_2$CH$_2$NHC(O)CH$_2$CH$_2$CH$_2$C≡CH;

L$_1$ is a bond, —CHR$_x$—, —CH$_2$C(O)—, —(CH$_2$)$_2$NR$_x$(CH$_2$)$_{0-1}$—, —CH$_2$C(O)NR$_x$(CH$_2$)$_{0-4}$—, —C(O)(CH$_2$)$_{0-3}$—, —C(O)CH$_2$NH—, —C(O)CH$_2$O—, or —C(O)NH(CH$_2$)$_{1-2}$—;

A is a ring selected from adamantanyl, azabicyclo[3.2.1]octanyl, azepanyl, cyclohexyl, cyclopentyl, cyclopropyl, diazepanyl, furanyl, imidazolyl, indolyl, isoquinolinyl, morpholinyl, naphthalenyl, oxetanyl, phenyl, piperazinyl, piperidinyl, pyrazinyl, pyrazolyl, pyridinyl, pyrrolidinonyl, pyrrolidinyl, pyrrolyl, quinolinyl, tetrahydropyranyl, tetrazolyl, thiadiazolyl, and thiazolyl, each substituted with -L$_2$-R$_a$ and zero to 4 R$_b$;

L$_2$ is a bond or —CHR$_x$—;

R$_a$ is:
(a) H, —CN, —OH, C$_{1-6}$ alkyl, —CF$_3$, —CH$_2$CH$_2$CF$_3$, —CH$_2$OH, —C(CH$_3$)$_2$OH, —CH$_2$CH$_2$CH(CH$_3$)OH, —CH$_2$C(CH$_3$)$_2$CH$_2$OH, —CH$_2$CH(OH)CH$_2$OH, —CH(OH)CH$_2$CH$_2$CH$_2$OH, —CH₂CH₂CH₂SCH₃, —CH₂CH₂CH₂CH₂CH₂OCH₃, —CH₂CH₂CH₂C(O)OH, —OCF₃, —OCH₂CH₂CH₂N(CH₃)₂, —NH₂, —N(CH₃)₂, —N(CH₃)(CH₂CH(CH₃)₂), —NH(CH(CH₃)₂), —S(O)₂NH₂, —NHS(O)₂CH₃, —CH₂C(O)NHCH(CH₃)₂, —C(O)H, —C(O)CH₃, —C(O)OCH₂CH₃, —C(O)CH₂N(CH₃)₂, —C(O)NHCH₂CN, —C(O)NHCH(CH₃)₂, —C(O)N(C₁₋₂ alkyl)₂, —C(O)N(CH₃)CH(CH₃)₂, —C(O)NHCH₂C(O)NH₂, or —C(O)NHCH₂CH₂NHC(O)CH₃;

(b) C₃₋₆ cycloalkyl or —C(O)NH(C₃₋₆ cycloalkyl), wherein each cycloalkyl is substituted with zero to 1 substituent selected from —OH, —CH₃, —CH₂OH, —CF₃, and —C(O)OCH₂CH₃; or (c) A₁, —CH₂A₁, —C(O)A₁, or —C(O)NHA₁, wherein A₁ is furanyl, imidazolyl, indolyl, isoxazolyl, octahydropyrrolo[3,4-c]pyrrolyl, oxazolyl, oxetanyl, phenyl, piperazinyl, piperidinyl, pyrazolyl, pyridinyl, pyrimidinyl, pyrrolidinyl, pyrrolyl, tetrahydrofuranyl, tetrahydropyranyl, thiadiazolyl, thiazolyl, thiophenyl, or triazolyl, each substituted with zero to three substituents independently selected from —OH, —CH₃, —CH(CH₃)₂, —CH₂OH, —C(O)CH₃, —C(O)OCH₂CH₃, —N(CH₃)₂, phenyl, trifluoromethyl-phenyl, —CH₂(bromophenyl), and —CH₂CH₂(pyrrolidinyl); and each R₄ is independently F or —OH; or two R₄ attached to the same carbon atom form =O.

5. The compound according to claim 1 or a salt thereof, wherein:
R₃ is -L₁-A.

6. The compound according to claim 1 or a salt thereof, wherein:
R₃ is H, —CH₃, —CH₂CH(CH₃)₂, —CH₂CH(CH₃)CF₃, —CH₂CH₂CH₂OH, —CH(CH₃)CH₂OH, —CH₂CH₂NHC(O)OC(CH₃)₃, —CH₂CH₂NH₂, —CH₂CH₂NH(CH₃), —CH₂CH₂N(CH₃)(CH₂CH₃), —CH₂CH₂N(CH₃)(CH₂CH(CH₃)₂), —CH₂CH₂CH₂NH(CH₃), —CH(CH₃)CH₂N(CH₃)₂, —C(O)OC(CH₃)₃, —C(O)CH₃, —C(O)CH₂OH, —C(O)CH₂Cl, —C(O)CH₂CF₃, —C(O)CH₂CH₂CF₃, —C(O)CH₂OCH(CH₃)₂, —C(O)CH₂S(O)₂CH₃, —C(O)CH(CH₃)OH, —C(O)C(CH₃)₂OC(O)CH₃, —C(O)NHCH₂CH₃, —C(O)NHCH(CH₃)₂, —C(O)CH₂NHCH₃, —C(O)CH₂NHCH₂CN, —C(O)CH₂NHCH₂C(O)CH₃, —C(O)CH₂N(CH₃)CH₂C(O)N(CH₂CH₃)₂, —C(O)CH₂N(CH₃)₂, —C(O)CH₂NHCH₂CH₃, —C(O)CH₂NHCH₂CH₂OH, —C(O)CH₂NHCH₂CF₃, —C(O)CH₂NHCH₂CH₂OCH₂CH₂OH, —C(O)CH₂N(CH₃)CH₂CH₂C(O)N(CH₂CH₃)₂, —C(O)CH₂NH(CH₂OH)CH₂CH₃, —C(O)CH₂NHCH(CH₂OH)₂, —C(O)CH₂N(CH₃)CH₂CH₂OH, —C(O)CH₂NHCH₂CH(CH₃)OH, —C(O)CH₂NHCH(OH)CH₂OH, —C(O)CH₂N(CH₃)CH(CH₃)₂, —C(O)CH₂NHCH₂CH(CH₃)₂, —C(O)CH₂NHCH(CH₃)CH(CH₃)₂, —C(O)CH₂NHCH₂CH(CH₃)OH, —C(O)CH₂NH(CH₂OH)(CH₂CH₂CH₂CH₃), —C(O)CH₂NH(CH₂OH)CH₂CH(CH₃)₂, —C(O)CH₂NH(CH(CH₂CH₃)₂), —C(O)CH₂NHCH₂CHFC(CH₃)₂OH, —C(O)CH₂NHCH₂C(CH₃)₂CH₂OH, —C(O)CH₂NHCH(CH₂OH)CH₂CH(CH₃)₂, —C(O)CH₂CH₂N(CH₃)₂, —C(O)CH₂CH₂N(CH₃)₂, —C(O)CH₂CH₂NHCH(CH₃)₂, —C(O)CH₂CH(CH₃)NH₂, —C(O)CH₂CH₂C(O)NH₂, —C(O)CH₂CH₂C(O)N(CH₃)₂, —CH₂C(O)N(CH₃)₂, —CH₂C(O)NHCH₂CN, —CH₂C(O)NHCH₂C(O)NH₂, —CH₂C(O)NHCH₂CH₂OH, —CH₂C(O)NHCH₂CH₂S(O)₂OH, —CH₂C(O)NHCH₂CH₂N(CH₃)₂, —CH₂C(O)NHCH₂NHC(O)CH₃, —CH₂C(O)NHCH₂CH₂NHC(O)CH₃, —CH₂C(O)N(CH₃)CH₂CH₂N(CH₃)₂, —CH₂C(O)N(CH₂CH₃)CH₂CH₂N(CH₃)₂, —CH₂C(O)NHCH(CH₃)₂, —CH₂C(O)NHCH₂CH₂OH, —CH₂C(O)NHCH₂CH₂CH₂N(CH₃)₂, —CH₂C(O)N(CH₃)CH₂CH₂CH₂N(CH₃)₂, —CH₂C(O)NHCH(CH₃)(CH₂CH₃), —CH₂C(O)NHCH(CH₂CH₃)₂, —C(O)CH₂NHC(O)CH₂CH₂CH₂CN, or —C(O)CH₂CH₂CH₂NHC(O)CH₃.

7. The compound according to claim 1 or a salt thereof, wherein said compound is selected from 2-(3,4-dimethoxyphenyl)-3-methyl-5-(piperidin-4-yl)-1H-indole hydrochloride (1); 5-([1,4'-bipiperidin]-4-yl)-2-(3,4-dimethoxyphenyl)-3-methyl-1H-indole dihydrochloride (2); 5-(1'-(cyclopropylmethyl)-[1,4'-bipiperidin]-4-yl)-2-(3,4-dimethoxyphenyl)-3-methyl-1H-indole (3); 2-(3,4-dimethoxyphenyl)-3-methyl-5-(1-((2-methyl-1H-imidazol-5-yl)methyl)piperidin-4-yl)-1H-indole (4); 3-(4-(2-(3,4-dimethoxyphenyl)-3-methyl-1H-indol-5-yl)piperidin-1-yl)propan-1-ol (5); 2-(3,4-dimethoxyphenyl)-5-(1'-isobutyl-[1,4'-bipiperidin]-4-yl)-3-methyl-1H-indole (6); 2-(3,4-dimethoxyphenyl)-3-methyl-5-(1-(oxetan-3-yl)piperidin-4-yl)-1H-indole (7); 2-(3,4-dimethoxyphenyl)-3-methyl-5-(1-(1-phenylpyrrolidin-3-yl)piperidin-4-yl)-1H-indole (8); 5-(1'-benzyl-[1,4'-bipiperidin]-4-yl)-2-(3,4-dimethoxyphenyl)-3-methyl-1H-indole (9); 2-(3,4-dimethoxyphenyl)-5-(1'-isopropyl-[1,4'-bipiperidin]-4-yl)-3-methyl-1H-indole (10); 2-(3,4-dimethoxyphenyl)-3-methyl-5-(1'-methyl-[1,4'-bipiperidin]-4-yl)-1H-indole (11); 1-(4-(2-(3,4-dimethoxyphenyl)-3-methyl-1H-indol-5-yl)-[1,4'-bipiperidin]-1'-yl)ethan-1-one (12); ethyl 3-(4-(2-(3,4-dimethoxyphenyl)-3-methyl-1H-indol-5-yl)piperidin-1-yl) pyrrolidine-1-carboxylate (13); 4-((4-(2-(3,4-dimethoxyphenyl)-3-methyl-1H-indol-5-yl) piperidin-1-yl)methyl)thiazol-2-amine (14); 5-((4-(2-(3,4-dimethoxyphenyl)-3-methyl-1H-indol-5-yl)piperidin-1-yl)methyl)quinoline (15); 2-(3,4-dimethoxyphenyl)-3-methyl-5-(1-((1-methyl-1H-imidazol-2-yl)methyl)piperidin-4-yl)-1H-indole (16); 2-(3,4-dimethoxyphenyl)-3-methyl-5-(1-((tetrahydro-2H-pyran-4-yl)methyl)piperidin-4-yl)-1H-indole (17); 2-((4-(2-(3,4-dimethoxyphenyl)-3-methyl-1H-indol-5-yl)piperidin-1-yl) methyl)quinoline (18); 4-((4-(2-(3,4-dimethoxyphenyl)-3-methyl-1H-indol-5-yl) piperidin-1-yl)methyl)-N,N-dimethylnaphthalen-1-amine (19); 2-(3,4-dimethoxyphenyl)-3-methyl-5-(1-(pyridin-4-ylmethyl)piperidin-4-yl)-1H-indole (20); 2-(3,4-dimethoxyphenyl)-3-methyl-5-(1-((1R,5S)-8-methyl-8-azabicyclo[3.2.1]octan-3-yl) piperidin-4-yl)-1H-indole (21); 2-(3,4-dimethoxyphenyl)-3-methyl-5-(1',2',2',6',6'-pentamethyl-[1,4'-bipiperidin]-4-yl)-1H-indole (22); 5-(1'-cyclopropyl-[1,4'-bipiperidin]-4-yl)-2-(3,4-dimethoxyphenyl)-3-methyl-1H-indole (23); 2-(3,4-dimethoxyphenyl)-5-(1'-ethyl-[1,3'-bipiperidin]-4-yl)-3-methyl-1H-indole (24); 3-(4-(2-(3,4-dimethoxyphenyl)-3-methyl-1H-indol-5-yl)piperidin-1-yl)-N,N-dimethylcyclohexan-1-amine (25); 2-(3,4-dimethoxyphenyl)-3-methyl-5-(1'-(tetrahydro-2H-pyran-4-yl)-[1,4'-bipiperidin]-4-yl)-1H-indole (26); 2-(3,4-dimethoxyphenyl)-3-methyl-5-(1-(1-phenylethyl)piperidin-4-yl)-1H-indole (27); 2-(3,4-dimethoxyphenyl)-3-methyl-5-(1-(pyridin-2-ylmethyl) piperidin-4-yl)-1H-indole (28); 2-(3,4-dimethoxyphenyl)-3-methyl-5-(1-((1-methyl-1H-pyrrol-2-yl) methyl)piperidin-4-yl)-1H-indole (29); 2-(4-(2-(3,4-dimethoxyphenyl)-3-methyl-1H-indol-5-yl)piperidin-1-yl)-N,N-dimethylpropan-1-amine (30); 6-((4-(2-(3,4-dimethoxyphenyl)-3-methyl- 1H-indol-5-yl)piperidin-1-yl)methyl)isoquinoline (31); 4-((4-(2-(3,4-dimethoxyphenyl)-3-methyl-1H-indol-5-yl)piperidin-1-yl)methyl)quinoline (32); 2-(3,4-dimethoxyphenyl)-3-methyl-5-(1-((1-methyl-1H-indol-2-yl)methyl) piperidin-4-yl)-1H-indole (33); 5-(1-(4-(1H-1,2,4-triazol-1-yl)benzyl)piperidin-4-yl)-2-(3,4-dimethoxyphenyl)-3-methyl-1H-indole (34); 2-((4-(2-(3,4-dimethoxyphenyl)-3-methyl-1H-indol-5-yl)piperidin-1-yl)methyl)quinoline (35); 8-((4-(2-(3,4-dimethoxyphenyl)-3-methyl-1H-indol-5-yl)piperidin-1-yl)methyl)quinoline (36); 4-((4-(2-(3,4-dimethoxyphenyl)-3-methyl-1H-indol-5-yl)piperidin-1-yl)methyl)-N,N-dimethylaniline (37); 3-(4-((4-(2-(3,4-dimethoxyphenyl)-3-methyl-1H-indol-5-yl) piperidin-1-yl)methyl)phenoxy)-N,N-dimethylpropan-1-amine (38); 5-(1-(4-(1H-imidazol-1-yl)benzyl)piperidin-4-yl)-2-(3,4-dimethoxyphenyl)-3-methyl-1H-indole (39); 2-(3,4-dimethoxyphenyl)-3-methyl-5-(1-((1-methyl-1H-imidazol-5-yl)methyl)piperidin-4-yl)-1H-indole (40); 4-((4-(2-(3,4-dimethoxyphenyl)-3-methyl-1H-indol-5-yl)piperidin-1-yl)methyl)-1,2,3-thiadiazole (41); 2-(3,4-dimethoxyphenyl)-3-methyl-5-(1-(4-(4-methylpiperazin-1-yl)benzyl)piperidin-4-yl)-1H-indole (42); 2-(4-(2-(3,4-dimethoxyphenyl)-3-methyl-1H-indol-5-yl)piperidin-1-yl)propan-1-ol (43); 2-(3,4-dimethoxyphenyl)-5-(1'-ethyl-[1,4'-bipiperidin]-4-yl)-3-methyl-1H-indole (44); 5-(1-((1-benzylpyrrolidin-3-yl)methyl)piperidin-4-yl)-2-(3,4-dimethoxyphenyl)-3-methyl-1H-indole (45); 2-(3,4-dimethoxyphenyl)-3-methyl-5-(1-(4-(pyrrolidin-1-yl)benzyl) piperidin-4-yl)-1H-indole (46); 2-(3,4-dimethoxyphenyl)-3-methyl-5-(1-(pyridin-3-ylmethyl)piperidin-4-yl)-1H-indole (47); 2-(3,4-dimethoxyphenyl)-3-methyl-5-(2',2',6',6'-tetramethyl-[1,4'-bipiperidin]-4-yl)-1H-indole (48); 2-(3,4-dimethoxyphenyl)-3-methyl-5-(1-((1-methylpiperidin-2-yl)methyl)piperidin-4-yl)-1H-indole (49); 2-(3,4-dimethoxyphenyl)-3-methyl-5-(1'-(3,3,3-trifluoropropyl)-[1,4'-bipiperidin]-4-yl)-1H-indole (50); 2-(3,4-dimethoxyphenyl)-3-methyl-5-(1'-(2-methylbutyl)-[1,4'-bipiperidin]-4-yl)-1H-indole (51); 3-(4-(2-(3,4-dimethoxyphenyl)-3-methyl-1H-indol-5-yl)-[1,4'-bipiperidin]-1'-yl)propane-1,2-diol (52); 2-(3,4-dimethoxyphenyl)-3-methyl-5-(1'-(3-(methylthio)propyl)-[1,4'-bipiperidin]-4-yl)-1H-indole (53); 2-(3,4-dimethoxyphenyl)-5-(1'-(2-ethylbutyl)-[1,4'-bipiperidin]-4-yl)-3-methyl-1H-indole (54); 2-(3,4-dimethoxyphenyl)-3-methyl-5-(1'-pentyl-[1,4'-bipiperidin]-4-yl)-1H-indole (55); 4-(4-(2-(3,4-dimethoxyphenyl)-3-methyl-1H-indol-5-yl)-[1,4'-bipiperidin]-1'-yl)butan-2-ol (56); 2-(3,4-dimethoxyphenyl)-5-(1'-(5-methoxypentyl)-[1,4'-bipiperidin]-4-yl)-3-methyl-1H-indole (57); 5-(1'-(cyclohexylmethyl)-[1,4'-bipiperidin]-4-yl)-2-(3,4-dimethoxyphenyl)-3-methyl-1H-indole (58); 2-(3,4-dimethoxyphenyl)-3-methyl-5-(1'-((1-methyl-1H-imidazol-5-yl)methyl)-[1,4'-bipiperidin]-4-yl)-1H-indole (59); ethyl 2-((4-(2-(3,4-dimethoxyphenyl)-3-methyl-1H-indol-5-yl)-[1,4'-bipiperidin]-1'-yl)methyl)cyclopropane-1-carboxylate (60); 5-(1'-cyclobutyl-[1,4'-bipiperidin]-4-yl)-2-(3,4-dimethoxyphenyl)-3-methyl-1H-indole (61); 5-(1'-cyclopentyl-[1,4'-bipiperidin]-4-yl)-2-(3,4-dimethoxyphenyl)-3-methyl-1H-indole (62); 2-(3,4-dimethoxyphenyl)-3-methyl-5-(1'-propyl-[1,4'-bipiperidin]-4-yl)-1H-indole (63); 2-(3,4-dimethoxyphenyl)-3-methyl-5-(1'-(thiophen-2-ylmethyl)-[1,4'-bipiperidin]-4-yl)-1H-indole (64); 5-(1'-(cyclopentylmethyl)-[1,4'-bipiperidin]-4-yl)-2-(3,4-dimethoxyphenyl)-3-methyl-1H-indole (65); 5-(1'-(sec-butyl)-[1,4'-bipiperidin]-4-yl)-2-(3,4-dimethoxyphenyl)-3-methyl-1H-indole (66); 2-(3,4-dimethoxyphenyl)-3-methyl-5-(1'-(3-methylcyclohexyl)-[1,4'-bipiperidin]-4-yl)-1H-indole (67); 5-(1'-cyclohexyl-[1,4'-bipiperidin]-4-yl)-2-(3,4-dimethoxyphenyl)-3-methyl-1H-indole (68); 3-(4-(2-(3,4-dimethoxyphenyl)-3-methyl-1H-indol-5-yl)-[1,4'-bipiperidin]-1'-yl)-2,2-dimethylpropan-1-ol (69); 4-(4-(2-(3,4-dimethoxyphenyl)-3-methyl-1H-indol-5-yl)-[1,4'-bipiperidin]-1'-yl)butanoic acid (70); 5-(1'-(sec-butyl)-[1,4'-bipiperidin]-4-yl)-2-(3,4-dimethoxyphenyl)-3-methyl-1H-indole (71); 2-((4-(2-(3,4-dimethoxyphenyl)-3-methyl-1H-indol-5-yl)-[1,4'-bipiperidin]-1'-yl)methyl) thiazole (72); 2-(3,4-dimethoxyphenyl)-3-methyl-5-(1'-(3-(trifluoromethyl)cyclohexyl)-[1,4'-bipiperidin]-4-yl)-1H-indole (73); 2-(3,4-dimethoxyphenyl)-3-methyl-5-(1'-(tetrahydrofuran-3-yl)-[1,4'-bipiperidin]-4-yl)-1H-indole (74); 2-(3,4-dimethoxyphenyl)-3-methyl-5-(1'-neopentyl-[1,4'-bipiperidin]-4-yl)-1H-indole (75); 2-(3,4-dimethoxyphenyl)-5-(1'-(furan-2-ylmethyl)-[1,4'-bipiperidin]-4-yl)-3-methyl-1H-indole (76); 2-(3,4-dimethoxyphenyl)-5-(1'-isopentyl-[1,4'-bipiperidin]-4-yl)-3-methyl-1H-indole (77); 2-(3,4-dimethoxyphenyl)-3-methyl-5-(1'-((1-methyl-1H-pyrrol-2-yl)methyl)-[1,4'-bipiperidin]-4-yl)-1H-indole (78); 2-(3,4-dimethoxyphenyl)-3-methyl-5-(1'-(3-methylcyclohexyl)-[1,4'-bipiperidin]-4-yl)-1H-indole (79); 2-(3,4-dimethoxyphenyl)-3-methyl-5-(1'-(4-methylcyclohexyl)-[1,4'-bipiperidin]-4-yl)-1H-indole (80); 2-(3,4-dimethoxyphenyl)-3-methyl-5-(1''-methyl-[1,4':1',4''-terpiperidin]-4-yl)-1H-indole (81); 5-(1'-butyl-[1,4'-bipiperidin]-4-yl)-2-(3,4-dimethoxyphenyl)-3-methyl-1H-indole (82); 2-(3,4-dimethoxyphenyl)-3-methyl-5-(1'-(oxetan-3-yl)-[1,4'-bipiperidin]-4-yl)-1H-indole (83); 4-(4-(2-(3,4-dimethoxyphenyl)-3-methyl-1H-indol-5-yl)-[1,4'-bipiperidin]-1'-yl) cyclohexan-1-ol (84); 2-(3,4-dimethoxyphenyl)-5-(1-(1-isobutylpyrrolidin-3-yl)piperidin-4-yl)-3-methyl-1H-indole (85); 3-(4-(2-(3,4-dimethoxyphenyl)-3-methyl-1H-indol-5-yl)piperidin-1-yl)-N-isobutyl-N-methylcyclohexan-1-amine (89); 3-(4-(2-(3,4-dimethoxyphenyl)-3-methyl-1H-indol-5-yl)piperidin-1-yl)-N-isobutylcyclohexan-1-amine (90); 2-(3,4-dimethoxyphenyl)-3-methyl-5-(1-(1-methylazepan-4-yl)piperidin-4-yl)-1H-indole (91); 2-(3,4-dimethoxyphenyl)-5-(1-(1-isopropylazepan-4-yl)piperidin-4-yl)-3-methyl-1H-indole (92); 5-(1-(1-cyclopentylazepan-4-yl)piperidin-4-yl)-2-(3,4-dimethoxyphenyl)-3-methyl-1H-indole (93); 5-(1-(1-(cyclopropylmethyl)azepan-4-yl) piperidin-4-yl)-2-(3,4-dimethoxyphenyl)-3-methyl-1H-indole (94); 2-(3,4-dimethoxyphenyl)-5-(1-(1-isobutylazepan-4-yl) piperidin-4-yl)-3-methyl-1H-indole (95); 2-(3,4-dimethoxyphenyl)-3-methyl-5-(1-(1-(oxetan-3-yl)azepan-4-yl)piperidin-4-yl)-1H-indole (96); 2-(3,4-dimethoxyphenyl)-5-(1-(1-ethylazepan-4-yl)piperidin-4-yl)-3-methyl-1H-indole (97); tert-butyl (2-(4-(2-(3,4-dimethoxyphenyl)-3-methyl-1H-indol-5-yl) piperidin-1-yl) ethyl) carbamate (99); 2-(4-(2-(3,4-dimethoxyphenyl)-3-methyl-1H-indol-5-yl)piperidin-1-yl) ethan-1-amine (100); 2-(3,4-dimethoxyphenyl)-3-methyl-5-(1-(piperidin-2-ylmethyl) piperidin-4-yl)-1H-indole (101); 3-(4-(2-(3,4-dimethoxyphenyl)-3-methyl-1H-indol-5-yl)piperidin-1-yl)-N-methylpropan-1-amine (102); 5-(1-(azepan-4-yl)piperidin-4-yl)-2-(3,4-dimethoxyphenyl)-3-methyl-1H-indole (103); 2-(3,4-dimethoxyphenyl)-3-methyl-5-(1-(pyrrolidin-3-yl)piperidin-4-yl)-1H-indole (104); 3-(4-(2-(3,4-dimethoxyphenyl)-3-methyl-1H-indol-5-yl)piperidin-1-yl)cyclohexan-1-amine (105); 5-([1,3'-bipiperidin]-4-yl)-2-(3,4-dimethoxyphenyl)-3-methyl-1H-indole (106); (S)-2-(3,4-dimethoxyphenyl)-3-methyl-5-(1-(pyrrolidin-2-ylmethyl)piperidin-4-yl)-1H-indole (107); (R)-2-(3,4-dimethoxyphenyl)-3-methyl-5-(1-(pyrrolidin-2-ylmethyl) piperidin-4-yl)-1H-indole (108); N-(2-(4-(2-(3,4-dimethoxyphenyl)-3-methyl-1H-indol-5-yl)piperidin-1-yl) ethyl)-N-methyloxetan-3-amine (109); N-(2-(4-(2-(3,4-dimethoxyphenyl)-3-methyl-1H-indol-5-yl)piperidin-1-yl)

ethyl)-N,2-dimethylpropan-1-amine (110); 2-(4-(2-(3,4-dimethoxyphenyl)-3-methyl-1H-indol-5-yl)piperidin-1-yl)-N-ethyl-N-methylethan-1-amine (111); N-(cyclopropylmethyl)-2-(4-(2-(3,4-dimethoxyphenyl)-3-methyl-1H-indol-5-yl)piperidin-1-yl)-N-methylethan-1-amine (112); 1-(4-(2-(3,4-dimethoxyphenyl)-3-methyl-1H-indol-5-yl)piperidin-1-yl)-2-(ethylamino)ethan-1-one (113); 2-(4-(2-(3,4-dimethoxyphenyl)-1,3-dimethyl-1H-indol-5-yl)piperidin-1-yl)-N-methylethan-1-amine (114); 2-(3,4-dimethoxyphenyl)-5-(1'-isopropyl-[1,4'-bipiperidin]-4-yl)-3,6-dimethyl-1H-indole-di-trifluoroacetic acid (115); 1-(4-(2-(3,4-dimethoxyphenyl)-3-isobutyl-1H-indol-5-yl)piperidin-1-yl)-2-(ethylamino) ethanone trifluoroacetic acid (116); 2-(4-(3-(cyclopropylmethyl)-2-(3,4-dimethoxyphenyl)-1H-indol-5-yl)piperidin-1-yl)-N-methylethanamine di-trifluoroacetic acid (117); 2-(3,4-dimethoxyphenyl)-5-(1-(2-(methylamino)ethyl)piperidin-4-yl)-1H-indole-3-carbonitrile-di-trifluoroacetic acid (118); 2-(3,4-2-(4-(3-chloro-2-(3,4-dimethoxyphenyl)-1H-indol-5-yl)piperidin-1-yl)-N-methylethanamine-di-trifluoroacetic acid (119); 3-chloro-2-(3,4-dimethoxyphenyl)-5-(1'-isobutyl-[1,4'-bipiperidin]-4-yl)-1H-indole di-trifluoroacetic acid (120); 2-(3,4-dimethoxyphenyl)-5-(1'-isobutyl-[1,4'-bipiperidin]-4-yl)-3-propyl-1H-indole-di-trifluoroacetic acid (121); 2-(3,4-dimethoxyphenyl)-3-ethyl-5-(piperidin-4-yl)-1H-indole (122); 2-(3,4-dimethoxyphenyl)-3-ethyl-5-(1'-isobutyl-[1,4'-bipiperidin]-4-yl)-1H-indole-di-trifluoroacetic acid (123); 5-((4-(2-(3,4-dimethoxyphenyl)-3-ethyl-1H-indol-5-yl)-[1,4'-bipiperidin]-1'-yl)methyl)-2-methyloxazole (124); 5-(1'-((1H-imidazol-4-yl) methyl)-[1,4'-bipiperidin]-4-yl)-2-(3,4-dimethoxyphenyl)-3-ethyl-1H-indole (125); 4-((4-(2-(3,4-dimethoxyphenyl)-3-ethyl-1H-indol-5-yl)-[1,4'-bipiperidin]-1'-yl)methyl)-2-methyloxazole (126); ethyl 5-((4-(2-(3,4-dimethoxyphenyl)-3-ethyl-1H-indol-5-yl)-[1,4'-bipiperidin]-1'-yl)methyl)-2,4-dimethyl-1H-pyrrole-3-carboxylate (127); 5-(1'-((1H-indol-2-yl)methyl)-[1,4'-bipiperidin]-4-yl)-2-(3,4-dimethoxyphenyl)-3-ethyl-1H-indole (128); 2-(3,4-dimethoxyphenyl)-3-ethyl-5-(1'-((2-methyl-1H-indol-3-yl)methyl)-[1,4'-bipiperidin]-4-yl)-1H-indole (129); 4-((4-(2-(3,4-dimethoxyphenyl)-3-ethyl-1H-indol-5-yl)-[1,4'-bipiperidin]-1'-yl)methyl)-1,2,3-thiadiazole (130); 2-(3,4-dimethoxyphenyl)-3-ethyl-5-(1'-((3-methyl-1H-pyrazol-5-yl) methyl)-[1,4'-bipiperidin]-4-yl)-1H-indole (131); 2-(3,4-dimethoxyphenyl)-5-(1'-((1,3-dimethyl-1H-pyrazol-5-yl)methyl)-[1,4'-bipiperidin]-4-yl)-3-ethyl-1H-indole (132); 2-(3,4-dimethoxyphenyl)-3-ethyl-5-(1'-((1-methyl-1H-pyrazol-3-yl)methyl)-[1,4'-bipiperidin]-4-yl)-1H-indole (133); 5-((4-(2-(3,4-dimethoxyphenyl)-3-ethyl-1H-indol-5-yl)-[1,4'-bipiperidin]-1'-yl)methyl)oxazole (134); 2-(1-(4-(2-(3,4-dimethoxyphenyl)-3-ethyl-1H-indol-5-yl)-[1,4'-bipiperidin]-1'-yl)ethyl) oxazole (135); 2-(3,4-dimethoxyphenyl)-3-ethyl-5-(1'-((1-methyl-1H-imidazol-2-yl) methyl)-[1,4'-bipiperidin]-4-yl)-1H-indole (136); 2-(3,4-dimethoxyphenyl)-3-ethyl-5-(1'-((1-methyl-1H-indol-2-yl) methyl)-[1,4'-bipiperidin]-4-yl)-1H-indole (137); 4-((4-(2-(3,4-dimethoxyphenyl)-3-ethyl-1H-indol-5-yl)-[1,4'-bipiperidin]-1'-yl)methyl)-3,5-dimethylisoxazole (138); 2-(3,4-dimethoxyphenyl)-3-ethyl-5-(1'-((3-methylthiophen-2-yl)methyl)-[1,4'-bipiperidin]-4-yl)-1H-indole (139); 2-(3,4-dimethoxyphenyl)-3-ethyl-5-(1'-((5-methylthiophen-2-yl)methyl)-[1,4'-bipiperidin]-4-yl)-1H-indole (140); 2-(3,4-dimethoxyphenyl)-3-ethyl-5-(1'-((5-phenylthiophen-2-yl)methyl)-[1,4'-bipiperidin]-4-yl)-1H-indole (141); 2-(3,4-dimethoxyphenyl)-3-ethyl-5-(1'-(thiophen-3-ylmethyl)-[1,4'-bipiperidin]-4-yl)-1H-indole (142); 2-(3,4-dimethoxyphenyl)-3-ethyl-5-(1'-((5-phenylfuran-2-yl) methyl)-[1,4'-bipiperidin]-4-yl)-1H-indole (143); 2-(3,4-dimethoxyphenyl)-5-(1'-((1,5-dimethyl-1H-pyrazol-3-yl) methyl)-[1,4'-bipiperidin]-4-yl)-3-ethyl-1H-indole (144); 1-(4-(2-(3,4-dimethoxyphenyl)-3-ethyl-1H-indol-5-yl)-[1,4'-bipiperidin]-1'-yl)butane-1,4-diol (145); 2-(3,4-dimethoxyphenyl)-3-ethyl-5-(1'-(furan-3-ylmethyl)-[1,4'-bipiperidin]-4-yl)-1H-indole (146); 5-(1'-benzyl-[1,4'-bipiperidin]-4-yl)-2-(3,4-dimethoxyphenyl)-3-ethyl-1H-indole (147); 2-(3,4-dimethoxyphenyl)-3-ethyl-5-(1'-ethyl-[1,4'-bipiperidin]-4-yl)-1H-indole (149); 2-(3,4-dimethoxyphenyl)-3-ethyl-5-(1'-methyl-[1,4'-bipiperidin]-4-yl)-1H-indole (150); 2-(3,4-dimethoxyphenyl)-3-ethyl-5-(1'-isopropyl-[1,4'-bipiperidin]-4-yl)-1H-indole (151); 5-(1'-cyclopentyl-[1,4'-bipiperidin]-4-yl)-2-(3,4-dimethoxyphenyl)-3-ethyl-1H-indole (152); 2-(3,4-dimethoxyphenyl)-3-ethyl-5-(1'-((2-methyl-1H-imidazol-5-yl)methyl)-[1,4'-bipiperidin]-4-yl)-1H-indole (153); 2-(4-(2-(3,4-dimethoxyphenyl)-3-ethyl-1H-indol-5-yl)piperidin-1-yl)-N-methylethanamine di-trifluoroacetic acid (155); 1-(4-(2-(3,4-dimethoxyphenyl)-3-ethyl-1H-indol-5-yl) piperidin-1-yl)-2-((2-hydroxypropyl)amino)ethan-1-one (157); 2-([1,4'-bipiperidin]-1'-yl)-1-(4-(2-(3,4-dimethoxyphenyl)-3-ethyl-1H-indol-5-yl)piperidin-1-yl)ethan-1-one (158); 1-(4-(2-(3,4-dimethoxyphenyl)-3-ethyl-1H-indol-5-yl)piperidin-1-yl)-2-((2-hydroxyethyl)amino) ethan-1-one (159); 1-(4-(2-(3,4-dimethoxyphenyl)-3-ethyl-1H-indol-5-yl)piperidin-1-yl)-2-((1-(hydroxymethyl)cyclopentyl)amino) ethan-1-one (160); 2-((2-(4-(2-(3,4-dimethoxyphenyl)-3-ethyl-1H-indol-5-yl)piperidin-1-yl)-2-oxoethyl) amino) acetonitrile (161); 1-(4-(2-(3,4-dimethoxyphenyl)-3-ethyl-1H-indol-5-yl) piperidin-1-yl)-2-((4-(dimethylamino) cyclohexyl)amino)ethan-1-one (162); 1-(4-(2-(3,4-dimethoxyphenyl)-3-ethyl-1H-indol-5-yl)piperidin-1-yl)-2-(((1r,3s,5R,7S)-3-hydroxyadamantan-1-yl)amino) ethan-1-one (163); 1-(4-(2-(3,4-dimethoxyphenyl)-3-ethyl-1H-indol-5-yl)piperidin-1-yl)-2-((3-hydroxy-2,2-dimethylpropyl)amino)ethan-1-one (164); 2-((1,3-dihydroxypropan-2-yl)amino)-1-(4-(2-(3,4-dimethoxyphenyl)-3-ethyl-1H-indol-5-yl)piperidin-1-yl) ethan-1-one (165); 2-(4-acetyl-1,4-diazepan-1-yl)-1-(4-(2-(3,4-dimethoxyphenyl)-3-ethyl-1H-indol-5-yl)piperidin-1-yl)ethan-1-one (166); 1-(4-(2-(3,4-dimethoxyphenyl)-3-ethyl-1H-indol-5-yl)piperidin-1-yl)-2-morpholinoethan-1-one (167); 1-(2-(4-(2-(3,4-dimethoxyphenyl)-3-ethyl-1H-indol-5-yl)piperidin-1-yl)-2-oxoethyl)-N,N-diethylpiperidine-3-carboxamide (168); 1-(4-(2-(3,4-dimethoxyphenyl)-3-ethyl-1H-indol-5-yl)piperidin-1-yl)-2-(3-(hydroxymethyl)piperidin-1-yl)ethan-1-one (169); 1-(4-(2-(3,4-dimethoxyphenyl)-3-ethyl-1H-indol-5-yl)piperidin-1-yl)-2-(isopropyl(methyl)amino) ethan-1-one (170); 2-(4-acetylpiperazin-1-yl)-1-(4-(2-(3,4-dimethoxyphenyl)-3-ethyl-1H-indol-5-yl)piperidin-1-yl)ethan-1-one (171); 1-(4-(2-(3,4-dimethoxyphenyl)-3-ethyl-1H-indol-5-yl)piperidin-1-yl)-2-(4-(tetrahydrofuran-2-carbonyl)piperazin-1-yl) ethan-1-one (172); (R)-1-(4-(2-(3,4-dimethoxyphenyl)-3-ethyl-1H-indol-5-yl)piperidin-1-yl)-2-(3-hydroxypyrrolidin-1-yl)ethan-1-one (173); (S)-1-(4-(2-(3,4-dimethoxyphenyl)-3-ethyl-1H-indol-5-yl)piperidin-1-yl)-2-((1-hydroxyhexan-2-yl)amino)ethan-1-one (174); 1-(4-(2-(3,4-dimethoxyphenyl)-3-ethyl-1H-indol-5-yl) piperidin-1-yl)-2-methyl-1-oxopropan-2-yl acetate (175); 1-(2-(4-(2-(3,4-dimethoxyphenyl)-3-ethyl-1H-indol-5-yl)piperidin-1-yl)-2-oxoethyl)piperidine-3-carboxylic acid (176); 1-(4-(2-(3,4-dimethoxyphenyl)-3-ethyl-1H-indol-5-yl)piperidin-1-yl)-2-(thiazol-2-ylamino)ethanone (177); 1-(2-(4-(2-(3,4-dimethoxyphenyl)-3-ethyl-1H-indol-5-yl)piperidin-1-yl)-2-oxoethyl)-N,N-diethylpiperidine-3-carboxamide (178 and 179); 2-(3,4-dimethoxyphenyl)-3-ethyl-5-(1-(3,3,3-trifluoro-2-methylpropyl)piperidin-4-yl)-1H-indole (180); 1-(4-(2-(3,4-dimethoxyphenyl)-3-ethyl-1H-indol-5-yl)piperidin-1-yl)-2-(dimethylamino) ethanone (181); 4-(2-(3,4-dimethoxyphenyl)-3-ethyl-1H-indol-5-yl)-N-isopropylpiperidine-1-carboxamide (182); (4-(2-(3,4-dimethoxyphenyl)-3-ethyl-1H-indol-5-yl)piperidin-1-yl) (pyridin-4-yl)methanone (183); tert-butyl 3-(4-(2-(3,4-dimethoxyphenyl)-3-ethyl-1H-indol-5-yl)piperidine-1-carbonyl)piperidine-1-carboxylate (184); 1-(4-(2-(3,4-dimethoxyphenyl)-3-ethyl-1H-indol-5-yl)piperidin-1-yl)ethan-1-one (185); (4-(2-(3,4-dimethoxyphenyl)-3-ethyl-1H-indol-5-yl)piperidin-1-yl)(piperidin-4-yl)methanone (186); (4-(2-(3,4-dimethoxyphenyl)-3-ethyl-1H-indol-5-yl)piperidin-1-yl)(4-methylpiperidin-4-yl)methanone (187); 2-(4-(2-(3,4-dimethoxyphenyl)-3-ethyl-6-methyl-1H-indol-5-yl) piperidin-1-yl)-N-methylethanamine-di-trifluoroacetic acid (188); 2-(3,4-dimethoxyphenyl)-3-ethyl-7-fluoro-5-(piperidin-4-yl)-1H-indole (189); 2-(3,4-dimethoxyphenyl)-3-ethyl-7-fluoro-5-(1'-isobutyl-[1,4'-bipiperidin]-4-yl)-1H-indole (190); 2-(4-(2-(3,4-dimethoxyphenyl)-3-ethyl-7-fluoro-1H-indol-5-yl)piperidin-1-yl)-N-methylethan-1-amine (191); 2-(3,4-dimethoxyphenyl)-3-ethyl-5-(1'-isopropyl-[1,4'-bipiperidin]-4-yl)-6-methoxy-1H-indole (192); 2-(4-(2-(3,4-dimethoxyphenyl)-3-ethyl-6-methoxy-1H-indol-5-yl)piperidin-1-yl)-N-methylethanamine (193); 2-(3,4-dimethoxyphenyl)-3-isopropyl-5-(piperidin-4-yl)-1H-indole hydrochloride (194); 2-(4-(2-(3,4-dimethoxyphenyl)-3-isopropyl-1H-indol-5-yl)piperidin-1-yl)-N-methylethan-1-amine (195); 5-([1,4'-bipiperidin]-4-yl)-2-(3,4-dimethoxyphenyl)-3-isopropyl-1H-indole dihydrochloride (197); 5-(1'-(cyclopropylmethyl)-[1,4'-bipiperidin]-4-yl)-2-(3,4-dimethoxyphenyl)-3-isopropyl-1H-indole di trifluoroacetic acid (198); 2-(3,4-dimethoxyphenyl)-5-(1'-isobutyl-[1,4'-bipiperidin]-4-yl)-3-isopropyl-1H-indole (199); 2-(3,4-dimethoxyphenyl)-3-isopropyl-5-(1'-methyl-[1,4'-bipiperidin]-4-yl)-1H-indole (200); 2-(3,4-dimethoxyphenyl)-3-isopropyl-5-(1'-isopropyl-[1,4'-bipiperidin]-4-yl)-1H-indole (201); 5-(1'-cyclopentyl-[1,4'-bipiperidin]-4-yl)-2-(3,4-dimethoxyphenyl)-3-isopropyl-1H-indole (202); 2-((2-(4-(2-(3,4-dimethoxyphenyl)-3-isopropyl-1H-indol-5-yl) piperidin-1-yl)-2-oxoethyl)(methyl)amino)-N,N-diethylacetamide, TFA (203); 3-((2-(4-(2-(3,4-dimethoxyphenyl)-3-isopropyl-1H-indol-5-yl) piperidin-1-yl)-2-oxoethyl)(methyl) amino)-N,N-diethylpropanamide (204); 2-(3,4-dimethoxyphenyl)-3-isopropyl-6-methyl-5-(piperidin-4-yl)-1H-indole (205); 2-(3,4-dimethoxyphenyl)-3-isopropyl-5-(1'-isopropyl-[1,4'-bipiperidin]-4-yl)-6-methyl-1H-indole di trifluoroacetic acid (206); 2-(3,4-dimethoxyphenyl)-3-isopropyl-5-(1'-isopropyl-[1,4'-bipiperidin]-4-yl)-6-methyl-1H-indole-ditrifluoroacteic acid (207); 2-(4-(2-(3,4-dimethoxyphenyl)-6-fluoro-3-isopropyl-1H-indol-5-yl)piperidin-1-yl)-N-methylethan-1-amine (208); 1-(4-(2-(3,4-dimethoxyphenyl)-3-isopropyl-1H-indol-5-yl)piperidin-1-yl)-2-(dimethylamino)ethan-1-one (209); 1-(4-(2-(3,4-dimethoxyphenyl)-3-isopropyl-1H-indol-5-yl)piperidin-1-yl)-2-((2-hydroxypropyl)amino) ethan-1-one (210); 2-([1,4'-bipiperidin]-1'-yl)-1-(4-(2-(3,4-dimethoxyphenyl)-3-isopropyl-1H-indol-5-yl)piperidin-1-yl)ethan-1-one (211); 1-(4-(2-(3,4-dimethoxyphenyl)-3-isopropyl-1H-indol-5-yl)piperidin-1-yl)-2-((2-hydroxyethyl) amino)ethan-1-one (212); 1-(4-(2-(3,4-dimethoxyphenyl)-3-isopropyl-1H-indol-5-yl) piperidin-1-yl)-2-((1-(hydroxymethyl)cyclopentyl)amino)ethan-1-one (213); 2-((2-(4-(2-(3,4-dimethoxyphenyl)-3-isopropyl-1H-indol-5-yl)piperidin-1-yl)-2-oxoethyl)amino) acetonitrile (214); 1-(4-(2-(3,4-dimethoxyphenyl)-3-isopropyl-1H-indol-5-yl)piperidin-1-yl)-2-((4-(dimethylamino)cyclohexyl) amino)ethan-1-one (215); 2-((3-(tert-butyl)-1H-pyrazol-5-yl)amino)-1-(4-(2-(3,4-dimethoxyphenyl)-3-isopropyl-1H-indol-5-yl)piperidin-1-yl)ethan-1-one (216); 2-(((3s,5s,7s)-adamantan-1-yl)amino)-1-(4-(2-(3,4-dimethoxyphenyl)-3-isopropyl-1H-indol-5-yl)piperidin-1-yl)ethan-1-one (217); 1-(4-(2-(3,4-dimethoxyphenyl)-3-isopropyl-1H-indol-5-yl)piperidin-1-yl)-2-(((1r,3s,5R,7S)-3-hydroxyadamantan-1-yl)amino)ethan-1-one (218); 1-(4-(2-(3,4-dimethoxyphenyl)-3-isopropyl-1H-indol-5-yl)piperidin-1-yl)-2-((3-hydroxy-2,2-dimethylpropyl)amino)ethan-1-one (219); 2-((1,3-dihydroxypropan-2-yl)amino)-1-(4-(2-(3,4-dimethoxyphenyl)-3-isopropyl-1H-indol-5-yl)piperidin-1-yl) ethan-1-one (220); 1-(4-(2-(3,4-dimethoxyphenyl)-3-isopropyl-1H-indol-5-yl)piperidin-1-yl)-2-((2,2,2-trifluoroethyl) amino)ethan-1-one (221); 2-(4-acetyl-1,4-diazepan-1-yl)-1-(4-(2-(3,4-dimethoxyphenyl)-3-isopropyl-1H-indol-5-yl)piperidin-1-yl)ethan-1-one (222); 1-(4-(2-(3,4-dimethoxyphenyl)-3-isopropyl-1H-indol-5-yl)piperidin-1-yl)-2-morpholinoethan-1-one (223); 1-(2-(4-(2-(3,4-dimethoxyphenyl)-3-isopropyl-1H-indol-5-yl)piperidin-1-yl)-2-oxoethyl)-N,N-diethylpiperidine-3-carboxamide (224); 1-(4-(2-(3,4-dimethoxyphenyl)-3-isopropyl-1H-indol-5-yl)piperidin-1-yl)-2-(2-(((S)-1-methylpyrrolidin-2-yl)methyl) piperidin-1-yl)ethan-1-one (225); 1-(4-(2-(3,4-dimethoxyphenyl)-3-isopropyl-1H-indol-5-yl)piperidin-1-yl)-2-(3-(hydroxymethyl)piperidin-1-yl)ethan-1-one (226); 1-(4-(2-(3,4-dimethoxyphenyl)-3-isopropyl-1H-indol-5-yl)piperidin-1-yl)-2-(isopropyl(methyl)amino) ethan-1-one (227); 2-((2-(4-(2-(3,4-dimethoxyphenyl)-3-isopropyl-1H-indol-5-yl) piperidin-1-yl)-2-oxoethyl)amino)acetamide (228); 2-(4-(2-(4-(2-(3,4-dimethoxyphenyl)-3-isopropyl-1H-indol-5-yl)piperidin-1-yl)-2-oxoethyl)piperazin-1-yl)-N-isopropylacetamide (229); 1-(4-(2-(3,4-dimethoxyphenyl)-3-isopropyl-1H-indol-5-yl) piperidin-1-yl)-2-((2-(2-hydroxyethoxy)ethyl)amino)ethan-1-one (230); (S)-1-(4-(2-(3,4-dimethoxyphenyl)-3-isopropyl-1H-indol-5-yl)piperidin-1-yl)-2-((1-hydroxy-4-methylpentan-2-yl)amino)ethan-1-one (231); 2-(((1r,4r)-4-aminocyclohexyl)amino)-1-(4-(2-(3,4-dimethoxyphenyl)-3-isopropyl-1H-indol-5-yl)piperidin-1-yl)ethan-1-one (232); 1-(4-(2-(3,4-dimethoxyphenyl)-3-isopropyl-1H-indol-5-yl)piperidin-1-yl)-2-((1-hydroxybutan-2-yl)amino)ethan-1-one (233); (R)-1-(4-(2-(3,4-dimethoxyphenyl)-3-isopropyl-1H-indol-5-yl)piperidin-1-yl)-2-((1-hydroxy-4-methylpentan-2-yl)amino) ethan-1-one (234); (S)-2-((2,3-dihydroxypropyl)amino)-1-(4-(2-(3,4-dimethoxyphenyl)-3-isopropyl-1H-indol-5-yl)piperidin-1-yl)ethan-1-one (235); 1-(4-(2-(3,4-dimethoxyphenyl)-3-isopropyl-1H-indol-5-yl)piperidin-1-yl)-2-((2-hydroxycyclopentyl) amino)ethan-1-one (236); 1-(4-(2-(3,4-dimethoxyphenyl)-3-isopropyl-1H-indol-5-yl) piperidin-1-yl)-2-((3-hydroxybutyl)amino)ethan-1-one (237); 1-(4-(2-(3,4-dimethoxyphenyl)-3-isopropyl-1H-indol-5-yl)piperidin-1-yl)-2-(4-hydroxypiperidin-1-yl) ethan-1-one (238); 1-(4-(2-(3,4-dimethoxyphenyl)-3-isopropyl-1H-indol-5-yl)piperidin-1-yl)-2-(4-methyl-1,4-diazepan-1-yl) ethan-1-one (239); 1-(4-(2-(3,4-dimethoxyphenyl)-3-isopropyl-1H-indol-5-yl)piperidin-1-yl)-2-(4-isopropylpiperazin-1-yl)ethan-1-one (240); 1-(4-(2-(3,4-dimethoxyphenyl)-3-isopropyl-1H-indol-5-yl)piperidin-1-yl)-2-(4-(4-methylpiperazin-1-yl)piperidin-1-yl)ethan-1-one (241); 1-(4-(2-(3,4-dimethoxyphenyl)-3-isopropyl-1H-indol-5-yl)piperidin-1-yl)-2-((2-hydroxyethyl)(methyl) amino)ethan-1-one (242); 1-(4-(2-(3,4-dimethoxyphenyl)-3-isopropyl-1H-indol-5-yl)piperidin-1-yl)-2-(4-(hydroxymethyl)piperidin-1-yl)ethan-1-one (243); 1-(4-(2-(3,4-dimethoxyphenyl)-3-isopropyl-1H-indol-5-yl) piperidin-1-yl)-2-(4-(dimethylamino)piperidin-1-yl)ethan- 1-one (244); 1-(4-(2-(3,4-dimethoxyphenyl)-3-isopropyl-1H-indol-5-yl)piperidin-1-yl)-2-((4-(2-hydroxypropan-2-yl)cyclohexyl)amino)ethan-1-one (245); 1-(4-(2-(3,4-dimethoxyphenyl)-3-isopropyl-1H-indol-5-yl)piperidin-1-yl)-2-((4-hydroxycyclohexyl) amino)ethan-1-one (246); 1-(2-(4-(2-(3,4-dimethoxyphenyl)-3-isopropyl-1H-indol-5-yl)piperidin-1-yl)-2-oxoethyl)-N,N-diethylpiperidine-3-carboxamide (247 and 248); 1-(4-(2-(3,4-dimethoxyphenyl)-3-isopropyl-1H-indol-5-yl)piperidin-1-yl)-2-(3-(hydroxymethyl)piperidin-1-yl)ethan-1-one (249 and 250); (R)-1-(4-(2-(3,4-dimethoxyphenyl)-3-isopropyl-1H-indol-5-yl)piperidin-1-yl)-2-((2-fluoro-3-hydroxy-3-methylbutyl)amino)ethan-1-one (251); N-(2-(4-(2-(3,4-dimethoxyphenyl)-3-isopropyl-1H-indol-5-yl)piperidin-1-yl)-2-oxoethyl) hex-5-ynamide (252); (S)-3-amino-1-(4-(2-(3,4-dimethoxyphenyl)-3-isopropyl-1H-indol-5-yl)piperidin-1-yl)butan-1-one (253); (S)-1-(4-(2-(3,4-dimethoxyphenyl)-3-isopropyl-1H-indol-5-yl)piperidin-1-yl)-3-hydroxybutan-1-one (254 and 255); 1-(4-(2-(3,4-dimethoxyphenyl)-3-isopropyl-1H-indol-5-yl)piperidin-1-yl)-2-(methylamino)ethan-1-one (256); 1-(4-(2-(3,4-dimethoxyphenyl)-3-isopropyl-1H-indol-5-yl)piperidin-1-yl)-4-(isopropylamino)butan-1-one (257); 2-(3,4-dimethoxyphenyl)-3-isopropyl-5-(1-(((1-methyl-1H-imidazol-5-yl) methyl)piperidin-4-yl)-1H-indole (258); 2-(3,4-dimethoxyphenyl)-3-isopropyl-5-(1-(((1-methyl-1H-pyrazol-4-yl)methyl)piperidin-4-yl)-1H-indole (259); N-(3-((4-(2-(3,4-dimethoxyphenyl)-3-isopropyl-1H-indol-5-yl)piperidin-1-yl)methyl)phenyl)methanesulfonamide (260); 2-((4-(2-(3,4-dimethoxyphenyl)-3-isopropyl-1H-indol-5-yl) piperidin-1-yl)methyl)thiazole (261); 2-(3,4-dimethoxyphenyl)-3-isopropyl-5-(1-(((1-methyl-1H-imidazol-2-yl)methyl)piperidin-4-yl)-1H-indole (262); 5-(1-(4-(1H-imidazol-1-yl)benzyl)piperidin-4-yl)-2-(3,4-dimethoxyphenyl)-3-isopropyl-1H-indole (263); 3-((4-(2-(3,4-dimethoxyphenyl)-3-isopropyl-1H-indol-5-yl)piperidin-1-yl)methyl)benzonitrile (264); 2-(3,4-dimethoxyphenyl)-5-(1-(2-ethylbutyl)piperidin-4-yl)-3-isopropyl-1H-indole (265); 2-(3,4-dimethoxyphenyl)-3-isopropyl-5-(1-((2-methyl-1H-imidazol-5-yl)methyl)piperidin-4-yl)-1H-indole (266); 2-(3,4-dimethoxyphenyl)-3-isopropyl-5-(1-((4-methyl-1H-imidazol-5-yl)methyl)piperidin-4-yl)-1H-indole (267); 5-(1-((1H-imidazol-5-yl)methyl)piperidin-4-yl)-2-(3,4-dimethoxyphenyl)-3-isopropyl-1H-indole (268); 2-(3,4-dimethoxyphenyl)-3-isopropyl-5-(1-(3-(trifluoromethyl)benzyl)piperidin-4-yl)-1H-indole (269); 4-((4-(2-(3,4-dimethoxyphenyl)-3-isopropyl-1H-indol-5-yl)piperidin-1-yl)methyl)-N,N-dimethylaniline (270); 2-(3,4-dimethoxyphenyl)-3-isopropyl-5-(1-(4-(trifluoromethoxy)benzyl)piperidin-4-yl)-1H-indole (271); 1-(2-(4-(2-(3,4-dimethoxyphenyl)-3-isopropyl-1H-indol-5-yl)piperidin-1-yl)acetyl)-N,N-diethylpiperidine-3-carboxamide (272); 2-(4-(2-(3,4-dimethoxyphenyl)-3-isopropyl-1H-indol-5-yl)piperidin-1-yl)-N-(1-isopropylpiperidin-4-yl)acetamide (273); 2-(4-(2-(3,4-dimethoxyphenyl)-3-isopropyl-1H-indol-5-yl)piperidin-1-yl)-1-(4-methylpiperazin-1-yl)ethan-1-one (274); 2-(4-(2-(3,4-dimethoxyphenyl)-3-isopropyl-1H-indol-5-yl)piperidin-1-yl)-1-(3-(hydroxymethyl)piperidin-1-yl)ethan-1-one (275); 2-(4-(2-(3,4-dimethoxyphenyl)-3-isopropyl-1H-indol-5-yl)piperidin-1-yl)-N-(2-hydroxyethyl) acetamide (276); 2-(4-(2-(3,4-dimethoxyphenyl)-3-isopropyl-1H-indol-5-yl)piperidin-1-yl)-N-(3-hydroxypropyl)acetamide (277); (S)-2-(4-(2-(3,4-dimethoxyphenyl)-3-isopropyl-1H-indol-5-yl)piperidin-1-yl)-1-(3-hydroxypyrrolidin-1-yl)ethan-1-one (278); 2-(4-(2-(3,4-dimethoxyphenyl)-3-isopropyl-1H-indol-5-yl)piperidin-1-yl)-N-((1r,4r)-4-(2-hydroxypropan-2-yl)cyclohexyl)acetamide (279); 1-(2-(4-(2-(3,4-dimethoxyphenyl)-3-isopropyl-1H-indol-5-yl)piperidin-1-yl)-2-oxoethyl)-N-(1-isopropylpiperidin-4-yl) piperidine-3-carboxamide (280 and 281); 1-(4-(2-(3,4-dimethoxyphenyl)-3-isopropyl-1H-indol-5-yl)piperidin-1-yl)-2-(3-(3-hydroxypyrrolidine-1-carbonyl)piperidin-1-yl) ethan-1-one (282 and 283); (S)-2-(3-(4-acetylpiperazine-1-carbonyl)piperidin-1-yl)-1-(4-(2-(3,4-dimethoxyphenyl)-3-isopropyl-1H-indol-5-yl)piperidin-1-yl)ethan-1-one (284); (S)-1-(2-(4-(2-(3,4-dimethoxyphenyl)-3-isopropyl-1H-indol-5-yl)piperidin-1-yl)-2-oxoethyl)-N-isopropylpiperidine-3-carboxamide (285); (S)-1-(4-(2-(3,4-dimethoxyphenyl)-3-isopropyl-1H-indol-5-yl)piperidin-1-yl)-2-(3-(4-isopropylpiperazine-1-carbonyl)piperidin-1-yl)ethan-1-one (286); (S)-1-(4-(2-(3,4-dimethoxyphenyl)-3-isopropyl-1H-indol-5-yl)piperidin-1-yl)-2-(3-(pyrrolidine-1-carbonyl)piperidin-1-yl)ethan-1-one (287); (S)-1-(2-(4-(2-(3,4-dimethoxyphenyl)-3-isopropyl-1H-indol-5-yl)piperidin-1-yl)-2-oxoethyl)-N-isopropyl-N-methylpiperidine-3-carboxamide (288); (S)-1-(4-(2-(3,4-dimethoxyphenyl)-3-isopropyl-1H-indol-5-yl) piperidin-1-yl)-2-(3-(4-(dimethylamino)piperidine-1-carbonyl)piperidin-1-yl)ethan-1-one (289); (S)-1-(4-(2-(3,4-dimethoxyphenyl)-3-isopropyl-1H-indol-5-yl)piperidin-1-yl)-2-(3-(4-(3-(trifluoromethyl)phenyl)piperazine-1-carbonyl)piperidin-1-yl)ethan-1-one (290); (S)-1-(4-(2-(3,4-dimethoxyphenyl)-3-isopropyl-1H-indol-5-yl)piperidin-1-yl)-2-(3-(4-(2-hydroxyethyl)piperidine-1-carbonyl)piperidin-1-yl)ethan-1-one (291); 1-(4-(2-(3,4-dimethoxyphenyl)-3-isopropyl-1H-indol-5-yl)piperidin-1-yl)-2-((3S)-3-(3-hydroxypiperidine-1-carbonyl)piperidin-1-yl) ethan-1-one (292); (S)-1-(4-(2-(3,4-dimethoxyphenyl)-3-isopropyl-1H-indol-5-yl)piperidin-1-yl)-2-(3-(4-(2-(pyrrolidin-1-yl) ethyl)piperazine-1-carbonyl)piperidin-1-yl)ethan-1-one (293); (S)-2-(3-(4-(4-bromobenzyl)piperazine-1-carbonyl)piperidin-1-yl)-1-(4-(2-(3,4-dimethoxyphenyl)-3-isopropyl-1H-indol-5-yl)piperidin-1-yl)ethan-1-one (294); (S)—N-(2-acetamidoethyl)-1-(2-(4-(2-(3,4-dimethoxyphenyl)-3-isopropyl-1H-indol-5-yl)piperidin-1-yl)-2-oxoethyl) piperidine-3-carboxamide (295); (S)-1-(2-(4-(2-(3,4-dimethoxyphenyl)-3-isopropyl-1H-indol-5-yl)piperidin-1-yl)-2-oxoethyl)-N-(1-(hydroxymethyl)cyclopentyl)piperidine-3-carboxamide (296); (S)—N-(cyanomethyl)-1-(2-(4-(2-(3,4-dimethoxyphenyl)-3-isopropyl-1H-indol-5-yl)piperidin-1-yl)-2-oxoethyl)piperidine-3-carboxamide (297); (S)—N-(2-amino-2-oxoethyl)-1-(2-(4-(2-(3,4-dimethoxyphenyl)-3-isopropyl-1H-indol-5-yl) piperidin-1-yl)-2-oxoethyl)piperidine-3-carboxamide (298): 1-(2-(3,4-dimethoxyphenyl)-3-isopropyl-1H-indol-5-yl)piperidin-1-yl)-2-((3S)-3-(octahydropyrrolo[3,4-c]pyrrole-2-carbonyl)piperidin-1-yl) ethan-1-one (299); 1-(4-(2-(3,4-dimethoxyphenyl)-3-isopropyl-1H-indol-5-yl)piperidin-1-yl)-2-((3S)-3-(2,5-dimethylpyrrolidine-1-carbonyl)piperidin-1-yl)ethan-1-one (300); 1-(4-(2-(3,4-dimethoxyphenyl)-3-isopropyl-1H-indol-5-yl)piperidin-1-yl)-2-((S)-3-((S)-3-hydroxypyrrolidine-1-carbonyl)piperidin-1-yl)ethan-1-one (301); (R)-1-(4-(2-(3,4-dimethoxyphenyl)-3-isopropyl-1H-indol-5-yl)piperidin-1-yl)-2-(3-(4-isopropylpiperazine-1-carbonyl)piperidin-1-yl)ethan-1-one (302); (R)-1-(4-(2-(3,4-dimethoxyphenyl)-3-isopropyl-1H-indol-5-yl)piperidin-1-yl)-2-(3-(pyrrolidine-1-carbonyl)piperidin-1-yl)ethan-1-one (303); (R)-1-(2-(4-(2-(3,4-dimethoxyphenyl)-3-isopropyl-1H-indol-5-yl)piperidin-1-yl)-2-oxoethyl)-N-isopropyl-N-methylpiperidine-3-carboxamide (304); (R)-1-(4-(2-(3,4-dimethoxyphenyl)-3-isopropyl-1H-indol-5-yl) piperidin-1-yl)-2-(3-(4-(dimethylamino)piperidine-1-carbonyl)piperidin-1-yl)ethan-1-one (305); (R)-1-(4-(2-(3,4-dimethoxyphenyl)-3-isopropyl-1H-indol-5-yl)piperidin-1- yl)-2-(3-(4-(2-hydroxyethyl)piperidine-1-carbonyl) piperidin-1-yl)ethan-1-one (306); (R)-1-(4-(2-(3,4-dimethoxyphenyl)-3-isopropyl-1H-indol-5-yl)piperidin-1-yl)-2-(3-(4-(2-(pyrrolidin-1-yl)ethyl)piperazine-1-carbonyl) piperidin-1-yl)ethan-1-one (307); (R)—N-(cyanomethyl)-1-(2-(4-(2-(3,4-dimethoxyphenyl)-3-isopropyl-1H-indol-5-yl) piperidin-1-yl)-2-oxoethyl)piperidine-3-carboxamide (308); (R)—N-(2-amino-2-oxoethyl)-1-(2-(4-(2-(3,4-dimethoxyphenyl)-3-isopropyl-1H-indol-5-yl)piperidin-1-yl)-2-oxoethyl)piperidine-3-carboxamide (309); 1-(4-(2-(3,4-dimethoxyphenyl)-3-isopropyl-1H-indol-5-yl) piperidin-1-yl)-2-((3R)-3-(octahydropyrrolo[3,4-c]pyrrole-2-carbonyl) piperidin-1-yl) ethan-1-one (310); 1-(4-(2-(3,4-dimethoxyphenyl)-3-isopropyl-1H-indol-5-yl)piperidin-1-yl)-2-((3R)-3-(2,5-dimethylpyrrolidine-1-carbonyl) piperidin-1-yl)ethan-1-one (311); 2-(4-(2-(3,4-dimethoxyphenyl)-3-isopropyl-1H-indol-5-yl)piperidin-1-yl)-N,N-dimethylacetamide (312); 1-(4-(2-(3,4-dimethoxyphenyl)-3-isopropyl-1H-indol-5-yl) piperidin-1-yl)-2-hydroxyethanone (313); 1-(4-(2-(3,4-dimethoxyphenyl)-3-isopropyl-1H-indol-5-yl) piperidin-1-yl)-2-isopropoxyethan-1-one (314); 1-(4-(2-(3,4-dimethoxyphenyl)-3-isopropyl-1H-indol-5-yl)piperidin-1-yl)-2-((1-methylpiperidin-4-yl) oxy)ethan-1-one (315); tert-butyl 5-(1-(tert-butoxycarbonyl)-3-hydroxypiperidin-4-yl)-2-(3,4-dimethoxyphenyl)-3-isopropyl-1H-indole-1-carboxylate (316); 4-(2-(3,4-dimethoxyphenyl)-3-isopropyl-1H-indol-5-yl)piperidin-3-ol 2,2,2-trifluoroacetate (317 and 318); 2-(3,4-dimethoxyphenyl)-5-(3-fluoropiperidin-4-yl)-3-isopropyl-1H-indole (319 and 320); 2-(3,4-dimethoxyphenyl)-5-(3-fluoropiperidin-4-yl)-3-isopropyl-1H-indole (321, 322, 323, and 324); 5-(3,3-difluoropiperidin-4-yl)-2-(3,4-dimethoxyphenyl)-3-isopropyl-1H-indole (325); 4-(2-(3,4-dimethoxyphenyl)-3-isopropyl-1H-indol-5-yl) piperidin-2-one (326); 3-(2,2-difluoroethyl)-2-(3,4-dimethoxyphenyl)-5-(piperidin-4-yl)-1H-indole (328); 2-(3,4-dimethoxyphenyl)-5-(piperidin-4-yl)-3-(2,2,2-trifluoroethyl)-1H-indole (329); 1-(4-(2-(3,4-dimethoxyphenyl)-3-(2,2,2-trifluoroethyl)-1H-indol-5-yl) piperidin-1-yl)-3-(piperidin-1-yl)propan-1-one (330); 1-(4-(2-(3,4-dimethoxyphenyl)-3-(2,2,2-trifluoroethyl)-1H-indol-5-yl)piperidin-1-yl)-4-(1H-imidazol-1-yl)butan-1-one (331); 1-(4-(2-(3,4-dimethoxyphenyl)-3-(2,2,2-trifluoroethyl)-1H-indol-5-yl)piperidin-1-yl)-2-(1H-indol-3-yl)ethan-1-one (332); 4-(4-(2-(3,4-dimethoxyphenyl)-3-(2,2,2-trifluoroethyl)-1H-indol-5-yl)piperidin-1-yl)-4-oxobutanamide (333); 1-(4-(2-(3,4-dimethoxyphenyl)-3-(2,2,2-trifluoroethyl)-1H-indol-5-yl)piperidin-1-yl)-2-(1H-imidazol-4-yl)ethan-1-one (334); 1-(4-(2-(3,4-dimethoxyphenyl)-3-(2,2,2-trifluoroethyl)-1H-indol-5-yl) piperidin-1-yl)-2-(pyridin-3-yl)ethan-1-one (335); (S)-1-(2-(4-(2-(3,4-dimethoxyphenyl)-3-(2,2,2-trifluoroethyl)-1H-indol-5-yl)piperidine-1-carbonyl) pyrrolidin-1-yl)ethan-1-one (336); 1-(4-(2-(3,4-dimethoxyphenyl)-3-(2,2,2-trifluoroethyl)-1H-indol-5-yl)piperidin-1-yl)-3-(1H-indol-1-yl)propan-1-one (337); 1-(4-(2-(3,4-dimethoxyphenyl)-3-(2,2,2-trifluoroethyl)-1H-indol-5-yl)piperidin-1-yl)-2-(4-(dimethylamino)phenyl)ethan-1-one (338); 1-(4-(2-(3,4-dimethoxyphenyl)-3-(2,2,2-trifluoroethyl)-1H-indol-5-yl) piperidin-1-yl)-3,3,3-trifluoropropan-1-one (339); 1-(4-(2-(3,4-dimethoxyphenyl)-3-(2,2,2-trifluoroethyl)-1H-indol-5-yl)piperidin-1-yl)-3-(dimethylamino)propan-1-one (340); 1-(4-(2-(3,4-dimethoxyphenyl)-3-(2,2,2-trifluoroethyl)-1H-indol-5-yl)piperidin-1-yl)-2-(1H-tetrazol-5-yl)ethan-1-one (341); 1-(4-(2-(3,4-dimethoxyphenyl)-3-(2,2,2-trifluoroethyl)-1H-indol-5-yl)piperidin-1-yl)-2-(pyrazin-2-yl)ethan-1-one (342); N-(4-(4-(2-(3,4-dimethoxyphenyl)-3-(2,2,2-trifluoroethyl)-1H-indol-5-yl)piperidin-1-yl)-4-oxobutyl) acetamide (343); 1-(4-(2-(3,4-dimethoxyphenyl)-3-(2,2,2-trifluoroethyl)-1H-indol-5-yl)piperidin-1-yl)-3-(1H-pyrrol-1-yl)propan-1-one (344); 1-(4-(4-(2-(3,4-dimethoxyphenyl)-3-(2,2,2-trifluoroethyl)-1H-indol-5-yl) piperidine-1-carbonyl)piperidin-1-yl)ethan-1-one (345); 4-(4-(2-(3,4-dimethoxyphenyl)-3-(2,2,2-trifluoroethyl)-1H-indol-5-yl)piperidin-1-yl)-N,N-dimethyl-4-oxobutanamide (346); 1-(4-(2-(3,4-dimethoxyphenyl)-3-(2,2,2-trifluoroethyl)-1H-indol-5-yl)piperidin-1-yl)-2-(methylsulfonyl)ethan-1-one (347); 1-(4-(2-(3,4-dimethoxyphenyl)-3-(2,2,2-trifluoroethyl)-1H-indol-5-yl)piperidin-1-yl)-3-(pyridin-3-yl) propan-1-one (348); 1-(4-(2-(3,4-dimethoxyphenyl)-3-(2,2,2-trifluoroethyl)-1H-indol-5-yl)piperidin-1-yl)-2-(pyridin-3-yloxy)ethan-1-one (349); 1-(4-(2-(3,4-dimethoxyphenyl)-3-(2,2,2-trifluoroethyl)-1H-indol-5-yl) piperidin-1-yl)-4,4,4-trifluorobutan-1-one (350); 1-(4-(2-(3,4-dimethoxyphenyl)-3-(2,2,2-trifluoroethyl)-1H-indol-5-yl) piperidin-1-yl)-4-(dimethylamino)butan-1-one (351); (S)-1-(4-(2-(3,4-dimethoxyphenyl)-3-(2,2,2-trifluoroethyl)-1H-indol-5-yl)piperidin-1-yl)-3-hydroxybutan-1-one (352); (R)-1-(4-(2-(3,4-dimethoxyphenyl)-3-(2,2,2-trifluoroethyl)-1H-indol-5-yl)piperidin-1-yl)-3-hydroxybutan-1-one (353); 1-(4-(2-(3,4-dimethoxyphenyl)-3-(2,2,2-trifluoroethyl)-1H-indol-5-yl)piperidin-1-yl)-2-(dimethylamino)ethan-1-one (354); 2-(3,4-dimethoxyphenyl)-5-(1-methylpiperidin-4-yl)-3-(2,2,2-trifluoroethyl)-1H-indole (355); 4-(2-(3,4-dimethoxyphenyl)-3-(2,2,2-trifluoroethyl)-1H-indol-5-yl)-N-ethylpiperidine-1-carboxamide (356); 4-(2-(3,4-dimethoxyphenyl)-3-(2,2,2-trifluoroethyl)-1H-indol-5-yl)-N-phenethylpiperidine-1-carboxamide (357); 4-(2-(3,4-dimethoxyphenyl)-3-(2,2,2-trifluoroethyl)-1H-indol-5-yl)-N-(furan-2-ylmethyl) piperidine-1-carboxamide (358); 1-([1,4'-bipiperidin]-1'-yl)-2-(4-(2-(3,4-dimethoxyphenyl)-3-(2,2,2-trifluoroethyl)-1H-indol-5-yl)piperidin-1-yl)ethan-1-one (359); 2-(4-(2-(3,4-dimethoxyphenyl)-3-(2,2,2-trifluoroethyl)-1H-indol-5-yl)piperidin-1-yl)-N-(2-(1-methylpyrrolidin-2-yl)ethyl) acetamide (360); 1-(4-acetylpiperazin-1-yl)-2-(4-(2-(3,4-dimethoxyphenyl)-3-(2,2,2-trifluoroethyl)-1H-indol-5-yl)piperidin-1-yl)ethan-1-one (361); 2-(4-(2-(3,4-dimethoxyphenyl)-3-(2,2,2-trifluoroethyl)-1H-indol-5-yl) piperidin-1-yl)-1-(4-isopropylpiperazin-1-yl)ethan-1-one (362); 2-(4-(2-(3,4-dimethoxyphenyl)-3-(2,2,2-trifluoroethyl)-1H-indol-5-yl) piperidin-1-yl)-1-(4-(4-methylpiperazin-1-yl)piperidin-1-yl) ethan-1-one (363); 2-(4-(2-(3,4-dimethoxyphenyl)-3-(2,2,2-trifluoroethyl)-1H-indol-5-yl) piperidin-1-yl)-1-(4-(dimethylamino)piperidin-1-yl) ethan-1-one (364); 2-(4-(2-(3,4-dimethoxyphenyl)-3-(2,2,2-trifluoroethyl)-1H-indol-5-yl) piperidin-1-yl)-N-(3-(dimethylamino)propyl)-N-methylacetamide (365); 2-(4-(2-(3,4-dimethoxyphenyl)-3-(2,2,2-trifluoroethyl)-1H-indol-5-yl)piperidin-1-yl)-1-(4-(pyridin-4-yl)piperazin-1-yl) ethan-1-one (366); 2-(4-(2-(3,4-dimethoxyphenyl)-3-(2,2,2-trifluoroethyl)-1H-indol-5-yl) piperidin-1-yl)-N-(2-(dimethylamino)ethyl)-N-methylacetamide (367); 2-(4-(2-(3,4-dimethoxyphenyl)-3-(2,2,2-trifluoroethyl)-1H-indol-5-yl)piperidin-1-yl)-1-(4-(pyrimidin-2-yl)piperazin-1-yl)ethan-1-one (368); 1-(2-(4-(2-(3,4-dimethoxyphenyl)-3-(2,2,2-trifluoroethyl)-1H-indol-5-yl) piperidin-1-yl)acetyl) piperidine-4-carboxamide (369); 2-(4-(2-(3,4-dimethoxyphenyl)-3-(2,2,2-trifluoroethyl)-1H-indol-5-yl)piperidin-1-yl)-N-methyl-N-(1-methylpyrrolidin-3-yl)acetamide (370); (R)-2-(4-(2-(3,4-dimethoxyphenyl)-3-(2,2,2-trifluoroethyl)-1H-indol-5-yl)piperidin-1-yl)-1-(2-(hydroxymethyl)pyrrolidin-1-yl)ethan-1-one (371); 2-(4-(2-(3,4-dimethoxyphenyl)-3-(2,2,2-trifluoroethyl)-1H-indol-5-yl)piperidin-1-yl)-N-(2-(dimethylamino)ethyl)-N- ethylacetamide (372); (R)-2-(4-(2-(3,4-dimethoxyphenyl)-3-(2,2,2-trifluoroethyl)-1H-indol-5-yl)piperidin-1-yl)-1-(3-(dimethylamino)pyrrolidin-1-yl) ethan-1-one (373); (S)-2-(4-(2-(3,4-dimethoxyphenyl)-3-(2,2,2-trifluoroethyl)-1H-indol-5-yl)piperidin-1-yl)-1-(3-(dimethylamino)pyrrolidin-1-yl)ethan-1-one (374); 2-(4-(2-(3,4-dimethoxyphenyl)-3-(2,2,2-trifluoroethyl)-1H-indol-5-yl)piperidin-1-yl)-N-(2-(pyrrolidin-1-yl)ethyl)acetamide (375); 2-(4-(2-(3,4-dimethoxyphenyl)-3-(2,2,2-trifluoroethyl)-1H-indol-5-yl)piperidin-1-yl)-N-(3-(2-oxopyrrolidin-1-yl)propyl) acetamide (376); N-(sec-butyl)-2-(4-(2-(3,4-dimethoxyphenyl)-3-(2,2,2-trifluoroethyl)-1H-indol-5-yl)piperidin-1-yl) acetamide (377); 2-(4-(2-(3,4-dimethoxyphenyl)-3-(2,2,2-trifluoroethyl)-1H-indol-5-yl)piperidin-1-yl)-N-(pentan-3-yl)acetamide (378); N-(2-acetamidoethyl)-2-(4-(2-(3,4-dimethoxyphenyl)-3-(2,2,2-trifluoroethyl)-1H-indol-5-yl)piperidin-1-yl)acetamide (379); 2-(4-(2-(3,4-dimethoxyphenyl)-3-(2,2,2-trifluoroethyl)-1H-indol-5-yl)piperidin-1-yl)-N-(2-(dimethylamino)ethyl)acetamide (380); N-(cyanomethyl)-2-(4-(2-(3,4-dimethoxyphenyl)-3-(2,2,2-trifluoroethyl)-1H-indol-5-yl)piperidin-1-yl)acetamide (381); 2-(4-(2-(3,4-dimethoxyphenyl)-3-(2,2,2-trifluoroethyl)-1H-indol-5-yl)piperidin-1-yl)-N-(3-(dimethylamino)propyl)acetamide (382); N-(3-(1H-imidazol-1-yl)propyl)-2-(4-(2-(3,4-dimethoxyphenyl)-3-(2,2,2-trifluoroethyl)-1H-indol-5-yl)piperidin-1-yl)acetamide (383); 2-(4-(2-(3,4-dimethoxyphenyl)-3-(2,2,2-trifluoroethyl)-1H-indol-5-yl)piperidin-1-yl)-N-(4-sulfamoylphenethyl)acetamide (384); N-(2-amino-2-oxoethyl)-2-(4-(2-(3,4-dimethoxyphenyl)-3-(2,2,2-trifluoroethyl)-1H-indol-5-yl)piperidin-1-yl)acetamide (385); 2-(2-(4-(2-(3,4-dimethoxyphenyl)-3-(2,2,2-trifluoroethyl)-1H-indol-5-yl)piperidin-1-yl) acetamido)ethane-1-sulfonic acid (386); N-(5-(tert-butyl)-1H-pyrazol-3-yl)-2-(4-(2-(3,4-dimethoxyphenyl)-3-(2,2,2-trifluoroethyl)-1H-indol-5-yl)piperidin-1-yl)acetamide (387); 2-(4-(2-(3,4-dimethoxyphenyl)-3-(2,2,2-trifluoroethyl)-1H-indol-5-yl)piperidin-1-yl)-N-(4-(pyrrolidin-1-yl)butyl)acetamide (388); 2-(3,4-dimethoxyphenyl)-5-(piperidin-4-yl)-3-(tetrahydro-2H-pyran-4-yl)-1H-indole (389); 1-(2-(4-(2-(3,4-dimethoxyphenyl)-3-(tetrahydro-2H-pyran-4-yl)-1H-indol-5-yl)piperidin-1-yl)-2-oxoethyl)-N,N-diethylpiperidine-3-carboxamide (391 and 392); 1-(4-(2-(3,4-dimethoxyphenyl)-3-(tetrahydro-2H-pyran-4-yl)-1H-indol-5-yl)piperidin-1-yl)-2-(dimethylamino)ethan-1-one (393); (R)-1-(4-(2-(3,4-dimethoxyphenyl)-3-(tetrahydro-2H-pyran-4-yl)-1H-indol-5-yl)piperidin-1-yl)-2-((3-methylbutan-2-yl)amino)ethan-1-one (394); 1-(4-(2-(3,4-dimethoxyphenyl)-3-(2,2,2-trifluoro-1-hydroxyethyl)-1H-indol-5-yl) piperidin-1-yl)-2-(dimethylamino)ethan-1-one (395); 2-(3,4-dimethoxyphenyl)-3-ethyl-6-methyl-5-(piperidin-4-yl)-1H-indole, HCl (396); 2-(3,4-dimethoxyphenyl)-3-ethyl-6-methoxy-5-(piperidin-4-yl)-1H-indole (397); 2-(3,4-dimethoxyphenyl)-3-ethyl-5-(1'-isopropyl-[1,4'-bipiperidin]-4-yl)-6-methoxy-1H-indole (398); 1-(4-(3-(2,2-difluoroethyl)-2-(3,4-dimethoxyphenyl)-1H-indol-5-yl) piperidin-1-yl)-2-(dimethylamino)ethan-1-one (399); 2-(4-(3-(2,2-difluoroethyl)-2-(3,4-dimethoxyphenyl)-1H-indol-5-yl)piperidin-1-yl)-N,N-dimethylacetamide (400); 2-(4-(3-(2,2-difluoroethyl)-2-(3,4-dimethoxyphenyl)-1H-indol-5-yl)piperidin-1-yl)-N-methylacetamide (401); 1-(4-(2-(3,4-dimethoxyphenyl)-3-methyl-1H-indol-5-yl)piperidin-1-yl)-2-(dimethylamino)ethan-1-one (402); 1-(2-(4-(2-(3,4-dimethoxyphenyl)-3-methyl-1H-indol-5-yl)piperidin-1-yl)-2-oxoethyl)-N,N-diethylpiperidine-3-carboxamide (404); (R)-2-((2,3-dihydroxypropyl) amino)-1-(4-(2-(3,4-dimethoxyphenyl)-3-methyl-1H-indol-5-yl)piperidin-1-yl)ethan-1-one (405); 1-(4-(2-(3,4-dimethoxyphenyl)-3-methyl-1H-indol-5-yl)piperidin-1-yl)-2-((3-hydroxybutyl) amino) ethan-1-one (406); 1-(4-(2-(3,4-dimethoxyphenyl)-3-methyl-1H-indol-5-yl) piperidin-1-yl)-2-(4-(dimethylamino)piperidin-1-yl)ethan-1-one (407); 1-(4-(2-(3,4-dimethoxyphenyl)-3-methyl-1H-indol-5-yl)piperidin-1-yl)-2-((2-hydroxyethyl)(methyl) amino)ethan-1-one (408); 1-(4-(2-(3,4-dimethoxyphenyl)-3-methyl-1H-indol-5-yl) piperidin-1-yl)-2-(4-methylpiperazin-1-yl)ethan-1-one (409); 1-(4-(2-(3,4-dimethoxyphenyl)-3-methyl-1H-indol-5-yl)piperidin-1-yl)-2-(4-methyl-1,4-diazepan-1-yl)ethan-1-one (410); N-(2-(4-(2-(3,4-dimethoxyphenyl)-3-isopropyl-1H-indol-5-yl) piperidin-1-yl)ethyl)hept-6-ynamide (411); 2-(3,4-dimethoxyphenyl)-5-(1'-isopropyl-[1,4'-bipiperidin]-4-yl)-3-(2,2,2-trifluoroethyl)-1H-indole (412); 2-(4-(2-(3,4-dimethoxyphenyl)-3-(2,2,2-trifluoroethyl)-1H-indol-5-yl)piperidin-1-yl)-N-methylethanamine (413); tert-butyl (2-(4-(2-(3,4-dimethoxyphenyl)-3-(2,2,2-trifluoroethyl)-1H-indol-5-yl) piperidin-1-yl)-2-oxoethyl) (methyl)carbamate (414); 2-(4-(2-(3,4-dimethoxyphenyl)-3-methyl-1H-indol-5-yl)piperidin-1-yl)-N,N-dimethylethan-1-amine (415); 2-(3,4-dimethoxyphenyl)-5-(1'-isobutyl-[1,3'-bipiperidin]-4-yl)-3-methyl-1H-indole (416); 2-(3,4-dimethoxyphenyl)-5-(1'-isobutyl-[1,3'-bipiperidin]-4-yl)-3-methyl-1H-indole (417); 1-(2-(4-(2-(3,4-dimethoxyphenyl)-3-(2,2,2-trifluoroethyl)-1H-indol-5-yl)piperidin-1-yl)-2-oxoethyl)-N,N-diethylpiperidine-3-carboxamide (418, 420-421); and 1-(2-(4-(2-(3,4-dimethoxyphenyl)-3-(2,2,2-trifluoroethyl)-1H-indol-5-yl)piperidin-1-yl)-2-oxoethyl)-N,N-dimethylpiperidine-3-carboxamide (419).

8. A pharmaceutical composition comprising a compound according to claim 1 or a pharmaceutically-acceptable salt thereof; and a pharmaceutically acceptable carrier.

9. A method of treating an autoimmune disease or a chronic inflammatory disease, comprising administering to a mammalian patent a compound according to claim 1 or a pharmaceutically acceptable salt thereof, wherein said autoimmune disease or chronic inflammatory disease is selected from systemic lupus erythematosus (SLE), rheumatoid arthritis, multiple sclerosis (MS), and Sjögren's syndrome.

10. The method according to claim 9 wherein said autoimmune disease or chronic inflammatory disease is systemic lupus erythematosus.

11. The method according to claim 9 wherein said autoimmune disease or chronic inflammatory disease is rheumatoid arthritis.

12. The compound according to claim 1 or a salt thereof, wherein said compound is:

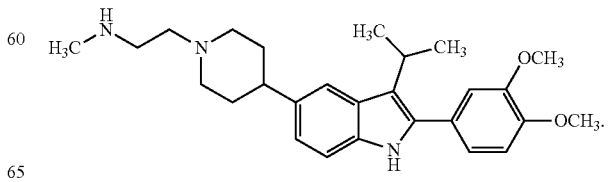

13. The compound according to claim 1 or a salt thereof, wherein said compound is:
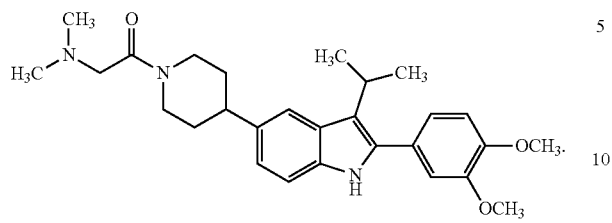
14. The compound according to claim 1 or a salt thereof, wherein said compound is:
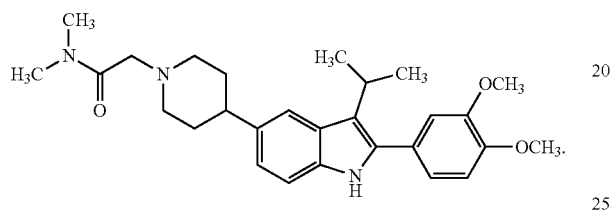
* * * * *